US008815239B2

(12) United States Patent
Mulard et al.

(10) Patent No.: US 8,815,239 B2
(45) Date of Patent: Aug. 26, 2014

(54) GLYCOCONJUGATES AND USE THEREOF AS VACCINE AGAINST SHIGELLA FLEXNERI SEROTYPE 3A AND X

(75) Inventors: Laurence Mulard, Le Kremlin Bicetre (FR); Julien Boutet, La Plaine sur Mer (FR); Catherine Guerreiro, Combes la Ville (FR); Farida Nato, Antony (FR); Philippe Sansonetti, Paris (FR); Armelle Phalipon, Paris (FR)

(73) Assignees: Institut Pasteur, Paris (FR); Centre National de la Recherche Scientifique, Paris (FR); Universite Paris Descartes, Paris (FR)

( * ) Notice: Subject to any disclaimer, the term of this patent is extended or adjusted under 35 U.S.C. 154(b) by 589 days.

(21) Appl. No.: 12/663,454

(22) PCT Filed: May 16, 2008

(86) PCT No.: PCT/FR2008/000687
§ 371 (c)(1),
(2), (4) Date: Jun. 1, 2010

(87) PCT Pub. No.: WO2008/155487
PCT Pub. Date: Dec. 24, 2008

(65) Prior Publication Data
US 2010/0239584 A1 Sep. 23, 2010

(30) Foreign Application Priority Data

Jun. 5, 2007 (CA) ..................................... 2591253

(51) Int. Cl.
*A61K 39/395* (2006.01)
*A61K 39/112* (2006.01)
*A61P 31/04* (2006.01)
*C12N 15/13* (2006.01)

(52) U.S. Cl.
USPC .............. 424/137.1; 435/72; 514/53; 514/54; 536/123.1; 536/123.13

(58) Field of Classification Search
USPC ....................... 424/137.1; 435/72; 514/53, 54; 536/123.1, 123.13
See application file for complete search history.

(56) References Cited

U.S. PATENT DOCUMENTS

2003/0235818 A1* 12/2003 Katritch et al. ................... 435/5
2008/0112951 A1 5/2008 Phalipon et al.

FOREIGN PATENT DOCUMENTS

WO       2005 003775       1/2005
WO   WO 2005/003775 A2 *  1/2005 ........... G01N 33/569

OTHER PUBLICATIONS

Polotsky et al, Infection and Immunity, 1994, 62(1), 210-214.*
Carlin et al, Infection and Immunity, 1986, 53 (1), 103-109.*
Wright et al, Org. Biomal.Chem. 2004, 2, 1518-1527.*
Noriega et al, Infection and Immunity, 1999, 67(2), 782-88.*
Phalipon et al, Journal of Immunology, 2006, 176, 1686-94.*
Pozsgay, V., "Synthesis of Glycoconjugate Vaccines against *Shigella dysenteriae* Type 1", J. Org. Chem., vol. 63, pp. 5983-5999 (Jan. 1, 1998) XP-002305374.
Wright, K. et al., "Preparation of Synthetic Glycoconjugates as Potential Vaccines Against *Shigella flexneri* Serotype 2a Disease", Organic and Biomolecular Chemistry, vol. 2, No. 10, pp. 1518-1527 (May 21, 2004) XP-002305375.
Pozsgay, V. et al., "Towards an Oligosaccharide-Based Glycoconjugate Vaccine Against *Shigella dysenteriae* Type 1", Synlett, No. 6, pp. 743-767 (2003) XP-002535551.
Noriega, F. R. et al., "Strategy for Cross-Protection Among *Shigella flexneri* Serotypes", Infection and Immunity, vol. 67, No. 2, pp. 782-788 (Feb. 1999) XP-002535552.
Ekwall, E. et al., "*Shigella flexneri* O-Antigen-Specific Enzyme Immunoassay: Class-Specific Antibody Titres Against Lipopolysaccharide Antigen in Healthy Vietnamese and Swedish Populations", Serodiagnosis and Immunotherapy, vol. 2, No. 1, pp. 47-61 (Feb. 1, 1988) XP-023250134.
Witkowska, D. et al., "Enterobacterial 38-kDa Outer Membrane Protein is an Age-Dependent Molecular Marker of Innate Immunity and Immunoglobulin Deficiency as Results From its Reactivity With IgG and IgA Antibody", FEMS, Immunology and Medical Microbiology, vol. 48, No. 2, pp. 205-214 (Nov. 1, 2006) XP-002478615.
Carlin, N. I. A., et al., "Monoclonal Antibodies Specific for *Shigella flexneri* Lipopolysaccharides: Clones Binding to Type I and Type III:6,7,8 Antigens, Group 6 Antigen, and a Core Epitope", Infection and Immunity, vol. 53, No. 1, pp. 103-109 (1986) XP-002535553.
Carlin, N. I. A., et al., "Monoclonal Antibodies Specific for *Shigella flexneri* Lipopolysaccharides: Clones Binding to Type IV, V, and VI Antigens, Group 3,4 Antigen, and an Epitope Common to All *Shigella flexneri* and *Shigella dysenteriae* Type 1 Strains", Infection and Immunity, vol. 55, No. 6, pp. 1412-1420 (1987) XP-002535554.

* cited by examiner

*Primary Examiner* — Ganapathy Krishnan
(74) *Attorney, Agent, or Firm* — Oblon, Spivak, McClelland, Maier & Neustadt, L.L.P.

(57) ABSTRACT

The present invention relates to compounds derived from sugars which reproduce the epitopes of *Shigella flexneri* serotypes 3a and X and to the use thereof for the preparation of vaccine compositions. More specifically, the subject matter of the present invention relates to novel glycoconjugated compounds comprising oligosaccharides or polysaccharides described hereinafter, to the method for synthesizing these oligosaccharides or polysaccharides and glycoconjugates, to derivatives of these oligosaccharides or polysaccharides, to compositions containing same, and also to the use of the glycoconjugates for vaccination purposes. Finally, the present invention relates to methods for diagnosing a *Shigella flexneri* infection using one or more oligosaccharides or polysaccharides or conjugates thereof.

19 Claims, 9 Drawing Sheets

Figure 1:
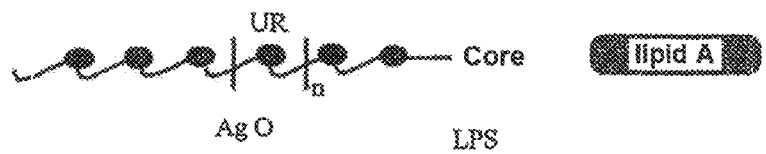

GLYCOCONJUGATES AND USE THEREOF AS VACCINE AGAINST *SHIGELLA FLEXNERI* SEROTYPE 3A AND X

The present invention relates to compounds derived from sugars, which reproduce the epitopes of serotypes 3a and X of *Shigella flexneri* and use thereof for the preparation of vaccine compositions.

More specifically, the object of the present invention relates to novel glycoconjugated compounds comprising oligo- or polysaccharides described hereunder, to the method of synthesis of said oligo- or polysaccharides and glycoconjugates, to derivatives of said oligo- or polysaccharides, to compositions containing them, as well as to the use of the glycoconjugates for vaccination purposes.

The present invention finally relates to methods of diagnosis of a *Shigella flexneri* infection using one or more oligo- or polysaccharides or conjugates thereof.

The polysaccharide-protein conjugated vaccines represent a major advance in the development of antibacterial vaccines compatible with use in young children. It should therefore prove useful to develop a chemically defined vaccine of the glycoconjugated type against the infections linked to the prevailing serotypes of *Shigella flexneri*, a Gram-negative bacterium responsible for the endemic form of bacillary dysentery. So as to avoid certain limitations connected with the use of polysaccharides extracted from bacterial cultures, the use of synthetic saccharide antigens that mimic the polysaccharide (PS) moiety of the lipopolysaccharide (LPS) of *S. flexneri*, the main target of the host's humoral protective response to the infection, was preferred.

Shigellosis or bacillary dysentery is responsible for about 1 million deaths a year, corresponding to 165 million cases, mainly occurring in the developing countries (only 1.5 million cases in the developed countries). Children under 5 years of age are the most affected.

This diarrheal disease, transmitted by the fecal-oral route, is caused by a Gram-negative enterobacterium called *Shigella*. Among the various known types of *Shigella*, *Shigella dysenteria* type 1 is the cause of devastating epidemics, whereas *Shigella flexneri* and *Shigella sonnei* are responsible for the endemic form of the disease. In the case of *Shigella flexneri*, several serotypes are prevalent, in particular serotypes 2a, 1b, 3a and 6. Improving the hygiene conditions in the affected regions would make it possible to reduce the number of cases of shigellosis, but this is still difficult. Thus, the only realistic approach in terms of prevention is still the development of a vaccine with a broad coverage of serotypes. There is still no vaccine against shigellosis.

The immune response to the infection is essentially humoral. The immune response protecting against reinfection is directed against the main surface antigen, the lipopolysaccharide or LPS. The latter is composed of three entities: a lipid moiety, lipid A anchored in the membrane; a polysaccharide of low molecular weight, called O antigen, exposed to the external environment and whose repeating unit characterizes the serotype of the bacterium; and a short oligosaccharide called the core, which joins the two together (cf. FIG. 1).

The data available in this area show that the protective immune response is specific to the infectious serotype, which suggests the O antigen as preferred target. By analogy with the vaccines based on capsular polysaccharides that are already marketed, it is to be hoped that vaccines derived from LPS can be developed.

Now, owing to the presence of lipid A, LPS is toxic, and cannot be used as such in vaccine preparations of the glycoconjugated type. A preliminary stage of detoxification is essential. Detoxified LPS is a polymer of low molecular weight that has to be conjugated to a carrier molecule in order to be used in a vaccine preparation.

This approach has certain limitations:
low yields
high cost
keeping the O antigen and therefore the epitopes involved in protection intact during the various purification stages and the various stages of chemical detoxification and activation.

No LPS-based glycoconjugated vaccine has yet been commercialized.

The alternative developed consists of designing chemically defined glycoconjugated vaccines based on the use of synthetic oligosaccharides that are representative of the glycoside epitopes involved in protection.

Figure 2:
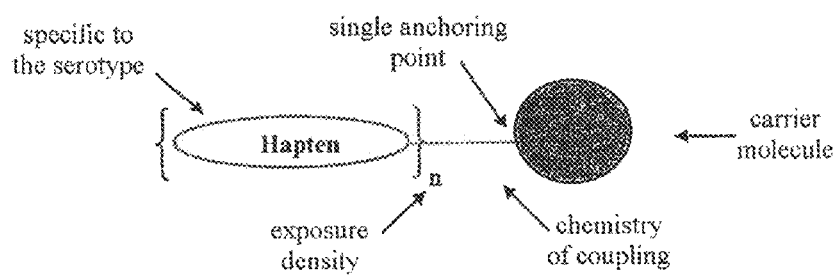

The strategy of the targeted vaccine constructions is to couple, by covalent bonding and via a single anchoring point, a hapten specific to the infectious serotype to a carrier molecule, endowing it with the required immunogenicity (cf. FIG. 2). In addition to the nature of the hapten and that of the carrier molecule, various parameters must be taken into account such as the exposure density of the hapten on the carrier molecule or the chemistry of coupling.

This is the approach that the inventors have developed for the prevailing serotypes 3a and X; thus, firstly, the saccharide epitope(s) "protecting" against infection with *S. flexneri* 3a were identified. To do this, various oligosaccharides representative of the natural polymeric antigen whose biological repeating unit is the branched pentasaccharide (shown in FIG. 21) were synthesized, notably in series of tri-, tetra- and pentasaccharides.

Figure 21:
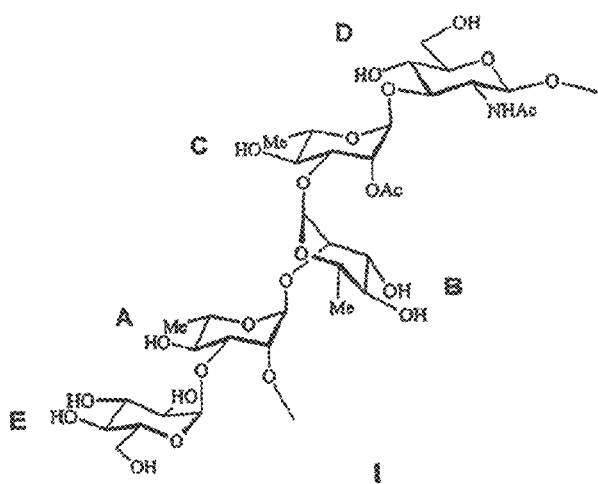

The O antigen of the bacterium *S. flexneri* serotype 3a has a branched pentasaccharide $(E)AB_{Ac}CD$ as the repeating unit. The linear moiety is a tetrasaccharide composed of three L-rhamnose residues A, B and C and an N-acetyl-D-glucosamine residue D. Serotype specificity is linked to the presence of an α-D-glucose residue E in position 3 of rhamnose A as well as to the presence of an acetyl function in position 2 of rhamnose C (FIG. 21).

The O antigen of the bacterium *S. flexneri* serotype X is the branched pentasaccharide (E)ABCD.

Once the protective epitopes had been identified, the inventors then synthesized protein or peptide glycoconjugates, inducing raised titers of anti-PS antibodies in the mouse. These glycoconjugates incorporate saccharide haptens that mimic natural PS optimally. The haptens are selected on the basis of the antigenicity data of the synthesized oligosaccharides (evaluated by ELISA).

FIGURE CAPTIONS

Figure 3:
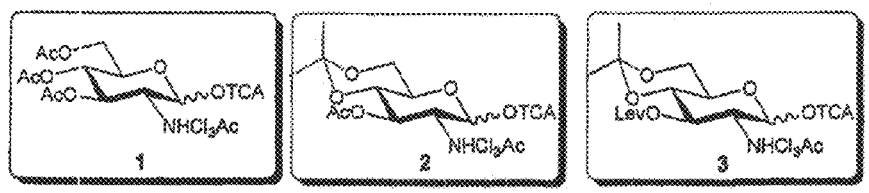
Figure 6:
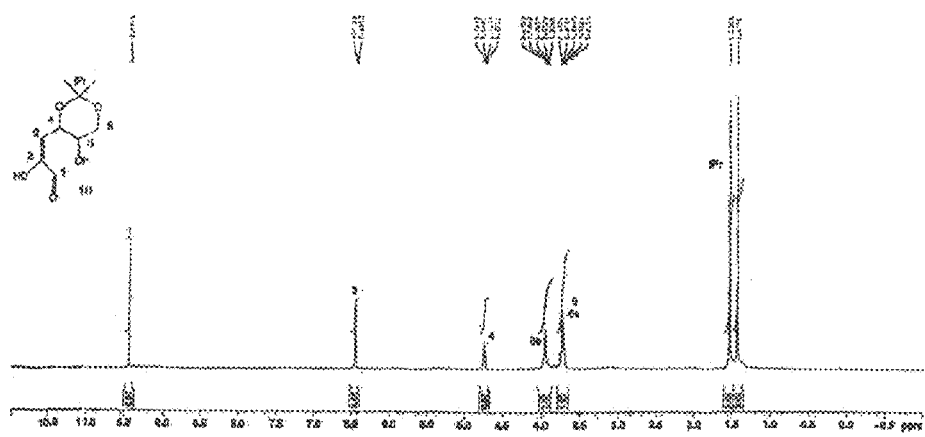
Figure 7:
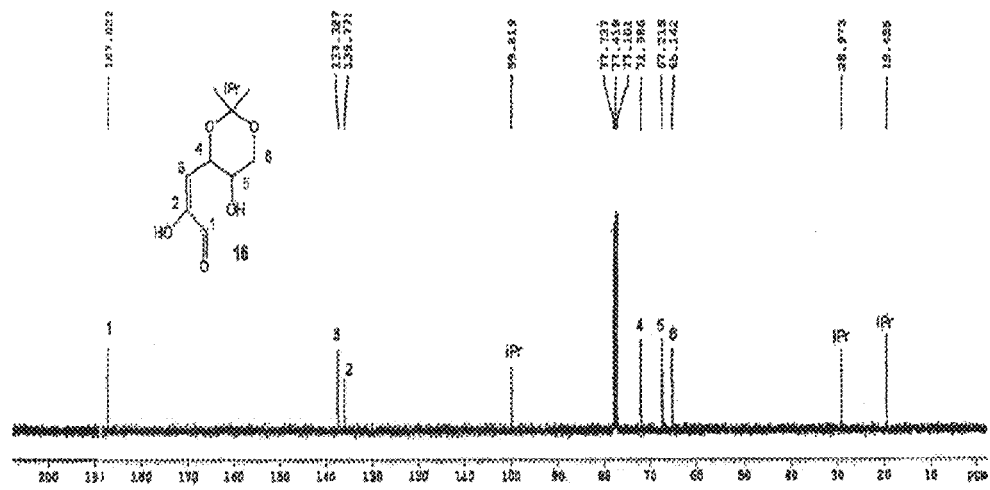

FIG. 1: Composition of the LPS
FIG. 2: Vaccine constructions
FIG. 3: Donors 1, 2 and 3
FIG. 4: Structure of secondary product 11
FIG. 5: Structure of secondary product 13
FIG. 6: Proton NMR of the keto-aldehyde 16
FIG. 7: Carbon NMR of the keto-aldehyde 16
FIG. 8: Structure of the diol 26
FIG. 9: Structure of the thiophenyl donor 34
FIG. 10: Structure of 33' resulting from Chapman rearrangement of 33
FIG. 11: Structure of oxazoline 2'
FIG. 12: Structure of the donor 39
FIG. 13: Comparison of the proton spectra of 40 and 41

Figure 14:
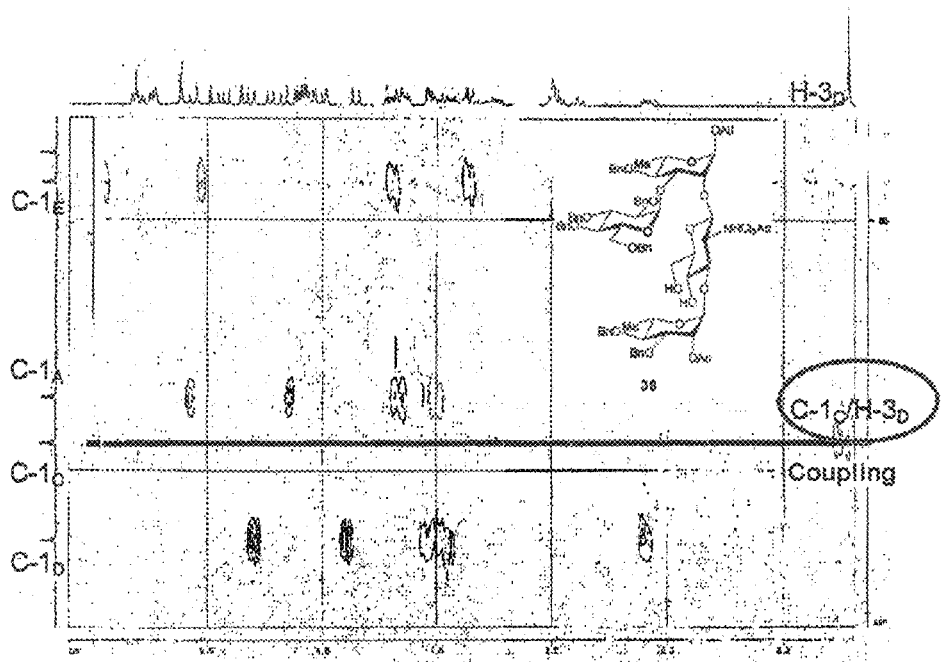

FIG. 14: HMBC of the coupling product 41

Figure 15:
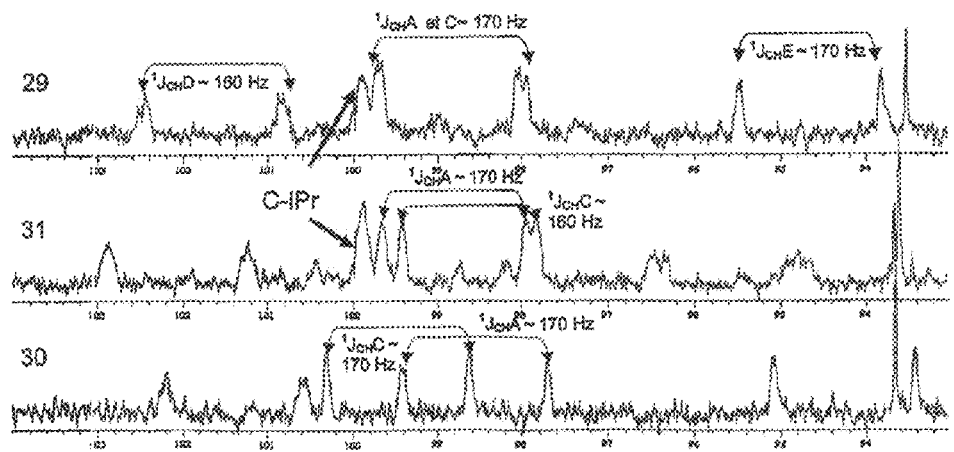

FIG. 15: Superposition of the $C^{13}$GD spectra of 40, 41 and 42

Figure 16:
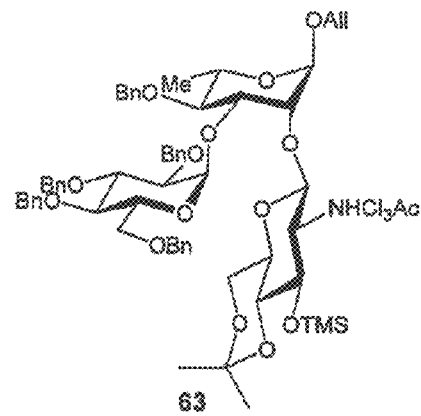

FIG. 16: Structure of the silylated product observed during coupling between 38 and 47

Figure 17:
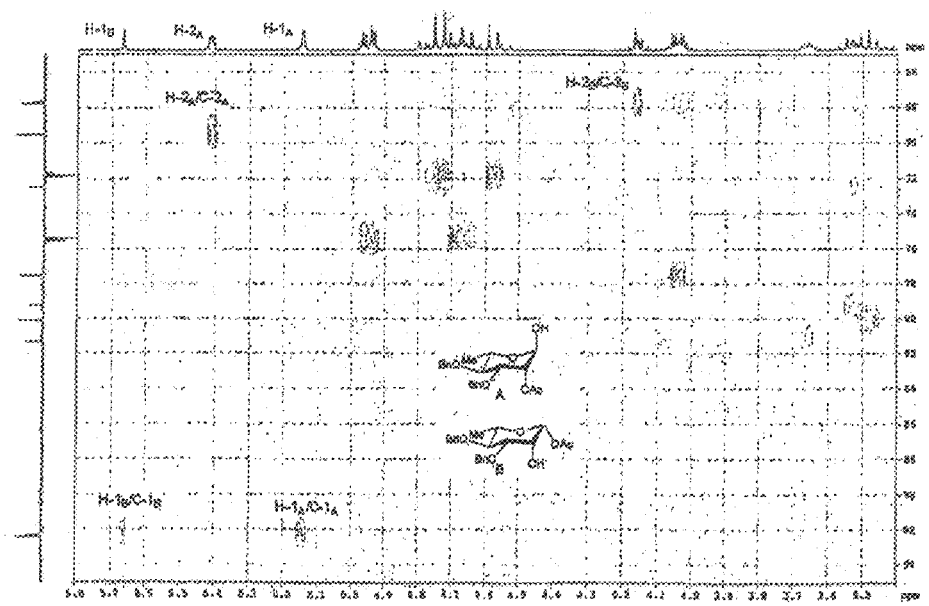

FIG. 17: HSQC of the mixture 77 and 78

Figure 18:
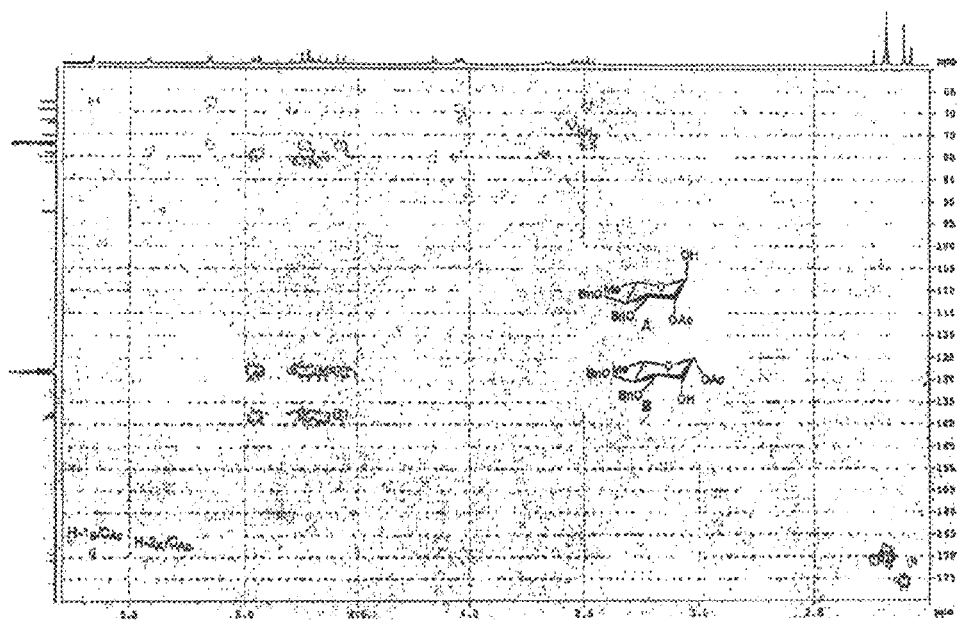

FIG. 18: HMBC of the mixture 77 and 78

Figure 19:
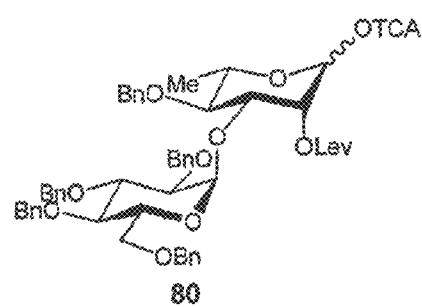

FIG. 19: Structure of the donor 80

Figure 20:
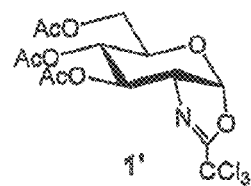

FIG. 20: Structure of oxazoline 1'

FIG. 21: O antigen of the bacterium S. flexneri 3a

Figure 22:
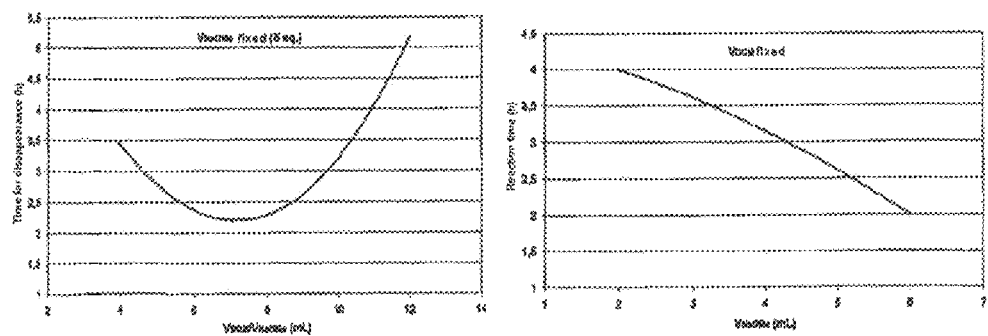

FIG. 22: Investigation of reduction of the trichloroacetamide function

DETAILED DESCRIPTION OF THE INVENTION

Thus, the present invention relates to conjugates specific to Shigella flexneri of serotype 3a and/or X, comprising a saccharide (oligosaccharide or polysaccharide) selected from the group comprising list L1:

$(X)_x$-$\{D(E)A\}_n$-$(Y)_y$
$(X)_x$-$\{(E)AB\}_n$-$(Y)_y$
$(X)_x$-$\{CD(E)A\}_n$-$(Y)_y$
$(X)_x$-$\{D(E)AB\}_n$-$(Y)_y$
$(X)_x$-$\{(E)ABC\}_n$-$(Y)_y$
$(X)_x$-$\{BCD(E)A\}_n$-$(Y)_y$
$(X)_x$-$\{CD(E)AB\}_n$-$(Y)_y$
$(X)_x$-$\{D(E)ABC\}_n$-$(Y)_y$
$(X)_x$-$\{(E)ABCD\}_n$-$(Y)_y$, and in which:

A represents a residue α-L-Rhap-(1,2),

B represents a residue α-L-Rhap-(1,3),

C represents a residue α-L-Rhap-(1,3) or a residue [2-O-acetyl] α-L-Rhap-(1,3),

D represents a residue β-D-GlcNAcp-(1,2) and

E represents a residue α-D-Glcp-(1,3), x and y independently represent 0 or 1,

X and Y represent a mono-, di- or oligosaccharide and are selected independently from the group comprising A, B, C, D, E, AB, BC, CD, DA, (E)A, ABC, BCD, CDA, DAB, (E)AB, D(E)A, ABCD, BCDA, CDAB, DABC, (E)ABC, D(E)AB, CD(E)A, (E)ABCD, D(E)ABC, CD(E)AB and BCD(E)A, X and Y are such that the sequence of the group -ABCD- is always conserved, and n is an integer between 1 and 10, preferably between 2 and 6 said saccharides (oligosaccharides and polysaccharides) being bound to a preferred substrate molecule M.

X and Y are such that the saccharide according to the invention always has a sequence or a group with a partial or complete sequence of the natural saccharide -ABCD-, see for example compounds I to XXVIII.

The abbreviations used are: Rhap: rhamnopyranosyl; Glcp: glucopyranosyl; GlcNAcp: 2-acetamido-2-deoxy-glucopyranosyl.

DEFINITIONS

In the sense of the invention, an oligosaccharide is a carbohydrate containing from 2 to 20 monosaccharide units joined together; in the present invention the term oligosaccharide is used broadly and includes all the saccharides defined in the present invention; this usage differs from the standard definition of the oligosaccharides, which in general do not contain more than 10 monosaccharide units (Joint Commission on Biological Nomenclature, Eur. J. Biochem., 1982, 126, 433-437).

Polysaccharide means, in the present invention, a carbohydrate containing more than 20 monosaccharide units joined together.

The term saccharide will be used hereinafter to denote both oligosaccharides and polysaccharides.

The term "functional group" refers to groups of atoms characterized by their elementary compositions; said functional groups impart reactivity to the molecule containing them. Common functional groups include: primary amines (R—$NH_2$); primary imines (—C(=NH)—R'); azo: [azo, —N=N—R']; nitrile: —C≡N; carboxylic acid; carboxyl: —C(=O)OH; carboxylic acid and its derivatives such as esters: [—C(=O)O—R'] or activated esters; carbonyl: [aldehyde: —C(=O)H; ketone, —C(=O)—R'], or derivatives of said carbonyls such as masked carbonyls (acetal or thioacetal; alkenes: [—CH=CH—R']; alkynes: [—C≡C—R']; isocyanates: [—N=C=O]; isothiocyanate: [—N=C=S]; thioacyl: [—SCO—R'], [thiol —SH, dithiol: —S—S—R']; azide —$N_3$: hydrazide: —$CONHNH_2$, hydrazine, maleimide, O-alkyl hydroxylamine, halogen. The functional groups according to the invention also comprise the thioglycoside donors and the donors of the phosphate type or trichloroacetimidate or trifluoroacetimidate.

The "structurally similar oligo- or polysaccharides" in the sense of the present invention correspond to a modified oligo- or polysaccharide from list L1, characterized by its ability to mimic, immunologically, the antigenic determinant of the O—SP of S. flexneri, in particular S. flexneri type 3a or X. Said modified oligo- or polysaccharides can be obtained by structural modification, which makes the modified polysaccharides antigenically similar to the antigenic determinant of the O—SP of S. flexneri 3a or X. Said modified oligo- or polysaccharides can be obtained for example by means of a specific spacer that makes it possible to put these oligosaccharides in the same conformation as the native O—SP.

The term "immunoreactive" denotes a specific bond between a molecule containing an antigenic determinant and a molecule containing an antibody.

An antibody corresponds to the immunoglobulins or to fragments thereof comprising a recognition site and an antigen binding site. Antibodies are either complete immunoglobulins or active fragments such as the fragments ab, ab', (ab')$_2$ and scv, as well as the chimeric antibodies.

The expression "immunologically similar" refers to the capacity of the oligo- or polysaccharide according to the invention to immuno-react or to bind to an antibody as defined in the present invention which recognizes and binds to a native antigenic determinant of the O—SP of S. flexneri of type 3a or X.

The term "substrate molecule M" refers to any molecule that can be bound covalently to an oligo- or polysaccharide of the invention, to form the glycoconjugates of the invention. It includes various substrate molecules (carriers) to be used as vaccine or for preparing diagnostic reagents.

The term "immunocarrier" refers to an immunogenic molecule or to a fragment of the latter that is recognized by the T cells and is capable of inducing an immune response.

The term "other molecules M for the preparation of diagnostic reagents" means, in the sense of the present invention, agents usually employed for immobilizing the molecules on a solid substrate or for labeling the molecules.

A marker refers to any substance that can produce a signal that can be detected by any means.

The term glycoconjugate refers to an oligo- or polysaccharide on list L1 bound covalently to a substrate molecule M (carrier).

"Prevention and treatment" means, in the sense of the present invention, the prevention of infection or reinfection, reduction or elimination of symptoms and reduction or complete elimination of the pathogen. The treatment can be carried out prophylactically or therapeutically.

The oligo- and polysaccharides of the invention are called conjugates or glycoconjugates when they are bound covalently to a substrate molecule M.

Within the scope of the methods described hereunder, cleavage means, indiscriminately, a reaction of deprotection by deacetalation or acid hydrolysis.

Within the scope of the present invention and unless stated otherwise, C represents an acetylated or non-acetylated residue α-L-Rhap-(1,3).

According to an advantageous embodiment of said conjugates, they are combined with a molecule M selected from the group comprising peptides and proteins having at least one epitope T or a derivative of the latter.

According to another embodiment of said conjugates, the substrate molecule M is selected from the group comprising the protein IpaD, the peptide PADRE, tetanus toxin, the protein KLH or the protein $CRM_{197}$.

The oligo- or polysaccharide is preferably conjugated with a molecule M, via a linker molecule or a crosslinking agent, which is preferably a linear molecule having a molecular weight >500 dalton, said molecule being neither pyrogenic nor toxic in the final form of the product.

For conjugation via a linker molecule, either the oligo- or polysaccharide, or the molecule M, or both are first bound covalently to said linker molecule.

Said linker molecule is advantageously a homobifunctional or heterobifunctional molecule (Bioconjugate techniques, G. T. Hermanson, Ed., Academic Press San Diego, 1995), e.g. adipic dihydrazide, ethylenediamine, cystamine, N-succinimidyl-3-(2-pyridyldithio)propionate (SPDP), N-succinimidyl-[N-(2-iodoacetyl)]-β-alanyl propionate-propionate (SIAP), succinimidyl-4-(N-maleimido-methyl) cyclohexane-1 carboxylate (SMCC), 3,3'-dithiodipropionic acid. Among the heterobifunctional linker molecules, we may mention the omega-hydroxy alkanoic acids.

The methods for binding oligo- and/or polysaccharides to nontoxic proteins are well known by a person skilled in the art. For example, in U.S. Pat. No. 5,204,098 and U.S. Pat. No. 5,738,855 it is stated that a saccharide containing at least one carboxyl group can, by means of a carbodiimide condensation, be thiolated with cystamine or aminated with an adipic dihydrazide, diamino esters or ethylenediamine. The groups that can be introduced by this method or by other methods known by a person skilled in the art include the following groups: thiols, hydrazides, amines and carboxylic acids. Both the thiolated intermediates and the aminated intermediates are stable, can be lyophilized and stored in the cold. The thiolated intermediate can be reduced and bound covalently to a polymeric substrate molecule M containing a disulfide group such as a 2-pyridyldithio group. The aminated intermediate can be bound covalently to a polymeric substrate molecule M containing a carboxyl group by a reaction of carbodiimide condensation.

The saccharides can be bound covalently to the substrate molecule M with or without a linker molecule or spacer. A substrate molecule M can be a natural, modified, synthetic, semisynthetic or recombinant molecule and contains one or more functional groups, for example primary or secondary amino groups, azido groups or carboxyl groups. The substrate molecule M can be water-soluble or water-insoluble. The immunogenic substrate molecules M are selected for increasing the immunogenicity of the saccharide and/or for inducing the production of antibodies to said substrate molecule M that are of interest medically.

The immunogenic substrate molecules M include proteins, peptides, polysaccharides, polylactic acids, polyglycolic acids, lipid aggregates and inactivated viral particles.

Said conjugates can advantageously be derivatized with functional groups, so as to make them capable of binding to chemical ligands such as biotin or physical substrates such as plates, beads or particles (metal particles, such as gold particles or others).

Said conjugates can react with the molecule M via the saccharide residue either directly, or via a spacer, which can be monovalent or polyvalent (i.e. comprising several copies of said saccharide residue).

According to another advantageous embodiment of said conjugate, the ratio of saccharide to molecule M is between 1:1 and 200:1, preferably between 30:1 and 10:1.

The present invention also relates to conjugates, characterized in that the saccharide is selected from the group comprising tetrasaccharides, pentasaccharides and multimers of the latter conforming to the group sequence of the natural saccharides of serotypes 3a and X, namely -ABCD-.

According to another embodiment, said saccharide is selected from the group comprising:

[CD(E)A], [D(E)AB], [(E)ABC], [BCD(E)A], [CD(E)AB], [D(E)ABC], [(E)ABCD], [BCD(E)A]$_n$, [CD(E)AB]$_n$, [D(E)ABC]$_n$, [(E)ABCD]$_n$, [BCD(E)AB], [D(E)ABCD], [D(E)ABCD(E)A], [BCD(E)ABCD], [BCD(E)ABCD(E)A], [D(E)ABCD(E)ABC], with n being between 2 and 5.

The present invention also comprises the saccharide derivatives selected from the group comprising:

{D(E)A}$_n$-WQ
{(E)AB}$_n$-WQ
{CD(E)A}$_n$-WQ
{D(E)AB}$_n$-WQ
{(E)ABC}$_n$-WQ
{BCD(E)A}$_n$-WQ
{CD(E)AB}$_n$-WQ
{D(E)ABC}$_n$-WQ
{(E)ABCD}$_n$-WQ in which A, B, C, D, E and n have the same definition as in claim 1, W is an oxygen or sulfur atom and Q represents one of the following groups: alkyl, alkenyl, acyl, or a donor group having from 1 to 12 carbon atoms, optionally functionalized.

The present invention also includes the saccharides in list L1 comprising a spacer of the type O—R—Z and preferably of the type O—R—$NH_2$ (Z=$NH_2$), in which R represents an alkyl group having from 1 to 12 carbon atoms and preferably from 1 to 6 carbon atoms and Z is a functional group. We thus obtain, starting from list L1, the following derivatized saccharides:

{D(E)A}$_m$-O—R—Z
{(E)AB}$_m$-O—R—Z
{CD(E)A}$_m$-O—R—Z
{D(E)AB}$_m$-O—R—Z
{(E)ABC}$_m$-O—R—Z
{BCD(E)A}$_n$-O—R—Z
{CD(E)AB}$_n$-O—R—Z
{D(E)ABC}$_n$-O—R—Z
{(E)ABCD}$_n$-O—R—Z

The functional group can be masked, for example an S-acetyl or a disulfide bridge for generating —SH, which is not isolated but which is the active species. Starting from the allyl, transformation to aldehyde is also conceivable.

The present invention also relates to an immunogenic composition comprising a conjugate as defined above in a pharmaceutically acceptable excipient, i.e. acceptable from the physiological standpoint.

The conjugate notably comprises pentasaccharides such as those included in list L1 as well as the multimers of said pentasaccharides.

Said immunogenic composition advantageously further comprises an immunogen capable of protecting against another pathogenic agent, such as *S. flexneri* of serotype 1b, 2a and 6 or other species of *Shigella*, such as *S. dysenteriae* and *S. sonnei* or other pathogens responsible for diarrhea in humans.

Vaccines

The immunogenic compositions according to the invention used as vaccines include one or more pharmaceutical vehicles such as water, physiological serum, glycerol and ethanol. In addition, auxiliary substances such as wetting agents or emulsifiers, buffer substances and others can also be used as excipients.

The immunogenic compositions that induce antibodies protecting against infection with *S. flexneri*, in particular *S. flexneri* of serotype 3a or X are administered to a subject, preferably to a human in sufficient amount to prevent or attenuate the severity or the duration of infection with *S. flexneri*, in particular *S. flexneri* of serotype 3a or X.

Each vaccine dose comprises an effective amount of conjugate according to the invention. Said amount varies according to the subject to be treated, the age and the general condition of the subject to be treated, the capacity of the immune response of the subject to be treated, the desired degree of protection, the severity of the condition to be treated, the conjugate selected and its method of administration, among other factors. An appropriate effective amount can easily be determined by a person skilled in the art.

More particularly, the conjugate according to the invention can be administered in a therapeutically effective amount between 1 and 1000 µg of saccharide, preferably between 1 and 50 µg.

An optimal amount for a particular vaccine can be established by standard tests involving measurement of the titer of anti-LPS 3a or X antibodies in the subjects.

Following a first vaccination, the subjects can be given one or two booster injections at intervals of about 4 weeks.

The immunogenic composition according to the invention can be administered with or without adjuvant. The adjuvants can be added directly to the vaccine composition or they can be administered separately either simultaneously or after administration of the vaccine. Said adjuvants include but are not limited to the aluminum salts (aluminum hydroxide) but also include the oil-in-water emulsions with or without agents for specific stimulation such as: muramyl peptides, saponin, cytokines, detoxified mutants of bacterial toxins such as cholera toxin, *Pertussis* toxin or heat-sensitive *E. coil* toxin.

The immunogenic composition according to the invention can be administered with other immunogens or immunoregulating agents, for example immunoglobulins, cytokines, lymphokines and chemokines.

The invention further relates to a method of preparation of a conjugate according to list L1, characterized in that it comprises the covalent reaction of a saccharide-ORZ molecule as defined above with a suitable substrate molecule M.

According to an advantageous embodiment of said method, the covalent reaction comprises preliminary activation of molecule M.

According to another advantageous embodiment of said method, it comprises the following stages:

a) conjugation of a saccharide-ORZ, as defined above, with a spacer to obtain a derivatized molecule containing said spacer, and
b) reaction of the molecule that has been derivatized and contains the spacer with the molecule M.

As a variant, said method comprises the following stages:

a) conjugation of a suitable molecule M with a spacer to obtain a derivatized substrate molecule M containing the spacer,
b) reaction of said derivatized substrate molecule M with a saccharide-ORZ, as defined above.

According to an advantageous embodiment, the spacer is a small molecule with a molecular weight of less than 500 dalton, either homobifunctional, or heterobifunctional.

The present invention also relates to an IgG monoclonal antibody that is immunoreactive with the LPS of *S. flexneri* of serotype 3a or an IgG monoclonal antibody that is immunoreactive with the LPS of *S. flexneri* of serotype X.

The present invention also relates to a polynucleotide coding for the light chain and/or the heavy chain of an antibody as defined above or a fragment thereof.

The present invention also relates to an expression vector comprising the polynucleotide as defined above.

The present invention also relates to a host cell modified with a polynucleotide or a vector as defined above.

The present invention further relates to a nonhuman transgenic animal or a transgenic plant, characterized in that some or all of the cells are modified with a polynucleotide or a vector as defined above.

Passive Protection

The invention also relates to a pharmaceutical composition comprising an antibody as defined above or a functional fragment thereof and a pharmaceutically acceptable vehicle or excipient.

The antibodies according to the present invention that have a protective effect against infection with *S. flexneri*, in particular *S. flexneri* type 3a or X are administered to a subject, preferably a human, in sufficient amount to prevent or attenuate the severity or the duration of infection with *S. flexneri*, in particular *S. flexneri* type 3a or X.

Administration of the antibody can be either prophylactic (before any exposure to *S. flexneri*) or therapeutic (before infection or at the very start of infection).

The antibody doses vary depending on various factors such as the subject's age and weight. In general, the antibody doses are between 1 mg/kg and 10 mg/kg.

Preferably, the antibody is an antibody of class IgG.

The route of administration of the antibody can be either oral or systemic, for example subcutaneous, intramuscular or intravenous.

Diagnostics

The antibodies and the saccharides according to the present invention are used in vitro as diagnostic reagents specific to *S. flexneri* type 3a or X in standard immunoassays.

The antibodies according to the present invention are used for testing for the presence of *S. flexneri* type 3a or X in biological samples for establishing a diagnosis of shigellosis in an individual presenting diarrheal symptoms.

Alternatively, the saccharides according to the present invention can be used for testing for the presence of anti *S. flexneri* type 3a or X antibodies. These saccharides can be used for epidemiological studies, for example for determining the geographical distribution or the development of infections with *S. flexneri* type 3a or X in the world as well as for evaluating the antibody response induced by an immunogen.

The antibodies and the saccharides according to the present invention can advantageously be labeled and/or immobilized on a solid substrate according to standard protocols known by a person skilled in the art. Such markers include but are not limited to enzymes (alkaline phosphatase, peroxidase), luminescent molecules or fluorescent molecules. For example, the saccharides according to the invention conjugated with biotin can be immobilized on a solid substrate for detecting the presence of anti *S. flexneri* type 3a or X antibodies in biological samples.

Said immunoassays include but are not limited to agglutination tests, radioimmunoassays, ELISA, fluorescence assays, Western blots etc.

Thus, the invention further relates to a kit for diagnosis of an infection with *Shigella flexneri* of serotype 3a or X, characterized in that it comprises at least one conjugate or one saccharide as defined above.

The invention also relates to an intermediate for the preparation of an oligo- or polysaccharide on list L1, characterized in that it is selected from the following list L2:

3-(O-Acetyl-2-deoxy-4,6-O-isopropylidene-2-trichloroacetamido-α/β-D-glucopyranose trichloroacetimidate 2, 2-Deoxy-4,6-O-isopropylidene-3-O-levulinoyl-2-trichloroacetamido-α-D-glucopyranose trichloroacetimidate 3, Allyl 2-deoxy-4,6-O-isopropylidene-2-trichloroacetamido-β-D-glucopyranoside 20, Allyl(3,4,6-tri-O-acetyl-2-deoxy-2-trichloroacetamido-β-D-glucopyranosyl)-(1→2)-[2,3,4,6-tetra-O-benzyl-α-D-glucopyranosyl-(1→3)]-4-O-benzyl-α-L-rhamnopyranoside 22, Allyl(3-O-acetyl-2-deoxy-4,6-O-isopropylidene-2-trichloroacetamido-β-D-glucopyranosyl)-(1→2)-[2,3,4,6-tetra-O-benzyl-α-D-glucopyranosyl-(1→3)]-4-O-benzyl-α-L-rhamnopyranoside 23, 2,3,4,6-Tetra-O-benzyl-α/β-D-glucopyranose trichloroacetimidate 33, Allyl(2,3,4,6-tetra-O-benzyl-α-D-glucopyranosyl)-(1→3)-2-O-acetyl-4-O-benzyl-α-L-rhamnopyranoside 35, Allyl(2-deoxy-2-trichloroacetamido-β-D-glucopyranosyl)-(1→2)-[2,3,4,6-tetra-O-benzyl-α-D-glucopyranosyl-(1→3)]-4-O-benzyl-α-L-rhamnopyranoside 37, Allyl(2-deoxy-4,6-O-isopropylidene-2-trichloroacetamido-β-D-glucopyranosyl)-(1→2)-[2,3,4,6-tetra-O-benzyl-α-D-glucopyranosyl-(1→3)]-4-O-benzyl-α-L-rhamnopyranoside 38, Allyl(2-O-acetyl-3,4-di-O-benzyl-α-L-rhamnopyranosyl)-(1→3)-(2-deoxy-4,6-O-isopropylidene-2-trichloroacetamido-β-D-glucopyranosyl)-(1→2)-[2,3,4,6-tetra-O-benzyl-α-D-glucopyranosyl-(1→3)]-4-O-benzyl-α-L-rhamnopyranoside 40, Allyl(2-O-acetyl-3,4-di-O-benzyl-α-L-rhamnopyranosyl)-(1→3)-(2-deoxy-2-trichloroacetamido-β-D-glucopyranosyl)-(1→2)-[2,3,4,6-tetra-O-benzyl-α-D-glucopyranosyl-(1→3)]-4-O-benzyl-α-L-rhamnopyranoside 41, Allyl(3,4-di-O-benzyl-α-L-rhamnopyranosyl)-(1→3)-(2-deoxy-2-trichloroacetamido-β-D-glucopyranosyl)-(1→2)-[2,3,4,6-tetra-O-benzyl-α-D-glucopyranosyl-(1→3)]-4-O-benzyl-α-L-rhamnopyranoside 69, (2,3,4-Tri-O-acetyl-α-L-rhamnopyranosyl)-(1→3)-2-O-acetyl-4-O-benzyl-α/β-L-rhamnopyranose trichloroacetimidate 46, (3,4-Di-O-benzyl-2-O-levulinoyl-α-L-rhamnopyranosyl)-(1→3)-2-O-acetyl-4-O-benzyl-α/β-L-rhamnopyranose trichloroacetimidate 47, Allyl(2,3,4-tri-O-acetyl-α-L-rhamnopyranosyl)-(1→3)-(2-O-acetyl-4-O-benzyl-α-L-rhamnopyranosyl)-(1→3)-(2-deoxy-4,6-O-isopropylidene-2-trichloroacetamido-β-D-glucopyranosyl)-(1→2)-[2,3,4,6-tetra-O-benzyl-α-D-glucopyranosyl-(1→3)]-4-O-benzyl-α-L-rhamnopyranoside 52, Allyl α-L-rhamnopyranosyl-(1→3)-(2-O-acetyl-4-O-benzyl-α-L-rhamnopyranosyl)-(1→3)-(2-deoxy-4,6-O-isopropylidene-2-trichloroacetamido-β-D-glucopyranosyl)-(1→2)-[2,3,4,6-tetra-O-benzyl-α-D-glucopyranosyl-(1→3)]-4-O-benzyl-α-L-rhamnopyranoside 54, Allyl α-L-rhamnopyranosyl-(1→3)-(4-O-benzyl-α-L-rhamnopyranosyl)-(1→3)-(2-deoxy-4,6-O-isopropylidene-2-trichloroacetamido-β-D-glucopyranosyl)-(1→2)-[2,3,4,6-tetra-O-benzyl-α-D-glucopyranosyl-(1→3)]-4-O-benzyl-α-L-rhamnopyranoside 55, Allyl α-L-rhamnopyranosyl-(1→3)-(2-O-acetyl-4-O-benzyl-α-L-rhamnopyranosyl)-(1→3)-(2-deoxy-2-trichloroacetamamido-β-D-glucopyranosyl)-(1→2)-[2,3,4,6-tetra-O-benzyl-α-D-glucopyranosyl-(1→3)]-4-O-benzyl-α-L-rhamnopyranoside 56, Allyl α-L-rhamnopyranosyl-(1→3)-(4-O-benzyl-α-L-rhamnopyranosyl)-(1→3)-(2-deoxy-2-trichloroacetamido-β-D-glucopyranosyl)-(1→2)-[2,3,4,6-tetra-O-benzyl-α-D-glucopyranosyl-(1→3)]-4-O-benzyl-α-L-rhamnopyranoside 57, Allyl(3,4-di-O-benzyl-2-O-levulinoyl-α-L-rhamnopyranosyl)-(1→3)-(2-O-acetyl-4-O-benzyl-α-rhamnopyranoside 61, Allyl(3,4-di-O-benzyl-2-O-levulinoyl-α-L-rhamnopyranosyl)-(1→3)-(2-O-acetyl-4-O-benzyl-α-L-rhamnopyranosyl)-(1→3)-(2-deoxy-4,6-O-isopropylidene-2-trichloroacetamido-β-D-glucopyranosyl)-(1→2)-[2,3,4,6-tetra-O-benzyl-α-D-glucopyranosyl-(1→3)]-4-O-benzyl-α-L-rhamnopyranoside 64, Allyl(3,4-di-O-benzyl-α-L-rhamnopyranosyl)-(1→3)-(2-O-acetyl-4-O-benzyl-α-L-rhamnopyranosyl)-(1→3)-(2-deoxy-4,6-O-isopropylidene-2-trichloroacetamido-β-D-glucopyranosyl)-(1→2)-[2,3,4,6-tetra-O-benzyl-α-D-glucopyranosyl-(1→3)]-4-O-benzyl-α-L-rhamnopyranoside 66, Allyl(3,4-di-O-benzyl-α-L-rhamnopyranosyl)-(1→3)-(2-O-acetyl-4-O-benzyl-α-L-rhamnopyranosyl)-(1→3)-(2-deoxy-2-trichloroacetamido-β-D-glucopyranosyl)-(1→2)-[2,3,4,6-tetra-O-benzyl-α-D-glucopyranosyl-(1→3)]-4-O-benzyl-α-L-rhamnopyranoside 67, Allyl(3,4-di-O-benzyl-α-L-rhamnopyranosyl)-(1→3)-2-O-acetyl-4-O-benzyl-α-L-rhamnopyranoside 79, (2,3,4,6-Tetra-O-benzyl-α-D-glucopyranosyl)-(1→3)-4-O-benzyl-2-O-levulinoyl-α/β-L-rhamnopyranose trichloroacetimidate 80, (2,3,4,6-Tetra-O-benzyl-α-D-glucopyranosyl)-(1→3)-2-O-benzoyl-4-O-benzyl-α/β-L-rhamnopyranose trichloroacetimidate 80', Allyl(2,3,4,6-tetra-O-benzyl-α-D-glucopyranosyl)-(1→3)-(4-O-benzyl-α-L-rhamnopyranosyl)-(1→2)-(3,4-di-O-benzyl-α-L-rhamnopyranosyl)-(1→3)-2-O-acetyl-4-O-benzyl-α-L-rhamnopyranoside 85, (2,3,4,6-Tetra-O-benzyl-α-D-glucopyranosyl)-(1→3)-(4-O-benzyl-2-O-levulinoyl-α-L-rhamnopyranosyl)-(1→2)-(3,4-di-O-benzyl-α-L-rhamnopyranosyl)-(1→3)-2-O-acetyl-4-O-benzyl-α/β-L-rhamnopyranose trichloroacetimidate 86, Allyl(2,3,4,6-tetra-O-benzyl-α-D-glucopyranosyl)-(1→3)-(4-O-benzyl-2-O-levulinoyl-α-L-rhamnopyraosyl)-(1→2)-(3,4-di-O-benzyl-α-L-rhamnopyranosyl)-(1→3)-2-O-acetyl-4-O-benzyl-α-L-rhamnopyranoside 87, Allyl(2,3,4,6-tetra-O-benzyl-α-D-glucopyranosyl)-(1→3)-(4-O-benzyl-α-L-rhamnopyranosyl)-(1→2)-(3,4-di-O-benzyl-α-L-rhamnopyranosyl)-(1→3)-4-O-benzyl-α-L-rhamnopyranoside 89, Allyl(3,4,6-tri-O-acetyl-2-deoxy-2-trichloroacetamido-β-D-glucopyranosyl)-(1→2)-[2,3,4,6-tetra-O-benzyl-α-D-glucopyranosyl-(1→3)]-(4-O-benzyl-α-L-rhamnopyranosyl)-(1→2)-(3,4-di-O-benzyl-α-L-rhamnopyranosyl)-(1→3)-2-O-acetyl-4-O-benzyl-α-L-rhamnopyranoside 90, Allyl(2-deoxy-2-trichloroacetamido-β-D-glucopyranosyl)-(1→2)-[2,3,4,6-tetra-O-benzyl-α-D-glucopyranosyl-(1→3)]-(4-O-benzyl-α-L-rhamnopyranosyl)-(1→2)-(3,4-di-O-benzyl-α-L-rhamnopyranosyl)-(1→3)-2-O-acetyl-4-O-benzyl-α-L-rhamnopyranoside 91, Allyl(2-deoxy-2-trichloroacetamido-β-D-glucopyranosyl)-(1→2)-[2,3,4,6-tetra-O-benzyl-α-D-glucopyranosyl-(1→3)]-(4-O-benzyl-α-L-rhamnopyranosyl)-(1→2)-(3,4-di-O-benzyl-α-L-rhamnopyranosyl)-(1→3)-4-O-benzyl-α-L-rhamnopyranoside 92, Allyl(2,3,4,6-tetra-O-benzyl-α-D-glucopyranosyl)-(1→3)-(4-O-benzyl-2-O-levulinoyl-α-L-rhamnopyranosyl)-(1→2)-(3,4-di-O-benzyl-α-L-rhamnopyranosyl)-(1→3)-(2-O-acetyl-4-O-benzyl-α-L-rhamnopyranosyl)-(1→3)-2-acetamido-2-deoxy-4,6-O-isopropylidene-β-D-glucopyranoside 93, Allyl(2,3,4,6-tetra-O-benzyl-α-D-glucopyranosyl)-(1→3)-(4-O-benzyl-α-L-rhamnopyranosyl)-(1→2)-(3,4-di-O-benzyl-α-L-rhamnopyranosyl)-(1→3)-(2-O-acetyl-4-O-benzyl-α-L-rhamnopyranosyl)-(1→3)-2-acetamido-2-deoxy-4,6-O-isopropylidene-β-D-glucopyranoside 94, Allyl(2,3,4,6-tetra-O-benzyl-α-D-glucopyranosyl)-(1→3)-(4-O-benzyl-α-L-rhamnopyranosyl)-(1→2)-(3,4-di-O-benzyl-α-L-rhamnopyranosyl)-(1→3)-2-O-acetyl-4-O-benzyl-α-L-rhamnopyranosyl)-(1→3)-2-acetamido-2-deoxy-β-D-glucopyranoside 95, Allyl(2,3,4,6-tetra-O-benzyl-α-D-glucopyranosyl)-(1→3)-(4-O-benzyl-α-L-rhamnopyranosyl)-(1→2)-(3,4-di-O-benzyl-α-L-rhamnopyranosyl)-(1→3)-(4-O-benzyl-α-L-rhamnopyranosyl)-(1→3)-2-acetamido-2-deoxy-4,6-O-isopropylidene-β-D-glucopyranoside 96, Allyl(2,3,4,6-tetra-O-benzyl-α-D-glucopyranosyl)-(1→3)-(4-O-benzyl-α-L-rhamnopyranosyl)-(1→2)-(3,4-di-O-benzyl-α-L-rhamnopyranosyl)-(1→3)-(4-O-benzyl-α-L-rhamnopyranosyl)-(1→3)-2-acetamido-2-deoxy-β-D-glucopyranoside 97, Allyl(2,3,4,6-tetra-O-benzyl-α-D-glucopyranosyl)-(1→3)-(4-O-benzyl-2-O-levulinoyl-α-L-rhamnopyranosyl)-(1→2)-3,4-di-O-benzyl-α-L-rhamnopyranoside 107, Allyl(2,3,4,6-tetra-O-benzyl-α-D-glucopyranosyl)-(1→3)-(2-O-benzoyl-4-O-benzyl-α-L-rhamnopyranosyl)-(1→2)-3,4-di-O-benzyl-α-L-rhamnopyranoside 107', Allyl(2,3,4,6-tetra-O-benzyl-α-D-glucopyranosyl)-(1→3)-(4-O-benzyl-α-L-rhamnopyranosyl)-(1→2)-3,4-di-O-benzyl-α-L-rhamnopyranoside 108, Allyl(2-deoxy-4,6-O-isopropylidene-2-trichloroacetamido-β-D-glucopyranosyl)-(1→2)-[2,3,4,6-tetra-O-benzyl-α-D-glucopyranosyl-(1→3)]-(4-O-benzyl-α-L-rhamnopyranosyl)-(1→2)-3,4-di-O-benzyl-α-L-rhamnopyranoside 110, Allyl(3-O-acetyl-2-deoxy-4,6-O-isopropylidene-2-trichloroacetamido-β-D-glucopyranosyl)-(1→2)-[2,3,4,6-tetra-O-benzyl-α-D-glucopyranosyl-(1→3)]-(4-O-benzyl-α-L-rhamnopyranosyl)-(1→2)-3,4-di-O-benzyl-α-L-rhamnopyranoside 115, Allyl(2-deoxy-2,3,4-tri-O-acetyl-2-trichloroacetamido-β-D-glucopyranosyl)-(1→2)-[2,3,4,6-tetra-O-benzyl-α-D-glucopyranosyl-(1→3)]-(4-O-benzyl-α-L-rhamnopyranosyl)-(1→2)-3,4-di-O-benzyl-α-L-rhamnopyranoside 115', Allyl(2-deoxy-2-trichloroacetamido-β-D-glucopyranosyl)-(1→2)-[2,3,4,6-tetra-O-benzyl-α-D-glucopyranosyl-(1→3)]-(4-O-benzyl-α-L-rhamnopyranosyl)-(1→2)-3,4-di-O-benzyl-α-L-rhamnopyranoside 115"

Allyl(2-deoxy-4,6-O-isopropylidene-2-acetamido-β-D-glucopyranosyl)-(1→2)-[2,3,4,6-tetra-O-benzyl-α-D-glucopyranosyl-(1→3)]-(4-O-benzyl-α-L-rhamnopyranosyl)-(1→2)-3,4-di-O-benzyl-α-L-rhamnopyranoside 116, Allyl 2-O-acetyl-3,4-di-O-benzyl-α-L-rhamnopyranoside-(1→3)-(2-deoxy-4,6-O-isopropylidene-2-acetamido-β-D-glucopyranosyl)-(1→2)-[2,3,4,6-tetra-O-benzyl-α-D-glucopyranosyl-(1→3)]-(4-O-benzyl-α-L-rhamnopyranosyl)-(1→2)-3,4-di-O-benzyl-α-L-rhamnopyranoside 116', Allyl 2-O-acetyl-3,4-di-O-benzyl-α-L-rhamnopyranoside-(1→3)-(2-deoxy-2-acetamido-β-D-glucopyranosyl)-(1→2)-[2,3,4,6-tetra-O-benzyl-α-D-glucopyranosyl-(1→3)]-(4-O-benzyl-α-L-rhamnopyranosyl)-(1→2)-3,4-di-O-benzyl-α-L-rhamnopyranoside 116", Allyl(3,4-di-O-benzyl-2-O-levulinoyl-α-L-rhamnopyranosyl)-(1→3)-2-O-acetyl-4-O-benzyl-α-L-rhamnopyranosyl)-(1→3)-(2-deoxy-4,6-O-isopropylidene-2-trichloroacetamido-β-D-glucopyranosyl)-(1→2)-[2,3,4,6-tetra-O-benzyl-α-D-glucopyranosyl-(1→3)]-(4-O-benzyl-α-L-rhamnopyranosyl)-(1→2)-3,4-di-O-benzyl-α-L-rhamnopyranoside 122, Allyl(3,4-di-O-benzyl-2-O-levulinoyl-α-L-rhamnopyranosyl)-(1→3)-2-O-acetyl-4-O-benzyl-α-L-rhamnopyranosyl)-(1→3)-(2-deoxy-2-trichloroacetamido-β-D-glucopyranosyl)-(1→2)-[2,3,4,6-tetra-O-benzyl-α-D-glucopyranosyl-(1→3)]-(4-O-benzyl-α-L-rhamnopyranosyl)-(1→2)-3,4-di-O-benzyl-α-L-rhamnopyranoside 123, Allyl(3,4-di-O-benzyl-2-α-L-rhamnopyranosyl)-(1→3)-2-O-acetyl-4-O-benzyl-α-L-rhamnopyranosyl)-(1→3)-(2-deoxy-2-trichloroacetamido-β-D-glucopyranosyl)-(1→2)-[2,3,4,6-tetra-O-benzyl-α-D-glucopyranosyl-(1→3)]-(4-O-benzyl-α-L-rhamnopyranosyl)-(1→2)-3,4-di-O-benzyl-α-L-rhamnopyranoside 124, Allyl(3,4-di-O-benzyl-2-α-L-rhamnopyranosyl)-(1→3)-4-O-benzyl-α-L-rhamnopyranosyl)-(1→3)-(2-deoxy- 2-trichloroacetamido-β-D-glucopyranosyl)-(1→2)-[2,
3,4,6-tetra-O-benzyl-α-D-glucopyranosyl-(1→3)]-(4-
O-benzyl-α-L-rhamnopyranosyl)-(1→2)-3,4-di-O-
benzyl-α-L-rhamnopyranoside 125, Allyl(2,3,4,6-tetra-O-benzyl-α-D-glucopyranosyl)-
(1→3)-(4-O-benzyl-2-O-levulinoyl-α-L-rhamnopyra-
nosyl)-(1→2)-(3,4-di-O-benzyl-α-L-rhamnopyrano-
syl)-(1→3)-(2-O-acetyl-4-O-benzyl-α-L-
rhamnopyranosyl)-(1→3)-(2-deoxy-4,6-O-
isopropylidene-2-trichloroacetamido-β-D-
glucopyranosyl)-(1→2)-[2,3,4,6-tetra-O-benzyl-α-D-
glucopyranosyl-(1→3)]-4-O-benzyl-α-L-
rhamnopyranoside 126, Allyl(2,3,4,6-tetra-O-benzyl-α-D-glucopyranosyl)-
(1→3)-(4-O-benzyl-α-L-rhamnopyranosyl)-(1→2)-(3,
4-di-O-benzyl-α-L-rhamnopyranosyl)-(1→3)-(2-O-
acetyl-4-O-benzyl-α-L-rhamnopyranosyl)-(1→3)-(2-
deoxy-4,6-O-isopropylidene-2-trichloroacetamido-β-
D-glucopyranosyl)-(1→2)-[2,3,4,6-tetra-O-benzyl-α-
D-glucopyranosyl-(1→3)]-4-O-benzyl-α-L-
rhamnopyranoside 127, Allyl(2-deoxy-4,6-O-isopropylidene-3-O-levulinoyl-2-
trichloroacetamido-β-D-glucopyranose)-(1→2)-[2,3,4,
6-tetra-O-benzyl-α-D-glucopyranosyl-(1→3)]-(4-O-
benzyl-α-L-rhamnopyranosyl-(1→2)-(3,4-di-O-
benzyl-α-L-rhamnopyranosyl)-(1→3)-(2-O-acetyl-4-
O-benzyl-α-L-rhamnopyranosyl)-(1→3)-(2-deoxy-4,
6-O-isopropylidene-2-trichloroacetamido-β-D-
glucopyranosyl)-(1→2)-[2,3,4,6-tetra-O-benzyl-α-D-
glucopyranosyl-(1→3)]-4-O-benzyl-α-L-
rhamnopyranoside 128.

The invention also relates to an intermediate for the preparation of a saccharide as defined in list L1, characterized in that it is selected from the following list L3:

[CD(E)A] (III and IV),
[D(E)AB] (VIII),
[(E)ABC] (XI and XII),
[BCD(E)A] (V and VI),
[CD(E)AB] (IX and X),
[D(E)ABC] (XIII and XIV),
[(E)ABCD] (XV and XVI),
[BCD(E)AB] (XVII and XVIII),
[D(E)ABCD] (XXIII and XXIV),
[D(E)ABCD(E)A] (XIX and XX),
[BCD(E)ABCD] (XXV and XXVI),
[BCD(E)ABCD(E)A] (XXI and XXII),
[D(E)ABCD(E)ABC] (XXVII and XXVIII)

Detailed Description of the Method of Preparation of the Saccharides According to the Invention

TABLE 1

Oligosaccharides representative of the fragments of the O antigen

| Disaccharides | Trisaccharides | Tetrasaccharides | Pentasaccharides and > |
|---|---|---|---|
| (E)A I | D(E)A II | $_{Ac}$CD(E)A/III | B$_{Ac}$CD(E)A V |
|  |  | CD(E)A IV | BCD(E)A VI |
|  | (E)AB VII | D(E)AB VIII | $_{Ac}$CD(E)AB IX |
|  |  |  | CD(E)AB X |
|  |  | (E)AB$_{Ac}$C XI | D(E)AB$_{Ac}$C XIII |
|  |  | (E)ABC XII | D(E)ABC XIV |
|  |  |  | (E) AB$_{Ac}$CD XV |
|  |  |  | (E)ABCD XVI |
|  |  |  | B$_{Ac}$CD(E)AB XVII |
|  |  |  | BCD(E)AB XVIII |

All the syntheses are based on the use of these key synthons shown in scheme 1.

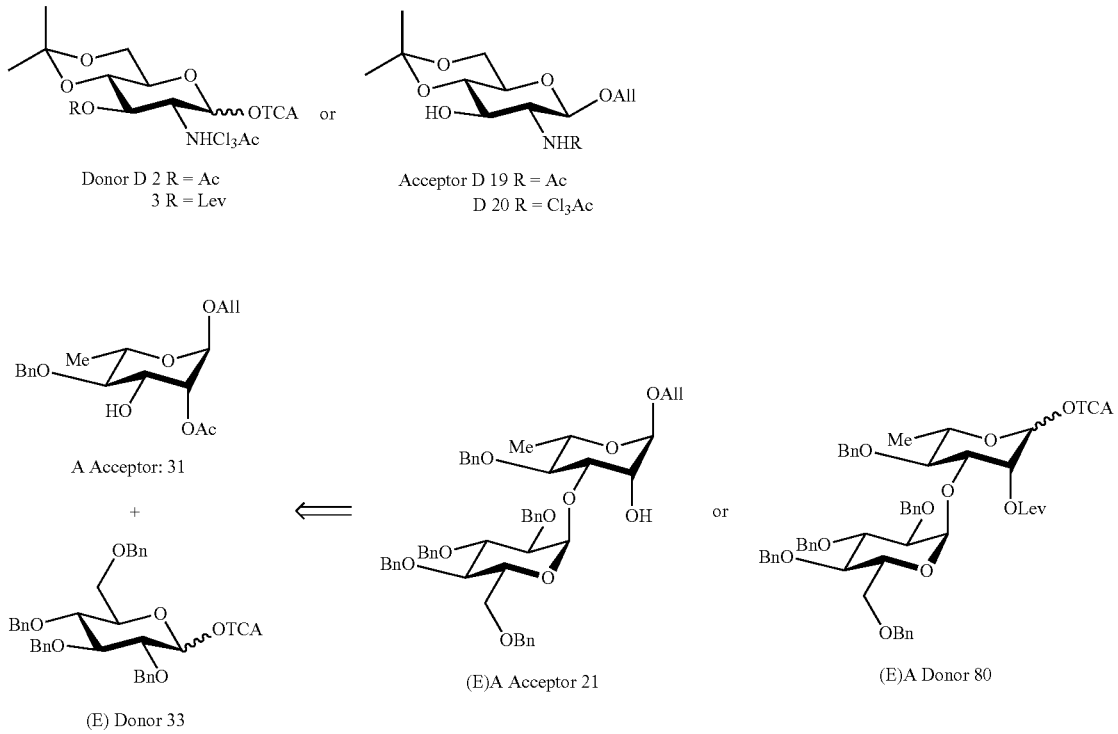

Scheme 1: Key synthons adopted

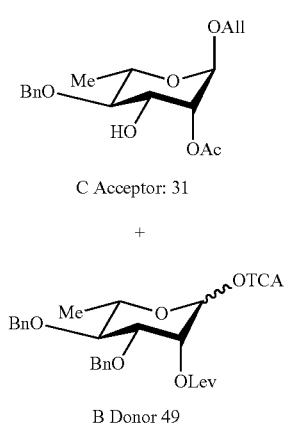

C Acceptor: 31

+

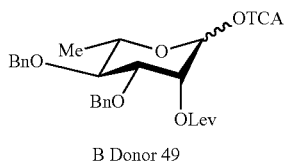

B Donor 49

⇐

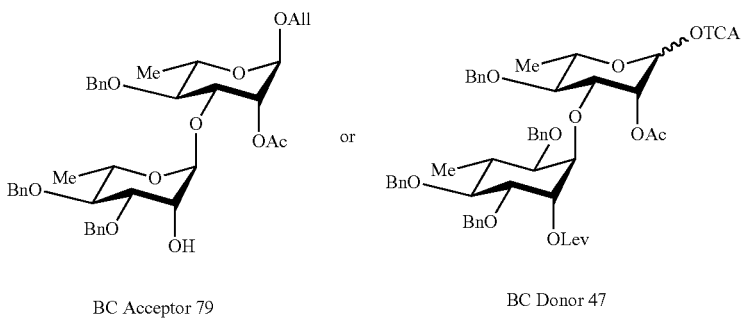

BC Acceptor 79   or   BC Donor 47

Thus, the acceptor synthons can be extended at their non-reducing end by iterative incorporation of the required suitably functionalized donor monosaccharides or disaccharides. Moreover, the allyl glycosides can be extended at their reducing end after selective deallylation and activation, permitting them to be coupled to the required suitably functionalized acceptor monosaccharides or disaccharides.

The following abbreviations are used in the methods of synthesis given below:

RT: room temperature
TLC: thin-layer chromatography
Ac: acetyl
Cl]Ac: trichloroacetyl
TCA: trichloroacetimidate
Bn: benzyl
Bz: benzoyl
Lev: levulinoyl
Et: ethyl
Me: methyl
Pr: propyl
iPr: isopropyl
DCM: dichloromethane
DCE: 1,2-dichloroethane
Chex: cyclohexane
$Et_2O$: diethyl ether
$iPr_2O$: diisopropyl ether
PE: petroleum ether
Tol: toluene
THF: tetrahydrofuran
DMF: N,N-dimethylformamide
PTSA: para-toluenesulfonic acid
TfOH: trifluoromethanesulfonic acid
TMSOTf: trimethylsilyl trifluoromethanesulfonate
CSA: camphor sulfonic acid
HCl: hydrochloric acid
DCC: dicyclohexylcarbodiimide
DCU: dicyclohexylurea
DMAP: N-dimethylaminopyridine
Rf: retardation factor
DBU: 1,8-diazo-bicyclo(5.4.0)undec-7-ene
Glc: glucose
Rha: rhamnose
Lit. literature eq.: equivalent
aq.: aqueous
quant.: quantitative
MS: mass spectroscopy
HRMS: high resolution mass spectroscopy
ESI: electrospray ionization
HPLC: high-performance liquid chromatography
NMR: nuclear magnetic resonance
COSY: COrrelation Spectroscopy
DEPT: Distortionless Enhancement by Polarization Transfer
HSQC: Heteronuclear Single Quantum Correlation
HMBC: Heteronuclear Multiple Bond Correlation
TOCSY: TOtal Correlation Spectroscopy
ROESY: ROtative frame Overhauser Enhancement Spectroscopy
NOESY: Nuclear Overhauser Enhancement SpectroscopY
DOWEX (H+): DOWEX SOWX8-200
HCl solution at 10%
$NaHCO_3$: sodium hydrogen carbonate
$K_2CO_3$: potassium carbonate
$Na_2SO_4$: sodium sulfate
$Cs_2CO_3$: cesium carbonate
$NaHSO_3$: sodium hydrogen sulfite
HCl 1M or SM
Sat. NaCl solution
Solution of acetic acid 80% (for dissach E(A))
Aqueous solution of TFA SO %

The schemes to which the methods refer are indicated to illustrate a particular embodiment without in any way limiting the conditions of application of these methods to these particular conditions.

Part I—Preparatory Stage of Synthesis of the Key Glucosamine Donor Synthons:

The O antigen of *S. flexneri* 3a has a structure of type 3)-β-D-pGlcNHAc-(1. As stated in the back-synthesis section, the donor precursors used are derived from 4,6-O-isopropylidene-2-trichloroacetamido-D-glucosamine. This section presents the synthesis of the novel donors 2 and 3. A route of access alternative to that published for analog 1,[1] much used in the laboratory, is also proposed.

1. Monosaccharide D Donor 1 and 2

The objective was to obtain these three donors in large quantity at good yields and limiting the number of purification stages. It should be noted that various acceptors and some glucosaminyl donors having a 4,6-O-isopropylidene function[2] have already been used in the synthesis of analogs of lipid A[3] or of peptidoglycan[4] but less often in the synthesis of complex oligosaccharides. To the best of our knowledge, two "trichloroacetimidate" donors derived from glucosamine in the azido series[2,5] and an analog in the 2-trichlorethoxycarbonyl series[6] have already been described. In the trichloroacetamide series, only one thiophenyl donor has already been described.[7]

a. Protection of the Amine Function

Conditions for Introducing the Trichloroacetamide Function Selected as Participating Group Use of the method of Bergmann and Zervas via an imine was known.[8-10] D-glucosamine hydrochloride 4 is reacted with sodium hydroxide and para-anisaldehyde to form the imine 5 (Scheme 2). After acetylation of all the hydroxyl functions and cleavage of the imine in acid conditions, the amine function generated can be protected with a trichloroacetyl function by means of trichloroacetyl chloride which leads to the pure β anomer 8 at an overall yield of 45%. This method is efficient as each intermediate can be crystallized. However, it involves 4 stages, and access to donor 2 is made impossible since degradation of the reaction mixture was observed during various attempts at deacetylation of the peracetyl 8.

Scheme 2: Method I for access to the per-acetyl 8

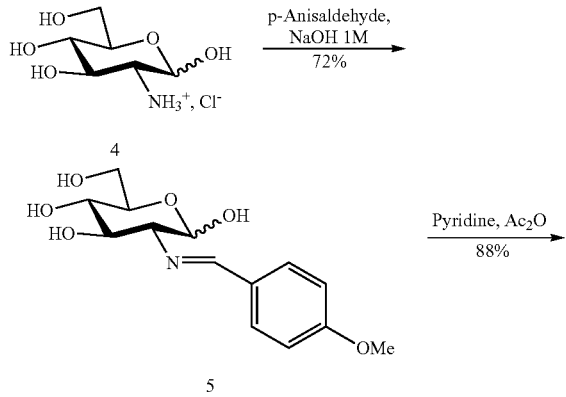

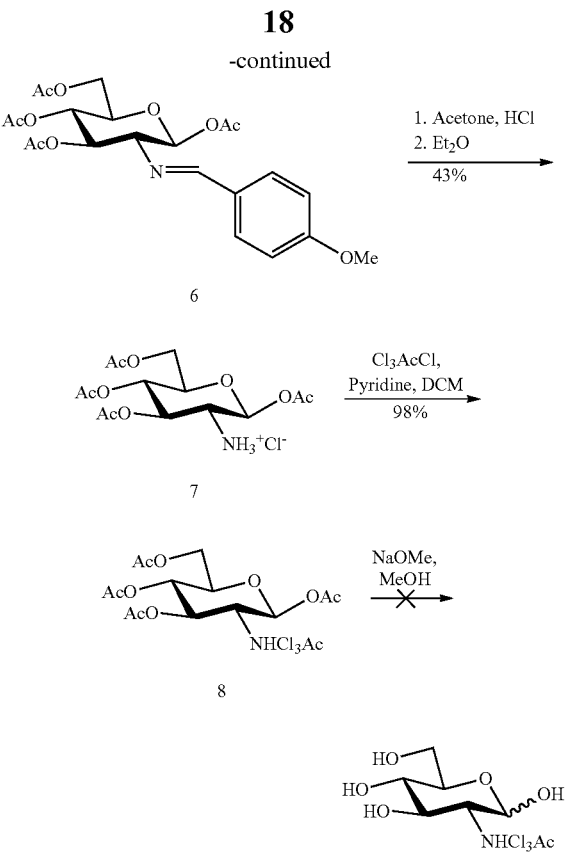

An alternative is the method described by Jacquinet et al.[1] (Method II, Scheme 3). D-glucosamine hydrochloride 4, reacted with a weak base, sodium hydrogen carbonate, then trichloroacetyl chloride, is converted regioselectively to hemiacetal 9 protected on the amine function by a trichloroacetyl function. This method is efficient for large quantities if linked with direct acetylation and crystallization of the peracetylated derivative 8 as described by the authors. However, crystallization of the trichloroacetamide 9 is difficult because of the high solubility of this compound in the crystallization medium (cold water). These two stages made it possible to isolate the mixture of α and β anomers 8 in 90/10 ratio at a yield of 45%, which is less than that described (63%).[1]

Scheme 3: Methods of access II and III to the per-acetylated derivative 8

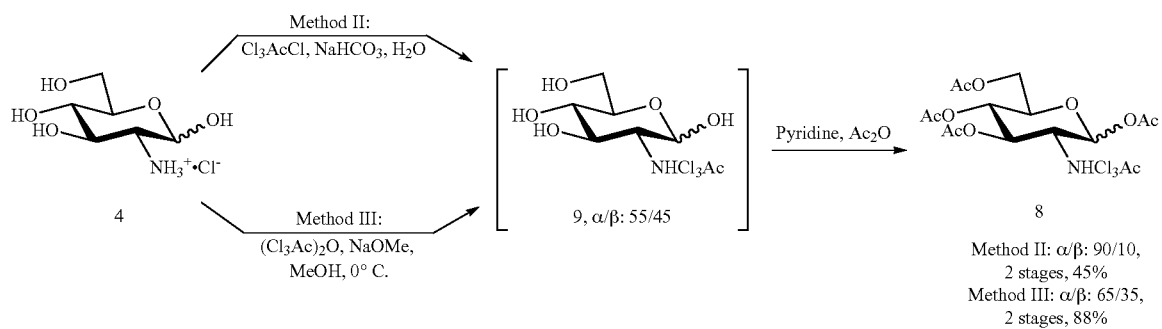

It has also been shown that it is possible to convert an amine function to amide with good results by introduction of groups such as acetyl, palmitoyl or butyroyl[11, 12] but also more recently the introduction of butanoyl or a 3,4,5,6-tetra-chlorophthaloyl[10, 13] in position $2_D$. The introduction of these acyl groups is based on the use of a strong base, sodium methylate (NaOMe) to deprotonate the amine function of commercial glucosamine hydrochloride. The free amine that is liberated reacts on the anhydride corresponding to the desired group. These conditions were tested for "trichloroacetylating" the amine function of commercial glucosamine. After optimization of the conditions, the D-glucosamine hydrochloride, reacted at 0° C. (this reaction is very sensitive) with NaOMe and trichloroacetic anhydride, is converted to trichloroacetamide 9 (Method III, Scheme 3). As recrystallization is difficult at this stage owing to the presence of salts, acetylation of all the hydroxyl functions is then carried out without prior purification of 9. The mixture of α and β anomers (65/35) 8 is isolated at a yield of 88% after chromatography. This method is therefore very interesting relative to the previous methods, as the yields obtained are in fact far greater than those described previously for the preparation of 8. Moreover, this first stage is easily reproducible at the scale of about ten grams.

b. Synthesis of 3,4,6-tri-O-acetyl-2-deoxy-2-trichloroacetamido-α-D-glucopyranose trichloroacetimidate 1

Figure 4:
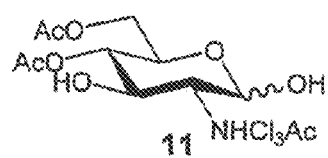

The per-acetylated derivative 8, obtained in the form of a pure β anomer (method I) or of a mixture of α/β anomers (method II or method III), must be deacetylated in the anomeric position. Among all the methods mentioned in the literature, two methods that are widely used were tested:
  hydrazinium acetate;[1, 14, 15]
  ethylenediamine in acid medium.[16, 17]
When the reaction is carried out in the presence of ethylenediamine and acetic acid, it is slower than in the presence of hydrazinium acetate, but the desired hemiacetal 10 is obtained with better regioselectivity and therefore a yield of 89%, higher than the 68% obtained with the first method. This better yield can be explained by the absence of formation of the byproduct 11, resulting from deacetylation in position 3, observed when hydrazinium acetate is used. The structure of compound 11 is confirmed by NMR analysis. A displacement of the chemical shift toward the strong fields of proton 3 of 11 ($\delta$=4.00 ppm) relative to the hemiacetal 10 ($\delta$=5.43 ppm) is observed (FIG. 4).

The hemiacetal is then activated with donor 1. As the latter is unstable in the conditions of purification on silica, an organic base that could be removed easily was selected on the basis of data in the literature.[18-20] Cesium carbonate seemed to be an interesting choice as only simple filtration is required to remove the salts formed. The alcohol 10 is therefore reacted in dichloromethane in the presence of cesium carbonate and trichloroacetonitrile to give the trichloroacetimidate 1 with a raw yield of 95% (Scheme 4). However, during the various coupling tests performed using this donor, the amount of acid (TMSOTf) to be added was increased, relative to classical conditions, to have a sufficiently acid pH of the reaction mixture. It is probable that there are still traces of cesium carbonate present. For this reason, the use of a strong base, also much used in the literature, DBU[21] was also tested. The alcohol 10 is reacted in 1,2-dichloroethane in the presence of DBU and trichloroacetonitrile to give, after quick purification on silica gel, the trichloroacetimidate 1 at a yield of 87%.[22, 23] Another optimization was introduced. If the stages of anomeric deacetylation and of activation are carried out successively without intermediate purification, donor 1 is obtained from precursor 8 at a yield of 84% over 2 stages, an improvement relative to the published data[1] (77%).

Scheme 4: Synthesis of donor 1

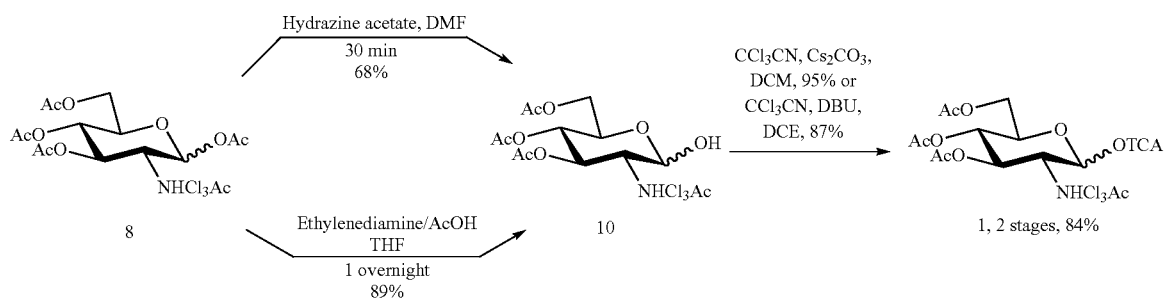

c. Synthesis of 3-O-acetyl-2-deoxy-4,6-O-isopropylidene-2-trichloroacetamido-α/β-D-glucopyranose trichloroacetimidate 2

Figure 5:
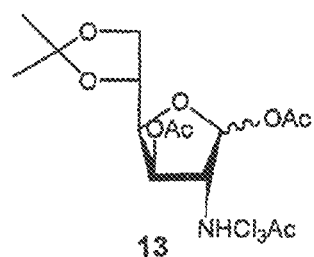

The trichloroacetamide 9 is prepared according to method III described above and used "as is". It is protected regioselectively in position 4 and 6 with an isopropylidene group by the action of 2-methoxypropene and CSA to give the hemiacetal 12.[24-29] The use of 2-methoxypropene[30, 31] was preferred to the more conventional use of 1,2-dimethoxypropane[32] as the latter makes it possible to limit the formation of furanose 13 to 10% (confirmed by the presence of the peak of the anomeric proton at 6.26 ppm with a coupling constant of 4.9 Hz in $^1$H NMR characteristic of a furanose a acetylated in anomeric position[33]), versus 30% if the reaction involves 1,2-dimethoxypropane (FIG. 5).

Then, the free hydroxyl positions 1 and 3 of the trichloroacetamide 12 are acetylated to obtain the diacetate 14 at a yield of 70% over the 3 stages (Scheme 5).

Scheme 5: Synthesis of the monosaccharide 14

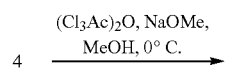

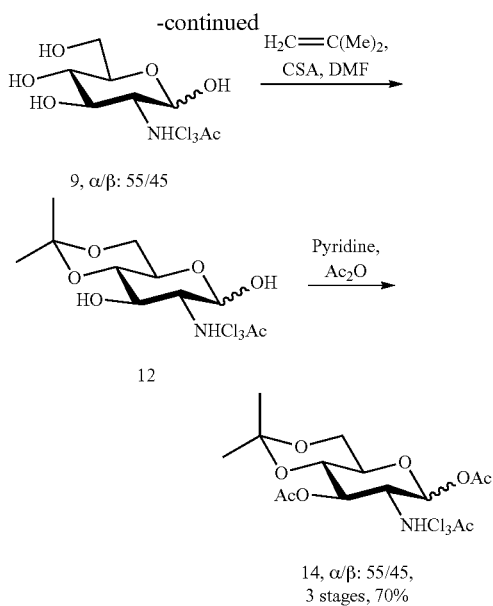

9, α/β: 55/45

12

14, α/β: 55/45, 3 stages, 70%

The penultimate stage is similar to that in the synthesis of the hemiacetal 10. It is an anomeric deacetylation. Once again, the best results are obtained with ethylenediamine[17] in the presence of acetic acid. The hemiacetal 15 is isolated at a yield of 87%, greater than the 78% obtained if hydrazinium acetate[15] is used (Scheme 6).

Just as for donor 1, weak organic bases such as cesium carbonate[20] or potassium carbonate[34-36] were tested for preparing donor 2. The activation reaction never went to completion, which is probably due to the instability of the trichloroacetimidate 2 that formed. The base was therefore replaced with a stronger base, DBU[21], which made it possible to isolate donor 2 at a yield of 87%.[22, 23]

chromatography. After forcing the formation of this secondary compound 16 by leaving the compound on the silica for a longer time, NMR analysis shows disappearance of the acetyl and of the trichloroacetamide function and the appearance of an aldehyde, with a characteristic chemical shift at 9.43 ppm in proton NMR and 187.0 ppm in carbon NMR. Whereas the loss of the isopropylidene could be considered to be due to the acidity of the silica, NMR analysis does confirm its presence with characteristic signals at 1.54 ppm and 1.43 ppm for proton as well as the signal characteristic of the carbon bearing the two methyls at 99.8 ppm. The rest of the structure is confirmed by comparison with the literature.[37]

The appearance of this keto-aldehyde 16 can be explained by elimination of the acetyl, due to the acidity of the silica, followed by hydrolysis of the imine that formed. To prevent the formation of this byproduct, the hemiacetal 15 is used directly in the activation reaction without any purification at this stage. The donor 2 is thus obtained at a yield of 80% over the two stages, anomeric deacetylation and activation (Scheme 6).

2. Coupling of the Functionalized Donor 2 with Various Acceptors

A Model Alcohol: Allyl Alcohol

Having obtained this first donor 2, the objective was to compare its properties as donor with precursor 1. Allyl alcohol was selected as acceptor, leading to a glycosylation product potentially usable in the synthesis of the oligosaccharides of S. flexneri 3a.

Allyl alcohol was therefore coupled, in classical conditions such as TMSOTf (0.2 eq.) in dichloromethane in the presence of a molecular sieve. With donor 2, formation of allyl β glycoside 17, isolated at a yield of 82%, is observed (Scheme 7). In comparison, coupling with the triacetate donor 1 also gives the analog 18 at an entirely comparable yield of 83%. This result suggests that the isopropylidene of the donor 2 is stable in the coupling conditions and that the stereoselectivity observed is just as good for donor 2 as for donor 1.

Scheme 6: Synthesis of donor 2

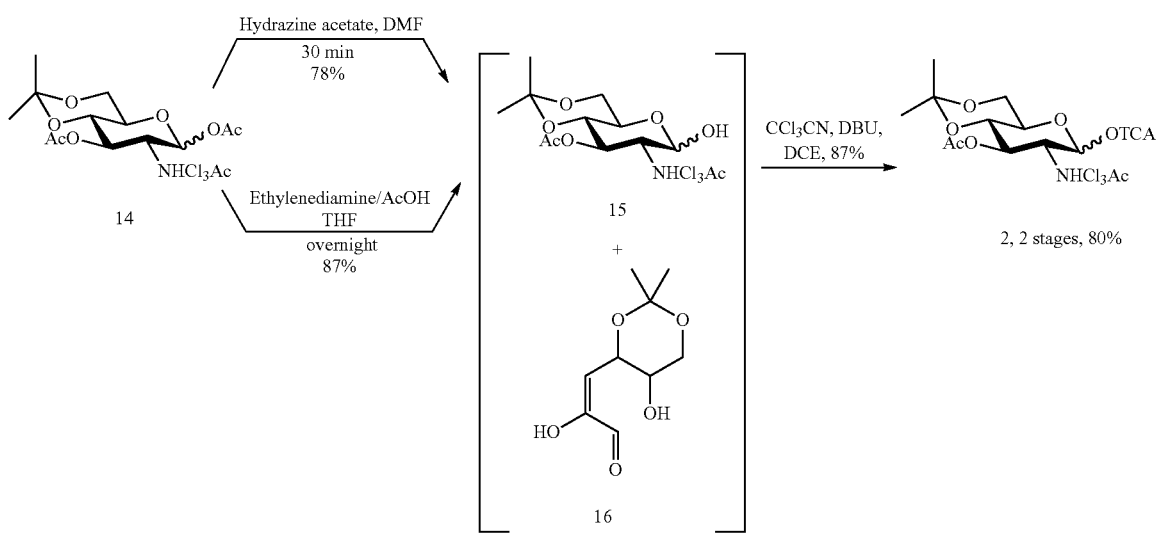

Conversely, when the reaction of anomeric deacetylation was carried out on a larger scale, degradation of the hemiacetal 15 on silica is observed with the presence, in TLC, of a more polar compound 16, which is difficult to isolate by To confirm that donor 2 can be used for future elongation in position $3_D$ after coupling, the allyl glycoside 17 was transformed to acceptor. Two routes were considered, the first is simultaneous saponification of the acetyl function in position 3 and of the trichloroacetyl function in position 2, followed by selective acetylation in situ of the amine function generated, to give the N-acetylated acceptor 19 at a yield of 71%.[4] The other strategy is the selective deacetylation of the acetyl in position 3. In this case, the trichloroacetamide function that masks the acetamide function is preserved. In fact, it has often been shown that an acetamide function of glucosamine can influence the coupling yields.[38] After optimization of the deacetylation conditions, the potassium carbonate, which can be removed by simple filtration, is retained since it leads to the best yield of acceptor 20 (94%). Acceptor 20 can also be obtained via donor 1. It is interesting to note that the yields are comparable for both routes, or even slightly better if 1 is involved. To summarize, acceptor 20 is obtained at a yield of 49% in 7 stages via 1 whereas with donor 2 and the same number of stages, it is obtained at a yield of 43% (Scheme 7).

Scheme 7: Synthesis of two new acceptors 19 and 20

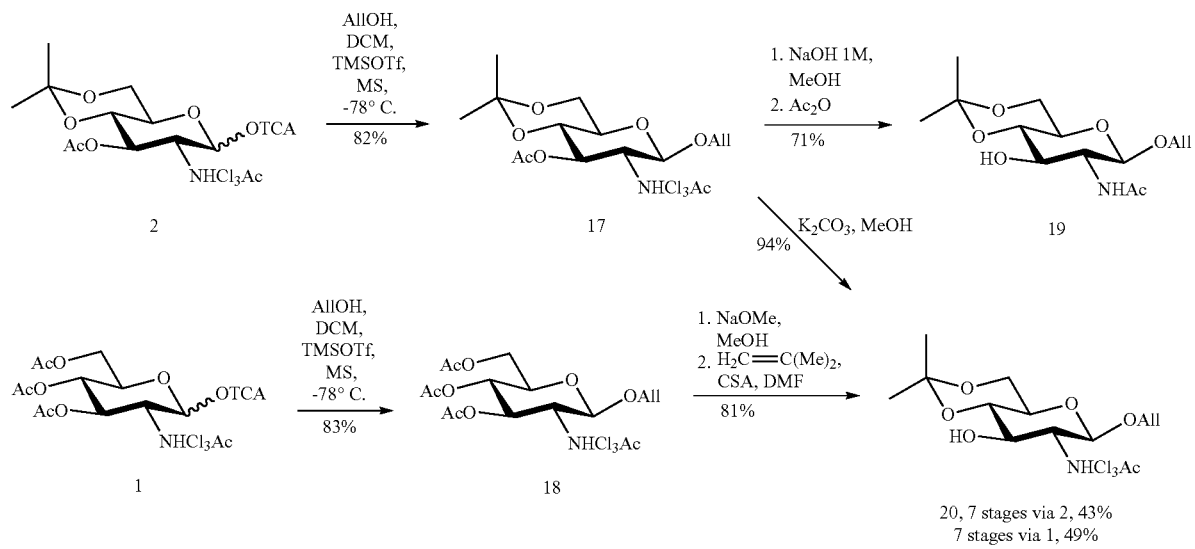

3. Taking Account of the Potential Presence of an Acetyl: Synthesis of Donor 3

However, the presence of an isolated acetyl function may prove restrictive in the case of subsequent elongation of sequences comprising residue C. Taking this limitation into account, it is a question of designing a donor equivalent to 2 but provided with a group orthogonal to the acetyl in position 3. As seen in the back-synthesis section, our choice fell on the levulinoyl group. Synthesis of the 3-O-levulinoyl analog of 2 was therefore envisaged.

Scheme 8: Synthesis of donor 3

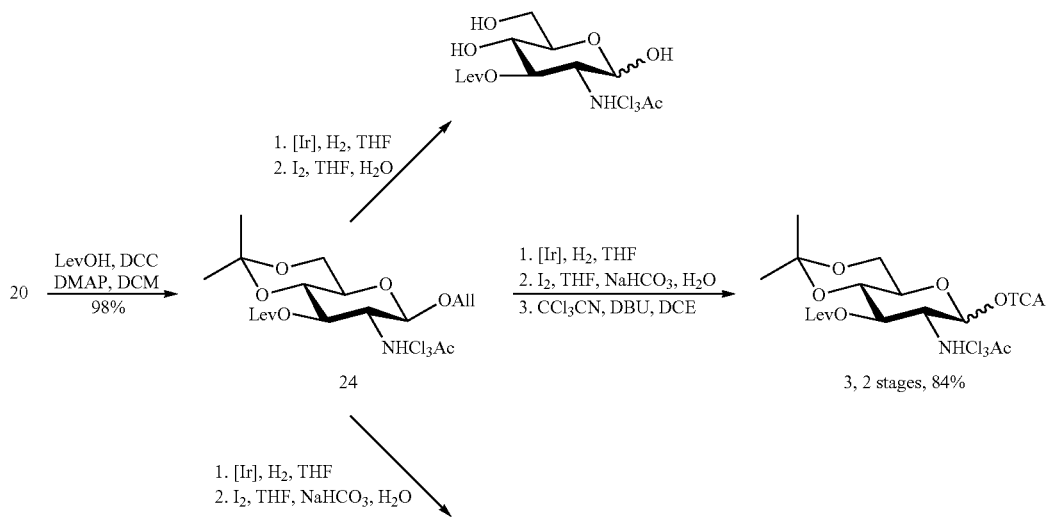

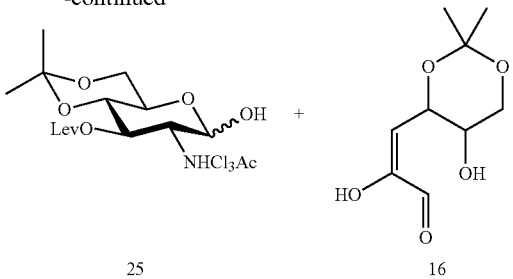

The key intermediate is the allyl glycoside 24, easily obtained from acceptor 20 by the action of levulinic acid activated by DCC in the presence of DMAP (98%). The conversion of the latter to donor 3 requires the hemiacetal 25 resulting from a stage of anomeric deallylation in classical conditions[33, 40] (Scheme 8). However, in the absence of base, loss of the isopropylidene was observed due to the formation in situ of hydriodic acid HI.[39] The loss of this group can be avoided if a weak base, for example sodium hydrogencarbonate[41] is added. Moreover, the hemiacetal 25 proved to be unstable since, during purification by silica gel chromatography, the keto-aldehyde 16 was isolated again. In these conditions, the hemiacetal could not be isolated without 10% of contamination. In contrast, if the two stages, deallylation and activation, are carried out successively without intermediate purification, donor 3 is isolated at a yield of 84% over the two stages.

4. Conclusion

At this stage, three donors, precursors of residue D, are available. An efficient synthesis was elaborated for each of them, including a 25% improvement in the synthesis of 1 relative to data in the literature.[1] In fact, the functionalized donor 2 is obtained at a yield of 56% in 5 stages and donor 3 at a yield of the order of 40% in 10 stages (Scheme 9).

Moreover, the synthesis of donors 1 and 2 only involves two stages of purification on silica gel. These precursors can thus be prepared on a large scale (of the order of about ten grams).

Experimental Conditions for Synthesis of Donors 1, 2 and 3:

2-Deoxy-2-[p-methoxybenzylidene(amino)]-β-D-glucopyranose[10] 5

1,3,4,6-Tetra-O-acetyl-2-deoxy-2-[p-methoxybenzylidene(amino)]-β-D-glucopyranose[10] 6

1,3,4,6-Tetra-O-acetyl-2-amino-2-deoxy-β-D-glucopyranose hydrochloride[10] 7

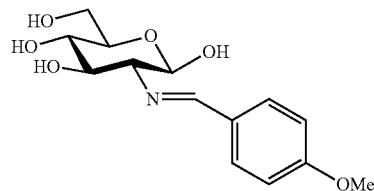

Chemical Formula: $C_{14}H_{19}NO_6$
Exact Mass: 297.1212
Molecular Weight: 297.3038

Scheme 9: Balance of the synthesis of donors 1, 2 and 3

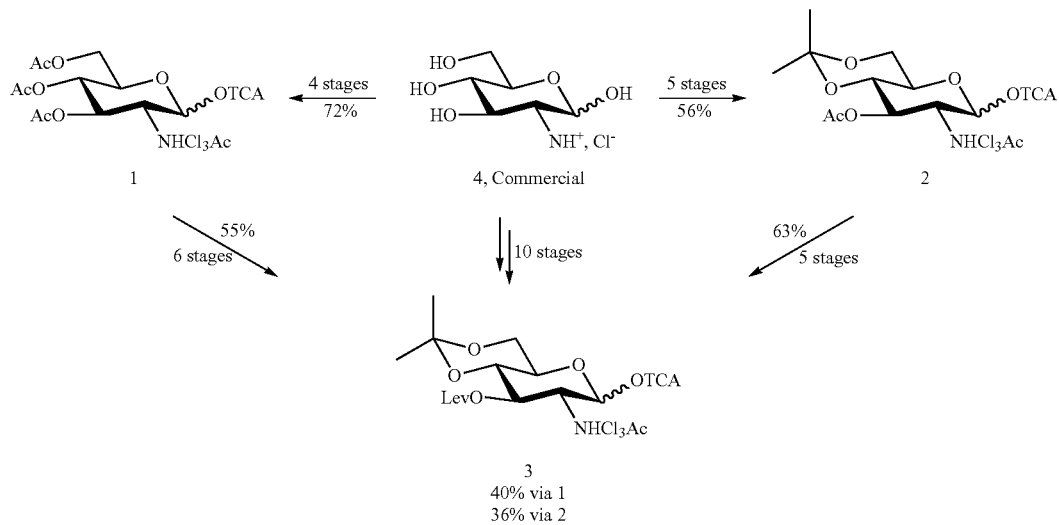

-continued

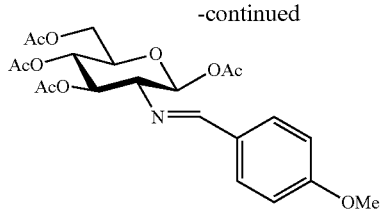

Chemical Formula: C$_{22}$H$_{27}$NO$_{10}$
Exact Mass: 465.1635
Molecular Weight: 465.4505

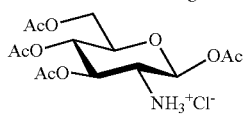

Chemical Formula: C$_{14}$H$_{22}$ClNO$_9$
Exact Mass: 383.0983
Molecular Weight: 383.7788 para-Anisaldehyde (17.0 mL, 140 mmol) is added to a freshly prepared solution of D-glucosamine hydrochloride 4 (25.0 g, 116 mmol) in 1M sodium hydroxide (120 mL), stirring vigorously. Crystallization begins after a few moments. The reaction mixture is adjusted to 4° C. and after 2 h, the precipitate is filtered and washed with cold water and then with EtOH/H$_2$O mixture (1/1) to give the imine 5 as a white solid (24.9 g, 72%).

$^1$H NMR (DMSO-d6), δ8.11 (s, 1H, CH), 7.68 (d, 2H, CH$_{Ph}$), 6.97 (d, 2H, CH$_{Ph}$), 4.69 (d, 1H, J$_{1,2}$=7.8 Hz, H-1), 3.78 (s, 3H, OMe), 3.71 (m, 1H, H-6a), 3.50 (pt, 1H, H-3), 3.43 (dd, 1H, J$_{5,6a}$=9.0 Hz, H6b), 3.25 (m, 1H, H-5), 3.15 (pt, 1H, J$_{3,4}$=9.5 Hz, H-4), 2.81 (dd, 1H, J$_{2,3}$=9.1 Hz, H-2).

$^{13}$C NMR (DMSO-d6), δ162.7 (CH), 161.9 (C$_{Ph}$), 130.4 (2C, CH$_{Ph}$), 129.7 (C$_{Ph}$), 114.8 (2C, CH$_{Ph}$), 96.2 (C-1, $^1$J$_{CH}$=153.9 Hz), 78.7 (C-2), 77.5 (C-5), 75.2 (C-3), 71.0 (C-4), 61.9 (C-6), 56.5 (OMe).

The imine 5 (24.9 g, 84 mmol) is added portion by portion to a pyridine/acetic anhydride mixture (1/1, 200 mL), stirred on an ice bath. The reaction mixture is stirred for 1 h and then at RT overnight. The yellow solution obtained is transferred to 500 mL of iced water. The resultant white precipitate is filtered, washed with cold water and then dried. The white solid obtained is identified as the tetra-O-acetyl 6 (34.3 g, 88%).

$^1$H NMR (CDCl$_3$), δ8.17 (s, 1H, CH), 7.68 (d, 2H, CH$_{Ph}$), 6.93 (d, 2H, CH$_{Ph}$), 5.96 (d, 1H, J$_{1,2}$=7.8 Hz, H-1), 5.44 (pt, 1H, J$_{2,3}$=9.6 Hz, H-3), 5.15 (pt, 1H, J$_{3,4}$=9.8 Hz, H-4), 4.38 (dd, 1H, J$_{5,6a}$=4.6 Hz, J$_{6a,6b}$=12.4 Hz, H-6a), 4.13 (dd, 1H, J$_{5,6b}$=2.1 Hz, H6b), 4.00 (m, 1H, H-5), 3.85 (s, 3H, OMe), 3.46 (dd, 1H, H-2), 2.13, 2.06, 2.05, 1.89 (4 s, 12H, H$_{Ac}$).

$^{13}$C NMR (CDCl$_3$), δ171.0, 170.2, 169.8, 169.1 (4C, C$_{Ac}$), 164.6 (CH), 162.7 (C$_{Ph}$), 130.6 (2C, CH$_{Ph}$), 128.7 (C$_{Ph}$), 114.7 (2C, CH$_{Ph}$), 93.5 (C-1, $^1$J$_{CH}$=167.0 Hz), 73.3 (C-3), 73.1 (C-2), 73.0 (C-5), 68.4 (C-4), 62.2 (C-6), 55.9 (OMe), 21.2, 21.1, 21.0, 20.9 (4C, C$_{Ac}$).

The tetra-O-acetyl 6 (34.3 g, 74.0 mmol) is dissolved in 300 mL of hot acetone, then HCl (5M, 15.0 mL) is added dropwise to the reaction mixture. A precipitate forms immediately, and the flask is immersed in an ice bath. After adding 300 mL of diethyl ether and stirring for 2 h, the flask is put in a refrigerator overnight. The precipitate obtained is filtered, washed with diethyl ether and dried with a vane pump to give glucosamine hydrochloride 7 as a white solid (19.0 g, 43%).

$^1$H NMR (D$_2$O), δ5.90 (d, 1H, J$_{1,2}$=8.8 Hz, H-1), 5.43 (pt, 1H, J$_{2,3}$=9.1 Hz, H-3), 5.06 (pt, 1H, J$_{3,4}$=9.6 Hz, H-4), 4.27 (dd, 1H, J$_{5,6a}$=3.8 Hz, J$_{6a,6b}$=12.6 Hz, H-6a), 4.16-4.11 (m, 2H, H-5, H-6b), 3.70 (dd, 1H, H-2), 2.13, 2.06, 1.99 (3 s, 12H, H$_{Ac}$).

$^{13}$C NMR (D$_2$O), δ173.9, 173.4, 173.0, 171.5 (4C, C$_{Ac}$), 90.7 (C-1, $^1$J$_{CH}$=161.0 Hz), 72.5 (C-5), 71.2 (C-3), 68.4 (C-4), 61.8 (C-6), 52.7 (C-2), 20.6, 20.5, 20.4, 20.3 (4C, C$_{Ac}$).

2-Deoxy-2-trichloroacetamido-α/β-D-glucopyranose)[1] 9

1,3,4,6-Tetra-O-acetyl-2-deoxy-2-trichloroacetamido-α/β-D-glucopyranose[1] 8

Chemical Formula: C$_8$H$_{12}$Cl$_3$NO$_8$
Exact Mass: 322.9730
Molecular Weight: 324.5430

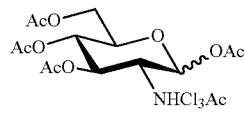

Chemical Formula: C$_{16}$H$_{20}$Cl$_3$NO$_{10}$
Exact Mass: 491.0153
Molecular Weight: 492.6897

Commercial D-glucosamine hydrochloride 4 (5.0 g, 23.2 mmol) is dissolved in MeOH (100 mL) and the solution is stirred for 2 h at RT. Then the flask is adjusted to 0° C. and stirred for 10 min, then 25% NaOMe (16.1 mL, 58.1 mmol, 2.5 eq.) is slowly added to the reaction mixture. After stirring for 15 min, a precipitate is observed, then trichloroacetic anhydride (6.4 mL, 34.9 mmol, 1.5 eq.) is added dropwise to the reaction mixture on an ice bath. After stirring for 1.5 h, monitoring by TLC (iPrOH/H$_2$O/NH$_3$, 4/1/0.5) shows disappearance of 4 (Rf=0.1) and appearance of a less polar product (Rf=0.6). The reaction mixture is then neutralized with DOWEX (H$^+$) ion-exchange resin, then filtered on a frit and concentrated in a rotary evaporator. The residue is dissolved in a minimum of H$_2$O and then lyophilized. The yellow foam obtained, which is a mixture of anomer 9$_{α/β}$ (6/4), is used in the next stage after NMR to check for absence of 4.

Rf=0.6 (iPrOH/H$_2$O/NH$_3$, 4/1/0.5).

$^1$H NMR (DMSO-d6), δ: α: 8.13 (bs, 1H, NH), 5.06 (d, 1H, J$_{1,2}$=3.5 Hz, H-1), 4.99 (bs, 1H, OH-4), 4.90 (bs, 1H, OH-2), 4.82 (bs, 1H, OH-3), 4.43 (bs, 1H, OH-6), 3.73 (m, 1H, H-3), 3.64 (m, 1H, H-6a), 3.61 (m, 1H, H-5), 3.56 (m, 1H, H-2), 3.53 (m, 1H, H-6b), 3.18 (pt, 1H, J$_{3,4}$=8.6 Hz, H-4).

$^{13}$C NMR (DMSO-d6), δ: α: 162.3 (C$_{NTCA}$), 93.5 (CCl$_3$), 90.5 (C-1, $^1$J$_{CH}$=167.4 Hz), 73.1 (C-5), 71.6 (C-4), 70.7 (C-3), 61.8 (C-6), 57.8 (C-2).

$^1$H NMR (DMSO-d6), δ: β: 8.59 (d, 1H, J$_{NH,2}$=8.5 Hz, NH), 4.95 (bs, 1H, OH-4), 4.65 (d, 1H, J$_{1,2}$=7.6 Hz, H-1), 4.50 (bs, 1H, OH-6), 3.68 (m, 1H, H-6a), 3.50 (m, 1H, H-5), 3.46 (m, 1H, H-6b), 3.41 (m, 1H, H-2), 3.18 (m, 2H, H-3, H-4).

$^{13}$C NMR (DMSO-d6), δ: β: 162.1 (C$_{NTCA}$), 95.4 (C-1, $^1$J$_{CH}$=157.0 Hz), 94.3 (CCl$_3$), 77.7 (C-4), 74.2 (C-5), 72.0 (C-3), 62.0 (C-6), 59.9 (C-2).

Route 1:

The raw reaction product 9 obtained is dissolved in a pyridine/acetic anhydride mixture (1/1, 50 mL) at 0° C. and the reaction mixture is stirred overnight at RT. After verifying, by TLC (DCM/EtOAc, 9/1), the appearance of two new compounds (Rf=0.45 and 0.2), the reaction mixture is concentrated in a rotary evaporator and then coevaporated with Tol (3×100 mL) and DCM (3×100 mL). The residue is dried with a vane pump to give the expected derivative in the form of a solid corresponding to a mixture of α/β anomers. The solid obtained is purified by silica gel chromatography (DCM/EtOAc, 97/3→9/1) to give, in the order of elution, the desired monosaccharide $8_\alpha$ (6.6 g, 57%) and then the stereoisomer $8_\beta$ (3.5 g, 31%). The two anomers $8_\alpha$ and $8_\beta$ (65/35) are isolated as a white solid (10.1 g, 88%).

Route 2:

Glucosamine hydrochloride 7 is added in portions (5 g, 13.1 mmol) to a solution of DCM (40 mL) and pyridine (5.2 mL, 65.3 mmol, 5 eq.). The reaction mixture is put on an ice bath and then trichloroacetyl chloride (4.1 mL, 36.0 mmol, 2.8 eq.) is added dropwise. After stirring for 15 min at 0° C., the reaction mixture is stirred for 30 min at RT. The reaction is monitored by TLC (DCM/EtOAc, 9/1), and the appearance of a less polar product (Rf=0.2) is observed. The reaction mixture is taken up in $H_2O$ (20 mL) and the aqueous phase is extracted with DCM (3×30 mL). The organic phases are combined and washed with a solution of 5% $NaHCO_3$ (3×50 mL), with $H_2O$ (3×50 mL) and then dried over $Na_2SO_4$ and concentrated in a rotary evaporator to give a white solid (6.3 g, 98%) corresponding to the anomer $8_\beta$.

$8_\alpha$: Rf=0.45 (DCM/EtOAc, 9/1).

$^1$H NMR (CDCl$_3$), δ6.83 (d, 1H, $J_{NH,2}$=8.3 Hz, NH$_\alpha$), 6.29 (d, 1H, $J_{1,2}$=3.7 Hz, H-1), 5.34 (pt, 1H, $J_{2,3}$=9.6 Hz, H-3), 5.23 (pt, 1H, $J_{3,4}$=9.8 Hz, H-4), 4.35-4.25 (m, 2H, H-2, H-6a), 4.07-4.01 (m, 2H, H-5, H-6b), 2.18, 2.08, 2.05 (3 s, 12H, H$_{Ac}$).

$^{13}$C NMR (CDCl$_3$), δ172.0, 171.0, 169.4, 168.7 (4C, C$_{Ac}$), 162.3 (C$_{NTCA}$), 92.1 (CCl$_3$), 89.9 (C-1, $^1J_{CH}$=179.2 Hz), 70.4 (C-5), 70.2 (C-3), 67.4 (C-4), 61.7 (C-6), 53.7 (C-2), 21.1, 21.0, 20.9, 20.8 (4C, C$_{Ac}$).

$8_\beta$: Rf=0.2 (DCM/EtOAc, 9/1).

$^1$H NMR (CDCl$_3$), δ7.19 (d, 1H, $J_{NH,2}$=9.4 Hz, NH), 5.83 (d, 1H, $J_{1,2}$=8.7 Hz, H-1), 5.37 (pt, 1H, $J_{2,3}$=9.4 Hz, H-3), 5.18 (pt, 1H, $J_{3,4}$=9.8 Hz, H-4), 4.32 (m, 2H, H-2, H-6a), 4.18 (m, 1H, $J_{5,6b}$=2.3 Hz, $J_{6a,6b}$=12.4 Hz, H-6b), 3.89 (ddd, 1H, $J_{4,5}$=10.0 Hz, $J_{5,6a}$=4.7 Hz, H-5), 2.13, 2.06 (2 s, 12H, H$_{Ac}$).

$^{13}$C NMR (CDCl$_3$), δ171.6, 171.0, 169.7, 169.6, (4C, C$_{Ac}$), 162.7 (C$_{NTCA}$), 92.5 (CCl$_3$), 92.4 (C-1, $^1J_{CH}$=159.6 Hz), 73.5 (C-5), 72.2 (C-3), 68.1 (C-4), 62.0 (C-6), 55.0 (C-2), 21.1, 21.0, 20.9, 20.8 (4C, C$_{Ac}$).

3,4,6-Tri-O-acetyl-2-deoxy-2-trichloroacetamido-α/β-glucopyranose[1] 10

4,6-Tri-O-acetyl-2-deoxy-2-trichloroacetamido-α/β-D-glucopyranose 11

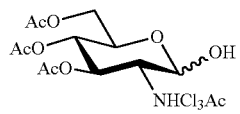

Chemical Formula: C$_{14}$H$_{16}$Cl$_3$NO$_9$
Exact Mass: 449.0047
Molecular Weight: 450.6530

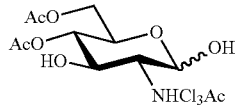

Chemical Formula: C$_{12}$H$_{16}$Cl$_3$NO$_6$
Exact Mass: 406.9941
Molecular Weight: 408.6163

Acetic acid (1.7 mL, 29.1 mmol, 1.4 eq.) is slowly added to a solution of ethylenediamine (1.8 mL, 25 mmol, 1.2 eq.) in THF (390 mL). A precipitate forms immediately. Then tetra-O-acetyl 8 (10.2 g, 20.8 mmol) is added to the reaction mixture, which is stirred at RT, and the reaction is monitored by TLC (DCM/MeOH, 95/5 and Chex/EtOAc, 1/1). After 24 h, the transformation of 8 (Rf=0.7 and 0.3, respectively) to a more polar compound is complete (Rf=0.4 and 0.3, respectively). The reaction mixture is taken up in cold water (100 mL) and ethyl acetate (100 mL) and the aqueous phase is extracted with ethyl acetate (3×100 mL). The organic phases are combined and washed with a solution of 5% NaHCO$_3$ (3×50 mL), with a solution of NaCl$_{sat}$ (3×50 mL), with H$_2$O (3×50 mL) and then dried over Na$_2$SO$_4$ and concentrated in a rotary evaporator. The white solid obtained is purified by silica gel chromatography (Chex/EtOAc, 8/2→1/1) to give, in the order of elution, the hemiacetal 10 in the form of a white solid (8.3 g, 89%) and then the unwanted diol 11 (420 mg, 5%).

10: Rf=0.3 (Chex/EtOAc, 1/1).

$^1$H NMR (CDCl$_3$), δ7.03 (d, 1H, $J_{NH,2}$=8.9 Hz, NH), 5.43 (pt, 1H, $J_{2,3}$=9.6 Hz, H-3), 5.43 (pt, 1H, $J_{1,2}$=3.6 Hz, H-1), 5.19 (pt, 1H, $J_{3,4}$=9.6 Hz, H-4), 4.33-4.24 (m, 3H, H-2, H-5, H-6a), 4.19 (m, 1H, H-6b), 3.47 (d, 1H, $J_{OH,1}$=2.6 Hz, OH), 2.13, 2.09, 2.05 (3 s, 9H, H$_{Ac}$).

$^{13}$C NMR (CDCl$_3$), δ170.3, 169.4, 168.5 (3C, C$_{Ac}$), 161.1 (C$_{NTCA}$), 91.0 (CCl$_3$), 89.9 (C-1, $^1J_{CH}$=172.6 Hz), 69.5 (C-3), 67.2 (C-4), 67.0 (C-5), 61.0 (C-6), 53.2 (C-2), 19.7, 19.6, 19.5 (3C, C$_{Ac}$).

11: Rf=0.2 (Chex/EtOAc, 1/1).

$^1$H NMR (CDCl$_3$), δ7.19 (d, 1H, $J_{NH,H-2}$=8.6 Hz, NH), 5.34 (pt, 1H, $J_{1,2}$=3.3 Hz, H-1), 5.19 (pt, 1H, $J_{3,4}$=9.5 Hz, H-4), 4.25-4.03 (m, 4H, H-6a, H-5, H-2, H-6b), 3.97 (pt, 1H, $J_{2,3}$=9.5 Hz, H-3), 2.10, 2.08 (2 s, 6H, H$_{Ac}$).

$^{13}$C NMR (CDCl$_3$), δ171.7, 171.4 (2C, C$_{Ac}$), 163.3 (C$_{NTCA}$), 92.6 (CCl$_3$), 91.3 (C-1, $^1J_{CH}$=171.9 Hz), 71.5 (C-4), 70.9 (C-3), 68.4 (C-5), 62.7 (C-6), 56.4 (C-2), 21.3, 21.2 (2C, C$_{Ac}$)

HRMS (ESI$^+$): [M+Na]$^+$ C$_{12}$H$_{16}$NO$_8$$^{35}$Cl$_3$Na m/z theoretical:
429.9839
m/z measured:
429.9864

3,4,6-Tri-O-acetyl-2-deoxy-2-trichloroacetamido-α/β-D-glucopyranose trichloroacetimidate[1] 1

2-Trichloromethyl-(3,4,6-tri-O-acetyl-1,2-dideoxy-α-D-glucopyrano)-[2,1-d]-2-oxazoline[1] 1'

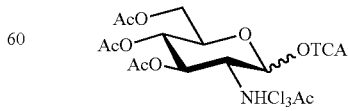

Chemical Formula: C$_{16}$H$_{18}$Cl$_6$N$_2$O$_9$
Exact Mass: 591.9143
Molecular Weight: 595.0401

-continued

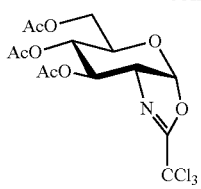

Chemical Formula: C$_{14}$H$_{16}$Cl$_3$NO$_8$
Exact Mass: 430.9941
Molecular Weight: 432.6377

Route 1:

The hemiacetal 10 (4.0 g, 8.9 mmol) is dissolved in DCE (30 mL) and stirred under argon at −5° C., and then DBU (372 µL, 2.5 mmol, 0.28 eq.) and trichloroacetonitrile (4.4 mL, 44.4 mmol, 5 eq.) are added. The reaction mixture is stirred at this temperature for 15 min and then it is loaded, without any treatment, in a silica gel column (flash chromatography, Chex/EtOAc+5% NEt$_3$, 7/3→1/1) to obtain the trichloroacetimidate 1 in the form of a white solid (4.6 g, 87%).

Route 2:

The hemiacetal 10 (1.5 g, 3.3 mmol) is dissolved in DCM (15 mL). Trichloroacetonitrile (1.7 mL, 16.7 mmol, 5 eq.) is added to the reaction mixture and then Cs$_2$CO$_3$ (217 mg, 670 µmol, 0.2 eq.) is added in small portions. The reaction mixture is stirred at RT and the reaction is monitored by TLC (Chex/EtOAc, 1/1). After stirring for 1.5 h, the transformation of 10 to a less polar product (Rf=0.8) is complete. The residue obtained is filtered and washed with DCM. The filtrate is then co-evaporated with Tol in a rotary evaporator. The trichloroacetimidate 1 obtained in the form of a yellow solid (1.9 g, 98%) is used directly in the next stage after checking by $^1$H NMR.

1: Rf=0.8 (Chex/EtOAc, 1/1)

$^1$H NMR (CDCl$_3$), δ: α: 8.85 (s, 1H, NH), 7.00 (d, 1H, J$_{NH,2}$=8.5 Hz, NH), 6.5 (d, 1H, J$_{1,2}$=3.6 Hz, H-1), 5.44 (pt, 1H, J$_{2,3}$=9.7 Hz, H-3), 5.3 (pt, 1H, J$_{3,4}$=10.0 Hz, H-4), 4.45 (ddd, 1H, H-2), 4.28 (dd, 1H, J$_{5,6a}$=4.2 Hz, J$_{6a,6b}$=12.7 Hz, H-6a), 4.18-4.12 (m, 2H, H-5, H-6b), 2.11, 2.08, 2.06 (3 s, 9H, H$_{Ac}$).

$^{13}$C NMR (CDCl$_3$), δ: α: 171.8, 170.9, 169.5 (3C, C$_{Ac}$), 162.4 (C=NH), 160.3 (C$_{NTCA}$), 94.0 (C-1, $^1$J$_{CH}$=181.4 Hz), 92.1 (CCl$_3$), 90.8 (CCl$_3$), 70.8 (C-5), 70.5 (C-3), 68.2 (C-4), 61.6 (C-6), 54.2 (C-2), 21.1, 21.0, 20.9 (3C, C$_{Ac}$)

The oxazoline 1', resulting from the degradation of 1 during purification, is isolated as the second product eluted during silica gel chromatography.

1': Rf=0.65 (Chex/EtOAc, 1/1)

$^1$H NMR (CDCl$_3$), δ: oxazoline: 6.35 (d, 1H, J$_{1,2}$=7.4 Hz, H-1), 5.41 (pt, 1H, J$_{2,3}$=2.3 Hz, H-3), 4.96 (m, 1H, J$_{4,5}$=8.2 Hz, J$_{2,4}$=1.6 Hz, H-4), 4.49 (m, 1H, H-2), 4.29 (dd, 1H, J$_{5,6a}$=3.0 Hz, J$_{6a,6b}$=12.1 Hz, H-6a), 4.20 (dd, 1H, J$_{5,6b}$=6.0 Hz, H-6b), 3.80 (m, 1H, H-5), 2.15, 2.13, 2.11 (3 s, 9H, H$_{Ac}$).

$^{13}$C NMR (CDCl$_3$), δ: oxazoline: 170.8, 169.8, 169.3 (3C, C$_{Ac}$), 163.4 (N=C), 103.5 (C-1, $^1$J$_{CH}$=183.6 Hz), 86.5 (CCl$_3$), 69.4 (C-5), 69.1 (C-3), 68.0 (C-4), 65.1 (C-2), 63.8 (C-6), 21.2, 21.1, 21.0 (3C, C$_{Ac}$).

2-Deoxy-4,6-O-isopropylidene-2-trichloroacetamido-α/β-D-glucopyranose 12

1,3-Di-O-acetyl-2-deoxy-4,6-O-isopropylidene-2-trichloroacetamido-α/β-D-glucopyranose 14

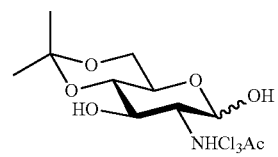

Chemical Formula: C$_{11}$H$_{16}$Cl$_3$NO$_6$
Exact Mass: 363.0043
Molecular Weight: 364.6068

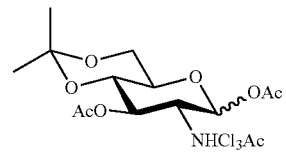

Chemical Formula: C$_{15}$H$_{20}$Cl$_3$NO$_8$
Exact Mass: 447.0254
Molecular Weight: 448.6802

Commercial D-glucosamine hydrochloride 4 (11.6 g, 54.0 mmol) is protected in position 2$_D$ with a trichloroacetamide group as described previously.

The raw product obtained 9 (54.0 mmol) is dissolved in DMF (185 mL) containing 2-methoxypropene (10.3 mL, 108.0 mmol, 2 eq.). CSA (24.0 g, 108.0 mmol, 2 eq.) is added in portions to the reaction mixture until pH 2 is obtained. The reaction mixture is stirred at RT and the reaction is monitored by TLC (DCM/MeOH, 8/2 and Chex/EtOAc, 1/1). After stirring for 2.5 h, the MeOH formed is evaporated in a rotary evaporator and 2-methoxypropene (2 mL, 21.6 mmol, 0.4 eq.) is added again. After stirring for 1 h, the transformation of 9 to a less polar product (Rf=0.3 in Chex/EtOAc, 1/1) is practically complete. The reaction mixture is neutralized with triethylamine (0.2 mL) and then concentrated in a rotary evaporator to give a yellow solid, corresponding to a mixture of anomers 12$_{α/β}$ (9/1).

Rf=0.3 (Chex/EtOAc, 1/1).

$^1$H NMR (DMSO-d6), δ: α: 8.37 (d, 1H, J$_{NH,2}$=7.8 Hz, NH), 6.88 (d, 1H, J$_{1,2}$=3.9 Hz, H-1), 5.0 (m, 2H, OH), 3.77 (m, 1H, H-3), 3.71-3.65 (m, 4H, H-2, H-5, H-6a, H-6b), 3.50 (m, 1H, H-4), 1.44 (s, 3H, H$_{iPr}$), 1.25 (s, 3H, H$_{iPr}$).

$^{13}$C NMR (DMSO-d6), δ: α: 162.4 (C$_{NTCA}$), 99.9 (C$_{iPr}$), 93.3 (CCl$_3$), 91.2 (C-1, $^1$J$_{CH}$=168.2 Hz), 75.0 (C-4), 67.5 (C-3), 63.9 (C-5), 62.3 (C-6), 58.0 (C-2), 29.8 (C$_{iPr}$), 21.6 (C$_{iPr}$).

HRMS (ESI$^+$): [M+Na]$^+$ C$_{11}$H$_{16}$NO$_6$$^{35}$Cl$_3$Na m/z theoretical:
385.9941
m/z measured:
385.9962

The raw reaction product 12 obtained is dissolved in a pyridine/acetic anhydride mixture (1/1, 100 mL) at 0° C. and the reaction mixture is stirred overnight at RT. After verifying the appearance of two new compounds (Rf=0.7 and 0.75) by monitoring with TLC (Chex/EtOAc, 1/1), the reaction mixture is concentrated in a rotary evaporator and then coevaporated with Tol (3×200 mL) and DCM (3×200 mL). The residue is dried with a vane pump to give the expected derivative in the form of a solid. The solid obtained is purified by silica gel chromatography (Chex/EtOAc, 8/2→75/25) to give the mixture of anomers 14$_{\alpha/\beta}$ in the proportions 55/45 in the form of a white solid (17.0 g, 70%)

14$_\alpha$: Rf=0.7 (Chex/EtOAc, 1/1).

$^1$H NMR (CDCl$_3$), δ 7.01 (d, 1H, J$_{NH,2}$=8.4 Hz, NH), 6.23 (d, 1H, J$_{1,2}$=3.9 Hz, H-1), 5.30 (pt, 1H, J$_{2,3}$=9.5 Hz, H-3), 4.28 (ddd, 1H, H-2), 3.93-3.83 (m, 2H, H-4, H-6a), 3.79-3.74 (m, 2H, H-5, H-6b), 2.16, 2.09 (2 s, 6H, H$_{Ac}$), 1.51 (s, 3H, H$_{iPr}$), 1.39 (s, 3H, H$_{iPr}$).

$^{13}$C NMR (CDCl$_3$), δ172.2, 169.4 (2C, C$_{Ac}$), 162.4 (C$_{NTCA}$), 100.4 (C$_{iPr}$), 92.2 (CCl$_3$), 90.5 (C-1, $^1$J$_{CH}$=178.6 Hz), 71.8 (C-4), 70.0 (C-3), 66.4 (C-5), 62.2 (C-6), 53.8 (C-2), 29.2 (C$_{iPr}$), 21.2, 21.1 (2C, C$_{Ac}$), 19.4 (C$_{iPr}$).

14$_\beta$ Rf=0.75 (Chex/EtOAc, 1/1).

$^1$H NMR (CDCl$_3$), δ 7.03 (d, 1H, J$_{NH,2}$=9.7 Hz, NH), 5.78 (d, 1H, J$_{1,2}$=8.7 Hz, H-1), 5.24 (pt, 1H, J$_{2,3}$=9.6 Hz, H-3), 4.25 (m, 1H, H-2), 4.01 (m, 1H, H-6a), 3.88-3.83 (m, 2H, H-4, H-6b), 3.55 (m, 1H, H-5), 2.11 (s, 3H, H$_{Ac}$), 2.09 (s, 3H, H$_{Ac}$), 1.52 (s, 3H, H$_{iPr}$), 1.45 (s, 3H, H$_{iPr}$).

$^{13}$C NMR (CDCl$_3$), δ171.8, 169.5 (2C, C$_{Ac}$), 162.8 (C$_{NTCA}$), 100.5 (C$_{iPr}$), 93.2 (C-1), 92.2 (CCl$_3$), 71.6 (C-4), 71.3 C-3), 69.1 (C-5), 62.1 (C-6), 55.9 (C-2), 30.1 (C$_{iPr}$), 21.2, 21.1 (2C, C$_{Ac}$), 19.3 (C$_{iPr}$).

HRMS (ESI$^+$): [M+Na]$^+$ C$_{15}$H$_{20}$NO$_8$$^{35}$Cl$_3$Na m/z theoretical:
470.0152
m/z measured:
470.0123

3-O-Acetyl-2-deoxy-4,6-O-isopropylidene-2-trichloroacetamido-α/β-D-glucopyranose 15

2,5-Hydroxy-4,6-O-isopropylidene-hex-2-enal 16

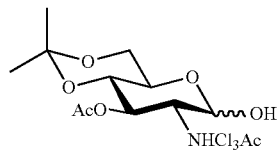

Chemical Formula: C$_{13}$H$_{18}$Cl$_3$NO$_7$
Exact Mass: 405.0149
Molecular Weight: 406.6435

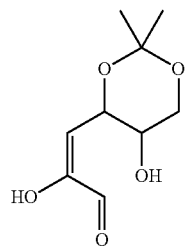

Chemical Formula: C$_9$H$_{14}$O$_5$
Exact Mass: 202.0841
Molecular Weight: 202.2045

Acetic acid (162 μL, 2.8 mmol, 1.4 eq.) is slowly added to a solution of ethylenediamine (177 μL, 2.4 mmol, 1.2 eq.) in THF (40 mL). A precipitate forms immediately. Then the di-O-acetyl 14 (900 mg, 2.0 mmol) is added to the reaction mixture, which is stirred at RT, and the reaction is monitored by TLC (DCM/MeOH, 95/5 and Chex/EtOAc, 1/1). After 20 h, the transformation of 14 (Rf=0.7 and 0.75 in Chex/EtOAc, 1/1) to a more polar compound is complete (Rf=0.6 in DCM/MeOH, 95/5 and 0.5 in Chex/EtOAc, 1/1). The reaction mixture is taken up in cold water (25 mL) and in ethyl acetate (25 mL) and the aqueous phase is extracted with ethyl acetate (3×20 mL). The organic phases are combined and washed with a solution of 5% NaHCO$_3$ (3×15 mL), with a solution of NaCl$_{sat}$ (3×15 mL), with H$_2$O (3×15 mL) and then dried over Na$_2$SO$_4$ and concentrated in a rotary evaporator. The solid obtained is purified by silica gel chromatography (Chex/EtOAc, 8/2→1/1) to give the mixture of anomers 15$_{\alpha/\beta}$ in the proportions 95/5 in the form of a white solid (710 mg, 87%) followed by the keto-aldehyde 16 (20 mg, 5%).

15$_\alpha$: Rf=0.5 (Chex/EtOAc, 1/1).

$^1$H NMR (CDCl$_3$), δ7.11 (d, 1H, J$_{NH,2}$=8.9 Hz, NH), 5.37-5.34 (m, 2H, H-1, H-3), 4.20 (ddd, 1H, J$_{1,2}$=3.7 Hz, J$_{2,3}$=9.5 Hz, J$_{2,OH}$=1.8 Hz, H-2), 4.02 (ddd, 1H, H-5), 3.91 (dd, 1H, J$_{5,6a}$=5.2 Hz, J$_{6a,6b}$=10.6 Hz, H-6a), 3.86-3.77 (m, 2H, J$_{3,4}$=10.6 Hz, H-4, H-6b), 2.09 (s, 3H, H$_{Ac}$), 1.53 (s, 3H, H$_{iPr}$), 1.45 (s, 3H, H$_{iPr}$).

$^{13}$C NMR (CDCl$_3$), δ 171.8 (C$_{Ac}$), 162.5 (C$_{NTCA}$), 100.4 (C$_{iPr}$), 92.4 (CCl$_3$), 92.1 (C-1, $^1$J$_{CH}$=173.5 Hz), 72.0 (C-4), 70.2 (C-3), 64.3 (C-5), 62.6 (C-6), 55.3 (C-2), 29.3 (C$_{iPr}$), 21.3 (C$_{Ac}$), 19.4 (C$_{iPr}$).

HRMS (ESI$^+$): [M+Na]$^+$ C$_{13}$H$_{18}$NO$_7$$^{35}$Cl$_3$Na m/z theoretical:
428.0047
m/z measured:
428.0048

16: Rf=0.25 (Chex/EtOAc, 6/4).

$^1$H NMR (CDCl$_3$), δ9.43 (s, 1H, H-1), 6.45 (d, 1H, J$_{3,4}$=5.7 Hz, H-3), 4.74 (m, 1H, H-4), 3.93 (m, 1H, H-6a), 3.77-3.69 (m, 2H, H-5, H-6b), 1.54 (s, 3H, H$_{iPr}$), 1.43 (s, 3H, H$_{iPr}$);

$^{13}$C NMR (CDCl$_3$), δ187.0 (CHO), 137.3 (C-3), 135.8 (C-2), 99.8 (C$_{iPr}$), 72.0 (C-4), 67.2 (C-5), 65.1 (C-6), 29.0 (C$_{iPr}$), 19.5 (C$_{iPr}$);

3-O-Acetyl-2-deoxy-4,6-O-isopropylidene-2-trichloroacetamido-α/β-D-glucopyranose trichloroacetimidate 2

2-Trichloromethyl-3-O-acetyl-1,2-dideoxy-4,6-O-isopropylidene-α-D-glucopyrano)-[2,1-d]-2-oxazoline 2'

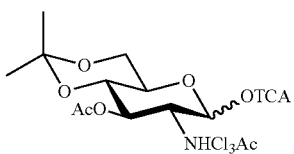

Chemical Formula: C$_{15}$H$_{18}$Cl$_6$N$_2$O$_7$
Exact Mass: 547.9245
Molecular Weight: 551.0306

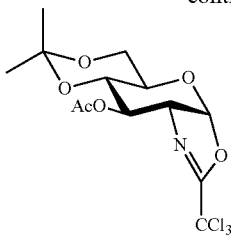

Chemical Formula: $C_{13}H_{16}Cl_3NO_6$
Exact Mass: 387.0043
Molecular Weight: 388.6282

Route 1:

The hemiacetal 15 (3.0 g, 7.4 mmol) is dissolved in DCE (12 mL) and stirred under argon at −5° C., then DBU (310 μL, 2.1 mmol, 0.28 eq.) and trichloroacetonitrile (3.7 mL, 36.9 mmol, 5 eq.) are added. The reaction mixture is stirred at this temperature for 15 min and then it is loaded, without any treatment, on a silica gel column (flash chromatography, Chex/EtOAc+5% NEt$_3$, 7/3) to obtain the trichloroacetimidate 2 as a white solid (3.5 g, 87%).

Route 2:

Acetic acid (1.0 mL, 17.6 mmol, 1.7 eq.) is slowly added to a solution of ethylenediamine (1.0 mL, 14.5 mmol, 1.4 eq.) in THF (180 mL). A precipitate forms immediately. Then the di-O-acetyl 14 (4.6 g, 10.4 mmol) is added to the reaction mixture, which is stirred at RT, and the reaction is monitored by TLC (DCM/MeOH, 95/5 and Chex/EtOAc, 1/1). After 20 h, the transformation of 14 (Rf=0.7 and 0.75 in Chex/EtOAc, 1/1) to a more polar compound is complete (Rf=0.6 in DCM/MeOH, 95/5 and 0.5 in Chex/EtOAc, 1/1). The reaction mixture is taken up in ethyl acetate (150 mL) and is washed with cold water (2×25 mL) and the aqueous phase is extracted with ethyl acetate (2×50 mL). The organic phases are combined, dried over Na$_2$SO$_4$ and concentrated in a rotary evaporator to give the desired compound as a white solid (4.2 g).

The aforementioned raw product (4.2 g, 10.4 mmol) is dissolved in DCE (15 mL) and stirred under argon at −5° C. and then DBU (434 μL, 2.9 mmol, 0.28 eq.) and trichloroacetonitrile (4.5 mL, 44.6 mmol, 4.3 eq.) are added. The reaction mixture is stirred at this temperature for 15 min and then it is loaded, without any treatment, on a silica gel column (flash chromatography, Chex/EtOAc+5% NEt$_3$, 7/3) to obtain the trichloroacetimidate 2 as a white solid (4.6 g, 80%).

2: Rf=0.5 (Chex/EtOAc, 7/3).

$^1$H NMR (CDCl$_3$), δ: α: 8.78 (s, 1H, NH), 7.10 (d, 1H, J$_{NH,2}$=8.5 Hz, NH), 6.45 (d, 1H, J$_{1,2}$=3.7 Hz, H-1), 5.40 (pt, 1H, J$_{2,3}$=9.2 Hz, H-3), 4.39 (m, 1H, H-2), 3.98-3.91 (m, 3H, H-4, H-5, H-6a), 3.81 (m, 1H, H-6b), 2.11 (s, 3H, H$_{Ac}$), 1.54 (s, 3H, H$_{iPr}$), 1.43 (s, 3H, H$_{iPr}$).

$^{13}$C NMR (CDCl$_3$), δ: α: 171.9 (C$_{Ac}$), 162.5 (C$_{NTCA}$), 160.7 (C=NH), 100.5 (C$_{iPr}$), 94.7 (C-1, $^1$J$_{CH}$=180.1 Hz), 92.2 (CCl$_3$), 91.0 (CCl$_3$), 71.4 (C-4), 69.9 (C-3), 67.0 (C-5), 62.3 (C-6), 55.0 (C-2), 29.3 (C$_{iPr}$), 21.2 (C$_{Ac}$), 19.4 (C$_{iPr}$).

The oxazoline 2', resulting from the degradation of 2 during purification, is isolated as the second product eluted during silica gel chromatography.

2': Rf=0.4 (Chex/EtOAc, 7/3).

$^1$H NMR (CDCl$_3$), δ: oxazoline: 7.18 (d, 1H, J$_{NH,2}$=8.5 Hz, NH), 6.28 (d, 1H, J$_{1,2}$=7.53 Hz, H-1), 5.05 (m, 1H, H-3), 4.34 (m, 1H, H-2), 4.05 (m, 1H, H-6a), 3.88 (m, 1H, H-4), 3.76 (m, 1H, H-6b), 3.59 (m, 1H, H-5), 2.11 (s, 3H, H$_{Ac}$), 1.52 (s, 3H, H$_{iPr}$), 1.43 (s, 3H, H$_{iPr}$).

$^{13}$C NMR (CDCl$_3$), δ: oxazoline: 170.0 (C$_{Ac}$), 163.1 (N=C), 105.9 (C-1), 100.5 (C$_{iPr}$), 92.2 (CCl$_3$), 74.2 (C-3), 70.8 (C-4), 68.5 (C-2), 65.2 (C-5), 62.1 (C-6), 29.0 (C$_{iPr}$), 21.4 (C$_{Ac}$), 19.3 (C$_{iPr}$).

Allyl 3-O-acetyl-2-deoxy-4,6-O-isopropylidene-2-trichloroacetamido-β-D-glucopyranoside 17

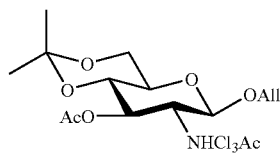

Chemical Formula: $C_{16}H_{22}Cl_3NO_7$
Exact Mass: 445.0462
Molecular Weight: 446.7074

TMSOTf (360.0 μL, 2.0 mmol, 0.2 eq.) is added to a solution of allyl alcohol (1.4 mL, 20.1 mmol, 2 eq.) and of donor 2 (5.5 g, 10.1 mmol, 1 eq.) in DCM (700 mL), in the presence of molecular sieve 4 Å (3.9 g), and stirred under argon at −78° C. After stirring for 30 min, monitoring by TLC (Tol/EtOAc, 8/2) indicates the disappearance of the donor (Rf=0.65) and the appearance of a new, more polar compound (Rf=0.45). The reaction is stopped by adding triethylamine (0.5 mL) and then the reaction mixture is filtered and concentrated in a rotary evaporator. The yellow oil obtained is purified by silica gel chromatography (Tol/EtOAc, 9/1→75/25) to obtain the allyl glycoside 17 in the form of a white solid (3.7 g, 82%).

Rf=0.45 (Tol/EtOAc, 1/1).

$^1$H NMR (CDCl$_3$), δ7.65 (d, 1H, J$_{NH,2}$=9.6 Hz, NH), 5.81 (m, 1H, CH=), 5.38 (pt, 1H, J$_{2,3}$=9.3 Hz, H-3), 5.25 (m, 1H, J$_{trans}$=17.2 Hz, =CH$_2$), 5.15 (m, 1H, J$_{cis}$=9.2 Hz, =CH$_2$), 4.62 (d, 1H, J$_{1,2}$=8.3 Hz, H-1), 4.29 (m, 1H, H$_{All}$), 4.18 (m, 1H, H-2), 4.10 (m, 1H, H$_{All}$), 3.99 (dd, 1H, J$_{5,6a}$=5.5 Hz, J$_{6a,6b}$=10.8 Hz, H-6a), 4.17 (m, 1H, H-6b), 3.81 (pt, 1H, J$_{3,4}$=9.5 Hz, H-4), 3.75 (ddd, 1H, J$_{4,5}$=9.9 Hz, H-5), 2.08 (s, 3H, H$_{Ac}$), 1.51 (s, 3H, H$_{iPr}$), 1.38 (s, 3H, H$_{iPr}$).

$^{13}$C NMR (CDCl$_3$), δ172.0 (C$_{Ac}$), 162.7 (C$_{NTCA}$), 133.7 (CH=), 118.0 (=CH$_2$), 100.9 (C-1, $^1$J$_{CH}$=158.1 Hz), 100.1 (C$_{iPr}$), 93.1 (CCl$_3$), 72.5 (C-3), 72.1 (C-4), 70.6 (C$_{All}$), 67.4 (C-5), 62.2 (C-6), 56.1 (C-2), 29.1 (C$_{iPr}$), 21.1 (C$_{Ac}$), 19.3 (C$_{iPr}$).

HRMS (ESI$^+$): [M+Na]$^+$ C$_{16}$H$_{22}$NO$_7$$^{35}$Cl$_3$Na m/z theoretical:
468.0359
m/z measured:
468.0359

Allyl 3,4,6-tri-O-acetyl-2-deoxy-2-trichloroacetamido-β-D-glucopyranoside 18

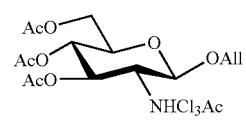

Chemical Formula: $C_{17}H_{22}Cl_3NO_9$
Exact Mass: 489.0360
Molecular Weight: 490.7169

TMSOTf (830.0 μL, 4.6 mmol, 0.2 eq.) is added to a solution of allyl alcohol (3.1 mL, 46.0 mmol, 2 eq.) and of donor 1 (13.7 g, 23.0 mmol, 1 eq.) in DCM (160 mL), in the presence of molecular sieve 4 Å (8.9 g), stirred under argon at −78° C. After stirring for 30 min, monitoring by TLC (Tol/EtOAc, 8/2) indicates the disappearance of the donor (Rf=0.5) and the appearance of a new, more polar compound (Rf=0.35). The reaction is stopped by adding triethylamine (1 mL) and then the reaction mixture is filtered and concentrated in a rotary evaporator. The yellow oil obtained is purified by silica gel chromatography (Tol/EtOAc, 9/1→75/25) to obtain the allyl glycoside 18 as a white solid (9.4 g, 83%).

Rf=0.35 (Tol/EtOAc, 1/1).

$^1$H NMR (CDCl$_3$), δ6.98 (d, 1H, $J_{NH,2}$=8.9 Hz, NH), 5.84 (m, 1H, CH═), 5.39 (pt, 1H, $J_{2,3}$=9.3 Hz, H-3), 5.28 (m, 1H, $J_{trans}$=17.2 Hz, ═CH$_2$), 5.19 (m, 1H, $J_{cis}$=10.4 Hz, ═CH$_2$), 5.12 (pt, 1H, $J_{3,4}$=9.6 Hz, H-4), 4.74 (d, 1H, $J_{1,2}$=8.3 Hz, H-1), 4.36 (m, 1H, H$_{All}$), 4.29 (dd, 1H, $J_{5,6a}$=5.0 Hz, $J_{6a,6b}$=12.3 Hz, H-6a), 4.17 (dd, 2H, $J_{5,6b}$=2.4 Hz, H-6b), 4.10 (m, 1H, H$_{All}$), 4.03 (m, 1H, H-2), 3.75 (ddd, 1H, $J_{4,5}$=9.9 Hz, H-5), 2.10, 2.04, 2.03 (3 s, 9H, H$_{Ac}$).

$^{13}$C NMR (CDCl$_3$), δ171.3, 171.1, 169.7 (3C, C$_{Ac}$), 162.4 (C$_{NTCA}$), 133.6 (CH═), 118.4 (═CH$_2$), 99.7 (C-1, $^1J_{CH}$=155.5 Hz), 92.7 (CCl$_3$), 72.4 (C-5), 72.0 (C-3), 70.6 (C$_{All}$), 69.0 (C-4), 62.5 (C-6), 56.3 (C-2), 21.1, 21.0, 20.9 (3C, C$_{Ac}$).

HRMS (ESI$^+$): [M+Na]$^+$ C$_{17}$H$_{23}$NO$_9{}^{35}$Cl$_3$Na m/z theoretical:
512.0258
m/z measured:
512.0258

Allyl 2-acetamido-2-deoxy-4,6-O-isopropylidene-β-D-glucopyranoside[4] 19

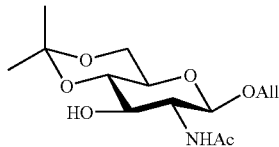

Chemical Formula: C$_{14}$H$_{23}$NO$_6$
Exact Mass: 301.1525
Molecular Weight: 301.3355

After adding 1M NaOH (6.7 mL, 6.7 mmol, 3 eq.) to the allyl glycoside 17 (1.0 g, 2.2 mmol) in solution in MeOH (40 mL), the reaction mixture is stirred overnight and its progress is monitored by TLC (DCM/MeOH, 9/1). After observing the disappearance of 17 (Rf=0.95) and the appearance of a more polar product (Rf=0.5), acetic anhydride (630 μL, 6.7 mmol, 3 eq.) is added to the reaction mixture. After stirring for 3 h, the yellow solid obtained is purified by silica gel chromatography (DCM/MeOH, 98/2→9/1) to obtain the alcohol 19 as a white solid (476 mg, 71%).

Rf=0.5 (DCM/MeOH, 9/1).

$^1$H NMR (CDCl$_3$), δ5.90 (m, 1H, CH═), 5.74 (d, 1H, $J_{NH,2}$=4.6 Hz, NH), 5.32 (m, 1H, $J_{trans}$=17.2 Hz, ═CH$_2$), 5.26 (m, 1H, $J_{cis}$=10.4 Hz, ═CH$_2$), 4.68 (d, 1H, $J_{1,2}$=8.3 Hz, H-1), 4.37 (m, 1H, H$_{All}$), 4.10 (m, 1H, H$_{All}$), 4.00-3.93 (m, 2H, H-3, H-6a), 3.82 (m, 1H, H-6b), 3.61 (pt, 1H, $J_{3,4}$=9.4 Hz, H-4), 3.49 (m, 1H, H-2), 3.31 (ddd, 1H, $J_{5,6b}$=5.4 Hz, $J_{4,5}$=10.0 Hz, H-5), 2.07 (s, 3H, H$_{NAc}$), 1.55 (s, 3H, H$_{iPr}$), 1.47 (s, 3H, H$_{iPr}$).

$^{13}$C NMR (CDCl$_3$), δ162.7 (C$_{NAc}$), 134.2 (CH═), 117.8 (═CH$_2$), 100.9 (C-1, $^1J_{CH}$=162.1 Hz), 100.1 (C$_{iPr}$), 74.6 (C-4), 71.8 (C-3), 70.5 (C$_{All}$), 67.5 (C-5), 62.4 (C-6), 57.9 (C-2), 29.4 (C$_{iPr}$), 23.7 (C$_{NAc}$), 19.5 (C$_{iPr}$).

HRMS (ESI$^+$): [M+Na]$^+$ C$_{14}$H$_{23}$NO$_6$Na m/z theoretical:
324.123
m/z measured:
321.1412
[M+Na]$^+$ C$_{14}$H$_{23}$NO$_6$ m/z theoretical:
302.1604
m/z measured:
302.1599

Allyl 2-deoxy-4,6-O-isopropylidene-2-trichloroacetamido-β-D-glucopyranoside 20

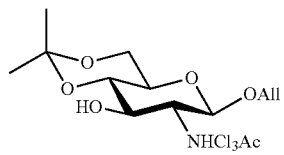

Chemical Formula: C$_{14}$H$_{20}$Cl$_3$NO$_6$
Exact Mass: 403.0356
Molecular Weight: 404.6707

Route 1:
After adding 0.5 M NaOMe (42.0 mL, 20.9 mmol, 1.1 eq.) to the allyl glycoside 18 (9.3 g, 19.0 mmol) in solution in MeOH (40 mL), the reaction mixture is stirred overnight and its development is monitored by TLC (Tol/EtOAc, 8/2, DCM/MeOH, 9/1). After observing the disappearance of 18 (Rf=0.35 and 0.85, respectively) and the appearance of a more polar product (Rf=0 and 0.3, respectively), the reaction mixture is neutralized by adding DOWEX (H$^+$) ion-exchange resin, and then filtered on a frit. The resin is washed with DCM/MeOH mixture and the solvents are evaporated. The yellow solid obtained is used directly in the next stage (6.8 g).

The previous raw product (6.8 g, 19.0 mmol) and 2-methoxypropene (3.4 mL, 38.0 mmol, 2 eq.) are dissolved in DMF (30 mL). CSA (1.2 g, 5.2 mmol, 0.15 eq.) is added in portions to the reaction mixture. While stirring at RT, the reaction is monitored by TLC (Tol/EtOAc, 6/4 and DCM/MeOH, 95/5). After stirring for 2.5 h, the MeOH formed is evaporated in a rotary evaporator and 2-methoxypropene (1.7 mL, 19.0 mmol, 1 eq.) is added again. After stirring for 1 h, the transformation of the starting product to a less polar product (Rf=0.3 in Tol/EtOAc, 6/4) is practically complete. The reaction mixture is neutralized with triethylamine (1 mL) and then concentrated in a rotary evaporator. The solid obtained is purified by silica gel chromatography (Tol/EtOAc, 8/2→7/3) to give the alcohol 20 as a white solid (6.2 g, 81%).

Route 2:
The allyl glycoside 17 (395 mg, 880 μmol) is dissolved in MeOH (5 mL) and then K$_2$CO$_3$ (37 mg, 260 μmol, 0.3 eq.) is added to the reaction mixture. After stirring for 25 min, monitoring by TLC (Chex/EtOAc, 6/4) indicates the disappearance of 17 (Rf=0.45) and the appearance of a more polar product (Rf=0.25). The reaction mixture is evaporated under reduced pressure. The solid obtained is purified by silica gel chromatography (Chex/EtOAc, 8/2→1/1) to give the alcohol 20 as a white solid (335 mg, 94%).

Rf=0.3 (Tol/EtOAc, 6/4).

$^1$H NMR (CDCl$_3$), δ7.26 (d, 1H, $J_{NH,2}$=7.4 Hz, NH), 5.84 (m, 1H, CH═), 5.27 (m, 1H, $J_{trans}$=17.2 Hz, ═CH$_2$), 5.19 (m, 1H, $J_{cis}$=10.4 Hz, ═CH$_2$), 4.89 (d, 1H, $J_{1,2}$=8.3 Hz, H-1), 4.33 (m, 1H, H$_{All}$), 4.20 (pt, 1H, J$_{2,3}$=9.2 Hz, H-3), 4.08 (m, 1H, H$_{All}$), 3.93 (dd, 1H, J$_{5,6a}$=5.4 Hz, J$_{6a,6b}$=10.8 Hz, H-6a), 3.79 (m, 1H, H-6b), 3.56 (pt, 1H, J$_{3,4}$=9.3 Hz, H-4), 3.50 (m, 1H, H-2), 3.32 (ddd, 1H, J$_{4,5}$=10.0 Hz, H-5), 1.52 (s, 3H, H$_{iPr}$), 1.42 (s, 3H, H$_{iPr}$).

$^{13}$C NMR (CDCl$_3$), δ162.3 (C$_{NTCA}$), 133.3 (CH=), 118.4 (=CH$_2$), 99.9 (C$_{iPr}$), 98.9 (C-1, $^1$J$_{CH}$=165.0 Hz), 92.5 (CCl$_3$), 74.4 (C-4), 70.6 (C$_{All}$), 69.8 (C-3), 67.0 (C-5), 61.9 (C-6), 59.3 (C-2), 29.0 (C$_{iPr}$), 19.1 (C$_{iPr}$).

HRMS (ESI$^+$): [M+Na]$^+$ C$_{14}$H$_{20}$NO$_6$$^{35}$Cl$_3$Na m/z theoretical:
426.0254
m/z measured:
426.0252

Allyl 2-deoxy-4,6-O-isopropylidene-3-O-levulinoyl-2-trichloroacetamido-β-D-glucopyranoside 24

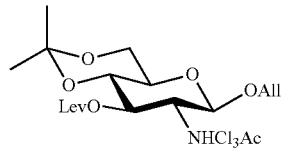

Chemical Formula: C$_{19}$H$_{26}$Cl$_3$NO$_6$
Exact Mass: 501.0724
Molecular Weight: 502.7706

The alcohol 20 (5.9 g, 14.6 mmol) is dissolved in DCM (100 mL) and then DMAP (3.6 g, 29.3 mmol, 2 eq.) is added to the reaction mixture. In another flask, DCC (4.5 g, 22.0 mmol, 1.5 eq.) and levulinic acid (2.7 mL, 26.4 mmol, 1.8 eq.) are stirred in DCM (100 mL) and then added to the reaction mixture. The reaction mixture is then stirred for 30 min, after which time monitoring by TLC (Tol/EtOAc, 7/3) shows the formation mainly of a less polar compound (Rf=0.35) and the disappearance of 20 (Rf=0.25). The DCU is filtered on Celite and the filtrate is taken up in H$_2$O (50 mL). The aqueous phase is extracted with DCM (3×200 mL). The organic phases are combined and washed with a solution of NaHCO$_{3sat}$ (3×100 mL), a solution of NaCl$_{sat}$ (3×100 mL), filtered on a phase-separating filter and concentrated in a rotary evaporator. The oil obtained is purified by silica gel chromatography (Chex/EtOAc, 85/15→75/25) to give the levulinoyl ester 24 (7.3 g, 98%).

Rf=0.35 (Tol/EtOAc, 7/3).

$^1$H NMR (CDCl$_3$), δ7.50 (d, 1H, J$_{NH,2}$=9.4 Hz, NH), 5.82 (m, 1H, CH=), 5.34 (pt, 1H, J$_{2,3}$=9.6 Hz, H-3), 5.24 (m, 1H, J$_{trans}$=17.2 Hz, =CH$_2$), 5.13 (m, 1H, J$_{cis}$=10.5 Hz, =CH$_2$), 4.66 (d, 1H, J$_{1,2}$=8.3 Hz, H-1), 4.29 (m, 1H, H$_{All}$), 4.11 (m, 1H, H-2), 4.06 (m, 1H, H$_{All}$), 3.96 (dd, 1H, J$_{5,6a}$=5.4 Hz, J$_{6a,6b}$=10.7 Hz, H-6a), 3.81 (m, 1H, H-6b), 3.78 (pt, 1H, J$_{3,4}$=9.6 Hz, H-4), 3.60 (ddd, 1H, J$_{4,5}$=9.9 Hz, H-5), 2.72 (m, 2H, CH$_{2Lev}$), 2.58 (m, 2H, CH$_{2Lev}$), 2.14 (s, 3H, CH$_{3Lev}$), 1.50 (s, 3H, H$_{iPr}$), 1.36 (s, 3H, H$_{iPr}$).

$^{13}$C NMR (CDCl$_3$), δ205.5 (C$_{Lev}$), 173.1 (C$_{Lev}$), 162.3 (C$_{NTCA}$), 133.3 (CH=), 117.5 (=CH$_2$), 100.4 (C-1, $^1$J$_{CH}$=162.5 Hz), 99.8 (C$_{iPr}$), 92.7 (CCl$_3$), 72.1 (C-3), 71.7 (C-4), 70.4 (C$_{All}$), 66.9 (C-5), 61.9 (C-6), 56.0 (C-2), 37.9 (CH$_{2Lev}$), 29.6 (CH$_{3Lev}$), 28.7 (C$_{iPr}$), 28.1 (CH$_{2Lev}$), 18.9 (C$_{iPr}$).

HRMS (ESI$^+$): [M+Na]$^+$ C$_{19}$H$_{26}$NO$_8$$^{35}$Cl$_3$Na m/z theoretical:
524.0622 m/z measured:
524.0657

[M+NH$_4$]$^+$ C$_{19}$H$_{26}$NO$_8$Cl$_3$NH$_4$ m/z theoretical:
519.1068
m/z measured:
519.1097

Deoxy-4,6-O-isopropylidene-3-O-levulinoyl-2-trichloroacetamido-β-D-glucopyranose 25

2-Deoxy-4,6-O-isopropylidene-3-O-levulinoyl-2-trichloroacetamido-α-D-glucopyranose trichloroacetimidate 3

2-Trichloromethyl-(1,2-dideoxy-4,6-O-isopropylidene-3-O-levulinoyl-α-D-glucopyrano)-[2,1-d]-2-oxazoline 3'

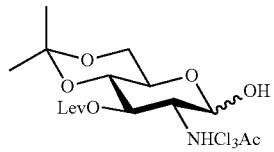

Chemical Formula: C$_{16}$H$_{22}$Cl$_3$NO$_5$
Exact Mass: 461.0411
Molecular Weight: 462.7608

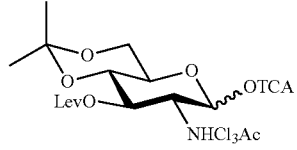

Chemical Formula: C$_{16}$H$_{22}$Cl$_3$N$_2$O$_8$
Exact Mass: 603.9507
Molecular Weight: 607.0939

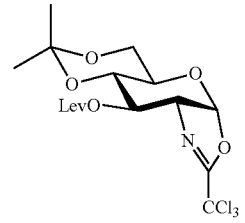

Chemical Formula: C$_{16}$H$_{20}$Cl$_3$NO$_7$
Exact Mass: 443.0305
Molecular Weight: 444.6915

(1,5-Cyclooctadienebis(methyldiphenyl-phosphine)iridium(I)hexafluorophosphate) (360 mg) is dissolved in THF (100 mL) with stirring. The mixture is submitted to 5 cycles of vacuum/argon degassing, 5 cycles of vacuum/hydrogen degassing and is then placed under hydrogen for 15 min. The mixture is then submitted to 5 cycles of vacuum/argon degassing for a second time. The solution of the levulinoyl ester 24 (6.0 g, 11.9 mmol) in THF (15 mL) is transferred to the solution of activated catalyst. Monitoring by TLC (Tol/EtOAc, 6/4) shows the disappearance of 24 (Rf=0.4) and the appearance of a somewhat less polar product (Rf=0.45).

Diiodine (6.0 g, 23.8 mmol, 2 eq.) and NaHCO$_3$ (3.0 g, 35.7 mmol, 3 eq.) in solution in a THF/H$_2$O mixture (8/2, 70 mL) are added to the reaction mixture. Monitoring by TLC (Tol/EtOAc, 6/4) indicates the disappearance of the intermediate (Rf=0.45) and the appearance of a new, much more polar compound (Rf=0.3). To stop the reaction, 10% NaHSO₃ aqueous solution (60 mL) is added in portions to the mixture until the black coloration disappears. The reaction mixture is taken up in DCM and the aqueous phase is extracted with DCM (3×200 mL). The organic phases are combined and washed with a solution of NaCl$_{sat}$ (3×100 mL), with H$_2$O (3×100 mL) and then dried on a phase-separating filter and concentrated in a rotary evaporator. The yellow oil obtained (5.5 g), corresponding to the hemiacetal 25, is used directly in the next stage without any purification.

25: Rf=0.3 (Tol/EtOAc, 6/4).

$^1$H NMR (CDCl$_3$), δ7.16 (m, 1H, NH), 5.33-5.28 (m, 2H, H-3, H-1), 4.44 (bs, 1H, OH), 4.16 (dd, 1H, $J_{1,2}$=3.6 Hz, $J_{2,3}$=10.0 Hz, H-2), 3.99 (ddd, 1H, $J_{4,5}$=10.1 Hz, H-5), 3.88 (dd, 1H, $J_{5,6a}$=5.2 Hz, $J_{6a,6b}$=10.7 Hz, H-6a), 3.82-3.76 (m, 2H, H-4, H-6b), 2.71 (m, 2H, CH$_{2Lev}$), 2.61 (m, 2H, CH$_{2Lev}$), 2.17 (s, 3H, CH$_{3Lev}$), 1.51 (s, 3H, H$_{iPr}$), 1.39 (s, 3H, H$_{iPr}$).

$^{13}$C NMR (CDCl$_3$), δ206.4 (C$_{Lev}$), 173.0 (C$_{Lev}$), 162.2 (C$_{NTCA}$), 100.0 (C$_{iPr}$), 92.1 (CCl$_3$), 91.6 (C-1, $^1J_{CH}$=158.9 Hz), 71.8 (C-4), 70.3 (C-3), 63.7 (C-5), 62.2 (C-6), 54.8 (C-2), 37.9 (CH$_{2Lev}$), 29.8 (CH$_{3Lev}$), 28.9 (C$_{iPr}$), 28.0 (CH$_{2Lev}$), 19.1 (C$_{iPr}$).

HRMS (ESI$^+$): [M+Na]$^+$ C$_{16}$H$_{22}$NO$_8$$^{35}$Cl$_3$Na m/z theoretical:
484.0309
m/z measured:
484.0332
[M+NH$_4$]$^+$ C$_{19}$H$_{26}$NO$_8$$^{35}$Cl$_3$NH$_4$ m/z theoretical:
479.0755
m/z measured:
479.0780

The raw product 25 (5.5 g, 11.9 mmol) is dissolved in DCE (50 mL) and stirred under argon at −5° C. and then DBU (500 μL, 3.3 mmol, 0.28 eq.) and trichloroacetonitrile (5.9 mL, 59.5 mmol, 5 eq.) are added. The reaction mixture is stirred at this temperature for 15 min and then it is loaded, without any treatment, on a silica gel column (flash chromatography, Tol/EtOAc+5% NEt$_3$, 9/1→7/3), obtaining the trichloroacetimidate 3 as a white solid (6.1 g, 84%).

Rf=0.55 (Tol/EtOAc, 6/4).

$^1$H NMR (CDCl$_3$), δ8.76 (s, 1H, NH), 7.09 (d, 1H, $J_{NH,2}$=8.3 Hz, NH), 6.42 (d, 1H, $J_{1,2}$=3.7 Hz, H-1), 5.33 (pt, 1H, $J_{2,3}$=10.4 Hz, $J_{3,4}$=9.2 Hz, H-3), 4.36 (m, 1H, H-2), 3.92 (dd, 1H, $J_{5,6a}$=4.7 Hz, $J_{6a,6b}$=9.2 Hz, H-6a), 3.90-3.84 (m, 2H, H-4, H-5), 3.81 (m, 1H, H-6b), 2.72 (m, 2H, CH$_{2Lev}$), 2.61 (m, 2H, CH$_{2Lev}$), 2.15 (s, 3H, CH$_{3Lev}$), 1.51 (s, 3H, H$_{iPr}$), 1.39 (s, 3H, H$_{iPr}$).

$^{13}$C NMR (CDCl$_3$), δ205.8 (C$_{Lev}$), 173.6 (C$_{Lev}$), 162.1 (C$_{NTCA}$), 160.2 (C=NH), 100.2 (C$_{iPr}$), 94.2 (C-1, $^1J_{CH}$=180.9 Hz), 91.7 (CCl$_3$), 90.5 (CCl$_3$), 71.0 (C-4), 69.7 (C-3), 66.5 (C-5), 61.8 (C-6), 54.6 (C-2), 37.8 (CH$_{2Lev}$), 29.7 (CH$_{3Lev}$), 28.8 (C$_{iPr}$), 27.9 (CH$_{2Lev}$), 19.0 (C$_{iPr}$).

The oxazoline 3', resulting from the degradation of 3 during purification, is isolated as the second product eluted during silica gel chromatography.

Rf=0.45 (Tol/EtOAc, 6/4).

$^1$H NMR (CDCl$_3$), δ 6.26 (d, 1H, $J_{1,2}$=7.5 Hz, H-1), 5.01 (dd 1H, $J_{2,3}$=3.4 Hz, $J_{3,4}$=7.8 Hz, H-3), 4.37 (dd, 1H, H-2), 4.00 (m, 1H, $J_{5,6a}$=5.6 Hz, $J_{6a,6b}$=11.0 Hz, H-6a), 3.90 (pt, 1H, $J_{4,5}$=10.2 Hz, H-4), 3.76 (pt, 1H, H-6b), 3.49 (m, 1H, H-5), 2.81 (m, 2H, CH$_{2Lev}$), 2.64 (m, 2H, CH$_{2Lev}$), 2.19 (s, 3H, CH$_{3Lev}$), 1.50 (s, 3H, H$_{iPr}$), 1.39 (s, 3H, H$_{iPr}$).

$^{13}$C NMR (CDCl$_3$), δ 206.6 (C$_{Lev}$), 171.9 (C$_{Lev}$), 162.7 (N=C), 105.2 (C-1), 100.1 (C$_{iPr}$), 86.2 (CCl$_3$), 74.0 (C-3), 70.5 (C-4), 68.0 (C-2), 64.4 (C-5), 61.7 (C-6), 38.0 (CH$_{2Lev}$), 29.8 (CH$_{3Lev}$), 28.7 (C$_{iPr}$), 28.0 (CH$_{2Lev}$), 18.8 (C$_{iPr}$).

Section II—Synthesis of the Targets I, II, III, IV, V and VI

This second section describes the methods leading to the saccharides I, II, III, IV, V and VI.

This section presents the synthesis of the di-, tri-, tetra- and pentasaccharide target fragments in reducing series A with or without the acetyl in position $2_C$.

|  | Acceptor | Donor | Target |
|---|---|---|---|
| Method 1 | 31 | 33 | I |
| Method 2 | 21 | 1 or 2 | II |
| Method 3 | 38 | 39 | III |
| Method 4 | 38 | 39 | IV |
| Method 5 | 38 | 46 or 47 | V |
| Method 6 | 38 | 46 or 47 | VI |

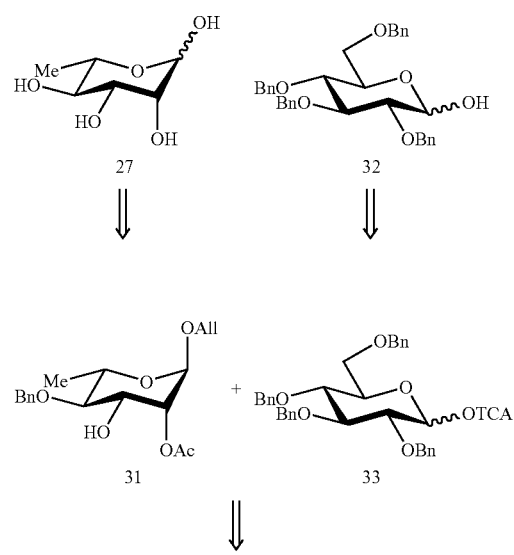

Back synthesis of the oligosaccharides in reducing series A 43     44
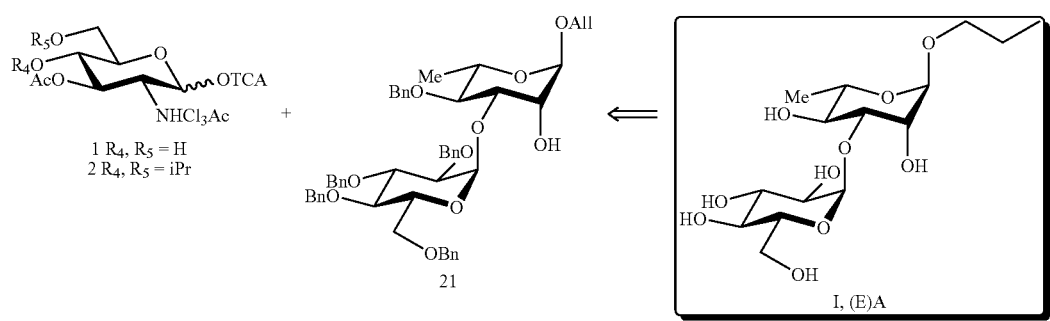
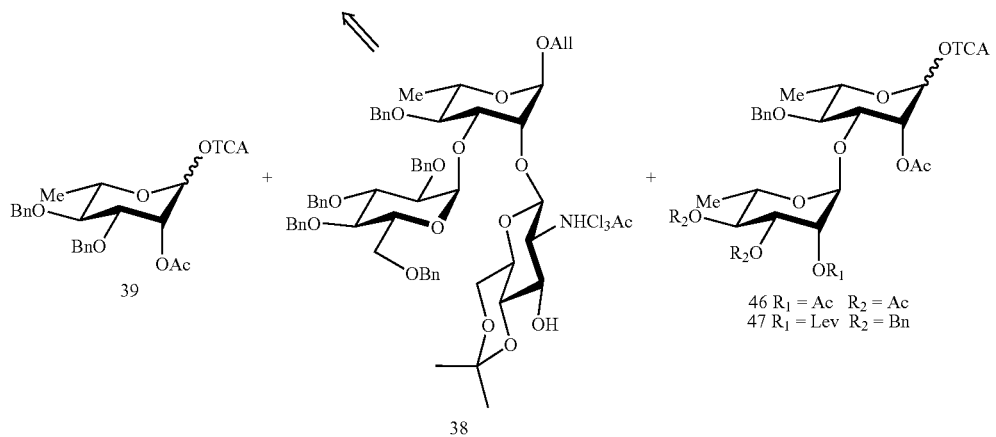
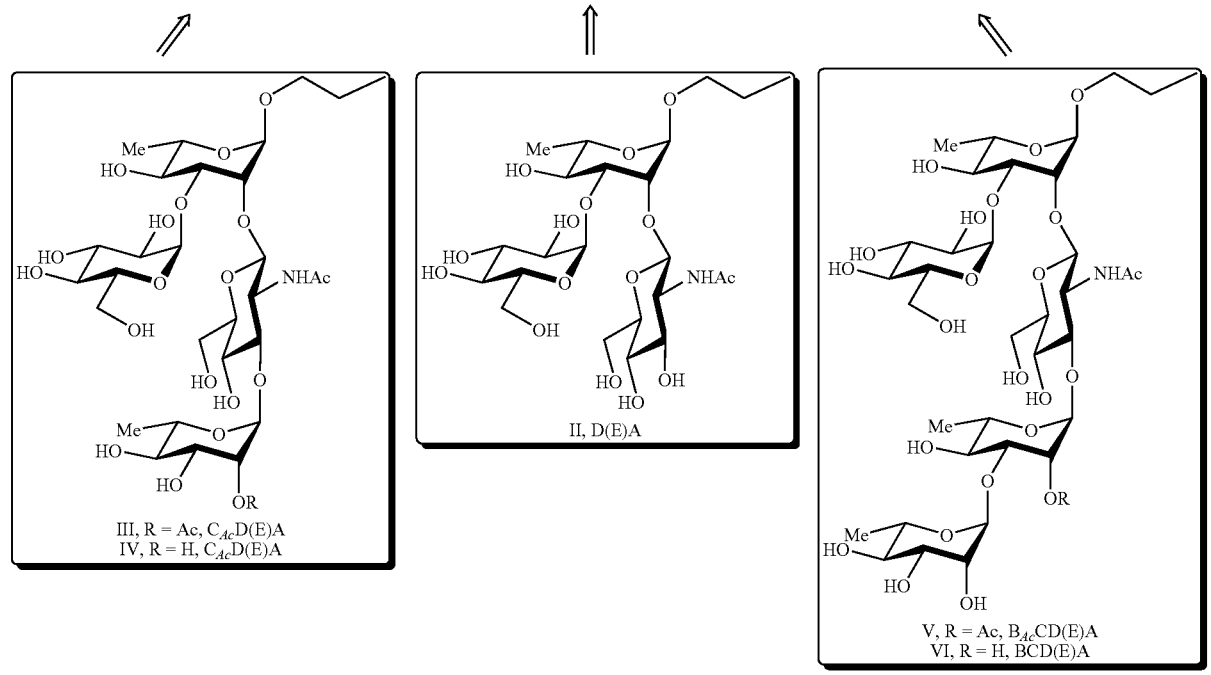

Method 1:

According to another of its objects, the present invention relates to a method of preparation of the disaccharide (E)A (I), an intermediate in the synthesis of a saccharide (oligo- or polysaccharide) as defined in list L1, characterized in that it comprises the following stages:

- condensation of the acceptor monosaccharide 31 with the donor monosaccharide 33 leading to the disaccharide 35, the condensation reaction preferably being carried out in a solvent such as dichloromethane, 1,2-dichloroethane, ether, toluene, acetonitrile or any other equivalent solvent, in the presence of a Lewis acid such as TMSOTf or triflic acid, preferably ether and at a temperature less than or equal to −20° C. (schemes 14 and 15);
- deacetylation of the disaccharide 35 to give the disaccharide 21, preferably in the presence of NaOMe with methanol reflux (schemes 14 and 15);
- deprotection of the disaccharide 21 by hydrogenolysis of the benzyl groups to give the disaccharide (E)A, preferably under hydrogen pressure in an alcohol such as ethanol in the presence of a palladium derivative, for example palladium on charcoal (scheme 16).

1. Synthesis of the Acceptor 31

Figure 8:
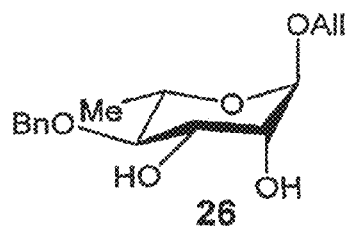
Figure 9:
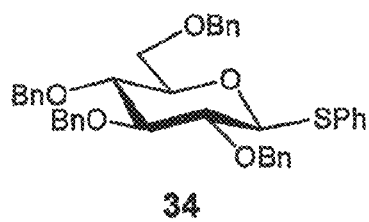

First, a quick and efficient synthesis of large amounts of the diol 26 was elaborated on the basis of the extensive data available in the literature and previous work in the laboratory[42-45] (FIG. 8).

The synthesis is carried out in 4 stages.[42] For the first glycosylation stage, numerous acids have been used, in the literature, for catalyzing this reaction, such as trifluoromethanesulfonic acid[43] (TMSOTf) or hydrochloric acid.[42] Other reagents for generating hydrochloric acid in situ have also been used, for example acetyl chloride.[46] In our case, the glycosylation of L-rhamnose monohydrate 27, in the presence of an excess of allyl alcohol, was tested in the presence of two different promoters: TMSOTf and hydrochloric acid resulting from the action of allyl alcohol on acetyl chloride.

By using TMSOTf, it was possible to isolate the triol 28 at a yield of 64%. Acetyl chloride proved to be more efficient. In fact, in this case, the α anomer is obtained at a yield of 89% in α/β ratio of 90/10, or an overall yield of 98%. The allyl glycoside 28 obtained is then protected regioselectively in position 2 and 3 by an isopropylidene function in the presence of 2,2-dimethoxypropane and of an acid catalyst (PTSA) in acetone. The acetal is introduced at positions 2 and 3 as they are cis-vicinal diols and the latter form rings at 5 that are more stable than the trans-vicinal diols. The acetal 29, obtained at a yield of 84%, is then benzylated on the hydroxyl function in position 4 by the action of the alcoholate resulting from the deprotonation of alcohol 29 by sodium hydride, on benzyl bromide. The fully protected intermediate 30 is isolated at a yield of 82%. Finally, the isopropylidene function of the intermediate 30 is cleaved by acid hydrolysis to regenerate the free hydroxyl functions in position 2 and 3 and lead to the desired diol 26 at a yield of 72% (Scheme 10).

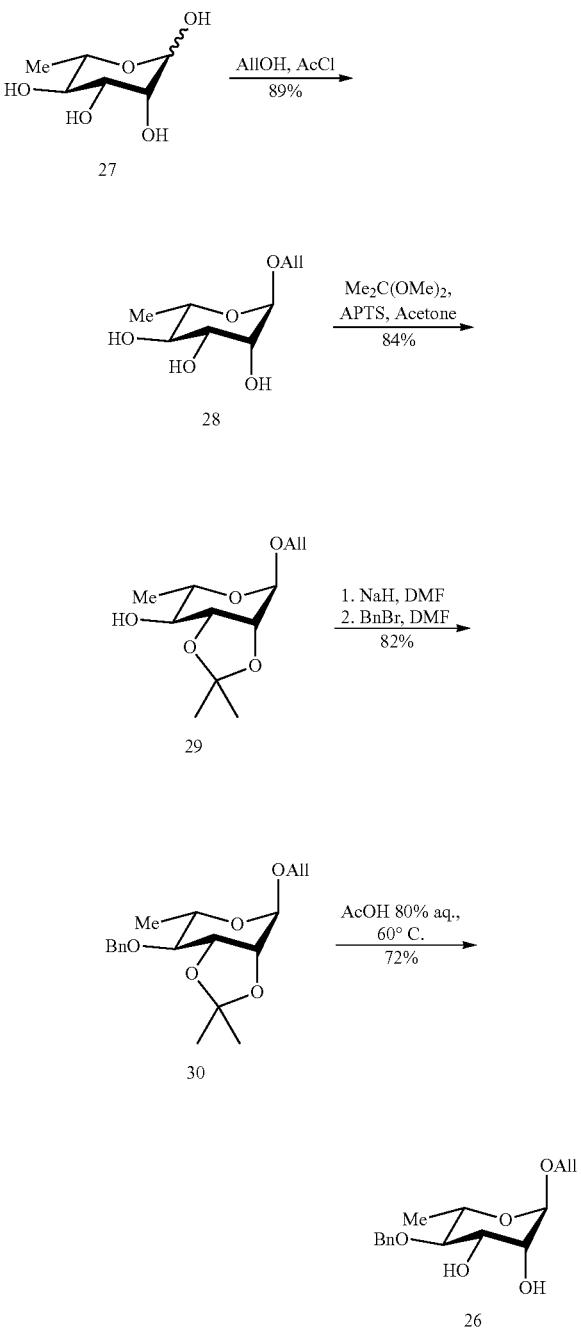

Scheme 10: Synthesis of the monosaccharide 26

After carrying out the synthesis of the diol 26 by purifying and characterizing each of the intermediates 28, 29 and 30, the synthesis was reproduced without intermediate chromatography. The expected diol 26 is simply isolated by recrystallization at an overall yield of 78%—well above that obtained previously (44% over the 4 stages) and that in the literature, which also had the four stages in succession[43] (46%) (Scheme 11). Interestingly, the crystalline nature of the diol 26 makes it possible to carry out the sequence of the 4 stages of protection/deprotection in succession with large amounts (20 g, for example).

Scheme 11: Balance of the synthesis of the monosaccharide 26 and access to the acceptor 31

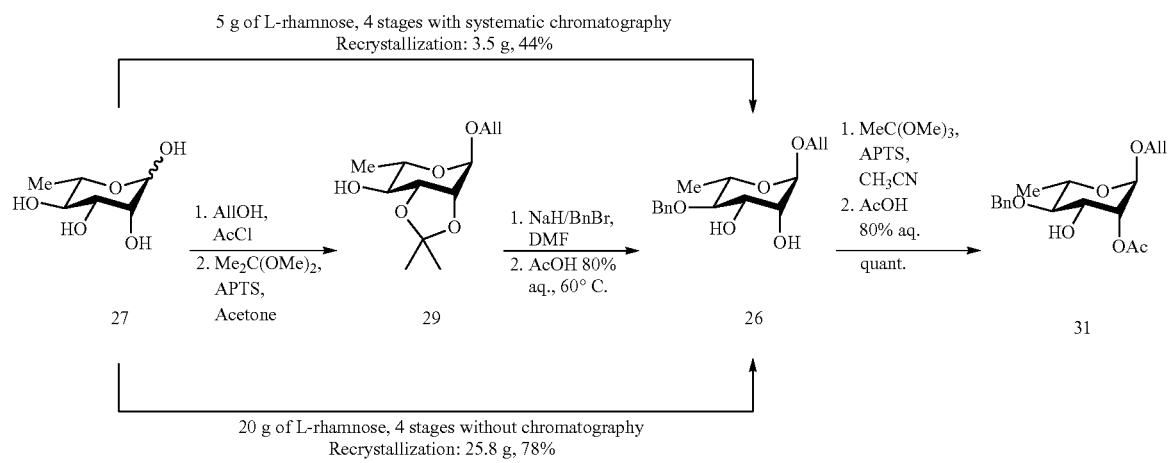

The last stage before glycosidic coupling with a glucose donor consists of regioselective protection of position 2.[47, 48] Owing to the cis-vicinal character of the hydroxyls 2 and 3 and their difference in basicity, position 2 can easily be protected selectively by regioselective opening of an intermediate cyclic orthoester. Thus, the diol 26 reacts with trimethyl orthoacetate in the presence of PTSA, being converted to acceptor 31 via a stage of acid hydrolysis. The acceptor 31 is obtained in the form of a mixture of regioisomers 2-OAc/3-OAc at a ratio of 97/3 (this ratio is determined by $^1$H NMR based on the signal from H-6 of the rhamnose). As this acceptor is not very stable on silica, it is used as it is in the coupling stage (migration of the acetyl function from OH-2 to OH-3 in an acid medium had previously been observed in the laboratory[45, 49]). A $^1$H NMR spectrum recorded before coupling makes it possible to verify that the acetyl has not migrated (Scheme 11).

2. Glucose Donors 33 and 34

Commercial 2,3,4,6-tetra-O-benzyl-3-D-glucopyranose 32 reacts at room temperature with trichloroacetonitrile in the presence of $K_2CO_3$ in dichloromethane to produce donor 33, activated in the anomeric position. The reaction is carried out under kinetic control[50, 34] at RT and in the presence of a weak base in order to promote formation of the β anomer[35] which crystallizes, slightly contaminated with the α anomer (α/β:7/93, ratio determined by $^1$H NMR based on the signal of the anomeric proton). Donor 33 is obtained at a yield of 76% (Scheme 12). The trichloroacetimidate is unstable on silica, making it difficult to monitor the reaction, but once it has crystallized it can be stored in the freezer for long periods.

Scheme 12: Synthesis of donor 33

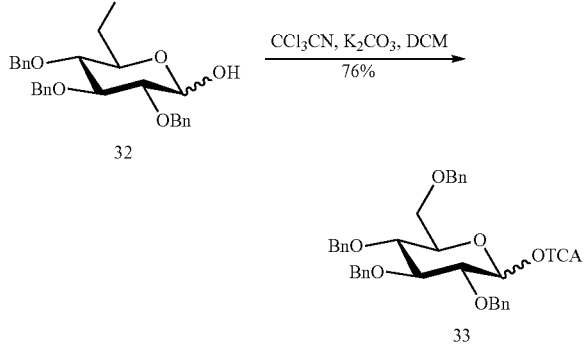

To ascertain the influence of the donor used during the glycosylation reactions, the thiophenyl donor 34 (FIG. 9), available in the laboratory, was also used.

3. Disaccharide (E)A Acceptor 21

Figure 10:
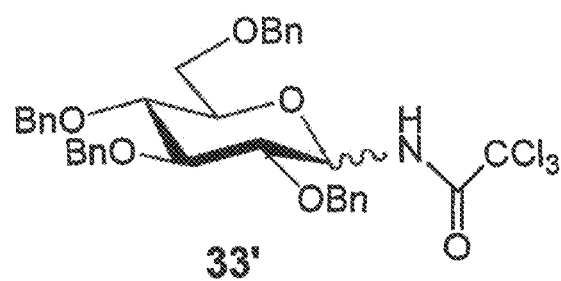

The disaccharide 35[45, 49, 51] is obtained by condensation of acceptor 31 and donor 33. It has been shown in the literature that a bond of the 1,2-cis type is obtained with better stereoselectivity by using Schmidt's inverse procedure[23, 52], i.e. the donor is added dropwise to the reaction mixture comprising acceptor and activator. Thus, rearrangement of donor 33 to 33'[53] according to the so-called Chapman rearrangement[54-56] is limited (FIG. 10).

The simplified mechanism of the reaction involves competition between an $S_N^1$ reaction and an $S_N^2$ reaction as shown in Scheme 13.

Scheme 13: Simplified mechanism of formation of the disaccharide 35

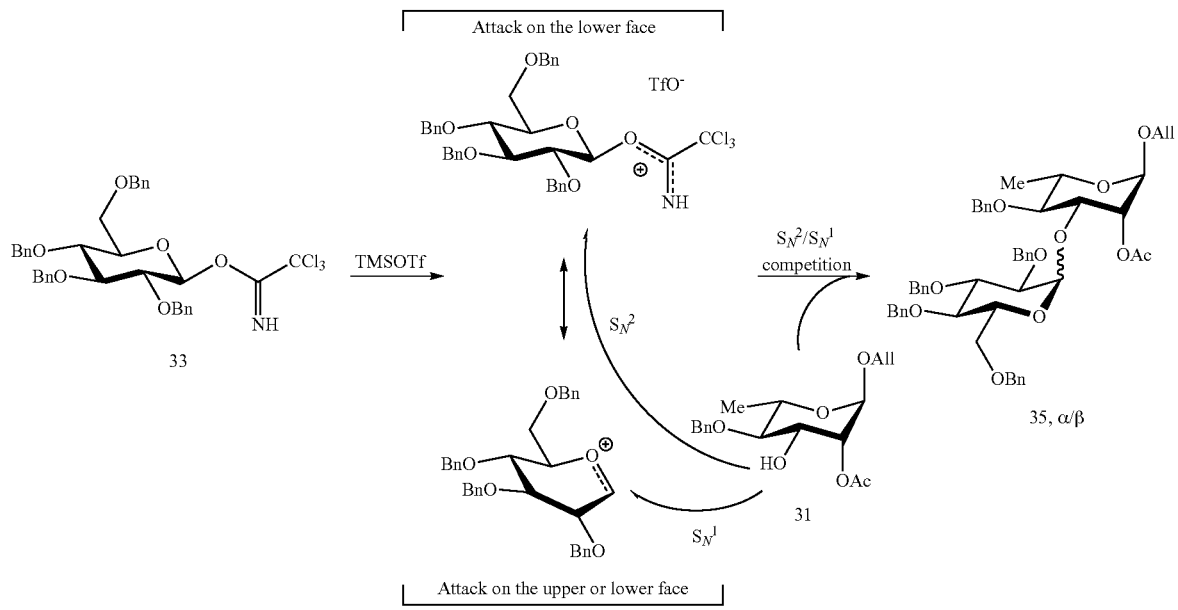

So that a 1,2-cis bond is mainly obtained, the $S_N^2$ mechanism must be favored. Thus, the effects of the solvent (ether or toluene), of the catalyst (TMSOTf or $BF_3.OEt_2$), of the temperature of addition of the donor and of the stereochemistry of the donor were investigated (Table 2).

Examining Table 2, the following conclusions can be drawn:

- Comparing entries 1 to 5 and 6 to 10, the best stereoselectivities are observed when using TMSOTf as catalyst and toluene as glycosylation solvent;
- Entries 4 and 9 show that neither the stereoselectivity nor the yield is increased by increasing the amount of catalyst or by adding molecular sieve;
- Comparison between entries 2 and 7 and, respectively, entries 1 and 6 shows that the stereoselectivity improves as the temperature of addition of the donor is lowered, proving that an $S_N^2$ mechanism is favored at low temperature;
- As expected, if the $S_N^2$ mechanism is favored, then using a donor in the form of α/β mixture does not improve the stereoselectivity (entry 3);
- The thiophenyl donor does not give better stereoselectivity than the trichloroacetimidate donor (entry 5).

TABLE 2

Optimization of the glycosylation of the disaccharide 35

| Entry | Solvent | Catalyst | Donor** | Temperature of addition of the donor*** | Yield and α/β ratio* |
|---|---|---|---|---|---|
| 1 | Et$_2$O | TMSOTf 0.02 eq. | 33$_\beta$ 1.2 eq. | RT | n.d., 60/40 |
| 2 | | | | −20° C. | 80%, 70/30 |
| 3 | | | 33$_{\alpha/\beta}$ (4/6) 1.2 eq. | | 58%, 70/30 |
| 4 | | TMSOTf 0.5 eq. | 33$_\beta$ 1.2 eq. | −78° C. | n.d., 65/35 |

TABLE 2-continued

Optimization of the glycosylation of the disaccharide 35

| Entry | Solvent | Catalyst | Donor** | Temperature of addition of the donor*** | Yield and α/β ratio* |
|---|---|---|---|---|---|
| 5 | | NIS 1.3 eq. TMSOTf 0.3 eq. | 34$_\beta$ 1.2 eq. | 0° C. | 77%, 55/45 |
| 6 | Tol | TMSOTf 0.02 eq. | 33$_\beta$ 1.2 eq. | −40° C. | 70%, 80/20 |
| 7 | | | | −78° C. | 82%, 85/15 |
| 8 | | | 33β 1.5 eq. | | 79%, 85/15 |
| 9 | | TMSOTf 0.1 eq. (Sieve) | 33$_\beta$ 1.2 eq. | −78° C. | 80%, 75/25 |
| 10 | | BF$_3$•OEt$_2$ 1 eq. | 33$_\beta$ 1.2 eq. | −45° C. | 35%, 75/25 |

*n.d.: non determined.
**The donor is dissolved in a minimum of DCM and then dissolved in the coupling solvent (2/1).
***All the reactions were stopped after return to RT.

Based on these results, the optimal conditions adopted are therefore: toluene as solvent, donor in its β anomer form, TMSOTf (0.02 eq.) as catalyst, use of the Schmidt inverse procedure.

After roughly isolating a mixture of α/β anomers (35), which are difficult to separate, said mixture is deacetylated in the presence of NaOMe with methanol reflux, since the acetyl function to be cleaved is isolated and hindered. The diastereoisomers are isolated by silica gel chromatography in this stage (Scheme 14). The disaccharide 21 of configuration α ($^1J_{CH}$=166.3 Hz) is obtained at a yield of 58% and the disaccharide 36 of β configuration ($J_{1,2}$=7.5 Hz, $^1J_{CH}$=159.5 Hz) at a yield of 12%.

51

Scheme 14: Synthesis of the disaccharide 21

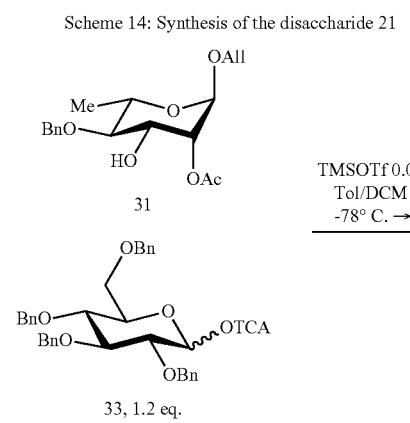

52

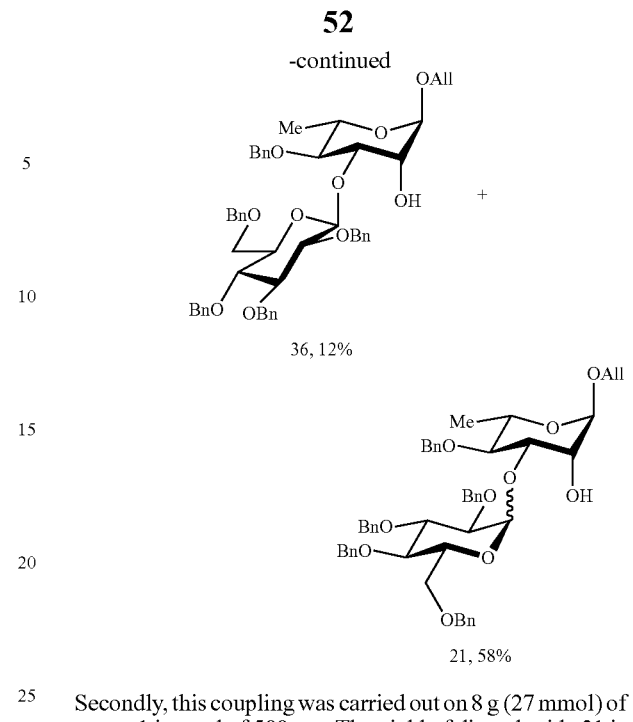

Secondly, this coupling was carried out on 8 g (27 mmol) of acceptor 1 instead of 500 mg. The yield of disaccharide 21 is increased slightly (61%) over the 3 stages, i.e. 48% yield of anomer a from the commercial L-rhamnose. Moreover, during coarse purification in the deacetylation stage, 10% of diol 26, resulting from the transesterification of 31 that has not reacted during the coupling stage, is isolated, leading to a corrected yield of disaccharide 21 of 69% over the 3 stages (Scheme 15).

Scheme 15: Large-scale synthesis of the disaccharide 21

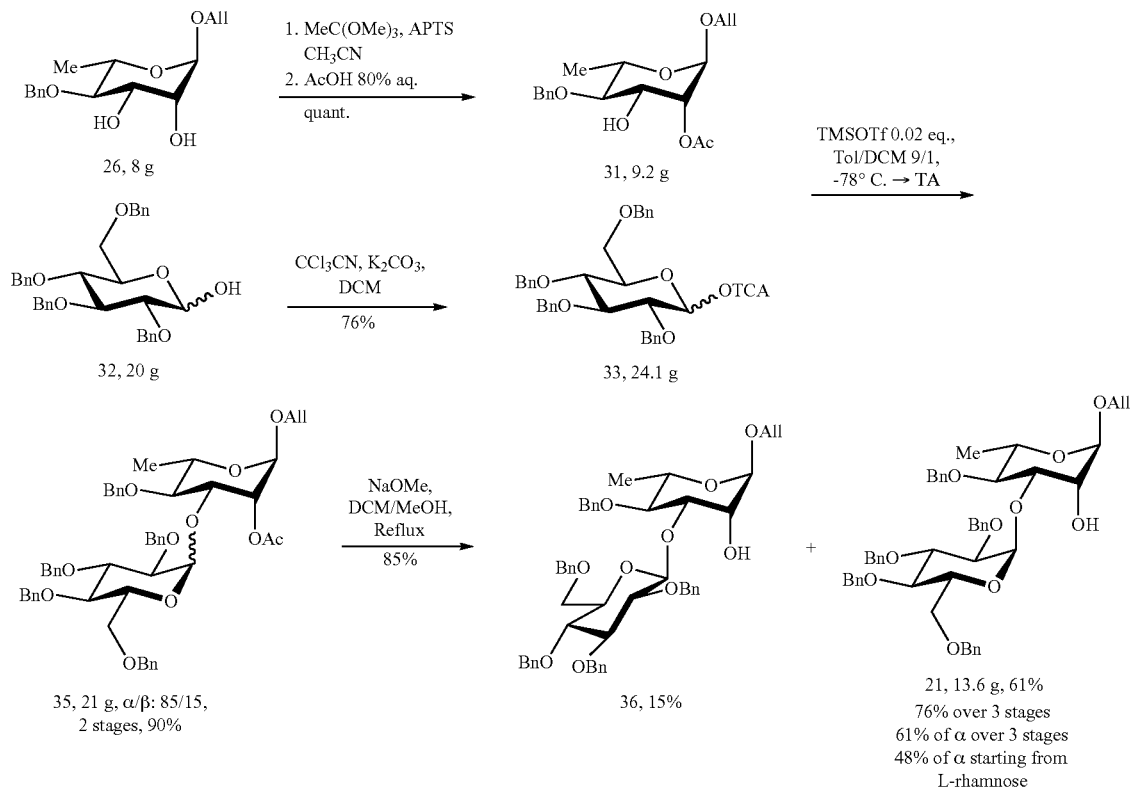

Another possible route to the disaccharide 21 is inspired by the work of Nifantev et al.[57] This showed that couplings in position 3 of the rhamnose could be carried out on the cis diol without prior protection of the axial hydroxyl function. The advantage of this strategy is that it reduces the number of stages of protection/deprotection even if the formation of regioisomers, coupled in position 2 or 3, and of the trisaccharide is observed. The first coupling tests performed in the laboratory between donor 6 and the acceptor diol 1 showed the presence of a complex mixture of products. It is clear that in the absence of a participating group, the formation of the two α regioisomers, coupled in position 2 or 3, as well as that of the two corresponding β stereoisomers, was to be expected. Therefore this strategy was quickly abandoned.

4. Final Deprotection of the Disaccharide (E)A 21

Hydrogenolysis[58, 59] of the benzyl groups of the disaccharide 21 is carried out under hydrogen pressure in ethanol in the presence of palladium on charcoal in a slightly acid medium to give propyl glycoside I at a yield of 83%.

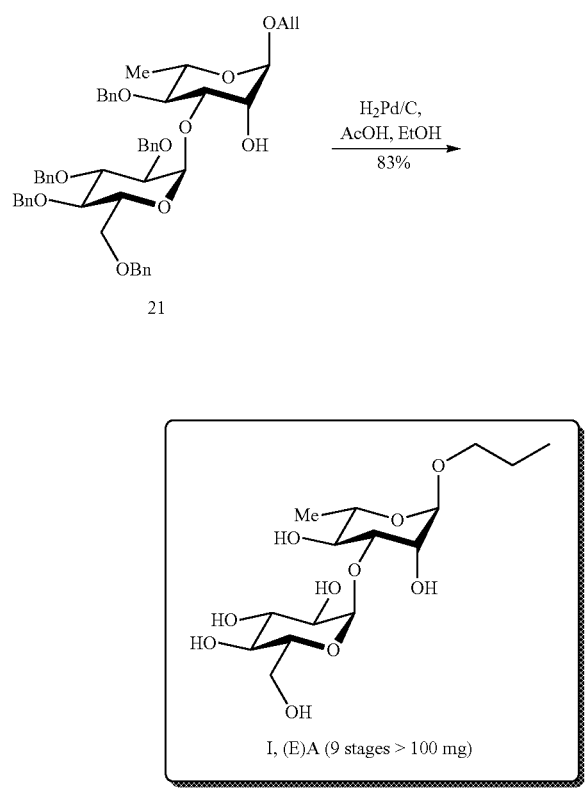

Scheme 16: Hydrogenolysis of the disaccharide 21

I, (E)A (9 stages > 100 mg)

Method 2

The invention also relates to the method of preparation of the trisaccharide D(E)A (II), the oligosaccharide intermediate in the synthesis of an oligo- or polysaccharide as defined in list L1, characterized in that it comprises the following stages:

condensation of the donor monosaccharide 1 with the acceptor disaccharide 21 leading to the trisaccharide 22, the condensation reaction preferably being carried out in a solvent such as dichloromethane, 1,2-dichloroethane, ether, toluene, acetonitrile or any other equivalent solvent, preferably in dichloromethane in the presence of a Lewis acid such as TMSOTf or triflic acid (scheme 17);

deacetylation of the trisaccharide 22 leading to the trisaccharide 37, preferably in the presence of NaOMe (scheme 19);

deprotection of the trisaccharide 37 by acid hydrogenolysis followed by hydrodechlorination to give the trisaccharide D(E)A, preferably under hydrogen pressure in the presence of palladium on charcoal in a basic medium (scheme 20).

The present invention further relates to the method of preparation of the trisaccharide D(E)A (II), the oligosaccharide intermediate in the synthesis of an oligo- or polysaccharide as defined in list L1 comprising the following stages:

condensation of the donor monosaccharide 2 with the acceptor disaccharide 21 leading to the trisaccharide 23, the condensation reaction preferably being carried out in a solvent such as dichloromethane, 1,2-dichloroethane, ether, toluene, acetonitrile or any other equivalent solvent, in the presence of a Lewis acid such as TMSOTf or triflic acid, preferably in dichloromethane, in the presence of TMSOTf at 0.3 eq (scheme 18);

deacetylation of the trisaccharide 23 leading to the acceptor trisaccharide 38, preferably in the presence of NaOMe (scheme 19);

cleavage of the isopropylene group of the trisaccharide 38 by acid hydrolysis leading to the trisaccharide 37;

deprotection of the trisaccharide 37 to give the trisaccharide D(E)A, preferably by acid hydrogenolysis followed by hydrodechlorination under hydrogen pressure in the presence of a palladium derivative such as palladium on charcoal in a basic medium.

5. Trisaccharide Acceptor D(E)A 38 a. Access to the Acceptor Trisaccharide 38 via the Allyl Glycoside 22

In addition to the synthesis of an acceptor trisaccharide that can be extended in position $3_D$ or $1_A$, our objective was to determine whether the introduction of an isopropylidene function in positions $4_D$ and $6_D$ is more effective at the monosaccharide stage or at the trisaccharide stage.

First, the condensation between the donor 1 and the acceptor 21 is carried out in dichloromethane in the presence of TMSOTf (0.2 eq.) and molecular sieve. The trisaccharide 22 is obtained with the expected β configuration ($^1J_{CH}$=161.0 Hz) and a yield of 95%, confirming the role of the trichloroacetamide as a participating group (Scheme 17) as well as the efficacy of 1 as donor, as already observed in the preceding series.

Scheme 17: Coupling between the donor 1 and the acceptor 21

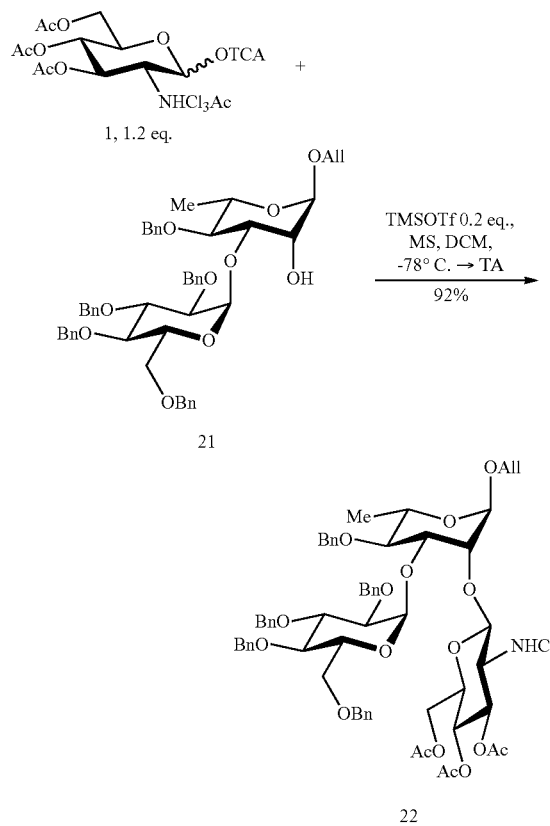

Scheme 18: Coupling between the donor 2 and the acceptor 21

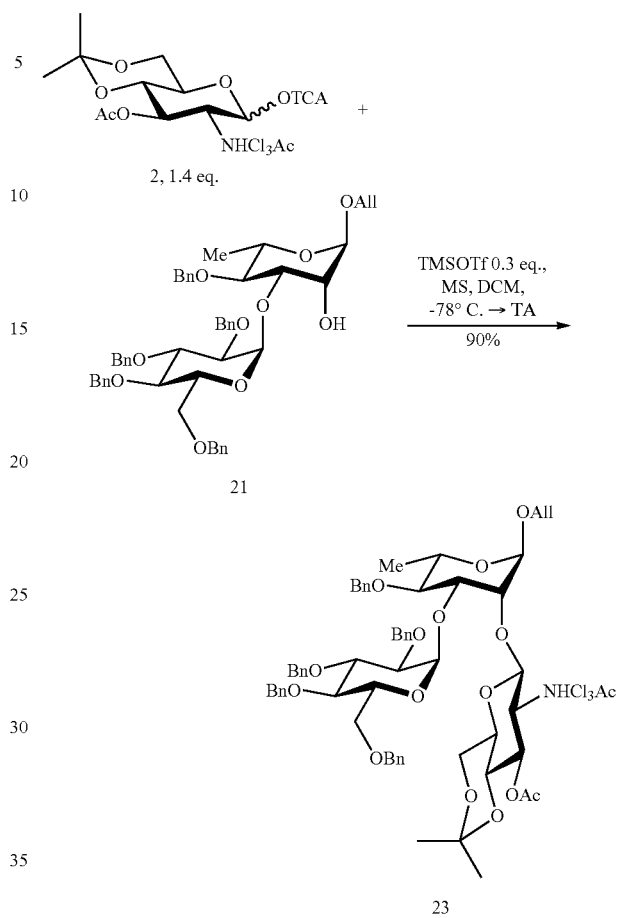

The allyl glycoside 22 is deacetylated in the presence of NaOMe in the Zemplen conditions[60] to obtain the triol 37 at a yield of 94%. The latter is then protected regioselectively in position $4_D$ and $6_D$ by an isopropylidene group in the presence of 2-methoxypropene[30, 31] and CSA to give the acceptor 38 at a yield of 76% (Scheme 19). It should be noted that the isopropylidene of the acceptor 38 proved to be unstable in a slightly acid medium (for example, the $CDCl_3$ used for NMR analysis). Equilibrium between 38 and the triol (ratio 65/35: 38/37), forming more or less quickly depending on the temperature of the sample and its concentration, is observed.

b. Access to the Acceptor Trisaccharide 38 Via the Allyl Glycoside 23

Figure 11:
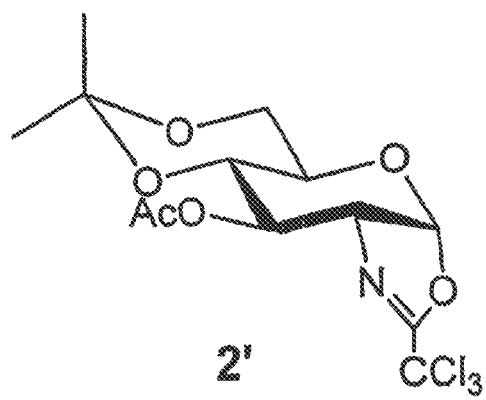
Figure 12:
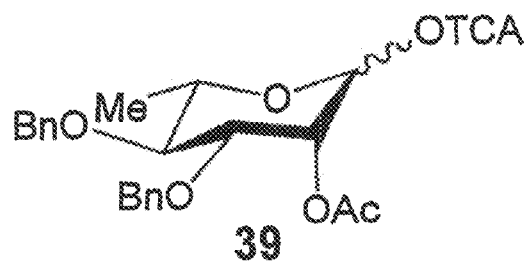

When the coupling conditions used previously (dichloromethane, 0.2 eq. of TMSOTf, molecular sieve) were applied to donor 2, the formation of the oxazoline 2' from donor 2 was observed, as confirmed by the presence of the signal from the anomeric proton at 7.18 ppm in $^1$H NMR characteristic of an oxazoline[33] (FIG. 11).

To compensate for this difference in reactivity, the next couplings were therefore carried out with 0.3 eq. of TMSOTf to permit opening of the oxazoline that formed.[61] In this case, condensation between the donor 11 and the acceptor 9 makes it possible to obtain the trisaccharide 23 with the expected β configuration ($^1J_{CH}$=164.4 Hz) and a yield of 92% (Scheme 18).

In order to introduce a pre-equipped glucosamine residue at sterically hindered positions as here, position $2_A$, it is therefore necessary to increase the amounts of TMSOTf and of donor 2. If we take into account the conditions of glycosylation, the combination of the two examples presented makes it possible to validate the donor potential of the already functionalized compound 2, permitting elongation, after coupling and simple selective deprotection, in position $3_D$ without other additional stages of protection at an advanced stage of the synthesis.

The advantage of this second strategy is that the isopropylidene has already been introduced during synthesis of the donor 2. Thus, the allyl glycoside 23 is deacetylated in the Zemplen conditions[60] to obtain, in one stage, the acceptor 38 at a yield of 84% (Scheme 19).

c. Conclusion Regarding the Synthesis of the Trisaccharide D(E)A

This time only involving two stages of purification by chromatography, the two routes of synthesis of the acceptor trisaccharide 38 were reproduced at the scale of 5 g and compared (Scheme 19). Based on these results, it therefore proves to be more advantageous to introduce the isopropylidene function at the trisaccharide stage rather than at the monosaccharide stage. In fact, the yields of the stages of coupling and of protection/deprotection do not change but the preparation of donor 2 (56% in 5 stages), bearing an isopropylidene function, offers poorer performance than that of the triacetate 1 (72% in 4 stages) (Section 1).

Scheme 19: Balance of the preparation of the acceptor 38

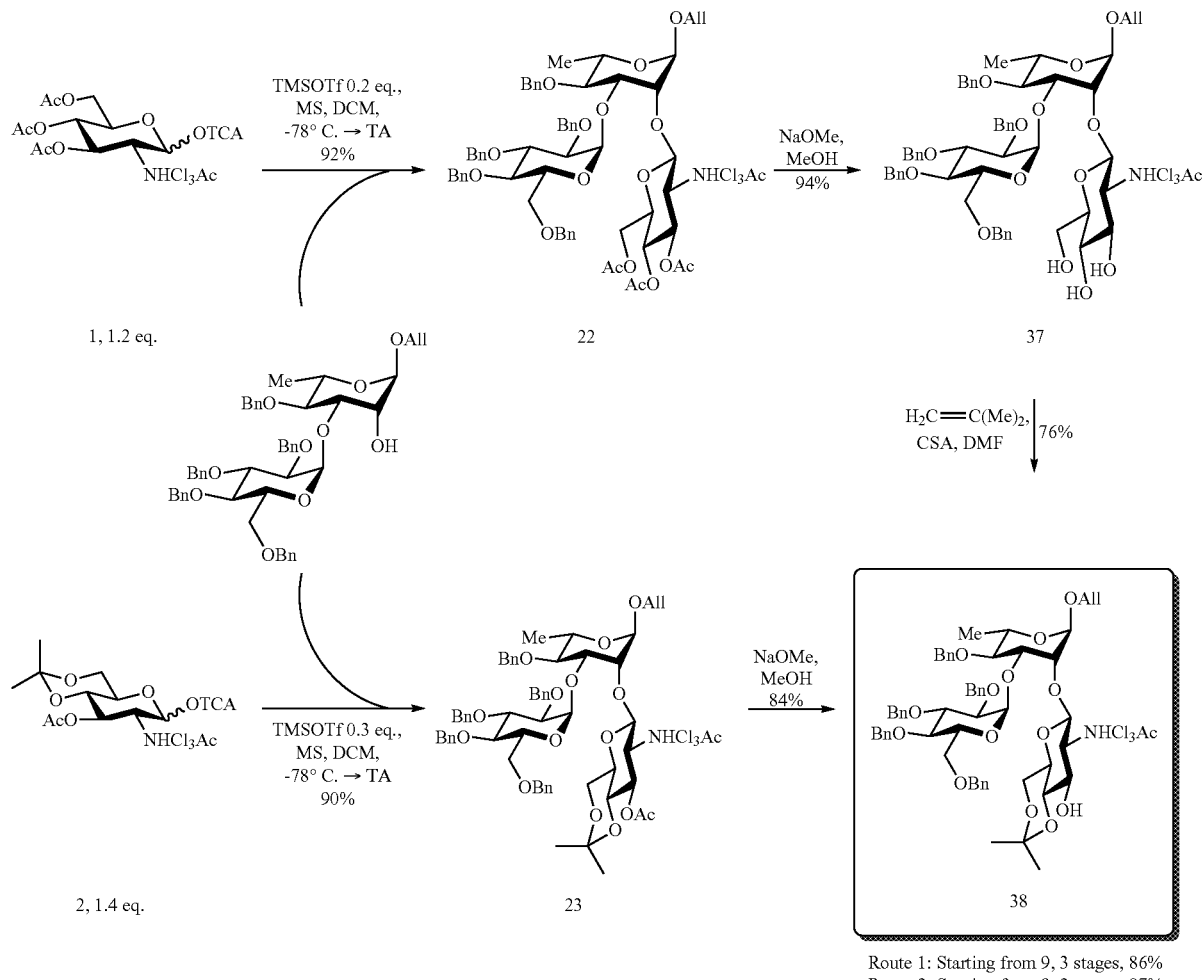

Route 1: Starting from 9, 3 stages, 86%
Route 2: Starting from 9, 2 stages, 87%

6. Final Deprotection of the Trisaccharide D(E)A 37

For the trisaccharide 37, two reactions are required: acid hydrogenolysis followed by hydrodechlorination.[62, 1] Thus, 37 is first treated in conditions identical to 21, then the reduction of the trichloroacetamide function to acetamide is carried out under hydrogen pressure in the presence of palladium on charcoal in a basic medium ($NEt_3$). The expected propyl glycoside II is obtained at a yield of 69% (Scheme 20).

Scheme 20: Hydrogenolysis of the trisaccharide 37

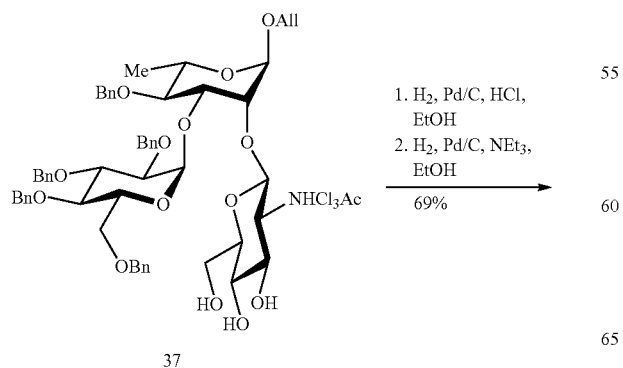

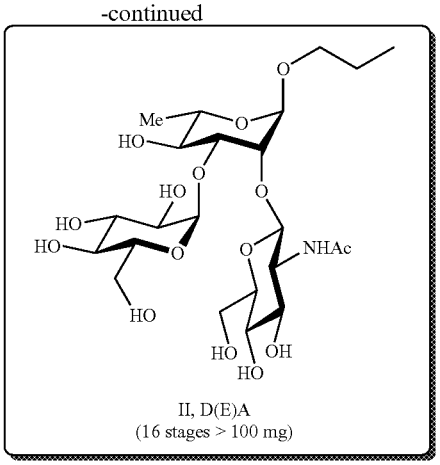

It should be pointed out that a synthesis of the analog of II in the methyl glycoside series had already been published in the 1980s by Kochetkov et al.[63-65] Apart from the choice of carrying out the synthesis of II in propyl glycoside series, which offers the advantage of having synthesis intermediates that are potentially both donor and acceptor, the difference between the two strategies lies in the choice of the protecting groups. In actual fact, Kochetkov et al. worked using the glycosyl bromide chemistry developed by Koenigs-Knorr[66], and the phthalimide as group protecting the amine function. In 8 stages, the trisaccharide is obtained at a yield of 11%, starting from methyl 4-O-benzyl-α-L-rhamnopyranoside (Scheme 21), whereas the synthesis proposed above makes it possible to obtain the trisaccharide D(E)A at a yield of 29% in 6 stages starting from the allyl 4-O-benzyl-α-L-rhamnopyranoside. It will be noted, however, that the main difference in yield occurs in the stage of regioselective acetylation of the acceptor A.

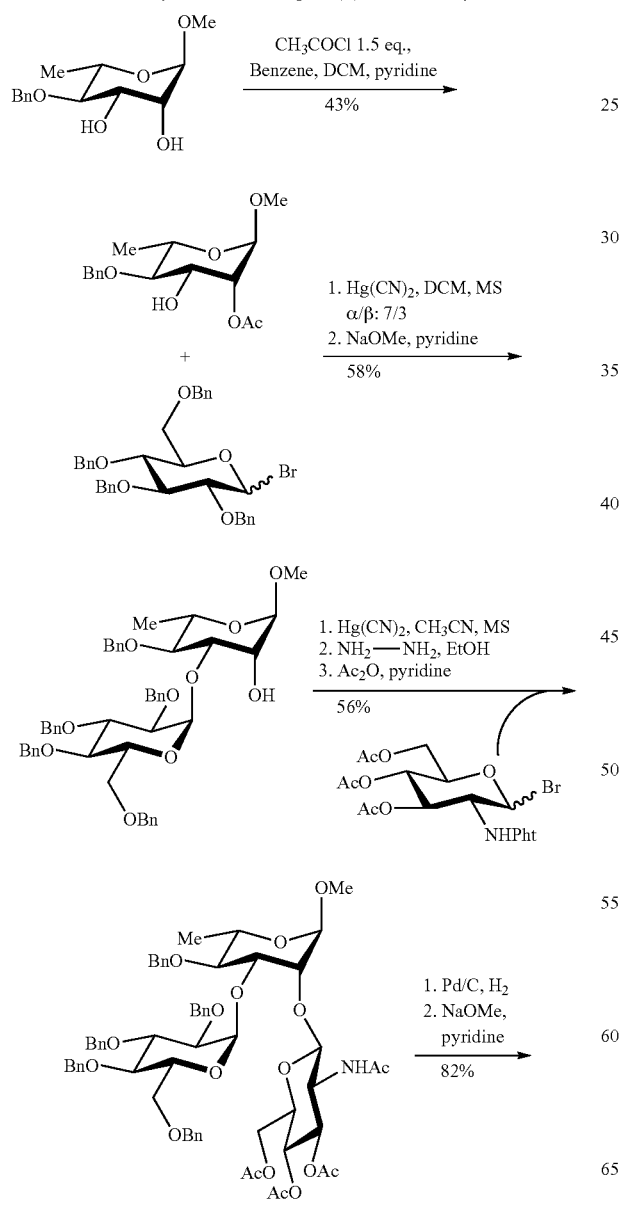

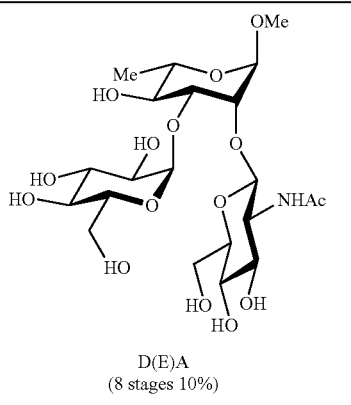

Method 3:

Another object of the invention relates to the method of preparation of the tetrasaccharide $_{Ac}$CD(E)A (III), as defined in list L1, comprising the following stages:

condensation of the donor monosaccharide 39 with the acceptor trisaccharide 38 leading to the tetrasaccharides 40 and 41, the condensation reaction preferably being carried out in a solvent such as dichloromethane, 1,2-dichloroethane, ether, toluene, acetonitrile or any other equivalent solvent, in the presence of a Lewis acid such as TMSOTf or triflic acid, preferably in toluene, in the presence of TMSOTf and at −78° C. (scheme 22);

cleavage of the isopropylidene group of the tetrasaccharide 40 by acid hydrolysis leading to the tetrasaccharide 41;

deprotection of the benzyl group and concomitant reduction of the trichloroacetamide of the tetrasaccharide 41 to give the tetrasaccharide $_{Ac}$CD(E)A, preferably under hydrogen pressure in an alcohol, for example ethanol in the presence of a palladium derivative such as palladium on charcoal.

7. Tetrasaccharide CD(E)A

The target tetrasaccharides III and IV result from the condensation of the donor 39[67] (FIG. 12), available in the laboratory, and of the acceptor trisaccharide 38.

In the first glycosylation test, in the conditions used for coupling donor 2 with acceptor 21 (dichloromethane, TMSOTf 0.3 eq., molecular sieve), three products could be isolated (entry 1 in Table 3 and Scheme 22), including the desired coupling product 40 with the α configuration ($^1J_{CH}$=169.1 Hz).

Scheme 22: Coupling between acceptor 35 and donor 39

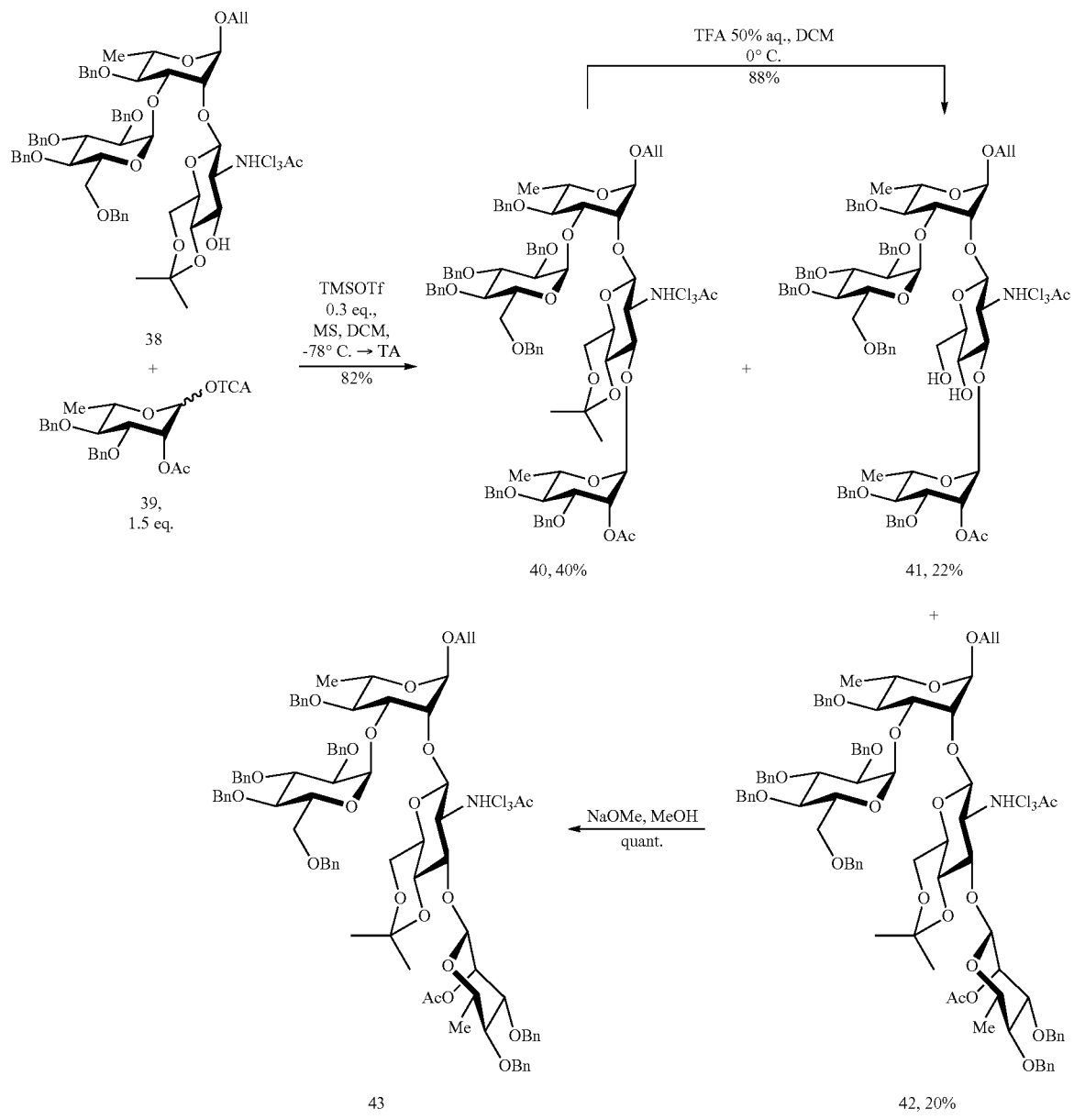

Figure 13:
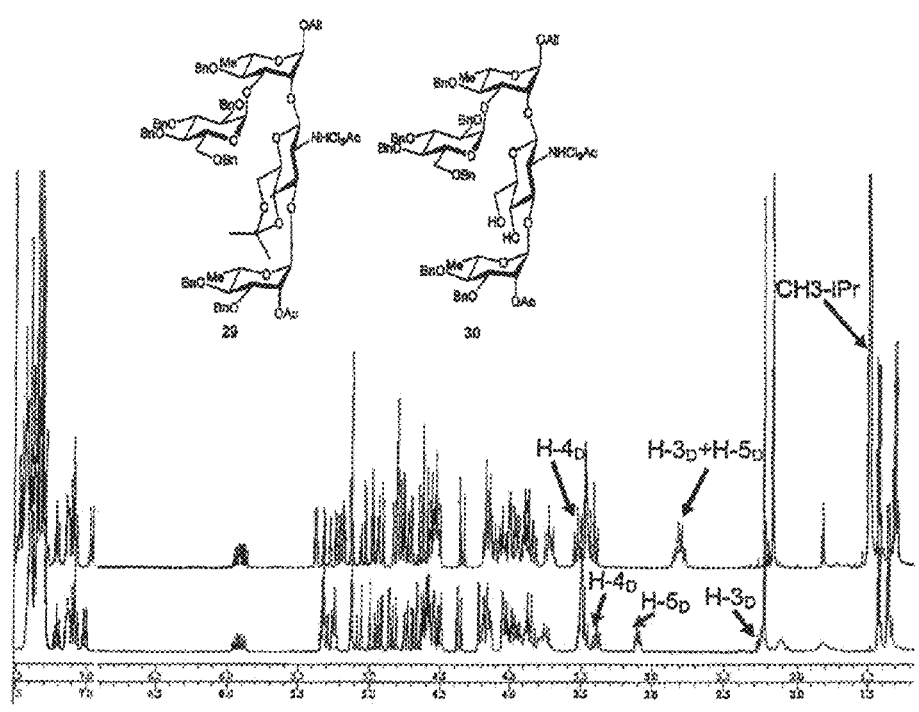

The allyl glycoside 41 also possesses the α configuration ($^1J_{CH}$=169.8 Hz) but, in the acid coupling conditions, has lost the isopropylidene function, as indicated by the absence of the peaks characteristic of isopropylidene in the proton spectrum and the carbon spectrum (41, FIG. 13). An HMBC NMR spectrum also showed that coupling had indeed taken place in position $3_D$ (FIG. 14) prior to deacetalation. To confirm this secondary reaction and therefore the loss of the isopropylidene of tetrasaccharide 41 in the acid coupling conditions, the coupling product 40 is treated with a 50% aqueous solution of TFA in dichloromethane at 0° C. After 4 h, the product isolated is equivalent, according to TLC and NMR analyses, to the allyl glycoside 41. This result shows that the glycosylation between 38 and 39 precedes the loss of the isopropylidene.

In contrast, the hypothesis made regarding the product 42 isolated is the formation of a tetrasaccharide whose unit C is joined in position $3_D$ by a β bond. To verify this hypothesis, and notably the presence of an acetyl in position $2_C$, the product 42 is deacetylated in the presence of NaOMe to give, after purification, the expected alcohol 43 confirmed by a full NMR analysis (absence of acetyl and presence of isopropylidene with a characteristic peak at 99.8 ppm in carbon NMR). By superimposing the three $C^{13}$GD spectra of 40, 41 and 42 it is possible to visualize the α bonds of 40 and 41 and the β bond of 42 (FIG. 15).

The presence of 42 and therefore the formation of this β bond ($^1J_{CH}$=156.6 Hz) proves that the acetyl in position $2_C$ has not fully performed its role of participating group, as already shown by examples in the literature.[68-75] Coupling conditions were investigated in order to increase the stereoselectivity but also to limit the degradation of the desired coupling product 40. In some works in the literature, the use of toluene can give better coupling results than the use of dichloromethane.[69, 76-79] Thus, toluene and diethyl ether were tested (Table 3).

TABLE 3

Influence of the solvent on the coupling between acceptor 38 and donor 39

| Entry | Solvents | Temperature | 40 | 41 | 42 |
|---|---|---|---|---|---|
| 1 | DCM | −78° C.→RT | 40% | 22% | 20% |
| 2 | Et$_2$O |  | 58% | 21% | n.o. |
| 3 | Toluene |  | n.o. | n.o. | n.o. |
| 4 | Toluene | −78° C. | 72% | 5% | n.o. |

* n.o.: not observed.

Formation of the expected tetrasaccharide was not observed in diethyl ether (entry 2 in Table 3). However, by carrying out the coupling in toluene it is possible to isolate compounds 40 and 41 in 75/25 ratio at an overall yield of 79% (entry 3). This time the coupling reaction is stereoselective, no trace of βC anomer being observed (Scheme 23). To limit the degradation of the isopropylidene function, the reaction is conducted at −78° C. for 15 minutes and the reaction mixture is neutralized by adding triethylamine at this temperature. In this case, a mixture of products 40 and 41 is then obtained at a ratio of 95/5 at a yield of 77% (entry 4).

The isopropylidene carried by 40 is cleaved by acid hydrolysis[80, 81] to give the diol 41 (88%), or a yield of 66% over the 2 stages (Scheme 23).

Scheme 23: Optimization of coupling between acceptor 38 and donor 39

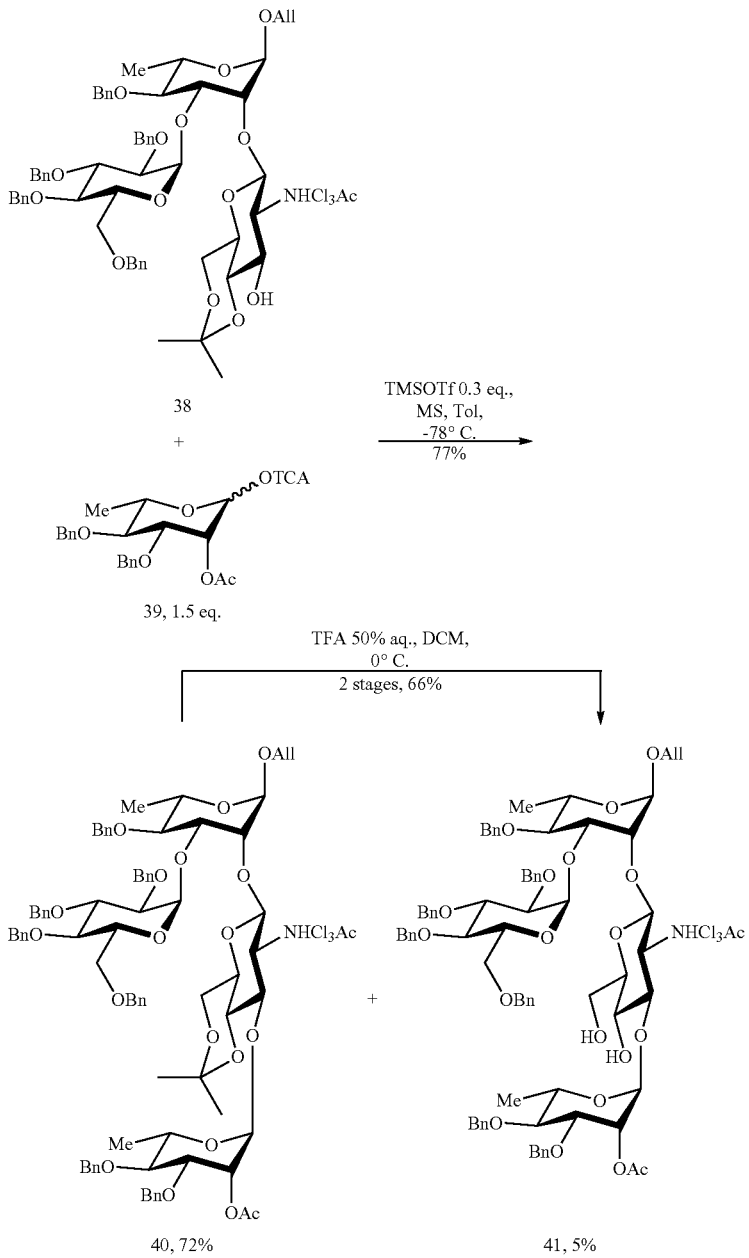

8. Final Deprotection of the Tetrasaccharides in Reducing Series A

In the case of the oligosaccharide 41, the possibility of cleavage of the acetyl function in acid or basic conditions excludes acid hydrogenolysis and basic hydrodechlorination. Moreover, as the target III possesses a free hydroxyl function in a position vicinal to position $2_C$, there is a risk of migration. Therefore suitable hydrogenation conditions were elaborated for the pentasaccharide 56 before hydrogenating the tetrasaccharide 41.

The various tests performed, in these conditions elaborated for the pentasaccharide 56, did not allow the target III to be isolated in a single form but, as we might have expected, in the form of a mixture of two regioisomers, acetylated in position $2_C$ or $3_C$ at a yield of 76% (Scheme 24).

Method 4:

The invention also relates to the method of preparation of the tetrasaccharide compound CD(E)A (IV), as defined in list L1, comprising the following stages:

condensation of the donor monosaccharide 39 with the acceptor trisaccharide 38 leading to the tetrasaccharides 40 and 41, the condensation reaction preferably being carried out in a solvent such as dichloromethane, 1,2-dichloroethane, ether, toluene, acetonitrile or any other equivalent solvent, in the presence of a Lewis acid such as TMSOTf or triflic acid, preferably in dichloromethane, in the presence of TMSOTf at 0.2 eq. as catalyst and at −78° C. (scheme 22);

cleavage of the isopropylidene group of the tetrasaccharide 40 by acid hydrolysis leading to the tetrasaccharide 41;

Scheme 24: Hydrogenolysis of the tetrasaccharides 41 and 69

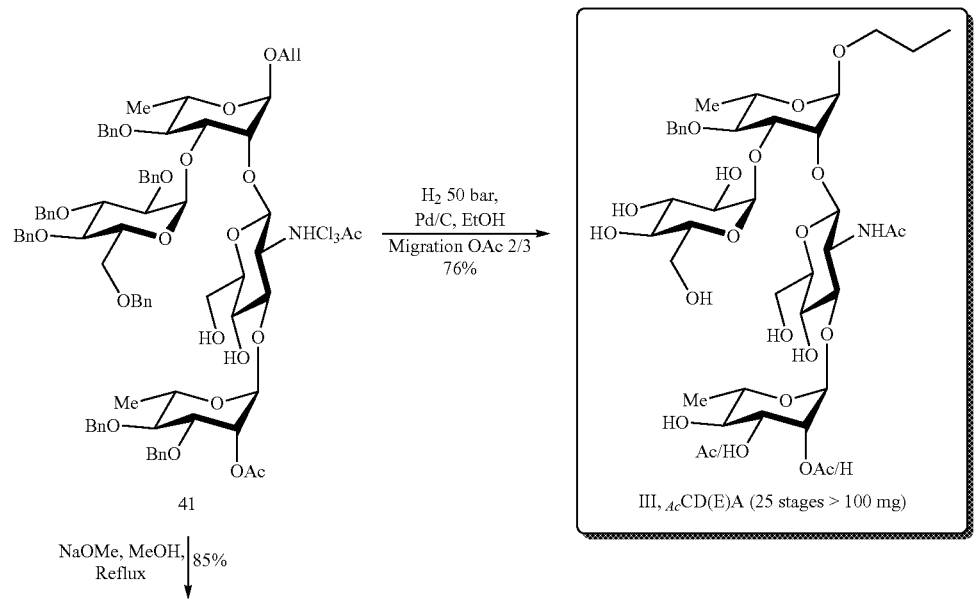

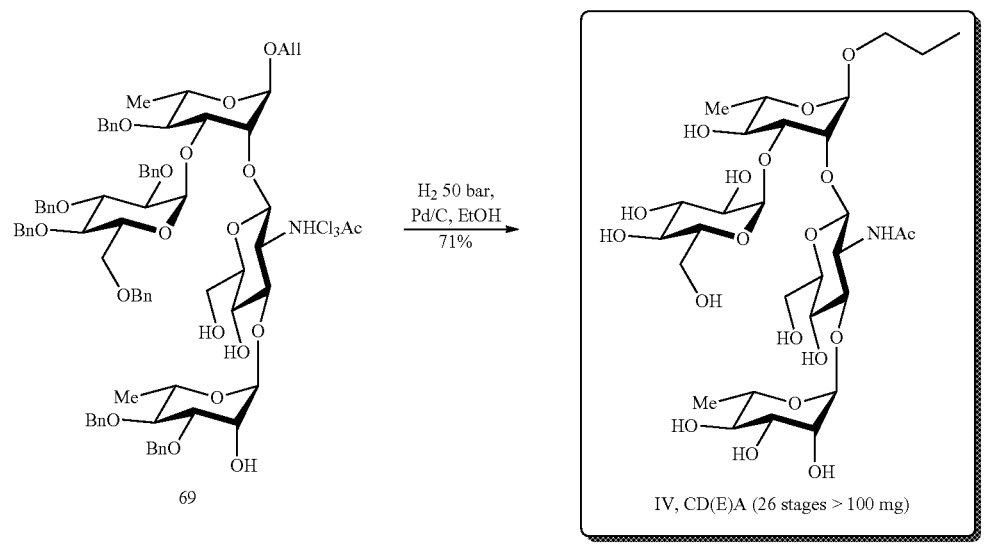

deacetylation of the tetrasaccharide 41 leading to the tetrasaccharide 69, preferably in the presence of NaOMe with methanol reflux (85%) (scheme 24);

deprotection by hydrogenolysis of the tetrasaccharide 69, preferably under hydrogen pressure in alcohol, for example ethanol, in the presence of a palladium derivative such as palladium on charcoal to give the tetrasaccharide CD(E)A.

The non-acetylated analog is obtained after deacetylation of the diol 41 in the presence of NaOMe with methanol reflux (85%). Finally, hydrogenation of 69 is carried out under 50 bar hydrogen pressure. The propyl glycoside IV is isolated at a yield of 71% (Scheme 24).

Method 5:

The invention relates to the method of preparation of the pentasaccharide $B_{Ac}CD(E)A$ (V) as defined in list L1 comprising the following stages:

condensation of the donor disaccharide 46 with the acceptor trisaccharide 38 leading to the pentasaccharide 52, the condensation reaction preferably being carried out in a solvent such as dichloromethane, 1,2-dichloroethane, ether, toluene, acetonitrile or any other equivalent solvent, in the presence of a Lewis acid such as TMSOTf or triflic acid, more preferably in toluene, in the presence of TMSOTf at 0.3 eq. and at −78° C. (scheme 27);

deacetylation of the pentasaccharide 52 leading to the pentasaccharide 54, preferably in basic conditions with $K_2CO_3$ (scheme 28);

cleavage of the isopropylidene group of the pentasaccharide 54 leading to the pentasaccharide 56, preferably in 50% aqueous TFA solution in dichloromethane at 0° C. (scheme 29);

deprotection of the pentasaccharide 56 to give the pentasaccharide $B_{Ac}CD(E)A$ preferably under hydrogen pressure in alcohol, for example ethanol, in the presence of a palladium derivative such as palladium on charcoal (scheme 35).

The present invention also relates to the method of preparation of the pentasaccharide $B_{Ac}CD(E)A$ (V) as defined in list L1, comprising the following stages:

condensation of the donor disaccharide 47 with the acceptor trisaccharide 38 leading to the pentasaccharide 64, the condensation reaction preferably being carried out in a solvent such as dichloromethane, 1,2-dichloroethane, ether, toluene, acetonitrile or any other equivalent solvent, in the presence of a Lewis acid such as TMSOTf or triflic acid, more preferably in toluene, in the presence of TMSOTf at 0.3 eq. and at −40° C. (scheme 33);

deprotection of the levulinoyl group of the pentasaccharide 64 leading to the pentasaccharide 66 preferably in a buffered medium (pyridine/AcOH) in the presence of hydrazine monohydrate (scheme 33);

cleavage of the isopropylidene group of the pentasaccharide 66 leading to the pentasaccharide 67 preferably in 50% aqueous TFA solution in dichloromethane at 0° C. (scheme 34);

deprotection of the pentasaccharide 67 to give the pentasaccharide $B_{Ac}CD(E)A$ preferably under hydrogen pressure in ethanol in the presence of palladium on charcoal (scheme 36).

9. Pentasaccharide $B_{Ac}CD(E)A$ V

As our analysis by back synthesis took into account access to oligosaccharides of higher order, the synthesis proposed for the target V involves the donor synthon 47. In the absence of elongation in position $2_B$, donor 46, which is more easily obtained than 47, can also be used successfully (Scheme 25). Both routes were investigated.

Scheme 25: Synthesis strategy for obtaining the target V

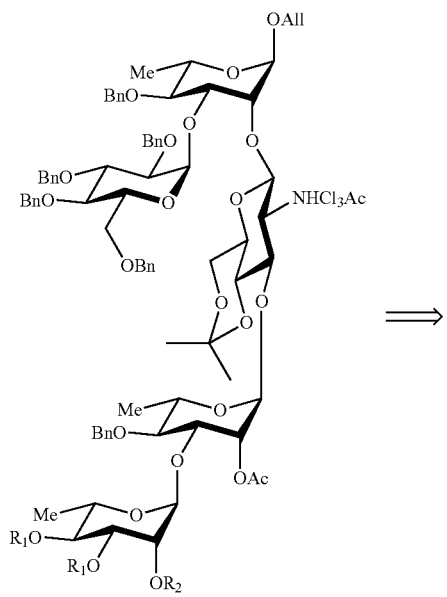

44 $R_1$ = Ac $R_2$ = Ac
45 $R_1$ = Bn $R_2$ = Lev

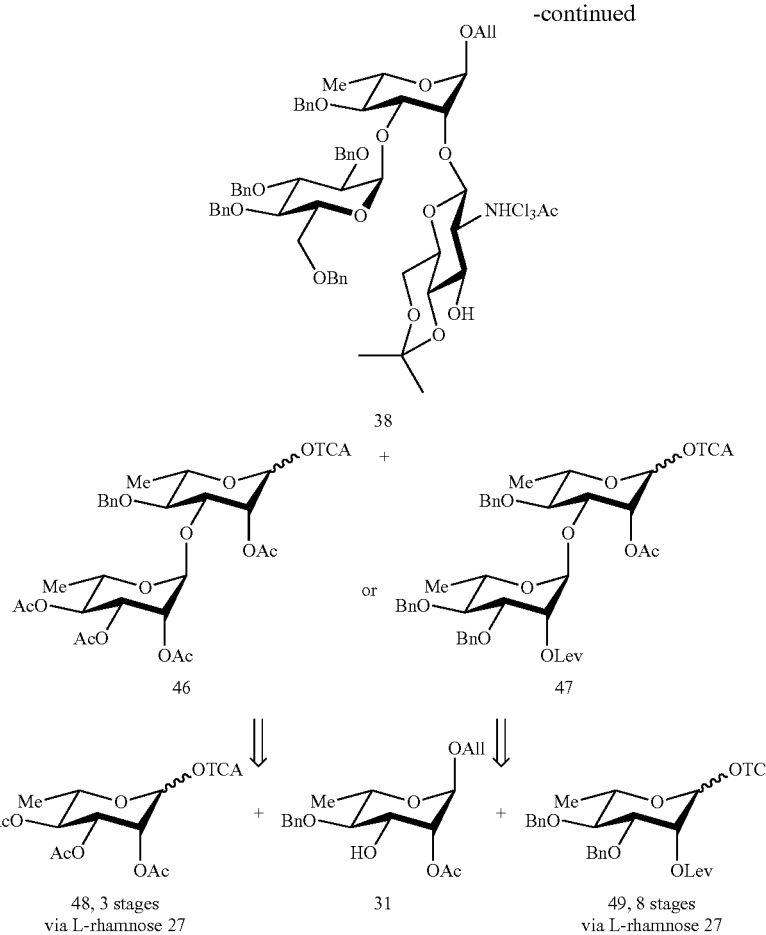

a. Route B Tritri-O-Acetyl

By analogy with the synthesis of the disaccharide 35, the acceptor 31 is condensed on the donor 48, available in the laboratory (3 stages, 76%[82, 49]). The glycosylation reaction is carried out in dichloromethane in the presence of TMSOTf (0.3 eq.) and molecular sieve. The allyl glycoside 50 is obtained with the expected α configuration ($J_{1,2}$=1.5 Hz, $^1J_{CH}$=173.0 Hz) and a yield of 95% (Scheme 26). The disaccharide 50 is deallylated[39, 40] in hemiacetal 51 (91%) and then converted by the action of trichloroacetonitrile and DBU[22, 23] to donor 46 at a yield of 89%.

Scheme 26: Synthesis of donor 46

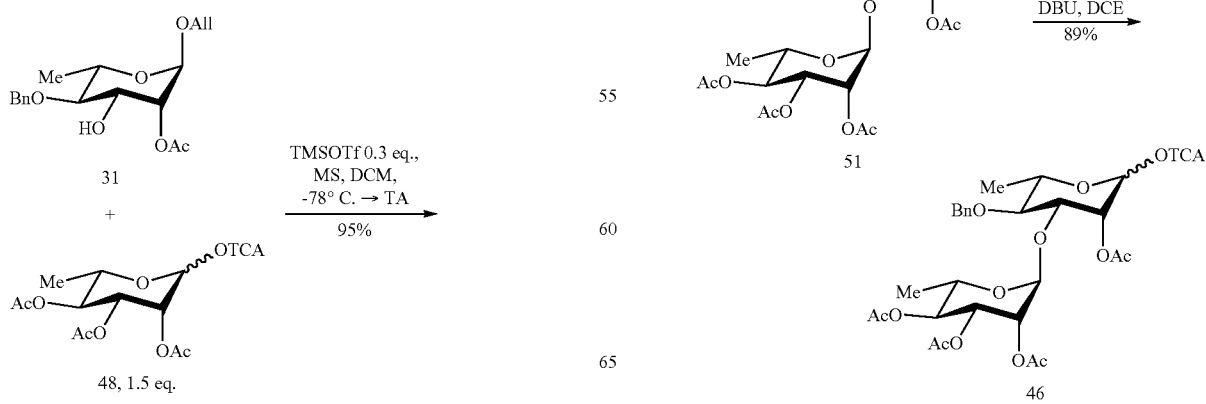

The initial strategic choice requires that it should be possible to carry out selective deacetylation with respect to an isolated acetyl. Disaccharide 50, the key synthon in the preparation of the donor 46, served as a model for confirming that all the acetyls of rhamnose B can be cleaved selectively when this is present in position $2_C$. Selective cleavage was therefore tested in various basic or acid conditions (Table 4). The best result was observed in basic conditions using $K_2CO_3$. The triol 50' and the tetraol 50" are obtained at a ratio of 70/30

TABLE 4

Investigation of the selective deacetylation of the disaccharide 50

| Conditions | Temperature | Reaction Time | Ratio 50'/50" |
|---|---|---|---|
| NaOMe/MeOH 0.2 eq.[60] | RT | 2.5 h | 60/40 |
| NaOMe/MeOH 0.2 eq.[60] | 0° C. | >2 days | n.d. |
| NEt$_3$/MeOH/H$_2$O[83, 84] | 0° C. | 2 days | 55/45 |
| K$_2$CO$_3$/MeOH 1 eq.[85] | RT | 15 min | 70/30 |
| K$_2$CO$_3$/MeOH 1 eq.[85] | 0° C. | 1.5 h | 65/35 |
| HBF$_4$ in Et$_2$O/MeOH[86, 87] | RT | >7 days | n.d. |

* n.d.: not determined.

As donor 46 is now available and the selective deacetylation of the disaccharide 50 to acetate 50' can be carried out, coupling with the acceptor 38 was considered for obtaining the target pentasaccharide.

The conditions elaborated during synthesis of the tetrasaccharide 40 (toluene, TMSOTf 0.3 eq., molecular sieve) were applied to this condensation reaction (Scheme 27). Two compounds could be isolated after chromatography, at a ratio of 78/22 and a yield of 90%, the coupling product 52, which does indeed have the desired α configuration ($^1J_{CH}$=170.5 Hz), and the diol 53. As in the case of 41, the latter, whose structure was confirmed by a full NMR analysis, results from the loss of the isopropylidene "post-condensation" in the acid coupling conditions. In the same a way as for the tetrasaccharide 40, to limit the loss of the isopropylidene, the temperature is maintained at −78° C. for 15 minutes and then the reaction is stopped by adding triethylamine. A mixture of pentasaccharides 52 and 53 is obtained, this time at a ratio of 92/8 and a yield of 87%.

Scheme 27: Coupling between the acceptor 38 and the donor 46

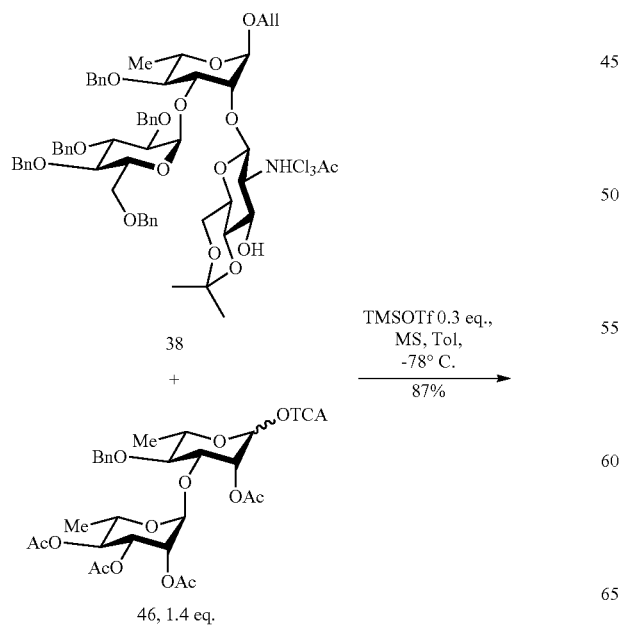

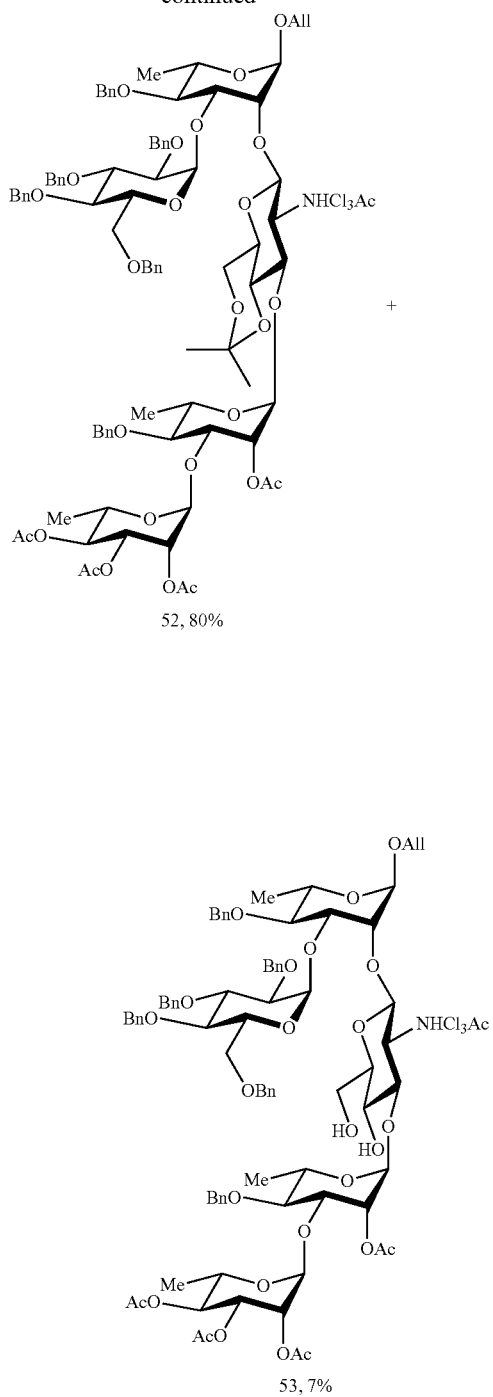

52, 80%

53, 7%

The pentasaccharide 52 is then deacetylated, in the conditions elaborated for the disaccharide 50 ($K_2CO_3$, MeOH) to obtain the triol 54 and the tetraol 55 at a ratio of 92/8 and a yield of 92% (Scheme 28). This selective deacetylation is more effective on the pentasaccharide 52 than on the disaccharide 50, undoubtedly, as was to be expected, because of the greater steric hindrance at the level of the acetyl function in position $2_C$.

Scheme 28: Selective deacetylation of the pentasaccharide 52
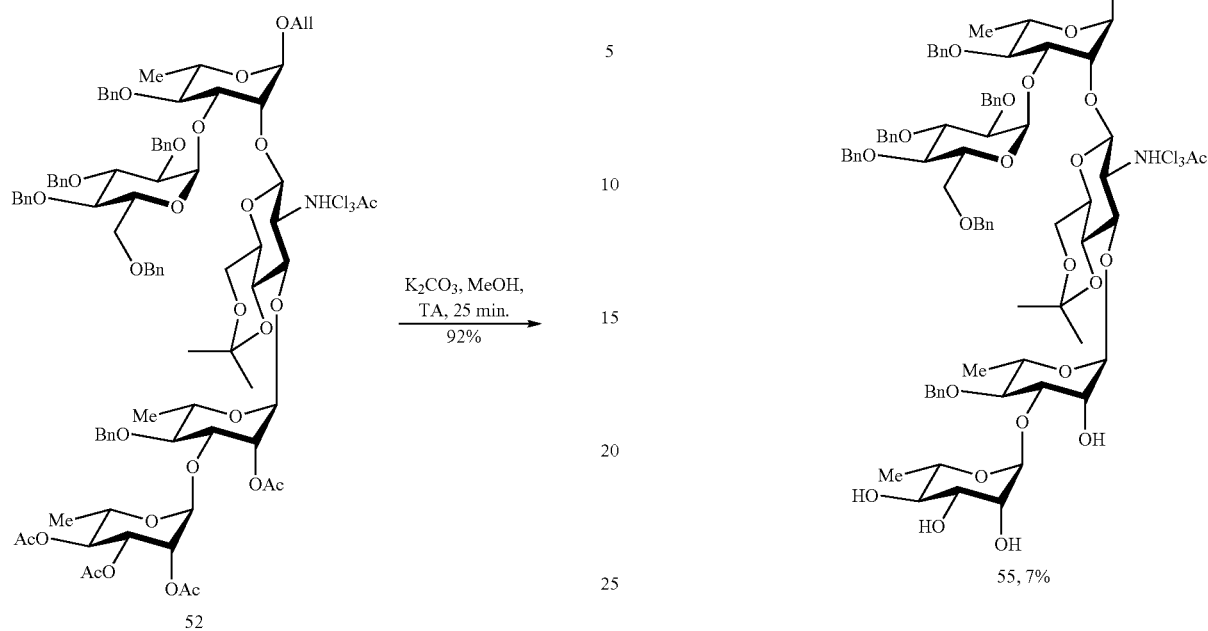
When treated with a 50% aqueous TFA solution in dichloromethane at 0° C.[80, 81] compounds 54 and 55 lead respectively to the pentasaccharides 56 and 57 at an identical yield of 95% (Scheme 29).
Scheme 29: Deacetalation of the compounds 54 and 55
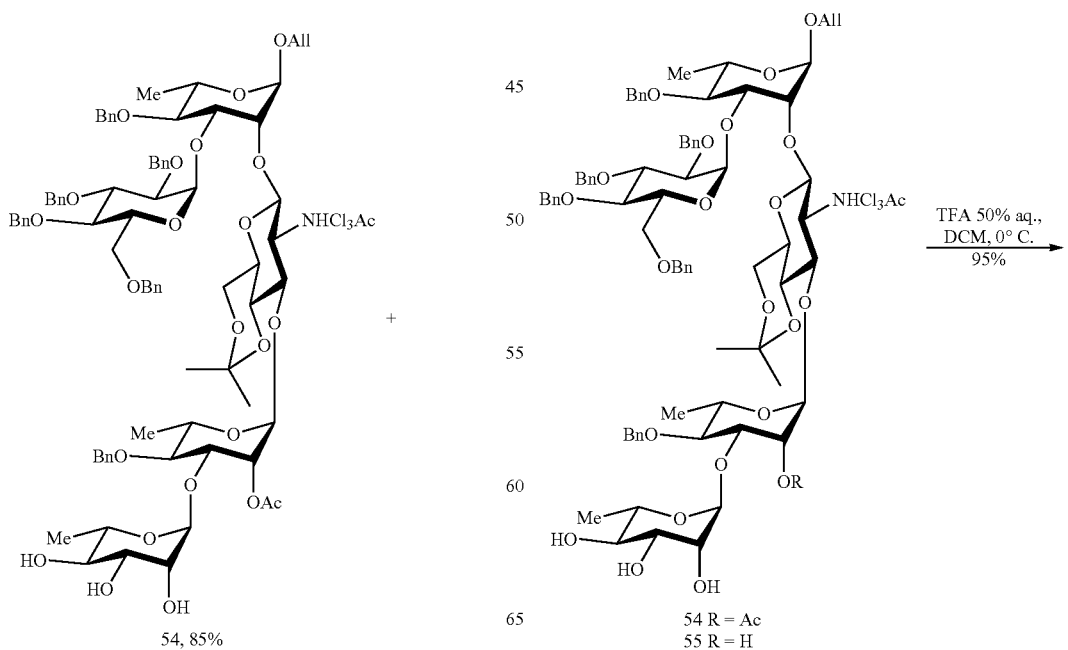

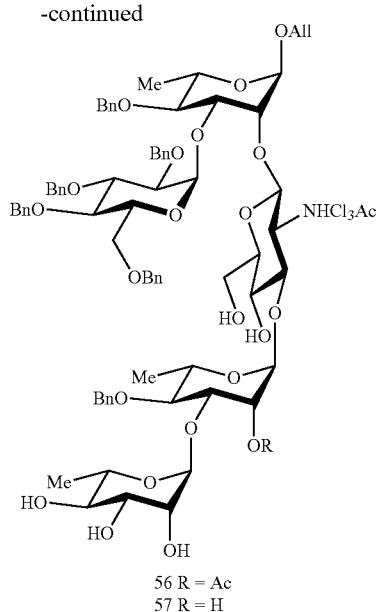

56 R = Ac
57 R = H b. Series B 2-O-Levulinoyl

The synthesis of precursor 49 (Scheme 25) was considered for carrying out the synthesis of the building block 47. In fact, as we saw in the back-synthesis section, the choice of a temporary, participating protecting group, in position $2_B$, fell on the levulinoyl group[88, 89]

Several strategies can be considered, but for large-scale synthesis of the diol 26, regioselective protection of position 3 of this diol with a benzyl group seems to be the best strategy. Thus, the diol 26 is heated under toluene reflux in Soxhlet apparatus in the presence of dibutyltin oxide used in stoichiometric amount in toluene to form the dibutylstannylene intermediate.[90] After formation of this intermediate, regioselective attack of the hydroxyl 3 on benzyl bromide was tested in the presence of tert-butyl ammonium iodide[91] or cesium fluoride.[92-94] The latter makes it possible to obtain the acceptor 58[95] at a yield of 88%, higher than the 70% obtained with tert-butyl ammonium iodide.

Scheme 30: Synthesis of the acceptor 58

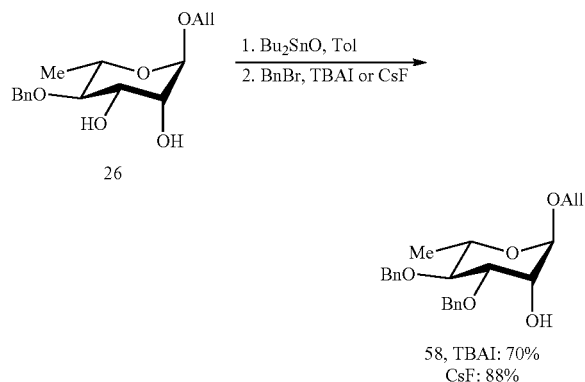

58, TBAI: 70%
CsF: 88%

Acceptor 58 is converted to levulinoyl ester 59 at a yield of 89% by the action of levulinic acid in the presence of DCC and DMAP in dichloromethane[89] (Scheme 31) then deallylated[96, 39, 40] in two stages (Back-Synthesis Section) allowing the hemiacetal 60 to be isolated at a yield of 94%. The latter is reacted in 1,2-dichloroethane in the presence of DBU and trichloroacetonitrile[22, 23] to give the trichloroacetimidate 49 at a yield of 92%.

Scheme 31: Synthesis of donor 49

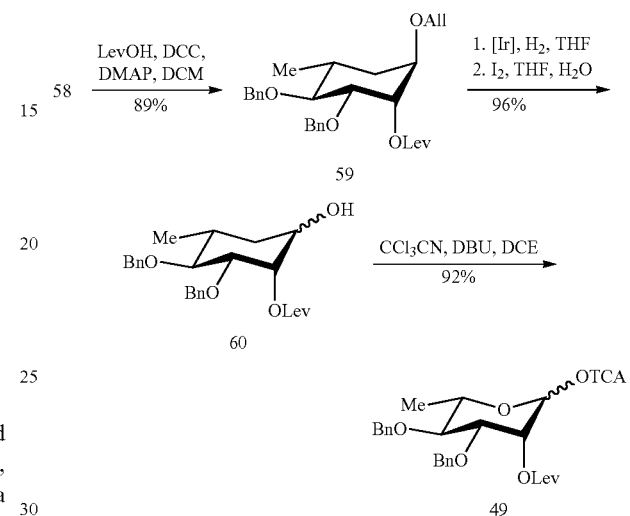

Coupling between donor 49 and acceptor 31 was investigated using various solvent conditions.[69, 76-79] If condensation is carried out in dichloromethane in the presence of TMSOTf (0.3 eq.) and molecular sieve, the disaccharide 61 is obtained with the expected α configuration ($J_{1,2}$=1.5 Hz, $^1J_{CH}$=169.5 Hz) and a yield of 66%, confirming the role of the levulinoyl as participating group (Scheme 32). In toluene in the presence of TMSOTf (0.3 eq.) and molecular sieve, the yield of disaccharide 61 is increased (77%) and reaches 90% when coupling is carried out on a large scale (7 g of acceptor 5). Then, as for the disaccharide 50, the disaccharide 61 is converted to donor 47 in two stages (Scheme 32), a deallylation stage[39, 40] (93%) followed by an activation stage[22, 23] (84%).

Scheme 32: Synthesis of donor 47

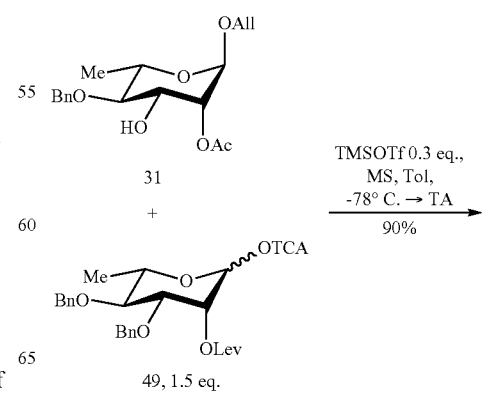

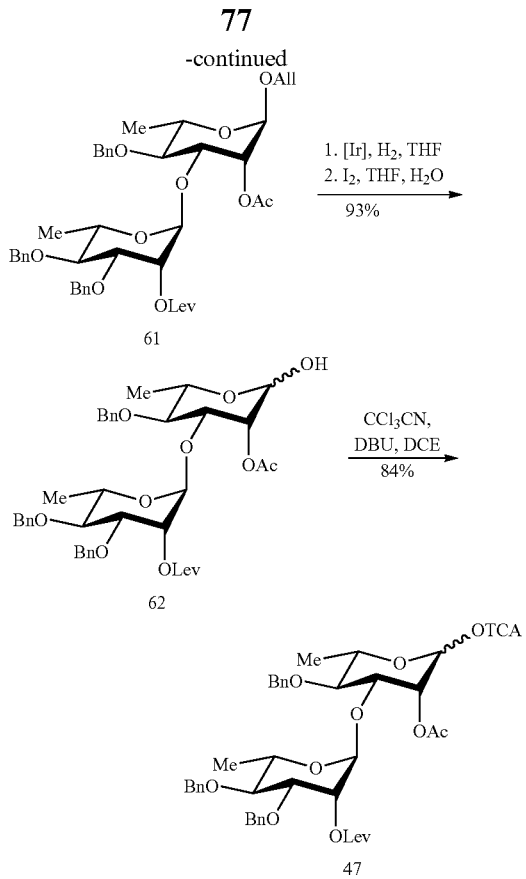

Various solvent conditions[69, 76-79] (dichloromethane, toluene) were tested during the coupling between the disaccharide donor 47 and the trisaccharide acceptor 38 (Scheme 33). The first two entries in Table 5 show, once again, the efficacy of toluene relative to dichloromethane but also the stability of the isopropylidene function at −78° C. In contrast, when coupling was carried out on a larger scale (of the order of 2 g of acceptor 38), the silylated acceptor 63 and the degradation of the donor 47, probably connected with low reactivity of the donor and/or of the acceptor, are observed (FIG. 16).

Two hypotheses were put forward:

1. The reaction mixture is not sufficiently acid to permit attack of the silylated acceptor 63 on the donor;
2. There is not enough donor in the reaction mixture.

No improvement is observed when coupling is carried out in more acid conditions (0.4 eq of TMSOTf) and, moreover, the addition of additional donor leads to its immediate degradation. As these two hypotheses do not enable us to evade the problem of reactivity of the donor 47, another factor, the influence of the temperature, was therefore investigated. In fact, entries 3 and 4 in Table 5 indicate that at −40° C. or at −20° C., neither the starting acceptor 38 nor the silylated acceptor 63 are observed, but again, as for the preceding couplings, the loss of isopropylidene is certainly real. However, if the temperature is raised too much, the yield drops. Analysis by NMR, and notably HMBC, was able to confirm the structure of pentasaccharide 64 and of pentasaccharide 65, which has lost the isopropylidene. Once again, glycosylation precedes the loss of this function.

TABLE 5

Investigation of coupling between donor 47 and acceptor 38

| Entry | Solvents | Temperature | Reaction time | Acceptor 38 remaining | 64 | 65 |
|---|---|---|---|---|---|---|
| 1 | DCM | −78° C. | 1 h | 30% | 42% | n.o. |
| 2 | Toluene | −78° C. | 1 h | 16% | 63% | n.o. |
| 3 | Toluene | −40° C. | 30 min | n.o. | 66% | 22% |
| 4 | Toluene | −20° C. | 30 min | n.o. | 66% | 13% |
| 5 | Toluene | −40° C. | 10 min | n.o. | 75% | n.o. |

* n.o.: not observed.

In conclusion, if the temperature is too low, the donor hydrolyzes faster than it reacts with the acceptor 38 or the silylated acceptor 63 and, conversely, if the temperature is too high, coupling does take place but at a yield which decreases as the temperature rises. Temperature control is therefore decisive, as illustrated in Scheme 33. Moreover, to limit the degradation of the isopropylidene during coupling, another factor was investigated: the reaction time before neutralization of the reaction mixture. Entries 3 and 5 in Table 5 can confirm that this factor influences the loss of the isopropylidene. The condensation between donor 47 and acceptor 38 is therefore carried out in toluene in the presence of TMSOTf (0.3 eq.) and molecular sieve at −40° C. After 10 min (entry 5 in Table 5), the reaction is stopped and the pentasaccharide 64, with the expected α configuration ($^1J_{CH}$=167.6 Hz), is isolated at a yield of 75%.

Scheme 33: Mechanism of coupling between donor 47 and acceptor 38

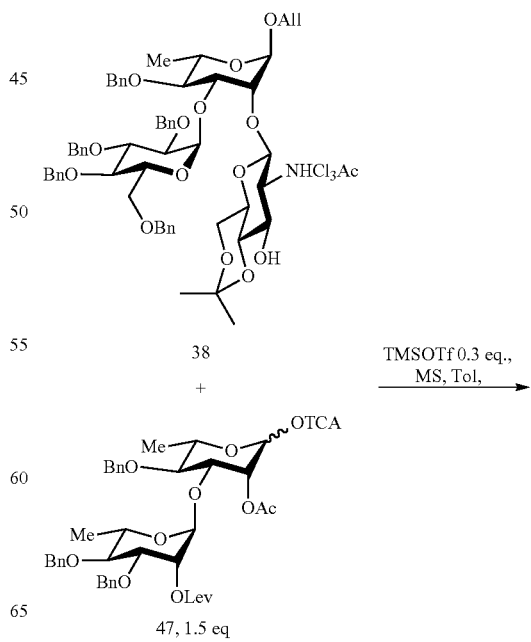

Scheme 34: Delevulinoylation of the levulinoyl ester 64 followed by its deacetalation

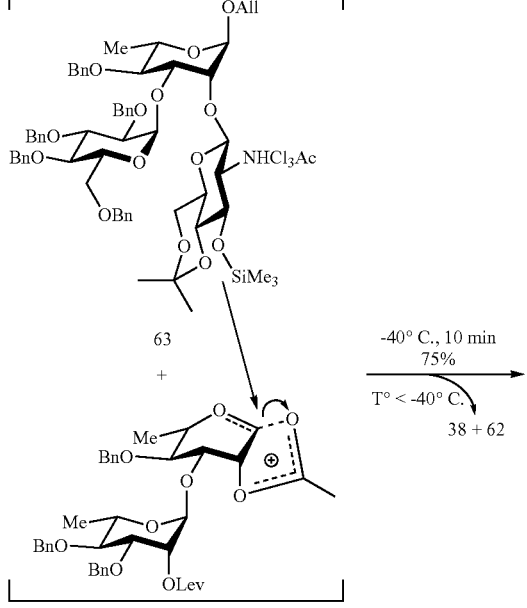

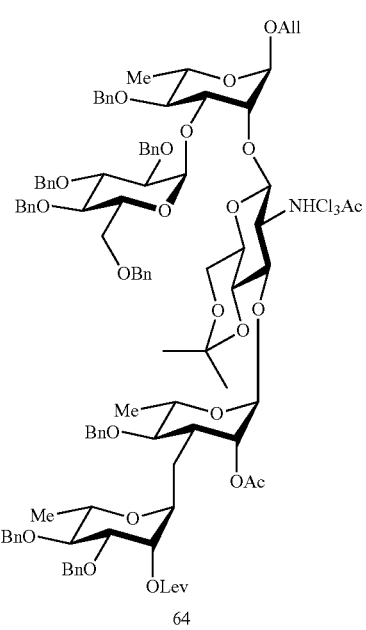

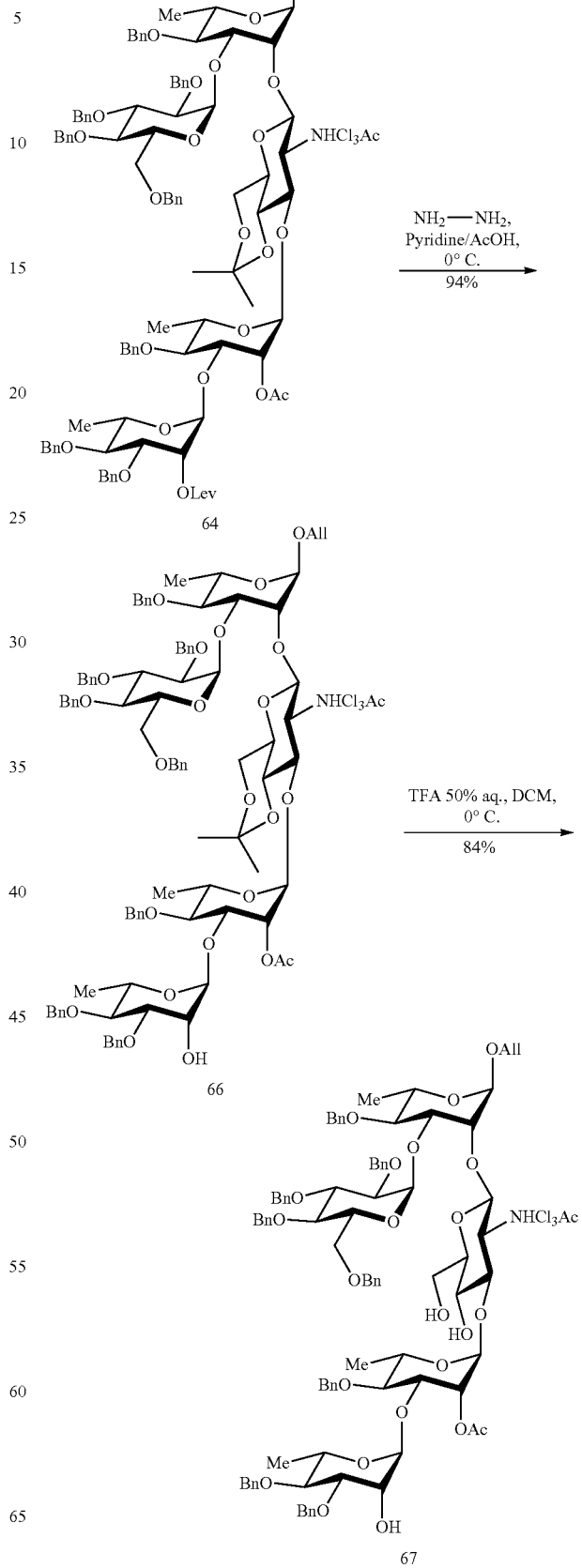

Deprotection of the levulinoyl group of the pentasaccharide 64 is carried out in a buffered medium (pyridine/AcOH) in the presence of hydrazine monohydrate.[89, 97-101] The alcohol 66 is obtained at a yield of 94%. When treated with a 50% aqueous TFA solution in dichloromethane at 0° C.[80, 81] the latter leads to the pentasaccharide 67 at a yield of 84% (Scheme 34).

10. Final Deprotection of the Pentasaccharides in Reducing Series A

With the possibility of cleavage of the acetyl function of 56 in acid or basic conditions, excluding acid hydrogenolysis and basic hydrodechlorination, suitable hydrogenation conditions were elaborated. The use of high pressure (50 bar) was preferred to an investigation of the choice of catalyst (Scheme 35).

Scheme 35: Hydrogenolysis of the pentasaccharide 56

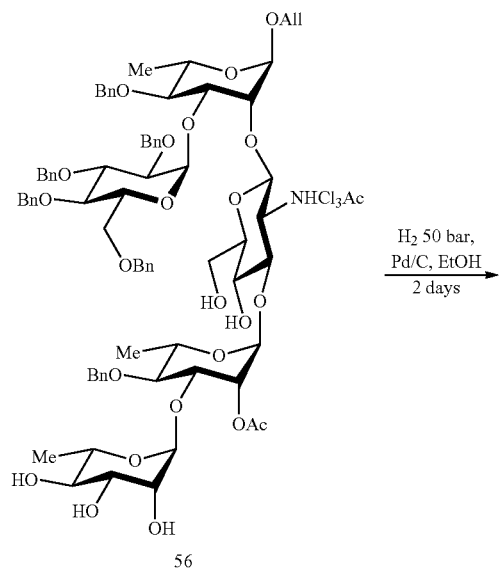

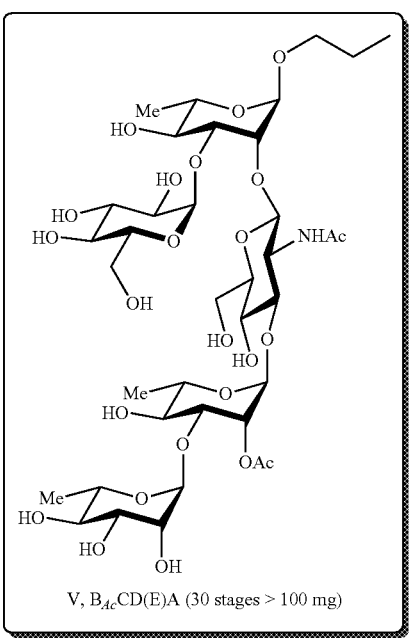

After two days, the chloroacetamide intermediate 68 was observed while monitoring with mass spectrometry (M=940.3429. found m/z=940.3425) and by NMR (proton singlet at 4.1 ppm and a carbon signal at 42.5 ppm) (Scheme 35). After a further eight days, the conversion to acetamide is total. Propyl glycoside V is isolated at a yield of 70%. The other possibility is to use the pentasaccharide 67 resulting from the coupling with the disaccharide synthon 47. The expected propyl glycoside V is obtained, in the same conditions, at a yield of 75% (Scheme 36).

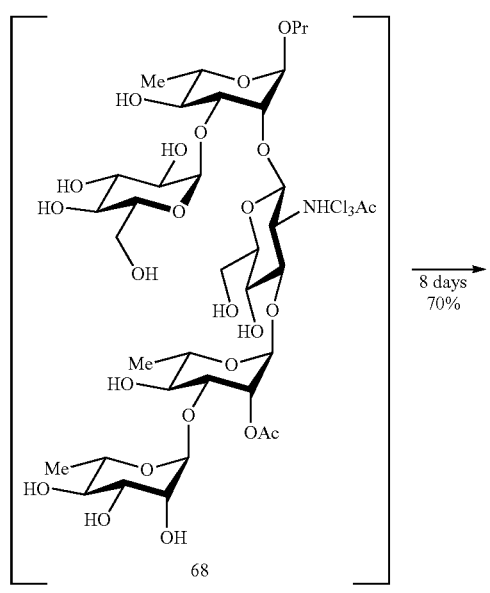

Scheme 36: Hydrogenolysis of the pentasaccharide 67

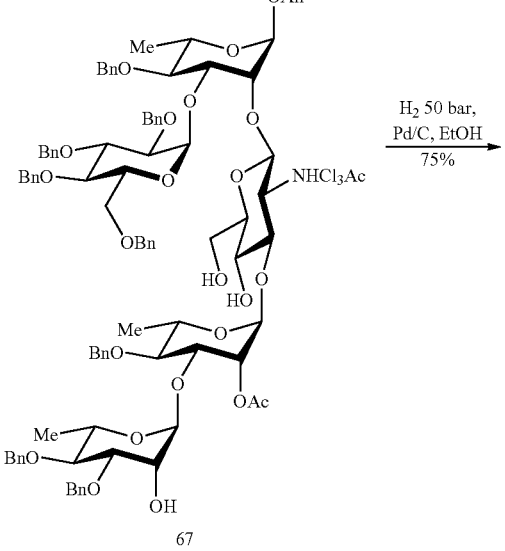

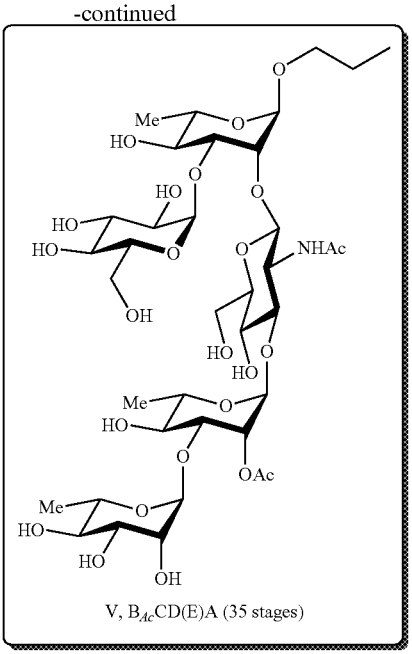

V, B$_{Ac}$CD(E)A (35 stages)

Method 6:

The invention further relates to the method of preparation of the pentasaccharide compound VI BCD(E)A (VI) as defined in list L1 comprising the following stages:

condensation of the donor disaccharide 46 with the acceptor trisaccharide 38 leading to the pentasaccharide 52, the condensation reaction preferably being carried out in a solvent such as dichloromethane, 1,2-dichloroethane, ether, toluene, acetonitrile or any other equivalent solvent, in the presence of a Lewis acid such as TMSOTf or triflic acid, preferably in toluene, in the presence of TMSOTf at 0.3 eq. and at −78° C. (scheme 27);

deacetylation of the pentasaccharide 52 leading to the pentasaccharide 55 preferably in basic conditions, notably with K$_2$CO$_3$ (scheme 28);

deacetylation of the pentasaccharide 55 leading to the pentasaccharide 57 preferably in 50% aqueous TFA solution in dichloromethane at 0° C. (scheme 29);

deprotection of the pentasaccharide 57 to give the pentasaccharide BCD(E)A preferably under hydrogen pressure in alcohol, for example ethanol, in the presence of a palladium derivative, such as palladium on charcoal (scheme 37).

In fact, by analogy with the preceding method, the hydrogenation of alcohol 57 at a pressure of 50 bar leads to the propyl glycoside VI, isolated at a yield of 71% (Scheme 37).

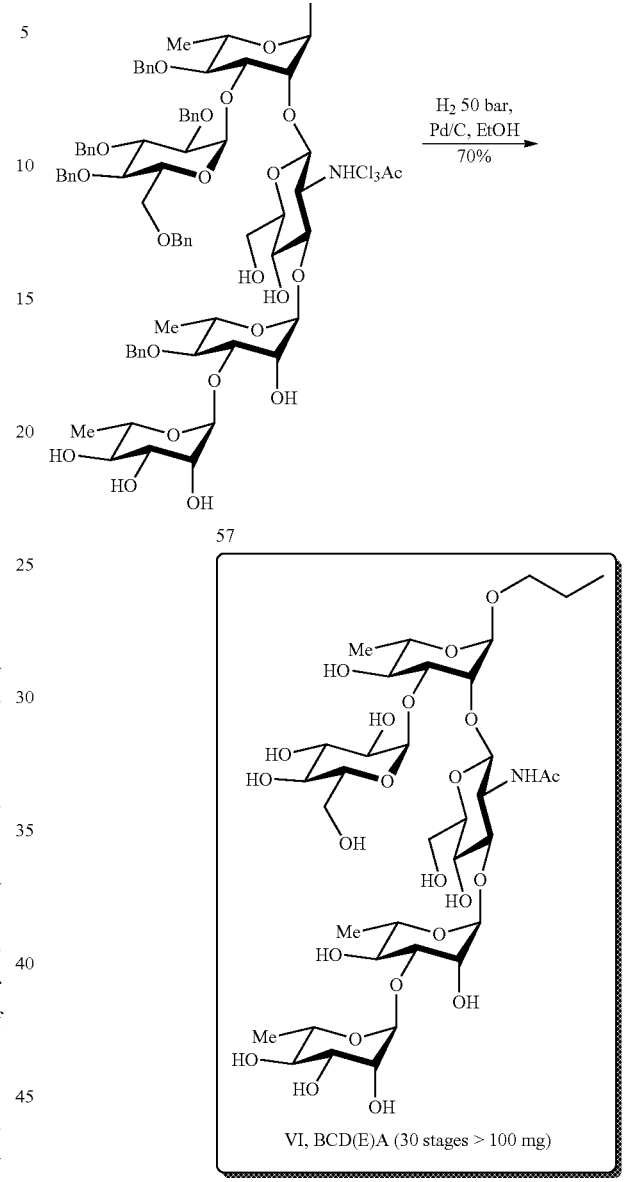

Scheme 37: Hydrogenolysis of the pentasaccharide 57

11. Conclusion

In this section, the synthesis of six oligosaccharides in reducing series A, mono-acetylated or not, corresponding to the serotypes 3a or X of *S. flexneri*, including one di-, one tri-, two tetra-, and two pentasaccharides as well as a comparative study of availability of the target pentasaccharide V were carried out. According to Scheme 38, access to this target, resulting from coupling between the acceptor trisaccharide 38 and the donor disaccharide 46, is a little more effective than that using donor 47. However, the advantage of the second route of synthesis is the possible elongation of the disaccharide synthon 61 as well as of the pentasaccharide 64, in reducing or nonreducing position, to arrive at larger oligosaccharide targets.

Scheme 38: Balance for access to the target $B_{Ac}CD(E)AV$

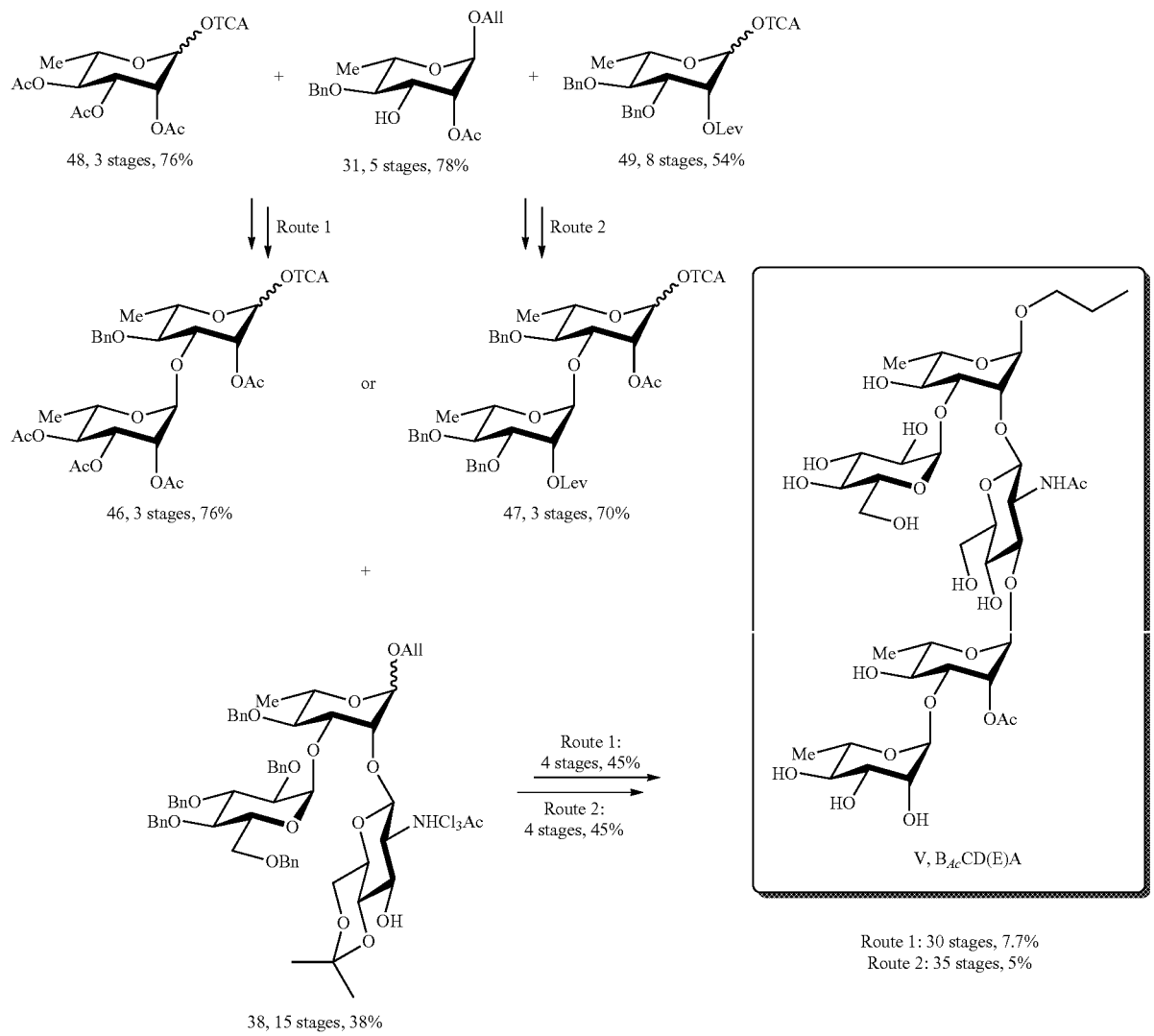

Route 1: 30 stages, 7.7%
Route 2: 35 stages, 5%

Experimental Application of Methods 1 to 6
Method 1:

Allyl α-L-rhamnopyranoside[42] 28

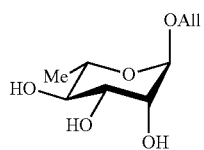

Chemical Formula: $C_9H_{16}O_5$
Exact Mass: 204.0998
Molecular Weight: 204.2203

Acetyl chloride (19.6 mL, 270.0 mmol, 2.5 eq.) is added in portions to allyl alcohol (250 mL) at 0° C. for 15 min, then commercial L(+)-rhamnose monohydrate 27 (20.0 g, 110.0 mmol) is added to the reaction mixture. The reaction mixture is then heated at 70° C. for 2.5 h and then at 40° C. overnight. Monitoring of the reaction by TLC (DCM/MeOH, 9/1) shows the disappearance of 27 (Rf=0.1) and the presence of a less polar main product (Rf=0.45). The reaction mixture is cooled to 0° C., neutralized by adding $NaHCO_3$ and then filtered on Celite and finally concentrated in a rotary evaporator. The volatile substances are coevaporated with Tol (2×100 mL) to give a yellow oil. The yellow oil is purified by silica gel chromatography (DCM/MeOH, 98/2→8/2), obtaining a mixture of the allyl glycoside $28_α$ (19.8 g, 88%) and its anomer $28_β$ (2.4 g, 11%) as a yellow oil.

$28_α$: Rf=0.45 (DCM/MeOH, 9/1).

$^1H$ NMR ($CDCl_3$), δ 5.92 (m, 1H, CH=), 5.30 (m, 1H, $J_{trans}$=15.7 Hz, =$CH_2$), 5.20 (m, 1H, $J_{cis}$=10.4 Hz, =$CH_2$), 4.81 (bs, 1H, H-1), 4.5 (bs, 1H, OH), 4.19-4.10 (m, 2H, $H_{All}$, OH), 3.98 (m, 1H, $H_{All}$), 3.96 (bs, 1H, H-2), 3.79 (m, 1H, H-3), 3.68 (dq, 1H, $J_{4,5}$=9.4 Hz, H-5), 3.50 (m, 2H, H-4, OH), 1.32 (d, 3H, $J_{5,6}$=6.2 Hz, H-6).

$^{13}C$ NMR ($CDCl_3$), δ 134.0 (CH=), 118.0 (=$CH_2$), 99.3 (C-1, $^1J_{CH}$=164.2 Hz), 73.1 (C-4), 72.4 (C-3), 71.5 (C-2), 68.5 (C-5), 68.4 ($C_{All}$), 17.9 (C-6).

Allyl 2,3-O-isopropylidene-α-L-rhamnopyranoside[42] 29

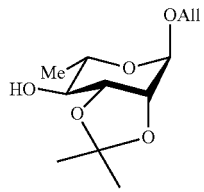

Chemical Formula: $C_{12}H_{20}O_5$
Exact Mass: 244.1311
Molecular Weight: 244.2842

The allyl glycoside 28 (3.5 g, 17.1 mmol) is dissolved in a mixture of acetone (16 mL) and 2,2-dimethoxypropane (6.9 mL, 51.3 mmol, 3 eq.) stirred under inert atmosphere at RT. PTSA (162 mg, 0.84 mmol, 0.05 eq.) is added, stirring for a further 2 h. Monitoring by TLC (DCM/MeOH, 9/1) shows the disappearance of 28 (Rf=0.45) and the formation of a less polar main compound (Rf=0.85). The reaction mixture is neutralized by adding triethylamine (1 mL) and then concentrated in a rotary evaporator. The yellow oil is taken up in DCM (100 mL) and washed with $H_2O$ (3×50 mL). The organic phases are combined, dried on a phase-separating filter and concentrated in a rotary evaporator to give a yellow oil. The yellow oil is purified by silica gel chromatography (Chex/EtOAc, 9/1→6/4) to obtain the alcohol 29 as a yellow oil (3.5 g, 84%).

Rf=0.85 (DCM/MeOH, 9/1).

$^1$H NMR (CDCl$_3$), δ5.89 (m, 1H, CH=), 5.32 (m, 1H, J$_{trans}$=15.6 Hz, =CH$_2$), 5.22 (m, 1H, J$_{cis}$=10.6 Hz, =CH$_2$), 5.01 (bs, 1H, H-1), 4.19 (m, 1H, H$_{All}$), 4.16 (d, 1H, J$_{1,2}$=0.6 Hz, J$_{2,3}$=5.8 Hz, H-2), 4.09 (pt, 1H, J$_{3,4}$=5.8 Hz, H-3), 4.01 (m, 1H, H$_{All}$), 3.68 (dq, 1H, J$_{4,5}$=9.3 Hz, H-5), 3.39 (m, 1H, H-4), 2.9 (s, 1H, OH), 1.53 (s, 3H, H$_{iPr}$), 1.35 (s, 3H, H$_{iPr}$), 1.32 (d, 3H, J$_{5,6}$=6.3 Hz, H-6).

$^{13}$C NMR (CDCl$_3$), δ134.0 (CH=), 118.2 (=CH$_2$), 110.0 (C$_{iPr}$), 96.6 (C-1), 78.5 (C-3), 76.2 (C-2), 74.7 (C-4), 68.3 (C$_{All}$), 66.2 (C-5), 28.3 (C$_{iPr}$), 26.5 (C$_{iPr}$), 17.8 (C-6).

Allyl 4-O-benzyl-2,3-O-isopropylidene-α-L-rhamnopyranoside[42] 30

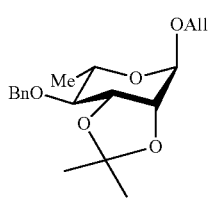

Chemical Formula: $C_{19}H_{26}O_5$
Exact Mass: 334.1780
Molecular Weight: 334.4067

In a three-necked flask, the alcohol 29 (3.5 g, 14.4 mmol) is dissolved in DMF (80 mL) under argon and cooled to −5° C., then 60% NaH in oil (1.7 g, 41.8 mmol, 2.9 eq.) is added in small portions. Stirring is continued at RT for 1 h. Following return to −5° C., benzyl bromide (1.9 mL, 15.8 mmol, 1.1 eq.) is added dropwise. After stirring at RT for 4 hours, monitoring by TLC (Chex/EtOAc, 8/2) shows the formation of a less polar main compound (Rf=0.7). After putting the flask in an ice bath, MeOH (1.2 mL) is slowly added and stirring is maintained for 2 h at RT. $H_2O$ is added (20 mL), then the reaction mixture is transferred to a separating funnel and the aqueous phase is extracted with ethyl acetate (3×100 mL). The organic phases are combined and washed successively with $H_2O$ (2×20 mL), 5% HCl (2×20 mL), NaCl$_{sat}$ (2×20 mL), then dried on a phase-separating filter and finally concentrated in a rotary evaporator. The yellow oil obtained is purified by silica gel chromatography (Chex/EtOAc, 99/1→8/2) to obtain compound 30 in the form of a yellow oil (3.9 g, 82%).

Rf=0.7 (Chex/EtOAc, 8/2).

$^1$H NMR (CDCl$_3$), δ7.41-7.31 (m, 5H, CH$_{Ph}$), 5.92 (m, 1H, CH=), 5.33 (m, 1H, J$_{trans}$=17.2 Hz, =CH$_2$), 5.23 (m, 1H, J$_{cis}$=10.4 Hz, =CH$_2$), 5.05 (bs, 1H, H-1), 4.94 (d, 1H, J=11.6 Hz, H$_{Bn}$), 4.67 (d, 1H, H$_{Bn}$), 4.32 (pt, 1H, J$_{3,4}$=6.8 Hz, H-3), 4.20 (m, 2H, H-2, H$_{All}$), 4.01 (m, 1H, H$_{All}$), 3.76 (dq, J$_{4,5}$=9.8 Hz, 1H, H-5), 3.25 (pt, 1H, H-4), 1.54 (s, 3H, H$_{iPr}$), 1.41 (s, 3H, H$_{iPr}$), 1.32 (d, 3H, J$_{5,6}$=6.3 Hz, H-6).

$^{13}$C NMR (CDCl$_3$), δ138.8 (C$_{Ph}$), 134.1 (CH=), 128.8-128.0 (CH$_{Ph}$), 118.1 (=CH$_2$), 109.5 (C$_{iPr}$), 96.5 (C-1, $^1$J$_{CH}$=167.8 Hz), 81.5 (C-4), 79.1 (C-3), 76.5 (C-2), 73.3 (C$_{Bn}$), 68.2 (C$_{All}$), 64.8 (C-5), 28.4 (C$_{iPr}$), 26.7 (C$_{iPr}$), 18.2 (C-6).

Allyl 4-O-benzyl-α-L-rhamnopyranoside[42] 26

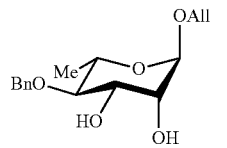

Chemical Formula: $C_{16}H_{22}O_5$
Exact Mass: 294.1467
Molecular Weight: 294.3429

Route 1:

Compound 30 (3.9 g, 11.8 mmol) is dissolved in 80% aq. acetic acid solution (60 mL) and heated to 60° C. After reaction for 3 h, monitoring by TLC (DCM/EtOAc, 1/1) shows the formation of a more polar main compound (Rf=0.6). The reaction mixture is cooled to RT and then concentrated and coevaporated with Tol/Chex mixture (1/1, 3×100 mL).

Recrystallization is carried out from iPr$_2$O/PE mixture (8/2, 10 mL). After storage overnight in a refrigerator, the white crystals are filtered and washed with an iPr$_2$O/PE mixture (1/1, 10 mL) to obtain the diol 26 in the form of white crystals (2.5 g, 72%, i.e. 44% over 4 stages).

Route 2:

Acetyl chloride (19.6 mL, 270.0 mmol, 2.5 eq.) is added in portions to allyl alcohol (250 mL) at 0° C. for 15 min, then commercial L(+)-rhamnose monohydrate 27 (20.0 g, 110.0 mmol) is added to the reaction mixture. The reaction mixture is then heated at 70° C. for 2.5 h and then at 40° C. overnight. Monitoring of the reaction by TLC (DCM/MeOH, 9/1) shows the disappearance of 27 (Rf=0.1) and the presence of a less polar main product (Rf=0.45). The reaction mixture is cooled to 0° C., neutralized by adding NaHCO$_3$ and then filtered on Celite and finally concentrated in a rotary evaporator. The volatile substances are coevaporated with Tol (2×100 mL) to give a yellow oil (27.6 g).

The raw reaction product obtained (27.6 g, 110.0 mmol) is dissolved in a mixture of acetone (121 mL) and 2,2-dimethoxypropane (40.5 mL, 330.0 mmol, 3 eq.) stirred under inert atmosphere at RT. PTSA (208 mg, 1.1 mmol, 0.01 eq.) is added and stirring is continued for 2 h. Monitoring by TLC (DCM/MeOH, 9/1) shows the disappearance of 28 (Rf=0.45) and the formation of a less polar main compound (Rf=0.85). The reaction mixture is neutralized by adding triethylamine (2 mL) and then concentrated in a rotary evaporator. The yellow oil is taken up in DCM (200 mL) and washed with $H_2O$ (3×100 mL). The organic phases are combined, dried on a phase-separating filter and concentrated in a rotary evaporator to give a yellow oil (25.1 g).

In a three-necked flask, the raw reaction product obtained (25.1 g, 110.0 mmol) is dissolved in DMF (320 mL) under argon and cooled to −5° C. and then 60% NaH in oil (13.2 g, 330.0 mmol, 3 eq.) is added in small portions. Stirring is continued at RT for 1 h. Following return to −5° C., benzyl bromide (25.5 mL, 210.0 mmol, 2 eq.) is added dropwise. After stirring at RT for 4 hours, monitoring by TLC (Chex/EtOAc, 8/2) shows the formation of a less polar main compound (Rf=0.7). After putting the flask in an ice bath, MeOH (9 mL) is slowly added and stirring is maintained for 2 h at RT. $H_2O$ is added (50 mL) and then the reaction mixture is transferred to a separating funnel and the aqueous phase is extracted with ethyl acetate (3×250 mL). The organic phases are combined and washed successively with $H_2O$ (2×50 mL), 5% HCl (2×50 mL), $NaCl_{sat}$ (2×50 mL), and then dried on a phase-separating filter and finally concentrated in a rotary evaporator to give a yellow oil (35.0 g). The raw reaction product obtained (35.0 g, 110.0 mmol) is dissolved in 80% aq. acetic acid solution (280 mL) and heated to 60° C. After reaction for 3 h, monitoring by TLC (DCM/EtOAc, 1/1) shows the formation of a more polar main compound (Rf=0.6). The reaction mixture is cooled to RT, then concentrated and coevaporated with Tol/Chex mixture (1/1, 3×250 mL). Recrystallization is carried out in $iPr_2O$/PE mixture (8/2, 100 mL). After storage overnight in a refrigerator, the white crystals are filtered and washed with $iPr_2O$/PE mixture (1/1). The mother liquor is concentrated and purified by silica gel chromatography (DCM/EtOAc, 9/1→7/3). The yellow oil obtained is recrystallized from $iPr_2O$/PE mixture to obtain the diol 26 in the form of white crystals (25.8 g, 78%).

Rf=0.6 (DCM/EtOAc, 8/2).

$^1$H NMR ($CDCl_3$), δ7.40-7.33 (m, 5H, $CH_{Ph}$), 5.88 (m, 1H, CH=), 5.31 (m, 1H, $J_{trans}$=17.2 Hz, =$CH_2$), 5.20 (m, 1H, $J_{cis}$=10.4 Hz, =$CH_2$), 4.83 (s, 1H, H-1), 4.81 (d, 1H, J=11.3 Hz, $H_{Bn}$), 4.72 (d, 1H, $H_{Bn}$), 4.19 (m, 1H, $H_{All}$), 4.00-3.96 (m, 2H, H-3, $H_{All}$), 3.95 (bs, 1H, H-2), 3.78 (dq, $J_{4,5}$=9.4 Hz, 1H, H-5), 3.37 (pt, 1H, $J_{3,4}$=9.0 Hz, H-4), 3.05 (bs, 2H, OH), 1.31 (d, 3H, $J_{5,6}$=6.3 Hz, H-6).

$^{13}$C NMR ($CDCl_3$), δ138.6 ($C_{Ph}$), 134.1 (CH=), 129.0-128.4 ($CH_{Ph}$), 117.7 (=$CH_2$), 98.8 (C-1, $^1J_{CH}$=168.2 Hz), 82.1 (C-4), 75.5 ($C_{Bn}$), 71.8, 71.6 (C-2*, C-3*), 68.3 ($C_{All}$), 67.6 (C-5), 18.4 (C-6).

2,3,4,6-Tetra-O-benzyl-α/β-D-glucopyranose trichloroacetimidate[35] 33

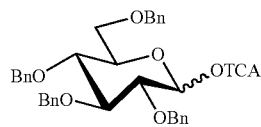

Chemical Formula: $C_{36}H_{36}Cl_3NO_6$
Exact Mass: 683.16
Molecular Weight: 685.03

Commercial 2,3,4,6-tetra-O-benzyl-β-D-glucopyranose 32 (25.0 g, 46.3 mmol) is dissolved in DCM (250 mL). Then $K_2CO_3$ (25.0 g, 180.0 mmol, 3.9 eq.) previously dried overnight at 300° C., and then trichloroacetonitrile (25.0 mL, 250.0 mmol, 5.4 eq.), are added. The reaction mixture is stirred vigorously for 3 h at RT. The reaction is monitored by TLC (Chex/EtOAc+5% $NEt_3$, 8/2). Although it has not gone to completion, the reaction is stopped in order to avoid isomerization of the β trichloroacetimidate (Rf=0.6) to a (Rf=0.7). The reaction mixture is filtered, and concentrated under vacuum. The trichloroacetimidate is obtained by recrystallization from $iPr_2O$/PE mixture (6/4, 100 mL). The first filtration, after 1 h on an ice bath, makes it possible to recover the starting product in the form of flocs (1.1 g, 2 mmol), and the second, after a week in a refrigerator, the feed product in the form of beads. It is predominantly the anomer $33_β$ (22.4 g, 71%) with a smaller amount of the anomer $33_α$ (1.7 g, 5%).

33β: Rf=0.6 (Chex/EtOAc, 8/2).

$^1$H NMR ($CDCl_3$), δ: β: 8.72 (s, 1H, NH), 7.36-7.29 (m, 20H, $CH_{Ph}$), 5.83 (d, 1H, $J_{1-2}$=7.3 Hz, H-1), 4.98-4.55 (m, 8H, $H_{Bn}$), 3.80-3.74 (m, 5H, H-2, H-3, H-4, H-6a, H-6b), 3.67 (m, 1H, H-5).

$^{13}$C NMR ($CDCl_3$), δ: β: 161.6 (C=NH), 138.8-138.3 ($C_{Ph}$), 128.7-127.9 ($CH_{Ph}$), 98.7 (C-1, $^1J_{CH}$=167.2 Hz), 84.9 (C-4), 81.3 (C-3), 77.7 (C-2), 76.3 (C-5), 76.0, 75.4, 75.3, 73.8 (4C, $C_{Bn}$), 68.6 (C-6).

Allyl 2-O-acetyl-4-O-benzyl-α-L-rhamnopyranoside[47] 31

Allyl(2,3,4,6-tetra-O-benzyl-α-D-glucopyranosyl)-(1→3)-2-O-acetyl-4-O-benzyl-α-L-rhamnopyranoside[51] 35

Allyl(2,3,4,6-tetra-O-benzyl-α-D-glucopyranosyl)-(1→3)-4-O-benzyl-α-L-rhamnopyranoside[45] 21

Allyl(2,3,4,6-tetra-O-benzyl-β-D-glucopyranosyl)-(1→3)-4-O-benzyl-α-L-rhamnopyranoside[45] 36

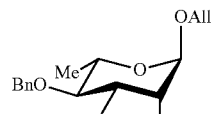

Chemical Formula: $C_{18}H_{24}O_6$
Exact Mass: 336.1573
Molecular Weight: 336.3796

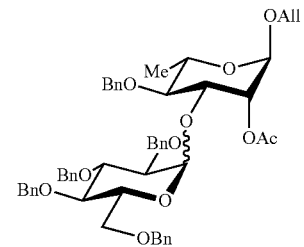

Chemical Formula: $C_{52}H_{58}O_{11}$
Exact Mass: 858.3979
Molecular Weight: 859.0103

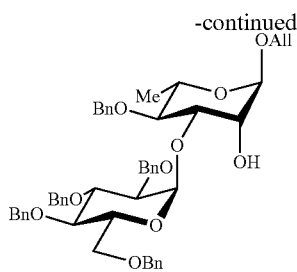

Chemical Formula: C$_{50}$H$_{56}$O$_{10}$
Exact Mass: 816.3873
Molecular Weight: 816.9736

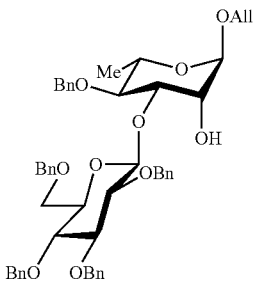

Chemical Formula: C$_{50}$H$_{56}$O$_{10}$
Exact Mass: 816.3873
Molecular Weight: 816.9736

Trimethyl orthoacetate (6.6 mL, 51.7 mmol, 1.9 eq.) and PTSA (72 mg, 400 µmol, 0.014 eq.) are added to the diol 26 (8.0 g, 27.2 mmol) in solution in acetonitrile (15 mL). The reaction mixture is stirred at RT and the reaction is monitored by TLC (Tol/EtOAc, 9/1, DCM/EtOAc, 1/1). After 1 h, the transformation of the diol 26 (Rf=0.5 in DCM/EtOAc, 1/1) to less polar orthoester (Rf=0.6 in Tol/EtOAc, 9/1) is total and the flask is immersed in an ice bath. Stirring is maintained for 10 min, then 80% aqueous acetic acid (15 mL) is added. After stirring vigorously at RT for 1 h, monitoring by TLC (Tol/EtOAc, 8/2) indicates complete transformation of the orthoester to a more polar compound (Rf=0.25). The reaction mixture is taken up in cold water (50 mL) and the aqueous phase is quickly extracted with DCM (3×100 mL). The organic phases are combined and washed with a solution of NaCl$_{sat}$ (3×20 mL), filtered on a phase-separating filter and concentrated in a rotary evaporator. The colorless oil (9.1 g, 98%) is used directly in the next stage after checking by $^1$H NMR. The latter indicates the presence of the desired acceptor 31 and of the acetylated regioisomer in position 3 at a ratio of 97/3.

Rf=0.25 (Tol/EtOAc, 8/2).

$^1$H NMR (CDCl$_3$), δ7.38-7.32 (m, 5H, CH$_{Ph}$), 5.88 (m, 1H, CH=), 5.31 (m, 1H, J$_{trans}$=17.2 Hz, =CH$_2$), 5.21 (m, J$_{cis}$=10.4 Hz, =CH$_2$), 5.14 (dd, 1H, J$_{1,2}$=1.7 Hz, J$_{2,3}$=3,6 Hz, H-2), 4.86 (d, 1H, J=11.1 Hz, H$_{Bn}$), 4.80 (d, 1H, H-1), 4.73 (d, 1H, H$_{Bn}$), 4.17 (m, 2H, H-3, H$_{All}$), 3.98 (m, 1H, H$_{All}$), 3.78 (dq, 1H, J$_{4,5}$=9.4 Hz, H-5), 3.37 (pt, 1H, J$_{3,4}$=9.5 Hz, H-4), 2.19 (s, 3H, H$_{Ac}$), 1.37 (d, 3H, J$_{5,6}$=6.3 Hz, H-6).

$^{13}$C NMR (CDCl$_3$), δ168.9 (C$_{Ac}$), 136.3 (C$_{Ph}$), 131.6 (CH=), 126.6-126.0 (CH$_{Ph}$), 115.6 (=CH$_2$), 94.6 (C-1), 79.9 (C-4), 73.4 (C$_{Bn}$), 70.9 (C-2), 68.3 (C-3), 66.2 (C$_{All}$), 65.6 (C-5), 19.2 (C$_{Ac}$), 16.1 (C-6).

TMSOTf (98.0 µL, 550 µmol, 0.02 eq.) is added to a solution of the raw oil obtained (9.1 g, 27.2 mmol) in Tol (112 mL), stirred under argon at −78° C. After stirring for 30 min at this temperature, a solution of donor 33 (22.4 g, 32.6 mmol, 1.2 eq.) in Tol/DCM mixture (2/1, 24 mL) is added dropwise. The ethanol-dry ice bath is withdrawn and stirring is continued for 1 h, after which time monitoring by TLC (Tol/EtOAc, 9/1, Chex/EtOAc, 73/27 and Tol/EtOAc, 8/2) indicates the disappearance of the acceptor 31 (Rf=0.15 and 0.2, respectively) and the appearance of a less polar compound (Rf=0.4 and 0.55, respectively). The reaction is stopped by adding triemylamine (0.2 mL) and then the reaction mixture is concentrated in a rotary evaporator. The yellow oil obtained is submitted to coarse purification by flash chromatography (Tol/EtOAc, 97/3→94/6). The mixture of anomers 35$_\alpha$ and 35$_\beta$ in the form of a yellow oil (21.0 g, 85/15, αE/βE, 90%) is used in the next stage without any other purification.

Rf=0.55 (Chex/EtOAc, 73/27).

$^1$H NMR (CDCl$_3$), δ: α: 7.46-7.15 (m, 25H, CH$_{Ph}$), 5.88 (m, 1H, CH=), 5.43 (dd, 1H, H-2$_A$), 5.31 (m, 1H, J$_{trans}$=17.3 Hz, =CH$_2$), 5.24-5.21 (m, 2H, H-1$_E$, =CH$_2$), 5.06 (d, 1H, J=11.0 Hz, H$_{Bn}$), 4.99 (d, 1H, J=10.2 Hz, H$_{Bn}$), 4.92 (d, 1H, H$_{Bn}$), 4.89 (d, 1H, H$_{Bn}$), 4.82 (d, 1H, J$_{1,2}$=1.6 Hz, H-1$_A$), 4.77 (d, 1H, J=11.9 Hz, H$_{Bn}$), 4.72 (d, 1H, H$_{Bn}$), 4.65 (d, 1H, H$_{Bn}$), 4.63 (d, 1H, H$_{Bn}$), 4.52 (d, 1H, J=11.0 Hz, H$_{Bn}$), 4.40 (d, 1H, J=12.1 Hz, H$_{Bn}$), 4.37 (dd, 1H, J$_{2,3}$=3.3 Hz, J$_{3,4}$=9.6 Hz, H-3$_A$), 4.19 (M$_{overlapped}$, 1H, H$_{All}$), 4.14 (pt$_{overlapped}$, 1H, J$_{3,4}$=9.5 Hz, H-3$_E$), 4.10 (M$_{overlapped}$, 1H, H-5$_E$), 4.00 (m, 1H, H$_{All}$), 3.84 (dq, 1H, J$_{4,5}$=9.4 Hz, H-5$_A$), 3.85 (pt, 1H, J$_{4,5}$=9.4 Hz, H-4$_E$), 3.68-3.61 (m, 3H, H-2$_E$, H-6a$_E$, H-4$_A$), 3.57 (dd, 1H, J$_{5,6b}$=1.8 Hz, J$_{6a,6b}$=10.9 Hz, H-6b$_E$), 1.99 (s, 3H, H$_{Ac}$), 1.43 (d, 3H, J$_{5,6}$=6.3 Hz, H-6$_A$).

$^{13}$C NMR (CDCl$_3$), δ: β: 170.5 (C$_{Ac}$), 138.9-137.7 (C$_{Ph}$), 133.6 (CH=), 128.6-127.4 (CHPh), 117.5 (=CH$_2$), 96.7 (C-1$_A$, $^1$J$_{CH}$=170.4 Hz), 92.7 (C-1$_E$, $^1$J$_{CH}$=167.0 Hz), 82.2 (C-3$_E$), 79.9 (C-4$_A$), 79.4 (C-2$_E$), 77.9 (C-4$_E$), 76.2, 75.5, 75.0, 73.3, 73.0 (5C, C$_{Bn}$), 72.2 (C-3$_A$), 70.2 (C-5$_E$), 68.3 (C-6$_E$), 68.1 (C$_{All}$), 68.0 (C-5$_A$), 67.9 (C-2$_A$), 20.9 (C$_{Ac}$), 18.0 (C-6$_A$).

After adding 0.5 M NaOMe (53.8 mL, 26.9 mmol, 1.1 eq.) to the oil obtained (21.0 g, 24.5 mmol) in solution in DCM/MeOH mixture (11/8, 250 mL), the reaction mixture is refluxed. After 2 h, as there is no further progress of the reaction (Tol/EtOAc, 9/1, Chex/EtOAc, 73/27), it is stopped. After return to RT, it is neutralized by adding DOWEX (H$^+$) ion-exchange resin, then filtered on a frit. The resin is washed with DCM/MeOH mixture and the solvents are evaporated. The yellow oil obtained is purified by silica gel chromatography (Tol/EtOAc 92/8→9/1) to give, in the order of elution, the desired disaccharide 21 (Rf=0.3 and 0.45, 13.6 g, 61% over three stages) then the β stereoisomer 36 (Rf=0.15 and 0.35, 3.4 g, 15% over three stages). The two disaccharides 21 and 36 are isolated in the form of colorless oils. The condensation products are obtained at an overall yield of 76% over three stages, in an α/β ratio of 8/2.

21: Rf=0.45 (Chex/EtOAc, 73/27)

$^1$H NMR (CDCl$_3$), δ7.25-7.02 (m, 25H, CH$_{Ph}$), 5.78 (m, 1H, CH=), 5.18 (m, 1H, J$_{trans}$=17.3 Hz, =CH$_2$), 5.10 (m, 1H, J$_{cis}$=10.4 Hz, =CH$_2$), 4.85 (d, 1H, J=11.0 Hz, H$_{Bn}$), 4.81 (m, 3H, H-1$_E$, H-1$_A$, H$_{Bn}$), 4.73 (d, 2H, J=11.5 Hz, H$_{Bn}$), 4.60 (m, 3H, H$_{Bn}$), 4.39 (d, 2H, J=12.0 Hz, H$_{Bn}$), 4.30 (d, 1H, H$_{Bn}$), 4.07 (m, 1H, H$_{All}$), 3.99 (pt, 1H, H-3$_E$), 3.95-3.92 (m, 2H, H-3$_A$, H$_{All}$), 3.90-3.83 (m, 2H, J$_{4,5}$=9.1 Hz, H-2$_A$, H-5$_E$), 3.68 (dq, 1H, J$_{4,5}$=9.3 Hz, H-5$_A$), 3.63 (pt, 1H, J$_{3,4}$=9.7 Hz, H-4$_E$), 3.51 (dd, 1H, J$_{1,2}$=3.6 Hz, J$_{2,3}$=9.6 Hz, H-2$_E$), 3.41 (pt, 1H, J$_{3,4}$=9.4 Hz, H-4$_A$), 3.37 (dd, 1H, J$_{5,6b}$=2.7 Hz, J$_{6a,6b}$=10.9 Hz, H-6b$_E$), 3.30 (bs, 1H, OH), 3.24 (dd, 1H, J$_{5,6a}$=1.8 Hz, H-6a$_E$), 1.27 (d, 3H, J$_{5,6}$=6.2 Hz, H-6$_A$).

$^{13}$C NMR (CDCl$_3$), δ: 139.0-137.9 (C$_{Ph}$), 134.2 (CH=), 129.4-127.9 (CH$_{Ph}$), 117.7 (=CH$_2$), 98.6 (C-1$_E$, $^1$J$_{CH}$=166.3 Hz), 94.4 (C-1$_A$, $^1$J$_{CH}$=166.9 Hz), 82.8 (C-3$_E$), 79.7 (C-4$_A$), 79.3 (C-2$_E$), 78.1 (C-4$_E$), 77.7 (C-3$_A$), 77.0, 76.0, 75.3, 74.7, 73.8 (5C, $C_{Bn}$), 71.1 (C-$5_E$), 68.3 (C-$6_E$), 68.2 ($C_{All}$), 67.8 (C-$2_A$), 67.6 (C-$5_A$), 18.3 (C-$6_A$).

36: Rf=0.35 (Chex/EtOAc, 73/27)

$^1$H NMR (CDCl$_3$), δ7.43-7.28 (m, 25H, CH$_{Ph}$), 5.95 (m, 1H, CH=), 5.36 (m, 1H, $J_{trans}$=17.2 Hz, =CH$_2$), 5.26 (m, 1H, $J_{cis}$=10.4 Hz, =CH$_2$), 5.04 (d, 1H, J=11.1 Hz, H$_{Bn}$), 4.98 (m, 2H, H$_{Bn}$), 4.93 (bs, 1H, H-$1_A$), 4.90 (m, 2H, H$_{Bn}$), 4.81 (d, 1H, $J_{1,2}$=7.5 Hz, H-$1_E$), 4.81 (m, 1H, J=11.2 Hz, H$_{Bn}$), 4.65 (m, 4H, H$_{Bn}$), 4.26 (m, 1H, H$_{All}$), 4.25-4.21 (m, 2H, H-$3_A$, H-$2_A$), 4.05 (m, 1H, H$_{All}$), 3.89 (m, 1H, H-$5_A$), 3.80-3.63 (m, 6H, H-$6a_E$, H-$3_E$, H-$4_E$, H-$6b_E$, H-$4_A$, H-$2_E$), 3.60 (m, 1H, H-$5_E$), 3.33 (bs, 1H, OH), 1.40 (d, 3H, $J_{5,6}$=6.3 Hz, H-$6_A$).

$^{13}$C NMR (CDCl$_3$), δ: 138.9-138.3 ($C_{Ph}$), 134.4 (CH=), 129.5-127.9 (CH$_{Ph}$), 117.8 (=CH$_2$), 103.0 (C-$1_E$, $^1J_{CH}$=159.5 Hz), 99.1 (C-$1_A$, $^1J_{CH}$=167.6 Hz), 85.3 (C-$3_E$), 82.6 (C-$2_E$), 81.4 (C-$3_A$), 80.5 (C-$4_A$), 78.2 (C-$4_E$), 76.0, 75.5, 75.4, 75.1 (4C, $C_{Bn}$), 75.0 (C-$5_E$), 74.0 ($C_{Bn}$), 70.5 (C-$2_A$), 69.3 (C-$6_E$), 68.3 ($C_{All}$), 68.0 (C-$5_A$), 18.4 (C-$6_A$).

Propyl α-D-glucopyranosyl-(1→3)-α-L-rhamnopyranoside I

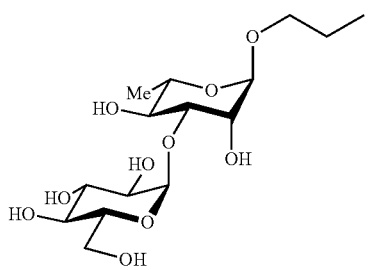

Chemical Formula: $C_{15}H_{28}O_{10}$
Exact Mass: 368.1682
Molecular Weight: 368.3768

Pd—C 10% (420 mg) is added to a degassed solution of disaccharide 21 (500 mg, 610 μmol) in a mixture of ethanol (24 mL) and acetic acid (70.0 μL, 1.2 mmol, 2 eq.). The suspension is saturated with hydrogen at atmospheric pressure and stirred at RT overnight. Monitoring by TLC (iPrOH/H$_2$O/NH$_3$, 7/1/2 and Chex/EtOAc, 73/27) shows the disappearance of 21 (Rf=1 and 0.45, respectively) and the appearance of a new, more polar compound (Rf=0.6 and 0, respectively). Then the reaction mixture is filtered on Celite and then concentrated in a rotary evaporator. The residue obtained is purified on a C-18 column (H$_2$O/CH$_3$CN, 100/0→9/1) to give the target I as a white solid (187 mg, 83%).

Rf=0.6 (iPrOH/H$_2$O/NH$_3$, 7/1/2).

$^1$H NMR (D$_2$O), δ5.03 (d, 1H, $J_{1,2}$=3.8 Hz, H-$1_E$), 4.81 (d, 1H, $J_{1,2}$=1.6 Hz, H-$1_A$), 4.10 (dd, 1H, $J_{2,3}$=2.2 Hz, H-$2_A$), 3.92 (m, 1H, H-$5_A$), 3.80-3.70 (m, 5H, H-$3_A$, H-$3_E$, H-$6a_E$, H-$6b_E$, H-$5_A$), 3.62 (m, 1H, H$_{Pr}$), 3.56-3.45 (m, 3H, H-$2_E$, H-$4_A$, H$_{Pr}$), 3.42 (pt, 1H, $J_{3,4}$=9.3 Hz, H-$4_E$), 1.63 (sex, 2H, CH$_2$), 1.27 (d, 3H, $J_{5,6}$=6.2 Hz, H-$6_A$), 0.88 (t, 3H, J=7.4 Hz, CH$_3$).

$^{13}$C NMR (D$_2$O), δ99.6 (C-$1_A$, $^1J_{CH}$=170.2 Hz), 95.9 (C-$1_E$, $^1J_{CH}$=172.7 Hz), 76.1 (C-$3_A$), 73.3 (C-$3_E$), 72.1 (C-$5_E$), 71.8 (C-$2_E$), 70.7 (C-$4_A$), 70.0 ($C_{Pr}$), 69.8 (C-$4_E$), 69.0 (C-$5_A$), 67.3 (C-$2_A$), 60.7 (C-$6_E$), 22.4 (CH$_2$), 17.1 (C-$6_A$), 10.3 (CH$_3$).

HRMS (ESI$^+$): [M+Na]$^+$ C$_{15}$H$_{28}$O$_{10}$Na m/z
theoretical: 391.1580
m/z measured: 391.1556

Method 2:

Allyl(3,4,6-tri-O-acetyl-2-deoxy-2-trichloroacetamido-β-D-glucopyranosyl)-(1→2)-[2,3,4,6-tetra-O-benzyl-α-D-glucopyranosyl-(1→3)]-4-O-benzyl-α-L-rhamnopyranoside 22

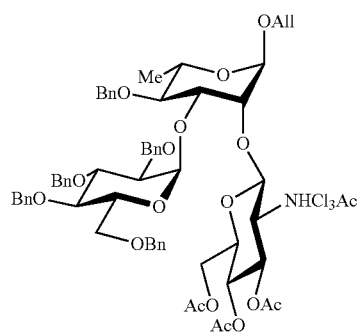

Chemical Formula: $C_{64}H_{72}Cl_3NO_{18}$
Exact Mass: 1247.3815
Molecular Weight: 1249.6114

TMSOTf (40.0 μL, 230 μmol, 0.2 eq.) is added to a solution of acceptor 21$^{45}$ (920 mg, 1.13 mmol) and of donor 1 (800 mg, 1.3 mmol, 1.2 eq.) in DCM (24 mL), in the presence of molecular sieve 4 Å (1.0 g), stirred under argon at −78° C. After stirring for 3 h, the ethanol-dry ice bath is withdrawn and stirring is continued for 30 min, after which time monitoring by TLC (Chex/EtOAc, 7/3) indicates the disappearance of the acceptor (Rf=0.5) and the appearance of a new, more polar compound (Rf=0.2). The reaction is stopped by adding triethylamine (0.2 mL), then the reaction mixture is filtered and then concentrated in a rotary evaporator. The yellow oil obtained is purified by silica gel chromatography (Chex/EtOAc, 8/2→7/3) to obtain the allyl glycoside 22 as a white solid (1.3 g, 92%).

Rf=0.2 (Chex/EtOAc, 7/3).

$^1$H NMR (CDCl$_3$), δ7.40-7.03 (m, 26H, NH, CH$_{Ph}$), 5.88 (m, 1H, CH=), 5.29 (m, 1H, $J_{trans}$=17.2 Hz, =CH$_2$), 5.20 (m, 1H, $J_{cis}$=10.4 Hz, =CH$_2$), 5.22-5.16 (m, 3H, H-$1_E$, 2H$_{Bn}$), 5.06 (s, 2H, H$_{Bn}$), 5.01 (pt, 1H, $J_{3,4}$=9.7 Hz, H-$4_D$), 4.85 (d, 1H, $J_{1,2}$=1.5 Hz, H-$1_A$), 4.86-4.75 (m, 3H, H-$1_D$, H-$3_D$, H$_{Bn}$), 4.72 (d, 1H, J=10.1 Hz, H$_{Bn}$), 4.55 (m, 2H, H$_{Bn}$), 4.45 (d, 1H, J=10.9 Hz, H$_{Bn}$), 4.30 (d, 1H, J=12.0 Hz, H$_{Bn}$), 4.25-4.12 (m, 4H, H-$2_D$, H-$3_A$, H-$3_E$, H$_{All}$), 4.07-3.99 (m, 3H, H-$6a_D$, H-$6b_D$, H-$5_E$), 3.98-3.90 (m, 2H, H-$2_A$, H$_{All}$), 3.91 (dd, 1H, $J_{1,2}$=3.6 Hz, H-$2_E$), 3.80 (pt, 1H, $J_{3,4}$=9.2 Hz, H-$4_E$), 3.71 (m, 1H, H-$5_A$), 3.45 (pt, 1H, $J_{3,4}$=9.8 Hz, H-$4_A$), 3.37 (m, 2H, H-$6a_E$, H-$6b_E$), 2.94 (m, 1H, H-$5_D$), 2.12, 2.02 (2 s, 9H, H$_{Ac}$), 1.40 (d, 3H, $J_{5,6}$=6.2 Hz, H-$6_A$).

$^{13}$C NMR (CDCl$_3$), δ170.6, 170.5, 169.1 (3C, $C_{Ac}$), 161.9 ($C_{NTCA}$), 138.5-137.6 ($C_{Ph}$), 133.7 (CH=), 128.9-127.2 (CH$_{Ph}$), 117.2 (=CH$_2$), 100.8 (C-$1_D$, $^1J_{CH}$=161.0 Hz), 98.1 (C-$1_A$, $^1J_{CH}$=172.2 Hz), 94.5 (C-$1_E$, $^1J_{CH}$=165.5 Hz), 92.7 (CCl$_3$), 83.4 (C-$3_E$), 79.6 (C-$4_A$), 78.9 (C-$2_E$), 78.5 (C-$4_E$), 76.0, 75.1, 74.8 (3C, $C_{Bn}$), 74.6 (C-$3_A$), 74.4 (C-$2_A$), 73.9, 73.3 (2C, $C_{Bn}$), 73.1 (C-$3_D$), 71.6 (C-$5_D$), 69.8 (C-$5_E$), 68.1 (C-$5_A$), 67.9 ($C_{All}$), 67.8 (C-$4_D$), 67.7 (C-$6_E$), 61.6 (C-$6_D$), 55.5 (C-$2_D$), 20.7, 20.6, 20.5 (3C, $C_{Ac}$), 17.8 (C-$6_A$).

HRMS (ESI⁺): [M+Na]⁺ $C_{64}H_{72}NO_{18}{}^{35}Cl_3Na$ m/z theoretical:
1270.3713
m/z measured:
1270.3662
[M+NH₄]⁺ $C_{64}H_{72}NO_{18}{}^{35}Cl_3NH_4$ m/z theoretical:
1265.4159
m/z measured:
1265.4180

Allyl(3-O-acetyl-2-deoxy-4,6-O-isopropylidene-2-trichloroacetarado-β-D-glucopyranosyl)-(1→2)-[2,3,4,6-tetra-O-benzyl-α-D-glucopyranosyl-(1→3)]-4-O-benzyl-α-L-rhamnopyranoside 23

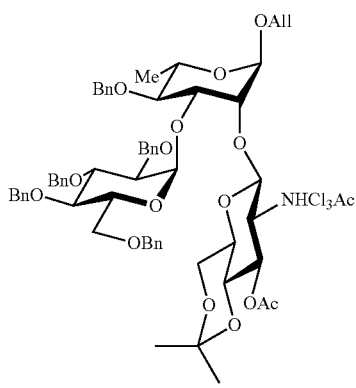

Chemical Formula: $C_{63}H_{72}Cl_3NO_{16}$
Exact Mass: 1203.3917
Molecular Weight: 1205.6019

TMSOTf (59.0 μL, 330 μmol, 0.3 eq.) is added to a solution of acceptor 21⁴⁵ (900 mg, 1.1 mmol) and of donor 2 (850 mg, 1.5 mmol, 1.4 eq.) in DCM (30 mL), in the presence of molecular sieve 4 Å (0.9 g), stirred under argon at −78° C. After stirring for 6 h, the ethanol-dry ice bath is withdrawn and stirring is continued for 30 min, after which time monitoring by TLC (Chex/EtOAc, 7/3) indicates the almost complete disappearance of the acceptor (Rf=0.5) and the appearance of a new, more polar compound (Rf=0.35). The reaction is stopped by adding triethylamine (0.1 mL), then the reaction mixture is filtered and concentrated in a rotary evaporator. The yellow oil obtained is purified by silica gel chromatography (Chex/EtOAc, 8/2→7/3) to obtain the allyl glycoside 23 as a white solid (1.2 g, 90%).

Rf=0.35 (Chex/EtOAc, 7/3).

¹H NMR (CDCl₃), δ7.42-7.04 (m, 26H, NH, $CH_{Ph}$), 5.89 (m, 1H, CH=), 5.28 (m, 1H, $J_{trans}$=17.2 Hz, =CH₂), 5.19 (m, 1H, $J_{cis}$=10.4 Hz, =CH₂), 5.13-5.1 (m, 3H, $J_{1,2}$=3.3 Hz, $2H_{Bn}$, $H-1_E$), 5.04 (d, 2H, $H_{Bn}$), 4.79-4.74 (m, 3H, $H-3_D$, $H-1_A$, $H_{Bn}$), 4.71 (m, 2H, $H-1_D$, $H_{Bn}$), 4.58-4.51 (m, 2H, $H_{Bn}$), 4.45 (d, 1H, J=10.9 Hz, $H_{Bn}$), 4.29 (d, 1H, J=12.0 Hz, $H_{Bn}$), 4.18-4.10 (m, 4H, $H-3_A$, $H-3_E$, $H_{All}$, $H-2_D$), 4.07 (m, 1H, $H-5_E$), 3.97 (bs, 1H, $H-2_A$), 3.94 (m, 1H, $H_{All}$), 3.91-3.83 (m, $2H, H-2_E, H-6a_D$), 3.78 (pt, 1H, $J_{3,4}$=9.4 Hz, $H-4_E$), 3.75-3.64 (m, 3H, $H-6b_D$, $H-5_A$, $H-4_D$), 3.43 (pt, 1H, $J_{3,4}$=9.6 Hz, $H-4_A$), 3.41 (m, 1H, $H-6a_E$, $H-6b_E$), 2.71 (m, 1H, $H-5_D$), 2.07 (s, 3H, $H_{Ac}$), 1.45 (s, 3H, $H_{iPr}$), 1.40 (S, 3H, $H_{iPr}$), 1.39 (d, 3H, $J_{5,6}$=6.2 Hz, $H-6_A$).

¹³C NMR (CDCl₃), δ171.2 ($C_{Ac}$), 162.5 ($C_{NTCA}$), 138.8-137.8 ($C_{Ph}$), 134.1 (CH=), 129.5-127.7 ($CH_{Ph}$), 117.6 (=CH₂), 101.8 ($C-1_D$, $^1J_{CH}$=164.4 Hz), 100.1 ($C_{iPr}$), 98.7 ($C-1_A$, $^1J_{CH}$=173.7 Hz), 94.9 ($C-1_E$, $^1J_{CH}$=168.6 Hz), 93.1 (CCl₃), 83.8 ($C-3_E$), 80.1 ($C-4_A$) 78.9 (2C, $C-2_E$, $C-4_E$), 76.5, 75.5, 75.3 (3C, $C_{Bn}$), 74.7 ($C-3_A$), 74.6 ($C-2_A$), 74.4, 73.8 (2C, $C_{Bn}$), 72.8 ($C-3_D$), 71.5 ($C-4_D$), 70.1 ($C-5_E$), 68.6 ($C-5_A$), 68.2 (2C, $C_{All}$, $C-6_E$), 67.6 ($C-5_D$), 62.4 ($C-6_D$), 56.8 ($C-2_D$), 29.4 ($C_{iPr}$), 21.3 ($C_{Ac}$), 19.3 ($C_{iPr}$), 18.3 ($C-6_A$).

HRMS (ESI⁺): [M+Na]⁺ $C_{63}H_{72}NO_{16}{}^{35}Cl_3Na$ m/z theoretical:
1226.3814
m/z measured:
1226.3860
[M+NH₄]⁺ $C_{63}H_{72}NO_{16}{}^{35}Cl_3NH_4$ m/z theoretical:
1221.4260
m/z measured:
1221.4227
[M+K]⁺ $C_{63}H_{72}NO_{16}{}^{35}Cl_3K$ m/z theoretical:
1242.3553
m/z measured:
1242.3586

Allyl(2-deoxy-2-trichloroacetamido-β-D-glucopyranosyl)-(1→2)-[2,3,4,6-tetra-O-benzyl-α-D-glucopyranosyl-(1→3)]-4-O-benzyl-α-L-rhamnopyranoside 37

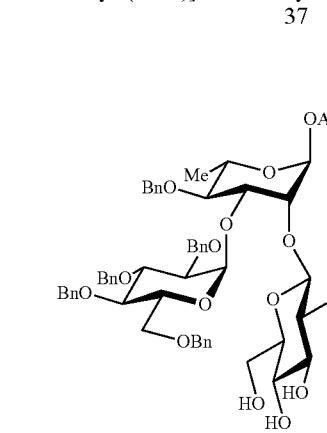

Chemical Formula: $C_{58}H_{66}Cl_3NO_{15}$
Exact Mass: 1121.3498
Molecular Weight: 1123.5013

After adding 0.5 M NaOMe (160 μL, 8.0 μmol, 0.2 eq.) to the tri-O-acetyl 22 (500 mg, 40 μmol) in solution in MeOH (3 mL), the reaction mixture is stirred for 15 min and its development is monitored by TLC (Chex/EtOAc, 1/1, DCM/MeOH, 95/5). After observing the disappearance of 22 (Rf=0.7 and 0.95, respectively) and the appearance of a more polar product (Rf=0.05 and 0.3, respectively), the reaction mixture is neutralized by adding DOWEX (H⁺) ion-exchange resin, and then filtered on a frit. The resin is washed with DCM/MeOH mixture and the solvents are evaporated. The yellow oil obtained is purified by silica gel chromatography (DCM/MeOH, 99/1→96/4) to give the triol 37 as a white solid (420 mg, 94%).

Rf=0.3 (DCM/MeOH, 7/3).

¹H NMR (CDCl₃), δ7.38-7.06 (m, 26H, NH, $CH_{Ph}$), 5.88 (m, 1H, CH=), 5.29 (m, 1H, $J_{trans}$=17.2 Hz, =CH₂), 5.20 (m, 1H, $J_{cis}$=10.4 Hz, =CH₂), 5.10 (d, 1H, $J_{1,2}$=3.7 Hz, $H-1_E$), 5.07 (m, 3H, J=10.0 Hz, $H_{Bn}$), 4.90-4.87 (m, 2H, $H-1_A$, $H_{Bn}$), 4.79-4.70 (m, 2H, J=11.0 Hz, $H_{Bn}$), 4.62 (d, 1H, $J_{1,2}$=8.3 Hz, $H-1_D$), 4.61-4.46 (m, 3H, J=11.0 Hz, $H_{Bn}$), 4.30 (d, 1H, J=12.0 Hz, $H_{Bn}$), 4.17-4.09 (m, 4H, $H-3_A$, $H-5_E$, $H_{All}$, H-3$_E$,), 4.01 (m, 2H, H-2$_A$, H$_{All}$), 3.84-3.78 (m, 5H, H-2$_E$, H-4$_E$, H-2$_D$, H-6a$_D$, H-6b$_D$), 3.63 (m, 1H, H-5$_A$), 3.51 (pt, H, J$_{3,4}$=9.2 Hz, H-4$_D$), 3.44 (m, 3H, H-4$_A$, H-6a$_E$, H-6b$_E$), 3.01 (m, 2H, H-5$_D$, OH), 2.57 (pt, 1H, J$_{2,3}$=9.6 Hz, H-3$_D$), 2.56 (bs, 1H, OH), 1.40 (d, 3H, J$_{5,6}$=6.2 Hz, H-6$_A$).

$^{13}$C NMR (CDCl$_3$), δ164.4 (C$_{NTCA}$), 138.9-137.8 (C$_{Ph}$), 129.5 (CH=), 129.1-127.7 (CH$_{Ph}$), 117.7 (=CH$_2$), 101.3 (C-1$_D$, $^1$J$_{CH}$=160.3 Hz), 98.6 (C-1$_A$, $^1$J$_{CH}$=171.6 Hz), 94.8 (C-1$_E$, $^1$J$_{CH}$=166.4 Hz), 92.9 (CCl$_3$), 83.6 (C-3$_E$), 80.2 (C-4$_A$), 79.5, 79.0 (2C, C-2$_E$, C-4$_E$), 76.6 (C$_{Bn}$), 76.0 (C-3$_D$), 75.6 (C$_{Bn}$), 75.5 (C-5$_D$), 75.4, 75.3 (2C, C$_{Bn}$), 74.8 (C-3$_A$), 74.6 (C-2$_A$), 73.8 (C$_{Bn}$), 71.6 (C-4$_D$), 70.3 (C-5$_E$), 68.7 (C-5$_A$), 68.3 (C$_{All}$), 66.2 (C-6$_E$), 62.4 (C-6$_D$), 58.6 (C-2$_D$), 18.3 (C-6$_A$).

HRMS (ESI$^+$): [M+Na]$^+$ C$_{58}$H$_{66}$NO$_{15}$$^{35}$Cl$_3$Na m/z theoretical:
1144.3396
m/z measured:
1144.3389
[M+NH$_4$]$^+$ C$_{58}$H$_{66}$NO$_{15}$$^{35}$Cl$_3$NH$_4$ m/z theoretical:
1139.3842
m/z measured:
1139.3890

Propyl(2-acetamido-2-deoxy-β-D-glucopyranosyl)-(1→2)-[α-D-glucopyranosyl-(1→3)]-4-O-benzyl-α-L-rhamnopyranoside II

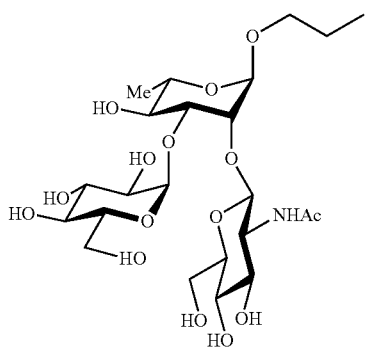

Chemical Formula: C$_{23}$H$_{41}$NO$_{15}$
Exact Mass: 571.2476
Molecular Weight: 571.5693

Pd—C 10% (280 mg) is added to a degassed solution of trisaccharide 37 (412 mg, 360 μmol) in a mixture of ethanol (30 mL) and 1M HCl (280 μL). The suspension is saturated with hydrogen at atmospheric pressure and stirred at RT overnight. Monitoring by TLC (iPrOH/H$_2$O/NH$_3$, 7/1/2 and DCM/MeOH, 92/8) shows the disappearance of 37 (Rf=1 and 0.35, respectively) and the appearance of a new, more polar compound (Rf=0.45 and 0, respectively). Then the reaction mixture is filtered on Celite and then concentrated in a rotary evaporator. The residue obtained is then dissolved in a mixture of ethanol (30 mL) and triethylamine (153 μL, 1.1 mmol, 3 eq.). Pd—C 10% (280 mg) is added to the reaction mixture. The suspension is then saturated with hydrogen at atmospheric pressure and stirred at RT overnight. Monitoring by TLC (iPrOH/H$_2$O/NH$_3$, 7/1/2) shows the disappearance of the intermediate (Rf=0.45) and the appearance of a new, more polar compound (Rf=0.4). Then the reaction mixture is filtered on Celite and then concentrated in a rotary evaporator. The residue obtained is purified on a C-18 column (H$_2$O/CH$_3$CN, 100/0→9/1) to give the target II as a white solid (144 mg, 69%).

Rf=0.45 (iPrOH/H$_2$O/NH$_3$, 7/1/2).

$^1$H NMR (D$_2$O), δ5.10 (d, 1H, J$_{1,2}$=3.7 Hz, H-1$_E$), 4.89 (d, 1H, J$_{1,2}$=1.8 Hz, H-1$_A$), 4.79 (d, 1H, J$_{1,2}$=8.5 Hz, H-1$_D$), 4.23 (dd, 1H, J$_{2,3}$=2.3 Hz, H-2$_A$), 4.01 (m, 1H, H-5$_E$), 3.89-3.86 (m, 3H, H-3$_A$, H-6a$_D$, H-6b$_D$), 3.80 (pt, 1H, J$_{3,4}$=9.7 Hz, H-3$_E$), 3.78-3.64 (m, 6H, H-6b$_D$, H-6a$_E$, H-6b$_E$, H-2$_D$, H-2$_E$, H-5$_A$), 3.60 (m, 1H, H$_{Pr}$), 3.50-3.44 (m, 2H, H-4$_E$, H$_{Pr}$), 3.42-3.38 (m, 3H, H-5$_D$, H-3$_D$, H-4$_D$), 3.32-3.34 (pt, 1H, J$_{3,4}$=9.7 Hz, H-4$_A$), 2.10 (s, 3H, H$_{Ac}$), 1.57 (sex, 2H, CH$_2$), 1.24 (d, 3H, J$_{5,6}$=6.2 Hz, H-6$_A$), 0.87 (t, 3H, J=7.4 Hz, CH$_3$).

$^{13}$C NMR (D$_2$O), δ174.8 (C$_{NAC}$), 102.3 (C-1$_D$, $^1$J$_{CH}$=163.4 Hz), 99.6 (C-1$_A$, $^1$J$_{CH}$=171.3 Hz), 95.1 (C-1$_E$, $^1$J$_{CH}$=169.5 Hz), 76.3 (C-4$_D$), 74.6 (2C, C-2$_A$, C-3$_D$), 74.5 (C-3$_A$), 73.5 (C-3$_E$), 71.8 (C-5$_E$), 71.7 (C-2$_E$), 71.3 (C-4$_E$), 70.2 (C5-$_D$), 70.0 (C$_{Pr}$), 69.8 (C-4$_E$), 69.3 (C-5$_A$), 61.0 (C-6$_D$), 60.7 (C-6$_E$), 56.0 (C-2$_D$), 23.0 (C$_{NAC}$), 22.4 (CH$_2$), 17.1 (C-6$_A$), 10.3 (CH$_3$).

HRMS (ESI$^+$): [M+Na]$^+$ C$_{23}$H$_{41}$NO$_{15}$Na m/z theoretical:
594.2374
m/z measured:
594.2379

Allyl(2-deoxy-4,6-O-isopropylidene-2-trichloroacetamido-β-D-glucopyranosyl)-(1→2)-[2,3,4,6-tetra-O-benzyl-α-D-glucopyranosyl-(1→3)]-4-O-benzyl-α-L-rhamnopyranoside 38

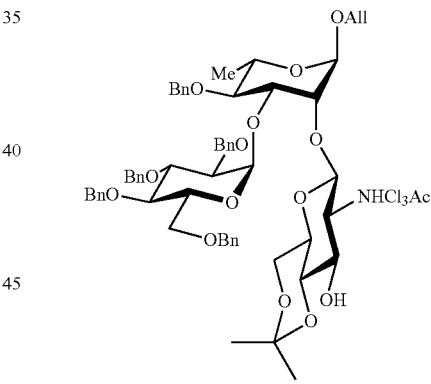

Chemical Formula: C$_{61}$H$_{70}$Cl$_3$NO$_{15}$
Exact Mass: 1161.3811
Molecular Weight: 1163.5652

Route 1:

The triol 37 (500 mg, 450 μmol) and 2-methoxypropene (85 μL, 890 μmol, 2 eq.) are dissolved in DMF (3 mL). CSA (10 mg, 23 μmol, 0.1 eq.) is added in portions to the reaction mixture. While stirring at RT, the reaction is monitored by TLC (Chex/EtOAc, 1/1 and DCM/MeOH, 96/4). After stirring for 6 h, the transformation of 37 (Rf=0.05 and 0.1, respectively) to a less polar product (Rf=0.75 and 0.85, respectively) is almost complete. The reaction mixture is neutralized with triethylamine (0.2 mL) and then concentrated in a rotary evaporator. The solid obtained is purified by silica gel chromatography (Chex/EtOAc, 9/1→1/1) to give the alcohol 38 as a white solid (390 mg, 76%).

Route 2:

TMSOTf (65.7 μL, 366 μmol, 0.2 eq.) is added to a solution of acceptor 21 (1.5 g, 1.8 mmol) and of donor 1 (1.3 g, 2.2 mmol, 1.2 eq.) in DCM (37 mL), in the presence of molecular sieve 4 Å (1.45 g), stirred under argon at −78° C. After stirring for 3 h, the ethanol-dry ice bath is withdrawn and stirring is continued for 30 min, after which time monitoring by TLC (Chex/EtOAc, 7/3) indicates the disappearance of 21 (Rf=0.5) and the appearance of a new, more polar compound (Rf=0.2). The reaction is stopped by adding triethylamine (0.2 mL), then the reaction mixture is filtered and then concentrated in a rotary evaporator. The yellow oil obtained is purified by silica gel chromatography (Chex/EtOAc, 8/2→7/3), obtaining a white solid (2.5 g).

After adding 0.5 M NaOMe (800 μL, 400 μmol, 0.2 eq.) to the preceding raw product (2.5 g, 2.0 mmol) in solution in MeOH (5 mL), the reaction mixture is stirred for 15 min and its development is monitored by TLC (Chex/EtOAc, 1/1, DCM/MeOH, 95/5). After observing the disappearance of the starting product (Rf=0.7 and 0.95, respectively) and the appearance of a more polar product (Rf=0.05 and 0.3, respectively), the reaction mixture is neutralized by adding DOWEX (H$^+$) ion-exchange resin, then filtered on a frit. The resin is washed with DCM/MeOH mixture and the solvents are evaporated. The yellow oil obtained is used directly in the next stage (2.2 g).

The preceding raw product (2.2 g, 2.0 mmol) is dissolved in DMF (15 mL) and 2-methoxypropene (385 μL, 4.0 mmol, 2 eq.). CSA (93 mg, 400 μmol, 0.2 eq.) is added in portions to the reaction mixture. While stirring at RT, the reaction is monitored by TLC (Chex/EtOAc, 1/1 and DCM/MeOH, 96/4). After stirring for 6 h, the transformation of the starting product (Rf=0.05 and 0.12, respectively) to a less polar product (Rf=0.75 and 0.85, respectively) is almost complete. The reaction mixture is neutralized with triethylamine (0.2 mL) and then concentrated in a rotary evaporator. The solid obtained is purified by silica gel chromatography (Chex/EtOAc, 9/1→1/1) to give the alcohol 38 as a white solid (1.8 g, 86%).

Route 3:

After adding 0.5 M NaOMe (108 μL, 54 μmol, 0.2 eq.) to the allyl glycoside 23 (328 mg, 270 μmol) in solution in MeOH (5 mL), the reaction mixture is stirred at RT and the reaction is monitored by TLC (Chex/EtOAc, 1/1, Chex/EtOAc, 7/3). After one night, the transformation of 23 (Rf=0.75 and 0.5, respectively) to a less polar product (Rf=0.6 and 0.2, respectively) is total. The reaction mixture is therefore neutralized by adding DOWEX (H$^+$) ion-exchange resin, then filtered on a frit. The resin is washed with DCM/MeOH mixture and the solvents are evaporated. The product obtained is purified by silica gel chromatography (Chex/EtOAc+NEt$_3$, 7/3→6/4) to give the alcohol 38 as a white solid (241 mg, 76%).

Route 4:

TMSOTf (245.0 μL, 1.4 mmol, 0.3 eq.) is added to a solution of acceptor 21 (3.6 g, 4.5 mmol) and of donor 2 (3.5 g, 6.3 mmol, 1.4 eq.) in DCM (8 mL), in the presence of molecular sieve 4 Å (3.7 g), stirred under argon at −78° C. After stirring for 6 h, the ethanol-dry ice bath is withdrawn and stirring is continued for 30 min, after which time monitoring by TLC (Chex/EtOAc, 7/3) indicates the disappearance of 21 (Rf=0.5) and the appearance of a new, more polar compound (Rf=0.35). The reaction is stopped by adding triethylamine (0.1 mL), then the reaction mixture is filtered and concentrated in a rotary evaporator. The yellow oil obtained is purified by silica gel chromatography (Chex/EtOAc, 8/2→7/3) to obtain a white solid (5.3 g).

After adding 0.5 M NaOMe (4.5 mL, 2.2 mmol, 0.5 eq.) to the preceding raw product (5.3 g, 4.5 mmol) in solution in MeOH (60 mL), the reaction mixture is stirred at RT and the reaction is monitored by TLC (Chex/EtOAc, 6/4). After 4 h, the transformation of the starting product (Rf=0.7) to a less polar product (Rf=0.5) is total. The reaction mixture is therefore neutralized by adding DOWEX (H$^+$) ion-exchange resin, then filtered on a frit. The resin is washed with DCM/MeOH mixture and the solvents are evaporated. The product obtained is purified by silica gel chromatography (Chex/EtOAc+NEt$_3$, 7/3→6/4) to give the alcohol 38 as a white solid (4.5 g, 87%).

Rf=0.45 (Chex/EtOAc, 6/4).

$^1$H NMR (CDCl$_3$), δ7.42-7.08 (m, 26H, NH, CH$_{Ph}$), 5.89 (m, 1H, CH=), 5.29 (m, 1H, J$_{trans}$=15.6 Hz, =CH$_2$), 5.21 (m, 1H, J$_{cis}$=10.4 Hz, =CH$_2$), 5.10 (d, 1H, J$_{1,2}$=3.6 Hz, H-1$_E$), 5.15-4.91 (m, 3H, H$_{Bn}$), 4.90 (d, 1H, J=12.1 Hz, H$_{Bn}$), 4.82-4.79 (m, 2H, H-1$_A$, H$_{Bn}$), 4.74 (d, 1H, J=10.0 Hz, H$_{Bn}$), 4.62-4.49 (m, 4H, H$_{Bn}$, H-1$_D$, 2H$_{Bn}$), 4.34 (d, 1H, J=10.9 Hz, H$_{Bn}$), 4.18-4.11 (m, 4H, H-3$_A$, H-5$_E$, H$_{All}$, H-3$_E$), 4.02 (bs, 1H, H-2$_A$), 4.01 (m, 1H, H$_{All}$), 3.91-3.82 (m, 4H, H-2$_E$, H-4$_E$, H-2$_D$, H-6a$_D$), 3.76-3.71 (m, 2H, H-6a$_E$, H-5$_A$), 3.51-3.42 (m, 4H, H-4$_A$, H-6a$_E$, H-6b$_E$, H-4$_D$), 2.84 (m, 2H, H-5$_D$, OH), 2.48 (pt, 1H, J$_{2,3}$=9.4 Hz, H-3$_D$), 1.51 (s, 3H, H$_{iPr}$), 1.50 (s, 3H, H$_{iPr}$), 1.40 (d, 3H, J$_{5,6}$=6.2 Hz, H-6$_A$).

$^{13}$C NMR (CDCl$_3$), δ164.1 (C$_{NTC4}$), 138.8-137.8 (C$_{Ph}$), 134.2 (CH=), 129.3-127.7 (CH$_{Ph}$), 117.6 (=CH$_2$), 101.5 (C-1$_D$, $^1$J$_{CH}$=163.6 Hz), 100.1 (C$_{iPr}$), 98.7 (C-1$_A$, $^1$J$_{CH}$=174.0 Hz), 94.5 (C-1$_E$, $^1$J$_{CH}$=167.5 Hz), 92.9 (CCl$_3$), 83.6 (C-3$_E$), 80.2 (C-4$_A$), 80.1 C-2$_E$), 79.1 (C-4$_E$), 76.6, 75.8, 75.7, 75.3 (4C, C$_{Bn}$), 74.7 (C-3$_A$), 74.4 (C-4$_D$), 74.0 (C-2$_A$), 73.8 (C$_{Bn}$), 73.4 (C-3$_D$), 70.2 (C-5$_E$), 68.7 (C-5$_A$), 68.2 (2C, C$_{All}$, C-6$_E$), 67.4 (C-5$_D$), 62.3 (C-6$_D$), 59.1 (C-2$_D$), 27.3 (C$_{iPr}$), 19.3 (C$_{iPr}$), 18.3 (C-6$_A$).

HRMS (ESI$^+$): [M+Na]$^+$ C$_{61}$H$_{70}$NO$_{15}$$^{35}$Cl$_3$Na m/z theoretical:
1184.3709
m/z measured:
1184.3669
[M+NH$_4$]$^+$ C$_{61}$H$_{70}$NO$_{15}$$^{35}$Cl$_3$NH$_4$ m/z theoretical:
1179.4155
m/z measured:
1179.4165

Method 3:

Allyl(2-O-acetyl-3,4-di-O-benzyl-α-L-rhamnopyranosyl)-(1→3)-(2-deoxy-4,6-O-isopropylidene-2-trichloroacetamido-β-D-glucopyranosyl)-(1→2)-[2,3,4,6-tetra-O-benzyl-α-D-glucopyranosyl-(1→3)]-4-O-benzyl-α-L-rhamnopyranoside 40

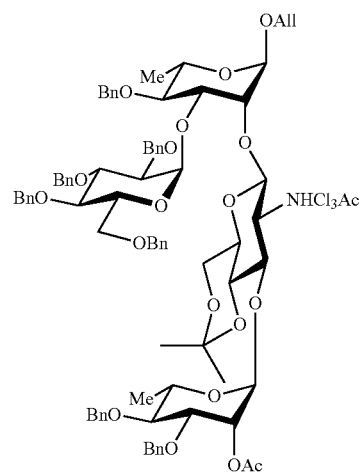

Chemical Formula: C$_{83}$H$_{94}$Cl$_3$NO$_{20}$
Exact Mass: 1529.5435
Molecular Weight: 1531.9882

TMSOTf (24.0 µL, 131 µmol, 0.3 eq.) is added to a solution of acceptor 38 (510 mg, 440 µmol) and of donor 39[67] (350 mg, 660 µmol, 1.5 eq.) in Tol (11 mL), in the presence of molecular sieve 4 Å (350 mg), stirred under argon at −78° C. After stirring for 30 min at −78° C., monitoring by TLC (Chex/EtOAc, 75/25 and Chex/EtOAc, 6/4) indicates the disappearance of 38 (Rf=0.1 and 0.45, respectively) and the appearance of a new, more polar compound (Rf=0.3 and 0.7, respectively). The reaction is stopped by adding triethylamine (0.1 mL), then the reaction mixture is filtered and concentrated in a rotary evaporator. The yellow oil obtained is purified by silica gel chromatography (Chex/EtOAc, 6.5/3.5→1/1), leading in the order of elution to the allyl glycoside 40 as a white solid (480 mg, 72%) and then the diol 41 as a white solid (33 mg, 5%).

Rf=0.7 (Chex/EtOAc, 6/4).

$^{1}$H NMR (CDCl$_3$), δ7.45-7.10 (m, 35H, CH$_{Ph}$), 6.98 (d, 1H, J$_{NH,2}$=8.6 Hz, NH), 5.92 (m, 1H, CH═), 5.37 (m, 1H, H-2$_C$), 5.29 (m, 1H, J$_{trans}$=16.9 Hz, ═CH$_2$), 5.21 (m, 1H, J$_{cis}$=10.6 Hz, ═CH$_2$), 5.17 (d, 1H, J$_{1,2}$=3.6 Hz, H-1$_E$), 5.05-4.90 (m, 3H, H$_{Bn}$), 4.83-4.69 (m, 6H, H-1$_C$, 2H$_{Bn}$, H-1$_A$, 2H$_{Bn}$), 4.64-4.50 (m, 7H, 3H$_{Bn}$, H-1$_D$, 3H$_{Bn}$), 4.34 (d, 1H, J=12.0 Hz, H$_{Bn}$), 4.17-4.14 (m, 3H, H-3$_E$, H$_{All}$, H-3$_A$), 4.12-4.03 (m, 3H, H-5$_E$, H-5$_C$, H-2$_D$), 4.00 (bs, 1H, H-2$_A$), 3.99-3.89 (m, 2H, H$_{All}$, H-3$_C$), 3.90-3.86 (m, 2H, H-2$_E$, H-6a$_D$), 3.84 (pt, 1H, J$_{3,4}$=9.8 Hz, H-4$_E$) 3.74-3.69 (m, 2H, H-6b$_D$, H-5$_A$), 3.50 (pt, 1H, J$_{3,4}$=9.4 Hz, H-4$_D$), 3.49-3.41 (m, 3H, H-4$_A$, H-6a$_E$, H-6b$_E$), 3.40 (pt, 1H, J$_{3,4}$=9.5 Hz, H-4$_C$), 2.84-2.76 (m, 2H, H-5$_D$, H-3$_D$), 2.16 (s, 3H, H$_{Ac}$), 1.51 (s, 3H, H$_{iPr}$), 1.50 (s, 3H, H$_{iPr}$), 1.41 (d, 3H, J$_{5,6}$=6.2 Hz, H-6$_A$), 1.41 (d, 3H, J$_{5,6}$=6.2 Hz, H-6$_C$).

$^{13}$C NMR (CDCl$_3$), δ170.1 (C$_{Ac}$), 162.2 (C$_{NTCA}$), 139.0-137.8 (C$_{Ph}$), 134.3 (CH═), 129.8-127.7 (CH$_{Ph}$), 117.5 (═CH$_2$), 101.7 (C-1$_D$, $^1$J$_{CH}$=161.0 Hz), 99.9 (C$_{iPr}$), 98.9 (C-1$_C$, $^1$J$_{CH}$=169.1 Hz), 98.8 (C-1$_A$, $^1$J$_{CH}$=171.2 Hz), 94.6 (C-1$_E$, $^1$J$_{CH}$=167.6 Hz), 93.5 (CCl$_3$), 83.5 (C-3$_E$), 80.6 (C-2$_E$), 80.2 (C-4$_C$), 80.1 (C-4$_A$), 79.1 (C-4$_E$), 79.0 (C-3$_D$), 78.5 (C-3$_C$), 76.5, 75.7, 75.6, 75.3, 75.2 (5C, C$_{Bn}$), 74.8 (C-3$_A$), 74.1 (C-2$_A$), 73.8 (C$_{Bn}$), 73.0 (C-4$_D$), 72.2 (C$_{Bn}$), 70.3 (C-5$_E$), 69.7 (C-2$_C$), 68.7 (C-5$_A$), 68.3 (C-6$_E$), 68.3 (C-5$_C$), 68.2 (C$_{All}$), 67.4 (C-5$_D$), 62.5 (C-6$_D$), 57.8 (C-2$_D$), 29.5 (C$_{iPr}$), 21.5 (C$_{Ac}$), 19.3 (C$_{iPr}$), 18.4, 18.3 (C-6$_A$, C-6$_C$).

HRMS (ESI$^+$): [M+Na]$^+$ C$_{83}$H$_{94}$NO$_{20}$$^{35}$Cl$_3$Na m/z theoretical:

1552.5332 m/z measured:

1552.5293

[M+NH$_4$]$^+$ C$_{83}$H$_{94}$NO$_{20}$$^{35}$Cl$_3$NH$_4$ m/z theoretical:

1547.5779 m/z measured:

1547.5818

[M+K]$^+$ C$_{83}$H$_{94}$NO$_{20}$$^{35}$Cl$_3$K m/z theoretical:

1568.5072 m/z measured:

1568.5120

Allyl(2-O-acetyl-3,4-di-O-benzyl-α-L-rhamnopyranosyl)-(1→3)-(2-deoxy-2-trichloroacetamido-β-D-glucopyranosyl)-(1→2)-[2,3,4,6-tetra-O-benzyl-α-D-glucopyranosyl-(1→3)]-4-O-benzyl-α-L-rhamnopyranoside 41

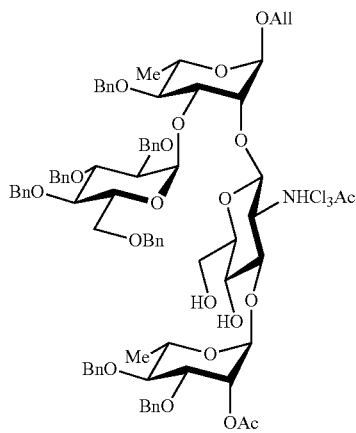

Chemical Formula: C$_{80}$H$_{90}$Cl$_3$NO$_{20}$
Exact Mass: 1489.5122
Molecular Weight: 1491.9243

50% aqueous TFA solution (1.6 mL) is slowly added to a solution of allyl glycoside 40 (79 mg, 52.0 µmol) in DCM (4 mL) at 0° C. The reaction mixture is stirred for 4 h at this temperature, after which time monitoring by TLC (Chex/EtOAc, 6/4) indicates the complete disappearance of 40 (Rf=0.65) and the appearance of a new, more polar compound (Rf=0.3). The reaction mixture is concentrated by coevaporation with Tol (3×10 mL). The yellow oil obtained is purified by silica gel chromatography (Chex/EtOAc, 7/3→6/4) to obtain a white solid corresponding to the expected diol 41 (68 mg, 88%).

Rf=0.3 (Chex/EtOAc, 6/4).

$^{1}$H NMR (CDCl$_3$), δ7.40-7.07 (m, 35H, CH$_{Ph}$), 6.99 (d, 1H, J$_{NH,2}$=8.3 Hz, NH), 5.91 (m, 1H, CH═), 5.31 (m, 1H, H-2$_C$), 5.29 (m, 1H, J$_{trans}$=16.9 Hz, ═CH$_2$), 5.25-5.23 (m, 2H, ═CH$_2$, H-1$_E$), 5.12 (m, 2H, H$_{Bn}$), 5.08 (d, 1H, J=12.6 Hz, H$_{Bn}$), 4.99-4.91 (m, 2H, H$_{Bn}$), 4.85 (d, 1H, J$_{1,2}$=1.5 Hz, H-1$_A$), 4.82 (d, 1H, J=11.1 Hz, H$_{Bn}$), 4.73 (d, 1H, J=10.1 Hz, H$_{Bn}$), 4.67 (d, 1H, J=11.4 Hz, H$_{Bn}$), 4.62-4.51 (m, 6H, 2H$_{Bn}$, H-1$_D$, 3H$_{Bn}$) 4.49 (d, 1H, J$_{1,2}$=1.8 Hz, H-1$_C$), 4.35 (d, 1H, J=11.9 Hz, H$_{Bn}$), 4.22-4.13 (m, 5H, OH-4$_D$, H-3$_A$, H-3$_E$, H$_{All}$, H-5$_E$), 4.04-4.01 (m, 3H, H$_{All}$, H-2$_A$, H-3$_C$), 3.98 (m, 1H, H-2$_D$), 3.96 (m, 1H, H-5$_C$) 3.87-3.82 (m, 3H, H-6a$_D$, H-2$_E$, H-4$_E$), 3.80-3.70 (m, 2H, H-6b$_D$, H-5$_A$), 3.52-3.49 (m, 3H, H-4$_A$, H-6a$_E$, H-6b$_E$), 3.46 (pt, 1H, J$_{3,4}$=9.4 Hz, H-4$_C$), 3.39 (pt, 1H, J$_{3,4}$=9.4 Hz, H-4$_D$), 3.09 (m, 1H, H-5$_D$), 2.09 (m, 4H, H$_{Ac}$, H-3$_D$), 1.41 (d, 3H, J$_{5,6}$=6.2 Hz, H-6$_A$), 1.34 (d, 3H, J$_{5,6}$=6.2 Hz, H-6$_C$).

$^{13}$C NMR (CDCl$_3$), δ170.5 (C$_{Ac}$), 162.3 (C$_{NTCA}$), 138.8-137.8 (C$_{Ph}$), 134.3 (CH═), 129.7-127.8 (CH$_{Ph}$), 117.8 (═CH$_2$), 101.4 (C-1$_D$, $^1$J$_{CH}$=158.6 Hz), 99.5 (C-1$_C$, $^1$J$_{CH}$=169.8 Hz), 98.6 (C-1$_A$, $^1$J$_{CH}$=174.0 Hz), 94.3 (C-1$_E$, $^1$J$_{CH}$=169.3 Hz), 93.7 (CCl$_3$), 87.3 (C-3$_D$), 83.4 (C-3$_E$), 81.0 (C-2$_E$), 80.2 (C-4$_A$), 79.6 (C-4$_C$), 79.2 (C-4$_E$), 77.5 (C-3$_C$), 76.6, 75.7, 75.6, 75.5, 75.3 (5C, C$_{Bn}$), 75.2 (C-5$_D$), 74.6 (C-3$_A$) 74.3 (C-2$_A$), 73.8, 72.2 (2C, C$_{Bn}$), 71.2 (C-4$_D$), 70.3

(C-5$_E$), 69.8 (C-5$_C$), 69.4 (C-2$_C$), 68.8 (C-5$_A$), 68.3 (C-6$_E$), 68.1 (C$_{All}$), 63.3 (C-6$_D$), 55.6 (C-2$_D$), 21.4 (C$_{Ac}$), 18.4 (C-6$_A$), 18.2 (C-6$_C$).

HRMS (ESI$^+$): [M+Na]$^+$ C$_{80}$H$_{90}$NO$_{20}$$^{35}$Cl$_3$Na m/z theoretical:
1512.5019
m/z measured:
1512.4950
[M+NH$_4$]$^+$ C$_{80}$H$_{90}$NO$_{20}$$^{35}$Cl$_3$NH$_4$ m/z theoretical:
1507.5465
m/z measured:
1507.5507
[M+K]$^+$ C$_{80}$H$_{90}$NO$_{20}$$^{35}$Cl$_3$K m/z theoretical:
1528.4758
m/z measured:
1528.4808

Allyl(3,4-di-O-benzyl-β-L-rhamnopyranosyl)-(1→3)-(2-deoxy-4,6-O-isopropylidene-2-trichloroacetamido-β-D-glucopyranosyl)-(1→2)-[2,3,4,6-tetra-O-benzyl-α-D-glucopyranosyl-(1→3)]-4-O-benzyl-α-L-rhamnopyranoside 43

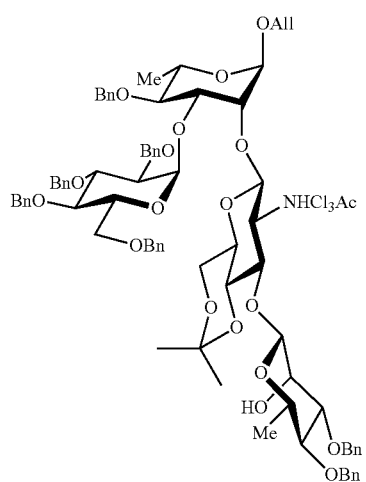

Chemical Formula: C$_{81}$H$_{92}$Cl$_3$NO$_{19}$
Exact Mass: 1487.5329
Molecular Weight: 1489.9515

TMSOTf (25.0 μL, 140 μmol, 0.5 eq.) is added to a solution of acceptor 38 (300 mg, 260 μmol) and of donor 39$^{67}$ (190 mg, 360 μmol, 1.4 eq.) in DCM (5 mL), in the presence of molecular sieve 4 Å (350 mg), stirred under argon at −78° C. After stirring for 30 min, the ethanol-dry ice bath is withdrawn and stirring is continued for 30 min, after which time monitoring by TLC (Chex/EtOAc, 75/25 and Chex/EtOAc, 6/4) indicates the disappearance of 38 (Rf=0.1 and 0.45, respectively). The reaction is stopped by adding triethylamine (0.1 mL), then the reaction mixture is filtered and concentrated in a rotary evaporator. The yellow oil obtained is purified by silica gel chromatography (Chex/EtOAc, 6.5/3.5→1/1), leading in the order of elution to the allyl glycoside as a white solid (170 mg, 40%), to compound 42 (80 mg, 20%), slightly contaminated, then to the diol 41 as a white solid (85 mg, 22%). After adding 0.5 M NaOMe (800 μL, 400 μmol) to 42 (25 mg) in solution in MeOH (1 mL), the reaction mixture is stirred at RT and its development is monitored by TLC (Chex/EtOAc, 6/4). After 4 h, the disappearance of 42 (Rf=0.65) and the appearance of a new, more polar compound (Rf=0.5) are observed. The reaction mixture is neutralized by adding DOWEX (H$^+$) ion-exchange resin, then the reaction mixture is filtered on a frit. The resin is washed with DCM/MeOH mixture and the solvents are evaporated. The yellow oil obtained is purified by silica gel chromatography (Chex/EtOAc, 8/2→6/4) to give the alcohol 43 as a white solid (8 mg).

Rf=0.5 (Chex/EtOAc, 6/4).

$^1$H NMR (CDCl$_3$), δ 7.55 (d, 1H, J$_{NH,2}$=8.3 Hz, NH), 7.40-7.03 (m, 35H, CH$_{Ph}$), 5.88 (m, 1H, CH═), 5.26 (m, 1H, J$_{trans}$=17.2 Hz, ═CH$_2$), 5.18 (m, 1H, J$_{cis}$=10.4 Hz, ═CH$_2$), 5.10-5.05 (m, 3H, H$_{Bn}$, H-1$_E$, H$_{Bn}$), 5.00-4.92 (m, 3H, H$_{Bn}$), 4.86 (d, 1H, J=12.1 Hz, H$_{Bn}$), 4.76 (m, 1H, H$_{1,2}$=1.5 Hz, H-1$_A$), 4.75-4.69 (m, 4H, H$_{Bn}$, H-1$_D$, 3H$_{Bn}$), 4.66-4.50 (m, 4H, 3H$_{Bn}$, H-1$_C$), 4.45 (d, 1H, J=10.9 Hz, H$_{Bn}$), 4.30 (d, 1H, J=11.9 Hz, H$_{Bn}$), 4.17-4.02 (m, 6H, H-3$_E$, H-3$_A$, H$_{All}$, H-5$_E$, H-2$_C$, H-2$_D$), 3.99 (m, 1H, H-2$_A$), 3.91 (m, 1H, H$_{All}$), 3.85-3.68 (m, 5H, H-6a$_D$, H-2$_E$, H-4$_E$, H-6b$_D$, H-5$_A$), 3.62 (pt, 1H, J$_{3,4}$=9.4 Hz, H-4$_D$), 3.52-3.39 (m, 6H, H-4$_C$, H-3$_D$, H-4$_A$, H-3$_C$, H-6a$_E$, H-6b$_E$), 3.24 (m, 1H, H-5$_C$), 2.72 (m, 1H, H-5$_D$), 1.45 (s, 6H, H$_{iPr}$), 1.40 (d, 3H, J$_{5,6}$=6.3 Hz, H-6$_A$), 1.18 (d, 3H, J$_{5,6}$=6.3 Hz, H-6$_C$).

$^{13}$C NMR (CDCl$_3$), δ 163.2 (C$_{NTCA}$), 138.8-137.8 (C$_{Ph}$), 134.2 (CH═), 129.5-127.6 (CH$_{Ph}$), 117.6 (═CH$_2$), 101.8 (C-1$_D$, $^1$J$_{CH}$=160.3 Hz), 99.8 (C$_{iPr}$), 99.1 (C-1$_C$, $^1$J$_{CH}$=156.6 Hz), 98.7 (C-1$_A$, $^1$J$_{CH}$=172.7 Hz), 95.0 (C-1$_E$, $^1$J$_{CH}$=166.1 Hz), 93.4 (CCl$_3$), 83.8 (C-3$_E$), 81.7 (C-3$_C$), 80.1 (C-4$_A$) 79.7 (C-4$_C$), 79.1 (C-4$_E$), 78.5 (C-2$_E$), 77.1 (C-3$_D$), 76.5, 75.8, 75.5, 75.1 (4C, C$_{Bn}$), 75.1 (C-3$_A$), 74.6 (C-4$_D$), 74.4 (C-2$_A$), 74.3, 73.8 (2C, C$_{Bn}$), 71.7 (C-5$_C$), 71.1 (C$_{Bn}$), 70.7 (C-5$_E$), 68.7 (C-5$_A$), 68.2 (C-2$_C$), 68.2, 68.1 (C-6$_E$, C$_{All}$), 67.1 (C-5$_D$), 62.4 (C-6$_D$), 56.6 (C-2$_D$), 29.4 (C$_{iPr}$), 19.5 (C$_{iPr}$), 18.5 (C-6$_C$), 18.2 (C-6$_A$).

Propyl (2/3-O-acetyl-α-L-rhamnopyranosyl)-(1→3)-(2-acetamido-2-deoxy-β-D-glucopyranosyl)-(1→2)-[α-D-glucopyranosyl-(1→3)]-α-L-rhamnopyranoside III

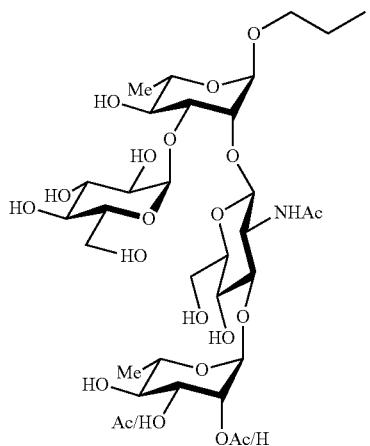

Chemical Formula: C$_{31}$H$_{53}$NO$_{20}$
Exact Mass: 759.3161
Molecular Weight: 759.7472

Pd—C 10% (300 mg) is added to a solution of tetrasaccharide 41 (340 mg, 320 μmol) in ethanol (30 mL). The suspension is saturated with hydrogen at 50 bar and stirred at RT for 10 days. Monitoring by TLC (iPrOH/H$_2$O/NH$_3$, 4/1/0.5 and Chex/EtOAc, 6/4) shows the disappearance of 41 (Rf=1 and 0.2, respectively) and the appearance of a new, more polar compound (Rf=0.5 and 0, respectively). The reaction mixture is filtered on an Acrodisc LC 25 mm filter, and the filtrate is concentrated in a rotary evaporator. The residue obtained is purified on a C-18 column ($H_2O/CH_3CN$, 100/0→7/3) to give the target III in the form of a mixture of two regioisomers $2_C$- and $3_C$-O-acetyl and a white solid (132 mg, 76%).

Rf=0.5 ($iPrOH/H_2O/NH_3$, 4/1/0.5).

$^1H$ NMR ($D_2O$), δ(partial) 5.05 (m, 1H, H-$1_E$), 4.83-4.72 (m, 4H, H-$1_A$, H-$1_C$, H-$1_D$, H-$2_C$), 4.17 (m, 1H, H-$2_A$), 3.93 (m, 1H, H-$5_E$), 3.82-3.3.79 (m, 2H, H-$3_A$, H-$5_C$), 3.73-3.52 (m, 10H, H-$2_D$, H-$6a_D$, H-$3_E$, H-$6a_E$, H-$6b_E$, H-$6b_D$, H-$3_C$, H-$5_A$, H-$2_E$, H$_{Pr}$), 3.42-3.32 (m, 6H, H-$4_E$, H$_{Pr}$, H-$5_D$, H-$4_C$, H-$4_D$, H-$3_D$), 3.21 (pt, 1H, $J_{3,4}$=9.7 Hz, H-$4_A$), 2.07-2.2.01 (m, 6H, H$_{Ac}$, H$_{NAc}$), 1.48 (sex, 2H, $CH_2$), 1.17-1.11 (d, 6H, H-$6_A$, H-$6_C$), 0.80 (t, 3H, J=7.4 Hz, $CH_3$).

$^{13}C$ NMR ($D_2O$), δ(partial) 174.9, 174.5, 174.1, 173.6 ($C_{NAC}$, $C_{Ac}$), 101.8 (C-$1_D$), 101.5, 101.2 (C-$1_C$), 99.0, 98.8 (C-$1_A$), 94.8, 94.7 (C-$1_E$), 82.6, 81.7 (C-$3_A$), 76.4 (C-$4_D$), 74.7 (C-$2_A$), 74.3-73.9 (C-$3_A$, C-$2_C$, C-$3_C$), 73.5, 73.3 (C-$3_E$), 72.4 (C-$4_C$), 71.7, 71.6 (C-$5_E$, C-$2_E$), 71.0 (C-$4_A$), 70.0 ($C_{Pr}$), 69.6-68.5 (C-$4_E$, C-$5_A$, C-$5_C$, C-$5_D$), 60.9 (C-$6_D$), 60.6 (C-$6_E$), 55.8 (C-$2_D$), 23.1, 22.8 ($C_{NAC}$), 22.3 ($CH_2$), 20.8, 20.6 ($C_{Ac}$), 17.1-16.6 (C-$6_A$, C-$6_C$), 10.2 ($CH_3$).

HRMS (ESI$^+$): [M+Na]$^+$ $C_{31}H_{53}NO_{20}Na$ m/z theoretical: 782.3058
m/z measured: 782.3066

Method 4:

Allyl(3,4-di-O-benzyl-α-L-rhamnopyranosyl)-(1→3)-(2-deoxy-2-trichloroacetamido-β-D-glucopyranosyl)-(1→2)-[2,3,4,6-tetra-O-benzyl-α-D-glucopyranosyl-(1→3)]-4-O-benzyl-α-L-rhamnopyranoside 69

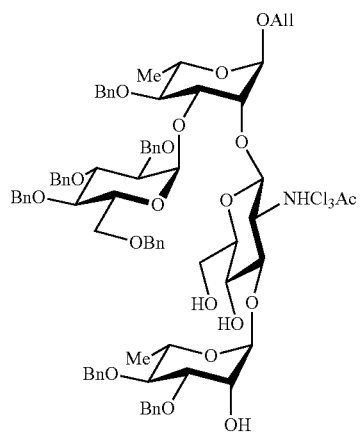

Chemical Formula: $C_{78}H_{88}Cl_3NO_{19}$
Exact Mass: 1447.5016
Molecular Weight: 1449.8876

After adding 0.5 M NaOMe (102 μL, 51 μmol, 1.1 eq.) to the diol 41 (69 mg, 46 μmol) in solution in MeOH (3 mL), the reaction mixture is refluxed. After 2 h, monitoring by TLC (Chex/EtOAc, 6/4) indicates the disappearance of the starting product (Rf=0.3) and the appearance of a more polar product (Rf=0.2). After return to RT, it is neutralized by adding DOWEX (H$^+$) ion-exchange resin, then filtered on a frit. The resin is washed with DCM/MeOH mixture and the solvents are evaporated. The solid obtained is purified by silica gel chromatography (Chex/EtOAc, 6/4→1/1) to give a white solid corresponding to the triol 69 (57 mg, 85%).

Rf=0.2 (Chex/EtOAc, 6/4).

$^1H$ NMR (CDCl$_3$), δ7.41-7.07 (m, 35H, CH$_{Ph}$), 6.93 (d, 1H, $J_{NH,2}$=7.7 Hz, NH), 5.89 (m, 1H, CH=), 5.29 (m, 1H, $J_{trans}$=17.2 Hz, =CH$_2$), 5.23 (m, 1H, $J_{cis}$=10.4 Hz, =CH$_2$), 5.21 (d, 1H, $J_{1,2}$=3.7 Hz, H-$1_E$), 5.13-4.88 (m, 5H, H$_{Bn}$), 4.84 (d, 1H, $J_{1,2}$=1.7 Hz, H-$1_A$), 4.79 (d, 1H, J=11.0 Hz, H$_{Bn}$), 4.73-4.67 (m, 3H, H$_{Bn}$), 4.62 (m, 1H, H$_{Bn}$), 4.58 (d, 1H, $J_{1,2}$=8.5 Hz, H-$1_D$), 4.58 (m, 1H, H$_{Bn}$), 4.55 (m, 1H, H-$1_C$), 4.51 (d, 2H, J=11.0 Hz, H$_{Bn}$), 4.34 (d, 1H, J=12.0 Hz, H$_{Bn}$), 4.19-4.11 (m, 4H, H-$3_A$, H$_{411}$, H-$3_E$, H-$5_E$), 4.03-4.00 (m, 3H, H-$2_A$, H-$2_C$, H$_{411}$), 3.96 (m, 1H, H-$2_D$), 3.93-3.87 (m, 3H, H-$5_C$, H-$3_C$, H-$6a_D$), 3.85 (m, 1H, H-$2_E$), 3.83 (m, 1H, H-$4_E$), 3.77 (m, 1H, H-$6b_D$), 3.73 (m, 1H, H-$5_A$), 3.50-3.44 (m, 4H, H-$4_C$, H-$6a_E$, H-$6b_E$, H-$4_A$), 3.38 (pt, 1H, $J_{3,4}$=8.9 Hz, H-$4_D$), 3.08 (m, 1H, H-$5_D$), 2.30 (m, 1H, $J_{3,4}$=8.8 Hz, H-$3_D$), 1.40 (d, 3H, $J_{5,6}$=6.2 Hz, H-$6_A$), 1.32 (d, 3H, $J_{5,6}$=6.2 Hz, H-$6_C$).

$^{13}C$ NMR (CDCl$_3$), δ162.0 ($C_{NTCA}$), 138.7-138.2 ($C_{Ph}$), 134.3 (CH=), 129.7-127.6 (CH$_{Ph}$), 117.8 (=CH$_2$), 101.4 (C-$1_D$, $^1J_{CH}$=161.7 Hz), 101.0 (C-$1_C$, $^1J_{CH}$=168.3 Hz), 98.6 (C-$1_A$, $^1J_{CH}$=168.3 Hz), 94.3 (C-$1_E$, $^1J_{CH}$=17.6 Hz), 93.7 (CCl$_3$), 87.1 (C-$3_D$), 83.5 (C-$3_E$), 80.8 (C-$2_E$), 80.2 (C-$4_A$), 79.5 (C-$4_C$), 79.4 (C-$3_C$), 79.3 (C-$4_E$), 76.6, 75.7, 75.6, 75.5, 75.3 (5C, $C_{Bn}$), 75.3 (C-$5_D$), 74.5 (2C, C-$2_A$, C-$3_A$), 73.8, 72.2 (2C, $C_{Bn}$), 71.1 (C-$4_D$), 70.3 (C-$5_E$), 69.5 (C-$5_C$), 68.9 (C-$2_C$), 68.8 (C-$5_A$), 68.4 (C-$6_E$), 68.1 (C$_{411}$), 63.3 (C-$6_D$), 55.9 (C-$2_D$), 21.4 ($C_{Ac}$), 18.3, 18.2 (C-$6_A$*, C-$6_C$*).

HRMS (ESI$^+$): [M+Na]$^+$ $C_{78}H_{88}NO_{19}^{35}Cl_3Na$ m/z theoretical: 1470.4913
m/z measured: 1470.5050
[M+NH$_4$]$^+$ $C_{78}H_{88}NO_{19}^{35}Cl_3NH_4$ m/z theoretical: 1465.5360
m/z measured: 1465.5448
[M+K]$^+$ $C_{78}H_{88}NO_{19}^{35}Cl_3K$ m/z theoretical: 1486.4653
m/z measured: 1486.4777

Propyl α-L-rhamnopyranosyl-(1→3)-(2-acetamido-2-deoxy-β-D-glucopyranosyl)-(1→2)-[α-D-glucopyranosyl-(1→3)]-α-L-rhamnopyranoside IV

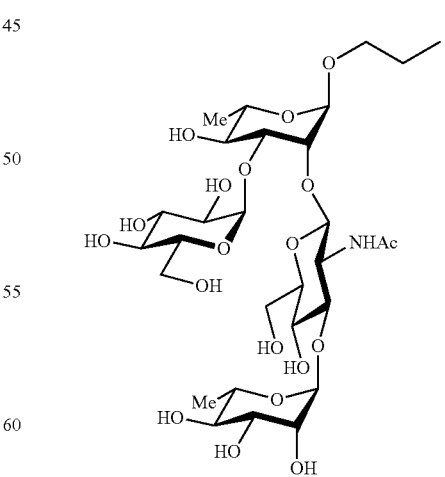

Chemical Formula: $C_{29}H_{51}NO_{19}$
Exact Mass: 717.3055
Molecular Weight: 717.7105

Pd—C 10% (300 mg) is added to a degassed solution of tetrasaccharide 68 (320 mg, 220 μmol) in ethanol (30 mL). The suspension is saturated with hydrogen at 50 bar and stirred at RT for 2 days. Monitoring by TLC (iPrOH/H$_2$O/NH$_3$, 4/1/0.5 and Chex/EtOAc, 6/4) shows the disappearance of 68 (Rf=1 and 0.2, respectively) and the appearance of a new, more polar compound (Rf=0.65 and 0, respectively). The reaction mixture is filtered on an Acrodisc LC 25 mm filter, and the filtrate is concentrated in a rotary evaporator. The residue obtained is purified on a C-18 column (H$_2$O/CH$_3$CN, 100/0→7/3) to give the target IV as a white solid (119 mg, 71%).

Rf=0.65 (iPrOH/H$_2$O/NH$_3$, 4/1/0.5).

$^1$H NMR (D$_2$O), δ5.06 (d, 1H, J$_{1,2}$=3.7 Hz, H-1$_E$), 4.83 (d, 1H, J$_{1,2}$=1.6 Hz, H-1$_A$), 4.76 (d, 1H, J$_{1,2}$=1.3 Hz, H-1$_C$), 4.73 (d, 1H, J$_{1,2}$=8.6 Hz, H-1$_D$), 4.18 (m, 1H, H-2$_A$), 3.95 (m, 1H, H-5$_E$), 3.88 (m, 1H, H-5$_C$), 3.83-3.79 (m, 2H, H-3$_A$, H-6a$_D$), 3.74 (m, 1H, H-2$_D$), 3.72 (m, 1H, H-3$_E$), 3.70-3.67 (m, 3H, H-2$_C$, H-6a$_E$, H-6b$_E$), 3.65-3.59 (m, 4H, H-6b$_D$, H-3$_C$, H-5$_A$, H-2$_E$), 3.52 (m, 1H, H$_{Pr}$), 3.42-3.28 (m, 6H, H-4$_E$, H$_{Pr}$, H-4$_D$, H-5$_D$, H-3$_D$, H4$_C$), 3.23 (pt, 1H, J$_{3,4}$=9.7 Hz, H-4$_A$), 2.01 (s, 3H, H$_{NAc}$), 1.49 (sex, 2H, CH$_2$), 1.16 (d, 3H, J$_{5,6}$=6.2 Hz, H-6$_A$), 1.12 (d, 3H, J$_{5,6}$=6.3 Hz, H-6$_C$), 0.80 (t, 3H, J=7.4 Hz, CH$_3$).

$^{13}$C NMR (D$_2$O), δ174.5 (C$_{NAc}$), 101.8 (C-1$_D$, $^1$J$_{CH}$=160.3 Hz), 101.6 (C-1$_C$, $^1$J$_{CH}$=170.5 Hz), 99.0 (C-1$_A$, $^1$J$_{CH}$=172.7 Hz), 94.8 (C-1$_E$, $^1$J$_{CH}$=169.8 Hz), 81.7 (C-3$_D$), 76.4 (C-4$_D$), 74.7 (C-2$_E$), 74.1 (C-3$_A$), 73.5 (C-3$_E$), 72.2 (C-4$_C$), 71.7 (C-5$_E$), 71.6 (C-2$_A$), 71.2 (C-2$_C$), 71.0 (C-4$_A$), 70.5 (C-3$_C$), 70.0 (C$_{Pr}$), 69.6 (C-5$_D$), 69.3 (C-5$_C$), 69.1 (C-5$_A$), 68.6 (C-4$_E$), 60.9 (C-6$_D$), 60.6 (C-6$_E$), 55.9 (C-2$_D$), 22.8 (C$_{NAc}$), 22.3 (CH$_2$), 17.0, 16.7 (C-6$_A$, C-6$_C$), 10.2 (CH$_3$).

HRMS (ESI$^+$): [M+Na]$^+$ C$_{29}$H$_{51}$NO$_{19}$Na m/z theoretical: 740.2953
m/z measured: 740.2941

Method 5:

Allyl (2,3,4-tri-O-acetyl-α-L-rhamnopyranosyl)-(1-3)-2-O-acetyl-4-O-benzyl-α-L-rhamnopyranoside 50

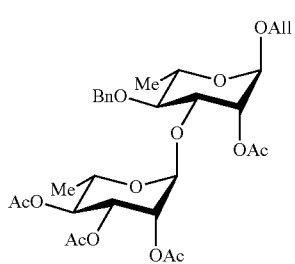

Chemical Formula: C$_{30}$H$_{40}$O$_{13}$
Exact Mass: 608.2469
Molecular Weight: 608.6308

TMSOTf (124.0 μL, 690 μmol, 0.3 eq.) is added to a solution of acceptor 31 (780 mg, 2.3 mmol) and donor 48$^{82, 49}$ (1.5 g, 3.5 mmol, 1.5 eq.) in DCM (60 mL), in the presence of molecular sieve 4 Å (2.0 g), stirred under argon at −78° C. After 6 h at this temperature, the ethanol-dry ice bath is withdrawn and stirring is continued for 30 min, after which time monitoring by TLC (Tol/EtOAc, 8/2) indicates the disappearance of 31 (Rf=0.3) and the appearance of a new, less polar compound (Rf=0.35). The reaction is stopped by adding triethylamine (0.1 mL), then the reaction mixture is filtered and concentrated in a rotary evaporator. The yellow oil obtained is purified by silica gel chromatography (Tol/EtOAc, 9/1→8/2), obtaining the allyl glycoside 50 as a white solid (1.3 g, 95%).

Rf=0.35 (Tol/EtOAc, 8/2).

$^1$H NMR (CDCl$_3$), δ7.34-7.02 (m, 5H, CH$_{Ph}$), 5.87 (m, 1H, CH=), 5.33 (m, 1H, H-2$_B$), 5.28 (m, 1H, =CH$_2$), 5.25 (m, 1H, H-3$_B$), 5.20 (m, 1H, =CH$_2$), 5.18 (m, 1H, H-2$_C$), 5.07 (pt, 1H, J$_{3,4}$=9.9 Hz, H-4$_B$), 5.04 (d, 1H, J$_{1,2}$=1.5 Hz, H-1$_B$), 4.82 (d, 1H, J=10.8 Hz, H$_{Bn}$), 4.75 (d, 1H, J$_{1,2}$=1.6 Hz, H-1$_C$), 4.67 (d, 1H, J=10.9 Hz, H$_{Bn}$), 4.17-4.12 (m, 2H, H-3$_C$, H$_{All}$), 4.00-3.91 (m, 2H, H$_{All}$, H-5$_B$), 3.77 (m, 1H, H-5$_C$), 3.51 (pt, 1H, J$_{3,4}$=9.5 Hz, H-4$_C$), 2.21, 2.08, 2.07, 1.99 (4 s, 12H, H$_{Ac}$), 1.34 (d, 3H, J$_{5,6}$=6.2 Hz, H-6$_C$), 1.21 (d, 3H, J$_{5,6}$=6.3 Hz, H-6$_B$).

$^{13}$C NMR (CDCl$_3$), δ170.9, 170.4, 170.3, 170.2 (4C, C$_{Ac}$), 138.3 (C$_{Ph}$), 133.8 (CH=), 129.4-128.1 (CH$_{Ph}$), 117.9 (=CH$_2$), 99.8 (C-1$_B$, $^1$J$_{CH}$=173.0 Hz), 96.8 (C-1$_C$, $^1$J$_{CH}$=170.0 Hz), 81.1 (C-4$_C$), 77.2 (C-3$_C$), 75.6 (C$_{Bn}$), 72.5 (C-2$_C$), 71.1 (C-4$_B$), 70.2 (C-2$_B$), 69.5 (C-3$_B$), 68.5 (C$_{All}$), 68.3 (C-5$_C$), 67.6 (C-5$_B$), 21.4, 21.2, 21.1, 21.0 (4C, C$_{Ac}$), 18.3 (C-6$_C$), 17.7 (C-6$_B$).

HRMS (ESI$^+$): [M+Na]$^+$ C$_{30}$H$_{40}$O$_{13}$Na m/z theoretical: 631.2367
m/z measured: 631.2368
[M+K]$^+$ C$_{30}$H$_{40}$O$_{13}$K m/z theoretical: 647.2106
m/z measured: 647.2124

(2,3,4-Tri-O-acetyl-α-L-rhamnopyranosyl)-(1→3)-2-O-acetyl-4-O-benzyl-α-L-rhamnopyranose 51

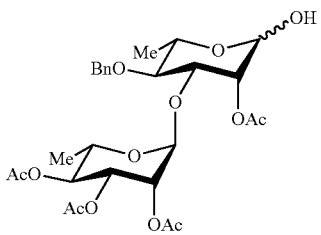

Chemical Formula: C$_{27}$H$_{36}$O$_{13}$
Exact Mass: 568.2156
Molecular Weight: 568.5669

(1,5-Cyclooctadienebis(methyldiphenylphosphine)-iridium(I)hexafluorophosphate (170 mg) is dissolved in THF (16 mL) while stirring. The mixture is submitted to cycles of vacuum/argon degassing, 5 cycles of vacuum/hydrogen degassing and is then placed under hydrogen for 15 min. The mixture is then submitted to 5 cycles of vacuum/argon degassing for a second time. The solution of allyl glycoside 50 (1.3 g, 2.2 mmol) in THF (8 mL) is transferred to the solution of activated catalyst. Monitoring by TLC (Tol/EtOAc, 8/2) shows the disappearance of 50 (Rf=0.35) and the appearance of a similar, less polar product (Rf=0.4).

Diiodine (1.1 g, 4.4 mmol) in solution in THF/H$_2$O mixture (8/2, 15 mL) is added to the reaction mixture. Monitoring by TLC (Tol/EtOAc, 8/2 and DCM/MeOH, 95/5) indicates the disappearance of the intermediate (Rf=0.35 and 0.95, respectively) and the appearance of a new, much more polar compound (Rf=0 and 0.55, respectively). To stop the reaction, 10% NaHSO₃ aqueous solution (10 mL) is added in portions to the mixture until the black coloration disappears. The reaction mixture is taken up in DCM (30 mL) and the aqueous phase is extracted with DCM (3×20 mL). The organic phases are combined and washed with a solution of NaCl$_{sat}$ (3×15 mL), with H₂O (3×15 mL) and then dried on a phase-separating filter and concentrated in a rotary evaporator. The yellow oil obtained is purified by silica gel chromatography (DCM/MeOH, 99/1,9/1) to obtain the hemiacetal 51 in the form of a yellow oil (1.1 g, 910).

Rf=0.55 (DCM/MeOH, 95/5).

¹H NMR (CDCl₃), δ: α: 7.33-7.26 (m, 5H, CH$_{Ph}$), 5.34 (m, 1H, H-2$_B$), 5.25 (m, 1H, H-3$_B$), 5.18 (m, 1H, H-2$_C$), 5.10 (s, 1H, H-1$_C$), 5.05 (pt, 1H, J$_{3,4}$=9.9 Hz, H-4$_B$), 5.04 (d, 1H, J$_{1,2}$=1.7 Hz, H-1$_B$), 4.80 (d, 1H, J=10.9 Hz, H$_{Bn}$), 4.65 (d, 1H, J=10.9 Hz, H$_{Bn}$), 4.19 (m, 1H, H3$_C$), 4.01-3.91 (m, 2H, H-5$_C$, H-5$_B$), 3.58 (s, 1H, OH), 3.49 (pt, 1H, J$_{3,4}$=9.5 Hz, H-4$_C$), 2.21, 2.08, 2.07, 1.99 (4 s, 12H, H$_{Ac}$), 1.31 (d, 3H, J$_{5,6}$=6.2 Hz, H-6$_C$), 1.19 (d, 3H, J$_{5,6}$=6.3 Hz, H-6$_B$).

¹³C NMR (CDCl₃), δ: δ: 171.7, 171.0, 170.6, 170.3 (4C, C$_{Ac}$), 138.3-137.9 (C$_{Ph}$), 128.8-128.1 (CH$_{Ph}$), 99.7 (C-1$_B$, ¹J$_{CH}$=172.7 Hz), 92.3 (C-1$_C$, ¹J$_{CH}$=170.5 Hz), 81.1 (C-4$_C$), 76.6 (C-3$_C$), 75.9 (C$_{Bn}$), 72.9 (C-2$_C$), 71.1 (C-4$_B$), 70.2 (C-2$_B$), 69.5 (C-3$_B$), 68.2 (C-5$_C$), 67.6 (C-5$_B$), 21.4, 21.2, 21.1, 21.0 (4C, C$_{Ac}$), 18.3 (C-6$_C$), 17.6 (C-6$_B$).

HRMS (ESI⁺): [M+Na]⁺ C₂₇H₃₆O₁₃Na m/z theoretical: 591.2054 m/z measured: 591.2037

[M+K]⁺ C₂₇H₃₆O₁₃K m/z theoretical: 607.1793 m/z measured: 607.1838

(2,3,4-Tri-O-acetyl-α-L-rhamnopyranosyl)-(1→3)-2-O-acetyl-4-O-benzyl-α/β-L-rhamnopyranose trichloroacetimidate 46

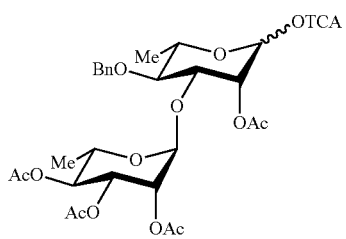

Chemical Formula: C₂₉H₃₆Cl₃NO₁₃
Exact Mass: 711.1252
Molecular Weight: 712.9540

The hemiacetal 51 (1.0 g, 1.7 mmol) is dissolved in DCE (7 mL) and stirred under argon at −5° C., and then DBU (72 μL, 476 μmol, 0.28 eq.) and trichloroacetonitrile (2.2 mL, 21.5 mmol, 12 eq.) are added. The reaction mixture is stirred at this temperature for 15 min and then it is loaded, without any treatment, on a silica gel column (flash chromatography, Chex/EtOAc+5% NEt₃, 7/3) to obtain the trichloroacetimidate 46 in the form of a yellow oil (1.1 g, 89%).

Rf=0.5 (Chex/EtOAc, 6/4).

¹H NMR (CDCl₃), δ: α: 8.70 (s, 1H, NH), 7.33-7.27 (m, 5H, CH$_{Ph}$), 6.18 (d, 1H, J$_{1,2}$=1.7 Hz, H-1$_C$), 5.35 (m, 2H, H-2$_B$, H-2$_C$), 5.22 (m, 1H, H-3$_B$), 5.08 (s, 1H, J$_{1,2}$=1.5 Hz, H-1$_B$), 5.07 (pt, 1H, J$_{3,4}$=9.9 Hz, H-4$_B$), 4.80 (d, 1H, J=10.8 Hz, H$_{Bn}$), 4.68 (d, 1H, J=10.8 Hz, H$_{Bn}$), 4.23 (m, 1H, H-3$_C$), 4.00-3.92 (m, 2H, H-5$_C$, H-5$_B$), 3.62 (pt, 1H, J$_{3,4}$=9.6 Hz, H-4$_C$), 2.26, 2.08, 2.07, 1.99 (4 s, 12H, H$_{Ac}$), 1.37 (d, 3H, J$_{5,6}$=6.3 Hz, H-6$_C$), 1.19 (d, 3H, J$_{5,6}$=6.3 Hz, H-6$_B$).

¹³C NMR (CDCl₃), δ: α: 170.6, 170.5, 170.4, 170.2 (4C, C$_{Ac}$), 164.0 (C=NH), 137.8 (C$_{Ph}$), 128.8-128.3 (CH$_{Ph}$), 99.6 (C-1$_B$, ¹J$_{CH}$=173.4 Hz), 95.1 (C-1$_C$, ¹J$_{CH}$=178.6 Hz), 91.2 (CCl₃), 80.5 (C-4$_C$), 76.2 (C$_{Bn}$), 75.6 (C-3$_C$), 71.3 (C-5$_C$), 70.9 (C-4$_B$), 70.7 (C-2$_C$), 70.0 (C-2$_B$), 69.4 (C-3$_B$), 67.8 (C-5$_B$), 21.3, 21.2, 21.1, 21.0 (4C, C$_{Ac}$), 18.3 (C-6$_C$), 17.7 (C-6$_B$).

Allyl (2,3,4-tri-O-acetyl-α-L-rhamnopyranosyl)-(1→3)-(2-O-acetyl-4-O-benzyl-α-L-rhamnopyranosyl)-(1→3)-(2-deoxy-4,6-O-isopropylidene-2-trichloroacetamido-β-D-glucopyranosyl)-(1→2)-(2,3,4,6-tetra-O-benzyl-α-D-glucopyranosyl-(1→3))-4-O-benzyl-α-L-rhamnopyranoside 52

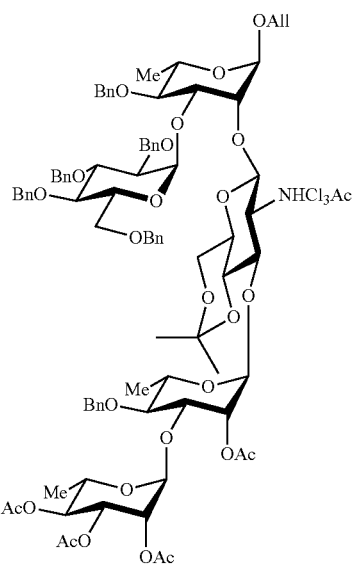

Chemical Formula: C₈₈H₁₀₄Cl₃NO₂₇
Exact Mass: 1711.5861
Molecular Weight: 1714.1169

TMSOTf (50.0 μL, 280 μmol, 0.3 eq.) is added to a solution of acceptor 38 (1.1 g, 935 μmol) and donor 46 (935 mg, 1.3 mmol, 1.4 eq.) in Tol (5.6 mL), in the presence of molecular sieve 4 Å (765 mg), stirred under argon at −78° C. After stirring for 15 min, monitoring by TLC (Tol/EtOAc, 7/3) indicates the disappearance of (Rf=0.35) and the appearance of a new, more polar compound (Rf=0.55). The reaction is stopped by adding triethylamine (0.1 mL), then the reaction mixture is filtered and concentrated in a rotary evaporator. The yellow oil obtained is purified by silica gel chromatography (Tol/EtOAc, 9/1→4/6), obtaining, in the order of elution, a white solid corresponding to the allyl glycoside 52 (1.3 g, 80%) then the diol 53, namely allyl (2,3,4-tri-O-acetyl-α-L-rhamnopyranosyl)-(1→3)-(2-O-acetyl-4-O-benzyl-α-L-rhamnopyranosyl)-(1→3)-(2-deoxy-2-trichloroacetamido-β-D-glucopyranosyl)-(1,2)-[2,3,4,6-tetra-O-benzyl-α-D-glucopyranosyl-(1,3)]-4-O-benzyl-α-L-rhamnopyranoside (Rf=0.25, 108 mg, 7%) contaminated with the hydrolyzed donor.

Rf=0.55 (Tol/EtOAc, 7/3).

¹H NMR (CDCl₂), δ7.48-7.12 (m, 35H, CH$_{Ph}$), 6.95 (d, 1H, J$_{NH,2}$=8.8 Hz, NH), 5.92 (m, 1H, CH=), 5.38 (m, 1H, H-2$_8$), 5.29 (m, 1H, J$_{trans}$=16.9 Hz, =CH₂), 5.28 (m, 1H, H-3$_B$), 5.22 (d, 1H, J$_{1,2}$=4.1 Hz, H-1$_E$), 5.21 (m, 1H, J$_{cis}$=10.6 Hz, =CH₂), 5.17 (m, 1H, H-2$_C$), 5.15 (m, 4H, H-1$_B$, H-4$_8$, 2H$_{Bn}$), 5.05 (d, 1H, J=12.2 Hz, H$_{Bn}$), 4.95 (d, 1H, J=12.2 Hz, $H_{Bn}$), 4.86-4.82 (m, 3H, H-1$_A$, 2H$_{Bn}$), 4.76-4.70 (m, 3H, H$_{Bn}$, H-1$_C$, H$_{Bn}$), 4.62-4.53 (m, 4H, 2H$_{Bn}$, H-1$_D$, H$_{Bn}$), 4.36 (d, 1H, J=12.0 Hz, H$_{Bn}$), 4.22-4.14 (m, 6H, H-3$_E$, H$_{A11}$, H-3$_C$, H-3$_A$, H-5$_B$, H-5$_E$), 4.09-4.04 (m, 3H, H-2$_D$, H-5$_C$, H-2$_A$), 3.99 (m, 1H, H$_{A11}$), 3.93-3.88 (m, 2H, H-2$_E$, H-6a$_D$), 3.85 (pt, 1H, J$_{3,4}$=9.6 Hz, H-4$_E$), 3.77-3.72 (m, 2H, H-5$_A$, H-6b$_D$), 3.57 (pt, 1H, J$_{3,4}$=9.2 Hz, H-4$_D$), 3.52-3.45 (m, 4H, H-4$_C$, H-4$_A$, H-6a$_E$, H-6b$_E$), 2.84-2.80 (m, 2H, H-5$_D$, H-3$_D$), 2.26, 2.13, 2.11, 2.03 (4 s, 12H, H$_{Ac}$), 1.52 (s, 3H, H$_{iPr}$), 1.50 (s, 3H, H$_{iPr}$), 1.44 (d, 3H, J$_{5,6}$=6.2 Hz, H-6$_A$), 1.37 (d, 3H, J$_{5,6}$=6.2 Hz, H-6$_B$), 1.33 (d, 3H, J$_{5,6}$=6.2 Hz, H-6$_C$).

$^{13}$C NMR (CDCl$_3$), δ170.6, 170.5, 170.3, 170.2 (4C, C$_{Ac}$), 162.4 (C$_{NTCA}$), 138.6-137.8 (C$_{Ph}$), 134.3 (CH=), 129.8-127.7 (CH$_{Ph}$), 117.6 (=CH$_2$), 101.6 (C-1$_D$, $^1$J$_{CH}$=164.7 Hz), 99.9 (C$_{iPr}$), 99.2 (C-1$_E$, $^1$J$_{CH}$=174.2 Hz), 98.8 (C-1$_A$, $^1$J$_{CH}$=171.2 Hz), 98.4 (C-1$_C$, $^1$J$_{CH}$=170.5 Hz), 94.7 (C-1$_E$, $^1$J$_{CH}$=166.9 Hz), 93.4 (CCl$_3$), 83.5 (C-3$_E$), 81.5 (C-4$_C$), 80.7 (C-2$_E$), 80.2 (C-4$_A$), 79.2 (C-4$_E$), 78.7 (C-3$_D$), 76.5 (C$_{Bn}$), 75.6 (C-3$_C$), 75.7, 75.6, 75.4, 75.3 (4C, C$_{Bn}$), 74.9 (C-3$_A$), 74.1 (C-2$_C$), 73.8 (C$_{Bn}$), 72.9 (C-4$_D$), 72.5 (C-2$_C$), 71.2 (C-4$_B$), 70.3 (2C, C-2$_B$, C-5$_E$), 69.6 (C-3$_E$), 68.8 (C-5$_A$), 68.4 (C-6$_E$), 68.3 (C-5$_C$), 68.2 (C$_{A11}$), 67.8 (C-5$_B$), 67.4 (C-5$_D$), 62.5 (C-6$_D$), 58.0 (C-2$_D$), 29.6 (C$_{iPr}$), 21.4, 21.3, 21.2, 21.1 (4C, C$_{Ac}$), 19.5 (C$_{iPr}$) 18.5 (C-6$_C$), 18.3 (C-6$_A$), 17.7 (C-6$_B$).

HRMS (ESI$^+$): [M+Na]$^+$ C$_{88}$H$_{104}{}^{35}$Cl$_3$NO$_{27}$Na m/z theoretical:
1734.5759
m/z measured:
1734.5825
[M+NH$_4$]$^+$ C$_{88}$H$_{104}{}^{35}$Cl$_3$NO$_{27}$NH$_4$ m/z theoretical:
1729.6205
m/z measured:
1729.6278

Allyl (α-L-rhamnopyranosyl)-(1→3)-(2-O-acetyl-4-O-benzyl-α-L-rhamnopyranosyl)-(1→3)-(2-deoxy-4,6-O-isopropylidene-2-trichloroacetamido-β-D-glucopyranosyl)-1-2)-[2,3,4,6-tetra-O-benzyl-α-D-glucopyranosyl-(1→3)]-4-O-benzyl-α-L-rhamnopyranoside 54

Allyl α-L-rhamnopyranosyl-(1→3)-(4-O-benzyl-α-L-rhamnopyranosyl)-(1→3)-(2-deoxy-4,6-O-isopropylidene-2-trichloroacetamido-β-D-glucopyranosyl)-(1→2)-[2,3,4,6-tetra-O-benzyl-α-D-glucopyranosyl-(1→3)]-4-O-benzyl-α-L-rhamnopyranoside 55

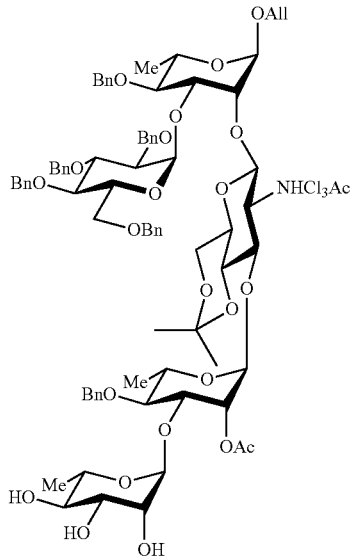

Chemical Formula: C$_{82}$H$_{98}$Cl$_3$NO$_{24}$
Exact Mass: 1585.5544
Molecular Weight: 1588.0068

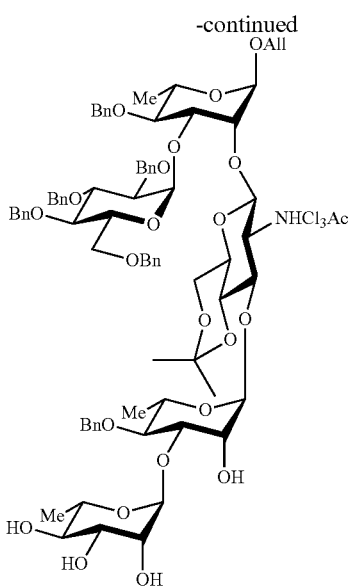

Chemical Formula: C$_{80}$H$_{96}$Cl$_3$NO$_{23}$
Exact Mass: 1543.5439
Molecular Weight: 1545.9701

The allyl glycoside 52 (525 mg, 300 μmol) is dissolved in MeOH (20 mL), and then potassium carbonate (42 mg, 300 μmol, 1 eq.) is added to the reaction mixture. After stirring for 25 min at RT, monitoring by TLC (DCM/MeOH, 96/4 and Tol/EtOAc, 8/2) indicates the disappearance of 52 (Rf=0.35 and 1, respectively) and the appearance of two more-polar products (Rf=0.3 and 0.25 in Tol/EtOAc, 8/2). The reaction mixture is then neutralized by adding DOWEX (H$^+$) ion-exchange resin, then filtered on a frit. The resin is washed with DCM/MeOH mixture and the solvents are evaporated. The yellow oil obtained is purified by silica gel chromatography (Chex/Acetone, 6/4→4/6), giving, in the order of elution, the mono-acetylated product 54 as a white solid (414 mg, 85%) and the non-acetylated product 55 as a white solid (33 mg, 7%).

54: Rf=0.3 (DCM/MeOH, 96/4).

$^1$H NMR (CDCl$_3$), δ7.42-7.07 (m, 35H, CH$_{Ph}$), 6.95 (d, 1H, J$_{NH,2}$=8.8 Hz, NH), 5.92 (m, 1H, CH=), 5.26 (m, 1H, J$_{trans}$=17.2 Hz, =CH$_2$), 5.18 (m, 1H, J$_{cis}$=10.4 Hz, =CH$_2$), 5.15 (d, 1H, J$_{1,2}$=3.4 Hz, H-1$_E$), 5.09-5.05 (m, 4H, H-2$_C$, H-1$_B$, 2H$_{Bn}$), 4.98 (d, 1H, J=12.2 Hz, H$_{Bn}$), 4.87 (d, 1H, J=12.2 Hz, H$_{Bn}$), 4.80-4.74 (m, 3H, H-1$_A$, 2H$_{Bn}$), 4.70 (d, 1H, J=11.2 Hz, H$_{Bn}$), 4.66-4.63 (m, 3H, H$_{Bn}$, H-1$_C$, H$_{Bn}$), 4.56-4.47 (m, 3H, 2H$_{Bn}$, H-1$_D$), 4.30 (d, 1H, J=11.9 Hz, H$_{Bn}$), 4.14-4.05 (m, 5H, H$_{A11}$, H-3$_E$, H-3$_A$, H-5$_E$, H-3$_C$), 4.00-3.94 (m, 4H, H-2$_D$, H$_{A11}$, H-2$_A$, H-5$_C$), 3.87-3.84 (m, 4H, H-6a$_D$, H-2$_B$, H-5$_B$, H-2$_E$), 3.79 (pt, 1H, J$_{3,4}$=9.1 Hz, H-4$_E$), 3.70-3.65 (m, 3H, H-6b$_D$, H-5$_A$, H-3$_B$), 3.53 (pt, 1H, J$_{3,4}$=9.2 Hz, H-4$_D$), 3.46-3.37 (m, 5H, H-4$_B$, H-6a$_E$, H-6b$_E$, H-4$_C$, H-4$_A$), 2.81-2.71 (m, 2H, H-5$_D$, H-3$_D$), 2.14 (s, 3H, H$_{Ac}$), 1.47 (s, 3H, H$_{iPr}$), 1.43 (s, 3H, H$_{iPr}$), 1.38 (d, 3H, J$_{5,6}$=5.9 Hz, H-6$_A$), 1.36 (d, 3H, J$_{5,6}$=6.0 Hz, H-6$_B$), 1.25 (d, 3H, J$_{5,6}$=6.2 Hz, H-6$_C$).

$^{13}$C NMR (CDCl$_3$), δ170.5 (C$_{Ac}$) 162.6 (C$_{NTCA}$), 138.7-138.1 (C$_{Ph}$), 134.2 (CH=), 129.8-127.7 (CH$_{Ph}$), 117.7 (=CH$_2$), 101.6 (C-1$_B$, $^1$J$_{CH}$=170.5 Hz), 101.4 (C-1$_D$, $^1$J$_{CH}$=159.5 Hz), 99.9 (C$_{iPr}$), 98.7 (C-1$_A$, $^1$J$_{CH}$=172.0 Hz), 98.2 (C-1$_C$, $^1$J$_{CH}$=169.1 Hz), 94.6 (C-1$_E$, $^1$J$_{CH}$=166.9 Hz), 93.3 (CCl$_3$), 83.4 (C-3$_E$), 81.3 (C-4$_C$), 80.6 (C-2$_E$), 80.1 (C-4$_A$), 79.1 (C-4$_E$), 78.7 (C-3$_D$), 76.5 (C$_{Bn}$), 76.0 (C-3$_C$), 75.7, 75.6, 75.5, 75.3 (4C, $C_{Bn}$), 74.8 (C-3$_A$), 73.9 (C-2$_A$), 73.8 (C-4$_B$), 73.7 ($C_{Bn}$), 72.9 (C-2$_C$), 72.7 (C-4$_D$), 71.8 (C-3$_B$), 71.4 (C-2$_B$), 70.2 (C-5$_E$), 69.2 (C-5$_B$), 68.7 (C-5$_A$), 68.3 (C-5$_C$), 68.2 (2C, C-6$_E$, C$_{A11}$), 67.3 (C-5$_D$), 62.4 (C-6$_D$), 57.9 (C-2$_D$), 29.6 ($C_{iPr}$) 21.6 ($C_{Ac}$), 19.5 ($C_{iPr}$), 18.4 (C-6$_A$), 18.3 (C-6$_C$), 17.8 (C-6$_B$).

HRMS (ESI$^+$): [M+Na]$^+$ $C_{82}H_{98}{}^{35}Cl_3NO_{24}Na$ m/z theoretical:

1608.5542 m/z measured:

1608.5582

[M+NH$_4$]$^+$ $C_{82}H_{98}{}^{35}Cl_3NO_{24}NH_4$ m/z theoretical:

1603.5889 m/z measured:

1603.6035

[M+K]$^+$ $C_{82}H_{98}{}^{35}Cl_3NO_{24}K$ m/z theoretical:

1624.5182 m/z measured:

1624.5436

55: Rf=0.25 (DCM/MeOH, 96/4).

$^1$H NMR (CDCl$_3$), δ7.38-7.04 (m, 35H, CH$_{Ph}$), 6.93 (d, 1H, $J_{NH,2}$=8.8 Hz, NH), 5.86 (m, 1H, CH=), 5.26 (m, 1H, $J_{trans}$=17.2 Hz, =CH$_2$), 5.18 (m, 1H, $J_{cis}$=10.4 Hz, =CH$_2$), 5.15 (d, 1H, $J_{1,2}$=3.5 Hz, H-1$_E$), 5.09-4.95 (m, 4H, H-1$_B$, 3H$_{Bn}$), 4.89 (d, 1H, J=12.3 Hz, H$_{Bn}$), 4.78 (d, 1H, J=11.0 Hz, H$_{Bn}$), 4.75 (d, 1H, $J_{1,2}$=1.0 Hz, H-1$_A$), 4.73-4.61 (m, 4H, 2H$_{Bn}$, H-1$_C$, H$_{Bn}$), 4.57 (d, 1H, J=12.0 Hz, H$_{Bn}$), 4.51-4.47 (m, 2H, H$_{Bn}$), 4.41 (d, 1H, $J_{1,2}$=8.4 Hz, H-1$_D$), 4.32 (d, 1H, J=12.0 Hz, H$_{Bn}$), 4.14-4.07 (m, 4H, H$_{All}$, H-3$_A$, H-3$_E$, H-5$_E$), 4.03 (d, 1H, $J_{1,2}$=9.2 Hz, H-2$_D$), 4.00-3.91 (m, 4H, H-5$_C$, H-2$_A$, H-3$_C$, H$_{A11}$), 3.89-3.79 (m, 6H, H-2$_C$, H-2$_B$, H-2$_E$, H-6a$_D$, H-4$_E$, H-3$_B$), 3.75-3.64 (m, 3H, H-5$_B$, H-6b$_D$, H-5$_A$), 3.52-3.48 (pt, 2H, $J_{3,4}$=9.2 Hz, H-4$_D$, H-4$_B$), 3.44 (m, 2H, H-6a$_E$, H-6b$_E$), 3.48 (pt, 1H, $J_{3,4}$=9.9 Hz, H-4$_C$), 3.48 (pt, 1H, $J_{3,4}$=9.5 Hz, H-4$_A$), 2.74-2.69 (m, 2H, H-3$_D$, H-5$_D$), 1.46 (s, 3H, H$_{iPr}$), 1.42 (s, 3H, H$_{iPr}$), 1.41 (d, 3H, $J_{5,6}$=6.0 Hz, H-6$_B$), 1.37 (d, 3H, $J_{5,6}$=6.2 Hz, H-6$_A$), 1.22 (d, 3H, $J_{5,6}$=6.2 Hz, H-6$_C$).

$^{13}$C NMR (CDCl$_3$), δ162.3 ($C_{NTCA}$), 138.8-138.2 ($C_{Ph}$), 134.2 (CH=), 129.8-127.7 (CH$_{Ph}$), 117.6 (=CH$_2$), 102.0 (C-1$_B$, $^1J_{CH}$=175.6 Hz), 101.4 (C-1$_D$, $^1J_{CH}$=162.5 Hz), 100.2 (C-1$_C$, $^1J_{CH}$=171.2 Hz), 99.8 ($C_{iPr}$), 98.7 (C-1$_A$, $^1J_{CH}$=172.0 Hz), 94.4 (C-1$_E$, $^1J_{CH}$=166.1 Hz), 93.3 (CCl$_3$), 83.5 (C-3$_E$), 80.7 (C-4$_C$), 80.5 (C-2$_E$), 80.1 (C-4$_A$), 79.4 (C-3$_C$), 79.1 (C-4$_E$), 78.0 (C-3$_D$), 76.6, 75.8, 75.6, 75.4, 75.3 (5C, $C_{Bn}$), 74.5 (C-3$_A$), 73.8 (C-4$_B$), 73.7 ($C_{Bn}$), 73.6 (C-2$_A$), 72.5 (C-4$_D$), 72.0 (C-3$_B$), 71.5 (C-2$_C$), 71.4 (C-2$_B$), 70.1 (C-5$_E$), 69.2 (C-5$_B$), 68.7 (C-5$_A$), 68.2 (2C, C6$_E$, C$_{A11}$), 68.0 (C-5$_C$), 67.3 (C-5$_D$), 62.4 (C-6$_D$), 58.1 (C-2$_D$), 30.1 ($C_{iPr}$), 19.5 ($C_{iPr}$), 18.3, 18.2 (C-6$_A$*, C-6$_C$*), 17.8 (C-6$_B$).

HRMS (ESI$^+$): [M+Na]$^+$ $C_{80}H_{96}{}^{35}Cl_3NO_{23}Na$ m/z theoretical:

1566.5337 m/z measured:

1566.5404

[M+NH$_4$]$^+$ $C_{80}H_{96}{}^{35}Cl_3NO_{23}NH_4$ m/z theoretical:

1561.5782 m/z measured:

1561.5812

Allyl (α-L-rhamnopyranosyl)-(1→3)-(2-O-acetyl-4-O-benzyl-α-L-rhamnopyranosyl)-(1→3)-(2-deoxy-2-trichloroacetamido-β-D-glucopyranosyl)-(1→2)-[2,3,4,6-tetra-O-benzyl-α-D-glucopyranosyl-(1→3)]-4-O-benzyl-α-L-rhamnopyranoside 56

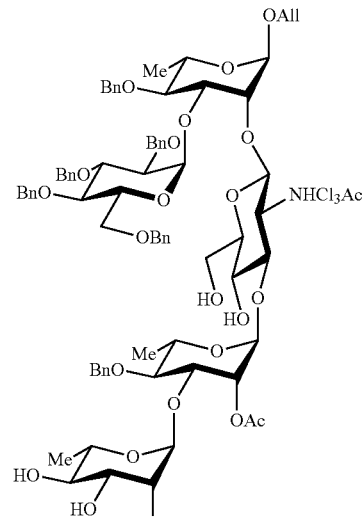

Chemical Formula: $C_{79}H_{94}Cl_3NO_{24}$
Exact Mass: 1545.5231
Molecular Weight: 1547.9430

50% aqueous TFA solution (2 mL) is slowly added to a solution of triol 54 (292 mg, 180 μmol) in DCM (5 mL) at 0° C. The reaction mixture is stirred for 2 h at this temperature, after which time monitoring by TLC (DCM/MeOH, 95/5) indicates the complete disappearance of 54 (Rf=0.35) and the appearance of a new, more polar compound (Rf=0.3). The reaction mixture is concentrated by coevaporation with Tol (3×10 mL). The yellow oil obtained is purified by silica gel chromatography (DCM/MeOH, 95/5→93/7) to obtain the mono-acetylated compound 56 as a white solid (274 mg, 95%).

Rf=0.3 (DCM/MeOH, 95/5).

$^1$H NMR (CDCl$_3$), δ7.39-7.05 (m, 36H, CH$_{Ph}$, NH), 5.88 (m, 1H, CH=), 5.28 (m, 1H, $J_{trans}$=17.2 Hz, =CH$_2$), 5.22-5.20 (m, 2H, H-1$_E$, =CH$_2$), 5.11 (m, 1H, H-2$_C$), 5.09-5.02 (m, 3H, H$_{Bn}$), 4.98 (m, 1H, H-1$_B$), 4.93 (d, 1H, J=12.5 Hz, H$_{Bn}$), 4.84 (d, 1H, $J_{1,2}$=1.3 Hz, H-1$_A$), 4.81-4.73 (m, 3H, H$_{Bn}$), 4.63-4.60 (m, 3H, H$_{Bn}$, H-1$_D$, H$_{Bn}$), 4.57 (m, 1H, H-1$_C$), 4.54-4.49 (m, 2H, H$_{Bn}$), 4.33 (d, 1H, J=12.0 Hz, H$_{Bn}$), 4.17-4.07 (m, 6H, H-3$_A$, H$_{A11}$, H-3$_E$, H-5$_E$, H-3$_C$, H-2$_A$), 4.00-3.95 (m, 2H, H-2$_D$, H$_{A11}$), 3.90 (m, 1H, H-5$_C$), 3.88-3.85 (m, 2H, H-2$_B$, H-6a$_D$), 3.84-3.78 (m, 2H, H-2$_E$, H-4$_E$), 3.77-3.61 (m, 4H, H-6b$_D$, H-5$_B$, H-3$_B$, H-5$_A$), 3.51-3.41 (m, 5H, H-4$_A$, H-6a$_E$, H-6b$_E$, H-4$_C$, H-4$_B$), 3.53 (pt, 1H, $J_{3,4}$=8.9 Hz, H-4$_D$), 3.04 (m, 1H, H-5$_D$), 2.29 (m, 1H, H-3$_D$), 2.19 (s, 3H, H$_{Ac}$), 1.25 (d, 3H, $J_{5,6}$=6.2 Hz, H-6$_B$), 1.36 (d, 3H, $J_{5,6}$=6.2 Hz, H-6$_C$), 1.38 (d, 3H, $J_{5,6}$=6.2 Hz, H-6$_A$).

$^{13}$C NMR (CDCl$_3$), δ170.5 ($C_{Ac}$), 162.8 ($C_{NTCA}$), 138.9-138.2 ($C_{Ph}$), 134.3 (CH=), 129.7-127.8 (CH$_{Ph}$), 117.7 (=CH$_2$), 102.1 (C-1$_B$, $^1J_{CH}$=167.9 Hz), 101.1 (C-1$_D$, $^1J_{CH}$=164.0 Hz), 98.7 (C-1$_C$, $^1J_{CH}$=170.3 Hz), 98.6 (C-1$_A$, $^1J_{CH}$=170.3 Hz), 94.5 (C-1$_E$, $^1J_{CH}$=167.9 Hz), 93.2 (CCl$_3$), 86.6 (C-3$_D$), 83.4 (C-3$_E$), 80.7 (C-2$_E$), 80.3 (C-4$_C$), 79.9 (C-4$_A$), 79.1 (C-4$_E$), 77.7 (C-3$_C$), 76.6, 75.9, 75.7, 75.4, 75.3 (5C, C$_{Bn}$), 75.2 (C-5$_D$), 74.8 (C-3$_A$), 74.0 (C-2$_A$), 73.8 (C-4$_B$), 73.7 (C$_{Bn}$), 72.5 (C-2$_C$), 71.9 (C-3$_B$), 71.4 (C-2$_B$), 70.9 (C-4$_D$), 70.3 (C-5$_E$), 69.5 (C-5$_C$), 69.4 (C-5$_A$), 68.8 (C-5$_B$), 68.4 (C-6$_E$), 68.2 (C$_{A11}$), 63.1 (C-6$_D$), 55.8 (C-2$_D$), 21.4 (C$_{Ac}$), 18.4 (C-6$_C$), 18.3 (C-6$_B$), 17.8 (C-6$_A$).

HRMS (ESI$^+$): [M+Na]$^+$ C$_{79}$H$_{94}$$^{35}$Cl$_3$NO$_{24}$Na m/z theoretical:
1568.5129
m/z measured:
1568.5162
[M+NH$_4$]$^+$ C$_{79}$H$_{94}$$^{35}$Cl$_3$NO$_{24}$NH$_4$ m/z theoretical:
1563.5575
m/z measured:
1563.5681

Allyl α-L-rhamnopyranosyl-(1→3)-(4-O-benzyl-α-L-rhamnopyranosyl)-(1→3)-(2-deoxy-2-trichloroacetamido-β-D-glucopyranosyl)-(1→2)-[2,3,4,6-tetra-O-benzyl-α-D-glucopyranosyl-(1→3)]-4-O-benzyl-α-L-rhamnopyranoside 57

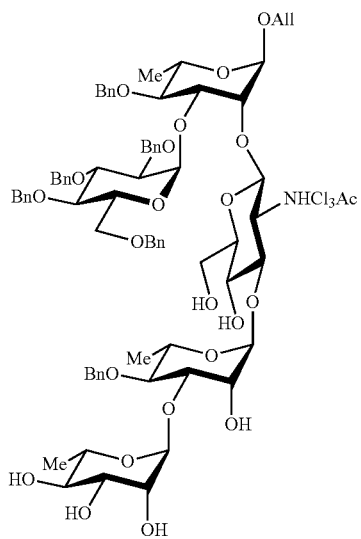

Chemical Formula: C$_{77}$H$_{92}$Cl$_3$NO$_{23}$
Exact Mass: 1503.5126
Molecular Weight: 1505.9063

50% aqueous TFA solution (2 mL) is slowly added to a solution of tetraol 55 (340 mg, 180 μmol) in DCM (5 mL) at 0° C. The reaction mixture is stirred for 2 h at this temperature, after which time monitoring by TLC (DCM/MeOH, 94/6) indicates the complete disappearance of 55 (Rf=0.35) and the appearance of a new, more polar compound (Rf=0.2). The reaction mixture is concentrated by coevaporation with Tol (3×10 mL). The yellow oil obtained is purified by silica gel chromatography (DCM/MeOH, 95/5,93/7) to obtain the non-acetylated compound 57 as a white solid (314 mg, 95%).
Rf=0.2 (DCM/MeOH, 94/6).

$^1$H NMR (CDCl$_3$), δ7.34-7.05 (m, 35H, CH$_{Ph}$, NH), 6.93 (d, 1H, J$_{NH,2}$=8.7 Hz, NH), 5.86 (m, 1H, CH=), 5.26 (m, 1H, J$_{trans}$=17.2 Hz, =CH$_2$), 5.20 (m, 1H, J$_{cis}$=10.4 Hz, =CH$_2$), 5.17 (d, 1H, J$_{1,2}$=3.6 Hz, H-1$_E$), 5.06 (d, 1H, J=11.0 Hz, H$_{Bn}$), 5.02 (m, 1H, H-1$_B$), 5.01-4.97 (m, 2H, H$_{Bn}$), 4.88 (d, 1H, J=12.3 Hz, H$_{Bn}$), 4.81 (d, 1H, J$_{1,2}$=1.4 Hz, H-1$_A$), 4.78-4.69 (m, 3H, H$_{Bn}$), 4.62-4.56 (m, 3H, H$_{Bn}$, H-1$_D$, H$_{Bn}$), 4.51-4.47 (m, 3H, H$_{Bn}$, H-1$_C$, H$_{Bn}$), 4.32 (d, 1H, J=12.0 Hz, H$_{Bn}$), 4.15-4.13 (m, 2H, H-3$_A$, H$_{A11}$), 4.11-4.07 (m, 2H, H-3$_E$, H-5$_E$), 4.02 (m, 1H, H-2$_A$), 3.98-3.95 (m, 2H, H-3$_C$, H$_{A11}$), 3.93-3.87 (m, 4H, H-2$_C$, H-2$_D$, H-5$_C$, H-2$_B$), 3.84 (m, 1H, H-6a$_D$), 3.82-3.71 (m, 5H, H-5$_B$, H-2$_E$, H-4$_E$, H-6b$_D$, H-3$_B$), 3.69 (m, 1H, H-5$_A$), 3.48 (pt, 1H, J$_{3,4}$=9.2 Hz, H-4$_E$), 3.47-3.37 (m, 5H, H-4$_C$, H-6a$_E$, H-6b$_E$, H-4$_A$, H-4$_D$), 3.04 (m, 1H, H-5$_D$), 2.38 (pt, 1H, J$_{3,4}$=9.1 Hz, H-3$_D$), 1.27 (d, 3H, J$_{5,6}$=6.5 Hz, H-6$_C$), 1.36 (d, 3H, J$_{5,6}$=6.2 Hz, H-6$_A$), 1.37 (d, 3H, J$_{5,6}$=6.2 Hz, H-6$_B$).

$^{13}$C NMR (CDCl$_3$), δ162.4 (C$_{NTCA}$), 138.2-137.9 (C$_{Ph}$), 134.2 (CH=), 129.2-127.7 (CH$_{Ph}$), 117.7 (=CH$_2$), 101.4 (C-1$_B$, $^1$J$_{CH}$=167.6 Hz), 101.1 (C-1$_D$, $^1$J$_{CH}$=159.5 Hz), 100.9 (C-1$_C$, $^1$J$_{CH}$=168.3 Hz), 98.6 (C-1$_A$, $^1$J$_{CH}$=174.2 Hz), 94.3 (C-1$_E$, $^1$J$_{CH}$=169.1 Hz), 93.3 (CCl$_3$), 85.8 (C-3$_D$), 83.4 (C-3$_E$), 80.6 (C-2$_E$), 80.3 (C-4$_A$), 80.0 (C-4$_C$), 79.2 (C-4$_E$), 78.8 (C-3$_C$), 76.6, 75.7, 75.6, 75.5 (4C, C$_{Bn}$), 75.3 (C-5$_D$), 75.2 (C$_{Bn}$), 74.5 (C-3$_A$), 74.0 (C-2$_A$), 73.7 (C$_{Bn}$), 73.6 (C-4$_B$), 71.9 (C-3$_E$), 712 (C-2$_B$), 70.9 (C-2$_C$), 70.6 (C-4$_D$), 70.3 (C-5$_E$), 69.4 (2C, C-5$_B$, C-5$_C$), 68.8 (C-5$_A$), 68.3 (C-6$_E$), 68.1 (C$_{A11}$), 63.0 (C-6$_D$), 56.3 (C-2$_D$), 18.2, 18.1, 18.0 (C-6$_A$*, C-6$_B$*, C-6$_C$*).

HRMS (ESI$^+$): [M+Na]$^+$ C$_{77}$H$_{92}$$^{35}$Cl$_3$NO$_{23}$Na m/z theoretical:
1526.5023
m/z measured:
1526.5076
[M+NH$_4$]$^+$ C$_{77}$H$_{92}$$^{35}$Cl$_3$NO$_{23}$NH$_4$ m/z theoretical:
1521.5470
m/z measured:
1521.5582
[M+K]$^+$ C$_{77}$H$_{92}$$^{35}$Cl$_3$NO$_{23}$K m/z theoretical:
1542.4763
m/z measured:
1542.4871

Allyl 3,4-di-O-benzyl-α-L-rhamnopyranoside[96, 102] 58

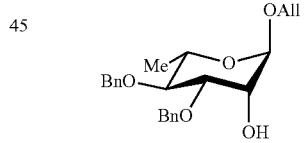

Chemical Formula: C$_{23}$H$_{28}$O$_5$
Exact Mass: 384.1937
Molecular Weight: 384.4654

The diol 26 (1.9 g, 6.6 mmol) and dibutyltin oxide (1.8 g, 7.2 mmol, 1.1 eq.) are dissolved in Tol (52 mL). The reaction mixture is heated under reflux for 2 h equipped with Soxhlet apparatus containing activated molecular sieve. The solution is cooled to 60° C. and the Soxhlet is removed. Cesium fluoride (1.5 mL, 13.1 mmol, 2 eq.) is added and the reaction mixture is evaporated. The residue is taken up in DMF (50 mL), and benzyl bromide (1.6 mL, 13.1 mmol, 2 eq.) is added. The reaction mixture is then stirred overnight at RT, after which time monitoring by TLC (Chex/EtOAc, 7/3) shows the appearance of a new, less polar compound (Rf=0.35). The reaction mixture is then filtered, taken up in dichloromethane (200 mL) and washed with saturated NaCl solution (3×50 mL), with H$_2$O (3×50 mL) and then dried over Na$_2$SO$_4$ and concentrated in a rotary evaporator. The yellow oil obtained is purified by silica gel chromatography (Chex/EtOAc, 8/2.4/6) to give the alcohol 58 in the form of a colorless oil (2.2 g, 88% i.e. 68% via 27).

Rf=0.35 (Chex/EtOAc, 7/3).

$^1$H NMR (CDCl$_3$), δ7.41-7.36 (m, 10H, CH$_{Ph}$), 5.93 (m, 1H, CH=), 5.32 (m, 1H, J$_{trans}$=17.2 Hz, =CH$_2$), 5.23 (m, 1H, J$_{cis}$=10.4 Hz, =CH$_2$), 4.94 (d, 1H, J=10.9 Hz, H$_{Bn}$), 4.90 (d, 1H, J$_{1,2}$=1.5 Hz, H-1), 4.74 (m, 2H, H$_{Bn}$), 4.70 (d, 1H, J=10.9 Hz, H$_{Bn}$), 4.19 (m, 1H, H$_{A11}$), 4.10 (m, 1H, H-2), 4.03 (m, 1H, H$_{A11}$), 3.93 (dd, 1H, J$_{2,3}$=3.3 Hz, J$_{3,4}$=9.1 Hz, H-3), 3.81 (m, 1H, H-5), 3.53 (pt, 1H, J$_{4,5}$=9.3 Hz, H-4), 2.69 (bs, 1H, OH), 1.38 (d, 3H, J$_{5,6}$=6.3 Hz, H-6).

$^{13}$C NMR (CDCl$_3$), δ138.8-138.4 (C$_{Ph}$), 134.3 (CH=), 128.9-128.1 (CH$_{Ph}$), 117.7 (=CH$_2$), 98.7 (C-1, $^1$J$_{CH}$=167.6 Hz), 80.5 (C-4), 80.4 (C-3), 75.8, 72.4 (2C, C$_{Bn}$), 69.0 (C-2), 68.3 (C$_{A11}$), 67.8 (C-5), 18.3 (C-6).

Allyl 3,4-di-O-benzyl-2-O-levulinoyl-α-L-rhamnopyranoside 59

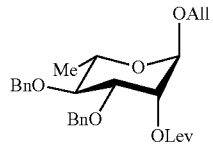

Chemical Formula: C$_{28}$H$_{34}$O$_7$
Exact Mass: 482.2305
Molecular Weight: 482.5654

The alcohol 58 (2.2 g, 5.7 mmol) is dissolved in DCM (120 mL), and then DCC (1.8 g, 8.5 mmol, 1.5 eq.), DMAP (1.4 g, 11.3 mmol, 2 eq.), and levulinic acid (1.1 mL, 10.2 mmol, 1.8 eq.) are added in portions. The reaction mixture is stirred overnight, after which time monitoring by TLC (DCM/EtOAc, 9/1) shows the formation of a less polar main compound (Rf=0.75) and the disappearance of 58 (Rf=0.65). The DCU is filtered on Celite and the filtrate is taken up in H$_2$O (50 mL). The aqueous phase is extracted with DCM (3×200 mL). The organic phases are combined and washed with 10% HCl solution (3×100 mL), NaHCO$_{3sat}$ solution (3×100 mL), NaCl$_{sat}$ solution (3×100 mL), filtered on a phase-separating filter and concentrated in a rotary evaporator. The oil obtained is purified by silica gel chromatography (Chex/EtOAc, 85/15→8/2) to give the levulinoyl ester 59 in the form of a colorless oil (2.4 g, 89%).

Rf=0.4 (Chex/EtOAc, 7/3).

$^1$H NMR (CDCl$_3$), δ7.39-7.30 (m, 10H, CH$_{Ph}$), 5.91 (m, 1H, CH=), 5.43 (m, 1H, H-2), 5.28 (m, 1H, J$_{trans}$=15.8 Hz, =CH$_2$), 5.22 (m, 1H, J$_{cis}$=10.4 Hz, =CH$_2$), 4.95 (d, 1H, J=10.8 Hz, H$_{Bn}$), 4.81 (d, 1H, J$_{1,2}$=1.5 Hz, H-1), 4.72 (d, 1H, J=11.2 Hz, H$_{Bn}$), 4.65 (d, 1H, J=10.8 Hz, H$_{Bn}$), 4.55 (d, 1H, J=11.2 Hz, H$_{Bn}$), 4.16 (m, 1H, H$_{A11}$), 3.99 (m, 2H, H$_{A11}$, H-3), 3.81 (m, 1H, H-5), 3.46 (pt, 1H, J$_{4,5}$=9.4 Hz, H-4), 2.74 (m, 4H, 2CH$_{2Lev}$), 2.19 (s, 3H, CH$_{3Lev}$), 1.37 (d, 3H, J$_{5,6}$=6.2 Hz, H-6).

$^{13}$C NMR (CDCl$_3$), δ206.6 (C$_{Lev}$), 172.5 (C$_{Lev}$), 138.9-138.5 (C$_{Ph}$), 133.9 (CH=), 128.9-128.1 (CH$_{Ph}$), 118.0 (=CH$_2$), 97.1 (C-1, $^1$J$_{CH}$=169.8 Hz), 80.5 (C-4), 78.5 (C-3), 75.8, 72.0 (2C, C$_{Bn}$), 69.5 (C-2), 68.4 (C$_{A11}$), 68.1 (C-5), 38.4 (CH$_{2Lev}$), 30.1 (CH$_{3Lev}$), 28.6 (CH$_{2Lev}$) 18.4 (C-6).

HRMS (ESI$^+$): [M+Na]$^+$ C$_{28}$H$_{34}$O$_7$Na m/z theoretical: 505.2202
m/z measured: 505.2201

3,4-Di-O-benzyl-2-O-levulinoyl-α/β-L-rhamnopyranose 60

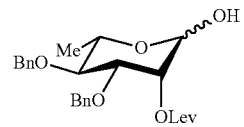

Chemical Formula: C$_{25}$H$_{30}$O$_7$
Exact Mass: 442.1992
Molecular Weight: 442.5015

(1,5-Cyclooctadienebis(methyldiphenylphosphine)-iridium(I)hexafluorophosphate) (120 mg) is dissolved in THF (60 mL) with stirring. The mixture is submitted to cycles of vacuum/argon degassing, 5 cycles of vacuum/hydrogen degassing and is then placed under hydrogen for 15 min. The mixture is then submitted to 5 cycles of vacuum/argon degassing for a second time. The solution of allyl glycoside 59 (2.7 g, 5.7 mmol) in THF (8 mL) is transferred to the solution of activated catalyst. Monitoring by TLC (Chex/EtOAc, 7/3) shows the disappearance of 59 (Rf=0.4) and the appearance of a somewhat less polar product (Rf=0.5).

Diiodine (2.9 g, 11.3 mmol, 2 eq.) in solution in THF/H$_2$O mixture (8/2, 30 mL) is added to the reaction mixture. Monitoring by TLC (Chex/EtOAc, 7/3 and DCM/MeOH, 98/2) indicates the disappearance of the intermediate (Rf=0.5 and 0.8, respectively) and the appearance of a new, much more polar compound (Rf=0.05 and 0.25, respectively). To stop the reaction, 10% NaHSO$_3$ aqueous solution (20 mL) is added in portions to the mixture until the black coloration disappears. The reaction mixture is taken up in DCM (50 mL) and the aqueous phase is extracted with DCM (3×30 mL). The organic phases are combined and washed with NaCl$_{sat}$ solution (3×30 mL), with H$_2$O (3×30 mL) and then dried on a phase-separating filter and concentrated in a rotary evaporator. The yellow oil obtained is purified by silica gel chromatography (DCM/MeOH, 99/1→9/1) to obtain a mixture of α/β anomers in the proportions 75/25 of the hemiacetal 60 in the form of a yellow oil (2.4 g, 96%).

Rf=0.25 (DCM/MeOH, 98/2) 60$_α$: $^1$H NMR (CDCl$_3$), δ7.37-7.28 (m, 10H, CH$_{Ph}$), 5.40 (m, 1H, H-2), 5.13 (m, 1H, H-1), 4.95 (d, 1H, J=10.9 Hz, H$_{Bn}$), 4.75-4.51 (m, 2H, H$_{Bn}$), 4.20 (d, 1H, J=10.7 Hz, H$_{Bn}$), 4.03-3.98 (m, 2H, H-3, H-5), 3.43 (pt, 1H, J$_{3,4}$=9.4 Hz, H-4), 2.73 (m, 4H, 2CH$_{2Lev}$), 2.18 (s, 3H, CH$_{3Lev}$) 1.33 (d, 3H, J$_{5,6}$=6.2 Hz, H-6).

$^{13}$C NMR (CDCl$_3$), δ 206.8 (C$_{Lev}$) 172.5 (C$_{Lev}$), 138.9-138.0 (C$_{Ph}$), 128.8-128.0 (CH$_{Ph}$), 92.7 (C-1, $^1$J$_{CH}$=170.3 Hz), 80.5 (C-4), 77.9 (C-3), 75.7, 72.0 (2C, C$_{Bn}$), 70.0 (C-2), 68.1 (C-5), 38.5 (CH$_{2Lev}$), 30.1 (CH$_{3Lev}$) 28.6 (CH$_{2Lev}$), 18.4 (C-6).

60$_β$: $^1$H NMR (CDCl$_3$), δ7.37-7.28 (m, 10H, CH$_{Ph}$), 5.56 (m, 1H, H-2), 4.95 (d, 1H, J=10.9 Hz, H$_{Bn}$), 4.77 (d, 1H, H-1), 4.75-4.51 (m, 2H, H$_{Bn}$), 4.20 (d, 1H, J=10.7 Hz, H$_{Bn}$), 3.66 (dd, 1H, J$_{2,3}$=3.3 Hz, J$_{3,4}$=8.9 Hz, H-3), 3.38 (m, 1H, H-5), 3.21 (m, 1H, H-4), 2.73 (m, 4H, 2CH$_{2Lev}$), 2.20 (s, 3H, CH$_{3Lev}$), 1.38 (d, 3H, J$_{5,6}$=5.9 Hz, H-6).

$^{13}$C NMR (CDCl$_3$), δ 208.2 (C$_{Lev}$) 173.0 (C$_{Lev}$), 138.9-138.0 (C$_{Ph}$), 128.8-128.0 (CH$_{Ph}$), 93.5 (C-1β, $^1$J$_{CH}$=158.8 Hz), 80.4 (C-3), 79.9 (C-4) 75.8, 71.9 (2C, C$_{Bn}$), 72.1 (C-5), 70.5 C 2), 39.0 (CH$_{2Lev}$) 30.2 (CH$_{3Lev}$), 28.8 (CH$_{2Lev}$) 18.4 (C-6).

HRMS (ESI$^+$): [M+Na]$^+$ C$_{25}$H$_{30}$O$_7$Na m/z theoretical: 465.1889
m/z measured: 465.1876

3,4-Di-O-benzyl-2-O-levulinoyl-α-L-rhamnopyranose trichloroacetimidate 49

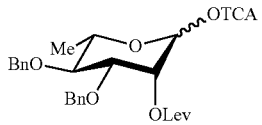

Chemical Formula: $C_{27}H_{30}Cl_3NO_7$
Exact Mass: 585.1088
Molecular Weight: 586.8886

The hemiacetal 60 (2.1 g, 4.8 mmol) is dissolved in DCE (15 mL) and stirred under argon at −5° C., and then DBU (202 µL, 1.3 mmol, 0.28 eq.) and trichloroacetonitrile (2.4 mL, 24.2 mmol, 5 eq.) are added. The reaction mixture is stirred at this temperature for 15 min and then it is loaded, without any treatment, on a silica gel column (flash chromatography, Chex/EtOAc+5% NEt$_3$, 7/3→1/1) to obtain the trichloroacetimidate 49 in the form of a yellow oil (2.6 g, 92%).

Rf=0.4 (Chex/EtOAc, 7/3).

$^1$H NMR (CDCl$_3$), δ8.68 (s, 1H, NH), 7.37-7.28 (m, 10H, CH$_{Ph}$) 6.20 (d, 1H, J$_{1,2}$=1.9 Hz, H-1), 5.50 (m, 1H, H-2), 4.97 (d, 1H, J=10.8 Hz, H$_{Bn}$), 4.74 (d, 1H, J=11.3 Hz, H$_{Bn}$), 4.67 (d, 1H, J=10.8 Hz, H$_{Bn}$), 4.58 (d, 1H, J=11.3 Hz, H$_{Bn}$), 4.03-3.94 (m, 2H, H-3, H-5), 3.53 (pt, 1H, J$_{4,5}$=9.5 Hz, H-4), 2.78 (m, 4H, 2CH$_{2Lev}$), 2.19 (s, 3H, CH$_{3Lev}$), 1.37 (d, 3H, J$_{5,6}$=6.2 Hz, H-6).

$^{13}$C NMR (CDCl$_3$), δ206.4 (C$_{Lev}$), 172.2 (C$_{Lev}$), 160.7 (C=NH), 138.5-138.0 (C$_{Ph}$), 128.8-128.2 (CH$_{Ph}$), 95.5 (C-1, $^1$J$_{CH}$=178.6 Hz), 91.3 (CCl$_3$), 79.7 (C-4), 77.6 (C-3), 76.0, 72.3 (2C, C$_{Bn}$), 71.1 (C-5), 68.2 (C-2), 38.4 (CH$_{2Lev}$), 30.2 (CH$_{3Lev}$), 28.5 (CH$_{2Lev}$), 18.4 (C-6).

Allyl (3,4-di-O-benzyl-2-O-levulinoyl-α-L-rhamnopyranosyl)-(1→3)-2-O-acetyl-4-O-benzyl-α-L-rhamnopyranoside 61

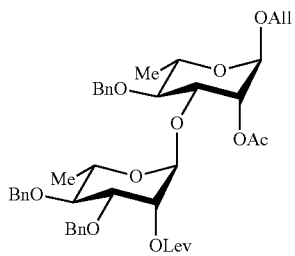

Chemical Formula: $C_{43}H_{52}O_{12}$
Exact Mass: 760.3459
Molecular Weight: 760.8658

TMSOTf (1.1 mL, 6.0 mmol, 0.3 eq.) is added to a solution of acceptor 31 (6.8 g, 20.2 mmol) and donor 49 (14.2 g, 24.2 mmol, 1.2 eq.) in Tol (250 mL), in the presence of molecular sieve 4 Å (17 g), stirred under argon at −78° C. After 1 h at this temperature, the ethanol-dry ice bath is withdrawn and stirring is continued for 30 min, after which time monitoring by TLC (Tol/EtOAc, 8/2, Chex/EtOAc, 6/4) indicates the disappearance of 31 (Rf=0.3 and 0.4, respectively) and the appearance of a new compound (Rf=0.45 and 0.5, respectively). The reaction is stopped by adding triethylamine (1 mL), then the reaction mixture is filtered and concentrated in a rotary evaporator. The yellow oil obtained is purified by silica gel chromatography (Tol/EtOAc, 95/5→85/15) to obtain the allyl glycoside 61 in the form of a colorless oil (13.3 g, 89%).

Rf=0.5 (Chex/EtOAc, 6/4).

$^1$H NMR (CDCl$_3$), δ7.39-7.27 (m, 15H, CH$_{Ph}$), 5.89 (m, 1H, CH=), 5.46 (m, 1H, H-2$_B$), 5.29 (m, 1H, J$_{trans}$=17.2 Hz, =CH$_2$), 5.21 (m, 1H, J$_{cis}$=10.4 Hz, =CH$_2$), 5.17 (m, 1H, H-2$_C$), 5.05 (d, 1H, J$_{1,2}$=1.5 Hz, H-1$_B$), 4.91 (d, 1H, J=11.0 Hz, H$_{Bn}$), 4.87 (d, 1H, J=10.9 Hz, H$_{Bn}$), 4.80 (d, 1H, J$_{1,2}$=1.5 Hz, H-1$_C$), 4.67-4.60 (d, 3H, H$_{Bn}$), 4.45 (d, 1H, J=11.3 Hz, H$_{Bn}$), 4.20-4.13 (m, 2H, H-3$_C$, H$_{All}$), 3.98 (m, 1H, H$_{All}$), 3.90 (dd, 1H, J$_{2,3}$=3.3 Hz, J$_{3,4}$=9.3 Hz, H-3$_B$), 3.83-3.74 (m, 2H, H-5$_B$, H-5$_C$), 3.47 (pt, 1H, J$_{3,4}$=9.5 Hz, H-4$_C$), 3.43 (pt, 1H, J$_{3,4}$=9.4 Hz, H-4$_B$), 2.71 (m, 4H, 2CH$_{2Lev}$), 2.18 (s, 3H, CH$_{3Lev}$), 2.14 (s, 3H, H$_{Ac}$), 1.31 (m, 6H, H-6$_C$, H-6$_B$).

$^{13}$C NMR (CDCl$_3$), δ206.4 (C$_{Lev}$) 172.2 (C$_{Lev}$), 170.6 (C$_{Ac}$), 138.9-138.4 (C$_{Ph}$), 133.9 (CH=), 128.9-128.0 (CH$_{Ph}$), 117.8 (=CH$_2$), 100.0 (C-1$_B$, $^1$J$_{CH}$=169.5 Hz), 96.6 (C-1$_C$, $^1$J$_{CH}$=170.0 Hz), 80.7 (C-4$_C$), 80.2 (C-4$_B$), 78.1 (C-3$_C$), 78.0 (C-3$_B$), 75.9, 75.6 (2C, C$_{Bn}$), 72.7 (C-2$_C$), 71.9 (C$_{Bn}$), 69.7 (C-2$_B$), 69.0 (C-5$_B$), 68.6 (C$_{All}$), 68.2 (C-5$_C$), 38.4 (CH$_{2Lev}$), 30.2 (CH$_{3Lev}$), 28.6 (CH$_{2Lev}$), 21.4 (C$_{Ac}$), 18.3 (2C, C-6$_B$, C-6$_C$).

HRMS (ESI$^+$): [M+Na]$^+$ C$_{43}$H$_{52}$O$_{12}$Na m/z theoretical: 783.3356
m/z measured: 783.3364
[M+NH$_4$]$^+$ C$_{43}$H$_{52}$O$_{12}$NH$_4$ m/z theoretical: 778.3802
m/z measured: 778.3829

(3,4-Di-O-benzyl-2-O-levulinoyl-α-L-rhamnopyranosyl)-(1→3)-2-O-acetyl-4-O-benzyl-α/β-L-rhamnopyranose 62

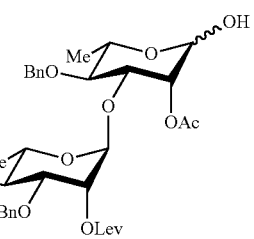

Chemical Formula: $C_{40}H_{48}O_{12}$
Exact Mass: 720.3146
Molecular Weight: 720.8019

(1,5-Cyclooctadienebis(methyldiphenylphosphine)-iridium(I)hexafluorophosphate) (175 mg) is dissolved in THF (90 mL) with stirring. The mixture is submitted to 5 cycles of vacuum/argon degassing, 5 cycles of vacuum/hydrogen degassing and is then placed under hydrogen for 15 min. The mixture is then submitted to 5 cycles of vacuum/argon degassing for a second time. The solution of allyl glycoside 61 (8.0 g, 10.6 mmol) in THF (15 mL) is transferred to the solution of activated catalyst. Monitoring by TLC (Tol/EtOAc, 8/2) shows the disappearance of the starting product (Rf=0.45) and the appearance of a somewhat less polar product (Rf=0.5).

Diiodine (5.4 g, 21.2 mmol, 2 eq.) in solution in THF/H$_2$O mixture (8/2, 30 mL) is added to the reaction mixture. Monitoring by TLC (Tol/EtOAc, 8/2 and DCM/MeOH, 98/2) indicates the disappearance of the intermediate (Rf=0.5 and 0.95, respectively) and the appearance of a new, much more polar compound (Rf=0.05 and 0.45, respectively). To stop the reaction, 10% NaHSO$_3$ aqueous solution (25 mL) is added in portions to the mixture until the black coloration disappears.

The reaction mixture is taken up in DCM (100 mL) and the aqueous phase is extracted with DCM (3×100 mL). The organic phases are combined and washed with NaCl$_{sat}$ solution (3×50 mL), with H$_2$O (3×50 mL) and then dried on a phase-separating filter and concentrated in a rotary evaporator. The yellow oil obtained is purified by silica gel chromatography (DCM/MeOH, 99/1→9/1) to obtain predominantly the hemiacetal 62 in the form of a yellow oil (7.1 g, 93%).

Rf=0.45 (DCM/MeOH, 98/2).

$^1$H NMR (CDCl$_3$), δ7.39-7.28 (m, 15H, CH$_{Ph}$), 5.44 (dd, 1H, J$_{1,2}$=1.9 Hz, J$_{2,3}$=3.2 Hz, H-2$_B$), 5.16 (dd, 1H, J$_{1,2}$=1.8 Hz, J$_{2,3}$=3.1 Hz, H-2$_C$), 5.12 (d, 1H, J$_{1,2}$=1.5 Hz, H-1$_C$), 5.05 (d, 1H, J$_{1,2}$=1.5 Hz, H-1$_B$), 4.92 (d, 1H, J=11.0 Hz, H$_{Bn}$), 4.83 (d, 1H, J=10.9 Hz, H$_{Bn}$), 4.67-4.60 (m, 3H, H$_{Bn}$), 4.45 (d, 1H, J=11.3 Hz, H$_{Bn}$), 4.20 (dd, 1H, J$_{2,3}$=3.3 Hz, J$_{3,4}$=9.5 Hz, H-3$_C$), 3.98 (dq, 1H, H-5$_C$), 3.89 (dd, 1H, J$_{2,3}$=3.3 Hz, J$_{3,4}$=9.3 Hz, H-3$_B$), 3.83 (dq, 1H, H-5$_B$), 3.77 (m, 1H, OH), 3.47 (pt, 1H, J$_{3,4}$=9.5 Hz, H-4$_C$), 3.43 (pt, 1H, J$_{3,4}$=9.3 Hz, H-4$_B$), 2.70 (m, 4H, 2CH$_{2Lev}$), 2.18 (s, 3H, CH$_{3Lev}$) 2.14 (s, 3H, H$_{Ac}$), 1.29 (d, 3H, J$_{5,6}$=6.3 Hz, H-6$_B$), 1.30 (d, 3H, J$_{5,6}$=6.2 Hz, H-6$_C$).

$^{13}$C NMR (CDCl$_3$), δ206.8 (C$_{Lev}$), 172.6 (C$_{Lev}$), 171.6 (C$_{Ac}$), 138.8-138.4 (C$_{Ph}$), 128.9-128.1 (CH$_{Ph}$), 99.9 (C-1$_B$, $^1$J$_{CH}$=173.3 Hz), 92.0 (C-1$_C$, $^1$J$_{CH}$=170.0 Hz), 80.7 (C-4$_C$), 80.2 (C-4$_B$), 78.0 (C-3$_B$), 77.7 (C-3$_C$), 75.8, 75.6 (2C, C$_{Bn}$), 73.2 (C-2$_C$), 72.0 (C$_{Bn}$), 69.7 (C-2$_B$), 69.0 (C-5$_B$), 68.0 (C-5$_C$), 38.4 (CH$_{2Lev}$), 30.2 (CH$_{3Lev}$), 28.5 (CH$_{2Lev}$), 21.5 (C$_{Ac}$), 18.5, 18.4 (C-6$_B$*, C-6$_C$*).

HRMS (ESI$^+$): [M+Na]$^+$ C$_{40}$H$_{48}$O$_{12}$Na m/z theoretical: 743.3043
m/z measured:
743.3173
[M+NH$_4$]$^+$ C$_{43}$H$_{52}$O$_{12}$NH$_4$ m/z theoretical:
738.3489
m/z measured:
738.3627

(3,4-Di-O-benzyl-2-O-levulinoyl-α-L-rhamnopyranosyl)-(1→3)-2-O-acetyl-4-O-benzyl-α/β-L-rhamnopyranose trichloroacetimidate 47

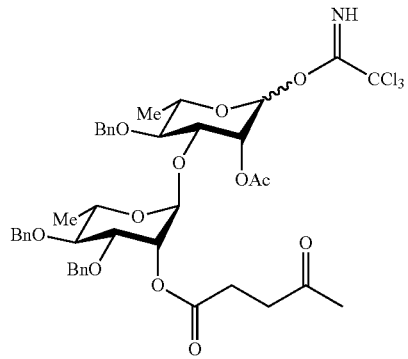

Chemical Formula: C$_{42}$H$_{48}$Cl$_3$NO$_{12}$
Exact Mass: 863.22
Molecular Weight: 865.19

The hemiacetal 62 (8.7 g, 12.1 mmol) is dissolved in DCE (50 mL) and stirred under argon at −5° C., and then DBU (508 µL, 3.3 mmol, 0.28 eq.) and trichloroacetonitrile (6.1 mL, 60.7 mmol, 5 eq.) are added. The reaction mixture is stirred at this temperature for 15 min and then it is loaded, without any treatment, on a silica gel column (flash chromatography, Chex/EtOAc+5% NEt$_3$, 7/3→1/1) to obtain the trichloroacetimidate 47 in the form of a yellow oil (8.7 g, 84%).

Rf=0.5 (Chex/EtOAc, 7/3).

$^1$H NMR (CDCl$_3$), δ8.72 (s, 1H, NH), 7.42-7.29 (m, 15H, CH$_{Ph}$), 6.22 (d, 1H, J$_{1,2}$=1.9 Hz, H-1$_C$), 5.48 (dd, 1H, J$_{1,2}$=1.8 Hz, J$_{2,3}$=3.2 Hz, H-2$_B$), 5.31 (dd, 1H, J$_{1,2}$=2.1 Hz, J$_{2,3}$=3.1 Hz, H-2$_C$), 5.10 (d, 1H, J$_{1,2}$=1.4 Hz, H-1$_B$), 4.92 (d, 1H, J=11.0 Hz, H$_{Bn}$), 4.85 (d, 1H, J=10.8 Hz, H$_{Bn}$), 4.68-4.62 (m, 3H, H$_{Bn}$), 4.51 (d, 1H, J=11.3 Hz, H$_{Bn}$), 4.26 (dd, 1H, J$_{2,3}$=3.3 Hz, J$_{3,4}$=9.5 Hz, H-3$_C$), 3.96 (dq, 1H, H-5$_C$), 3.89 (dd, 1H, J$_{2,3}$=3.3 Hz, J$_{3,4}$=9.3 Hz, H-3$_B$), 3.82 (dq, 1H, H-5$_B$), 3.58 (pt, 1H, J$_{3,4}$=9.5 Hz, H-4$_C$), 3.44 (pt, 1H, J$_{3,4}$=9.4 Hz, H-4$_B$), 2.72 (m, 4H, 2CH$_{2Lev}$), 2.18 (s, 3H, CH$_{3Lev}$), 2.17 (s, 3H, H$_{Ac}$), 1.36 (d, 3H, J$_{5,6}$=6.2 Hz, H-6$_C$), 1.29 (d, 3H, J$_{5,6}$=6.2 Hz, H-6$_B$).

$^{13}$C NMR (CDCl$_3$), δ206.5 (C$_{Lev}$), 172.3 (C$_{Lev}$), 170.3 (C$_{Ac}$), 160.5 (C=NH), 138.8-138.0 (C$_{Ph}$), 129.2-127.9 (CH$_{Ph}$), 99.9 (C-1$_B$, $^1$J$_{CH}$=137.3 Hz), 94.5 (C-1$_C$, $^1$J$_{CH}$=177.8 Hz), 91.2 (CCl$_3$), 80.2 (C-4$_C$), 80.1 (C-4$_B$), 77.9 (C-3$_B$), 76.5 (C-3$_C$), 76.1, 75.7, 72.0 (3C, C$_{Bn}$), 71.2 (C-2$_C$), 71.1 (C-5$_C$), 69.6 (C-2$_B$), 69.1 (C-5$_B$), 38.4 (CH$_{2Lev}$), 30.2 (CH$_{3Lev}$), 28.5 (CH$_{2Lev}$), 21.3 (C$_{Ac}$), 18.4, 18.3 (C-6$_B$*, C-6$_C$*).

Allyl (3,4-di-O-benzyl-2-O-levulinoyl-α-L-rhamnopyranosyl)-(1→3)-(2-O-acetyl-4-O-benzyl-α-L-rhamnopyranosyl)-(1→3)-(2-deoxy-4,6-O-isopropylidene-2-trichloroacetamido-β-D-glucopyranosyl)-(1→2)-[2,3,4,6-tetra-O-benzyl-α-D-glucopyranosyl-(1→3)]-4-O-benzyl-α-L-rhamnopyranoside 64

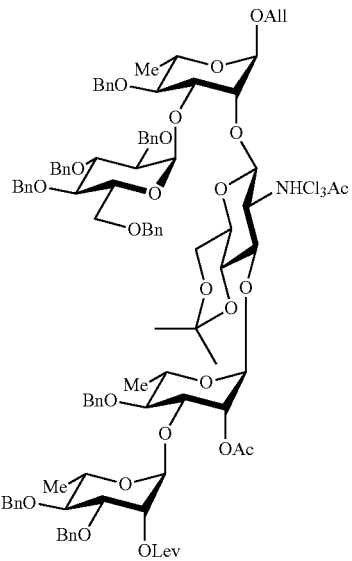

Chemical Formula: C$_{101}$H$_{116}$Cl$_3$NO$_{26}$
Exact Mass: 1863.6851
Molecular Weight: 1866.3518

TMSOTf (49.0 µL, 270 µmol, 0.3 eq.) is added to a solution of acceptor 38 (1.1 g, 0.9 mmol) and donor 47 (1.2 g, 1.4 mmol, 1.5 eq.) in Tol (30 mL), in the presence of molecular sieve 4 Å (1.1 g), stirred under argon at −40° C. After stirring for 15 min, monitoring by TLC (Tol/EtOAc, 8/2) indicates the disappearance of (Rf=0.25) and the appearance of a new, more polar compound (Rf=0.35). The reaction is stopped by adding triethylamine (0.1 mL), then the reaction mixture is filtered and concentrated in a rotary evaporator. The yellow oil obtained is purified by silica gel chromatography (Tol/EtOAc, 9/1→7/3) to obtain the allyl glycoside 64 as a white solid (1.4 g, 75%).

Rf=0.35 (Tol/EtOAc, 8/2).

$^1$H NMR (CDCl$_3$), δ7.51-7.13 (m, 40H, CH$_{Ph}$), 6.95 (d, 1H, J$_{NH,2}$=8.0 Hz, NH), 5.94 (m, 1H, CH=), 5.48 (dd, 1H, J$_{1,2}$=1.1 Hz, J$_{2,3}$=3.0 Hz, H-2$_B$), 5.33 (m, 1H, J$_{trans}$=17.2 Hz, =CH$_2$), 5.24 (m, 1H, J$_{cis}$=10.4 Hz, =CH$_2$), 5.24 (d, 1H, J$_{1,2}$=3.5 Hz, H-1$_E$), 5.16 (m, 2H, H$_{An}$), 5.12 (dd, 1H, J$_{2,3}$=2.8 Hz, H-2$_C$), 5.11 (d, 1H, J$_{1,2}$=1.3 Hz, H-1$_B$), 5.07 (d, 1H, J=12.2 Hz, H$_{Bn}$), 4.96 (m, 2H, H$_{Bn}$), 4.87 (d, 2H, J=11.0 Hz, H$_{Bn}$), 4.84 (d, 1H, J$_{1,2}$=1.7 Hz, H-1$_A$), 4.79 (d, 1H, J$_{1,2}$=1.6 Hz, H-1$_C$), 4.77-4.54 (d, 8H, H$_{Bn}$, H-1$_D$), 4.46 (d, 1H, J=11.3 Hz, H$_{Bn}$), 4.36 (d, 1H, J=12.0 Hz, H$_{Bn}$), 4.24-4.15 (m, 5H, H-3$_E$, H-3$_C$, H$_{A11}$, H-3$_A$, H-5$_E$), 4.09-3.98 (m, 5H, H-2$_D$, H-2$_A$, H-5$_C$, H$_{A11}$, H-5$_B$), 3.95 (dd, 1H, H-2$_4$, H-2$_D$, H$_{411}$), 3.90 (dd, 1H, J$_{5,6a}$5.3 Hz, J$_{6a,6b}$=10.7 Hz, H-6a$_D$), 3.83-3.72 (m, 4H, H-2$_E$, H-4$_E$, H-6b$_D$, H-5$_A$), 3.55 (pt, 1H, J$_{3,4}$=9.1 Hz, H-4$_D$), 3.54 (pt, 1H, J$_{3,4}$=9.5 Hz, H-4$_A$), 3.43 (m, 2H, H-6a$_E$, H-6b$_E$), 3.36 (pt, 1H, J$_{2,3}$=9.2 Hz, H-3$_D$), 2.94 (m, 1H, H-5$_D$), 1.51 (s, 3H, H$_{iPr}$), 1.45 (s, 3H, H$_{iPr}$), 1.44 (d, 3H, J$_{5,6}$=6.2 Hz, H-6$_A$), 0.13 (s, 9H, H$_{Si}$).

$^{13}$C NMR (CDCl$_3$), δ206.5 (C$_{Lev}$), 172.1 (C$_{Lev}$), 169.9 (C$_{Ac}$), 162.4 (C$_{NTCA}$), 139.1-138.8 (C$_{Ph}$), 134.4 (CH=), 129.5-127.8 (CH$_{Ph}$), 117.5 (=CH$_2$), 101.7 (C-1$_D$, $^1$J$_{CH}$=163.9 Hz), 99.9 (C$_{iPr}$), 99.4 (C-1$_B$, $^1$J$_{CH}$=174.7 Hz), 98.8 (C-1$_A$, $^1$J$_{CH}$=171.5 Hz), 98.1 (C-1$_C$, $^1$J$_{CH}$=167.6 Hz), 94.9 (C-1$_E$, $^1$J$_{CH}$=165.3 Hz), 93.5 (CCl$_3$), 83.5 (C-3$_E$), 80.9 (C-2$_E$), 80.8 (C-4$_B$), 80.3 (C-4$_C$), 80.1 (C-4$_A$), 79.2 (C-3$_D$), 79.1 (C-4$_E$), 78.0 (C-3$_B$), 77.1 (C-3$_C$), 76.4, 75.8, 75.7, 75.4, 75.3, 75.2 (6C, C$_{Bn}$), 75.1 (C-3$_A$), 74.2 (C-2$_A$), 73.8 (C$_{Bn}$), 73.1 (C-4$_D$), 72.8 (C-2$_C$), 71.9 (C$_{Bn}$), 70.3 (C-5$_E$), 69.9 (C-2$_B$), 69.0 (C-5$_B$), 68.8 (C-5$_A$), 68.4 (C-6$_E$), 68.3 (C-5$_C$), 68.2 (C$_{A11}$), 67.4 (C-5$_D$), 62.5 (C-6$_D$), 57.8 (C-2$_D$), 38.6 (CH$_{2Lev}$), 30.3 (CH$_{3Lev}$) 29.6 (C$_{iPr}$), 28.7 (CH$_{2Lev}$) 21.5 (C$_{Ac}$), 19.4 (C$_{iPr}$), 18.5 (C-6$_C$), 18.4 (C-6$_A$), 18.3 (C-6$_B$).

HRMS (ESI$^+$): [M+Na]$^+$ C$_{101}$H$_{116}$$^{35}$Cl$_3$NO$_{26}$Na m/z theoretical:
1886.6749
m/z measured:
1886.6445
[M+NH$_4$]$^+$ C$_{88}$H$_{104}$$^{35}$Cl$_3$NO$_{27}$NH$_4$ m/z theoretical:
1881.7195
m/z measured:
1881.6897

Allyl (2-deoxy-4,6-O-isopropylidene-2-trichloroacetamido-3-trimethylsilyl-β-D-glucopyranosyl)-(1,2)-[2,3,4,6-tetra-O-benzyl-α-D-glucopyranosyl-(1→3)]-4-O-benzyl-α-L-rhamnopyranoside 63

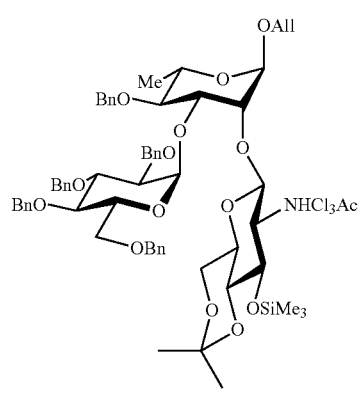

Chemical Formula: C$_{64}$H$_{78}$Cl$_3$NO$_{15}$Si
Exact Mass: 1233.4206
Molecular Weight: 1235.7463

TMSOTf (49.0 μL, 270 μmol, 0.3 eq.) is added to a solution of acceptor 38 (2.0 g, 1.7 mmol) and donor 47 (2.3 g, 2.6 mmol, 1.5 eq.) in Tol (30 mL), in the presence of molecular sieve 4 Å (1.1 g), stirred under argon at −78° C. After stirring for 15 min, monitoring by TLC (Tol/EtOAc, 8/2) indicates the disappearance of 38 (Rf=0.25) and the appearance of a new, more polar compound (Rf=0.35). The reaction is stopped by adding triethylamine (0.1 mL), then the reaction mixture is filtered and concentrated in a rotary evaporator. The yellow oil obtained is purified by silica gel chromatography (Tol/AcOEt: 9/1→7/3), obtaining, in the order of elution, the silylated compound 63 (233 mg, 11%) and then the allyl glycoside 64 (1.4 g, 66%).

Rf=0.5 (Tol/EtOAc, 8/2).

$^1$H NMR (CDCl$_3$), δ7.47-7.08 (m, 26H, NH, CH$_{Ph}$), 5.89 (m, 1H, CH=), 5.32 (m, 1H, J$_{trans}$=17.2 Hz, =CH$_2$), 5.23 (m, 1H, J$_{cis}$=10.6 Hz, =CH$_2$), 5.12 (d, 1H, J$_{1,2}$=3.6 Hz, H-1$_E$), 5.11-5.05 (m, 3H, H$_{Bn}$), 4.93 (d, 1H, J=12.8 Hz, H$_{Bn}$) 4.86 (d, 1H, J$_{1,2}$=1.6 Hz, H-1$_A$), 4.83-4.76 (m, 3H, H$_{Bn}$, H-1$_D$, H$_{Bn}$), 4.61-4.56 (m, 2H, H$_{Bn}$), 4.50 (d, 1H, J=11.0 Hz, H$_{Bn}$), 4.32 (d, 1H, J=12.0 Hz, H$_{Bn}$), 4.22-4.10 (m, 4H, H-3$_E$, H$_{A11}$, H-3$_A$, H-5$_E$), 4.08-3.97 (m, 3H, H-2$_A$, H-2$_D$, H$_{A11}$), 3.90 (dd, 1H, J$_{5,6a}$5.3 Hz, J$_{6a,6b}$=10.7 Hz, H-6a$_D$), 3.83-3.72 (m, 4H, H-2$_E$, H-4$_E$, H-6b$_D$, H-5$_A$), 3.55 (pt, 1H, J$_{3,4}$=9.1 Hz, H-4$_D$), 3.54 (pt, 1H, J$_{3,4}$=9.5 Hz, H-4$_A$), 3.43 (m, 2H, H-6a$_E$, H-6b$_E$), 3.36 (pt, 1H, J$_{2,3}$=9.2 Hz, H-3$_D$), 2.94 (m, 1H, H-5$_D$), 1.51 (s, 3H, H$_{iPr}$), 1.45 (s, 3H, H$_{iPr}$), 1.44 (d, 3H, J$_{5,6}$=6.2 Hz, H-6$_A$), 0.13 (s, 9H, H$_{Si}$).

$^{13}$C NMR (CDCl$_3$), δ161.7 (C$_{NTCA}$), 138.7-137.7 (C$_{Ph}$), 134.0 (CH=), 129.1-127.3 (CH$_{Ph}$), 117.1 (=CH$_2$), 101.5 (C-1$_D$, $^1$J$_{CH}$=163.6 Hz), 99.4 (C$_{iPr}$), 98.5 (C-1$_A$, $^1$J$_{CH}$=174.0 Hz), 95.2 (C-1$_E$, $^1$J$_{CH}$=167.5 Hz), 93.3 (CCl$_3$), 83.3 (C-3$_E$), 79.8 (C-4$_A$), 78.7, 78.6 (2C, C-2$_E$*, C-4$_E$*), 75.9 (C$_{Bn}$), 75.4 (C-3$_A$), 75.3, 74.9 (2C, C$_{Bn}$), 74.3 (C-3$_D$), 74.3 (C$_{Bn}$), 74.2 (C-4$_D$), 74.1 (C-2$_A$), 73.4 (C$_{Bn}$), 70.0 (C-5$_E$), 68.5 (C-5$_A$), 67.9 (C-6$_E$), 67.8 (C$_{A11}$), 67.2 (C-5$_D$), 62.1 (C-6$_D$), 58.6 (C-2$_D$), 29.1 (C$_{iPr}$) 19.0 (C$_{iPr}$), 18.0 (C-6$_A$), 0.7 (C$_{Si}$).

HRMS (ESI$^+$): [M+Na]$^+$ C$_{64}$H$_{78}$NO$_{15}$$^{35}$Cl$_3$SiNa m/z theoretical:
1256.4104
m/z measured:
1256.4188
[M+NH$_4$]$^+$ C$_{64}$H$_{78}$NO$_{15}$$^{35}$Cl$_3$SiNH$_4$ m/z theoretical:
1251.4550
m/z measured:
1251.4548

Allyl (3,4-di-O-benzyl-α-L-rhamnopyranosyl)-(1→3)-(2-O-acetyl-4-O-benzyl-α-L-rhamnopyranosyl)-(1→3)-(2-deoxy-4,6-O-isopropylidene-2-trichloroacetamido-β-D-glucopyranosyl)-(1→2)-[2,3,4,6-tetra-O-benzyl-α-D-glucopyranosyl-(1→3)]-4-O-benzyl-α-L-rhamnopyranoside 66

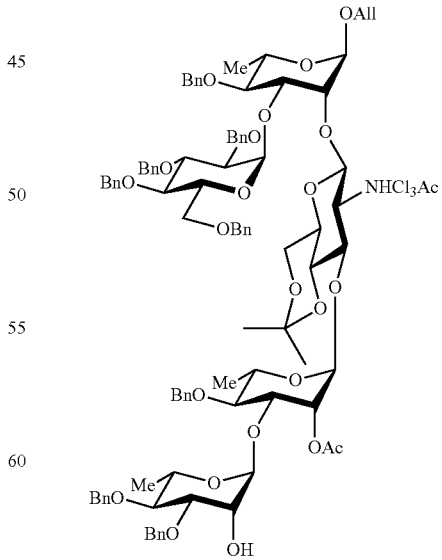

Chemical Formula: C$_{96}$H$_{110}$Cl$_3$NO$_{24}$
Exact Mass: 1765.6483
Molecular Weight: 1768.2519

The allyl glycoside 64 (1.2 g, 570 µmol) is dissolved in pyridine/acetic acid mixture (3/2, 10 mL). Hydrazine monohydrate (280 µL, 5.7 mmol, 10 eq.) is added dropwise to the reaction mixture. After stirring for 25 min at 0° C., monitoring by TLC (Tol/EtOAc, 7/3) indicates the disappearance of 64 (Rf=0.5) and the appearance of a more polar product (Rf=0.35). The reaction mixture is then taken up in cold water (10 mL) and the aqueous phase is quickly extracted with DCM (3×50 mL). The organic phases are combined and washed with NaCl$_{sat}$ solution, filtered on a phase-separating filter and concentrated in a rotary evaporator. The oil obtained is purified by silica gel chromatography (Tol/EtOAc, 9/1→7/3) to obtain the alcohol 66 as a white solid (950 mg, 94%).

Rf=0.35 (Tol/EtOAc, 7/3).

$^1$H NMR (CDCl$_3$), δ7.48-7.06 (m, 40H, CH$_{Ph}$), 6.87 (d, 1H, J$_{NH,2}$=8.9 Hz, NH), 5.90 (m, 1H, CH=), 5.29 (m, 1H, J$_{trans}$=17.2 Hz, =CH$_2$), 5.24 (m, 1H, J$_{cis}$=11.5 Hz, =CH$_2$), 5.16 (d, 1H, J$_{1,2}$=3.6 Hz, H-1$_E$), 5.10-5.07 (m, 4H, H$_{Bn}$, H-1$_B$, H-2$_C$, H$_{Bn}$), 5.02 (d, 1H, J=12.1 Hz, H$_{Bn}$) 4.89 (m, 2H, H$_{Bn}$), 4.81 (d, 1H, J=11.0 Hz, H$_{Bn}$), 4.78 (d, 1H, J$_{1,2}$=1.7 Hz, H-1$_A$), 4.76 (d, 1H, J$_{1,2}$=1.7 Hz, H-1$_C$), 4.75-4.49 (m, 10H, 9H$_{Bn}$, H-1$_D$), 4.32 (d, 1H, J=11.9 Hz, H$_{Bn}$), 4.19-4.10 (m, 5H, H-3$_E$, H$_{A11}$, H-3$_A$, H-3$_C$, H-5$_E$), 4.04-3.93 (m, 5H, H-2$_D$, H-2$_A$, H$_{A11}$, H-5$_C$, H-2$_B$), 3.90-3.82 (m, 4H, H-5$_B$, H-6a$_D$, H-2$_E$, H-4$_E$), 3.77 (dd, 1H, J$_{2,3}$=3.2 Hz, J$_{3,4}$=9.1 Hz, H-3$_B$), 3.74-3.67 (m, 2H, H-6b$_D$, H-5$_A$), 3.54 (pt, 1H, J$_{3,4}$=9.2 Hz, H-4$_D$), 3.51-3.44 (m, 4H, H-4$_A$, H-4$_B$, H-6a$_E$, H-6b$_E$) 3.40 (pt, 1H, J$_{3,4}$=9.4 Hz, H-4$_C$), 2.81 (m, 1H, H-5$_D$), 2.68 (pt, 1H, J$_{2,3}$=9.2 Hz, H-3$_D$), 2.13 (s, 3H, H$_{Ac}$), 1.48 (s, 3H, H$_{iPr}$), 1.46 (s, 3H, H$_{iPr}$), 1.40 (d, 3H, J$_{5,6}$=6.2 Hz, H-6$_A$), 1.33 (d, 3H, J$_{5,6}$=6.2 Hz, H-6$_B$), 1.25 (d, 3H, J$_{5,6}$=6.2 Hz, H-6$_C$).

$^{13}$C NMR (CDCl$_3$), δ169.6 (C$_{Ac}$), 162.0 (C$_{NTCA}$), 138.6-137.6 (C$_{Ph}$), 133.9 (CH=), 129.4-127.4 (CH$_{Ph}$), 117.1 (=CH$_2$), 101.2 (C-1$_D$, $^1$J$_{CH}$=158.9 Hz), 100.7 (C-1$_B$, $^1$J$_{CH}$=172.6 Hz), 99.4 (C$_{iPr}$), 98.4 (C-1$_A$, $^1$J$_{CH}$=172.4 Hz), 97.4 (C-1$_C$, $^1$J$_{CH}$=170.7 Hz), 94.3 (C-1$_E$, $^1$J$_{CH}$=166.4 Hz), 93.0 (CCl$_3$), 83.1 (C-3$_E$), 80.4 (C-4$_C$), 80.3 (C-2$_E$), 79.9, 79.7 (2C, C-4$_A$*, C-4$_B$*), 79.6 (C-3$_B$), 78.7 (C-4$_E$), 78.5 (C-3$_D$), 77.0 (C-3$_C$), 76.0, 75.3, 75.4, 75.0, 74.9, 74.8 (6C, C$_{Bn}$) 74.5 (C-3$_A$), 73.7 (C-2$_A$), 73.3 (C$_{Bn}$), 72.6 (C-4$_D$), 72.4 (C-2$_C$), 71.8 (C$_{Bn}$) 69.9 (C-5$_E$), 69.0 (C-2$_B$), 68.4 (C-5$_A$), 68.2 (C-5$_B$), 68.0 (C-6$_E$), 67.8 (C-5$_C$), 67.7 (C$_{A11}$), 66.9 (C-5$_D$) 62.1 (C-6$_D$), 57.3 (C-2$_D$), 29.2 (C$_{iPr}$), 21.1 (C$_{Ac}$), 19.0 (C$_{iPr}$) 18.1, 17.9, 17.8 (C-6$_A$*, C-6$_B$*, C-6$_C$*).

HRMS (ESI$^+$) [M+Na]$^+$ C$_{96}$H$_{110}$$^{35}$Cl$_3$NO$_{24}$Na m/z theoretical:

1788.6381 m/z measured:

1788.6537

[M+H]$^+$ C$_{96}$H$_{110}$$^{35}$Cl$_3$NO$_{24}$ m/z theoretical:

1766.6561 m/z measured:

1766.6667

Allyl (3,4-di-O-benzyl-α-L-rhamnopyranosyl)-(1→3)-(2-O-acetyl-4-O-benzyl-α-L-rhamnopyranosyl)-(1→3)-(2-deoxy-2-trichloroacetamido-β-D-glucopyranosyl)-(1→2)-[2,3,4,6-tetra-O-benzyl-α-D-glucopyranosyl-(1→3)]-4-O-benzyl-α-L-rhamnopyranoside 67

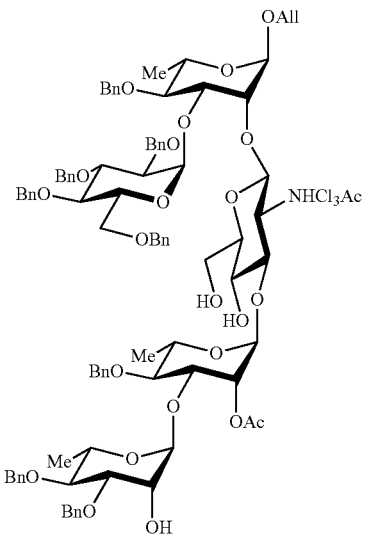

Chemical Formula: C$_{93}$H$_{106}$Cl$_3$NO$_{24}$
Exact Mass: 1725.6170
Molecular Weight: 1728.1880

50% aqueous TFA solution (4 mL) is slowly added to a solution of alcohol 66 (367 mg, 210 µmol) in DCM (10 mL) at 0° C. The reaction mixture is stirred for 2 h at this temperature, after which time monitoring by TLC (DCM/MeOH, 95/5) indicates the complete disappearance of the starting product (Rf=0.85) and the appearance of a new, more polar compound (Rf=0.3). The reaction mixture is concentrated by coevaporation with Tol (3×10 mL). The yellow oil obtained is purified by silica gel chromatography (Tol/EtOAc, 7/3→6/4) to obtain the triol 67 as a white solid (300 mg, 84%).

Rf=0.3 (DCM/MeOH, 95/5).

$^1$H NMR (CDCl$_3$), δ7.44-7.06 (m, 40H, CH$_{Ph}$), 7.02 (d, 1H, J$_{NH,2}$=8.8 Hz, NH), 5.90 (m, 1H, CH=), 5.30 (m, 1H, J$_{trans}$=18.7 Hz, =CH$_2$), 5.24-5.22 (m, 2H, =CH$_2$, H-1$_E$), 5.14 (dd, 1H, J, J$_{1,2}$=2.0 Hz, J$_{2,3}$=2.9 Hz, H-2$_C$), 5.10 (d, 1H, J$_{1,2}$=1.1 Hz, H-1$_B$), 5.10-5.05 (m, 2H, H$_{Bn}$), 4.96 (d, 1H, J=12.7 Hz, H$_{Bn}$), 4.90 (d, 1H, J=11.0 Hz, H$_{Bn}$), 4.84 (d, 1H, J$_{1,2}$=1.6 Hz, H-1$_A$), 4.83-4.73 (m, 4H, H$_{Bn}$), 4.66 (d, 1H, J=10.9 Hz, H$_{Bn}$), 4.51-4.50 (m, 8H, H$_{Bn}$, H-1$_C$, H$_{Bn}$, H-1$_D$, 4H$_{Bn}$), 4.34 (d, 1H, J=12.0 Hz, H$_{Bn}$), 4.21 (bs, 1H, OH-4$_D$), 4.20-4.12 (m, 5H, H3$_A$, H$_{A11}$, H-3$_E$, H-3$_C$, H-5$_E$), 4.00-3.91 (m, 5H, H-2$_B$, H-2$_A$, H$_{A11}$, H-2$_D$, H-5$_C$), 3.86-3.69 (m, 7H, H-6a$_D$, H-2$_E$, H-3$_B$, H-4$_E$, H-5$_E$, H-6b$_D$, H-5$_A$), 3.50-3.45 (m, 4H, H-6a$_E$, H-6b$_E$, H-4$_A$, H-4$_E$), 3.40 (pt, 1H, J$_{3,4}$=9.5 Hz, H-4$_C$), 3.36 (pt, 1H, J$_{3,4}$=9.2 Hz, H-4$_D$), 3.03 (m, 1H, H-5$_D$), 2.31 (bs, 1H, OH-4$_D$), 2.24 (pt, 1H, J$_{2,3}$=9.8 Hz, H-3$_D$), 2.18 (s, 3H, H$_{Ac}$), 1.41 (d, 3H, J$_{5,6}$=6.2 Hz, H-6$_A$), 1.30 (m, 3H, H-6$_C$), 1.26 (d, 3H, J$_{5,6}$=6.2 Hz, H-6$_B$).

$^{13}$C NMR (CDCl$_3$), δ170.0 (C$_{Ac}$), 162.2 (C$_{NTCA}$), 138.5-137.6 (C$_{Ph}$), 133.9 (CH=), 129.4-127.4 (CH$_{Ph}$), 117.3 (=CH$_2$), 101.0 (C-1$_D$, $^1J_{CH}$=160.2 Hz), 100.7 (C-1$_B$, $^1J_{CH}$=165.1 Hz), 98.2 (2C, C-1$_A$, C-1$_C$, $^1J_{CH}$=169.6 Hz), 94.3 (C-1$_E$, $^1H_{CH}$=166.7 Hz), 93.0 (CCl$_3$), 86.7 (C-3$_D$), 83.1 (C-3$_E$), 80.4 (C-2$_E$), 79.9, 79.7 (C-4$_A$*, C-4$_B$*), 79.6 (C-4$_E$), 79.2 (C-4$_C$), 78.7 (C-3$_E$), 77.9 (C-3$_C$), 76.2, 75.4, 75.3, 75.0 (6C, C$_{Bn}$), 74.6 (C-5$_B$), 74.3 (C-3$_A$), 74.2 (C-2$_A$), 73.4 (C$_{Bn}$), 72.0 (C-2$_C$), 71.6 (C$_{Bn}$), 70.8 (C-4$_D$), 69.9 (C-5$_E$), 69.1 (C-5$_C$), 68.7 (C-2$_B$), 68.5 (C-5$_A$), 68.4 (C-5$_B$), 68.0 (C-6$_E$), 67.7 (C$_{All}$), 62.9 (C-6$_D$), 55.1 (C-2$_D$), 21.1 (C$_{Ac}$), 18.0, 17.9, 17.8 (C-6$_A$*, C-6$_B$*, C-6$_C$*).

HRMS (ESI$^+$): [M+Na]$^+$ C$_{93}$H$_{106}$$^{35}$Cl$_3$NO$_{24}$Na m/z theoretical:
1748.6068
m/z measured:
1748.6008

Propyl α-L-rhamnopyranosyl-(1→3)-(2-O-acetyl-α-L-rhamnopyranosyl)-(1→3)-(2-acetamido-2-deoxy-O-D-glucopyranosyl)-(1→2)-[α-D-glucopyranosyl-(1→3)]-α-L-rhamnopyranoside V

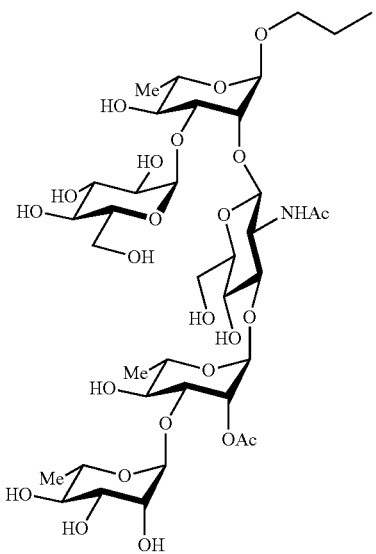

Chemical Formula: C$_{37}$H$_{63}$NO$_{24}$
Exact Mass: 905.3740
Molecular Weight: 905.8884

Route 1:
Pd—C 10% (280 mg) is added to a degassed solution of pentasaccharide 56 (270 mg, 180 µmol) in ethanol (20 mL). The suspension is saturated with hydrogen at 50 bar and stirred at RT for 10 days. Monitoring by TLC (iPrOH/H$_2$O/NH$_3$, 4/1/0.5 and DCM/MeOH, 95/5) shows the disappearance of 56 (Rf=1 and 0.3, respectively) and the appearance of a new, more polar compound (Rf=0.3 and 0, respectively). The reaction mixture is filtered on an Acrodisc LC 25 mm filter, and the filtrate is concentrated in a rotary evaporator. The residue obtained is purified on a C-18 column (H$_2$O/CH$_3$CN, 100/0→7/3) to give the target V as a white solid (111 mg, 70%).

Route 2:
Pd—C 10% (70 mg) is added to a degassed solution of pentasaccharide 67 (100 mg, 58 µmol) in ethanol (10 mL). The suspension is saturated with hydrogen at 50 bar and stirred at RT for 10 days. Monitoring by TLC (iPrOH/H$_2$O/NH$_3$, 4/1/0.5 and DCM/MeOH, 95/5) shows the disappearance of 67 (Rf=1 and 0.3, respectively) and the appearance of a new, more polar compound (Rf=0.3 and 0, respectively). The reaction mixture is filtered on an Acrodisc LC 25 mm filter, and the filtrate is concentrated in a rotary evaporator. The residue obtained is purified on a C-18 column (H$_2$O/CH$_3$CN, 100/0→7/3) to give the target V as a white solid (40 mg, 75%).

Rf=0.3 (iPrOH/H$_2$O/NH$_3$, 4/1/0.5).

$^1$H NMR (D$_2$O), δ5.04 (d, 1H, J$_{1,2}$=3.7 Hz, H-1$_E$), 4.91 (m, 1H, H-2$_C$), 4.90 (d, 1H, J$_{1,2}$=1.4 Hz, H-1$_B$), 4.83 (d, 1H, J$_{1,2}$=1.7 Hz, H-1$_A$), 4.79 (d, 1H, J$_{1,2}$=1.4 Hz, H-1$_C$), 4.72 (d, 1H, H-1$_D$), 4.17 (m, 1H, H-2$_A$), 4.00 (m, 1H, H-5$_C$), 3.96 (m, 1H, H-5$_E$), 3.91 (m, 1H, H-2$_B$), 3.86 (dd, 1H, J$_{2,3}$=3.2 Hz, J$_{3,4}$=9.7 Hz, H-3$_C$), 3.82-3.79 (m, 2H, H-3$_A$, H-6a$_D$), 3.76 (m, 1H, H-2$_D$), 3.71 (pt, 1H, J$_{3,4}$=9.5 Hz, H-3$_E$), 3.69 (m, 2H, H-6a$_E$, H-6b$_E$), 3.67-3.52 (m, 5H, H-6b$_D$, H$_{Pr}$, H-5$_A$, H-2$_E$, H-3$_B$), 3.48 (pt, 1H, J$_{3,4}$=9.9 Hz, H-4$_C$), 3.44 (m, 1H, H-5$_B$), 3.40 (m, 1H, H$_{Pr}$), 3.38 (m, 1H, H-4$_E$), 3.33 (m, 1H, H-4$_B$), 3.33-3.28 (m, 3H, H-5$_D$, H-4$_D$, H-3$_D$), 3.23 (pt, 1H, J$_{3,4}$=9.7 Hz, H-4$_A$), 2.07 (s, 3H, H$_{Ac}$), 2.04 (s, 3H, H$_{NAc}$), 1.49 (sex, 2H, CH$_2$), 1.17 (d, 3H, J$_{5,6}$=6.1 Hz, H-6$_A$), 1.16 (m, 3H, J$_{5,6}$=6.0 Hz, H-6$_B$), 1.15 (d, 3H, J$_{5,6}$=6.4 Hz, H-6$_C$), 0.80 (t, 3H, J=7.4 Hz, CH$_3$).

$^{13}$C NMR (D$_2$O), δ174.7 (C$_{NAc}$), 173.5 (C$_{Ac}$), 103.1 (C-1$_B$, $^1J_{CH}$=172.0 Hz), 101.9 (C-1$_D$, $^1J_{CH}$=163.9 Hz), 99.0 (C-1$_A$, $^1J_{CH}$=174.2 Hz), 98.7 (C-1$_C$, $^1J_{CH}$=171.2 Hz), 94.7 (C-1$_E$, $^1J_{CH}$=170.5 Hz), 83.0 (C-3$_D$), 77.4 (C-3$_C$), 76.4 (C-4$_D$), 74.7 (C-2$_A$), 74.0 (C-3$_A$), 73.5 (C-3$_E$), 72.8 (C-2$_C$), 72.1 (C-4$_B$), 71.7 (C-5$_E$), 71.6 (C-2$_E$), 71.5 (C-4$_C$), 71.2 (C-4$_A$), 70.5 (C-2$_B$), 70.3 (C-3$_B$), 70.0 (C$_{Pr}$), 69.4 (2C, C-4$_E$, C-5$_D$), 69.2 (C-5$_C$), 69.1 (C-5$_A$), 68.5 (C-5$_B$), 61.0 (C-6$_D$), 60.6 (C-6$_E$) 55.8 (C-2$_D$), 23.1 (C$_{NAc}$), 22.3 (CH$_2$), 20.6 (C$_{Ac}$), 17.1, 16.9, 16.7 (C-6$_A$*, C-6$_B$*, C-6$_C$*), 10.2 (CH$_3$).

HRMS (ESI$^+$): [M+H]$^+$ C$_{37}$H$_{64}$NO$_{24}$ m/z theoretical:
906.3818
m/z measured:
906.3823
[M+Na]$^+$ C$_{37}$H$_{63}$NO$_{24}$Na m/z theoretical:
928.3638
m/z measured:
928.3630

Method 6

Propyl α-L-rhamnopyranosyl-(1→3)-α-L-rhamnopyranosyl-(1→3)-(2-acetamido-2-deoxy-β-D-glucopyranosyl)-(1→2)-[α-D-glucopyranosyl-(1→3)]-α-L-rhamnopyranoside VI

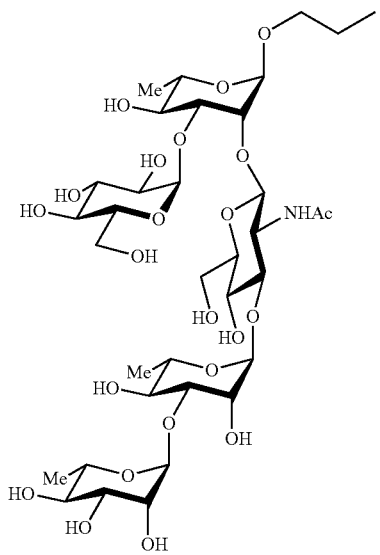

Chemical Formula: C$_{35}$H$_{61}$NO$_{23}$
Exact Mass: 863.3634
Molecular Weight: 863.8517

Pd—C 10% (250 mg) is added to a degassed solution of pentasaccharide 57 (200 mg, 130 μmol) in ethanol (15 mL). The suspension is saturated with hydrogen at 50 bar and stirred at RT for 2 days. Monitoring by TLC (iPrOH/H$_2$O/NH$_3$, 4/1/0.5 and DCM/MeOH, 95/5) shows the disappearance of 57 (Rf=1 and 0.2, respectively) and the appearance of a new, more polar compound (Rf=0.2 and 0, respectively). The reaction mixture is filtered on an Acrodisc LC 25 mm filter, and the filtrate is concentrated in a rotary evaporator. The residue obtained is purified on a C-18 column (H$_2$O/CH$_3$CN, 100/0→7/3) to give the target VI as a white solid (81 mg, 71%).

Rf=0.2 (iPrOH/H$_2$O/NH$_3$, 4/1/0.5).

$^1$H NMR (D$_2$O), δ4.94 (d, 1H, J$_{1,2}$=3.6 Hz, H-1$_E$), 4.78 (bs, 1H, H-1$_B$), 4.71 (bs, 1H, H-1$_A$), 4.63 (bs, 1H, H-1$_D$), 4.61 (bs, 1H, H-1$_C$), 4.07 (m, 1H, H-2$_A$), 3.83-3.78 (m, 3H, H-2$_B$, H-5$_E$, H-5$_C$), 3.71-3.68 (m, 2H, H-3$_A$, H-6a$_D$), 3.66-3.64 (m, 2H, H-2$_C$, H-2$_D$), 3.62-3.59 (m, 2H, H-3$_E$, H-3$_B$), 3.59-3.52 (m, 5H, H-6a$_E$, H-6b$_E$, H-3$_C$, H-5$_B$, H-6b$_D$), 3.50-3.39 (m, 2H, H-5$_A$, H-2$_E$), 3.41 (m, 1H, H$_{Pr}$), 3.32-3.18 (m, 7H, H-4$_E$, H-4$_C$, H$_{Pr}$, H-3$_D$, H-5$_D$, H-4$_B$, H-4$_D$), 3.10 (pt, 1H, J$_{3,4}$=9.7 Hz, H-4$_A$), 1.89 (s, 3H, H$_{NAc}$), 1.38 (sex, 2H, CH$_2$), 1.09 (m, 3H, J$_{5,6}$=6.2 Hz, H-6$_D$), 1.05 (d, 3H, J$_{5,6}$=6.2 Hz, H-6$_A$), 1.01 (d, 3H, J$_{5,6}$=6.2 Hz, H-6$_B$), 0.29 (t, 3H, J=7.4 Hz, CH$_3$).

$^{13}$C NMR (D$_2$O), δ174.4 (C$_{NAc}$), 102.8 (C-1$_E$, $^1$J$_{CH}$=172.0 Hz), 102.0 (C-1$_D$, $^1$J$_{CH}$=163.2 Hz), 101.7 (C-1$_C$, $^1$J$_{CH}$=171.2 Hz), 99.1 (C-1$_A$, $^1$J$_{CH}$=172.7 Hz), 95.0 (C-1$_E$, $^1$J$_{CH}$=170.5 Hz), 82.1 (C-3$_E$), 78.5 (C-3$_C$), 76.5 (C-4$_D$), 74.8 (C-2$_A$), 74.4 (C-3$_A$), 73.6 (C-3$_E$), 72.5 (C-4$_E$), 71.9 (C-5$_E$), 71.8 (C-2$_E$), 71.7 (C-4$_C$), 71.3 (C-4$_A$), 71.0 (C-2$_C$), 70.7 (C-3$_B$), 70.6 (C-2$_B$), 70.1 (C$_{Pr}$), 69.9 (C-5$_D$), 69.5 (2C, C-5$_B$, C-5$_C$), 69.3 (C-5$_A$), 68.8 (C-4$_E$), 61.2 (C-6$_D$), 60.8 (C-6$_E$), 55.9 (C-2$_D$), 23.1 (C$_{NAc}$), 22.5 (CH$_2$), 17.2, 17.1, 16.9 (C-6$_A$*, C-6$_B$*, C-6$_C$*), 10.3 (CH$_3$).

HRMS (ESI$^+$): [M+H]$^+$ C$_{35}$H$_{62}$NO$_{23}$ m/z theoretical: 864.3713
m/z measured: 864.3652
[M+Na]$^+$ C$_{35}$H$_{62}$NO$_{23}$Na m/z theoretical: 886.3532
m/z measured: 886.3461

Section III—Synthesis of the targets XI, XII, XIII, XIV, XV and XVI

In this section we shall describe the synthesis of all of the target tetra- and pentasaccharides bearing a residue C or D at their reducing end. As previously, the targets were synthesized in the form of propyl glycoside so as to block the reducing position in accordance with the anomerism adopted by the residue in the natural polysaccharide. The residue C is acetylated or non-acetylated, corresponding respectively to representative fragments of the O antigens of serotypes 3a and X of S. flexneri.

| | Acceptor | Donor | Target |
|---|---|---|---|
| Method 7 | 79 | 80 | XI |
| Method 8 | 79 | 80 | XII |
| Method 9 | 85 | 1 | XIII |
| Method 10 | 85 | 1 | XIV |
| Method 11 | 86 | 19 | XV |
| Method 12 | 86 | 19 | XVI |

Back synthesis of the oligosaccharides in reducing series C and D

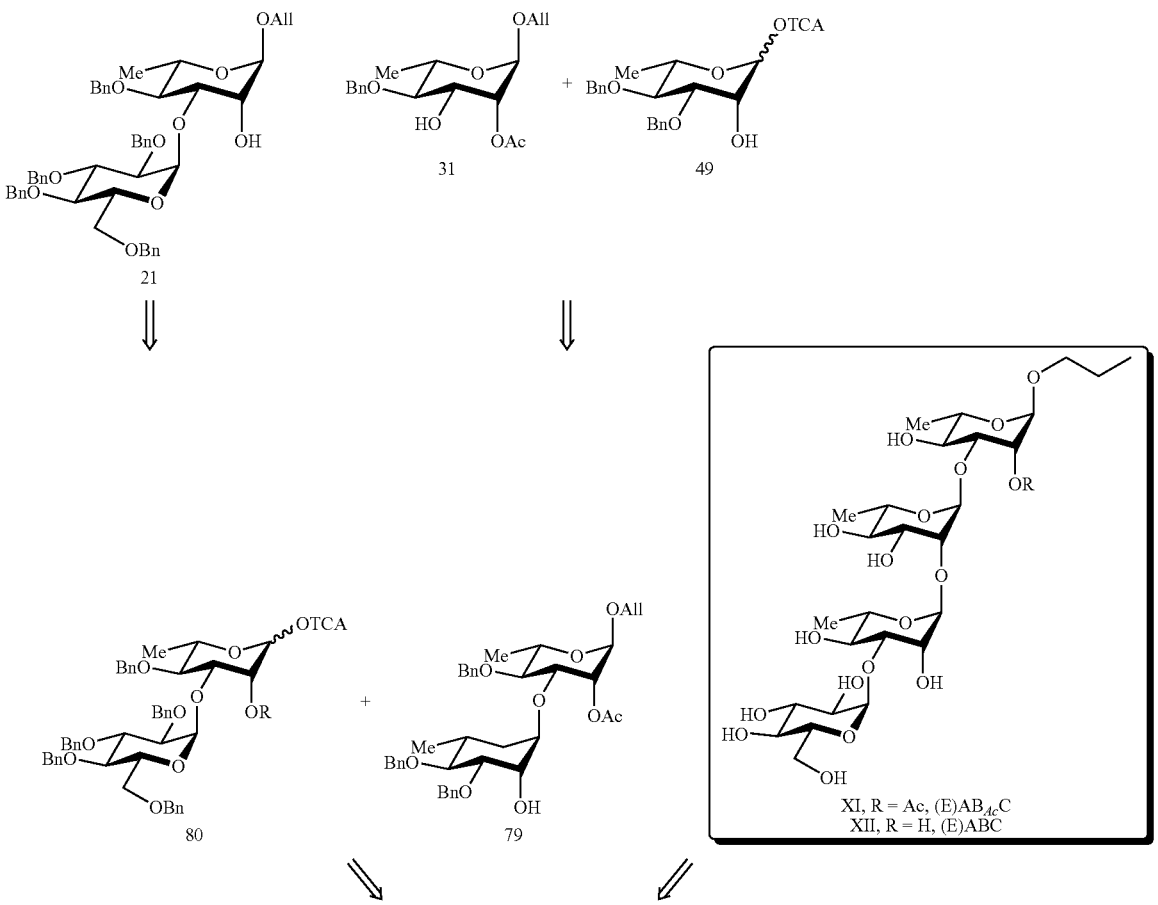

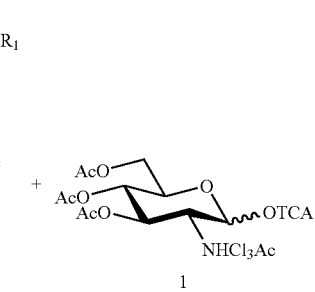
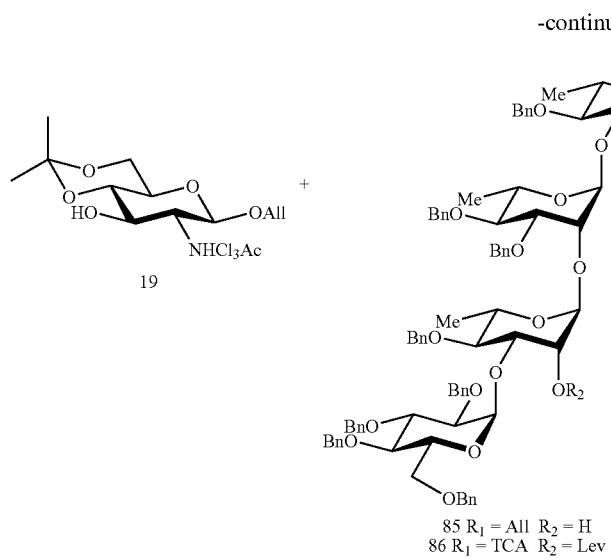

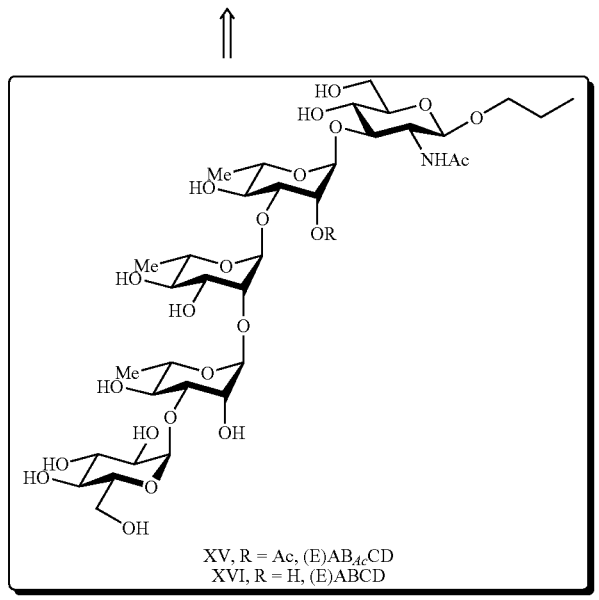

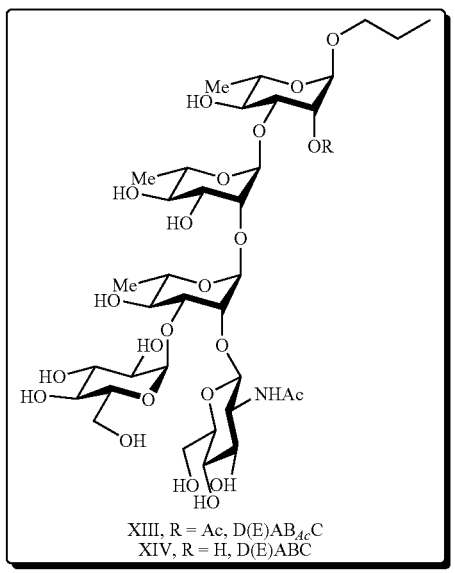

Method 7:

The invention relates to the method of preparation of compound XI (tetrasaccharide (E)AB$_{Ac}$C) as defined in list L1 comprising the following stages:

- condensation of the acceptor disaccharide 79 (BC) with the donor disaccharide 80 ((E)A) leading to the tetrasaccharide 87, the condensation reaction preferably being carried out in a solvent such as dichloromethane, 1,2-dichloroethane, ether, toluene, acetonitrile or any other equivalent solvent, in the presence of a Lewis acid such as TMSOTf or triflic acid, preferably in toluene or dichloromethane in the presence of TMSOTf (scheme 49);
- deprotection of the tetrasaccharide 87 leading to the acceptor tetrasaccharide 85 preferably in a pyridine/AcOH mixture in the presence of hydrazine monohydrate (scheme 49);
- deprotection by hydrogenolysis of the benzyl groups of the tetrasaccharide 85 leading to the tetrasaccharide (E)AB$_{Ac}$C preferably under hydrogen atmosphere in ethanol in the presence of palladium in neutral conditions (scheme 50).

1. Donor Monosaccharide B

Access to the synthon BC 61 involves the donor 49 protected in position 2 by a levulinoyl group[88, 89] (back-synthesis section). Synthesis of the latter, scaling-up the success of the synthesis of diol 26, is described in section 1. Here, we describe the optimization of the synthesis of acceptor 69, the precursor of the donor 49.

A method for quick access to a fully protected compound at a yield of the order of 94% starting from the commercial L-rhamnose 27 obtained from a key intermediate, the methyl orthoester 70 has been described[67] (Scheme 39). Following the protocol described[67] our yield of di-O-benzyl orthoester 70 was only 75%. Since our objective was to obtain the synthon BC 61, which is both acceptor and donor, preparation of the allyl orthoester was preferred to that of the methyl orthoester, with the aim of synthesizing the acceptor 58, after regioselective opening of the orthoester.[103]

Scheme 39: Access to the methyl orthoester 70 according to the Castro-Palomino et al.[67]

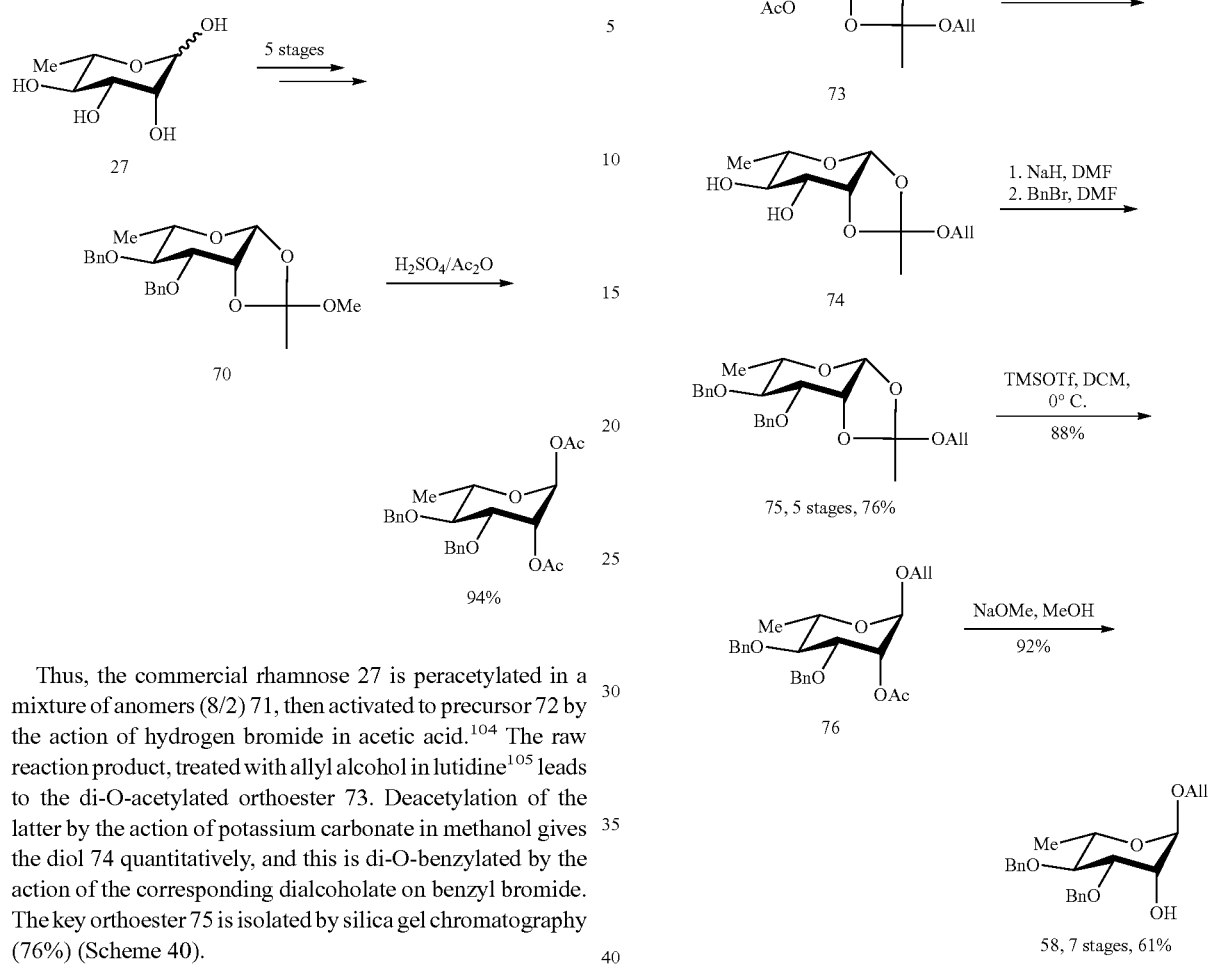

Thus, the commercial rhamnose 27 is peracetylated in a mixture of anomers (8/2) 71, then activated to precursor 72 by the action of hydrogen bromide in acetic acid.[104] The raw reaction product, treated with allyl alcohol in lutidine[105] leads to the di-O-acetylated orthoester 73. Deacetylation of the latter by the action of potassium carbonate in methanol gives the diol 74 quantitatively, and this is di-O-benzylated by the action of the corresponding dialcoholate on benzyl bromide. The key orthoester 75 is isolated by silica gel chromatography (76%) (Scheme 40).

Scheme 40: Method I for access to the acceptor 58

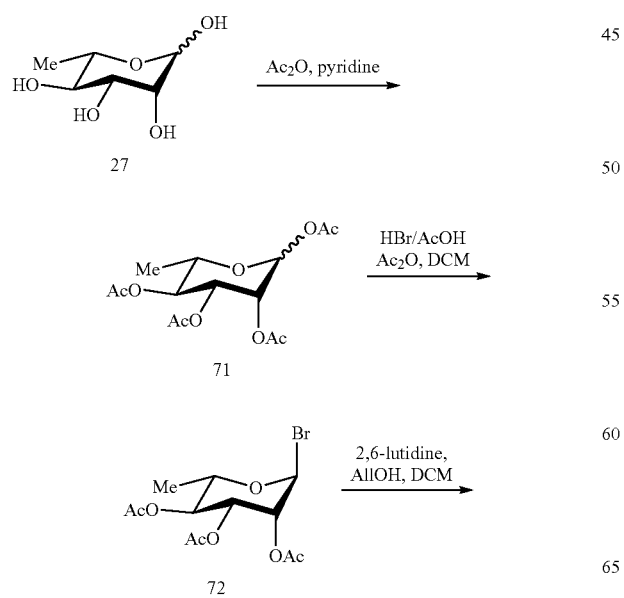

According to this strategy, the first option consists of regioselective opening in an acid environment. Various methods have been described[103] including the use of TMSOTf.[106] In the presence of this promoter, opening of the orthoester 75 is regio- and stereoselective. In fact, only the α anomer 76 is isolated (88%) (Scheme 40). A mechanism for explaining this good stereoselectivity has been proposed[106] (Scheme 41). Most interestingly, the presence of benzyl functions seems essential. In fact, when treated in the same conditions, the di-O-acetylated analog reacts very differently.[106]

Scheme 41: Mechanism of stereoselective opening of the 3,4-di-O-benzyl orthoesters proposed by Lindhorst[116]

Hindrance of the lower face of the intermediate species
Attack on the upper face

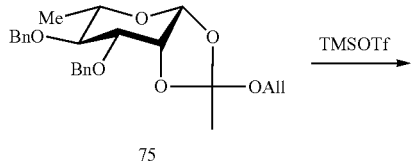

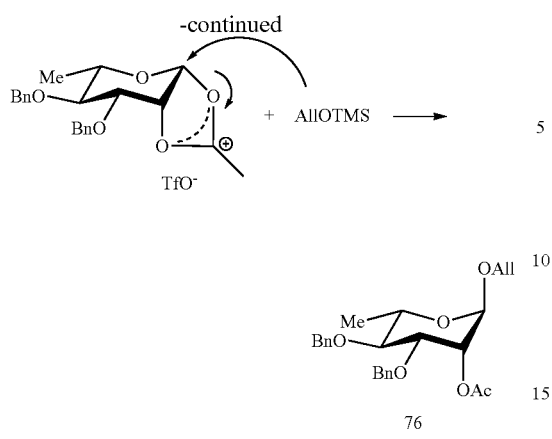

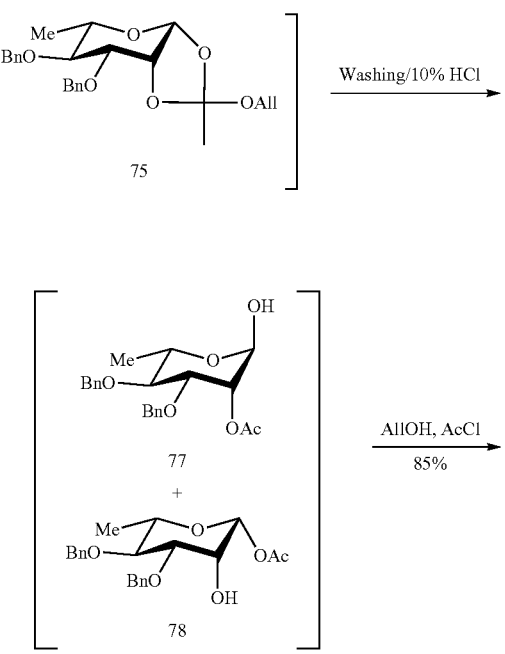

Scheme 43: Method II for access to the acceptor 58

Simple deacetylation of 76 carried out in the presence of NaOMe leads to the alcohol 58 at a yield of 92%, i.e. 61% in 7 stages starting from the commercial L-rhamnose. Moreover, we observed that treatment of the allyl orthoester 75 with 10% HCl solution results in a mixture of two monoacetylated regioisomers 77 and 78 that are less polar, and difficult to separate, at a ratio of 3/2 (Scheme 43). Moreover, the $C^{13}GD$ spectrum shows that the main compound 77 corresponds to an α anomer whereas 78 corresponds to a β anomer. Furthermore, the HMBC and HSQC spectra (FIG. 17 and FIG. 18) can prove that compound 77 is acetylated in position 2 whereas compound 78 is acetylated in position 1. This complete NMR analysis made it possible to confirm the structure of the two compounds 77 and 78, namely 2-O-acetyl-3,4-di-O-benzyl-α-L-rhamnopyranose and 1-O-acetyl-3,4-di-O-benzyl-β-L-rhamnopyranose, respectively. These results can be explained on the basis of data in the literature.[107, 108]

A mechanism of formation of compounds 77 and 78 is proposed (Scheme 42) on the basis of Kong's work.[103]

Scheme 42: Mechanism of formation of compounds 77 and 78 according to Kong et al.[103]

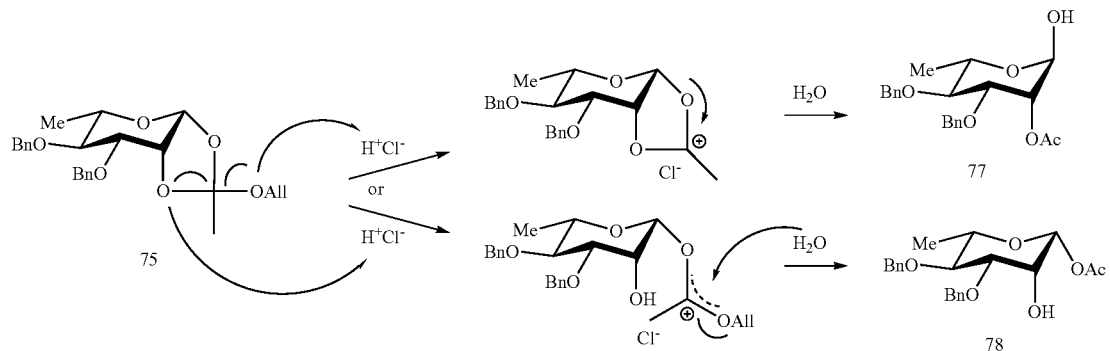

When the mixture of compounds 77 and 78 is heated in allyl alcohol in the presence of acetyl chloride, the allyl glycoside 58, deacetylated in position 2, is obtained at a yield of 85%, or 65% in 6 stages starting from the commercial L-rhamnose (Scheme 43). In actual fact, the acetyl function, unstable in acid alcoholic medium, is probably cleaved during this stage of anomeric allylation. This route has proved more efficient than route I since it makes it possible to isolate alcohol 58 at a higher yield in fewer stages.

In the preceding section, the acceptor 58 was obtained at a yield of 68% in 5 stages involving the diol 26 (Scheme 44). Despite this slightly higher yield, route II proposed above is still the most efficient as the use of tin is avoided and the 6 stages can be carried out in succession without any intermediate purification. In this case, the alcohol 58 is isolated by simple chromatography at an overall yield of 72%, instead of the 65% obtained otherwise (Scheme 44).

Scheme 44: Comparison of the three methods for access to the acceptor 58

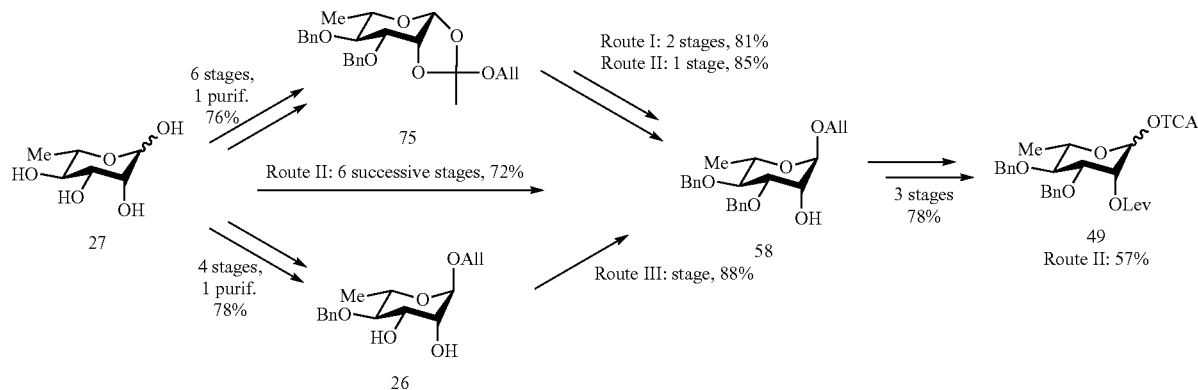

As a reminder (Section 2), the acceptor 58 is transformed to donor 49 in three stages, levulinoylation, deallylation, then activation at a yield of 78% (Scheme 44). Following optimization of the synthesis of alcohol 58, the donor 49 is now accessible in 9 stages at a yield of 57%.

2. Acceptor Disaccharide BC

The fully protected disaccharide 61 (Section 2) can be converted to acceptor 79 after deprotection of the levulinoyl group (81%) in a pyridine/AcOH mixture in the presence of hydrazine monohydrate[109] (Scheme 45).

Scheme 45: Conversion of the key intermediate 61 to acceptor 79

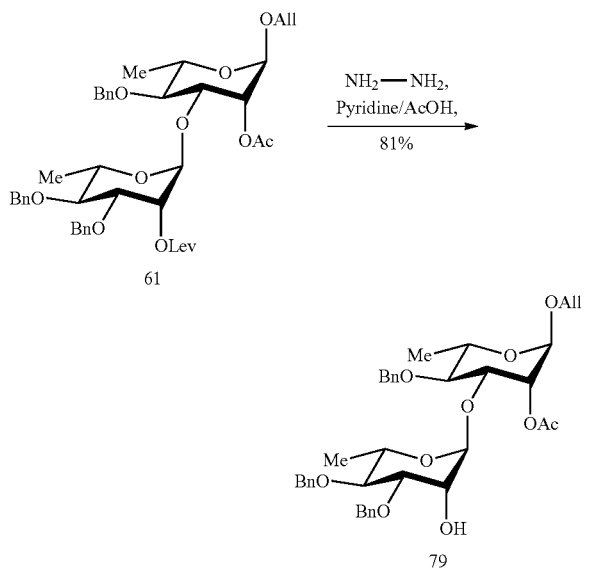

3. Donor Disaccharide (E)A

The levulinoyl function is the protecting group orthogonal to the acetyl function, said to be "participating", adopted following analysis by back synthesis conducted on the O antigen of *S. flexneri* 3a. In consequence, the donor disaccharide 80 is one of the key synthons, involved in the preparation of the targets XI and XII (FIG. 19).

The first test of levulinoylation of the acceptor 21 (Section 2) is carried out in the conditions used for preparing the levulinoyl ester 81, namely by action on levulinic acid in the presence of DCC and DMAP in dichloromethane.[89] This time, however, the reaction does not go to completion (Scheme 46).

Scheme 46: Test for levulinoylation of the acceptor 21

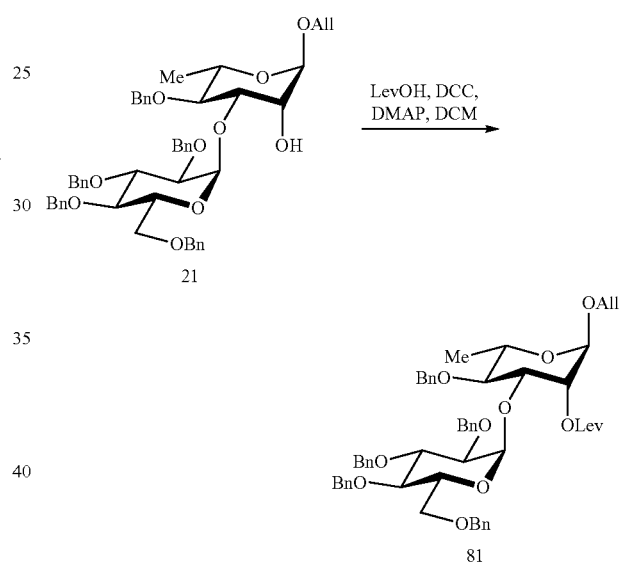

Varying certain parameters, such as the solvent or the reaction temperature, only at best made it possible to obtain the levulinoyl ester 81 mixed with alcohol 21 at a ratio of 4/1 (Table 6). This result can be explained by the presumed hindrance of the hydroxyl function in position $2_A$.

TABLE 6

| Levulinoylation of the allyl glycoside 21 | | | |
|---|---|---|---|
| Solvents | Temperature | Reaction time | Conversion* |
| DCM | RT | 3 days | 60% |
|  | 50° C. | 5 days | 80% |
| DCE | 80° C. | 5 days | 80% |
| CH₃CN |  | / | 0% |
| DMF | 80° C. | / | 0% |
| DCE | 90° C. | 5 days | 80% |

*The degrees of conversion are determined by TLC

As it is extremely difficult to separate the acceptor 21 and the levulinate 81, other conditions for introduction of the levulinoyl group were tested (Scheme 47). They involve levulinoyl chloride[110, 111] or levulinic anhydride.[112]

Scheme 47: Methods of activation of levulinic acid

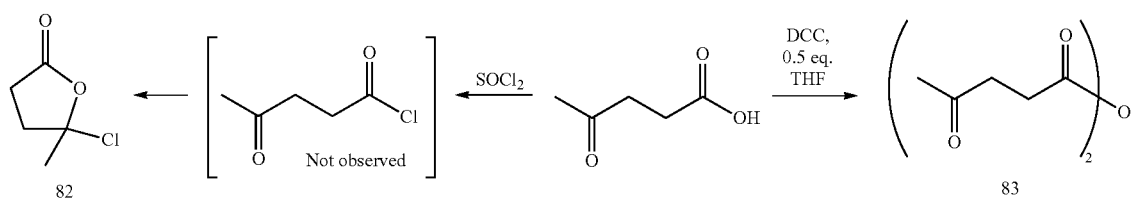

The action of thionyl chloride on levulinic acid does not make it possible to isolate levulinoyl chloride 82, as expected, but the cyclization product, confirmed by NMR analysis.[113] As the latter does not react with the acceptor 21[110] (Scheme 47), this route was abandoned. However, when levulinic acid is reacted with DCC[112] levulinic anhydride 83 is obtained quantitatively according to NMR analysis (Scheme 47). The action of this anhydride 83 on the acceptor 21 was investigated in classical conditions of esterification, pyridine and DMAP (Table 7). Comparison of entries 1 and 2 in Table 7 can confirm that increasing the temperature during this esterification increases the degree of conversion, whereas entry 3 shows that DMAP activates the reaction. The amount of levulinic anhydride added was also varied. In fact, the increase in the amounts of DMAP and levulinic anhydride in the reaction mixture (entry 3, 4 and 5 in Table 7) is correlated with the degree of conversion of 21 to 81.

TABLE 7

Optimization of the levulinoylation of the acceptor 21

| Entry | Levulinic anhydride (eq.) | DMAP (eq.) | Temperature | Conversion* |
|---|---|---|---|---|
| 1 | 4 | 0.5 | RT | 10% |
| 2 | | | 50° C. | 30% |
| 3 | | 2 | | 60% |
| 4 | 8 | 2 | | 80% |
| 5 | 10 | 5 | | 90% |
| 6 | | | 50° C.** | 100% |

*The degrees of conversion are determined by TLC
**In this case, the levulinic anhydride is added to the reaction mixture at 50° C.

Based on the results in Table 7 (entry 5 and 6), if 10 equivalents of levulinic anhydride are added at 50° C. then the conversion is maximal and makes it possible to isolate the desired levulinoyl ester 81 at a yield of 95%. Next, donor 80 is prepared in two stages. The disaccharide 81 is deallylated to hemiacetal 84 at a yield of 92%.[39, 40] The latter is activated by the action of trichloroacetonitrile to obtain the donor 80 at a of 97%.[22, 23]

Scheme 48: Synthesis of the donor 80

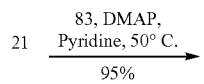

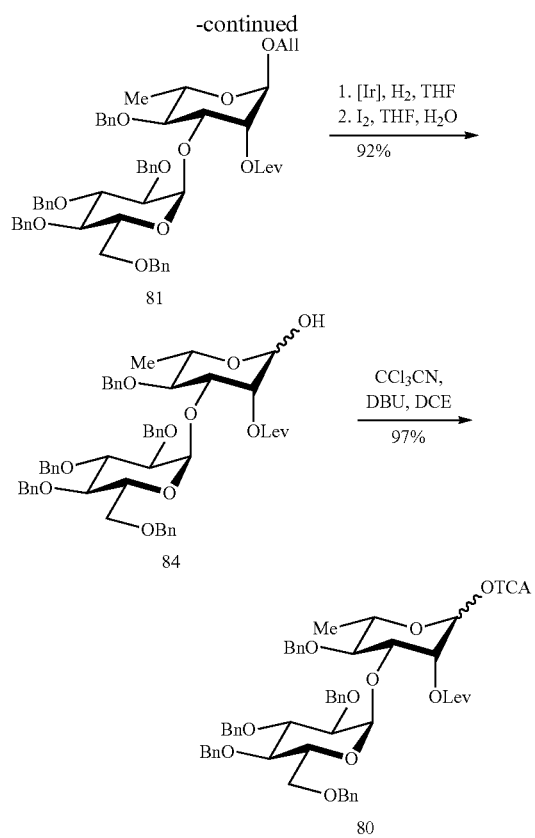

4. Tetrasaccharide (E)ABC

Once the acceptor disaccharide BC 79 and donor disaccharide (E)A 80 became available, synthesis of the acceptor 85 and donor 86 tetrasaccharides (E)ABC was carried out.

a. Series (E)ABC Acceptor

Just as for the syntheses in section 2, the glycosylation reaction between the donor 80 and the acceptor 79 was investigated in various solvents.[76-79] If the condensation is carried out in dichloromethane in the presence of TMSOTf (0.3 eq.) and molecular sieve, the tetrasaccharide 87 is obtained with the expected α configuration ($J_{1,2}$=1.6 Hz, $^1J_{CH}$=176.6 Hz) and a yield of 69% (Scheme 49). In contrast, in toluene, the tetrasaccharide 87 is obtained at a better yield (75%), which reaches 92% when the synthesis is reproduced on a large scale (4 g of acceptor 79 instead of 200 mg). This solvent system was therefore adopted.

Deprotection of the levulinoyl group carried by 87 in a pyridine/AcOH mixture in the presence of hydrazine monohydrate[109] leads to the required acceptor 85 at a yield of 89%, confirming the orthogonal character of the system of protecting groups employed (Scheme 49).

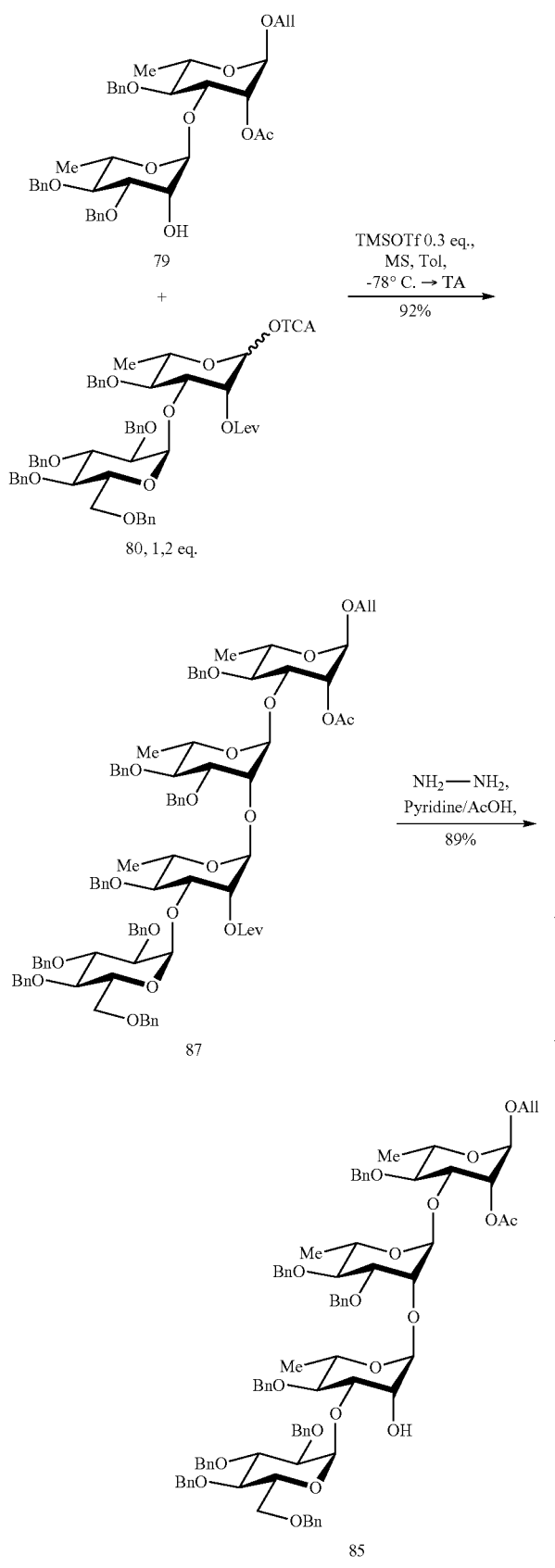

Scheme 49: Synthesis of the acceptor 85 b. Access to the Targets XI and XII

The presence of an acetyl group on the tetrasaccharide 85 excludes, a priori, conditions of hydrogenation in an acid medium. Hydrogenolysis of the benzyl groups of the tetrasaccharide 85 is therefore carried out under hydrogen atmosphere in ethanol in the presence of palladium in neutral conditions. The propyl glycoside XI is isolated at a yield of 76% (Scheme 50).

Scheme 50: Hydrogenolysis of the tetrasaccharides 63 and 69

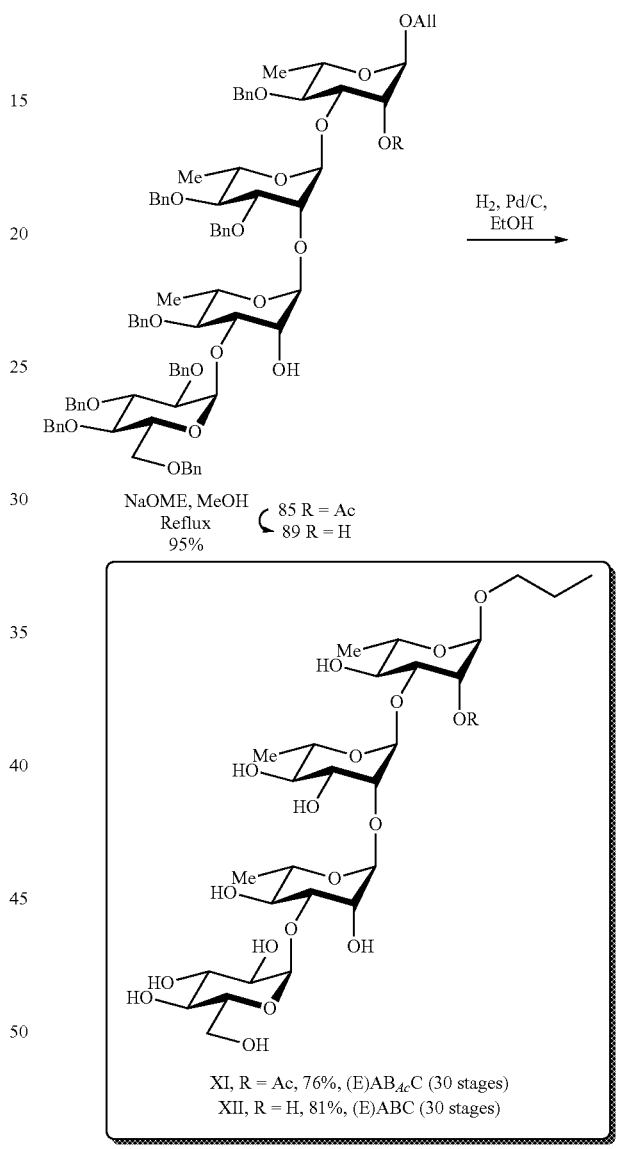

Method 8:

The invention also relates to the method of preparation of compound XII (tetrasaccharide (E)ABC) as defined in list L1 comprising the following stages:
  condensation of the acceptor disaccharide 79 (BC) with the donor disaccharide 80 ((E)A) leading to the tetrasaccharide 87, the condensation reaction preferably being carried out in a solvent such as dichloromethane, 1,2-dichloroethane, ether, toluene, acetonitrile or any other equivalent solvent, in the presence of a Lewis acid such as TMSOTf or triflic acid, preferably in toluene or dichloromethane in the presence of TMSOTf (scheme 49);

deprotection of the tetrasaccharide 87 leading to the acceptor tetrasaccharide 85 preferably in a pyridine/AcOH mixture in the presence of hydrazine monohydrate (scheme 49);

deacetylation of the acceptor tetrasaccharide 85 to the tetrasaccharide 89 preferably in the presence of NaOMe leading to reflux;

deprotection by hydrogenolysis of the benzyl groups of the tetrasaccharide 89 leading to the tetrasaccharide (E)ABC preferably under atmospheric hydrogen atmosphere in ethanol in the presence of palladium in neutral conditions (scheme 50).

To obtain the target XII, representative of the O antigen of the bacterium *S. flexneri* X, a deacetylation stage is required. The acceptor 85 is deacetylated in the presence of NaOMe under reflux to obtain the diol 89 (950), then debenzylated by hydrogenolysis. The expected target XII is obtained in the form of propyl glycoside at a yield of 81% (Scheme 50).

Method 9:

The invention relates to the method of preparation of compound XIII (pentasaccharide D(E)AB$_{Ac}$C) as defined in list L1 comprising the following stages:

condensation of the donor monosaccharide 1 and of the acceptor tetrasaccharide 85 leading to the pentasaccharide 90, the condensation reaction preferably being carried out in a solvent such as dichloromethane, 1,2-dichloroethane, ether, toluene, acetonitrile or any other equivalent solvent, in the presence of a Lewis acid such as TMSOTf or triflic acid, preferably in toluene or dichloromethane in the presence of TMSOTf (scheme 51);

deacetylation of the pentasaccharide 90 leading to the pentasaccharide 91 preferably in methanol in the presence of NaOMe (scheme 52);

deprotection of the pentasaccharide 91 to give the pentasaccharide D(E)AB$_{Ac}$C preferably under hydrogen pressure in ethanol in the presence of palladium on charcoal (scheme 53).

5. Pentasaccharide D(E)ABC

The pentasaccharide 90 is obtained by condensation of donor 1 and acceptor 85. Different solvent conditions were compared[69, 76-79] (Table 8). In the "usual" coupling conditions (dichloromethane or toluene, 0.3 eq. of TMSOTf, molecular sieve, entries 1 and 2), the oxazoline 1'[1] already described is isolated ($\delta_{H-1}$=6.35 ppm in $^1$H NMR) (FIG. 20). The following couplings were carried out with 0.5 eq. of TMSOTf to permit opening of the oxazoline.[61]

Comparison of entries 1 and 6 with, respectively, entries 2 and 7 shows, once again, that the use of toluene (30% and 72%) is preferable to the use of dichloromethane (20% and 67%) (Table 8).

TABLE 8

Optimization of coupling between acceptor 63 and donor 10

| Entry | TMSOTf | Temperature | Donor 1 | Solvents | Yield |
|---|---|---|---|---|---|
| 1 | 0.3 eq. | −78° C. | 1.3 eq. | Dichloromethane | 20% |
| 2 | | | | Toluene | 30% |
| 3 | 0.5 eq. | −78° C. | 1.3 eq. | Toluene | 50% |
| 4 | | −40° C. | | Toluene | 65% |
| 5 | | −20° C. | | Toluene | 60% |
| 6 | | −40° C. | 1.6 eq. | Dichloromethane | 67% |
| 7 | | | | Toluene | 72% |
| 8 | | | 2 eq. | Toluene | 82% |

Of the three temperature conditions tested, the best results are obtained at −40° C., therefore this temperature was adopted (entry 3, 4 and 5). In fact, at −20° C., donor 1 is probably less stable than at −40° C., which explains the lower yield at this temperature, whereas at −78° C., the acceptor 85 is not sufficiently reactive and hydrolysis of the donor 1 predominates. However, in all these couplings, the acceptor tetrasaccharide 85 is not consumed completely. In contrast, if 2 eq. of donor 1 are used (entry 7), the allyl glycoside 90 is isolated at a yield of 82% and with the expected β configuration ($^1J_{CH}$=161.0 Hz) (Scheme 51).

Scheme 51: Coupling between the acceptor 85 and the donor 1

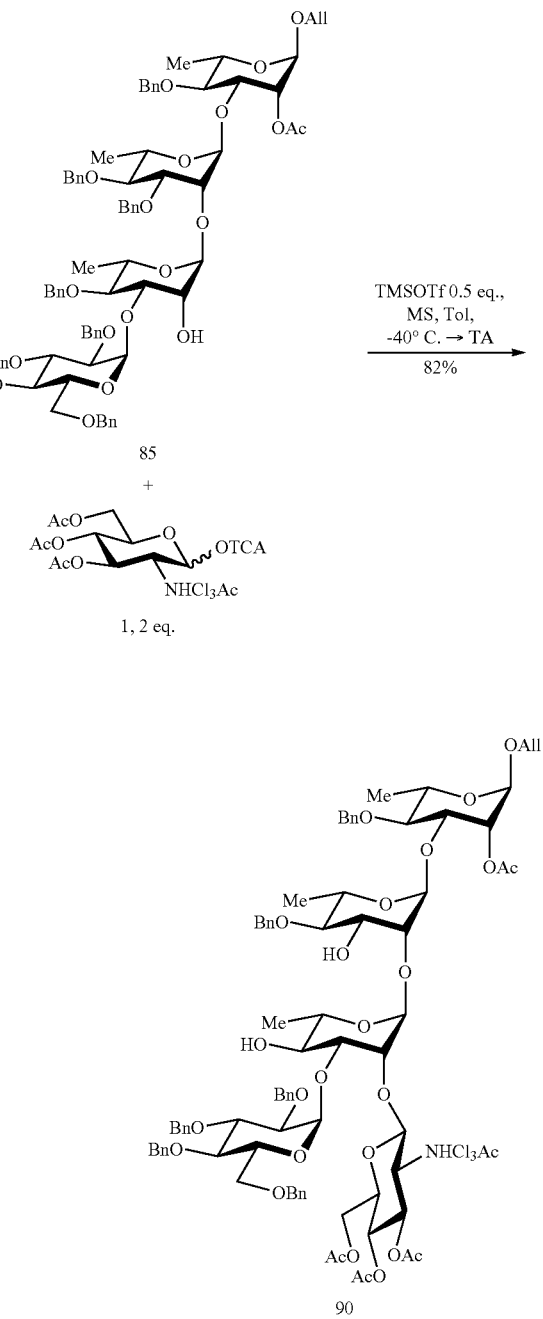

Secondly, the selective cleavage of the acetyls present on the glucosamine unit D was tested in various conditions (Table 9). In contrast to the results obtained in the deacetylation of 52, potassium carbonate does not permit selective deacetylation and the tetraol 92 is formed in large amounts at the expense of the triol 91 (entry 1). The same phenomenon is observed if triethylamine is used (entry 6). In Zemplen conditions[60] (entry 2), the reaction is too slow. If the amount of NaOMe is increased (entry 3, 4 and 5), the results are identical (ratio 65/35), only the reaction time varies. This difference in selectivity relative to the results described in reducing series A (Section 2) can be explained on the basis that there is far less hindrance of the acetyl function in position $2_C$. In fact, the residue in question is in the terminal position and therefore more accessible.

TABLE 9

Conditions of selective deacetylation

| Entry | Conditions | Reaction time | Ratio 91/92 |
|---|---|---|---|
| 1 | $K_2CO_3$/MeOH 1 eq.[85] | 30 min | 40/60 |
| 2 | NaOMe/MeOH 0.2 eq.[60] | 1 day | 65/35 |
| 3 | NaOMe/MeOH 1 eq. | 2 h | 65/35 |
| 4 | NaOMe/MeOH 2 eq. | 45 min | 65/35 |
| 5 | NaOMe/MeOH 3 eq. | 20 min | 65/35 |
| 6 | $NEt_3$/MeOH/$H_2O$[83, 84] | 7 h | 60/40 |

Product 90 is therefore deacetylated selectively in methanol in the presence of NaOMe (2 eq.) to obtain the monoacetylated compound 91 and the tetraol 92 at a ratio of 65/35 and a yield of 86% (Scheme 52).

Scheme 52: Selective deacetylation of the pentasaccharide 90

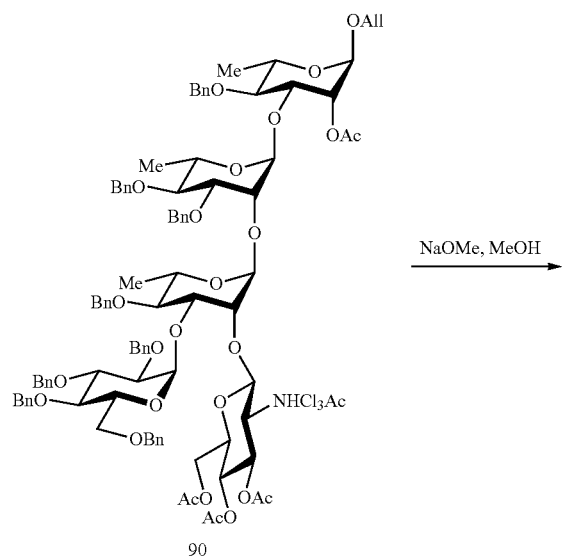

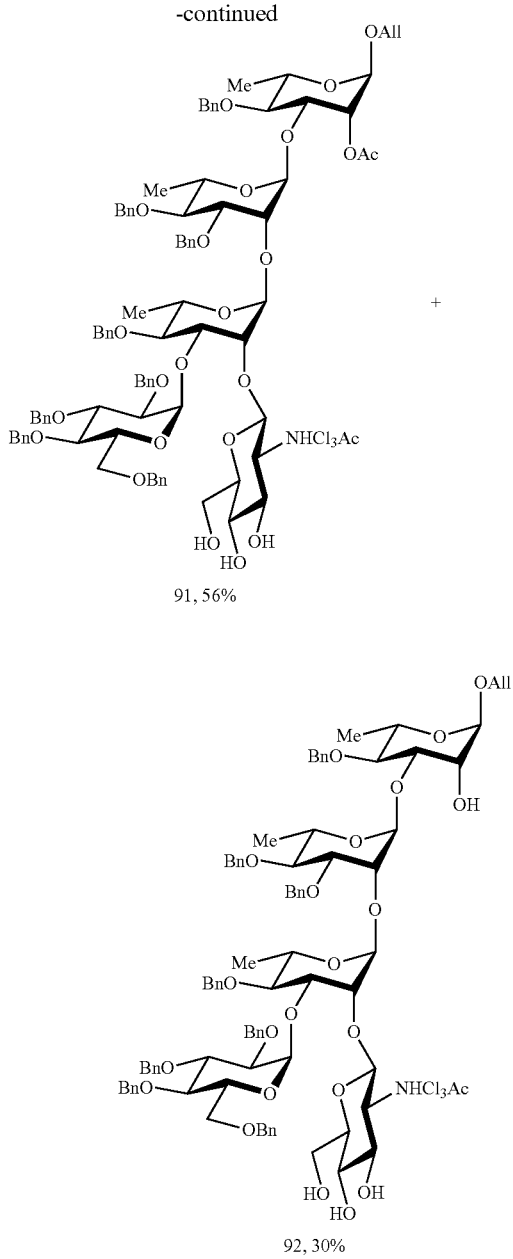

91, 56%

92, 30%

The conditions of hydrogenolysis of an oligosaccharide bearing, simultaneously, a trichloroacetamide function and benzyl functions elaborated for 56 (Section 2) were applied to the synthesis intermediates 91 and 92 at a pressure of 50 bar. The chloroacetamide intermediate was still observed, but by continuing the reaction for several days, the latter could be converted to acetamide completely. This reaction can in fact be monitored by mass or by NMR analysis based on the proton shift of the function $C(O)CH_2Cl$ ($\delta_{CH2}$=4.1 ppm) and of the carbon ($\delta_{CH2}$=42.5 ppm). Thus, hydrogenolysis of the two pentasaccharides 91 and 92 under hydrogen pressure (50 bar) makes it possible to isolate, after purification by reversed-phase chromatography (C18), the two propyl glycosides XIII and XIV at the same yield of 74% (Scheme 53).

Scheme 53: Hydrogenolysis of the pentasaccharides 91 and 92

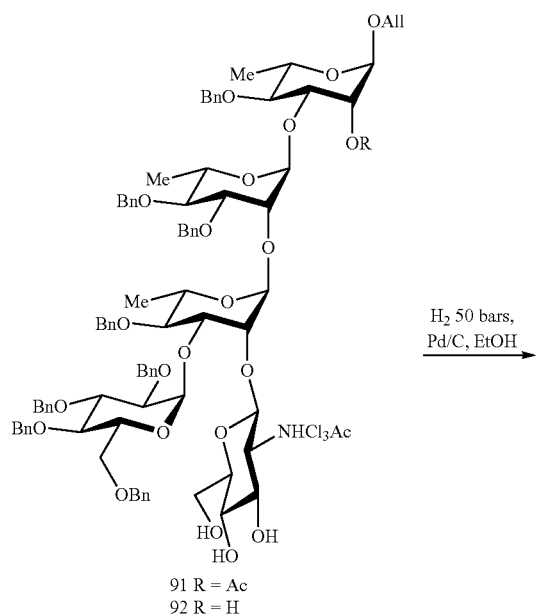

91 R = Ac
92 R = H

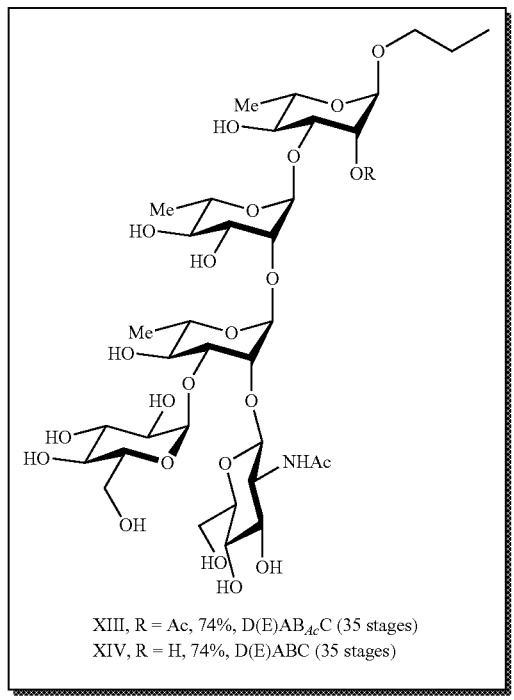

XIII, R = Ac, 74%, D(E)AB$_{Ac}$C (35 stages)
XIV, R = H, 74%, D(E)ABC (35 stages)

It should be noted that hydrogenolysis of these two pentasaccharides 91 and 92 was carried out in 2 days and 1 day, respectively, whereas for the two pentasaccharides 56 and 57—in 10 and 2 days, respectively. This difference in speed of conversion of the trichloroacetamide to acetamide can be explained by the greater hindrance of unit D, bearing the trichloroacetamide function, of the pentasaccharides in reducing series A relative to those in reducing series C.

Method 10:

The invention further relates to the method of preparation of compound XIV (pentasaccharide D(E)ABC) as defined in list L1 comprising the following stages:

condensation of the donor monosaccharide 1 and of the acceptor tetrasaccharide 85 leading to the pentasaccharide 90, the condensation reaction preferably being carried out in a solvent such as dichloromethane, 1,2-dichloroethane, ether, toluene, acetonitrile or any other equivalent solvent, in the presence of a Lewis acid such as TMSOTf or triflic acid, preferably in toluene or dichloromethane, in the presence of TMSOTf (scheme 51);

deacetylation of the pentasaccharide 90 leading to the pentasaccharide 92 preferably in methanol in the presence of NaOMe (scheme 52);

deprotection of the pentasaccharide 92 to give the pentasaccharide D(E)ABC preferably under hydrogen pressure in ethanol in the presence of palladium on charcoal (scheme 53).

Method 11:

The invention relates to the method of preparation of compound XV (pentasaccharide (E)AB$_{Ac}$CD) as defined in list L1 comprising the following stages:

condensation of the acceptor monosaccharide 19 and of the donor tetrasaccharide 86 leading to the pentasaccharide 93, the condensation reaction preferably being carried out in a solvent such as dichloromethane, 1,2-dichloroethane, ether, toluene, acetonitrile or any other equivalent solvent, in the presence of a Lewis acid such as TMSOTf or triflic acid, preferably in toluene at 70° C. (scheme 55);

cleavage of the levulinoyl function of the pentasaccharide 93 leading to the pentasaccharide 94, preferably in a pyridine/AcOH mixture in the presence of hydrazine monohydrate (scheme 56);

cleavage of the isopropylidene group of the pentasaccharide 94 by acid hydrolysis leading to the pentasaccharide 95;

hydrogenolysis of the pentasaccharide 95 leading to the pentasaccharide (E) $AB_{Ac}CD$, preferably under hydrogen atmosphere in alcohol, for example ethanol in the presence of a palladium derivative, such as palladium on charcoal (scheme 58).

6. Donor Series (E)ABC

The donor 86 is prepared in two stages, starting from the same intermediate 87. After deallylation39, 40 the hemiacetal obtained 88 (90%) is activated to trichloroacetimidate 86 at a yield of 88%[22, 30].

Scheme 54: Synthesis of the donor 86

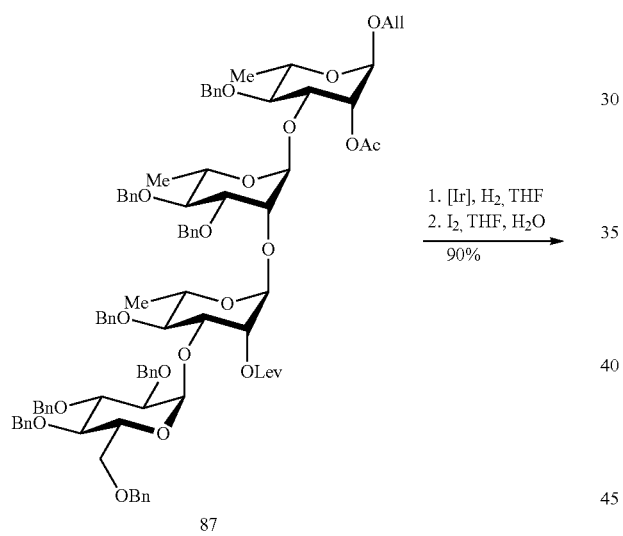

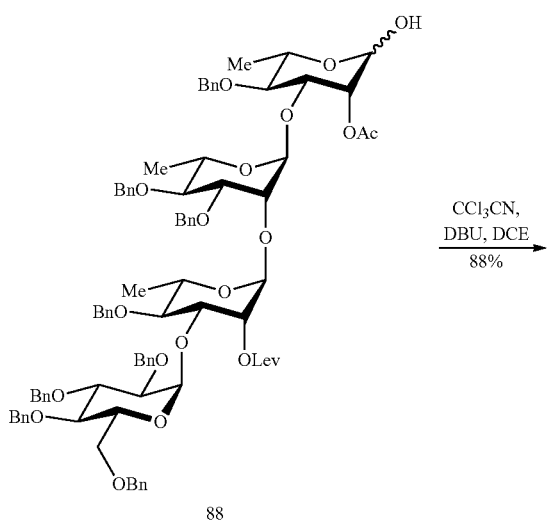

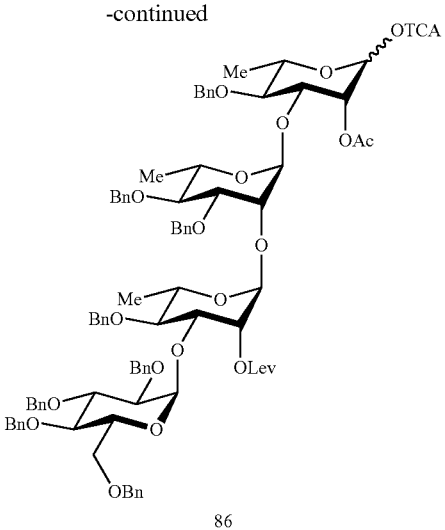

7. Pentasaccharide (E)ABCD

The pentasaccharide 93 is obtained by condensation of the acceptor 19 and of the donor 86. Now, the results in the literature[114] based on results obtained in the laboratory[115, 62] suggest that the reactivity of an acceptor of structure similar to that of 19, of low solubility owing to the presence of an acetamide function[38] could be improved by increasing the reaction temperature during coupling. In view of this observation, coupling between 19 and 86 was therefore carried out at 70° C. in toluene, based on the previous studies of glycosylation solvents (Section 2). Moreover, as the donor is an "expensive" tetrasaccharide, an insufficient amount is used, so as to ensure that it is consumed completely. During the first coupling test, the yield of pentasaccharide 93 is 43%, and 36% of hydrolyzed donor 88 was recovered, after purification. In contrast, in the presence of 2.5 eq. of acceptor, the donor 86 is consumed completely and the pentasaccharide 93 is isolated at a yield of 78%. Thus, the best results are obtained in conditions identical to those adopted in a similar study.[62]

Scheme 55: Coupling between the acceptor 19 and the donor 86

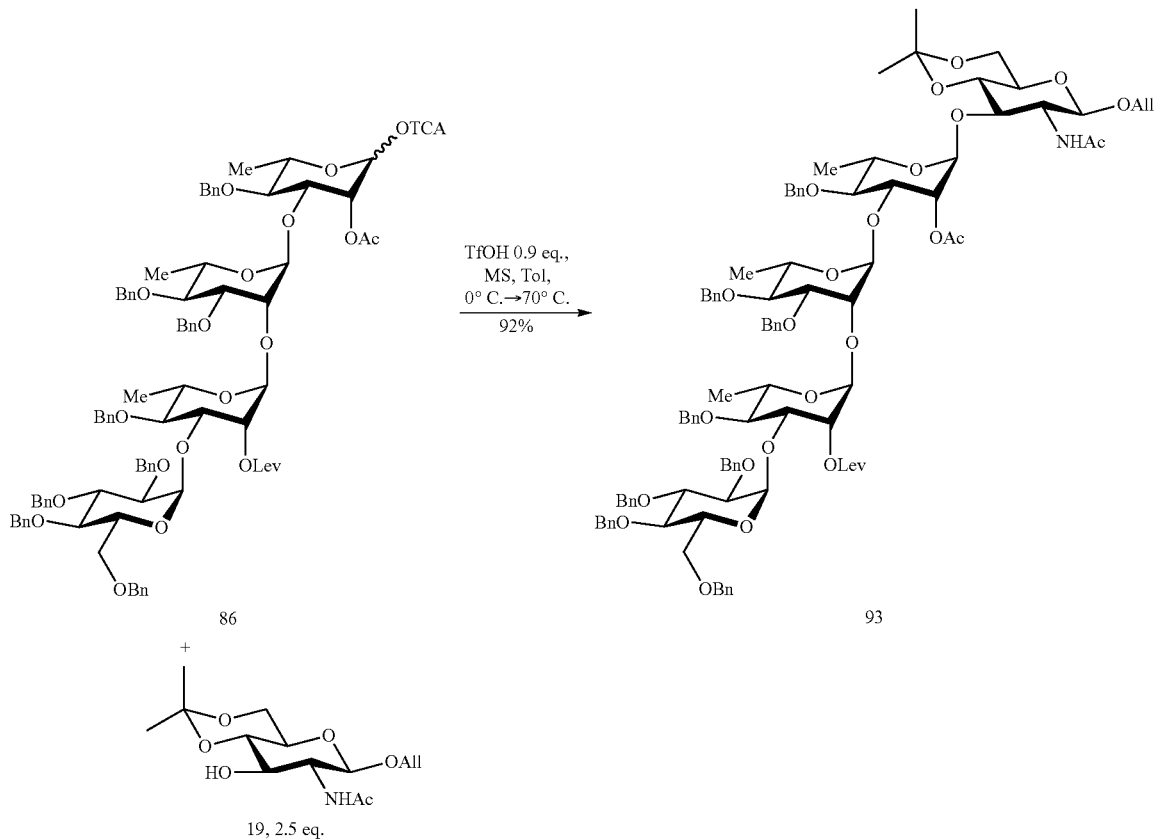

Cleavage of the levulinoyl function of 93, treated in a pyridine/AcOH mixture in the presence of hydrazine monohydrate, supplies the monoacetate 94[109] (85%), transformed to triol 95 after acid hydrolysis (92%) (Scheme 56).

Scheme 56: Conversion of 93 to triol 95

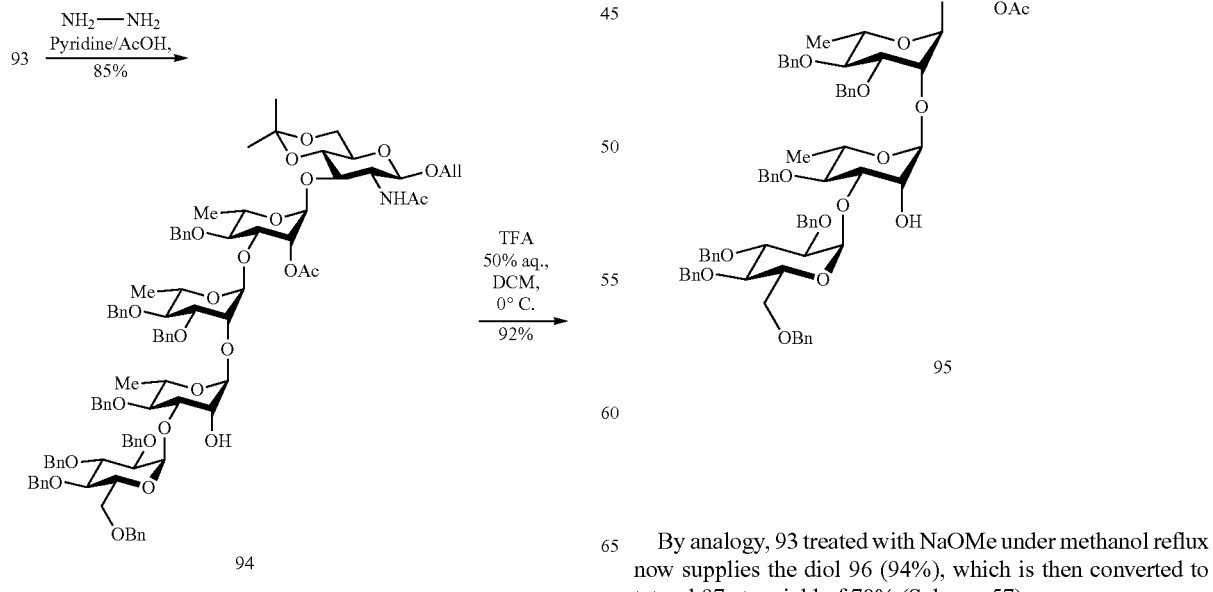

By analogy, 93 treated with NaOMe under methanol reflux now supplies the diol 96 (94%), which is then converted to tetraol 97 at a yield of 70% (Scheme 57).

153

Scheme 57: Conversion of 93 to tetraol 97

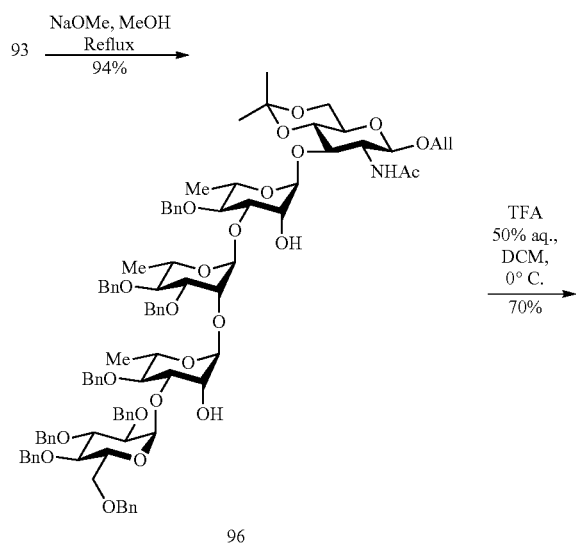

96

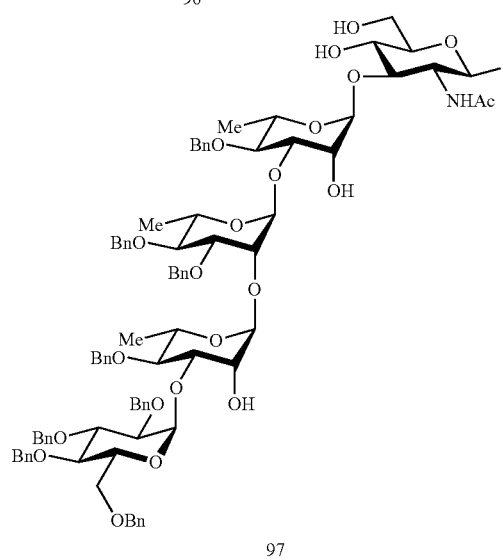

97

In the same way as for access to the targets XI and XII, hydrogenolysis of 95 and 97 leads to the target pentasaccharides XV and XVI in the form of propyl glycoside at respective yields of 77% and 70% (Scheme 58).

Scheme 58: Hydrogenolysis of the pentasaccharides 95 and 97

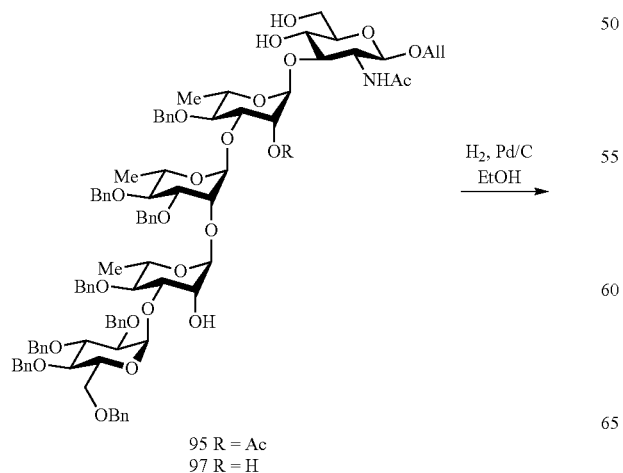

95 R = Ac
97 R = H

154

-continued

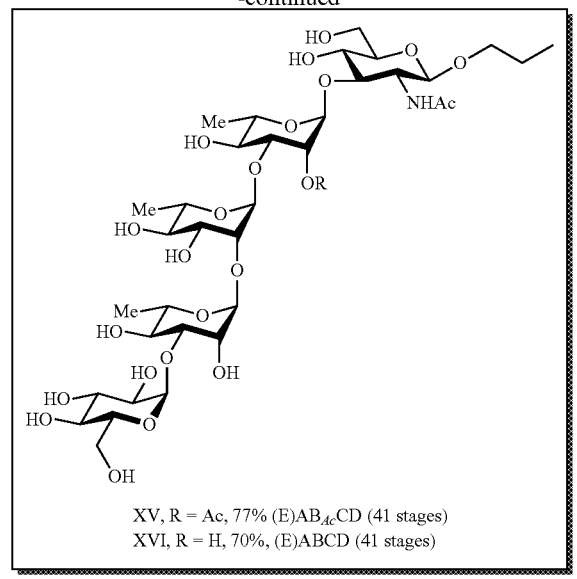

XV, R = Ac, 77% (E)AB$_{Ac}$CD (41 stages)
XVI, R = H, 70%, (E)ABCD (41 stages)

Method 12:

The invention relates to the method of preparation of compound XVI (pentasaccharide (E)ABCD) as defined in list L1 comprising the following stages:

condensation of the acceptor monosaccharide 19 and of the donor tetrasaccharide 86 leading to the pentasaccharide 93, the condensation reaction preferably being carried out in a solvent such as dichloromethane, 1,2-dichloroethane, ether, toluene, acetonitrile or any other equivalent solvent, in the presence of a Lewis acid such as TMSOTf or triflic acid, preferably in toluene at 70° C. (scheme 55);

deprotection of the pentasaccharide 93 leading to the pentasaccharide 96, preferably by transesterification (scheme 57);

cleavage of the isopropylidene group of the pentasaccharide 96 by acid hydrolysis leading to the pentasaccharide 97, preferably in 50% aqueous TFA solution in dichloromethane at 0° C. (scheme 57);

hydrogenolysis of the pentasaccharide 97 leading to the pentasaccharide (E)ABCD, preferably under hydrogen atmosphere in alcohol in the presence of palladium on charcoal (scheme 58).

8. Conclusion

In this section, the synthesis of a tetrasaccharide, potentially both acceptor and donor, was carried out in stages at a yield of 13% (Scheme 38). This key synthon provided access to six targets, including two tetra- and four pentasaccharides, mono-acetylated or non-acetylated corresponding to the fragments of the O antigen of the bacteria *S. flexneri* 3a and/or X.

Scheme 59: Balance for acess to the acceptor 85 and to the donor 86

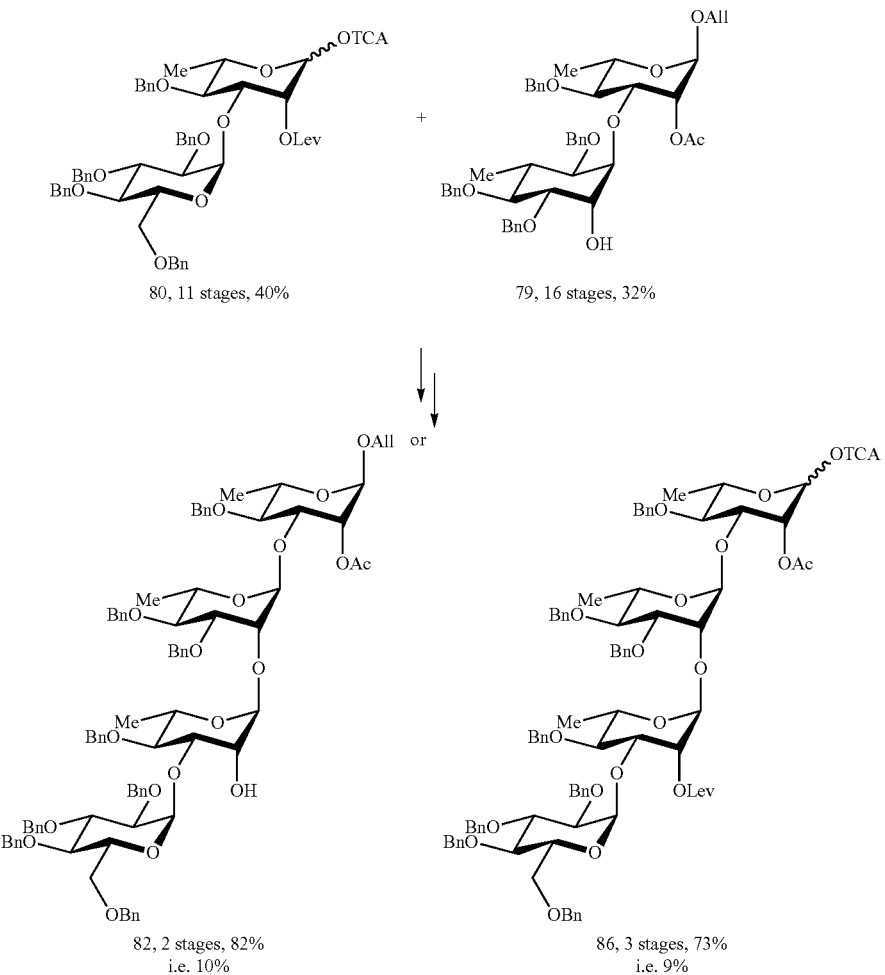

Experimental Application of Methods 7 to 12
Method 7:

3,4-Di-O-benzyl-1,2-(methyloxyethylidene)-β-L-rhamnopyranose[67] 70

1,2,3,4-Tetra-O-acetyl-α,β-L-rhamnopyranose 71

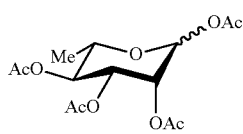

Chemical Formula: $C_{14}H_{20}O_9$
Exact Mass: 332.1107
Molecular Weight: 332.3032

Commercial L(+)-rhamnose monohydrate 27 (36.4 g, 200.0 mmol) is dissolved in a pyridine/acetic anhydride mixture (1/1, 200 mL). At the end of addition, the reaction mixture is stirred overnight at RT. After verifying, by monitoring by TLC (DCM/MeOH, 8/2), the disappearance of 27 (Rf=0.2) and the appearance of a new compound (Rf=0.9), the reaction mixture is concentrated in a rotary evaporator and then coevaporated with Tol (3×100 mL) and DCM (3×100 mL). The residue is dried with a vane pump to give the per-acetylated compound 71 in the form of a mixture of α/β, anomers (8/2) and a yellow oil (66.3 g, quant.). $71_α$: Rf=0.3 (Chex/EtOAc, 6/4).

$^1$H NMR (CDCl$_3$), δ5.98 (d, 1H, $J_{1,2}$=1.9 Hz, H-1), 5.27 (dd, 1H, $J_{3,4}$=10.1 Hz, $J_{2,3}$=3.5 Hz, H-3), 5.22 (m, 1H, H-2), 5.09 (pt, 1H, $J_{4,5}$=9.9 Hz, H-4), 3.91 (dq, 1H, H-5), 2.14, 2.13, 2.05, 1.98 (4 s, 12H, $H_{Ac}$) 1.20 (d, 3H, $J_{5,6}$=6.3 Hz, H-6).

RMN $^{13}$C (CDCl$_3$), δ170.5, 170.2, 170.0, 168.6 (4C, $C_{Ac}$), 91.0 (C-1, $^1J_{CH}$=177.0 Hz), 71.8 (C-5$_β$), 70.8 (C-4), 69.1 (C-3), 69.1 (C-5), 69.0 (C-2), 21.4, 21.2, 21.0, 20.8 (8C, $C_{Ac}$), 17.8 (C-6$_α$), 17.7 (C-6).

$71_β$: Rf=0.3 (Chex/EtOAc, 6/4).

$^1$H NMR (CDCl$_3$), δ5.84 (d, 1H, $J_{1,2}$=1.2 Hz, H-1), 5.45 (m, 1H, H-2), 5.05 (m, 2H, H-3, H-4), 3.65 (dq, 1H, H-5), 2.20, 2.12, 2.07, 1.95 (4 s, 12H, $H_{Ac}$), 1.26 (d, 3H, $J_{5,6}$=6.2 Hz, H-6).

$^{13}$C NMR (CDCl$_3$), 5170.3, 170.1, 169.9, 168.7 (4C, $C_{Ac}$), 91.0 (C-1, $^1J_{CH}$=162.6 Hz), 71.8 (C-5), 71.1, 70.6 (2C, C-3*, C-4*), 68.9 (C-2), 21.3, 21.1, 20.9, 20.7 (8C, $C_{Ac}$), 17.8 (C-6$_α$), 17.7 (C-6).

2,3,4-O-Acetyl-α-L-rhamnopyranose bromide 72

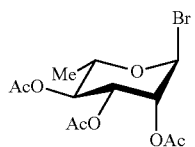

Chemical Formula: C$_{12}$H$_{17}$BrO$_7$
Exact Mass: 352.0158
Molecular Weight: 353.1632

The per-acetylated compound 71 (66.3 g, 200.0 mmol) is dissolved in DCM (500 mL), and then hydrobromic acid (100 mL) and acetic anhydride (23 mL) are added at 0° C. At the end of addition, the reaction mixture is stirred overnight at RT. After verifying, by monitoring by TLC (Chex/EtOAc, 6/4), the disappearance of 71 (Rf=0.25) and the appearance of a new compound (Rf=0.35), the excess hydrobromic acid is evaporated using a water-jet pump and then the reaction mixture is concentrated in a rotary evaporator and coevaporated with Tol (3×100 mL). The residue is dried with a vane pump to give the bromide 72 in the form of a yellow oil (70.6 g, quant.), which is used directly in the next stage after checking by $^1$H NMR.

Rf=0.35 (Chex/EtOAc, 6/4).

$^1$H NMR (CDCl$_3$), δ6.26 (d, 1H, J$_{1,2}$=0.8 Hz, H-1), 5.66 (dd, 1H, J$_{3,4}$=10.2 Hz, J$_{2,3}$=3.4 Hz, H-3), 5.44 (m, 1H, H-2), 5.14 (pt, 1H, J$_{4,5}$=10.0 Hz, H-4), 4.10 (dq, 1H, H-5), 2.14, 2.06, 1.99 (3 s, 9H, H$_{Ac}$), 1.25 (d, 3H, J$_{5,6}$=6.3 Hz, H-6).

$^{13}$C NMR (CDl$_3$), δ170.1, 170.0, 169.9 (3C, C$_{Ac}$), 84.1 (C-1, $^1$J$_{CH}$=184.3 Hz), 72.8 (C-2), 71.5 (C-5), 70.7 (C-4), 68.3 (C-3), 21.1, 21.0, 20.9 (3C, C$_{Ac}$), 17.3 (C-6).

3,4-Di-O-acetyl-1,2-(allyloxyethylidene)-β-L-rhamnopyranose 73

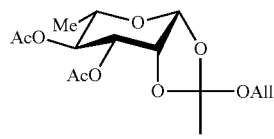

Chemical Formula: C$_{15}$H$_{22}$O$_8$
Exact Mass: 330.1315
Molecular Weight: 330.3304

2,6-Lutidine (28 mL) is added to a solution of bromide (70.6 g, 200.0 mmol) in an allyl alcohol/DCM mixture (1/1, 400 mL). At the end of addition, the reaction mixture is stirred overnight at RT. After verifying, by monitoring by TLC (Chex/EtOAc, 7/3), the disappearance of 72 (Rf=0.25) and the appearance of a new compound (Rf=0.35), the reaction mixture is taken up in a DCM/H$_2$O mixture (2/1, 150 mL) and the aqueous phase is extracted with DCM (3×150 mL). The organic phases are combined and washed with 10% citric acid solution (3×50 mL), NaHCO$_{3sat}$ solution (3×50 mL), and a solution of H$_2$O (3×30 mL) and then dried on a reparatory filter and concentrated in a rotary evaporator. The residue is dried with a vane pump to give the orthoester 73 in the form of a yellow oil (66.0 g) which is used directly in the next stage after checking by $^1$H NMR.

Rf=0.35 (Chex/EtOAc, 7/3).

$^1$H NMR (CDCl$_3$), δ5.85 (m, 1H, CH=), 5.39 (d, 1H, J$_{1,2}$=2.4 Hz, H-1), 5.22 (m, 1H, J$_{trans}$=17.2 Hz, =CH$_2$), 5.09 (m, 1H, J$_{cis}$=11.8 Hz, =CH$_2$), 5.06 (dd, 1H, J$_{2,3}$=3.9 Hz, J$_{3,4}$=9.7 Hz, H-3), 5.01 (pt, 1H, J$_{4,5}$=9.9 Hz, H-4), 4.56 (dd, 1H, J$_{1,2}$=2.4 Hz, J$_{2,3}$=3.9 Hz, H-2), 4.00 (m, 2H, H$_{A11}$), 3.49 (dq, 1H, H-5), 2.07, 2.02 (2 s, 6H, H$_{Ac}$), 1.72 (s, 3H, CH$_{3ortho}$) 1.20 (d, 3H, J$_{5,6}$=6.2 Hz, H-6).

$^{13}$C NMR (CDl$_3$), δ170.7, 170.3 (2C, C$_{Ac}$), 134.5 (CH=), 124.5 (C$_{ortho}$), 116.9 (=CH$_2$), 97.4 (C-1, $^1$J$_{CH}$=175.0 Hz), 77.0 (C-2), 71.1 (C-3), 70.7 (C-4), 69.5 (C-5), 64.0 (C$_{A11}$), 24.5 (CH$_{3ortho}$), 21.2, 21.0 (2C, C$_{Ac}$), 17.8 (C-6).

HRMS (ESI$^+$): [M+Na]$^+$ C$_{15}$H$_{22}$O$_8$Na m/z theoretical: 353.1212
m/z measured: 353.1235

1,2-(Allyloxyethylidene)-β-L-rhamnopyranose 74

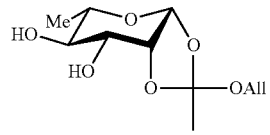

Chemical Formula: C$_{11}$H$_{18}$O$_6$
Exact Mass: 246.1103
Molecular Weight: 246.2570

The orthoester 73 (66.0 g, 200.0 mmol) is dissolved in MeOH (250 mL) and then potassium carbonate (1.1 g, 8.0 mmol, 0.04 eq.) is added to the reaction mixture. After stirring for 3 h, monitoring by TLC (Chex/EtOAc, 7/3 and DCM/MeOH, 95/5) indicates the disappearance of 73 (Rf=0.4 and 1, respectively) and the appearance of a more polar product (Rf=0 and 0.4, respectively). The reaction mixture is evaporated under reduced pressure to give the diol 74 in the form of a yellowish solid (49.2 g), which is used directly in the next stage after checking by $^1$H NMR.

Rf=0.5 (DCM/MeOH, 9/1).

$^1$H NMR (CDCl$_3$), δ5.85 (m, 1H, CH=), 5.39 (d, 1H, J$_{1,2}$=2.0 Hz, H-1), 5.26 (m, 1H, J$_{trans}$=17.2 Hz, =CH$_2$), 5.15 (m, 1H, J$_{cis}$=10.4 Hz, =CH$_2$), 4.48 (m, 1H, H-2), 4.07 (m, 2H, H$_{A11}$), 3.70 (dd, 1H, J$_{3,4}$=9.2 Hz, J$_{2,3}$=4.0 Hz, H-3), 3.42 (pt, 1H, J$_{4,5}$=9.2 Hz, H-4), 3.30 (dq, 1H, H-5), 1.71 (s, 3H, CH$_{3ortho}$), 1.31 (d, 3H, J$_{5,6}$=6.0 Hz, H-6).

$^{13}$C NMR (CDl$_3$), δ134.4 (CH=), 124.0 (C$_{ortho}$) 116.8 (=CH$_2$), 97.7 (C-1, $^1$J$_{CH}$=175.1 Hz), 79.6 (C-2), 72.9 (C-3), 72.7 (C-4), 71.1 (C-5), 64.0 (C$_{A11}$), 25.5 (CH$_{3ortho}$), 17.8 (C-6).

3,4-Di-O-benzyl-1,2-(allyloxyethylidene)-β-L-rhamnopyranose 75

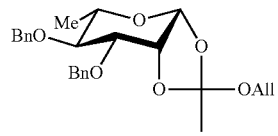

Chemical Formula: C$_{25}$H$_{30}$O$_6$
Exact Mass: 426.2042
Molecular Weight: 426.5021

60% NaH in oil (24.0 g, 600.0 mmol, 3 eq.) is added in small portions, at 0° C., to a solution of diol 74 (49.2 g, 200.0 mmol) in DMF (300 mL). The reaction mixture is then stirred for 15 min and then brought back to 0° C. Benzyl bromide (57.3 mL, 480.0 mmol, 2.4 eq.) is added dropwise and then the reaction mixture is stirred overnight at RT. After verifying, by monitoring by TLC (DCM/MeOH, 9/1 and Chex/EtOAc, 7/3), the disappearance of 73 (Rf=0.5 and 0, respectively) and the appearance of a new compound (Rf=0.9 and 0.5, respectively), the reaction mixture is adjusted to 0° C. and MeOH (30 mL) is added. The reaction mixture is then taken up in EtOAc/H$_2$O mixture (3/1, 400 mL) and the aqueous phase is extracted with EtOAc (3×150 mL). The organic phases are combined and washed with NaCl$_{sat}$ solution (3×50 mL), and a solution of H$_2$O (3×50 mL) and then dried over Na$_2$SO$_4$ and concentrated in a rotary evaporator. The oil obtained is purified by silica gel chromatography (Chex/EtOAc, 9/1→7/3) to give the di-O-benzyl 75 in the form of a colorless oil (64.8 g, 76%, 5 stages).

Rf=0.5 (Chex/EtOAc, 7/3).

$^1$H NMR (CDCl$_3$), δ7.47-7.35 (m, 10H, CH$_{Ph}$), 5.96 (m, 1H, CH=), 5.33 (m, 1H, J$_{trans}$=17.2 Hz, =CH$_2$), 5.31 (d, 1H, J$_{1,2}$=1.7 Hz, H-1), 5.22 (m, 1H, J$_{cis}$=10.4 Hz, =CH$_2$), 4.99 (d, 1H, J=10.8 Hz, H$_{Bn}$), 4.80 (m, 2H, H$_{Bn}$), 4.71 (d, 1H, J=10.8 Hz, H$_{Bn}$), 4.41 (dd, 1H, J$_{1,2}$=1.7 Hz, J$_{2,3}$=4.1 Hz, H-2), 4.08 (m, 2H, H$_{All}$), 3.73 (dd, 1H, J$_{3,4}$=9.1 Hz, J$_{2,3}$=4.1 Hz, H-3), 3.52 (pt, $^1$H, J$_{4,5}$=9.1 Hz, H-4), 3.37 (dq, 1H, H-5), 1.80 (s, 3H, CH$_{3ortho}$), 1.34 (d, 3H, J$_{5,6}$=6.2 Hz, H-6).

$^{13}$C NMR (CDl$_3$), δ138.7-138.3 (C$_{Ph}$), 135.0 (CH=), 129.0-128.3 (CH$_{Ph}$), 124.1 (C$_{ortho}$), 116.9 (=CH$_2$), 97.8 (C-1, $^1$J$_{CH}$=173.6 Hz), 79.9 (C-4), 79.6 (C-3), 77.5 (C-2), 76.6, 72.6 (2C, C$_{Bn}$), 70.7 (C-5), 64.0 (C$_{All}$), 25.4 (CH$_{3ortho}$), 18.4 (C-6).

HRMS (ESI$^+$): [M+Na]$^+$ C$_{25}$H$_{30}$O$_6$Na m/z theoretical: 449.1940
m/z measured:
449.1980

Allyl 2-O-acetyl-3,4-di-O-benzyl-α-L-rhamnopyranoside 76

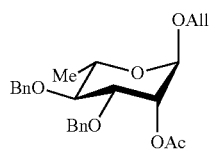

Chemical Formula: C$_{25}$H$_{30}$O$_6$
Exact Mass: 426.2042
Molecular Weight: 426.5021

TMSOTf (4.5 mL, 25.2 mmol, 0.2 eq.) is added to a solution of the di-O-benzyl 75 (53.8 g, 126.0 mmol) in DCM (300 mL), in the presence of molecular sieve 4 Å (55 g), stirred under argon at 0° C. After stirring for 3 h at RT, monitoring by TLC (Chex/EtOAc, 7/3) indicates the disappearance of 75 (Rf=0.5) and the appearance of a new, less polar compound (Rf=0.6). The reaction is stopped by adding triethylamine (2 mL), then the reaction mixture is filtered and concentrated in a rotary evaporator. The oil obtained is purified by silica gel chromatography (Chex/EtOAc, 9/1→7/3) to give the allyl glycoside 76 in the form of a colorless oil (47.5 g, 88%).

Rf=0.6 (Chex/EtOAc, 7/3).

$^1$H NMR (CDCl$_3$), δ7.42-7.33 (m, 10H, CH$_{Ph}$), 5.90 (m, 1H, CH=), 5.42 (dd, 1H, J$_{1,2}$=1.8 Hz, J$_{2,3}$=3.4 Hz, H-2), 5.29 (m, 1H, J$_{trans}$=17.2 Hz, =CH$_2$), 5.21 (m, 1H, J$_{cis}$=10.4 Hz, =CH$_2$), 4.95 (d, 1H, J=10.8 Hz, H$_{Bn}$), 4.80 (d, 1H, J$_{1,2}$=1.7 Hz, H-1), 4.73 (d, 1H, J=11.2 Hz, H$_{Bn}$), 4.64 (d, 1H, J=10.8 Hz, H$_{Bn}$), 4.56 (d, 1H, J=11.2 Hz, H$_{Bn}$), 4.19 (m, 1H, H$_{All}$), 4.01-3.97 (m, 2H, H$_{All}$, H-3), 3.37 (dq, 1H, H-5), 3.47 (pt, 1H, J$_{4,5}$=9.4 Hz, H-4), 2.17 (s, 3H, H$_{Ac}$), 1.36 (d, 3H, J$_{5,6}$=6.2 Hz, H-6).

$^{13}$C NMR (CDl$_3$), δ170.7 (C$_{Ac}$), 139.0-138.5 (C$_{Ph}$) 134.0 (CH=), 128.9-128.1 (CH$_{Ph}$), 118.0 (=CH$_2$), 97.3 (C-1, $^1$J$_{CH}$=169.6 Hz), 80.5 (C-4), 78.6 (C-3), 75.8, 72.2 (2C, C$_{Bn}$), 69.5 (C-2), 68.4 (C$_{All}$), 68.2 (C-5), 21.5 (C$_{Ac}$), 18.4 (C-6).

HRMS (ESI$^+$): [M+Na]$^+$ C$_{25}$H$_{30}$O$_6$Na m/z theoretical: 449.1940
m/z measured:
449.1951

Allyl 3,4-di-O-benzyl-α-L-rhamnopyranoside[96, 102]
58

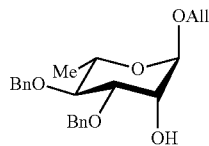

Chemical Formula: C$_{23}$H$_{28}$O$_5$
Exact Mass: 384.937
Molecular Weight: 384.4654

Route 1:
After adding 0.5 M NaOMe (222.7 mL, 111.0 mmol, 1 eq.) to the allyl glycoside 76 (47.5 g, 111.0 mmol) in solution in MeOH (150 mL), the reaction mixture is stirred for 2 h and its development is monitored by TLC (Chex/EtOAc, 7/3). After observing the disappearance of 76 (Rf=0.6) and the appearance of a more polar product (Rf=0.35), the reaction mixture is neutralized by adding DOWEX (H$^+$) ion-exchange resin, then filtered on a frit. The resin is washed with DCM/MeOH mixture and the solvents are evaporated. The yellow oil obtained is purified by silica gel chromatography (Chex/EtOAc, 8/2→7/3) to give the alcohol 58 in the form of a colorless oil (39.2 g, 92% or 61% starting from commercial L-rhamnose 27).

Route 2:
The raw product from 76 (65.2 g, 200.0 mmol) is taken up in EtOAc (300 mL). The organic phase is washed with 10% HCl solution (3×50 mL), NaCl$_{sat}$ solution (3×50 mL), and a solution of H$_2$O (3×50 mL) and then dried over Na$_2$SO$_4$ and concentrated in a rotary evaporator. Acetyl chloride is added (35.5 mL, 500.0 mmol, 2.5 eq.) in portions to allyl alcohol (300 mL) at 0° C. for 15 min, then the previous raw product is added to the reaction mixture. The reaction mixture is then heated at 70° C. for 2.5 h and then at 40° C. overnight. Monitoring of the reaction by TLC (Chex/EtOAc, 7/3) shows the disappearance of 76 (Rf=0.25) and the presence of a less polar main product (Rf=0.35). The reaction mixture is cooled to 0° C., neutralized by adding NaHCO$_3$ and then filtered on Celite and finally concentrated in a rotary evaporator. The volatile substances are coevaporated with Tol (2×100 mL) to give a yellow oil. The yellow oil is purified by silica gel chromatography (Chex/EtOAc, 8/2→1/1) to give the alcohol 58 in the form of a colorless oil (55 g, 72% starting from commercial L-rhamnose 27).

Route 3:
Part 2

Allyl(3,4-di-O-benzyl-α-L-rhamnopyranosyl)-
(1→3)-2-O-acetyl-4-O-benzyl-α-L-rhamnopyranoside 79

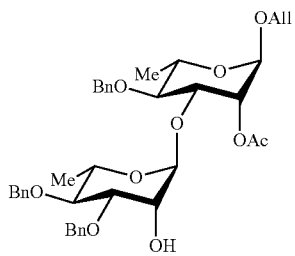

Chemical Formula: C$_{38}$H$_{46}$O$_{10}$
Exact Mass: 662.3091
Molecular Weigh: 662.7658

The allyl glycoside 61 (Section 2) (172 mg, 230 μmol) is dissolved in pyridine/acetic acid mixture (3/2, 5 mL). Hydrazine monohydrate (55 μL, 1.1 mmol, 5 eq.) is added dropwise to the reaction mixture. After stirring for 30 min at RT, monitoring by TLC (Tol/EtOAc, 8/2) indicates the disappearance of 61 (Rf=0.45) and the appearance of a more polar product (Rf=0.3). The reaction mixture is then taken up in cold water (10 mL) and the aqueous phase is quickly extracted with DCM (3×50 mL). The organic phases are combined and washed with NaCl$_{sat}$ solution, filtered on a phase-separating filter and concentrated in a rotary evaporator. The oil obtained is purified by silica gel chromatography (Tol/EtOAc, 9/1→75/25) to obtain the acceptor 79 in the form of a colorless oil (121 mg, 81%).

Rf=0.3 (Tol/EtOAc, 8/2).

$^1$H NMR (CDCl$_3$), δ7.40-7.28 (m, 15H, CH$_{Ph}$), 5.89 (m, 1H, CH=), 5.29 (m, 1H, J$_{trans}$=17.2 Hz, =CH$_2$), 5.21 (m, 1H, J$_{cis}$=10.4 Hz, =CH$_2$), 5.17 (m, 1H, H-2$_C$), 5.10 (d, 1H, J$_{1,2}$=1.5 Hz, H-1$_B$), 4.88 (d, 1H, J=11.0 Hz, H$_{Bn}$), 4.80 (d, 1H, J$_{1,2}$=1.6 Hz, H-1$_C$), 4.87 (d, 1H, J=11.0 Hz, H$_{Bn}$), 4.69-4.60 (d, 4H, H$_{Bn}$), 4.18-4.13 (m, 2H, H-3$_C$, H$_{All}$), 4.01-3.96 (m, 2H, H-2$_B$, H$_{All}$), 3.83-3.74 (m, 3H, H-3$_B$, H-5$_B$, H-5$_C$), 3.48 (pt, 1H, J$_{3,4}$=9.1 Hz, H-4$_B$), 3.46 (pt, 1H, J$_{3,4}$=9.4 Hz, H-4$_C$), 2.14 (s, 3H, H$_{Ac}$) 1.31 (m, 6H, H-6$_B$, H-6$_C$).

$^{13}$C NMR (CDCl$_3$), δ170.7 (C$_{Ac}$), 138.8-138.3 (C$_{Ph}$), 133.9 (CH=), 129.4-128.1 (CH$_{Ph}$), 117.9 (=CH$_2$), 101.8 (C-1$_B$, $^1$J$_{CH}$=171.0 Hz), 96.6 (C-1$_C$, $^1$J$_{CH}$=169.2 Hz), 80.7 (C-4$_C$), 80.2 (C-4$_B$), 80.1 (C-3$_B$), 78.5 (C-3$_C$), 75.9, 75.6 (2C, C$_{Bn}$), 72.9 (C-2$_C$), 72.4 (C$_{Bn}$), 69.4 (C-2$_B$), 68.7 (C-5$_B$), 68.6 (C$_{All}$), 68.1 (C-5$_C$), 21.5 (C$_{Ac}$), 18.3, 18.2 (C-6$_B$*, C-6$_C$*).

HRMS (ESI$^+$) [M+Na]$^+$ C$_{38}$H$_{46}$O$_{10}$Na m/z theoretical:
685.2989
m/z measured
685.2993
[M+NH$_4$]$^+$ C$_{38}$H$_{46}$O$_{10}$NH$_4$ m/z theoretical:
680.3434
m/z measured
680.3472
[M+K]$^+$ C$_{38}$H$_{46}$O$_{10}$K m/z theoretical:
701.2728
m/z measured
701.2731

5-Chloro-5-methyl-dihydro-furan-2-one[113] 82

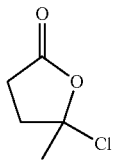

Chemical Formula: C$_5$H$_7$ClO$_2$
Exact Mass: 134.0135
Molecular Weight: 134.5609

Thionyl chloride (3.9 mL, 53.0 mmol, 1.1 eq.) is slowly added to a solution of levulinic acid (5.0 mL, 48.6 mmol, 1 eq.). The reaction mixture is stirred at RT for 1 h and then heated at 50° C. for 30 min. The excess thionyl chloride is then evaporated. The oil obtained is checked by $^1$H NMR and the data obtained are identical to the literature.[113]

Levulinic anhydride[112] 83

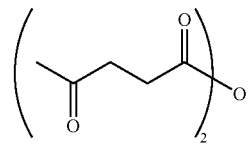

Chemical Formula: C$_{10}$H$_{14}$O$_5$
Exact Mass: 214.0841
Molecular Weight: 214.2152

DCC (80 g, 390 mmol) is added to a solution of levulinic acid (79.5 mL, 780.0 mmol, 2 eq.) in THF (500 mL) and the reaction mixture is stirred at RT overnight. The DCU that forms is then filtered on Celite and the filtrate is concentrated in a rotary evaporator. The white solid obtained (89.0 g) is used directly in the next stage after checking by $^1$H NMR.

Allyl(2,3,4,6-tetra-O-benzyl-α-D-glucopyranosyl)-
(1→3)-4-O-benzyl-2-O-levulinoyl-α-L-rhamnopyranoside 81

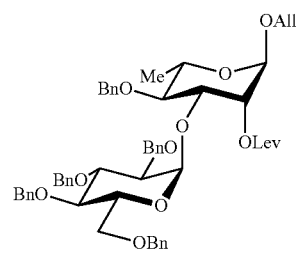

Chemical Formula: C$_{55}$H$_{62}$O$_{12}$
Exact Mass: 914.4241
Molecular Weight: 915.0736

The alcohol 21 (18.6 g, 22.8 mmol) is dissolved in pyridine (150 mL), then DMAP (13.9 g, 114 mmol, 5 eq.) is added and the reaction mixture is heated to 50° C. Levulinic anhydride 83 (48.8 g, 228.0 mmol, 10 eq.) dissolved in pyridine (200 mL) is added dropwise in the space of 1.5 h. After 3 h, monitoring by TLC (Chex/EtOAc, 7/3) indicates the disappearance of 21 (Rf=0.40) and the appearance of a more polar product (Rf=0.3). The reaction mixture is then concentrated in a rotary evaporator. The oil obtained is purified by silica gel chromatography (Chex/EtOAc, 9/1→75/25) to obtain the levulinoyl ester 81 in the form of a colorless oil (19.7 g, 95%).

Rf=0.3 (Chex/EtOAc, 7/3).

$^1$H NMR (CDCl$_3$), δ7.40-7.10 (m, 25H, CH$_{Ph}$), 5.87 (m, 1H, CH=), 5.39 (m, 1H, H-2$_A$), 5.28 (m, 1H, J$_{trans}$=17.2 Hz, =CH$_2$), 5.19 (d, 1H, J$_{1,2}$=5.6 Hz, H-1$_E$), 5.28 (m, 1H, J$_{cis}$=10.3 Hz, =CH$_2$), 5.02 (d, 1H, J=11.0 Hz, H$_{Bn}$), 4.96-4.85 (m, 3H, H$_{Bn}$), 4.78 (d, 1H, J$_{1,2}$=1.8 Hz, H-1$_A$), 4.78-4.59 (m, 4H, H$_{Bn}$), 4.50 (d, 1H, J=11.0 Hz, H$_{Bn}$), 4.36 (d, 1H, J=12.0 Hz, H$_{Bn}$), 4.26 (dd, 1H, J$_{2,3}$=3.2 Hz, J$_{3,4}$=9.6 Hz, H-3$_A$), 4.18-4.04 (m, 3H, H$_{All}$, H-3$_E$, H-5$_E$), 3.97 (m, 1H, H$_{All}$), 3.80 (m, 1H, H-5$_A$), 3.77 (pt, 1H, J$_{4,5}$=9.2 Hz, H-4$_E$), 3.64-3.52 (m, 4H, H-2$_E$, H-6a$_E$, H-4$_A$, H-6b$_E$), 2.55 (m, 4H, 2CH$_{2Lev}$), 2.09 (s, 3H, CH$_{3Lev}$) 1.40 (d, 3H, J$_{5,6}$=6.2 Hz, H-6$_A$).

$^{13}$C NMR (CDCl$_3$), δ206.5 (C$_{Lev}$) 172.5 (C$_{Lev}$), 139.2-138.1 (C$_{Ph}$), 134.0 (CH=), 129.0-127.8 (CH$_{Ph}$), 117.8 (=CH$_2$), 97.0 (C-1$_E$, $^1$J$_{CH}$=170.2 Hz), 93.3 (C-1$_A$, $^1$J$_{CH}$=167.5 Hz), 82.5 (C-3$_E$), 80.3 (C-4$_A$), 80.0 (C-2$_E$), 78.3 (C-4$_E$), 76.5, 75.9, 75.3, 73.7, 72.8 (5C, C$_{Bn}$), 72.8 (C-3$_A$), 70.6 (C-5$_E$), 68.7 (C-6$_E$), 68.6 (C-2$_A$), 68.5 (C$_{All}$), 68.4 (C-5$_A$), 38.2 (CH$_{2Lev}$), 30.0 (CH$_{3Lev}$), 28.4 (CH$_{2Lev}$), 18.3 (C-6$_A$).

HRMS (ESI$^+$): [M+Na]$^+$ C$_{55}$H$_{62}$O$_{12}$Na m/z theoretical:
937.4139
m/z measured
937.4109
[M+NH$_4$]$^+$ C$_{55}$H$_{62}$O$_{12}$NH$_4$ m/z theoretical:
932.4585
m/z measured
932.4542

(2,3,4,6-Tetra-O-benzyl-α-D-glucopyranosyl)-(1→3)-4-O-benzyl-2-O-levulinoyl-α/β-L-rhamnopyranose 84

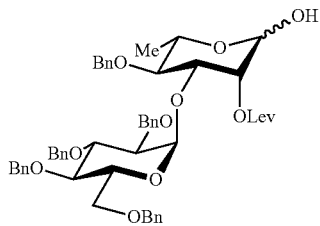

Chemical Formula: C$_{52}$H$_{58}$O$_{12}$
Exact Mass: 874.3928
Molecular Weight: 875.0097

(1,5-Cyclooctadienebis(methyldiphenylphosphine)-iridium(I)hexafluorophosphate) (250 mg) is dissolved in THF (100 mL) with stirring. The mixture is submitted to cycles of vacuum/argon degassing, 5 cycles of vacuum/hydrogen degassing and is then placed under hydrogen for 15 min. The mixture is then submitted to 5 cycles of vacuum/argon degassing for a second time. The solution of levulinoyl ester 81 (8.5 g, 9.3 mmol) in THF (15 mL) is transferred to a solution of activated catalyst. Monitoring by TLC (Chex/EtOAc, 7/3) shows the disappearance of 81 (Rf=0.3) and the appearance of a somewhat less polar product (Rf=0.35).

Diiodine (4.7 g, 18.6 mmol, 2 eq.) in solution in THF/H$_2$O mixture (8/2, 50 mL) is added to the reaction mixture. Monitoring by TLC (Chex/EtOAc, 7/3 and DCM/MeOH, 98/2) indicates the disappearance of the intermediate (Rf=0.35 and 0.85, respectively) and the appearance of a new, much more polar compound (Rf=0.05 and 0.2, respectively). To stop the reaction, 10% NaHSO$_3$ aqueous solution (40 mL) is added in portions to the mixture until the black coloration disappears. The reaction mixture is taken up in DCM (100 mL) and the aqueous phase is extracted with DCM (3×100 mL). The organic phases are combined and washed with NaCl$_{sat}$ solution (3×50 mL), with H$_2$O (3×50 mL) and then dried on a phase-separating filter and concentrated in a rotary evaporator. The yellow oil obtained is purified by silica gel chromatography (DCM/MeOH, 99/1→9/1) to obtain a mixture of α/β anomers of the hemiacetal 83 in the proportions 7/3 in the form of a yellow oil (7.5 g, 92%).

Rf=0.2 (DCM/MeOH, 98/2).

83$_α$: $^1$H NMR (CDCl$_3$), δ7.43-7.14 (m, 25H, CH$_{Ph}$), 5.43 (m, 1H, H-2$_A$), 5.25 (d, 1H, J$_{1,2}$=3.4 Hz, H-1$_E$), 5.15 (d, 1H, J$_{1,2}$=1.7 Hz, H-1$_A$), 5.07-4.87 (m, 3H, H$_{Bn}$), 4.80 (d, 1H, J=12.2 Hz, H$_{Bn}$), 4.74-4.59 (m, 3H, H$_{Bn}$), 4.52 (d, 1H, J=11.0 Hz, H$_{Bn}$), 4.46-4.36 (d, 2H, H$_{Bn}$), 4.34 (m, 1H, H-3$_A$), 4.20-4.10 (m, 2H, H-3$_E$, H-5$_E$), 4.05 (m, 1H, H-5$_A$), 3.78-3.73 (m, 2H, OH, H-4$_E$), 3.70-3.55 (m, 4H, H-2$_E$, H-6a$_E$, H-4$_A$, H-6b$_E$), 2.55 (m, 4H, 2CH$_{2Lev}$), 2.11 (s, 3H, CH$_{3Lev}$) 1.41 (d, 3H, J$_{5,6}$=6.2 Hz, H-6$_A$). RMN $^{13}$C (CDCl$_3$), δ 206.9 (C$_{Lev}$) 172.6 (C$_{Lev}$), 139.2-138.9 (C$_{Ph}$) 129.0-127.8 (CH$_{Ph}$), 93.0 (C-1$_E$, $^1$J$_{CH}$=169.0 Hz), 92.4 (C-1$_A$, $^1$J$_{CH}$=170.7 Hz), 82.5 (C-3$_E$), 80.3 (C-4$_A$) 79.9 (C-2$_E$), 78.3 (C-4$_E$), 76.5, 75.9, 75.4, 73.6, 73.2 (5C, C$_{Bn}$), 72.3 (C-3$_A$), 70.5 (C-5$_E$), 69.0 (C-2$_A$), 68.7 (C-6$_E$), 68.3 (C-5$_A$), 38.3 (CH$_{2Lev}$), 30.1 (CH$_{3Lev}$,) 28.6 (CH$_{2Lev}$), 18.5 (C-6$_A$).

83$_β$: $^1$H NMR (CDCl$_3$), δ7.43-7.14 (m, 25H, CH$_{Ph}$), 5.62 (d, 1H, J$_{2,3}$=2.7 Hz, H-2$_A$), 5.38 (d, 1H, J$_{1,2}$=3.4 Hz, H-1$_E$), 5.07-4.87 (m, 3H, H$_{Bn}$), 4.80 (d, 1H, J=12.2 Hz, H$_{Bn}$), 4.79 (s, 1H, H-1$_A$), 4.74-4.59 (m, 3H, H$_{Bn}$), 4.53 (d, 1H, J=11.0 Hz, H$_{Bn}$), 4.46-4.36 (d, 2H, H$_{Bn}$), 4.20-4.10 (m, 2H, H-3$_E$, H-5$_E$), 4.00 (m, 1H, H-3$_A$), 3.75 (m, 1H, H-4$_E$), 3.70-3.55 (m, 3H, H-2$_E$, H-6a$_E$, H-6b$_E$), 3.53 (pt, 1H, J$_{4,5}$=9.3 Hz, H-4), 3.44 (m, 1H, H-5$_A$), 2.55 (m, 4H, 2CH$_{2Lev}$), 2.14 (s, 3H, CH$_{3Lev}$) 1.47 (d, 3H, J$_{5,6}$=6.0 Hz, H-6$_A$).

$^{13}$C NMR (CDCl$_3$), δ208.6 (C$_{Lev}$), 173.1 (C$_{Lev}$), 139.2-138.9 (C$_{Ph}$), 129.0-127.8 (CH$_{Ph}$) 93.6 (C-1$_A$, $^1$J$_{CH}$=160.9 Hz), 92.6 (C-1$_E$, $^1$J$_{CH}$=169.1 Hz), 82.4 (C-3$_E$), 79.6 (C-4$_A$), 80.0 (C-2$_E$), 78.4 (C-4$_E$), 76.6, 76.0, 75.5 (3C, C$_{Bn}$), 74.2 (C-3$_A$), 73.6, 73.4 (2C, C$_{Bn}$), 72.3 (C-5$_A$), 70.5 (C-5$_E$), 69.0 (C-2$_A$), 68.8 (C-6$_E$), 39.1 (CH$_{2Lev}$), 30.0 (CH$_{3Lev}$), 28.5 (CH$_{2Lev}$), 18.5 (C-6$_A$).

HRMS: (ESI$^+$): [M+Na]$^+$ C$_{52}$H$_{58}$O$_{12}$Na m/z theoretical:
897.3826
m/z measured
897.3777
[M+NH$_4$]$^+$ C$_{52}$H$_{58}$O$_{12}$NH$_4$ m/z theoretical:
892.4272
m/z measured
892.4234

(2,3,4,6-Tetra-O-benzyl-α-D-glucopyranosyl)-(1→3)-4-O-benzyl-2-O-levulinoyl-α/β-L-rhamnopyranose trichloroacetimidate 80

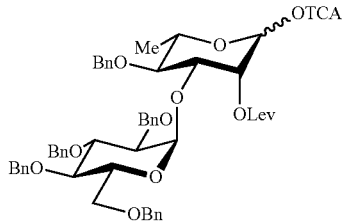

Chemical Formula: $C_{54}H_{58}Cl_3NO_{12}$
Exact Mass: 1017.3025
Molecular Weight: 1019.3968

The hemiacetal 83 (7.1 g, 8.1 mmol) is dissolved in DCE (30 mL) and stirred under argon at −5° C., and then DBU (340 μL, 2.3 mmol, 0.28 eq.) and trichloroacetonitrile (4.0 mL, 40.5 mmol, 5 eq.) are added. The reaction mixture is stirred at this temperature for 15 min and then it is loaded, without any treatment, on a silica gel column (flash chromatography, Chex/EtOAc+5% NEt$_3$, 7/3→1/1) to obtain the trichloroacetimidate 80 in the form of a yellow oil (8.0 g, 97%).
Rf=0.35 (Chex/EtOAc, 7/3).

$^1$H NMR (CDCl$_3$), δ8.72 (s, 1H, NH), 7.42-7.14 (m, 25H, CH$_{Ph}$), 6.24 (d, 1H, J$_{1,2}$=2.0 Hz, H-1$_A$), 5.61 (m, 1H, H-2$_A$), 5.27 (d, 1H, J$_{1,2}$=3.4 Hz, H-1$_E$), 5.05-4.99 (m, 2H, H$_{Bn}$), 4.92-4.88 (m, 2H, H$_{Bn}$), 4.80 (d, 1H, J=12.0 Hz, H$_{Bn}$), 4.74-4.53 (m, 4H, H$_{Bn}$), 4.42 (d, 1H, J=12.2 Hz, H$_{Bn}$), 4.34 (dd, 1H, J$_{2,3}$=3.1 Hz, J$_{3,4}$=9.7 Hz, H-3$_A$), 4.16-4.06 (m, 2H, H-3$_E$, H-5$_E$), 4.02 (m, 1H, H-5$_A$), 3.79 (pt, 1H, J$_{3,4}$=9.3 Hz, H-4$_E$), 3.71-3.62 (m, 3H, H-4$_A$, H-6a$_E$, H-2$_E$), 3.52 (m, 1H, H-6b$_E$), 2.59 (m, 4H, 2CH$_{2Lev}$) 2.11 (s, 3H, CH$_{3Lev}$), 1.45 (d, 3H, J$_{5,6}$=6.2 Hz, H-6$_A$).

$^{13}$C NMR (CDCl$_3$), δ206.3 (C$_{Lev}$), 172.5 (C$_{Lev}$), 160.5 (C=NH), 139.1-137.9 (C$_{Ph}$) 129.2-127.8 (CH$_{Ph}$), 95.4 (C-1$_A$, $^1$J$_{CH}$=178.9 Hz), 93.4 (C-1$_E$, $^1$J$_{CH}$=168.3 Hz), 91.3 (CCl$_3$), 82.4 (C-3$_E$), 79.8 (C-2$_E$), 79.5 (C-4$_A$), 78.2 (C-4$_E$), 76.8, 75.9, 75.4, 73.8, 73.2 (5C, C$_{Bn}$), 72.5 (C-3$_A$), 71.4 (C-5$_A$), 70.8 (C-5$_E$), 68.4 (C-6$_E$), 66.9 (C-2$_A$), 38.2 (CH$_{2Lev}$), 30.0 (CH$_{3Lev}$), 28.4 (CH$_{2Lev}$), 18.4 (C-6$_A$).

Allyl(2,3,4,6-tetra-O-benzyl-α-D-glucopyranosyl)-(1→3)-(4-O-benzyl-2-O-levulinoyl-α-L-rhamnopyranosyl)-(1→2)-(3,4-di-O-benzyl-α-L-rhamnopyranosyl)-(1→3)-2-O-acetyl-4-O-benzyl-α-L-rhamnopyranoside 87

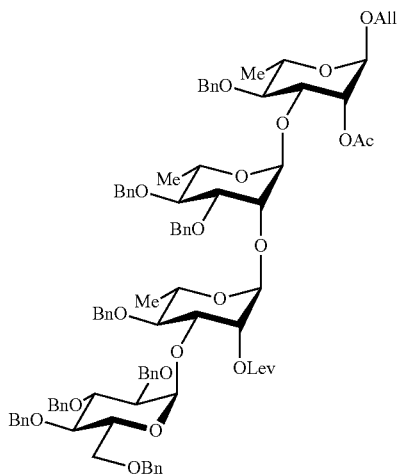

Chemical Formula: $C_{90}H_{102}O_{21}$
Exact Mass: 1518.6914
Molecular Weight: 1519.7603

TMSOTf (340.0 μL, 1.9 mmol, 0.3 eq.) is added to a solution of acceptor 79 (4.2 g, 6.3 mmol) and donor 80 (8.0 g, 7.8 mmol, 1.2 eq.) in Tol (100 mL), in the presence of molecular sieve 4 Å (5.3 g), stirred under argon at −78° C. After 1 h at this temperature, the ethanol-dry ice bath is withdrawn and stirring is continued for 30 min, after which time monitoring by TLC (Tol/EtOAc, 8/2, Chex/EtOAc, 7/3) indicates the disappearance of 79 (Rf=0.35 and 0.4, respectively) and the appearance of a new compound (Rf=0.65 and 0.45, respectively). The reaction is stopped by adding triethylamine (0.5 mL), then the reaction mixture is filtered and concentrated in a rotary evaporator. The yellow oil obtained is purified by silica gel chromatography (Tol/EtOAc, 95/5→85/15) to obtain the allyl glycoside 87 as a colorless oil (8.8 g, 92%). Rf=0.45 (Chex/EtOAc, 7/3).

$^1$H NMR (CDCl$_3$), δ7.42-7.15 (m, 40H, CH$_{Ph}$), 5.89 (m, 1H, CH=), 5.58 (m, 1H, H-2$_A$), 5.31 (m, 1H, J$_{trans}$=17.2 Hz, =CH$_2$), 5.28 (d, 1H, J$_{1,2}$=3.4 Hz, H-1$_E$), 5.21 (m, 1H, J$_{cis}$=10.4 Hz, =CH$_2$), 5.19 (m, 1H, H-2$_C$), 5.04 (d, 1H, J=11.0 Hz, H$_{Bn}$), 5.01 (d, 1H, J$_{1,2}$=1.4 Hz, H-1$_B$), 5.00 (d, 1H, J$_{1,2}$=1.6 Hz, H-1$_A$), 4.98-4.87 (m, 4H, H$_{Bn}$), 4.84 (d, 1H, J$_{1,2}$=1.6 Hz, H-1$_C$), 4.82-4.61 (m, 8H, H$_{Bn}$), 4.57 (d, 1H, J=11.1 Hz, H$_{Bn}$), 4.52 (d, 1H, J=11.0 Hz, H$_{Bn}$), 4.36 (d, 1H, J=12.0 Hz, H$_{Bn}$), 4.28 (dd, 1H, J$_{2,3}$=3.1 Hz, J$_{3,4}$=9.6 Hz, H-3$_A$), 4.19 (m, 1H, H$_{All}$), 4.17-4.07 (m, 3H, H-3$_E$, H-3$_C$, H-3$_E$), 4.04 (m, 1H, H$_{All}$), 3.99 (m, 1H, H-2$_E$), 3.90 (m, 1H, H-5$_A$), 3.88-3.81 (m, 2H, H-3$_B$, H-4$_E$), 3.79-3.74 (m, 3H, H-5$_C$), 3.73 (m, 1H, H-5$_E$), 3.69-3.65 (m, 2H, H-2$_E$, H-6a$_E$), 3.60-3.56 (m, 2H, H-6b$_E$, H-4$_A$), 3.54 (pt, 1H, J$_{3,4}$=9.4 Hz, H-4$_B$), 3.45 (pt, 1H, J$_{3,4}$=9.5 Hz, H-4$_C$), 2.57 (m, 4H, 2CH$_{2Lev}$), 2.17 (s, 3H, H$_{Ac}$), 2.11 (s, 3H, CH$_{3Lev}$), 1.35 (d, 3H, J$_{5,6}$=6.2 Hz, H-6$_A$), 1.30 (m, 6H, H-6$_C$, H-6$_B$).

$^{13}$C NMR (CDCl$_3$), δ206.6 (C$_{Lev}$) 172.1 (C$_{Lev}$), 170.8 (C$_{Ac}$), 138.6-138.4 (C$_{Ph}$), 134.0 (CH=), 129.0-127.9 (CH$_{Ph}$), 117.9 (=CH$_2$), 101.7 (C-1$_B$, $^1$J$_{CH}$=169.9 Hz), 99.5 (C-1$_A$, $^1$J$_{CH}$=176.6 Hz), 96.5 (C-1$_C$, $^1$J$_{CH}$=170.6 Hz), 93.3 (C-1$_E$, $^1$J$_{CH}$=168.8 Hz), 82.6 (C-3$_E$), 80.7 (C-4$_B$), 80.3 (C-4$_C$), 80.2 (C-4$_A$), 79.8 (C-2$_E$), 79.7 (C-3$_B$), 79.4 (C-3$_C$), 78.2 (C-4$_E$), 76.5, 76.0, 75.9 (3C, C$_{Bn}$), 75.8 (C-2$_B$), 75.7, 75.4, 73.8, 73.2 (4C, C$_{Bn}$), 72.9 (C-2$_C$), 72.6 (C-3$_A$), 72.5 (C$_{Bn}$), 70.6 (C-5$_E$), 69.4 (C-5$_B$), 69.0 (C-5$_A$), 68.7 (C$_{All}$), 68.6 (C-6$_E$), 68.4 (C-2$_A$), 68.1 (C-5$_C$), 38.3 (CH$_{2Lev}$) 30.1 (CH$_{3Lev}$), 28.5 (CH$_{2Lev}$), 21.5 (C$_{Ac}$), 18.4, 18.3, 18.2 (C-6$_A$*, C-6$_B$*, C-6$_C$*).

HRMS (ESI$^+$): [M+Na]$^+$ $C_{90}H_{102}O_{21}Na$ m/z theoretical:
1541.6812
m/z measured
1541.6769
[M+NH$_4$]$^+$ $C_{90}H_{102}O_{21}NH_4$ m/z theoretical:
1536.7257
m/z measured
1536.7207

Allyl(2,3,4,6-tetra-O-benzyl-α-D-glucopyranosyl)-(1→3)-(4-O-benzyl-α-L-rhamnopyranosyl)-(1→2)-(3,4-di-O-benzyl-α-L-rhamnopyranosyl)-(1→3)-2-O-acetyl-4-O-benzyl-α-L-rhamnopyranoside 85

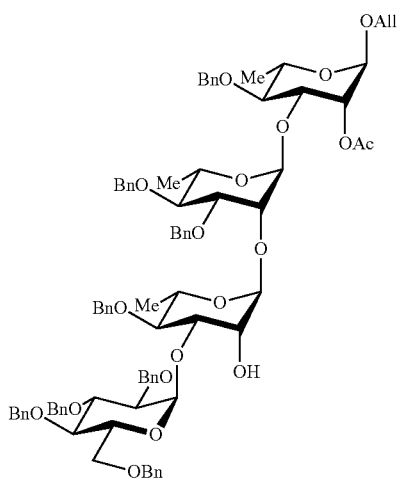

Chemical Formula: $C_{85}H_{96}O_{19}$
Exact Mass: 1420.6546
Molecular Weight: 1421.6603

The allyl glycoside 87 (552 mg, 360 μmol) is dissolved in pyridine/acetic acid mixture (3/2, 5 mL). Hydrazine monohydrate (88 μL, 1.8 mmol, 5 eq.) is added dropwise to the reaction mixture. After stirring for 30 min at RT, monitoring by TLC (Tol/EtOAc, 8/2) indicates the disappearance of 87 (Rf=0.65) and the appearance of a less polar product (Rf=0.7). The reaction mixture is then taken up in cold water (10 mL) and the aqueous phase is quickly extracted with DCM (3×100 mL). The organic phases are combined and washed with $NaCl_{sat}$ solution, filtered on a phase-separating filter and concentrated in a rotary evaporator. The oil obtained is purified by silica gel chromatography (Tol/EtOAc, 9/1) to obtain the acceptor 85 in the form of a colorless oil (456 mg, 89%).

Rf=0.7 (Tol/EtOAc, 8/2).

$^1$H NMR (CDCl$_3$), δ7.43-7.23 (m, 40H, CH$_{Ph}$), 5.89 (m, 1H, CH═), 5.35 (m, 1H, J$_{trans}$=17.2 Hz, ═CH$_2$), 5.25 (m, 1H, J$_{cis}$=10.4 Hz, ═CH$_2$), 5.22 (m, 1H, H-2$_C$), 5.19 (s, 1H, H-1$_A$), 5.06 (d, 1H, J$_{1,2}$=1.4 Hz, H-1$_E$), 5.03-4.96 (m, 3H, H$_{Bn}$) 4.97 (d, 1H, J$_{1,2}$=3.7 Hz, H-1$_E$), 4.91-4.89 (m, 3H, H$_{Bn}$), 4.81 (d, 1H, J$_{1,2}$=1.3 Hz, H-1$_C$), 4.81 (d, 1H, J=10.7 Hz, H$_{Bn}$), 4.75-4.68 (m, 3H, H$_{Bn}$), 4.66-4.53 (m, 5H, H$_{Bn}$), 4.36 (d, 1H, J=11.9 Hz, H$_{Bn}$), 4.19 (m, 1H, H$_{All}$), 4.17-4.08 (m, 5H, H-3$_C$, H-2$_A$, H-2$_B$, H-3$_E$, H-3$_A$), 4.03 (m, 1H, H$_{All}$), 4.01 (m, 1H, H-5$_E$), 3.93 (m, 1H, H-5$_A$), 3.89 (dd, 1H, J$_{2,3}$=2.8 Hz, J$_{3,4}$=9.4 Hz, H-3$_B$), 3.85 (m, 3H, H-5$_C$), 3.79 (pt, 1H, J$_{3,4}$=9.7 Hz, H-4$_E$), 3.74 (m, 1H, H-5$_B$), 3.66 (dd, 1H, J$_{1,2}$=3.6 Hz, J$_{2,3}$=9.6 Hz, H-2$_E$), 3.57 (pt, 1H, J$_{3,4}$=9.3 Hz, H-4$_A$), 3.54-3.43 (m, 4H, H-6a$_E$, H-4$_B$, H-4$_C$, H-6b$_E$), 2.19 (s, 3H, H$_{Ac}$), 1.37 (d, 3H, J$_{5,6}$=6.3 Hz, H-6$_A$), 1.35 (d, 3H, J$_{5,6}$=6.2 Hz, H-6$_B$), 1.33 (d, 3H, J$_{5,6}$=6.2 Hz, H-6$_C$).

$^{13}$C NMR (CDCl$_3$), δ170.8 (C$_{Ac}$), 138.8-138.6 (C$_{Ph}$), 134.0 (CH═), 129.1-128.1 (CH$_{Ph}$), 117.9 (═CH$_2$), 101.9 (C-1$_B$, $^1$J$_{CH}$=168.4 Hz), 101.3 (C-1$_A$, $^1$J$_{CH}$=173.1 Hz), 96.6 (C-1$_C$, $^1$J$_{CH}$=170.4 Hz), 94.3 (C-1$_E$, $^1$J$_{CH}$=167.2 Hz), 82.8 (C-3$_E$), 80.8 (C-4$_C$), 80.4 (C-4$_C$), 80.0 (C-3$_B$), 79.6 (C-4$_A$), 79.4 (2C, C-2$_E$, C-3$_C$), 78.2 (C-4$_E$), 76.8 (C-3$_A$), 76.0, 75.9, 75.7 (4C, C$_{Bn}$), 75.6 (C-2$_B$), 75.3, 74.8, 73.8 (3C, C$_{Bn}$), 73.0 (C-2$_C$), 72.7 (C$_{Bn}$), 71.1 (C-5$_E$), 69.4 (C-5$_B$), 68.7 (C$_{All}$), 68.7 (C-6$_E$), 68.3 (C-5$_A$), 68.2 (C-5$_C$), 67.8 (C-2$_A$), 21.6 (C$_{Ac}$), 18.4, 18.3, 18.2 (C-6$_A$*, C-6$_B$*, C-6$_C$*).

HRMS (ESI$^+$): [M+Na]$^+$ $C_{85}H_{96}O_{19}Na$ m/z theoretical: 1443.6444
m/z measured 1443.6505
[M+NH$_4$]$^+$ $C_{85}H_{96}O_{19}NH_4$ m/z theoretical 1438.6890
m/z measured 1438.6960

Propyl α-D-glucopyranosyl-(1→3)-α-L-rhamnopyranosyl-(1→2)-α-L-rhamnopyranosyl-(1→3)-2-O-acetyl-α-L-rhamnopyranoside XI

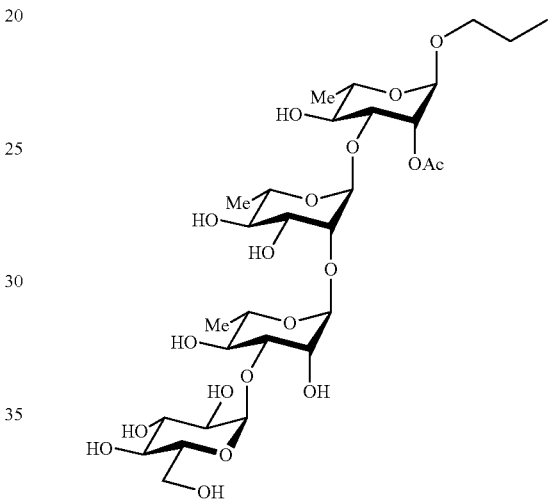

Chemical Formula: $C_{29}H_{50}O_{19}$
Exact Mass: 702.2946
Molecular Weight: 702.6959

Pd—C 10% (300 mg) is added to a degassed solution of alcohol 85 (400 mg, 281 μmol) in ethanol (30 mL). The suspension is saturated with hydrogen at atmospheric pressure and stirred at RT overnight. Monitoring by TLC (iPrOH/H$_2$O/NH$_3$, 4/1/0.5 and Tol/EtOAc, 8/2) shows the disappearance of 85 (Rf=1 and 0.7, respectively) and the appearance of a new, more polar compound (Rf=0.8 and 0, respectively). The reaction mixture is filtered on Celite, and the filtrate is concentrated in a rotary evaporator. The residue obtained is purified on a C-18 column (H$_2$O/CH$_3$CN, 100/0→8/2) to give the target XI as a white solid (150 mg, 76%).

Rf=0.8 (iPrOH/H$_2$O/NH$_3$, 4/1/0.5).

$^1$H NMR (D$_2$O), δ5.09 (d, 1H, J$_{1,2}$=1.0 Hz, H-1$_B$), 5.07 (m, 1H, H-2$_C$), 5.00 (d, 1H, J$_{1,2}$=3.8 Hz, H-1$_E$), 4.88 (d, 1H, J$_{1,2}$=1.5 Hz, H-1$_A$), 4.72 (d, 1H, J$_{1,2}$=1.5 Hz, H-1$_C$), 4.17 (dd, 1H, J$_{2,3}$=2.5 Hz, H-2$_A$), 3.91-3.83 (m, 3H, H-2$_B$, H-3$_C$, H-5$_E$), 3.75-3.61 (m, 7H, H-3$_A$, H-5$_C$, H-6a$_E$, H-6b$_E$, H-3$_E$, H-5$_A$, H-3$_B$), 3.60-3.54 (m, 2H, H$_{Pr}$, H-5$_E$), 3.49 (pt, 1H, J$_{3,4}$=9.7 Hz, H-4$_C$), 3.48-3.37 (m, 3H, H-2$_E$, H-4$_A$, H$_{Pr}$), 3.42 (pt, 1H, J$_{3,4}$=10.0 Hz, H-4$_B$), 3.42 (pt, 1H, J$_{3,4}$=9.2 Hz, H-4$_E$), 2.07 (s, 3H, H$_{Ac}$), 1.60 (sex, 2H, CH$_2$), 1.27 (d, 3H, J$_{5,6}$=6.2 Hz, H-6$_C$), 1.18-1.16 (m, 6H, H-6$_A$, H-6$_B$), 0.88 (t, 3H, J=7.4 Hz, CH$_3$).

$^{13}$C NMR (D$_2$O), δ173.4 (C$_{Ac}$), 102.4 (C-1$_A$, $^1J_{CH}$=175.5 Hz), 101.2 (C-1$_B$, $^1J_{CH}$=173.2 Hz), 97.2 (C-1$_C$, $^1J_{CH}$=172.3 Hz), 95.8 (C-1$_E$, $^1J_{CH}$=167.3 Hz), 78.8 (C-2$_B$), 76.2 (C-3$_C$), 75.7 (C-3$_A$), 73.3 (C-3$_E$), 72.5 (C-4$_C$), 72.4 (C-4$_E$), 72.3 (C-2$_C$), 72.1 (C-5$_E$), 71.8 (C-2$_E$), 70.7 (C-4$_A$), 70.3 (C$_{Pr}$), 70.2 (C-5$_A$), 69.8 (2C, C-4$_B$, C-5$_B$), 69.7 (C-3$_B$), 69.0 (C-5$_C$), 67.1 (C-2$_A$), 60.7 (C-6$_E$), 22.4 (CH$_2$), 20.7 (C$_{Ac}$), 17.2, 17.1, 16.9 (C-6$_A$*, C-6$_B$*, C-6$_C$*), 10.3 (CH$_3$).

HRMS (ESI$^+$): [M+Na]$^+$ C$_{29}$H$_{50}$O$_{19}$Na m/z theoretical: 725.2844
m/z measured
725.2827

Method 8:

Allyl(2,3,4,6-tetra-O-benzyl-α-D-glucopyranosyl)-(1→3)-(4-O-benzyl-α-L-rhamnopyranosyl)-(1→2)-(3,4-di-O-benzyl-α-L-rhamnopyranosyl)-(1→3)-4-O-benzyl-α-L-rhamnopyranoside 89

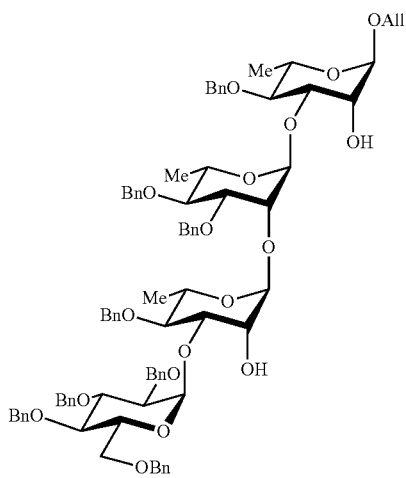

Chemical Formula: C$_{83}$H$_{94}$O$_{18}$
Exact Mass: 1378.6440
Molecular Weight: 1379.6237

After adding 0.5 M NaOMe (770 µL, 390 µmol, 1.1 eq.) to the alcohol 85 (500 mg, 350 µmol) in solution in MeOH (10 mL), the reaction mixture is refluxed and stirred for 3 h, after which time monitoring by TLC (Chex/EtOAc, 7/3) indicates the disappearance of 85 (Rf=0.5) and the appearance of a more polar product (Rf=0.3). After it returns to RT, the reaction mixture is neutralized by adding DOWEX (H$^+$) ion-exchange resin, then filtered on a frit. The resin is washed with DCM/MeOH mixture and the solvents are evaporated. The yellow oil obtained is purified by silica gel chromatography (Chex/EtOAc, 75/25→7/3) to give the diol 89 as a white solid (461 mg, 95%).

Rf=0.3 (Chex/EtOAc, 7/3).

$^1$H NMR (CDCl$_3$), δ7.42-7.20 (m, 40H, CH$_{Ph}$), 5.93 (m, 1H, CH=), 5.33 (m, 1H, J$_{trans}$=17.2 Hz, =CH$_2$), 5.23 (m, 1H, J$_{cis}$=10.4 Hz, =CH$_2$), 5.18 (s, 1H, H-1$_A$), 5.10 (d, 1H, J$_{1,2}$=1.5 Hz, H-1$_B$), 5.03-4.98 (m, 3H, H$_{Bn}$), 4.95 (d, 1H, J$_{1,2}$=3.3 Hz, H-1$_E$), 4.92-4.87 (m, 3H, H$_{Bn}$), 4.84 (d, 1H, J$_{1,2}$=1.5 Hz, H-1$_C$), 4.79 (d, 1H, J=11.4 Hz, H$_{Bn}$), 4.75-4.69 (m, 5H, H$_{Bn}$), 4.60-4.56 (m, 2H, H$_{Bn}$), 4.52 (d, 1H, J=11.0 Hz, H$_{Bn}$), 4.33 (d, 1H, J=12.0 Hz, H$_{Bn}$), 4.19 (m, 1H, H$_{All}$), 4.13-4.07 (m, 5H, H-2$_A$, H-3$_E$, H-2$_B$, H-3$_A$, H-2$_C$), 4.03 (m, 1H, H$_{All}$), 4.01-3.98 (m, 2H, H-3$_C$, H-5$_E$), 3.93-3.87 (m, 3H, H-3$_B$, H-5$_B$, H-5$_A$), 3.81-3.76 (m, 2H, H-4$_E$, H-5$_C$), 3.65 (dd, 1H, J$_{1,2}$=3.5 Hz, J$_{2,3}$=9.7 Hz, H-2$_E$), 3.56 (pt, 1H, J$_{3,4}$=9.5 Hz, H-4$_A$), 3.54-3.43 (m, 4H, H-4$_B$, H-6a$_E$, H-4$_C$, H-6b$_E$), 2.19 (s, 1H, OH), 1.37 (d, 3H, J$_{5,6}$=6.2 Hz, H-6$_A$), 1.34 (d, 3H, H-6$_A$, J$_{5,6}$=6.3 Hz, H-6$_B$), 1.30 (d, 3H, J$_{5,6}$=6.3 Hz, H-6$_C$).

$^{13}$C NMR (CDCl$_3$), δ138.6-138.2 (C$_{Ph}$), 134.0 (CH=), 129.0-128.1 (CH$_{Ph}$), 117.7 (=CH$_2$), 101.5 (C-1$_B$, $^1J_{CH}$=170.1 Hz), 10143 (C-1$_A$, $^1J_{CH}$=170.1 Hz), 98.8 (C-1$_C$, $^1J_{CH}$=167.2 Hz), 94.3 (C-1$_E$, $^1J_{CH}$=169.2 Hz), 82.8 (C-3$_E$), 81.5 (C-3$_C$), 80.7 (C-4$_B$), 80.2 (C-4$_C$), 80.0 (C-3$_B$), 79.6 (C-4$_A$), 79.3 (C-2$_E$), 78.2 (C-4$_E$), 76.8 (C-3$_A$), 76.0, 75.9, 75.8 (4C, C$_{Bn}$), 75.9 (C-2$_B$), 75.3, 74.8, 73.8, 72.7 (4C, C$_{Bn}$), 71.3 (C-2$_C$), 71.1 (C-5$_E$), 69.6 (C-5$_B$), 68.4 (C$_{All}$), 68.3 (C-6$_E$), 68.3 (C-5$_A$), 68.0 (C-5$_C$), 67.7 (C-2$_A$), 18.4, 18.3, 18.2 (C-6$_A$*, C-6$_B$*, C-6$_C$*).

HRMS (ESI$^+$): [M+Na]$^+$ C$_{83}$H$_{94}$O$_{18}$Na m/z theoretical: 1401.6338
m/z measured
1401.6403
[M+NH$_4$]$^+$ C$_{83}$H$_{94}$O$_{18}$NH$_4$ m/z theoretical: 1396.6783
m/z measured
1396.6854

Propyl α-D-glucopyranosyl-(1→3)-α-L-rhamnopyranosyl-(1→2)-α-L-rhamnopyranosyl-(1→3)-α-L-rhamnopyranoside XII

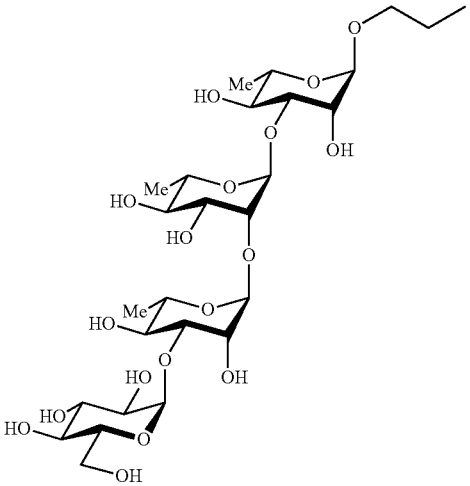

Chemical Formula: C$_{27}$H$_{48}$O$_{18}$
Exact Mass: 660.2841
Molecular Weight: 660.6592

Pd—C 10% (300 mg) is added to a degassed solution of diol 89 (360 mg, 261 µmol) in ethanol (30 mL). The suspension is saturated with hydrogen at atmospheric pressure and stirred at RT overnight. Monitoring by TLC (iPrOH/H$_2$O/NH$_3$, 4/1/0.5 and Chex/EtOAc, 7/3) shows the disappearance of 89 (Rf=1 and 0.3, respectively) and the appearance of a new, more polar compound (Rf=0.5 and 0, respectively). The reaction mixture is filtered on Celite, and the filtrate is concentrated in a rotary evaporator. The residue obtained is purified on a C-18 column (H$_2$O/CH$_3$CN, 100/0→8/2) to give the target XII as a white solid (140 mg, 81%). Rf=0.5 (iPrOH/H$_2$O/NH$_3$, 4/1/0.5).

$^1$H NMR (D$_2$O), δ5.10 (bs, 1H, H-1$_B$), 4.99 (d, 1H, J$_{1,2}$=3.8 Hz, H-1$_E$), 4.89 (d, 1H, J$_{1,2}$=1.5 Hz, H-1$_A$), 4.65 (d, 1H, J$_{1,2}$=1.4 Hz, H-1$_C$), 4.17 (dd, 1H, J$_{2,3}$=2.4 Hz, H-2$_A$), 3.95 (m, 1H, H-2$_B$) 3.88-3.81 (m, 3H, H-2$_C$, H-5$_E$, H-3$_B$), 3.73 (dd, 1H, J$_{2,3}$=3.0 Hz, J$_{3,4}$=9.7 Hz, H-3$_A$), 3.71-3.59 (m, 7H, H-3$_C$, H-6a$_E$, H-6b$_E$, H-5$_E$, H-3$_E$, H-5$_C$, H-5$_A$), 3.53 (m, 1H, H$_{Pr}$) 3.48-3.37 (m, 5H, H-2$_E$, H-4$_A$, H-4$_C$, H$_{Pr}$, H-4$_B$), 3.34 (pt, 1H, J$_{3,4}$=9.3 Hz, H-4$_E$), 1.50 (sex, 2H, CH$_2$), 1.18-1.16 (m, 9H, H-6$_A$, H-6$_B$, H-6$_C$), 0.81 (t, 3H, J=7.4 Hz, CH$_3$).

$^{13}$C NMR (D$_2$O), δ102.3 (C-1$_A$, $^1$H$_{CH}$=167.2 Hz), 101.0 (C-1$_B$, $^1$J$_{CH}$=173.1 Hz), 99.8 (C-1$_C$, $^1$J$_{CH}$=169.4 Hz), 95.7 (C-1$_E$, $^1$J$_{CH}$=169.5 Hz), 78.8 (C-2$_B$), 77.7 (C-3$_C$), 75.5 (C-3$_A$), 73.2 (C-3$_E$), 72.4 (C-4$_B$), 72.2 (C-4$_C$), 72.0 (C-5$_E$), 71.7 (C-4$_A$), 70.6 (C-2$_E$), 70.3 (C-2$_C$), 70.2 (C-3$_B$), 69.9 (C$_{Pr}$), 69.7 (C-5$_B$), 69.6 (C-4$_E$), 69.5 (C-5$_C$), 68.9 (C-5$_A$), 67.0 (C-2$_A$), 60.6 (C-6$_E$), 22.3 (CH$_2$), 17.1, 17.0, 16.8 (C-6$_A$*, C-6$_B$*, C-6$_C$*), 10.2 (CH$_3$).

HRMS (ESI$^+$) [M+Na]$^+$ C$_{27}$H$_{48}$O$_{18}$Na m/z theoretical:
683.2739
m/z measured
683.2729

Method 9:

Allyl(3,4,6-tri-O-acetyl-2-deoxy-2-trichloroacetamido-β-D-glucopyranosyl)-(1→2)-[2,3,4,6-tetra-O-benzyl-α-D-glucopyranosyl-(1→3)]-(4-O-benzyl-α-L-rhamnopyranosyl)-(1→2)-(3,4-di-O-benzyl-α-L-rhamnopyranosyl)-(1→3)-2-O-acetyl-4-O-benzyl-α-L-rhamnopyranoside 90

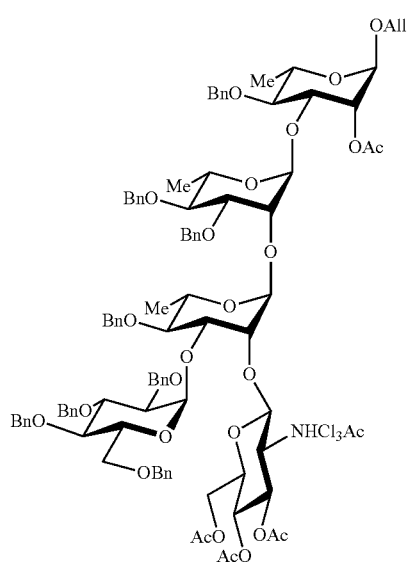

Chemical Formula: C$_{99}$H$_{112}$Cl$_3$NO$_{27}$
Exact Mass: 1851.6487
Molecular Weight: 1854.2981

TMSOTf (28.0 μL, 160 μmol, 0.5 eq.) is added to a solution of acceptor 85 (442 mg, 310 μmol) and donor 1 (370 mg, 620 μmol, 2 eq.) in Tol (8 mL), in the presence of molecular sieve 4 Å (253 mg), stirred under argon at −40° C. After 1 h at this temperature the ethanol-dry ice bath is withdrawn and stirring is continued for 30 min, after which time monitoring by TLC (Tol/EtOAc, 8/2) indicates the virtual disappearance of 85 (Rf=0.65) and the appearance of a new compound (Rf=0.45). The reaction is stopped by adding triethylamine (0.1 mL), then the reaction mixture is filtered and concentrated in a rotary evaporator.

The yellow oil obtained is purified by silica gel chromatography (Tol/EtOAc, 9/1→7/3) to obtain the allyl glycoside 90 as a white solid (469 mg, 82%).

Rf=0.45 (Tol/EtOAc, 8/2).

$^1$H NMR (CDCl$_3$), δ7.43-7.09 (m, 41H, CH$_{Ph}$, NH), 5.89 (m, 1H, CH=), 5.31 (m, 1H, J$_{trans}$=17.2 Hz, =CH$_2$), 5.26 (d, 1H, J$_{1,2}$=3.5 Hz, H-1$_E$), 5.22 (m, 1H, J$_{cis}$=10.4 Hz, =CH$_2$), 5.18 (m, 2H, H$_{Bn}$), 5.16 (m, 1H, H-2$_C$), 5.19 (d, 1H, J$_{1,2}$=1.1 Hz, H-1$_A$), 5.06 (m, 1H, H-4$_D$), 5.05 (m, 2H, H$_{Bn}$), 5.00 (d, 1H, J$_{1,2}$=1.0 Hz, H-1$_B$), 4.96 (m, 1H, H$_{Bn}$), 4.94 (m, 1H, H-1$_D$), 4.88 (pt, 1H, J$_{3,4}$=10.4 Hz, H-3$_D$), 4.81 (d, 1H, J$_{1,2}$=1.6 Hz, H-1$_C$), 4.77-4.85 (m, 4H, H$_{Bn}$), 4.62-4.56 (m, 4H, H$_{Bn}$), 4.52-4.47 (m, 2H, H$_{Bn}$), 4.32 (d, 1H, J=11.9 Hz, H$_{Bn}$), 4.26 (m, 1H, H-2$_D$), 4.20 (m, 1H, H-2$_A$), 4.18-4.14 (m, 3H, H$_{All}$, H-3$_A$, H-3$_E$), 4.12-4.08 (m, 2H, H-5$_E$, H-3$_C$), 4.01 (m, 1H, H$_{All}$), 3.98 (m, 1H, H-6a$_D$), 3.96-3.92 (m, 2H, H-2$_B$, H-2$_E$), 3.87-3.82 (m, 4H, H-6b$_D$, H-4$_E$, H-5$_A$, H-3$_B$), 3.79 (m, 3H, H-5$_C$), 3.74 (m, 1H, H-5$_B$), 3.50 (pt, 1H, J$_{3,4}$=9.3 Hz, H-4$_B$), 3.48 (pt, 1H, J$_{3,4}$=9.4 Hz, H-4$_A$), 3.54-3.40 (m, 3H, H-6a$_E$, H-6b$_E$, H-4$_C$), 2.97 (m, 1H, H-5$_D$), 2.15, 2.08, 2.03, 1.90 (4 s, 12H, H$_{Ac}$), 1.34 (d, 3H, J$_{5,6}$=6.2 Hz, H-6$_A$), 1.32 (d, 3H, J$_{5,6}$=6.2 Hz, H-6$_B$) 1.27 (d, 3H, J$_{5,6}$=6.2 Hz, H-6$_C$).

$^{13}$C NMR (CDCl$_3$), δ171.0, 170.9, 170.8, 169.6 (4C, C$_{Ac}$), 162.6 (C$_{NTCA}$), 139.0-138.0 (C$_{Ph}$), 134.0 (CH=), 129.0-127.8 (CH$_{Ph}$), 117.9 (=CH$_2$), 101.7 (C-1$_B$, $^1$J$_{CH}$=173.2 Hz), 101.3 (C-1$_A$, $^1$J$_{CH}$=171.0 Hz), 101.2 (C-1$_D$, $^1$J$_{CH}$=161.0 Hz), 96.5 (C-1$_C$, $^1$J$_{CH}$=168.8 Hz), 95.1 (C-1$_E$, $^1$J$_{CH}$=164.5 Hz), 93.1 (CCl$_3$), 82.8 (C-3$_E$), 80.8 (C-4$_E$), 80.3 (C-4$_C$), 80.1 (C-4$_A$), 79.3 (C-3$_C$), 79.2 (C-2$_E$), 79.1 (C4$_E$), 78.9 (C-3$_B$), 76.4 (C$_{Bn}$), 76.0 (C-2$_B$), 75.9, 75.7, 75.5, 75.3 (4C, C$_{Bn}$), 75.1 (C-3$_A$), 74.4 (C-2$_A$), 74.3, 73.8 (2C, C$_{Bn}$), 73.6 (C-3$_D$), 72.9 (C-2$_C$), 72.3 (C$_{Bn}$), 72.2 (C-5$_D$), 70.4 (C-5$_E$), 69.2 (C-5$_B$), 69.1 (C-5$_A$), 68.6 (C$_{All}$), 68.2 (C-4$_D$), 68.2 (C-6$_E$), 68.1 (C-5$_C$), 61.9 (C-6$_D$), 56.2 (C-2$_D$), 21.5, 21.0, 20.9, 20.8 (4C, C$_{Ac}$), 18.3, 18.2, 18.1 (C-6$_A$*, C-6$_B$*, C-6$_C$*).

HRMS (ESI$^+$) [M+Na]$^+$ C$_{99}$H$_{112}$$^{35}$Cl$_3$NO$_{27}$Na m/z theoretical:
1874.6385
m/z measured
1874.6638
[M+NH$_4$]$^+$ C$_{99}$H$_{112}$$^{35}$Cl$_3$NO$_{27}$NH$_4$ m/z theoretical:
1869.6831
m/z measured
1869.6978

Allyl(2-deoxy-2-trichloroacetamido-β-D-glucopyranosyl)-(1→2)-[2,3,4,6-tetra-O-benzyl-α-D-glucopyranosyl-(1→3)]-(4-O-benzyl-α-L-rhamnopyranosyl)-(1→2)-(3,4-di-O-benzyl-α-L-rhamnopyranosyl)-(1→3)-2-O-acetyl-4-O-benzyl-L-rhamnopyranoside 91

Allyl(2-deoxy-2-trichloroacetamido-β-D-glucopyranosyl)-(1→2)-[2,3,4,6-tetra-O-benzyl-α-D-glucopyranosyl-(1→3)]-(4-O-benzyl-α-L-rhamnopyranosyl)-(1→2)-(3,4-di-O-benzyl-α-L-rhamnopyranosyl)-(1→3)-4-O-benzyl-α-L-rhamnopyranoside 92

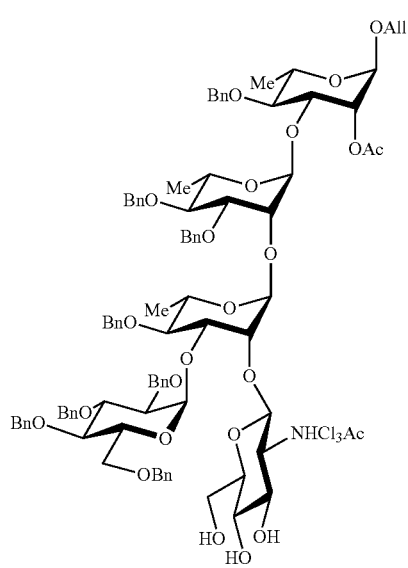

Chemical Formula: $C_{93}H_{106}Cl_3NO_{24}$
Exact Mass: 1725.6170
Molecular Weight: 1728.1880

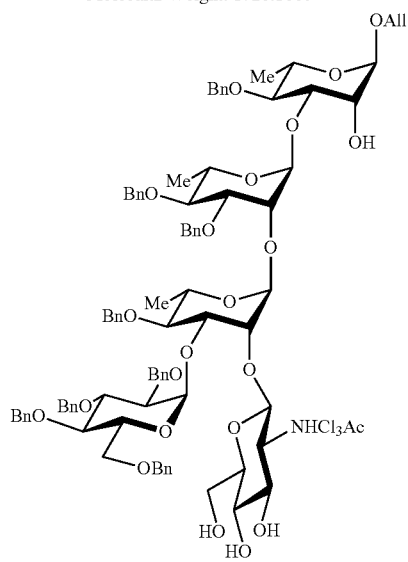

Chemical Formula: $C_{91}H_{104}Cl_3NO_{23}$
Exact Mass: 1683.6065
Molecular Weight: 1686.1514

The allyl glycoside 90 (200 mg, 100 μmol) is dissolved in MeOH (12.5 mL), and then 0.5 M NaOMe (431 μL, 200 μmol, 2 eq.) is added to the reaction mixture. After stirring for 25 min, monitoring by TLC (DCM/MeOH, 95/5 and Chex/EtOAc, 6/4) indicates the disappearance of 90 and the appearance of two more-polar products (Rf=0.3 and 0.2 in DCM/MeOH, 95/5). The reaction mixture is then neutralized by adding DOWEX (H$^+$) ion-exchange resin, then filtered on a frit. The resin is washed with DCM/MeOH mixture and the solvents are evaporated. The yellow oil obtained is purified by silica gel chromatography (Tol/EtOAc, 7/3→1/1), giving, in the order of elution, the mono-acetylated product 91 as a white solid (103 mg, 56%) and the non-acetylated product 92 as a white solid (55 mg, 30%).

91: Rf=0.3 (DCM/MeOH, 95/5).

$^1$H NMR (CDCl$_3$), δ7.41 (d, 1H, $J_{2,NH}$=6.1 Hz, NH), 7.39-7.08 (m, 40H, CH$_{Ph}$), 5.94 (m, 1H, CH=), 5.38 (bs, 1H, H-1$_A$), 5.33 (m, 1H, $J_{trans}$=17.2 Hz, =CH$_2$), 5.23 (m, 1H, $J_{cis}$=10.4 Hz, =CH$_2$), 5.19-5.15 (m, 4H, H-2$_C$, H-1$_E$, 2H$_{Bn}$), 5.12-5.01 (m, 2H, H$_{Bn}$), 4.96 (d, 1H, J=10.7 Hz, H$_{Bn}$), 4.91 (bs, 1H, H-1$_E$), 4.82 (d, 1H, $J_{1,2}$=1.5 Hz, H-1$_C$), 4.80-4.64 (m, 5H, H$_{Bn}$), 4.55 (m, 1H, H-1$_D$), 4.54-4.49 (m, 5H, H$_{Bn}$), 4.32 (d, 1H, J=11.9 Hz, H$_{Bn}$), 4.20 (m, 1H, H-2$_B$), 4.17 (m, 1H, H$_{All}$), 4.15 (m, 1H, H-2$_A$), 4.13-4.08 (m, 4H, H-3$_E$, H-3$_A$, H-3$_C$, H-5$_E$), 4.11 (m, 1H, H$_{All}$), 3.89-3.82 (m, 3H, H-4$_E$, H-3$_B$, H-2$_E$), 3.79-3.69 (m, 4H, H-2$_D$, H-5$_C$, H-5$_A$, H-5$_B$), 3.63 (m, 5H, H-4$_B$, H-4$_A$, H-6a$_E$, H-6b$_E$, H-4$_C$), 3.12 (pt, 1H, $J_{3,4}$=9.3 Hz, H-4$_D$), 3.05 (m, 1H, H-5$_D$), 2.92 (m, 1H, H-6b$_D$), 2.37 (m, 1H, H-3$_D$), 2.14 (s, 3H, H$_{Ac}$), 1.34-1.27 (m, 6H, H-6$_A$, H-6$_B$), 1.28 (d, 3H, $J_{5,6}$=6.1 Hz, H-6$_C$).

$^{13}$C NMR (CDCl$_3$), δ170.8 (C$_{Ac}$), 164.9 (C$_{NTCA}$), 138.7-138.1 (C$_{Ph}$), 134.0 (CH=), 129.5-127.7 (CH$_{Ph}$), 118.2 (=CH$_2$), 102.0 (C-1$_B$, $^1J_{CH}$=170.5 Hz), 101.3 (C-1$_D$, $^1J_{CH}$=161.0 Hz), 100.4 (C-1$_A$, $^1J_{CH}$=171.2 Hz), 96.5 (C-1$_C$, $^1J_{CH}$=171.2 Hz), 94.6 (C-1$_E$, $^1J_{CH}$=169.8 Hz), 92.9 (CCl$_3$), 83.4 (C-3$_E$), 80.6 (C-4$_E$), 80.5 (C-4$_E$), 80.1 (C-4$_C$), 80.1 (C-3$_C$), 79.9 (C-3$_B$), 79.4 (C-4$_A$), 79.0 (C-2$_E$), 76.6 (C$_{Bn}$), 76.5 (C-3$_D$), 76.1 (C-5$_D$), 75.9, 75.6, 75.4, 75.3 (5C, C$_{Bn}$), 74.4 (C-3$_A$), 74.1 (C-2$_A$), 73.9, 73.2 (2C, C$_{Bn}$), 72.9 (C-4$_D$), 72.8 (C-2$_C$), 72.1 (C-2$_B$), 70.4 (C-5$_B$), 69.7 (C-5$_E$), 69.2 (C-5$_A$), 68.8 (C$_{All}$), 68.0 (C-6$_E$), 67.9 (C-5$_C$), 62.9 (C-6$_D$), 58.8 (C-2$_D$), 21.5 (C$_{Ac}$), 18.3, 18.2, 18.1 (C-6$_A$*, C-6$_B$*, C-6$_C$*).

HRMS (ESI$^+$): [M+Na]$^+$ $C_{93}H_{106}{}^{35}Cl_3NO_{24}Na$ m/z theoretical:
1748.6068
m/z measured
1748.6366
[M+NH$_4$]$^+$ $C_{93}H_{106}{}^{35}Cl_3NO_{24}NH_4$ m/z theoretical:
1743.6514
m/z measured
1743.6545

92: Rf=0.2 (DCM/MeOH, 95/5).

$^1$H NMR (CDCl$_3$), δ7.41 (d, 1H, $J_{2,NH}$=6.6 Hz, NH), 7.40-7.11 (m, 40H, CH$_{Ph}$), 5.92 (m, 1H, CH=), 5.38 (bs, 1H, H-1$_A$), 5.31 (m, 1H, $J_{trans}$=17.2 Hz, =CH$_2$), 5.23 (m, 1H, $J_{cis}$=10.4 Hz, =CH$_2$), 5.19 (d, 1H, $J_{1,2}$=3.5 Hz, H-1$_E$), 5.14-4.98 (m, 4H, H$_{Bn}$), 4.96 (bs, 1H, H-1$_B$), 4.93 (d, 1H, J=12.3 Hz, H$_{Bn}$), 4.81 (d, 1H, $J_{1,2}$=1.3 Hz, H-1$_C$), 4.80 (d, 1H, J=10.7 Hz, H$_{Bn}$), 4.74-4.66 (m, 6H, H$_{Bn}$), 4.55 (m, 1H, $J_{1,2}$=4.4 Hz, H-1$_D$), 4.55-4.69 (m, 3H, H$_{Bn}$), 4.37 (d, 1H, J=11.9 Hz, H$_{Bn}$), 4.20 (m, 1H, H$_{All}$), 4.18-4.10 (m, 5H, H-2$_B$, H-2$_A$, H-3$_A$, H-3$_E$, H-5$_E$), 4.07 (m, 1H, H-2$_C$), 4.11 (m, 1H, H$_{All}$), 3.97 (m, 1H, H-3$_C$), 3.92 (m, 1H, H-3$_B$), 3.89-3.83 (m, 3H, H-4$_E$, H-2$_E$, H-2$_D$), 3.88 (m, 1H, H-5$_B$), 3.76 (m, 1H, H-5$_C$), 3.72 (m, 1H, H-5$_A$), 3.67 (m, 1H, H-6a$_D$), 3.56 (pt, 1H, $J_{3,4}$=9.4 Hz), 3.53-3.39 (m, 4H, H-6a$_E$, H-6b$_E$, H-4$_A$, H-4$_C$), 3.18 (pt, 1H, $J_{3,4}$=8.9 Hz, H-4$_D$), 3.13 (m, 1H, H-5$_D$), 3.08 (m, 1H, H-6b$_D$), 2.48 (m, 1H, H-3$_D$), 1.28 (d, 3H, $J_{5,6}$=6.2 Hz, H-6$_B$), 1.28 (d, 3H, $J_{5,6}$=6.2 Hz, H-6$_A$), 1.28 (d, 3H, $J_{5,6}$=6.2 Hz, H-6$_C$).

$^{13}$C NMR (CDCl$_3$), δ164.7 (C$_{NTCA}$), 138.7-138.2 (C$_{Ph}$), 134.2 (CH=), 129.6-127.7 (CH$_{Ph}$), 117.9 (=CH$_2$), 101.7 (C-1$_B$, $^1J_{CH}$=170.5 Hz), 101.4 (C-1$_D$, $^1J_{CH}$=158.1 Hz), 100.6 (C-1$_A$, $^1J_{CH}$=173.4 Hz), 98.8 (C-1$_C$, $^1J_{CH}$=169.8 Hz), 94.7 (C-1$_E$, $^1J_{CH}$=168.3 Hz), 93.0 (CCl$_3$), 83.7 (C-3$_E$), 81.9 (C-3$_C$), 80.7 (C-4$_B$), 80.3 (C-3$_B$), 80.1 (C-4$_A$), 80.0 (C-4$_C$), 79.4 (C-4$_E$), 79.1 (C-2$_E$), 76.6 (C$_{Bn}$), 76.5 (C-3$_D$), 76.2 (C-5$_D$), 75.8, 75.7, 75.4, 75.3 (5C, C$_{Bn}$), 74.4 (C-3$_A$), 74.3 (C-2$_A$), 73.9, 73.4 (2C, C$_{Bn}$), 72.8 (C-4$_D$), 72.7 (C-2$_B$), 71.3 (C-2$_C$), 70.4 (C-5$_E$), 69.7 (C-5$_B$), 69.3 (C-5$_A$), 68.4 (C-6$_E$), 68.2 (C$_{All}$), 67.9 (C-5$_C$), 63.0 (C-6$_D$), 58.8 (C-2$_D$), 18.4, 18.3, 18.2 (C-6$_A$*, C-6$_E$*, C-6$_C$*).

HRMS (ESI$^+$): [M+Na]$^+$ C$_{91}$H$_{104}$$^{35}$Cl$_3$NO$_{23}$Na m/z theoretical:
1706.5962
m/z measured
1706.6206
[M+NH$_4$]$^+$ C$_{91}$H$_{104}$$^{35}$Cl$_3$NO$_{23}$NH$_4$ m/z theoretical:
1701.6409
m/z measured
1701.6571

Propyl(2-acetamido-2-deoxy-β-D-glucopyranosyl)-(1→2)-[α-D-glucopyranosyl-(1→3)]-α-L-rhamnopyranosyl-(1→2)-α-L-rhamnopyranosyl-(1→3)-2-O-acetyl-α-L-rhamnopyranoside XIII Chemical Formula: C$_{37}$H$_{63}$NO$_{24}$
Exact Mass: 905.3740
Molecular Weight: 905.8884

Pd—C 10% (300 mg) is added to a degassed solution of triol 91 (310 mg, 180 μmol) in ethanol (20 mL). The suspension is saturated with hydrogen at 50 bar and stirred at RT for 2 days. Monitoring by TLC (iPrOH/H$_2$O/NH$_3$, 4/1/0.5 and DCM/MeOH, 95/5) shows the disappearance of 91 (Rf=1 and 0.3, respectively) and the appearance of a new, more polar compound (Rf=0.2 and 0, respectively). The reaction mixture is filtered on an Acrodisc LC 25 mm filter, and the filtrate is concentrated in a rotary evaporator. The residue obtained is purified on a C-18 column (H$_2$O/CH$_3$CN, 100/0→7/3) to give the target XIII as a white solid (119 mg, 74%).

Rf=0.2 (iPrOH/H$_2$O/NH$_3$, 4/1/0.5).

$^1$H NMR (D$_2$O), δ 5.09 (bs, 1H, H-1$_B$), 5.08 (m, 1H, H-2$_C$), 5.07 (d, 1H, J$_{1,2}$=3.5 Hz, H-1$_E$), 4.99 (d, 1H, J$_{1,2}$=1.5 Hz, H-1$_A$), 4.73 (bs, 1H, H-1$_C$), 4.72 (d, 1H, J$_{1,2}$=8.5 Hz, H-1$_D$), 4.33 (m, 1H, H-2$_A$), 3.95 (m, 1H, H-5$_E$), 3.93 (m, 1H, H-2$_B$), 3.88 (dd, 1H, J$_{2,3}$=3.4 Hz, J$_{3,4}$=9.6 Hz, H-3$_C$), 3.83-3.79 (m, 2H, H-3$_A$, H-6a$_D$), 3.76-3.68 (m, 4H, H-3$_E$, H-5$_C$, H-6a$_E$, H-6b$_E$), 3.66-3.52 (m, 7H, H-6b$_D$, H-2$_D$, H-3$_B$, H-5$_A$, H-2$_E$, H$_{Pr}$, H-5$_B$), 3.49 (pt, 1H, J$_{3,4}$=9.7 Hz, H-4$_C$), 3.42 (m, 1H, H$_{Pr}$), 3.38 (m, 1H, H-4$_E$), 3.37-3.29 (m, 4H, H-4$_B$, H-5$_D$, H-4$_D$, H-3$_D$), 3.26 (pt, 1H, J$_{3,4}$=9.7 Hz, H-4$_A$), 2.08 (s, 3H, H$_{Ac}$), 2.00 (s, 3H, H$_{NAc}$), 1.53 (sex, 2H, CH$_2$), 1.22 (d, 3H, J$_{5,6}$=6.2 Hz, H-6$_C$), 1.17 (m, 3H, J$_{5,6}$=6.4 Hz, H-6$_B$), 1.15 (d, 3H, J$_{5,6}$=6.2 Hz, H-6$_A$), 0.83 (t, 3H, J=7.4 Hz, CH$_3$).

$^{13}$C NMR (D$_2$O), δ174.8 (C$_{NAc}$), 173.3 (C$_{Ac}$), 102.2 (C-1$_D$, $^1J_{CH}$=163.9 Hz), 101.7 (C-1$_A$, $^1J_{CH}$=173.4 Hz), 101.0 (C-1$_B$, $^1J_{CH}$=172.7 Hz), 97.1 (C-1$_C$, $^1J_{CH}$=172.0 Hz), 94.9 (C-1$_E$, $^1J_{CH}$=170.5 Hz), 78.7 (C-2$_B$), 76.3 (C-4$_D$), 76.0 (C-3$_C$), 74.5 (C-3$_D$), 74.4 (C-2$_A$), 74.1 (C-3$_A$), 73.4 (C-3$_E$), 72.5 (C-4$_C$), 72.3 (C-2$_C$), 72.2 (C-4$_B$), 71.7 (C-5$_E$), 71.6 (C-2$_E$), 71.1 (C-4$_A$), 70.2 (C$_{Pr}$), 70.1 (C-5$_D$), 69.8 (C-3$_B$), 69.7 (3C, C-4$_E$, C-5$_A$, C-5$_B$), 68.9 (C-5$_C$), 61.0 (C-6$_D$), 60.6 (C-6$_E$), 56.0 (C-2$_D$), 23.0 (C$_{NAc}$), 22.3 (CH$_2$), 20.7 (C$_{Ac}$), 17.2, 17.0, 16.8 (C-6$_A$*, C-6$_B$*, C-6$_C$*), 10.2 (CH$_3$).

HRMS (ESI$^+$): [M+H]$^+$ C$_{37}$H$_{64}$NO$_{24}$ m/z theoretical:
906.3818
m/z measured
906.3831
[M+Na]$^+$ C$_{37}$H$_{63}$NO$_{24}$Na m/z theoretical:
928.3638
m/z measured
928.3652

Method 10:

Propyl(2-acetamido-2-deoxy-β-D-glucopyranosyl)-(1→2)-[α-D-glucopyranosyl-(1→3)]-α-L-rhamnopyranosyl-(1→2)-α-L-rhamnopyranosyl-(1→3)-α-L-rhamnopyranoside XIV Chemical Formula: C$_{37}$H$_{61}$NO$_{23}$
Exact Mass: 863.3634
Molecular Weight: 863.8517

Pd—C 100 (250 mg) is added to a degassed solution of tetraol 92 (240 mg, 143 μmol) in ethanol (15 mL). The suspension is saturated with hydrogen at 50 bar and stirred at RT for 24 h. Monitoring by TLC (iPrOH/H$_2$O/NH$_3$, 4/1/0.5 and DCM/MeOH, 95/5) shows the disappearance of 92 (Rf=1 and 0.2, respectively) and the appearance of a new, more polar compound (Rf=0.15 and 0, respectively). The reaction mixture is filtered on an Acrodisc LC 25 mm filter, and the filtrate is concentrated in a rotary evaporator. The residue obtained is purified on a C-18 column (H$_2$O/CH$_3$CN, 100/0→7/3) to give the target XIV as a white solid (91 mg, 74%).

Rf=0.15 (iPrOH/H₂O/NH₃, 4/1/0.5).

$^1$H NMR (D₂O), δ5.17 (bs, 1H, H-1$_B$), 5.14 (d, 1H, J$_{1,2}$=3.6 Hz, H-1$_E$), 5.06 (d, 1H, J$_{1,2}$=1.2 Hz, H-1$_A$), 4.78 (d, 1H, J$_{1,2}$=8.5 Hz, H-1$_D$), 4.73 (bs, 1H, H-1$_C$), 4.39 (m, 1H, H-2$_A$), 4.03 (m, 1H, H-2$_B$), 4.00 (m, 1H, H-5$_E$), 3.95 (m, 1H, H-2$_C$), 3.90 (m, 1H, H-3$_B$), 3.89-3.85 (m, 2H, H-3$_A$, H-6a$_D$), 3.82-3.72 (m, 5H, H-3$_E$, H-6a$_E$, H-6b$_E$, H-5$_B$, H-3$_C$), 3.73-3.65 (m, 5H, H-2$_D$, H-6b$_D$, H-5$_A$, H-2$_E$, H-5$_C$), 3.61 (m, 1H, H$_{Pr}$), 3.51 (pt, 1H, J$_{3,4}$=9.6 Hz, H-4$_C$), 3.47 (m, 1H, H$_{Pr}$), 3.45 (m, 1H, H-4$_E$), 3.43 (m, 1H, H-4$_B$), 3.41-3.3 (m, 3H, H-5$_D$, H-4$_D$, H-3$_D$), 3.32 (pt, 1H, J$_{3,4}$=9.7 Hz, H-4$_A$), 2.06 (s, 3H, H$_{NAc}$), 1.57 (sex, 2H, CH₂), 1.25 (m, 6H, H-6$_B$, H-6$_C$), 1.22 (d, 3H, J$_{5,6}$=6.2 Hz, H-6$_A$), 0.88 (t, 3H, J=7.4 Hz, CH₃).

$^{13}$C NMR (D₂O), δ174.8 (C$_{NAc}$), 102.3 (C-1$_D$, $^1$J$_{CH}$=163.2 Hz), 101.7 (C-1$_A$, $^1$J$_{CH}$=170.5 Hz), 101.0 (C-1$_B$, $^1$J$_{CH}$=172.7 Hz), 99.9 (C-1$_C$, $^1$J$_{CH}$=169.8 Hz), 95.0 (C-1$_E$, $^1$J$_{CH}$=170.5 Hz), 78.9 (C-2$_B$), 77.8 (C-3$_C$), 76.3 (C-4$_D$), 74.6 (C-3$_D$), 74.5 (C-2$_A$), 74.2 (C-3$_A$), 73.5 (C-3$_E$), 72.6 (C-4$_B$), 72.5 (C-4$_C$), 71.8 (C-5$_E$), 71.7 (C-2$_E$), 71.2 (C-4$_A$), 70.4 (C-2$_C$), 70.2 (2C, C-5$_D$, C-3$_B$), 70.0 (C$_{Pr}$), 69.9 (2C, C-5$_A$, C-4$_E$), 69.5 (C-5$_B$), 69.0 (C-5$_C$), 61.1 (C-6$_D$), 60.7 (C-6$_E$), 56.0 (C-2$_D$), 23.0 (C$_{NAc}$), 22.4 (CH₂), 17.2, 17.1, 16.9 (C-6$_A$*, C-6$_B$*, C-6$_C$*), 10.3 (CH₃).

HRMS (ESI⁺): [M+H]⁺ C₃₅H₆₂NO₂₃ m/z theoretical:
864.3713
m/z measured
864.3726
[M+Na]⁺ C₃₅H₆₁NO₂₃Na m/z theoretical:
886.3532
m/z measured
886.3522
Method 11:

(2,3,4,6-Tetra-O-benzyl-α-D-glucopyranosyl)-(1→3)-(4-O-benzyl-2-O-levulinoyl-α-L-rhamnopyranosyl)-(1→2)-(3,4-di-O-benzyl-α-L-rhamnopyranosyl)-(1→3)-2-O-acetyl-4-O-benzyl-α/β-L-rhamnopyranose 88

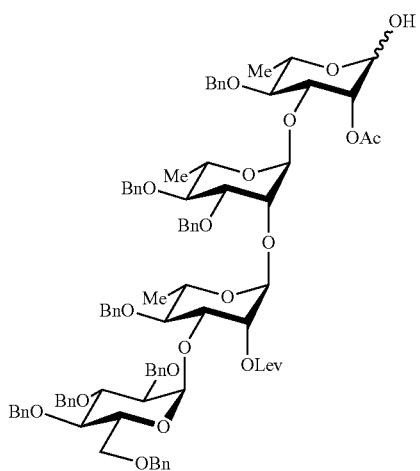

Chemical Formula: C₈₇H₉₈O₂₁
Exact Mass: 1478.6601
Molecular Weight: 1479.6964

(1,5-Cyclooctadienebis(methyldiphenylphosphine)-iridium(I)hexafluorophosphate (25 mg) is dissolved in THF (90 mL) with stirring. The mixture is submitted to 5 cycles of vacuum/argon degassing, 5 cycles of vacuum/hydrogen degassing and is then placed under hydrogen for 15 min. The mixture is then submitted to 5 cycles of vacuum/argon degassing for a second time. The solution of the allyl glycoside 87 (1.9 g, 1.2 mmol) in THF (15 mL) is transferred to the solution of activated catalyst. Monitoring by TLC (Tol/EtOAc, 9/1) shows the disappearance of 87 (Rf=0.3) and the appearance of a somewhat less polar product (Rf=0.35).

Diiodine (340 mg, 2.5 mmol, 2 eq.) in solution in

THF/H₂O mixture (8/2, 10 mL) is added to the reaction mixture. Monitoring by TLC (Tol/EtOAc, 9/1 and DCM/MeOH, 99/1) indicates the disappearance of the intermediate (Rf=0.35 and 0.95, respectively) and the appearance of a new, much more polar compound (Rf=0.05 and 0.25, respectively). To stop the reaction, 10% NaHSO₃ aqueous solution (2 mL) is added in portions to the mixture until the black coloration disappears. The reaction mixture is taken up in DCM (50 mL) and the aqueous phase is extracted with DCM (3×50 mL). The organic phases are combined and washed with NaCl$_{sat}$ solution (3×25 mL), with H₂O (3×25 mL) and then dried on a phase-separating filter and concentrated in a rotary evaporator. The yellow oil obtained is purified by silica gel chromatography (DCM/MeOH, 100/0→99/1) to obtain predominantly the a anomer of the hemiacetal 88 in the form of a yellow oil (1.7 g, 90%). Rf=0.25 (DCM/MeOH, 99/1).

$^1$H NMR (CDCl₃), δ7.42-7.15 (m, 40H, CH$_{Ph}$), 5.56 (m, 1H, H-2$_A$), 5.26 (d, 1H, J$_{1,2}$=3.4 Hz, H-1$_E$), 5.19 (m, 2H, H-2$_C$, H-1$_C$), 5.04 (d, 1H, J=10.9 Hz, H$_{Bn}$), 5.01 (d, 1H, J$_{1,2}$=1.2 Hz, H-1$_B$), 4.97 (d, 1H, J$_{1,2}$=1.4 Hz, H-1$_A$), 4.96-4.81 (m, 14H, H$_{Bn}$), 4.35 (d, 1H, J=12.0 Hz, H$_{Bn}$), 4.28 (dd, 1H, J$_{2,3}$=3.0 Hz, J$_{3,4}$=9.6 Hz, H-3$_A$), 4.17-3.97 (m, 5H, H-3$_C$, H-3$_E$, H-5$_E$, H-5$_C$, H-2$_B$), 3.88 (m, 1H, H-5$_A$), 3.86-3.78 (m, 2H, H-3$_B$, H-4$_E$), 3.71 (m, 1H, H-5$_B$), 3.67-3.63 (m, 2H, H-2$_E$, H-6a$_E$), 3.56 (pt, 1H, J$_{3,4}$=9.3 Hz, H-4$_A$), 3.55 (m, 1H, H-6b$_E$), 3.51 (pt, 1H, J$_{3,4}$=9.4 Hz, H-4$_B$), 3.43 (pt, 1H, J$_{3,4}$=9.4 Hz, H-4$_C$), 3.13 (m, 1H, OH), 2.53 (m, 4H, 2CH$_{2Lev}$), 2.16 (s, 3H, H$_{Ac}$), 2.10 (s, 3H, CH$_{3Lev}$), 1.34 (d, 3H, J$_{5,6}$=6.2 Hz, H-6$_A$), 1.29 (d, 3H, J$_{5,6}$=6.1 Hz, H-6$_B$), 1.27 (d, 3H, J$_{5,6}$=6.2 Hz, H-6$_C$).

$^{13}$C NMR (CDCl₃), δ206.7 (C$_{Lev}$), 172.1 (C$_{Lev}$), 170.9 (C$_{Ac}$), 139.1-138.8 (C$_{Ph}$), 129.1-127.9 (CH$_{Ph}$), 101.6 (C-1$_B$, $^1$J$_{CH}$=171.8 Hz), 99.5 (C-1$_A$, $^1$J$_{CH}$=169.9 Hz), 93.2 (C-1$_E$, $^1$J$_{CH}$=169.6 Hz), 92.0 (C-1$_C$, $^1$J$_{CH}$=170.2 Hz), 82.5 (C-3$_E$), 80.6 (C-4$_B$), 80.2 (C-4$_A$), 80.1 (C-4$_C$), 79.7 (C-2$_E$), 79.6 (C-3$_B$), 78.8 (C-3$_C$), 78.1 (C-4$_E$), 76.6, 76.0 (2C, C$_{Bn}$), 75.8 (C-2$_8$), 75.8, 75.7, 75.4, 74.0 (4C, C$_{Bn}$), 73.2 (C-2$_C$), 73.1 (C$_{Bn}$), 72.6 (C-3$_A$), 72.4 (C$_{Bn}$), 70.5 (C-5$_E$), 69.3 (C-5$_B$), 69.0 (C-5$_A$), 68.6 (C-6$_E$), 68.4 (C-2$_A$), 68.1 (C-5$_C$), 38.3 (CH$_{2Lev}$), 30.1 (CH$_{3Lev}$), 28.5 (CH$_{2Lev}$), 21.5 (C$_{Ac}$) 18.4, 18.3, 18.2 (C-6$_A$*, C-6$_B$*, C-6C*).

HRMS (ESI⁺): [M+Na]⁺ C₈₇H₉₈O₂₁Na m/z theoretical:
1501.6498
m/z measured
1501.6665
[M+NH₄]⁺ C₈₇H₉₈O₂₁NH₄ m/z theoretical:
1496.6945
m/z measured
1496.7114

(2,3,4,6-Tetra-O-benzyl-α-D-glucopyranosyl)-(1→3)-(4-O-benzyl-2-O-levulinoyl-α-L-rhamnopyranosyl)-(1→2)-(3,4-di-O-benzyl-α-L-rhamnopyranosyl)-(1→3)-2-O-acetyl-4-O-benzyl-α/β-L-rhamnopyranose trichloroacetimidate 86

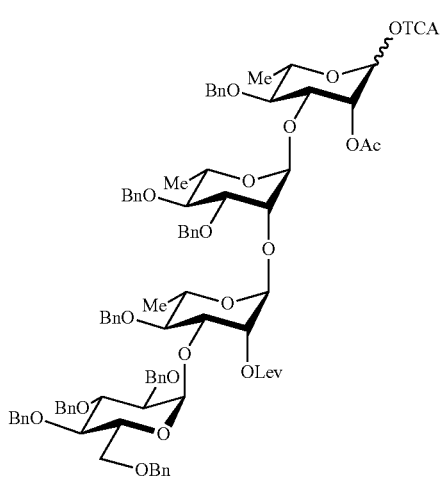

Chemical Formula: $C_{89}H_{98}Cl_3NO_{21}$
Exact Mass: 1621.5697
Molecular Weight: 1624.0835

The hemiacetal 88 (1.5 g, 1.0 mmol) is dissolved in DCE (5 mL) and stirred under argon at −5° C., and then DBU (42 µL, 280 µmol, 0.28 eq.) and trichloroacetonitrile (520 µL, 5.2 mmol, 5 eq.) are added. The reaction mixture is stirred at this temperature for 15 min and then it is loaded, without any treatment, on a silica gel column (flash chromatography, Chex/EtOAc+5% NEt$_3$, 8/2→7/3) to obtain the trichloroacetimidate 86 in the form of a yellow oil (1.5 g, 88%).

Rf=0.35 (Chex/EtOAc, 7/3).

$^1$H NMR (CDCl$_3$), δ8.73 (s, 1H, NH), 7.37-7.14 (m, 40H, CH$_{Ph}$), 6.24 (d, 1H, J$_{1,2}$=1.9 Hz, H-1$_C$), 5.56 (dd, 1H, J$_{1,2}$=2.7 Hz, J$_{1,2}$=4.9 Hz, H-2$_A$), 5.32 (dd, 1H, J$_{1,2}$=2.2 Hz, J$_{1,2}$=3.1 Hz, H-2$_C$), 5.26 (d, 1H, J$_{1,2}$=3.4 Hz, H-1$_E$), 5.04 (d, 1H, J=10.9 Hz, H$_{Bn}$), 5.03 (d, 1H, J$_{1,2}$=1.3 Hz, H-1$_B$), 4.99 (d, 1H, J$_{1,2}$=1.6 Hz, H-1$_A$), 4.97-4.79 (m, 6H, H$_{Bn}$), 4.73-4.49 (m, 8H, H$_{Bn}$), 4.35 (d, 1H, J=12.0 Hz, H$_{Bn}$), 4.25 (dd, 1H, J$_{2,3}$=3.1 Hz, J$_{3,4}$=9.6 Hz, H-3$_A$), 4.19 (dd, 1H, J$_{2,3}$=3.3 Hz, J$_{3,4}$=9.5 Hz, H-3$_C$), 4.14 (pt, 1H, J$_{3,4}$=9.3 Hz, H-3$_E$), 4.08 (m, 1H, H-5$_E$), 3.98-3.88 (m, 3H, H-2$_B$, H-5$_C$, H-5$_A$), 3.86-3.81 (m, 2H, H-3$_B$, H-4$_E$), 3.73 (m, 1H, H-5$_B$), 3.67-3.64 (m, 2H, H-2$_E$, H-6a$_E$), 3.58 (m, 1H, H-6b$_E$), 3.57 (pt, 1H !; J$_{3,4}$=9.6 Hz, H-4$_A$), 3.54 (pt, 1H, J$_{3,4}$=9.5 Hz, H-4$_C$), 3.52 (pt, 1H, J$_{3,4}$=9.4 Hz, H-4$_B$), 2.55 (m, 4H, 2CH$_{2Lev}$), 2.19 (s, 3H, H$_{Ac}$), 2.10 (s, 3H, CH$_{3Lev}$), 1.34 (d, 3H, J$_{5,6}$=6.3 Hz, H-6$_A$), 1.31 (d, 3H, J$_{5,6}$=6.1 Hz, H-6$_B$), 1.28 (d, 3H, J$_{5,6}$=6.0 Hz, H-6$_C$).

$^{13}$C NMR (CDCl$_3$), δ206.7 (C$_{Lev}$), 172.2 (C$_{Lev}$), 170.3 (C$_{Ac}$), 160.5 (C=NH), 139.1-138.8 (C$_{Ph}$), 129.1-127.9 (CH$_{Ph}$), 101.5 (C-1$_B$, $^1$J$_{CH}$=178.7 Hz), 99.8 (C-1$_A$, $^1$J$_{CH}$=174.2 Hz), 94.6 (C-1$_C$, $^1$J$_{CH}$=178.5 Hz), 93.3 (C-1$_E$, $^1$J$_{CH}$=170.0 Hz), 93.3 (CCl$_3$), 82.5 (C-3$_E$), 80.6 (C-4$_C$), 80.1 (C-4$_A$), 79.8 (C-4$_E$), 79.6 (C-2$_E$), 79.4 (C-3$_B$), 78.2 (C-3$_C$), 78.1 (C-4$_E$), 76.7 (C$_{Bn}$), 76.4 (C-2$_B$), 76.0, 75.9, 75.8, 75.4, 73.8, 73.2 (6C, C$_{Bn}$), 72.6 (C-3$_A$), 72.6 (C$_{Bn}$), 71.3 (C-2$_C$), 71.0 (C-5$_C$), 70.6 (C-5$_E$), 69.5 (C-5$_B$), 68.9 (C-5$_A$), 68.5 (C-6$_E$), 68.4 (C-2$_A$), 38.3 (CH$_{2Lev}$), 30.1 (CH$_{3Lev}$) 28.5 (CH$_{2Lev}$) 21.4 (C$_{Ac}$), 18.4, 18.3, 18.2 (C-6$_A$*, C-6$_B$*, C-6$_C$*).

Allyl(2,3,4,6-tetra-O-benzyl-α-D-glucopyranosyl)-(1→3)-(4-O-benzyl-2-O-levulinoyl-α-L-rhamnopyranosyl)-(1→2)-(3,4-di-O-benzyl-α-L-rhamnopyranosyl)-(1→3)-(2-O-acetyl-4-O-benzyl-α-L-rhamnopyranosyl)-(1→3)-2-acetamido-2-deoxy-4,6-O-isopropylidene-β-D-glucopyranoside 93

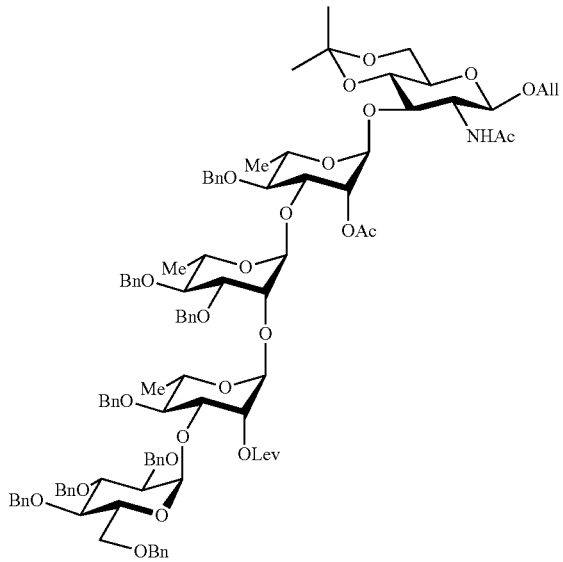

Chemical Formula: $C_{101}H_{119}NO_{26}$
Exact Mass: 1761.8020
Molecular Weight: 1763.0167

TfOH (45.0 µL, 515 µmol, 0.9 eq.) is added to a solution of acceptor 19 (432 mg, 1.4 mmol, 2.5 eq.) and donor 86 (926 mg, 571 µmol, 1 eq.) in Tol (25 mL), in the presence of molecular sieve 4 Å (3.2 g), stirred under argon at 0° C. The reaction mixture is then heated at 75° C. After 1 h at this temperature, monitoring by TLC (Tol/EtOAc, 7/3) indicates the appearance of a new compound (Rf=0.25). The reaction is stopped by adding triethylamine (0.2 mL), then the reaction mixture is filtered and concentrated in a rotary evaporator. The yellow oil obtained is purified by silica gel chromatography (Tol/EtOAc, 7/3→6/4) to obtain the allyl glycoside 93 as a white solid (780 mg, 78%).

Rf=0.45 (Tol/EtOAc, 6/4).

$^1$H NMR (CDCl$_3$), δ7.42-7.10 (m, 40H, CH$_{Ph}$), 5.89 (m, 2H, NH, CH=), 5.56 (dd, 1H, J$_{1,2}$=2.2 Hz, H-2$_A$), 5.30 (m, 1H, J$_{trans}$=17.2 Hz, =CH$_2$), 5.25 (d, 1H, J$_{1,2}$=3.4 Hz, H-1$_E$), 5.21 (m, 1H, J$_{cis}$=10.4 Hz, =CH$_2$), 5.15 (d, 1H, J$_{1,2}$=8.3 Hz, H-1$_D$), 5.07 (dd, 1H, J$_{1,2}$=1.6 Hz, J$_{1,2}$=3.2 Hz, H-2$_C$), 5.02 (d, 1H, J=11.0 Hz, H$_{Bn}$), 4.98 (d, 1H, J$_{1,2}$=1.5 Hz, H-1$_A$), 4.96 (d, 1H, J$_{1,2}$=1.3 Hz, H-1$_B$), 4.97-4.86 (m, 4H, H$_{Bn}$), 4.80 (bs, 1H, H-1$_C$), 4.78 (d, 1H, J=11.9 Hz, H$_{Bn}$), 4.73 (d, 1H, J=11.5 Hz, H$_{Bn}$), 4.67 (d, 1H, J=13.4 Hz, H$_{Bn}$), 4.62 (d, 1H, J=12.3 Hz, H$_{Bn}$), 4.61-4.53 (m, 6H, H$_{Bn}$), 4.50 (d, 1H, J=11.0 Hz, H$_{Bn}$), 4.39 (pt, 1H, J$_{3,4}$=9.2 Hz, H-3$_D$), 4.31 (m, 1H, H$_{All}$), 4.26 (dd, 1H, J$_{2,3}$=3.0 Hz, J$_{3,4}$=9.6 Hz, H-3$_A$), 4.15-4.06 (m, 3H, H-3$_E$, H$_{All}$, H-5$_E$), 4.04-3.94 (m, 4H, H-5$_C$, H-3$_C$, H-2$_B$, H-6a$_D$), 3.88 (dq, 1H, J$_{4,5}$=9.5 Hz, H-5$_A$), 3.84-3.77 (m, 3H, H-3$_B$, H-4$_E$, H-6b$_D$), 3.71-3.62 (m, 3H, H-5$_B$, H-6a$_E$, H-2$_E$), 3.60-3.52 (m, 3H, H-6b$_E$, H-4$_A$, H-4$_D$), 3.50 (pt, 1H, J$_{3,4}$=9.4 Hz, H-4$_B$), 3.40 (m, 1H, H-5$_D$), 3.38 (pt, 1H, J$_{3,4}$=9.6 Hz, H-4$_C$), 3.49 (m, 1H, J$_{2,NH}$=8.0 Hz, H-2$_D$), 2.53 (m, 4H, 2CH$_{2Lev}$), 2.11 (s, 3H, H$_{NAc}$), 2.09 (s, 3H, CH$_{3Lev}$), 2.04 (s, 3H, H$_{Ac}$), 1.50 (s, 3H, H$_{iPr}$), 1.42 (s, 3H, H$_{iPr}$), 1.35 (d, 3H, J$_{5,6}$=6.2 Hz, H-6$_A$), 1.26 (d, 3H, J$_{5,6}$=6.2 Hz, H-6$_B$), 1.20 (d, 3H, J$_{5,6}$=6.2 Hz, H-6$_C$).

$^{13}$C NMR (CDCl$_3$), δ206.1 (C$_{Lev}$), 171.7 (C$_{Lev}$), 171.3 (C$_{Ac}$), 170.5 (C$_{NAc}$), 138.8-137.6 (C$_{Ph}$), 133.8 (CH=), 129.1-127.4 (CH$_{Ph}$), 117.5 (=CH$_2$), 101.2 (C-1$_E$, $^1J_{CH}$=169.4 Hz), 99.4 (C$_{iPr}$), 99.0 (C-1$_A$, $^1J_{CH}$=173.7 Hz), 98.9 (C-1$_D$, $^1J_{CH}$=162.7 Hz), 97.6 (C-1$_C$, $^1J_{CH}$=171.0 Hz), 92.8 (C-1$_B$, $^1J_{CH}$=167.6 Hz), 82.1 (C-3$_E$), 80.2 (C-4$_B$), 79.8 (C-4$_A$), 79.6 (C-4$_C$), 79.5 (C-2$_E$), 79.4 (2C, C-3$_B$*, C-3$_C$*), 77.8 (C-4$_E$), 76.3 (C$_{Bn}$), 76.1 (C-3$_D$), 75.6, 75.5, 75.3 (3C, C$_{Bn}$), 75.2 (C-2$_B$), 75.1, 75.0, 73.4 (3C, C$_{Bn}$), 73.1 (C-4$_D$), 72.8 (C-2$_C$), 72.8 (C$_{Bn}$), 72.2 (C-3$_A$), 72.0 (C$_{Bn}$), 70.5 (C$_{All}$), 70.3 (C-5$_E$), 69.0 (C-5$_B$), 68.6 (C-5$_A$), 68.3 (C-6$_E$), 68.0 (C-2$_A$), 67.6 (C-5$_C$), 67.0 (C-5$_D$), 62.3 (C-6$_D$), 59.6 (C-2$_D$), 37.9 (CH$_{2Lev}$), 29.7 (CH$_3$ 1 Lev.), 29.1 (C$_{iPr}$), 28.1 (CH$_{2Lev}$), 23.5 (C$_{Ac}$), 21.2 (C$_{NAc}$), 19.3 (C$_{iPr}$), 18.0, 17.9, 17.8 (C-6$_A$*, C-6$_B$*, C-6$_C$*).

HRMS (ESI$^+$): [M+Na]$^+$ C$_{101}$H$_{119}$NO$_{26}$Na m/z theoretical:
1784.7917
m/z measured
1784.7917
[M+H]$^+$ C$_{101}$H$_{119}$NO$_{26}$ m/z theoretical:
1762.8098
m/z measured
1762.8038
[M+NH$_4$]$^+$ C$_{101}$H$_{119}$NO$_{26}$NH$_4$ m/z theoretical:
1779.8364
m/z measured
1779.8289

Allyl(2,3,4,6-tetra-O-benzyl-α-D-glucopyranosyl)-(1→3)-(4-O-benzyl-α-L-rhamnopyranosyl)-(1→2)-(3,4-di-O-benzyl-α-L-rhamnopyranosyl)-(1→3)-(2-O-acetyl-4-O-benzyl-α-L-rhamnopyranosyl)-(1→3)-2-acetamido-2-deoxy-4,6-O-isopropylidene-β-D-glucopyranoside 94

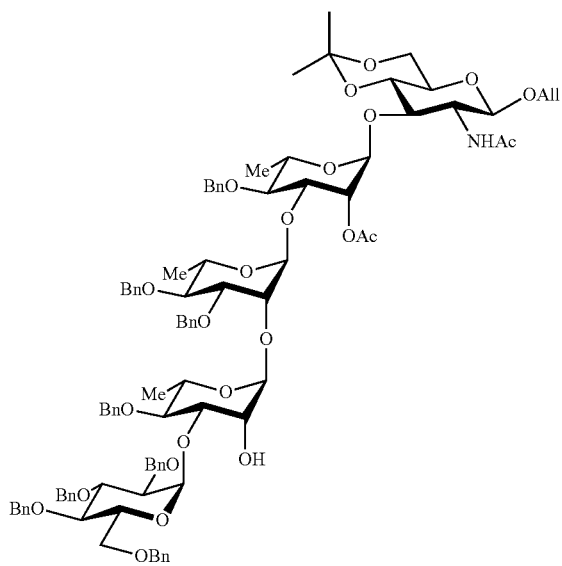

Chemical Formula: C$_{96}$H$_{113}$NO$_{24}$
Exact Mass: 1663.7653
Molecular Weight: 1664.9167

The allyl glycoside 93 (720 mg, 409 μmol) is dissolved in pyridine/acetic acid mixture (3/2, 20 mL). Hydrazine monohydrate (200 μL, 4.0 mmol, 10 eq.) is added dropwise to the reaction mixture. After stirring for 30 min at 0° C., the reaction mixture is taken up in cold water (20 mL) and the aqueous phase is quickly extracted with DCM (3×100 mL). The organic phases are combined and washed with NaCl$_{sat}$ solution (3×50 mL), filtered on a phase-separating filter and concentrated in a rotary evaporator. The oil obtained is purified by silica gel chromatography (Tol/EtOAc, 9/1→75/25) to obtain the alcohol 94 as a white solid (580 mg, 85%).

Rf=0.45 (Tol/EtOAc, 6/4).

$^1$H NMR (CDCl$_3$), δ7.44-7.18 (m, 40H, CH$_{Ph}$), 5.96 (d, 1H, J$_{NH,2}$=6.8 Hz, NH), 5.91 (m, 1H, CH=), 5.32 (m, 1H, J$_{trans}$=17.2 Hz, =CH$_2$), 5.24 (m, 1H, J$_{cis}$=10.4 Hz, =CH$_2$), 5.20 (bs, 1H, H-1$_A$), 5.16 (d, 1H, J$_{1,2}$=8.4 Hz, H-1$_D$), 5.12 (dd, 1H, J$_{1,2}$=1.6 Hz, J$_{1,2}$=3.2 Hz, H-2$_C$), 5.03 (d, 1H, J$_{1,2}$=1.3 Hz, H-1$_B$), 5.02-4.95 (d, 3H, J=11.0 Hz, H$_{Bn}$), 4.95 (d, 1H, J$_{1,2}$=3.9 Hz, H-1$_E$), 4.91-4.86 (m, 3H, H$_{Bn}$), 4.86 (bs, 1H, H-1$_C$), 4.84-4.81 (m, 2H, H$_{Bn}$), 4.72-4.70 (m, 3H, H$_{Bn}$), 4.63-4.58 (m, 4H, H$_{Bn}$), 4.53 (d, 1H, J=11.0 Hz, H$_{Bn}$), 4.41 (pt, 1H, J$_{3,4}$=9.3 Hz, H-3$_D$), 4.34 (m, 1H, H$_{All}$), 4.15-3.96 (m, 9H, H$_{All}$, H2$_B$, H-3$_E$, H-2$_A$, H-3$_A$, H-5$_C$, H-3$_C$, H-5$_E$, H-6a$_D$), 3.91 (dq, 1H, J$_{4,5}$=9.6 Hz, H-5$_A$), 3.88 (dd, 1H, J$_{2,3}$=2.7 Hz, J$_{3,4}$=9.4 Hz, H-3$_B$), 3.83 (m, 1H, H-6b$_D$), 3.80 (pt, 1H, J$_{3,4}$=10.1 Hz, H-4$_E$), 3.72 (dq, 1H, J$_{4,5}$=9.4 Hz, H-5$_B$), 3.66 (dd, 1H, J$_{2,3}$=3.6 Hz, J$_{3,4}$=9.6 Hz, H-2$_E$), 3.62-3.56 (m, 2H, H-4$_D$, H-4$_A$), 3.54-3.40 (m, 5H, H-6a$_E$, H-4$_B$, H-6b$_E$, H-4$_C$, H-5$_D$) 3.16 (m, 1H, J$_{2,NH}$=8.0 Hz, H-2$_D$), 2.16 (s, 3H, H$_{Ac}$), 2.09 (s, 3H, H$_{NAc}$), 1.54 (s, 3H, H$_{iPr}$), 1.46 (s, 3H, H$_{iPr}$), 1.38 (d, 3H, J$_{5,6}$=6.2 Hz, H-6$_A$), 1.33 (d, 3H, J$_{5,6}$=6.5 Hz, H-6$_B$), 1.26 (d, 3H, J$_{5,6}$=6.2 Hz, H-6$_C$).

$^{13}$C NMR (CDCl$_3$), δ171.3 (C$_{NAc}$), 170.5 (C$_{Ac}$), 138.7-137.6 (C$_{Ph}$), 133.9 (CH=), 129.1-127.7 (CH$_{Ph}$), 117.6 (=CH$_2$), 101.6 (C-1$_B$, $^1J_{CH}$=171.0 Hz), 100.8 (C-1$_A$, $^1J_{CH}$=175.0 Hz), 99.4 (C$_{iPr}$), 99.0 (C-1$_D$, $^1J_{CH}$=160.7 Hz), 97.6 (C-1$_C$, $^1J_{CH}$=170.8 Hz), 94.0 (C-1$_E$, $^1J_{CH}$=166.2 Hz), 82.4 (C-3$_E$), 80.4 (C-4$_B$), 79.7 (C-4$_C$, C-3$_B$), 79.5 (C-3$_C$), 79.3 (C-4$_A$), 79.0 (C-2$_E$), 77.8 (C-4$_E$), 76.5 (C-3$_A$), 76.2 (C-3$_D$), 75.7, 75.6, 75.4, 75.3, 75.0 (5C, C$_{Bn}$), 74.9 (C-2$_B$), 74.5, 73.5 (2C, C$_{Bn}$), 73.1 (C-4$_D$), 72.9 (C-2$_C$), 72.3 (C$_{Bn}$), 70.8 (C-5$_E$), 70.5 (C$_{All}$), 69.0 (C-5$_B$), 68.0 (C-6$_E$), 67.9 (C-5$_A$), 67.6 (C-5$_C$), 67.4 (C-2$_A$), 67.1 (C-5$_D$), 62.3 (C-6$_D$), 59.7 (C-2$_D$), 29.2 (C$_{iPr}$) 23.6 (C$_{NAc}$), 21.2 (C$_{Ac}$), 19.3 (C$_{iPr}$), 18.0, 17.9, 17.8 (C-6$_A$*, C-6$_B$*, C-6$_C$*).

HRMS (ESI$^+$): [M+Na]$^+$ C$_{96}$H$_{113}$NO$_{24}$Na m/z theoretical:
1686.7550
m/z measured
1686.7488
[M+H]$^+$ C$_{96}$H$_{113}$NO$_{24}$ m/z theoretical:
1664.7731
m/z measured
1664.7709
[M+NH$_4$]$^+$ C$_{96}$H$_{113}$NO$_{24}$NH$_4$ m/z theoretical:
1681.7997
m/z measured
1681.7993

Allyl(2,3,4,6-tetra-O-benzyl-α-D-glucopyranosyl)-(1→3)-(4-O-benzyl-α-L-rhamnopyranosyl)-(1→2)-(3,4-di-O-benzyl-α-L-rhamnopyranosyl)-(1→3)-(2-O-acetyl-4-O-benzyl-α-L-rhamnopyranosyl)-(1→3)-2-acetamido-2-deoxy-β-D-glucopyranoside 95

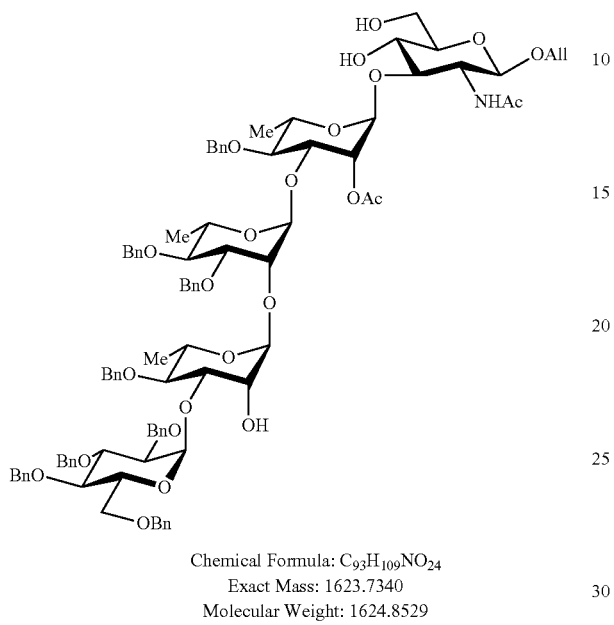

Chemical Formula: $C_{93}H_{109}NO_{24}$
Exact Mass: 1623.7340
Molecular Weight: 1624.8529

50% aqueous TFA solution (4 mL) is slowly added to a solution of alcohol 94 (400 mg, 240 µmol) in DCM (10 mL) at 0° C. The reaction mixture is stirred for 2 h at this temperature, after which time monitoring by TLC (Tol/EtOAc, 4/6) indicates the complete disappearance of 94 (Rf=0.6) and the appearance of a new, more polar compound (Rf=0.2). The reaction mixture is concentrated by coevaporation with Tol (3×10 mL). The yellow oil obtained is purified by silica gel chromatography (DCM/MeOH, 98/2→9/1) to obtain the triol 95 as a white solid corresponding to the expected tetrasaccharide (360 mg, 92%).

Rf=0.55 (DCM/MeOH, 95/5).

$^1$H NMR (CDCl$_3$), δ7.42-7.13 (m, 40H, CH$_{Ph}$), 6.09 (m, 1H, NH), 5.91 (m, 1H, CH=), 5.27 (m, 1H, =CH$_2$), 5.22 (bs, 1H, H-1$_A$), 5.18 (m, 1H, J$_{cis}$=10.4 Hz, =CH$_2$), 5.16 (m, 2H, H-1$_C$, H-2$_C$), 5.11 (d, 1H, J$_{1,2}$=8.3 Hz, H-1$_D$), 5.10-4.88 (m, 8H, H-1$_B$, H-1$_E$, H$_{BN}$), 4.83-4.49 (m, 9H, H$_{Bn}$), 4.35-4.29 (m, 2H, H$_{All}$, H$_{Bn}$) 4.14-3.96 (m, 9H, H-3$_E$, H$_{All}$, H-2$_A$, H-5$_C$, H-3$_A$, H-3$_C$, H-5$_E$, H-5$_A$), 3.87-3.73 (m, 4H, H-3$_B$, H-6a$_D$, H-6b$_D$, H-4$_E$), 3.68 (m, 1H, H-5$_B$) 3.65 (dd, 1H, J$_{2,3}$=3.6 Hz, J$_{3,4}$=9.6 Hz, H-2$_E$), 3.59 (d, 1H, J$_{4,5}$=9.3 Hz, H-4$_A$), 3.54-3.36 (m, 6H, H-6a$_E$, H-5$_D$, H-4$_B$, H-4$_C$, H-6b$_E$, H-4$_D$), 3.16 (m, 1H, H-2$_D$), 2.14 (s, 3H, H$_{Ac}$), 2.10 (s, 3H, H$_{NAc}$), 1.25 (m, 9H, H-6$_A$, H-6$_B$, H-6$_C$).

$^{13}$C NMR (CDCl$_3$), δ170.5 (2C, C$_{NAc}$, C$_{Ac}$), 138.6-137.5 (C$_{Ph}$), 133.9 (CH=), 128.6-127.5 (CH$_{Ph}$), 117.7 (=CH$_2$), 101.3 (C-1$_B$), 100.8 (C-1$_A$, C-1$_C$, $^1$J$_{CH}$=168.2 Hz), 98.4 (C-1$_D$, $^1$J$_{CH}$=169.0 Hz), 94.0 (C-1$_E$, $^1$J$_{CH}$=166.3 Hz), 82.4 (C-3$_E$), 80.2 (C-4$_C$), 79.4-79.1 (C-4$_B$*, C-3$_B$*, C-3$_C$*, C-4$_A$*), 79.0 (C-2$_E$), 77.8 (C-4$_E$), 76.5 (C-3$_A$), 75.9, 75.6, 75.4 (3C, C$_{Bn}$), 75.1 (C-4$_D$), 74.9, 74.5, 74.5, 73.5, 73.5 (5C, C$_{Bn}$), 72.2 (C-2$_C$), 70.8 (C-5$_E$), 70.5 (C$_{All}$), 70.3 (C-5$_D$), 69.0 (C-5$_B$), 68.0 (C-5$_A$), 67.9 (C-6$_E$), 67.4 (C-5$_C$, C-2$_A$), 62.3 (C-6$_D$), 59.7 (C-2$_D$), 23.2 (C$_{NAc}$), 21.1 (C$_{Ac}$), 18.3, 17.9, 17.7 (C-6$_A$*, C-6$_B$*, C-6$_C$*).

HRMS (ESI$^+$): [M+Na]$^+$ C$_{93}$H$_{109}$NO$_{24}$Na m/z theoretical: 1646.7238
m/z measured
1646.7377
[M+H]$^+$ C$_{93}$H$_{109}$NO$_{24}$ m/z theoretical:
1624.7418
m/z measured
1624.7565
[M+NH$_4$]$^+$ C$_{93}$H$_{109}$NO$_{24}$NH$_4$ m/z theoretical:
1641.7683
m/z measured
1641.7848

Propyl α-D-glucopyranosyl-(1→3)-α-L-rhamnopyranosyl-(1→2)-α-L-rhamnopyranosyl-(1→3)-(2-O-acetyl-α-L-rhamnopyranosyl)-(1→3)-2-acetamido-2-deoxy-β-D-glucopyranoside XV

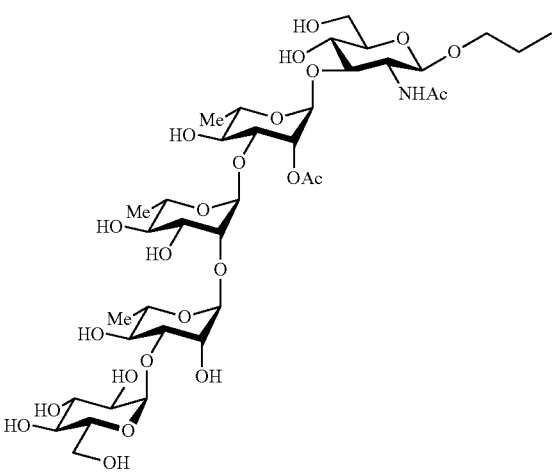

Chemical Formula: $C_{37}H_{63}NO_{24}$
Exact Mass: 905.3740
Molecular Weight: 905.8884

Pd—C 10% (200 mg) is added to a degassed solution of triol 95 (230 mg, 142 µmol) in ethanol (15 mL). The suspension is saturated with hydrogen and stirred at RT for 2 days. Monitoring by TLC (iPrOH/H$_2$O/NH$_3$, 4/1/0.5 and DCM/MeOH, 95/5) shows the disappearance of 95 (Rf=1 and 0.55, respectively) and the appearance of a new, more polar compound (Rf=0.35 and 0, respectively). The reaction mixture is filtered on an Acrodisc LC 25 mm filter, and the filtrate is concentrated in a rotary evaporator. The residue obtained is purified on a C-18 column (H$_2$O/CH$_3$CN, 100/0→7/3) to give the target XV as a white solid (100 mg, 77%).

Rf=0.35 (iPrOH/H$_2$O/NH$_3$, 4/1/0.5).

$^1$H NMR (D$_2$O), δ5.03 (bs, 1H, H-1$_B$), 5.00 (d, 1H, J$_{1,2}$=3.7 Hz, H-1$_E$), 4.90 (m, 2H, H-1$_A$, H-2$_C$), 4.76 (bs, 1H, H-1$_C$), 4.40 (d, 1H, J$_{1,2}$=8.6 Hz, H-1$_D$), 4.17 (m, 1H, H-2$_A$), 3.99 (m, 1H, J$_{5,6}$=6.3 Hz, J$_{4,5}$=9.8 Hz, H-5$_C$), 3.92 (dd, 1H, J$_{2,3}$=5.2 Hz, H-2$_B$), 3.88-3.80 (m, 3H, H-5$_E$, H-3$_C$, H-6a$_D$), 3.76-3.61 (m, 9H, H-3$_A$, H$_{Pr}$, H-2$_D$, H-6a$_E$, H-6b$_E$, H-3$_E$, H-5$_A$, H-3$_B$, H-6b$_D$), 3.51-3.40 (m, 7H, H-4$_C$, H-4$_A$, H-2$_E$, H-4$_D$, H$_{Pr}$, H-3$_D$, H-5$_E$), 3.38-3.31 (m, 3H, H-4$_E$, H-4$_B$, H-5$_E$), 2.07 (s, 3H, H$_{Ac}$), 1.94 (s, 3H, H$_{NAc}$), 1.49 (sex, 2H, J=7.1 Hz, CH$_2$), 1.19-1.14 (m, 9H, H-6$_A$, H-6$_B$, H-6$_C$), 0.76 (t, 3H, J=7.4 Hz, CH$_3$), $^{13}$C NMR (D$_2$O), δ174.4 (C$_{NAc}$), 173.0 (C$_{Ac}$), 101.9 (C-1$_A$, $^1J_{CH}$=175.6 Hz), 101.0 (C-1$_B$, $^1J_{CH}$=172.4 Hz), 100.6 (C-1$_D$, $^1J_{CH}$=162.7 Hz), 98.5 (C-1$_C$, $^1J_{CH}$=173.4 Hz), 95.3 (C-1$_E$, $^1J_{CH}$=170.3 Hz), 82.4 (C-3$_D$), 78.0 (C-2$_B$), 76.2 (C-3$_C$), 76.0 (C-5$_D$), 75.2 (C-3$_A$), 72.9 (C-3$_E$), 72.2 (C$_{Pr}$), 72.2 (C-2$_C$), 71.8 (C-4$_B$), 71.6 (C-5$_E$), 71.6 (C-4$_C$), 71.4 (C-4$_A$), 70.2 (C-4$_D$), 69.9 (C-3$_B$), 69.4 (C-2$_E$), 69.3 (C-4$_E$), 69.3 (C-5$_A$), 68.8 (C-5c), 68.3 (C-5$_B$), 66.6 (C-2$_A$), 60.7 (C-6$_D$), 60.2 (C-6$_E$), 55.2 (C-2$_D$), 22.2 (C$_{NAc}$), 22.1 (CH$_2$), 20.2 (C$_{Ac}$), 16.7 (C-6$_A$), 16.5 (C-6$_B$), 16.3 (C-6$_C$), 9.6 (CH$_3$).

HRMS (ESI$^+$): [M+H]$^+$ C$_{37}$H$_{63}$NO$_{24}$ m/z theoretical:
906.3818
m/z measured
906.3821
[M+Na]$^+$ C$_{37}$H$_{63}$NO$_{24}$Na m/z theoretical:
928.3638
m/z measured
928.3635
[M+K]$^+$ C$_{37}$H$_{63}$NO$_{24}$K m/z theoretical:
944.3377
m/z measured
944.3279

Method 12:

Allyl(2,3,4,6-tetra-O-benzyl-α-D-glucopyranosyl)-(1→3)-(4-O-benzyl-α-L-rhamnopyranosyl)-(1→2)-(3,4-di-O-benzyl-α-L-rhamnopyranosyl)-(1→3)-(4-O-benzyl-α-L-rhamnopyranosyl)-(1→3)-2-acetamido-2-deoxy-4,6-O-isopropylidene-β-D-glucopyranoside 96

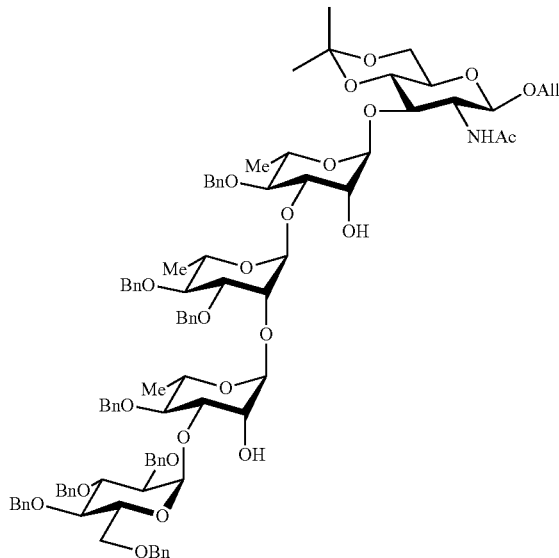

Chemical Formula: C$_{94}$H$_{111}$NO$_{23}$
Exact Mass: 1621.7547
Molecular Weight: 1622.8800

After adding 0.5 M NaOMe (830 μL, 414 μmol, 1 eq.) to the allyl glycoside 93 (729 mg, 414 μmol) in solution in MeOH (20 mL), the reaction mixture is refluxed and stirred for 3 h, after which time monitoring by TLC (Tol/EtOAc, 1/1) indicates the disappearance of 93 (Rf=0.5) and the appearance of a more polar product (Rf=0.2). After it returns to RT, the reaction mixture is neutralized by adding DOWEX (H$^+$) ion-exchange resin, then filtered on a frit. The resin is washed with DCM/MeOH mixture and the solvents are evaporated. The yellow oil obtained is purified by silica gel chromatography (Tol/EtOAc, 1/1→4/6) to give the diol 96 as a white solid (631 mg, 94%).

Rf=0.2 (Tol/EtOAc, 1/1).

$^1$H NMR (CDCl$_3$), δ7.41-7.16 (m, 40H, CH$_{Ph}$), 5.90 (m, 1H, CH=), 5.81 (d, 1H, J$_{NH,2}$=7.9 Hz, NH), 5.30 (m, 1H, J$_{trans}$=17.2 Hz, =CH$_2$), 5.22 (m, 1H, J$_{cis}$=10.4 Hz, =CH$_2$), 5.17 (bs, 1H, H-1$_E$), 5.07 (bs, 1H, H-1$_A$), 5.02-4.97 (m, 2H, H$_{Bn}$), 4.94 (d, 1H, J$_{1,2}$=4.0 Hz, H-1$_B$), 4.90-4.86 (m, 4H, 2H$_{Bn}$, H-1$_D$, H-1$_C$), 4.80-4.66 (d, 8H, H$_{Bn}$), 4.59-4.51 (m, 3H, H$_{Bn}$), 4.38-4.32 (m, 2H, H$_{All}$, H$_{Bn}$), 4.21 (pt, 1H, J$_{3,4}$=9.4 Hz, H-3$_D$), 4.12-4.05 (m, 6H, H$_{All}$, H-2$_B$, H-3$_E$, H-2$_A$, H-3$_A$, H-5$_C$), 3.99-3.84 (m, 7H, H-2$_C$, H-5$_E$, H-6a$_D$, H-3$_B$*, H-3$_C$*, H-5$_A$, H-5$_B$), 3.83 (m, 1H, H-6b$_D$), 3.78 (pt, 1H, J$_{3,4}$=9.6 Hz, H-4$_E$), 3.66-3.61 (m, 2H, H-2$_E$, H-4$_D$), 3.57-3.52 (m, 2H, H-4$_A$, H-4$_B$), 3.52-3.49 (m, 2H, H-2$_D$, H-6a$_E$), 3.43-3.35 (m, 3H, H-6b$_E$, H-4$_C$, H-5$_D$), 2.02 (s, 3H, H$_{NAc}$), 1.53 (s, 3H, H$_{iPr}$), 1.43 (s, 3H, H$_{iPr}$), 1.41, 1.28 (m, 6H, H-6$_A$*, H-6$_B$*), 1.23 (d, 3H, J$_{5,6}$=6.2 Hz, H-6$_C$).

$^{13}$C NMR (CDCl$_3$), δ170.4 (C$_{NAc}$), 138.6-137.6 (C$_{Ph}$), 133.8 (CH=), 129.1-127.5 (CH$_{Ph}$), 117.6 (=CH$_2$), 101.0 (C-1$_A$, $^1J_{CH}$=168.4 Hz), 100.9 (C-1$_B$, $^1J_{CH}$=172.3 Hz), 99.8 (C-1$_C$, $^1J_{CH}$=170.6 Hz), 99.6 (C-1$_D$, $^1J_{CH}$=160.5 Hz), 99.5 (C$_{iPr}$), 94.0 (C-1$_E$, $^1J_{CH}$=167.5. Hz), 82.4 (C-3$_E$), 80.4 (1C, C-4$_A$*, C-4$_B$*), 80.3 (1C, C-3$_B$*, C-3$_C$*), 79.7 (C-4$_C$), 79.5 (1C, C-3$_B$*, C-3$_C$*), 79.3 (1C, C-4$_A$*, C-4$_B$*), 79.0 (C-2$_E$), 77.8 (C-4$_E$), 76.5 (C-3$_A$), 76.0 (C-3$_D$), 75.6 (3C, C$_{Bn}$), 75.4 (C-2$_A$), 75.0, 74.9, 74.4, 73.5 (4C, C$_{Bn}$), 73.0 (C-4$_D$), 72.5 (C$_{Bn}$), 71.2 (C-2$_C$), 70.7 (C-5$_E$), 70.0 (C$_{All}$), 69.1 (1C, C-5$_A$*, C-5$_B$*), 68.0 (C-6$_E$), 67.9 (1C, C-5$_A$*, C-5$_B$*), 67.7 (C-5$_C$), 67.4 (C-2$_B$), 67.3 (C-5$_D$), 62.3 (C-6$_D$), 58.2 (C-2$_D$), 29.1 (C$_{iPr}$), 23.5 (C$_{NAc}$), 19.2 (C$_{iPr}$), 18.0, 17.8 (3C, C-6$_A$*, C-6$_B$*, C-6$_C$*).

HRMS (ESI$^+$): [M+H]$^+$ C$_{94}$H$_{111}$NO$_{23}$ m/z theoretical:
1622.7626
m/z measured
1622.7649
[M+Na]$^+$ C$_{94}$H$_{111}$NO$_{23}$Na m/z theoretical:
1644.7445
m/z measured
1644.7562

Allyl(2,3,4,6-tetra-O-benzyl-α-D-glucopyranosyl)-(1→3)-(4-O-benzyl-α-L-rhamnopyranosyl)-(1→2)-(3,4-di-O-benzyl-α-L-rhamnopyranosyl)-(1→3)-(4-O-benzyl-α-L-rhamnopyranosyl)-(1→3)-2-acetamido-2-deoxy-β-D-glucopyranoside 97

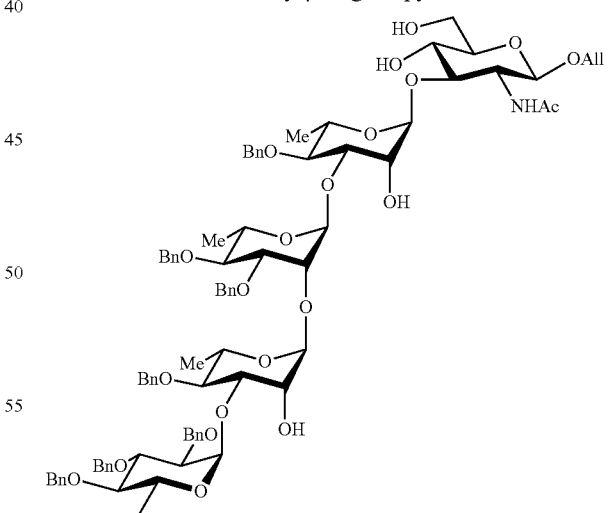

Chemical Formula: C$_{91}$H$_{107}$NO$_{23}$
Exact Mass: 1581.7234
Molecular Weight: 1582.8162

50% aqueous TFA solution (4 mL) is slowly added to a solution of diol 96 (515 mg, 318 μmol) in DCM (10 mL) at 0° C. The reaction mixture is stirred for 2 h at this temperature, after which time monitoring by TLC (DCM/MeOH, 95/5) indicates the complete disappearance of 96 (Rf=0.35) and the appearance of a new, more polar compound (Rf=0.2). The reaction mixture is concentrated by coevaporation with Tol (3×10 mL). The yellow oil obtained is purified by silica gel chromatography (Tol/EtOAc, 3/7→1/9) to obtain the tetraol 97 as a white solid (330 mg, 66%).

Rf=0.2 (DCM/MEOH, 95/5).

$^1$H NMR (CDCl$_3$), δ7.42-7.13 (m, 40H, CH$_{Ph}$), 5.90 (m, 1H, CH=), 5.78 (d, 1H, J$_{NH,2}$=7.2 Hz, NH), 5.30 (m, 1H, J$_{trans}$=17.3 Hz, =CH$_2$), 5.21 (m, 1H, J$_{cis}$=10.4 Hz, =CH$_2$), 5.17 (bs, 1H, H-1$_B$), 5.01-4.94 (m, 4H, H-1$_D$, H-1$_A$, 2H$_{Bn}$), 4.92 (d, 1H, J$_{1,2}$=3.7 Hz, H-1$_E$), 4.89-4.86 (m, 2H, H$_{Bn}$), 4.83 (m, 1H, J$_{1,2}$=2.4 Hz, H-1$_C$), 4.78-4.65 (d, 7H, H$_{Bn}$), 4.57-4.49 (m, 3H, H$_{Bn}$), 4.37-4.20 (m, 4H, H$_{All}$, 2H$_{Bn}$, H-3$_D$), 4.13 (m, 1H, H$_{All}$), 4.09-4.02 (m, 4H, H-3$_E$, H-2$_B$, H-2$_A$, H-3$_A$), 4.00-3.91 (m, 5H, H-2$_C$, H-5$_E$, H-5$_B$, H-3$_B$, H-6a$_D$), 3.88-3.82 (m, 4H, H-3$_C$, H-5$_C$, H-5$_A$, H-6b$_D$), 3.77 (pt, 1H, J$_{3,4}$=9.7 Hz, H-4$_E$), 3.63 (dd, 1H, J$_{2,3}$=9.6 Hz, H-2$_E$), 3.56-3.49 (m, 3H, H-4$_A$, H-6a$_E$, H-4$_B$), 3.47-3.37 (m, 4H, H-4$_D$, H-5$_D$, H-4$_C$, H-6b$_E$), 3.15 (m, 1H, H-2$_D$), 1.97 (s, 3H, H$_{NAc}$), 1.34-1.28 (m, 9H, H-6$_A$*, H-6$_B$*, H-6$_C$*).

$^{13}$C NMR (CDCl$_3$), δ170.6 (C$_{NAc}$), 138.6-137.5 (C$_{Ph}$), 133.9 (CH=), 128.6-127.5 (CH$_{Ph}$), 117.5 (=CH$_2$), 101.5 (C-1$_C$, $^1$J$_{CH}$=171.3 Hz), 100.9 (C-1$_A$, $^1$J$_{CH}$=168.8 Hz), 100.9 (C-1$_B$, $^1$J$_{CH}$=168.8 Hz), 98.7 (C-1$_D$, $^1$J$_{CH}$=163.1 Hz), 94.0 (C-1$_E$, $^1$J$_{CH}$=165.5 Hz), 84.1 (C-3$_D$), 82.4 (C-3$_E$), 80.2 (C-4$_B$), 79.8 (C-3$_B$), 79.4 (C-3$_C$), 79.3 (C-4$_A$), 79.2 (C-4$_C$), 79.0 (C-2$_E$), 77.8 (C-4$_E$), 76.5 (C-3$_A$), 75.8, 75.6, 75.5 (3C, C$_{Bn}$), 75.1 (C-4$_D$), 75.0 (C-2$_A$), 75.0, 74.5, 73.4, 72.6 (5C, C$_{Bn}$), 71.1 (C-5$_D$), 70.8 (2C, C-2$_C$, C-5$_E$), 70.3 (C$_{All}$), 69.3 (C-5$_B$), 69.0 (C-5$_C$), 68.0 (C-6$_E$), 67.9 (C-5$_A$), 67.3 (C-2$_B$), 62.8 (C-6$_D$), 57.3 (C-2$_D$), 23.6 (C$_{NAc}$), 18.0, 17.9, 17.8 (C-6$_A$*, C-6$_B$*, C-6$_C$*).

HRMS (ESI$^+$): [M+H]$^+$ C$_{91}$H$_{107}$NO$_{23}$ m/z theoretical: 1582.7312
m/z measured 1582.7300
[M+Na]$^+$ C$_{91}$H$_{107}$NO$_{23}$Na m/z theoretical: 1604.7131
m/z measured 1604.7180

Propyl α-D-glucopyranosyl-(1→3)-α-L-rhamnopyranosyl-(1→2)-α-L-rhamnopyranosyl-(1→3)-α-L-rhamnopyranosyl-(1→3)-2-acetamido-2-deoxy-β-D-glucopyranoside XVI Chemical Formula: C$_{35}$H$_{61}$NO$_{23}$
Exact Mass: 863.3634
Molecular Weight: 863.8517

Pd—C 10% (200 mg) is added to a degassed solution of tetraol 97 (260 mg, 164 μmol) in ethanol (15 mL). The suspension is saturated with hydrogen and stirred at RT for 2 days. Monitoring by TLC (iPrOH/H$_2$O/NH$_3$, 4/1/0.5 and DCM/MeOH, 95/5) shows the disappearance of 97 (Rf=1 and 0.2, respectively) and the appearance of a new, more polar compound (Rf=0.25 and 0, respectively). The reaction mixture is filtered on an Acrodisc LC 25 mm filter, and the filtrate is concentrated in a rotary evaporator. The residue obtained is purified on a C-18 column (H$_2$O/CH$_3$CN, 100/0→7/3), obtaining the target XVI as a white solid (99 mg, 70%).

Rf=0.25 (iPrOH/H$_2$O/NH$_3$, 4/1/0.5).

$^1$H NMR (D$_2$O), δ5.15 (bs, 1H, H-1$_B$), 5.08 (d, 1H, J$_{1,2}$=3.8 Hz, H-1$_E$), 4.98 (d, 1H, J$_{1,2}$=1.5 Hz, H-1$_A$), 4.79 (d, 1H, J$_{1,2}$=1.2 Hz, H-1$_C$), 4.50 (d, 1H, J$_{1,2}$=8.6 Hz, H-1$_D$), 4.17 (dd, 1H, J$_{2,3}$=2.6 Hz, H-2$_A$), 4.03 (dd, 1H, J$_{2,3}$=3.0 Hz, H-2$_B$), 3.99 (m, 1H, J$_{4,5}$=9.8 Hz, H-5$_C$), 3.94 (m, 1H, H-5$_E$), 3.92-3.87 (m, 2H, H-3$_B$, H-6a$_D$), 3.85-3.68 (m, 10H, H-3$_A$, H-2$_C$, H$_{Pr}$, H-2$_D$, H-6a$_E$, H-6b$_E$, H-3$_E$, H-3$_C$, H-6b$_D$, H-5$_A$, H-5$_B$), 3.58-3.40 (m, 9H, H-3$_D$, H-4$_A$, H-2$_E$, H$_{Pr}$, H-4$_C$, H-4$_D$, H-4$_B$, H-4$_E$, H-5$_D$), 2.01 (s, 3H, H$_{NAc}$), 1.51 (sex, 2H, J=7.2 Hz, CH$_2$), 1.29-1.24 (m, 6H, H-6$_A$*, H-6$_B$*), 1.20 (d, 3H, J$_{5,6}$=6.2 Hz, H-6$_C$), 0.83 (t, 3H, J=7.4 Hz, CH$_3$).

$^{13}$C NMR (D$_2$O), δ174.1 (C$_{NAc}$), 102.0 (C-1$_A$, $^1$J$_{CH}$=171.5 Hz), 101.3 (C-1$_C$, $^1$J$_{CH}$=173.6 Hz), 100.8 (C-1$_B$, $^1$J$_{CH}$=177.8 Hz), 100.6 (C-1$_D$, $^1$J$_{CH}$=156.2 Hz), 95.4 (C-1$_E$, $^1$J$_{CH}$=169.4 Hz), 81.7 (C-3$_D$), 78.3 (C-2$_B$), 77.3 (C-3$_C$), 76.0 (C-5$_D$), 75.3 (C-3$_A$), 73.0 (C-3$_E$), 72.3 (C$_{Pr}$), 72.2 (C-4$_B$), 71.7 (2C, C-4$_C$, C-5$_E$), 71.4 (C-4$_A$), 70.6 (C-2$_C$), 70.3 (C-2$_E$), 69.9 (C-3$_B$), 69.4 (C-4$_E$), 69.3 (2C, C-5$_A$, C-5$_B$), 68.9 (C-5$_C$), 68.5 (C-4$_D$), 66.7 (C-2$_A$), 60.9 (C-6$_D$), 60.3 (C-6$_E$), 55.4 (C-2$_D$), 22.1 (2C, C$_{NAc}$, CH$_2$), 20.2 (C$_{Ac}$), 16.8, 16.7 (C-6$_A$*, C-6$_B$*), 16.4 (C-6$_C$), 9.6 (CH$_3$).

HRMS (ESI$^+$): [M+H]$^+$ C$_{35}$H$_{61}$NO$_{23}$ m/z theoretical: 864.3713
m/z measured 864.3718
[M+Na]$^+$ C$_{35}$H$_{61}$NO$_{23}$Na m/z theoretical: 886.3532
m/z measured 886.3501

Section IV—Synthesis of the Targets VII, VIII, IX, XVII and XVIII

In addition to the tri-(VII), tetra-(VIII) and pentasaccharides (IX) having a residue B at their reducing end, in this section we undertook the synthesis of two hexasaccharides. As previously, these two targets, XVII in series *S. flexneri* 3a and its corresponding XVIII in series *S. flexneri* X, were synthesized in the form of propyl glycoside.

|  | Acceptor | Donor | Target |
| --- | --- | --- | --- |
| Method 13 | 58 | 80 or 80' | VII |
| Method 14 | 58 | 109 | VIII |
| Method 14a | 108 | 2 | VIII |
| Method 14b | 108 | 1 | VIII |
| Method 15 | 116 | 39 | IX |
| Method 16 | 110 | 47 | XVII |
| Method 17 | 110 | 47 | XVIII |

Back synthesis of the oligosaccharides in reducing series B
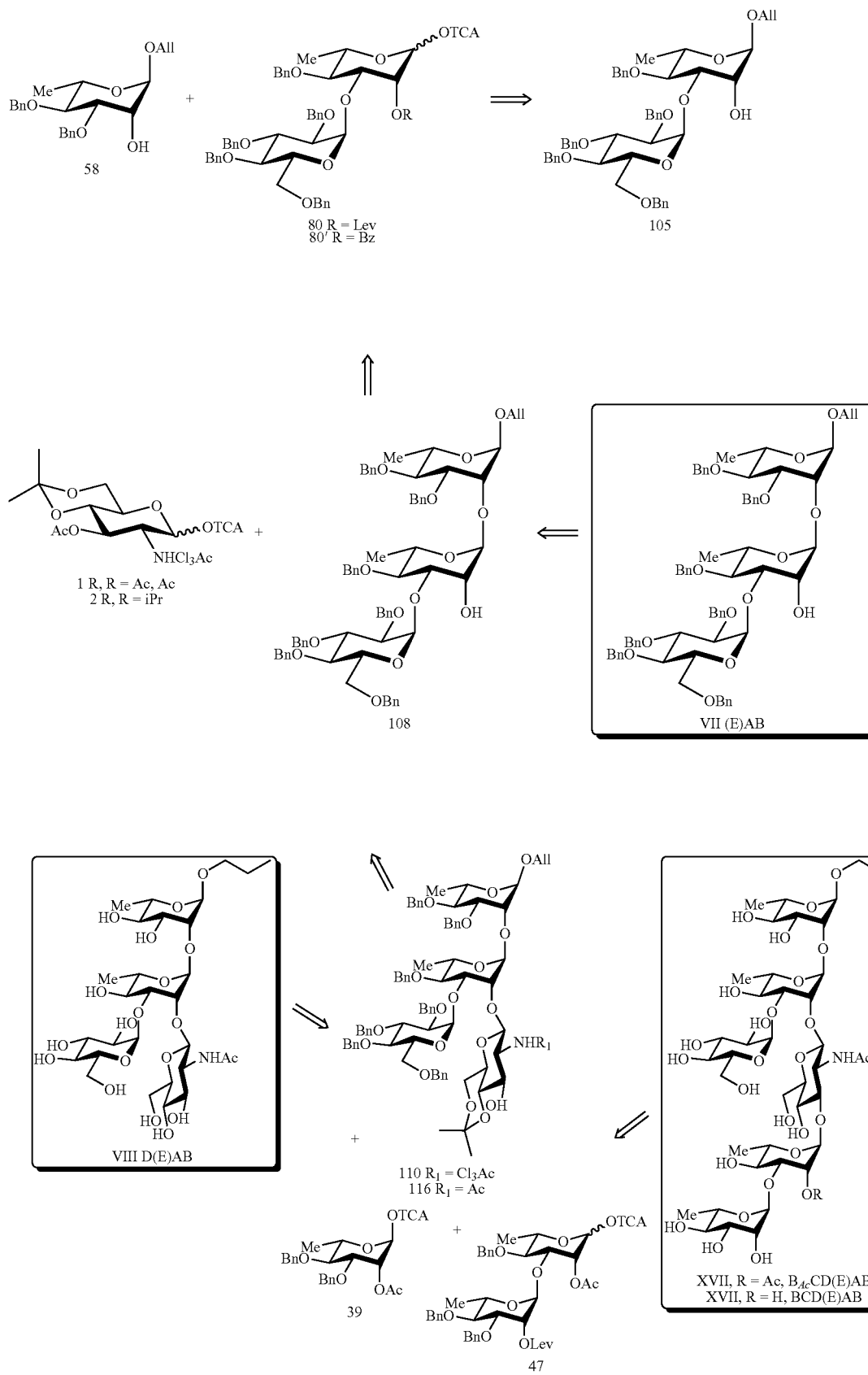

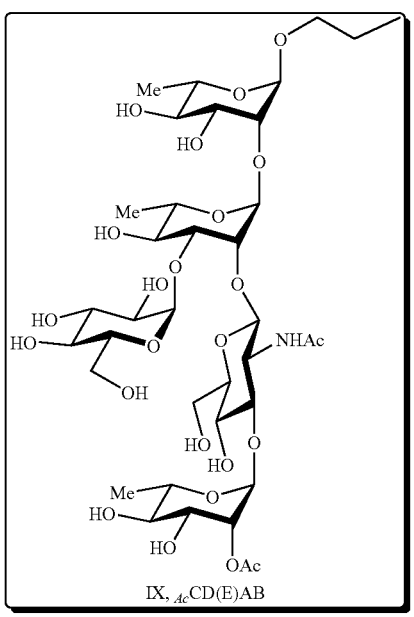

IX, $_{Ac}$CD(E)AB

Method 13:

The invention relates to the method of preparation of compound VII (trisaccharide (E)AB), an intermediate in the synthesis of a saccharide as defined in list L1 comprising the following stages:
- condensation of the acceptor monosaccharide 58 and of the donor disaccharide 80' leading to the trisaccharide 107', the condensation reaction preferably being carried out in a solvent such as dichloromethane, 1,2-dichloroethane, ether, toluene, acetonitrile or any other equivalent solvent, in the presence of a Lewis acid such as TMSOTf or triflic acid, preferably in toluene in the presence of a catalytic amount of triflic acid (scheme 55);
- debenzoylation of the trisaccharide 107' leading to the trisaccharide 108 preferably by the action of MeONa in a dichloromethane/methanol mixture;
- hydrogenolysis of the trisaccharide 108 leading to the trisaccharide (E)AB preferably under atmospheric hydrogen atmosphere in ethanol, for example ethanol, in the presence of palladium (scheme 60).

The invention also relates to the method of preparation of compound VII (trisaccharide (E)AB), an intermediate in the synthesis of a saccharide such as defined in list L1 comprising the following stages:
- condensation of the acceptor monosaccharide 58 and of the donor disaccharide 80 leading to the trisaccharide 107, the condensation reaction preferably being carried out in a solvent such as dichloromethane, 1,2-dichloroethane, ether, toluene, acetonitrile or any other equivalent solvent, in the presence of a Lewis acid such as TMSOTf or triflic acid, preferably in toluene in the presence of TMSOTf at 0.3 eq. (scheme 61);
- delevulinoylation of the trisaccharide 107' leading to the trisaccharide 108 preferably in NaOMe in the presence of methanol;
- hydrogenolysis of the trisaccharide 108 leading to the trisaccharide (E)AB, preferably under atmospheric hydrogen atmosphere in alcohol, for example ethanol, in the presence of palladium (scheme 60).

1. Trisaccharide (E)AB
a. Route $2_A$-O-benzoyl

Scheme 60: Synthesis of the trisaccharide VII via the acceptor 108

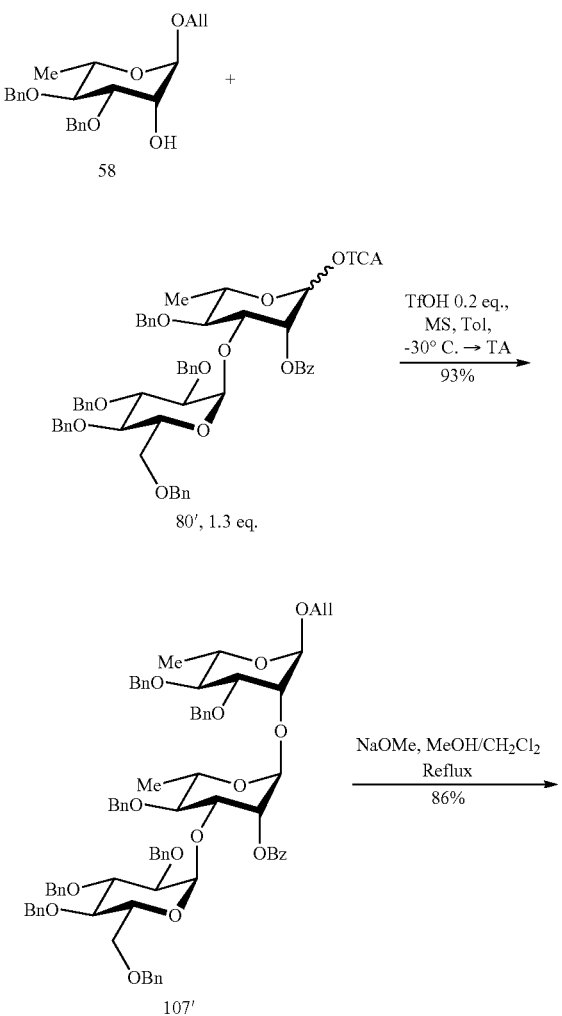

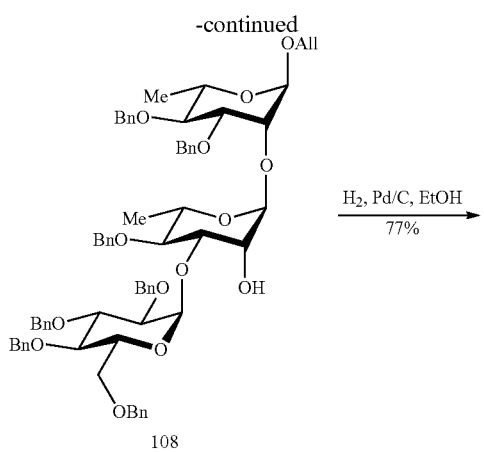

108

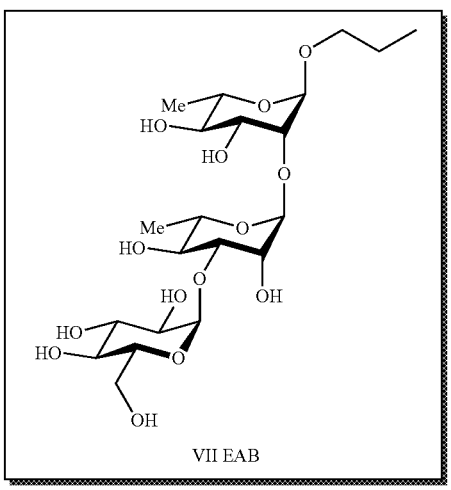

VII EAB

The donor disaccharide 80', bearing a benzoyl group in position $2_A$ and prepared according to the protocol already described[45] is condensed on the acceptor 58 in toluene in the presence of a catalytic amount of triflic acid to give the fully protected trisaccharide 107' at a yield of 930 (Scheme 60). The latter is debenzoylated by the action of MeONa in a dichloromethane/methanol mixture 2/3 under reflux to give the acceptor 108 (86%). The latter is debenzylated by hydrogenolysis in the presence of palladium on charcoal. The target trisaccharide VII is isolated after purification by HPLC (77%).

b. Route $2_A$-O-Levuniloyl

Having developed a new route for access to the disaccharide 21, precursor of the donor 80 and having optimized the synthesis of the rhamnose acceptor 58 in the preceding section, access to the target VII was considered starting from these two entities. Once again, the influence of the solvent[69, 76-79] in the glycosylation stage was evaluated.

In toluene, the trisaccharide 107 is obtained at a yield of 91%, greater than the yield obtained if dichloromethane is used (82%). On a large scale (1.5 g of acceptor 61), the yield even reaches 92%. This time the delevulinoylation is carried out in methanolic NaOMe, since no acetyl is present on the molecule, to obtain the acceptor 108 (94%) (Scheme 61).

Scheme 61: Alternative synthesis of the acceptor 108

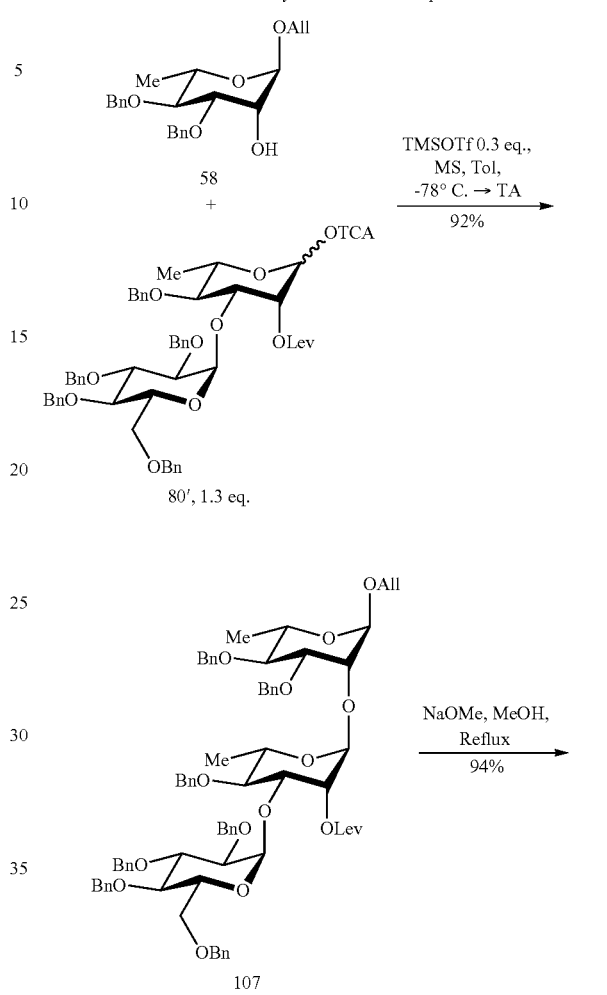

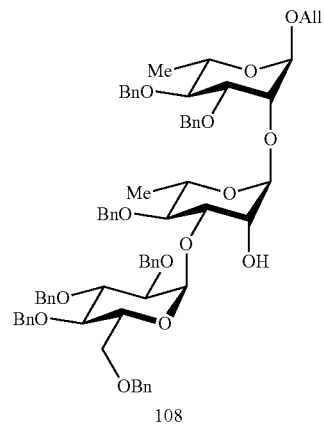

108

Method 14:

The invention relates to the method of preparation of compound VIII (tetrasaccharide D(E)AB) as defined in list L1 comprising the following stages:

condensation of the acceptor trisaccharide 108 with the donor monosaccharide 2 leading to the tetrasaccharide 115, the condensation reaction preferably being carried out in a solvent such as dichloromethane, 1,2-dichloroethane, ether, toluene, acetonitrile or any other equivalent solvent, in the presence of a Lewis acid such as TMSOTf or triflic acid, preferably in toluene in the presence of TMSOTf at a temperature between −20° C. and −40° C. (scheme 64);

deacetylation of the tetrasaccharide 115 leading to the tetrasaccharide 110 preferably in the presence of potassium carbonate (scheme 64);

cleavage of the isopropylidene group of the tetrasaccharide 110 and deprotection of the tetrasaccharide obtained leading to the tetrasaccharide D(E)AB preferably under hydrogen atmosphere of ethanol in the presence of palladium (scheme 29).

The invention also relates to the method of preparation of compound VIII (tetrasaccharide D(E)AB) as defined in list L1 comprising the following stages:

condensation of the acceptor trisaccharide 108 with the donor monosaccharide 1 leading to the tetrasaccharide 115', the condensation reaction preferably being carried out in a solvent such as dichloromethane, 1,2-dichloroethane, ether, toluene, acetonitrile or any other equivalent solvent, in the presence of a Lewis acid such as TMSOTf or triflic acid, preferably in toluene in the presence of a catalytic amount of triflic acid (scheme 65);

deacetylation of the tetrasaccharide 115' leading to the tetrasaccharide 115" preferably by a solution of MeONa in methanol;

deprotection of the tetrasaccharide 115" leading to the tetrasaccharide D(E)AB preferably under atmospheric hydrogen atmosphere in ethanol in the presence of palladium (scheme 65).

2. Tetrasaccharide D(E)AB

According to the back-synthesis study, the target VIII is accessible by coupling the acceptor 108 with the glucosamine donors 1, 2, or 3 described in the first section (Scheme 62).

However, as the long-term objective is the synthesis of large oligosaccharide targets, another strategy involving a smaller number of stages was also considered. The acceptor 58 can be coupled directly to a trisaccharide donor 109 instead of the disaccharide 80, resulting from glycosylation with donor 2 (Scheme 62). These two strategies were therefore compared. It should be noted that the new donor 109 does not have a participating group in position $2_A$, but data in the literature suggest that in the case of rhamnose and mannose, good stereoselectivity in favor of the α anomer can be envisaged in the absence of anchimeric assistance.

a. D(E)A+B Coupling

Synthesis of the donor 109 was undertaken in 3 stages: levulinoylation[89] of the acceptor 38 (90%), deallylation[39, 40] of the allyl glycoside 111 (80%) and then activation[22, 23] of the hemiacetal 112 (85%). Based on the previous studies, coupling between this donor 109 and the acceptor 54 was carried out in toluene. However, degradation of the donor 109 to hemiacetal 112 as well as the presence of the starting acceptor 58 were observed. In contrast, when the condensation was carried out in dichloromethane, two new compounds were isolated and characterized.

Scheme 63: First strategy for access to 110

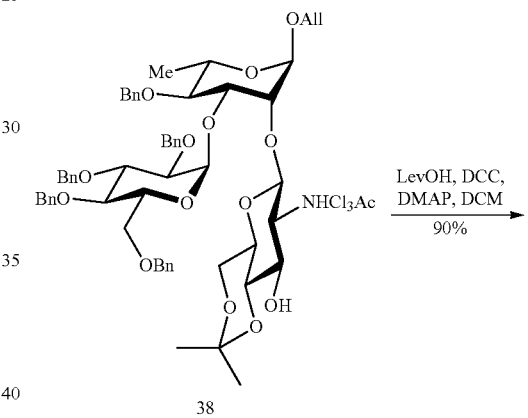

Scheme 62: Back synthesis of the tetrasaccharide 110

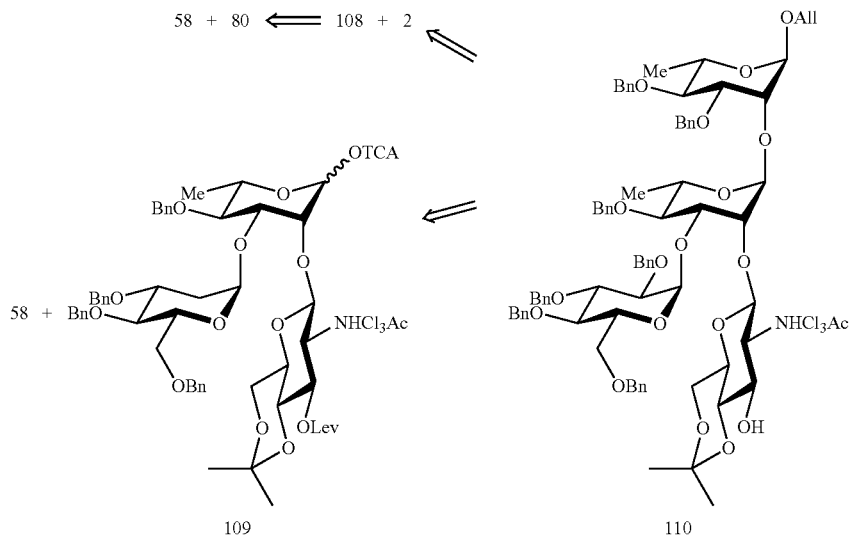

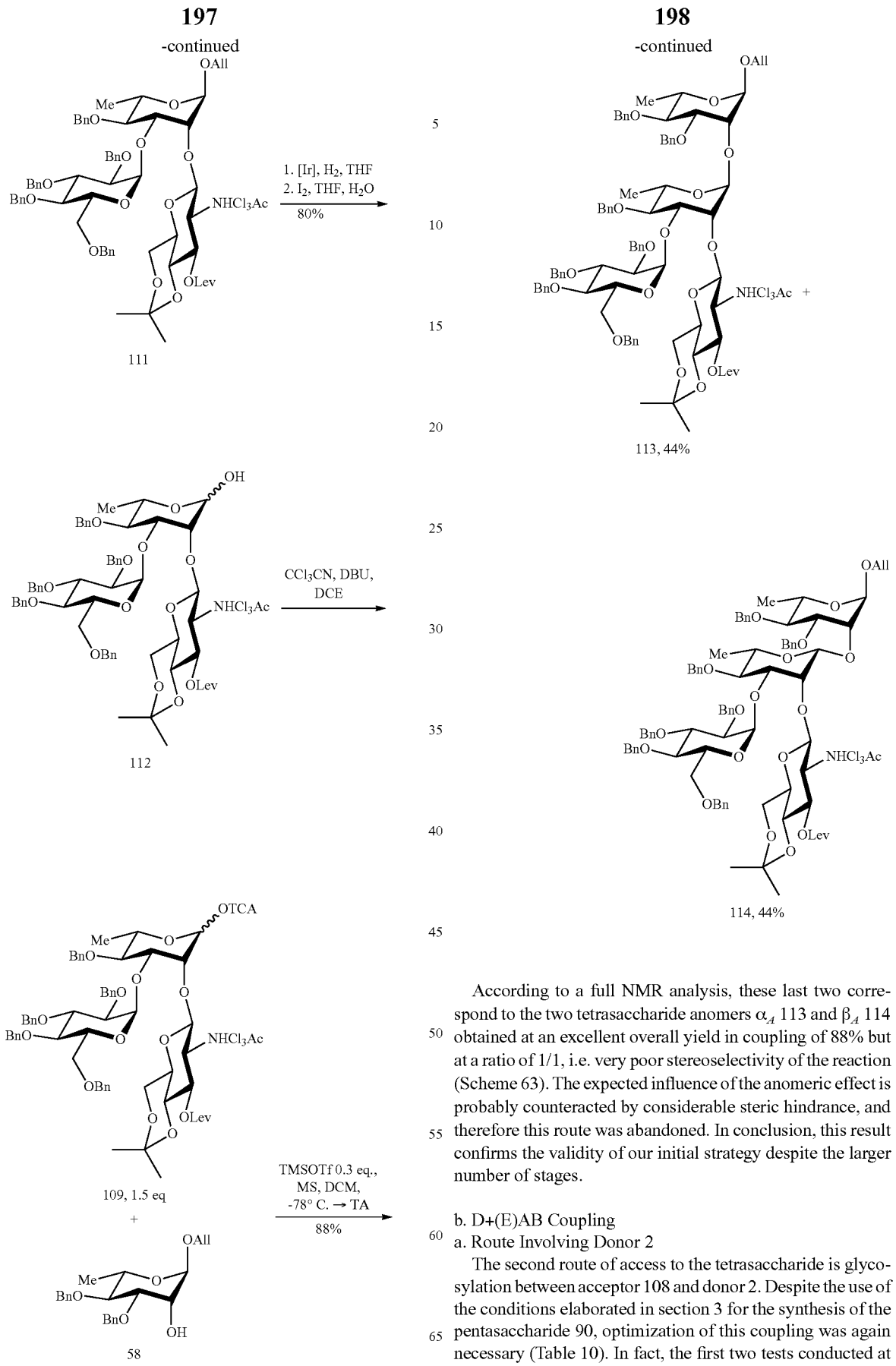

According to a full NMR analysis, these last two correspond to the two tetrasaccharide anomers $\alpha_A$ 113 and $\beta_A$ 114 obtained at an excellent overall yield in coupling of 88% but at a ratio of 1/1, i.e. very poor stereoselectivity of the reaction (Scheme 63). The expected influence of the anomeric effect is probably counteracted by considerable steric hindrance, and therefore this route was abandoned. In conclusion, this result confirms the validity of our initial strategy despite the larger number of stages.

b. D+(E)AB Coupling
a. Route Involving Donor 2

The second route of access to the tetrasaccharide is glycosylation between acceptor 108 and donor 2. Despite the use of the conditions elaborated in section 3 for the synthesis of the pentasaccharide 90, optimization of this coupling was again necessary (Table 10). In fact, the first two tests conducted at −40° C., in dichloromethane and toluene, did not give satisfactory results (entry 1 and 2). In fact, in TLC, acceptor 108 is still present in the reaction mixture whereas the donor 2 has been consumed. In the previous section, the glucosamine donor 2 was not sufficiently reactive at −78° C. and degraded too quickly at −20° C. Therefore comparative glycosylation was carried out at −20° C. and at −40° C., increasing both the amount of donor to give complete reaction, but also the amount of acid in order to increase the reaction rate. Based on entries 3 and 4, the previous results are again confirmed, since the ideal coupling temperature is −40° C. even if the reaction does not always go to completion. However, according to entries 3 and 5, the increase in the amount of acid did not have the desired effect.

TABLE 10

Investigation of coupling between 2 and 108

| Entry | TMSOTf | Temperature | Donor 2 | Solvents | Yield (corrected yield) |
|---|---|---|---|---|---|
| 1 | 0.3 eq. | −40° C. | 1.4 eq. | Dichloromethane | 35% |
| 2 | | | | Toluene | 56% |
| 3 | 0.4 eq. | −40° C. | 1.5 eq. | | 77% (84%) |
| 4 | | −20° C. | | | 70% (78%) |
| 5 | 0.3 eq. | −40° C. | 1.5 eq. | | 75% (82%) |
| 6 | | | 1.7 eq. | | 95% |

The presence of starting acceptor 108 in these various tests led to an increase in the amount of donor (entry 6 in Table 10).

Scheme 64: Second strategy for acess to 110

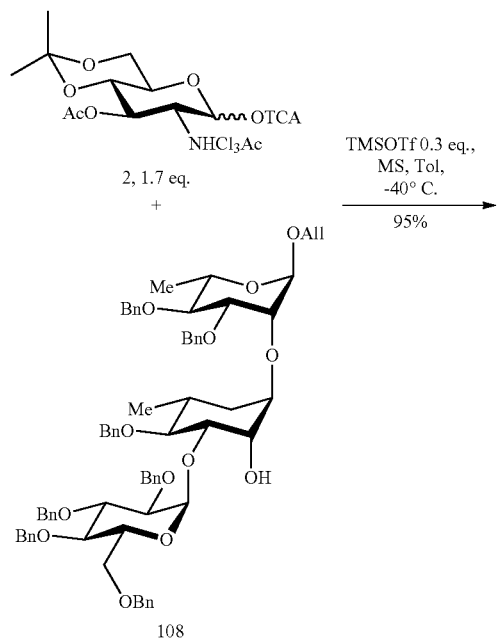

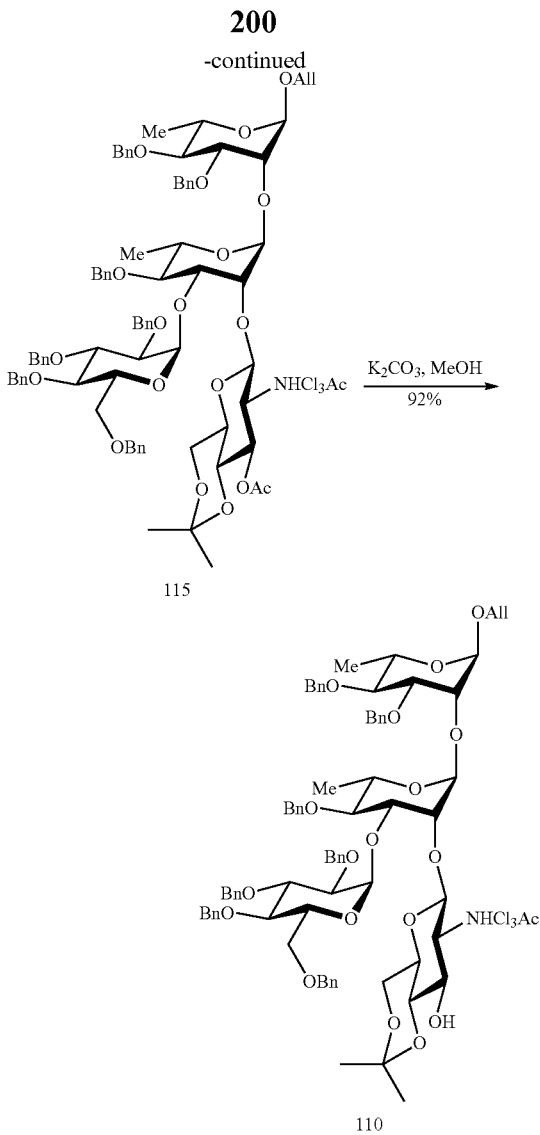

On a large scale (1.2 g of acceptor), reaction is total and the expected tetrasaccharide 115 can be isolated at a yield of 95% (Scheme 64). The latter is deacetylated in the presence of potassium carbonate[85] to obtain the acceptor tetrasaccharide 110 at an excellent yield of 92%.

b. Route Involving Donor 1

If chain extension in position $3_D$ is not required, it may be advisable to use the glucosaminyl residue donor 1, which is more easily accessible. This route was also considered (Scheme 65).

The triacetylated condensation product 115' is isolated (87%) as a result of coupling of acceptor 108 with donor 1, carried out in toluene in the presence of a catalytic amount of triflic acid. When treated at room temperature with a solution of MeONa in methanol, the tetrasaccharide 115' gives the triol 115" (79%). This intermediate is debenzylated by hydrogenolysis in a slightly acid medium, then converted to acetamide by hydrodechlorination in a slightly basic medium. The free tetrasaccharide VIII is isolated after purification by HPLC (68%).

A possible alternative consists of converting the fully protected tetrasaccharide 115' to acetamido triol by the action of MeONa in a dichloromethane/methanol mixture. This intermediate is debenzylated by hydrogenolysis to give the target tetrasaccharide VIII at an overall yield of 39% from acceptor 108. Note, however, that this yield is lower than the yield of 46% obtained for the full coupling/deprotection sequence (108→VIII) involving the trichloroacetamide 115'.

condensation of the acceptor tetrasaccharide 116 and donor monosaccharide 39 leading to the pentasaccharide 116', the condensation reaction preferably being carried out in a solvent such as dichloromethane, 1,2-

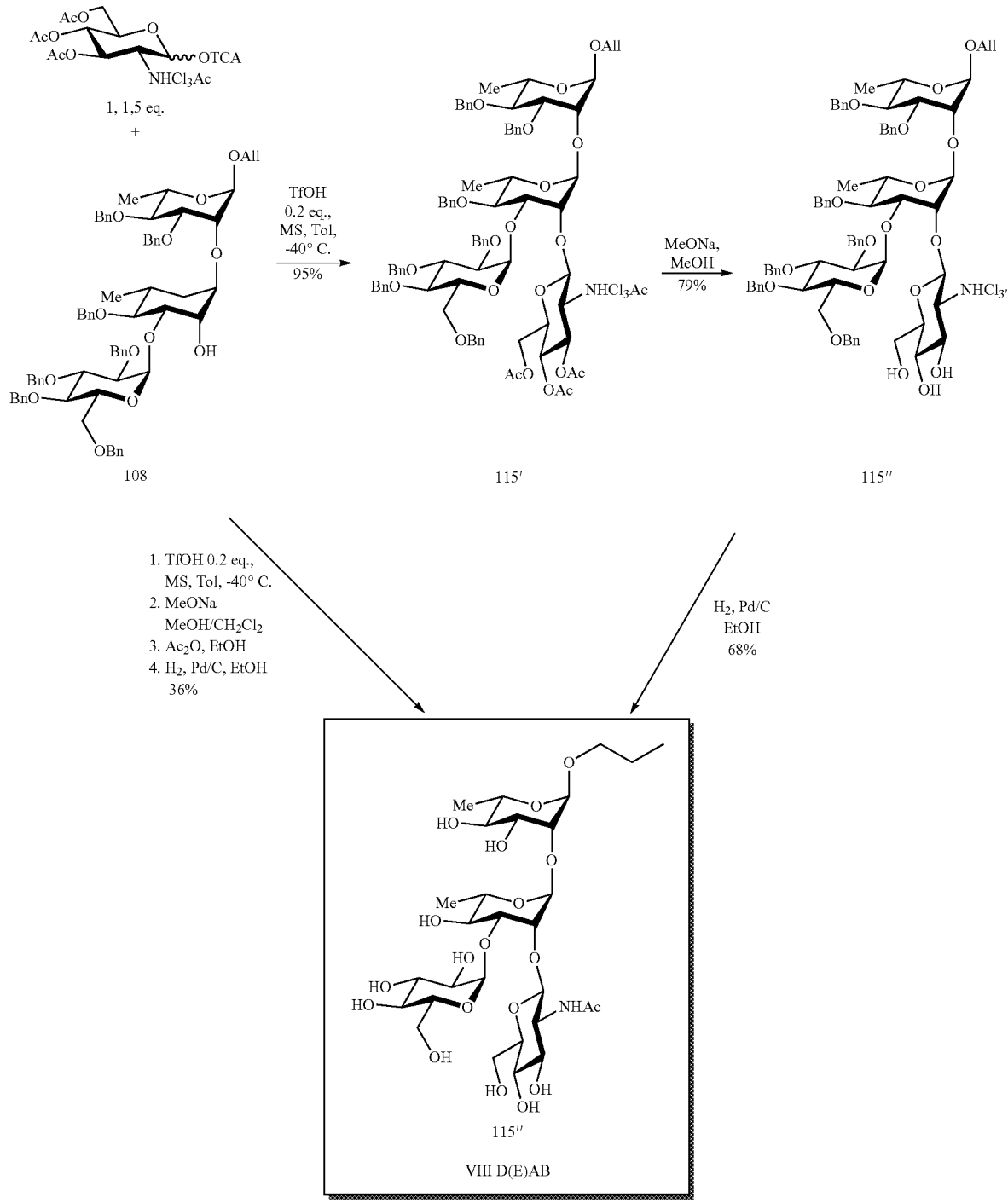

Scheme 65: Synthesis of the tetrasaccharide VIII via donor 1

Method 15:

The invention further relates to the method of preparation of compound IX (pentasaccharide $_{Ac}$CD(E)AB) as defined in list L1 comprising the following stages:

dichloroethane, ether, toluene, acetonitrile or any other equivalent solvent, in the presence of a Lewis acid such as TMSOTf or triflic acid, preferably in toluene in the presence of triflic acid (scheme 71);

cleavage of the isopropylidene group of the pentasaccharide 116' leading to the pentasaccharide 116";

deprotection of the pentasaccharide 116" leading to the pentasaccharide $_{Ac}$CD(E)AB preferably under hydrogen atmosphere in ethanol in the presence of palladium on charcoal (scheme 71).

3. New strategy: Conversion of the Trichloroacetamide to Acetamide During Synthesis Taking into account the presence of several trichloroacetamide functions on the same molecule during the synthesis of larger targets and the possible difficulties encountered during the final hydrogenolysis, conversion of the trichloroacetamide function to acetamide can also be considered before introduction of the acetyl function in position $2_C$ rather than in the last stage. Thus, synthesis of the acetamide analog of 116 was envisaged. Many methods of conversion are described in the literature (back-synthesis section), but as we wish to avoid tin, a new method was developed.

Elaboration of the Conditions

In accordance with the results that have just been described regarding the transformation of 115' into VIII, during deacetylation of the three acetyl functions of the trisaccharide 22, a surprising result was observed: if the reaction is carried out in methanol then only the triol 37 is obtained, whereas if dichloromethane is added to the reaction mixture, an extremely polar compound appears in TLC. As the latter is detected with ninhydrin, the most plausible hypothesis is the presence of the free amine form (Scheme 66). To verify this, an acetylation in an alcoholic medium, selective for the amine function postulated, was carried out. The structure of the reaction product 117 was determined by full NMR analysis and mass spectrometry, confirming the hypothesis.

Scheme 66: Deacetylation of 22 in various conditions of solvents

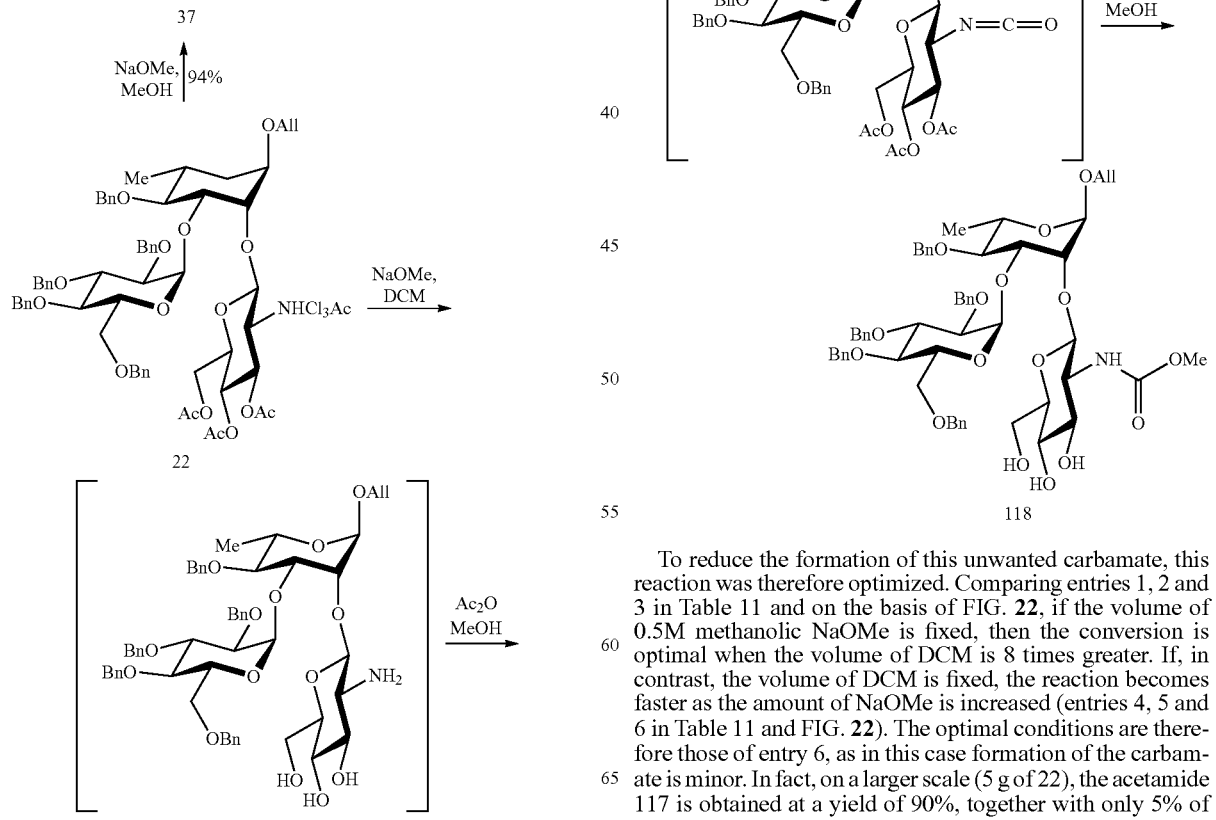

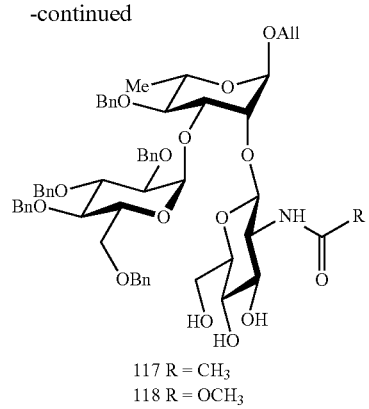

117 R = CH$_3$
118 R = OCH$_3$

However, conversion of the trichloroacetamide function to acetamide is made difficult by the presence of a secondary compound 118, a methyl carbamate, whose structure is very similar to that of the desired acetamide 117. Formation of this carbamate 118 can be explained by a probable transition via an unstable isocyanate, which then reacts with an alcohol, in this case the methanol used as solvent for the reaction, to give the corresponding carbamate[116] (Scheme 67).

Scheme 67: Mechanism assumed for formation of the byproduct 28

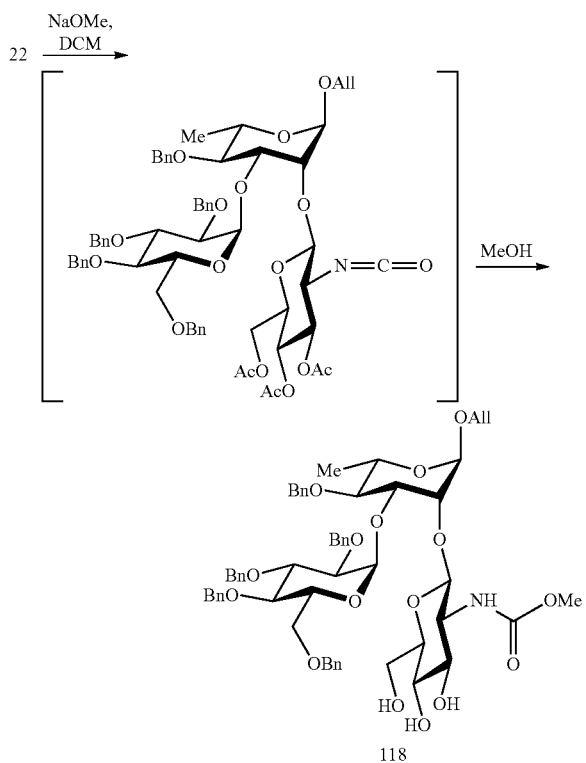

To reduce the formation of this unwanted carbamate, this reaction was therefore optimized. Comparing entries 1, 2 and 3 in Table 11 and on the basis of FIG. 22, if the volume of 0.5M methanolic NaOMe is fixed, then the conversion is optimal when the volume of DCM is 8 times greater. If, in contrast, the volume of DCM is fixed, the reaction becomes faster as the amount of NaOMe is increased (entries 4, 5 and 6 in Table 11 and FIG. 22). The optimal conditions are therefore those of entry 6, as in this case formation of the carbamate is minor. In fact, on a larger scale (5 g of 22), the acetamide 117 is obtained at a yield of 90%, together with only 5% of carbamate 118.

TABLE 11

Investigation of reduction of the trichloroacetamide function

| Entry | NaOMe (0.5M) | $V_{NaOMe}/V_{DCM}$ | Time of disappearance of 22 |
|---|---|---|---|
| 1 | 5 eq. | 4 | 3.75 h |
| 2 |  | 8 | 2.5 h |
| 3 |  | 12 | 5.25 h |
| 4 | 2 eq. | 8 | 4 h |
| 5 | 4 eq. |  | 3.25 h |
| 6 | 6 eq. |  | 2 h |

To prepare the equivalent of acceptor 38 in the acetamide series, the triol 117 is protected regioselectively in position $4_D$ and $6_D$ with an isopropylidene group to give the acceptor 119 at a yield of 85%[30, 31] (Scheme 68). It should be noted that the isopropylidene of this acceptor 119 is stable, in contrast to that of acceptor 38 (Section 2).

Scheme 68: First route for access to acceptor 119

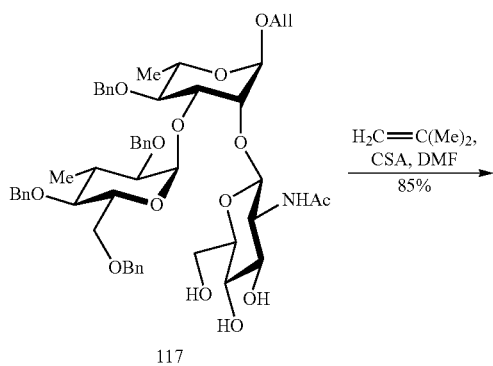

117

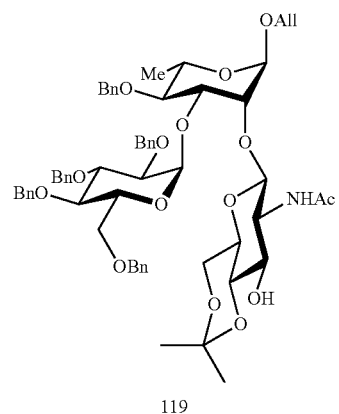

119

Investigation of the Reproducibility of Conversion of the Trichloroacetamide to Acetamide on Other Synthons As this new method of conversion is particularly efficient, it was applied to other intermediates used in our various syntheses, for example the trisaccharide for obtaining the same acceptor 119. Thus, deacetylation of the acetyl function combined with detrichloroacetylation of the amine function of the allyl glycoside 23 made it possible to isolate acceptor 119 at a yield of 90% (Scheme 69). To compare the two routes for access to acceptor 119, the different syntheses were carried out on a large scale (of the order of 5 g) while trying to limit the number of chromatography steps. The results presented in Scheme 69 show that the yields are comparable for these two routes, but are also comparable to the synthesis of acceptor 38 in the trichloroacetamide series (Section 2).

Scheme 69: Second route for access to acceptor 119

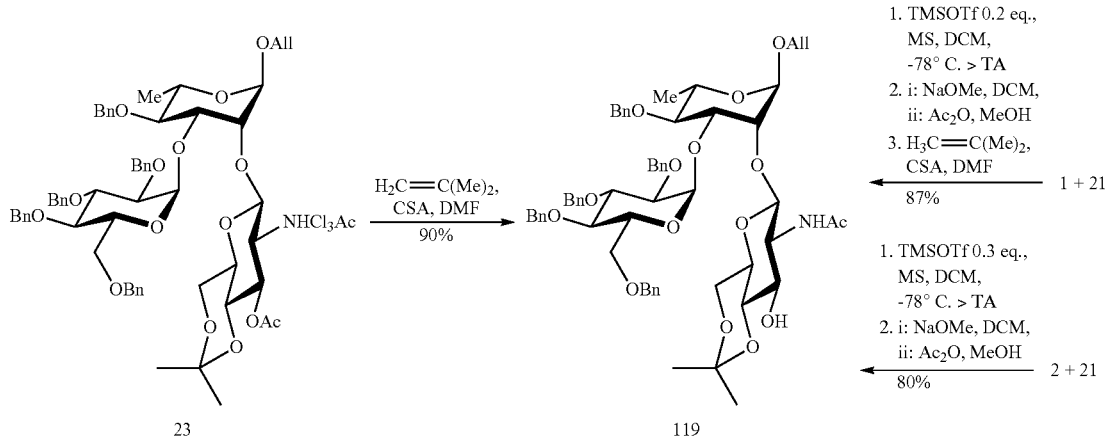

Next, two other synthons were converted to acetamide, according to the same protocol: the pentasaccharide 90 (D(E)ABC Section 3) (660) and the tetrasaccharide 115 at an excellent yield of 83% of 116 (Scheme 70). This new method of conversion has therefore demonstrated its full potential, so that elongation to large oligosaccharides can be envisaged.

Scheme 70: Synthesis of the acceptor 116

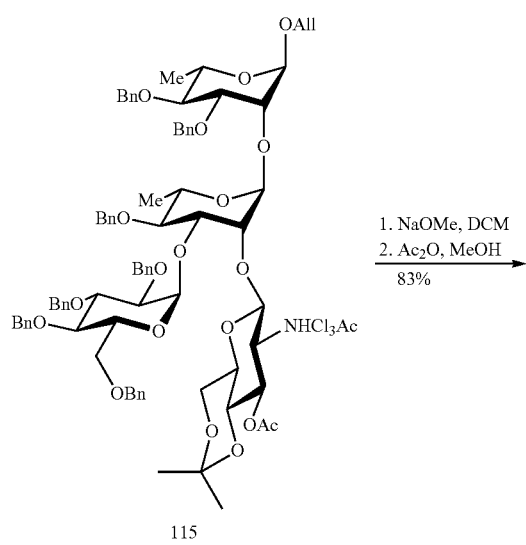

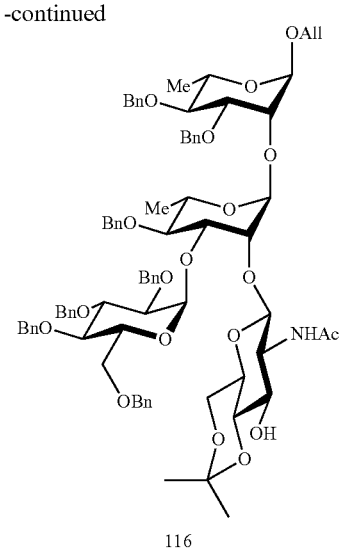

116

Application to Preparation of the Pentasaccharide IX

The tetrasaccharide 116 is condensed on donor 39 in the presence of triflic acid (Scheme 71). The reaction, carried out in toluene, leads to the fully protected pentasaccharide 106' (71%). The isopropylidene function is cleaved by acid hydrolysis to give the diol 106" quantitatively. The latter is debenzylated by hydrogenolysis in the presence of Pd/C. In accordance with the phenomenon already observed for the tetrasaccharide III, the pentasaccharide IX is isolated after purification in the form of a mixture of regioisomers corresponding to the desired product bearing an acetyl function in position $2_C$ and to the product of migration of the acetyl function on the cis-vicinal hydroxyl.

Scheme 71: Synthesis of the pentasaccharide IX

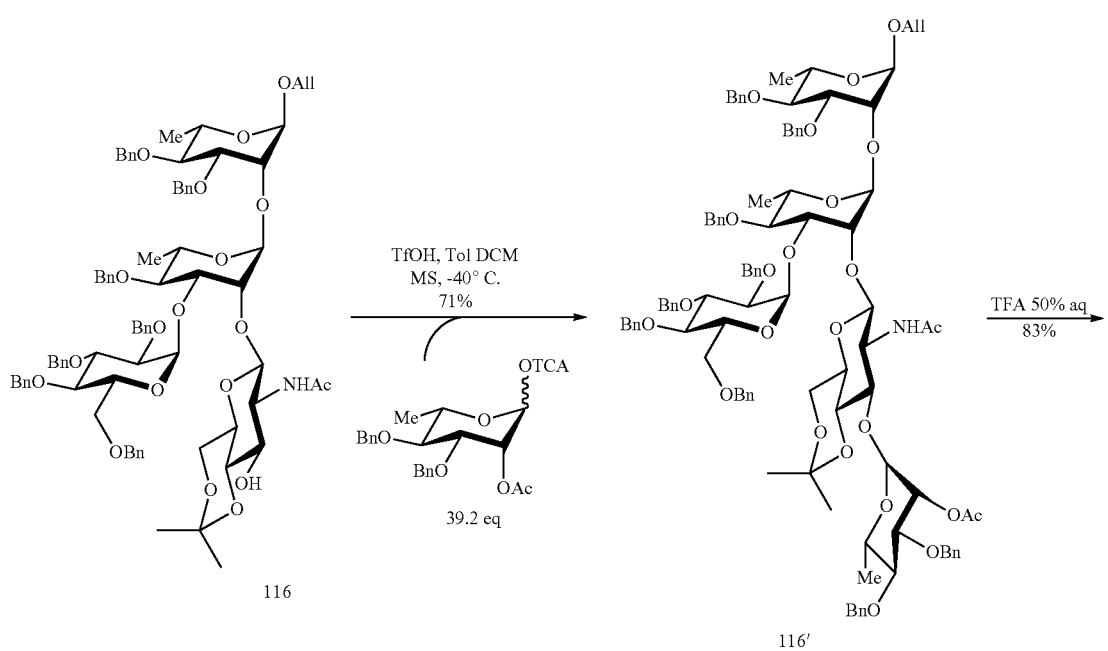

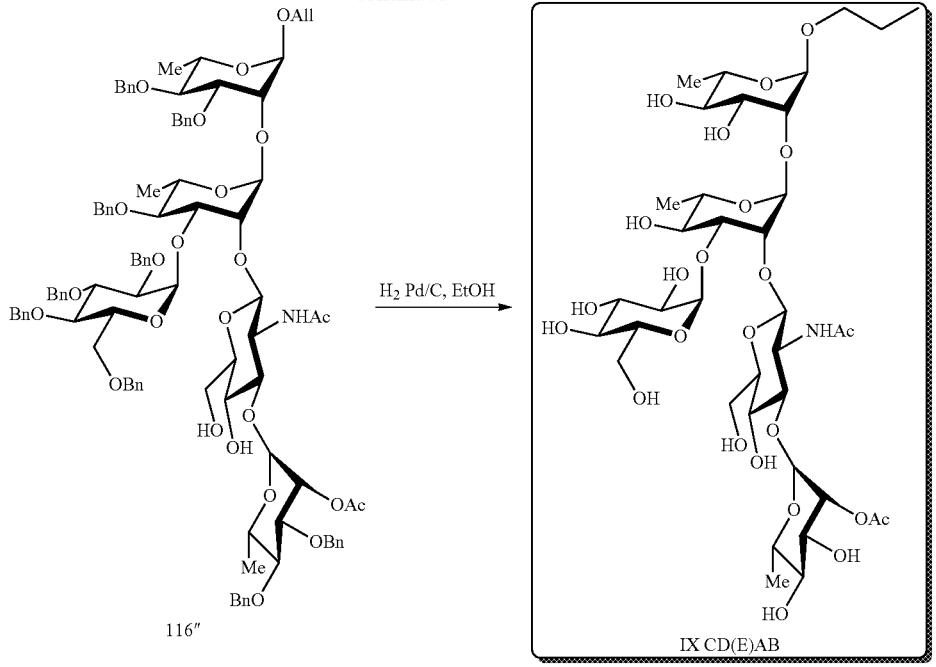

Method 16:

The invention relates to the method of preparation of compound XVII (hexasaccharide $B_{Ac}CD(E)AB$) as defined in list L1 comprising the following stages:

- condensation of the acceptor tetrasaccharide 110 and of the donor disaccharide 47 leading to the hexasaccharides 122 and 123, the condensation reaction preferably being carried out in a solvent such as dichloromethane, 1,2-dichloroethane, ether, toluene, acetonitrile or any other equivalent solvent, in the presence of a Lewis acid such as TMSOTf or triflic acid, preferably in toluene in the presence of TMSOTf (scheme 74);
- cleavage of the isopropylidene group of the hexasaccharide 122 leading to the hexasaccharide 123 preferably in 50% aqueous TFA solution in dichloromethane (scheme 75);
- delevulinoylation of the hexasaccharide 123 leading to the hexasaccharide 124 preferably in a buffered medium in the presence of hydrazine monohydrate (scheme 75);
- deprotection of the hexasaccharide 124 to the hexasaccharide $B_{Ac}CD(E)AB$ preferably at a pressure of 50 bar leading (scheme 76).

4. Hexasaccharide $B_{Ac}CD(E)AB$ (XVII)

As stated above, in the case of the derivative IX, migration of the acetyl function from position $2_C$ on the alcohol vicinal to $3_C$ is observed. To avoid this migration and for complete results of antigenicity, the synthesis of a longer fragment, namely the hexasaccharide $B_{Ac}CD(E)AB$ XVII was envisaged.

a. Investigation of Coupling in the Acetamide Series

Before carrying out the synthesis of this hexasaccharide and as a follow-up to the results obtained for the synthesis of IX, the feasibility of glycosylation in the acetamide series was investigated within the scope of preparation of a pentasaccharide resulting from coupling of acceptor 119 with donor 47 (Scheme 72). Data from the literature[114, 38] and from the laboratory[115, 62], together with the results from section 3, suggest that the acetamide acceptors are less reactive than their trichloroacetamide analogs. Various glycosylation conditions were evaluated (Table 12).

The first tests at −20° C., in toluene and dichloromethane (entries 1 and 2), confirm the low reactivity of acceptor 119. In fact, it is still present in the reaction mixture, whereas the donor 47 quickly decomposes. At −5° C., the yields of 120 are still quite low, whatever solvent is used (entries 3, 4 and 5). For coupling between 19 and 86 (Section 3), the amounts of molecular sieve and of acid were increased for carrying out glycosylation at higher temperature according to the conditions elaborated previously in the laboratory.

TABLE 12

Optimization of coupling of acceptor 119 with donor 47

| Entry | Solvent | Temperature | Activator | Yield |
|---|---|---|---|---|
| 1 | DCM | −20° C. | TMSOTf: 0.3 eq. | 20% |
| 2 | Toluene | −20° C. | | 25% |
| 3 | THF | −5° C. | | Not observed |
| 4 | Acetonitrile | −5° C. | | 35% |
| 5 | Ether | −5° C. | | 50% |
| 6 | Toluene | 0° C.→70° C. | TfOH: 0.9 eq. | 71% |
| 7 | Toluene | 0° C. | | 71% |

These conditions were therefore applied to this new coupling (entries 6 and 7). The yields of 120 are identical, which seems to indicate that the optimal temperature is 0° C. (Scheme 72).

Scheme 72: Glycosylation between acceptor 119 and donor 47

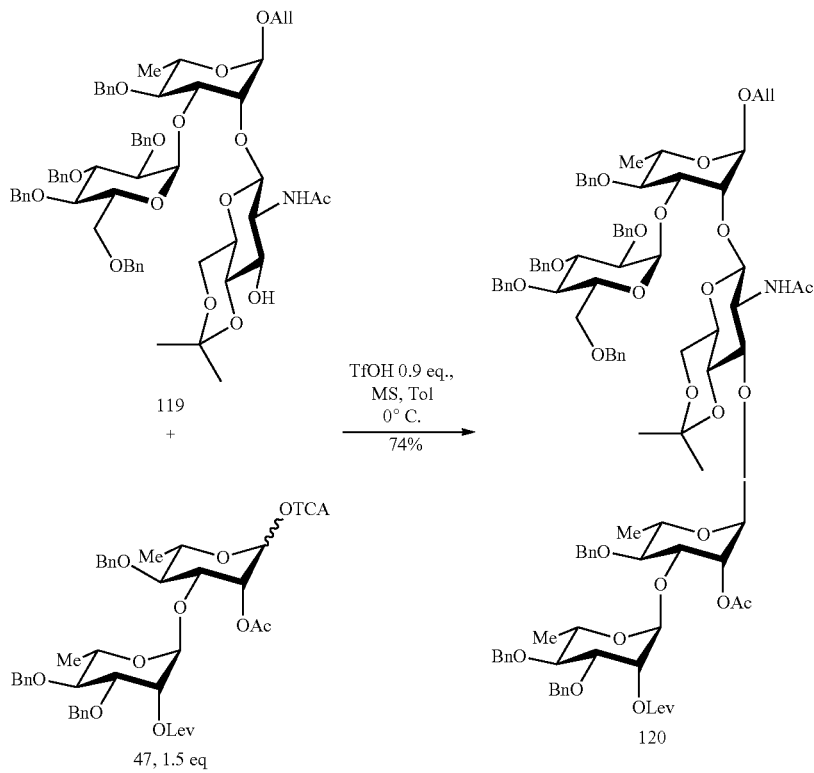

This result was confirmed for the acetamide acceptor 116. In fact, at 0° C. and in the presence of TMSOTf (0.9 eq.), the hexasaccharide 121 is isolated at a yield of 65% (Scheme 73). It should be noted that the use of TMSOTf or of TfOH (entry 7 or Scheme 73) did not, in our case, have any effect, since the yields are equivalent. Despite these encouraging results for the pentasaccharide 120 and the hexasaccharide 121, NMR analysis of all these glycosylation products shows that a contaminant, which is co-eluted with the latter, is always present. Separation of this contaminant was undertaken during the stages of deprotection, either of the acetal or of the levulinoyl function. However, the reaction of delevulinoylation of 120 never went to completion, and deacetalation of 120 made it possible to obtain the expected diol, but still contaminated. The contaminant could not be isolated or identified. Thus, before continuing the synthesis, a comparison was conducted with the trichloroacetamide series.

Scheme 73: Glycosylation between acceptor 116 and donor 47

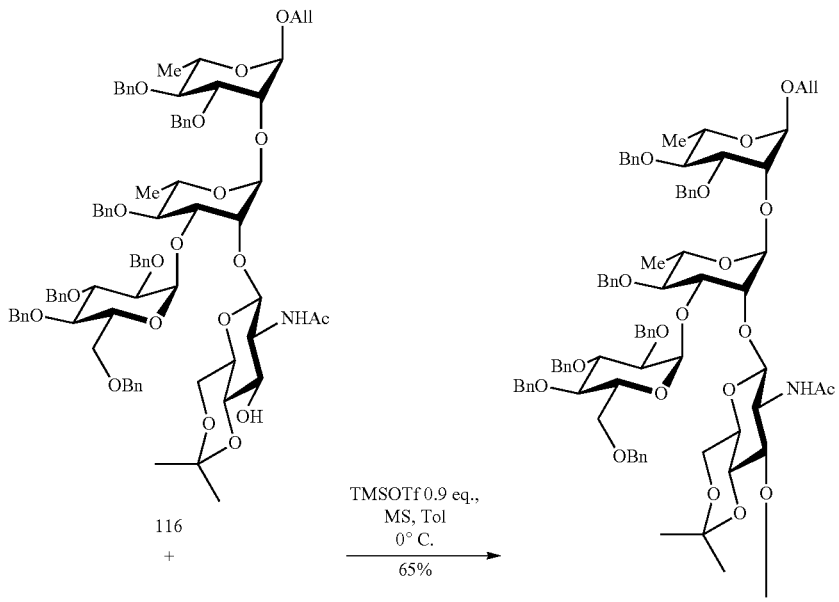

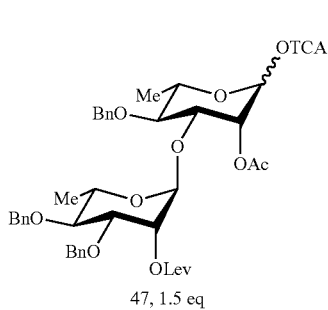

47, 1.5 eq

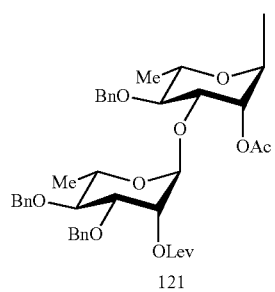

121 b. Investigation of Coupling in the Trichloroacetamide Series

The optimal temperature (−40° C.), determined during investigation of coupling between the trisaccharide 38 and the donor 47 (Section 2), was tested during glycosylation between the tetrasaccharide 110 and the same donor 47 (Table 13). In dichloromethane (entry 1), degradation of the isopropylidene function is greater than in toluene (entry 2), even if the overall yield of product is similar. As previously for 64, NMR analysis of 123, as well as isopropylidenation (93%, Scheme 74) of the latter made it possible to confirm the loss of isopropylidene as well as the position of glycosylation on the glucosamine unit.

TABLE 13

Investigation of coupling between donor 47 and acceptor 110

| Entry | Solvents | Reaction time | 122 | 123 |
|---|---|---|---|---|
| 1 | DCM | 25 min | 20% | 62% |
| 2 | Toluene | 25 min | 30% | 55% |

TABLE 13-continued

Investigation of coupling between donor 47 and acceptor 110

| Entry | Solvents | Reaction time | 122 | 123 |
|---|---|---|---|---|
| 3 | Toluene | 10 min | 59% | 23% |
| 4 | Toluene | 40 min | 59% | 21% |

Entry 3 shows, once again, that the degradation of the isopropylidene can be controlled by maintaining a very short reaction time. However, as the intermediate 123 is involved in the synthesis of the target XVII, glycosylation was reproduced on a large scale (1.7 g of acceptor 110) without controlling this factor, enabling 122 and 123 to be isolated in 75/25 ratio at an overall yield of 80% (entry 4, Scheme 74).

Scheme 74: Glycosylation between acceptor 110 and donor 47

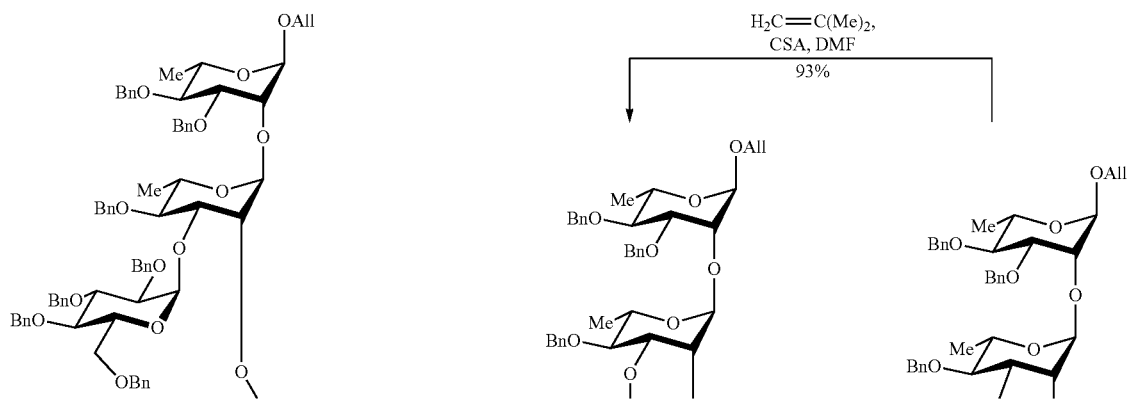

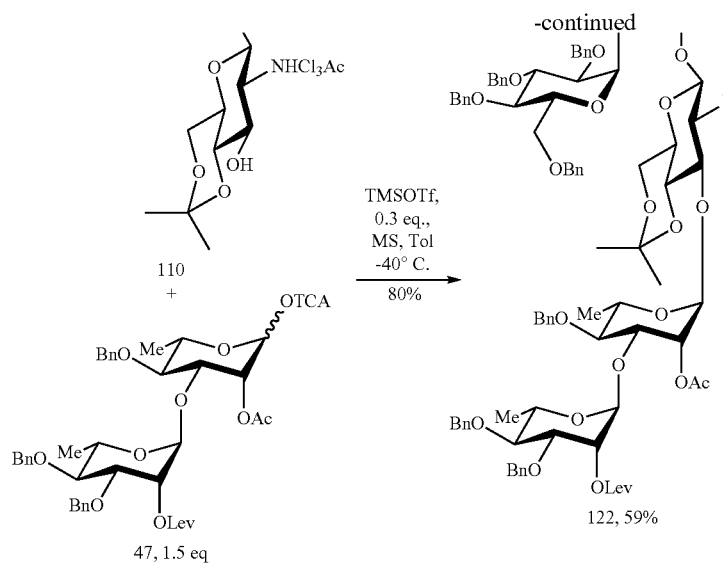
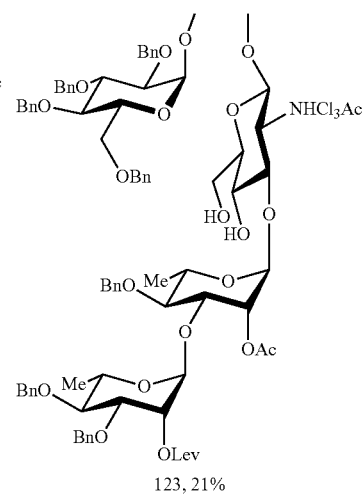
When treated with 50% aqueous TFA solution in dichloromethane[80, 81] the pentasaccharide 122 leads to the diol 123 at a yield of 89%.
Scheme 75: Deacetalation of 122 followed by delevulinoylation of the levulinoyl ester 123
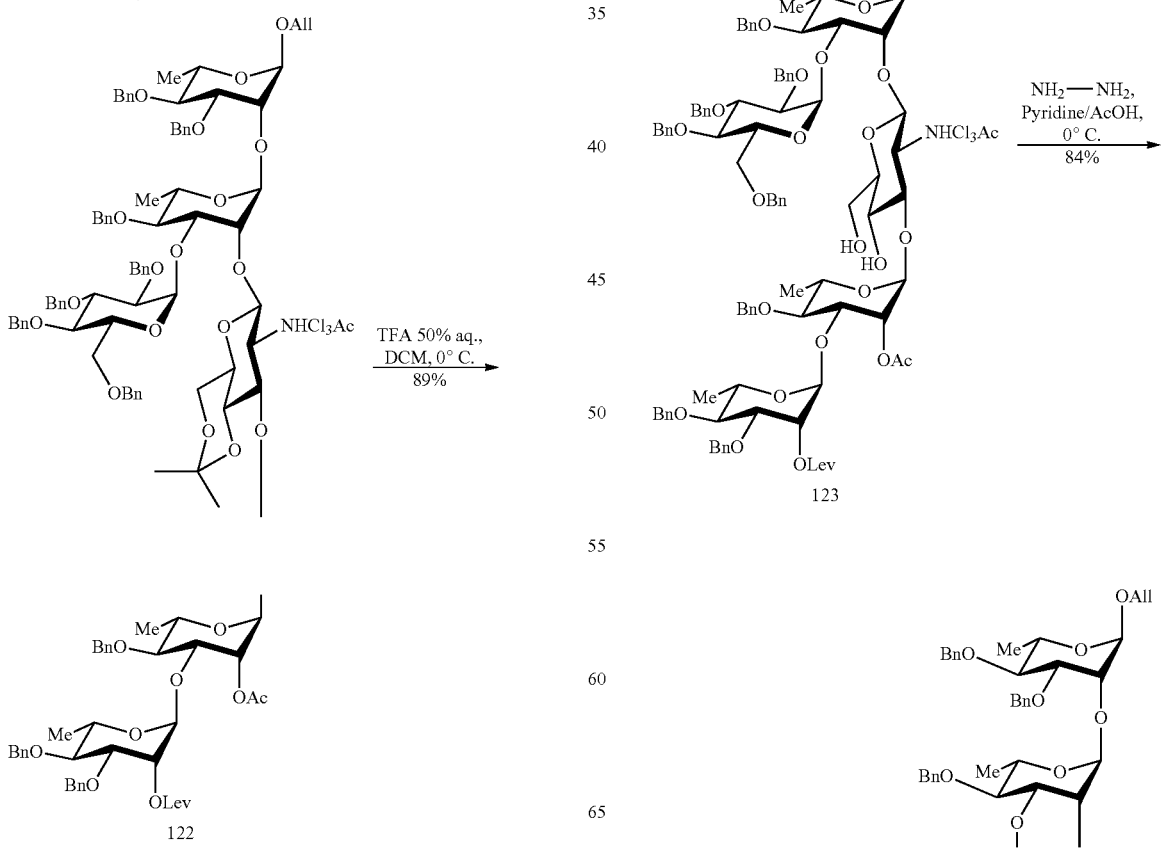

-continued

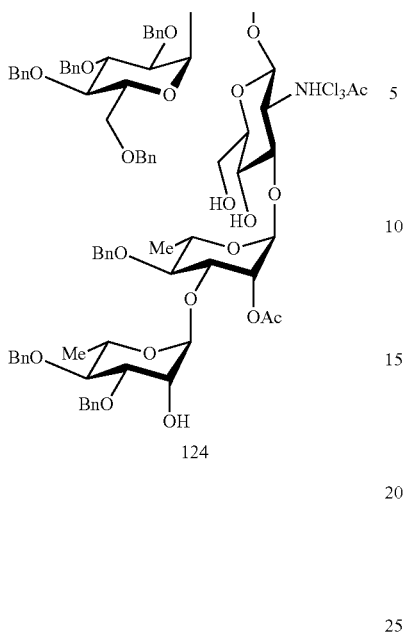

124

Then delevulinoylation is carried out in a buffered medium in the presence of hydrazine monohydrate[89, 97-101] to give the hexasaccharide 124 (84%). By analogy with the synthesis of the targets in Sections 2 and 3, hydrogenolysis of the triol 124 at a pressure of 50 bar leads to the propyl glycoside XVII at a yield of 64% (Scheme 76).

Scheme 76: Hydrogenolysis of the hexasaccharides 124 and 125

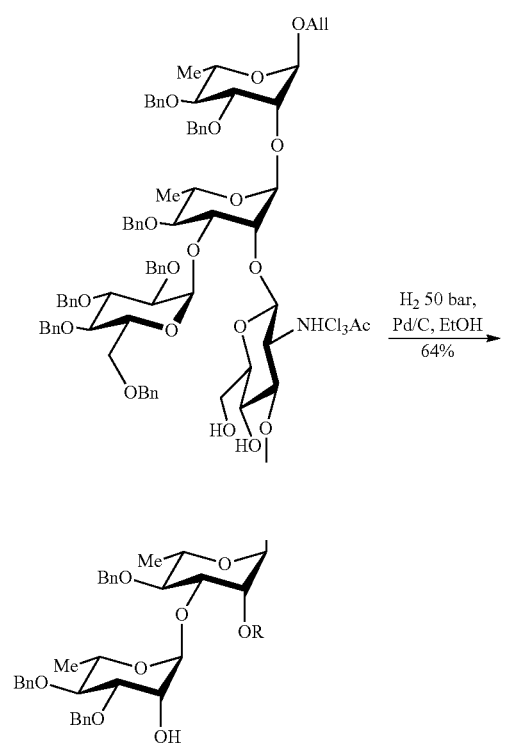

-continued

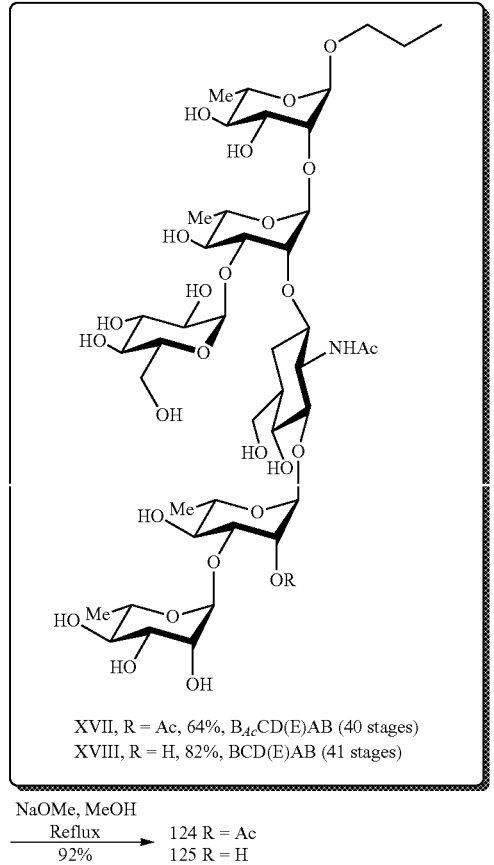

XVII, R = Ac, 64%, $B_{Ac}CD(E)AB$ (40 stages)
XVIII, R = H, 82%, BCD(E)AB (41 stages)

123 $\xrightarrow[92\%]{\text{NaOMe, MeOH} \atop \text{Reflux}}$ 124 R = Ac
125 R = H Method 17:
The invention relates to the method of preparation of compound XVIII (hexasaccharide $B_CCD(E)AB$) as defined in list L1 comprising the following stages:
  condensation of the acceptor tetrasaccharide 110 and of the donor disaccharide 47 leading to the hexasaccharides 122 and 123, the condensation reaction preferably being carried out in a solvent such as dichloromethane, 1,2-dichloroethane, ether, toluene, acetonitrile or any other equivalent solvent, in the presence of a Lewis acid such as TMSOTf or triflic acid, preferably in toluene in the presence of TMSOTf (scheme 74);
  cleavage of the isopropylidene group of the hexasaccharide 122 leading to the hexasaccharide 123 preferably in 50% aqueous TFA solution in dichloromethane (scheme 75);
  transesterification of the hexasaccharide 123 leading to the hexasaccharide 125 preferably in the presence of NaOMe with methanol reflux (scheme 76);
  deprotection of the hexasaccharide 125 leading to the hexasaccharide $B_{Ac}CD(E)AB$ preferably under pressure, for example at a pressure of 50 bar (scheme 76). Deacetylation of the triol 124 in the presence of NaOMe with methanol reflux leads to the tetraol 125 at a yield of 92%. Finally, hydrogenation, carried out in the same conditions as for the target XVII, makes it possible to isolate the propyl glycoside XVIII at a yield of 82% (Scheme 76).

5. Conclusion

In addition to the synthesis of the tri-(VII), tetra-(VIII), and pentasaccharides (IX), and synthesis of the two hexasaccharides XVII and XVIII, the difference in reactivity between the acetamide acceptors 119 and 116 with the trichloroacetamide acceptors 38 and 110, respectively, was also investigated, and the lower reactivity of acceptors of the N-acetylglucosamine type was confirmed. In fact, in all our tests with acceptors of this type, the yields remain lower and the presence of a contaminant means that the synthesis of the targets cannot continue. Even if loss of the isopropylidene is observed in the trichloroacetamide series, acetalation can be carried out again on the raw product from glycosylation without loss of product.

Moreover, the yields in hydrogenolysis of the trichloroacetamide derivatives 124 or 125 are comparable to the yields in deprotection of the acetamide intermediates (Section 2, 3 and 4). Continuing in the trichloroacetamide series throughout the synthesis and reducing this function during the stage of final deprotection is therefore the best strategy for the synthesis of higher oligosaccharides.

Experimental Application of Methods 13 to 17
Method 13:

Allyl(2,3,4,6-tetra-O-benzyl-α-D-glucopyranosyl)-(1→3)-(4-O-benzyl-2-O-levulinoyl-α-L-rhamnopyranosyl)-(1→2)-3,4-di-O-benzyl-α-L-rhamnopyranoside 107

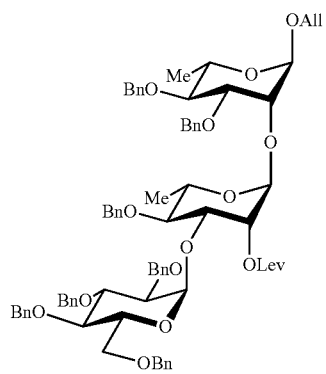

Chemical Formula: $C_{75}H_{84}O_{16}$
Exact Mass: 1240.5759
Molecular Weight: 1241.4599

TMSOTf (210.0 µL, 1.2 mmol, 0.3 eq.) is added to a solution of acceptor 58 (1.5 g, 3.9 mmol) and donor 80 (5.1 g, 5.1 mmol, 1.3 eq.) in Tol (100 mL), in the presence of molecular sieve 4 Å (3.4 g), stirred under argon at −78° C. After 15 min at this temperature, the ethanol-dry ice bath is withdrawn and stirring is continued for 30 min, after which time monitoring by TLC (Tol/EtOAc, 85/15) indicates the disappearance of 58 (Rf=0.25) and the appearance of a new, less polar compound (Rf=0.5). The reaction is stopped by adding triethylamine (1 mL), then the reaction mixture is filtered and concentrated in a rotary evaporator. The yellow oil obtained is purified by silica gel chromatography (Tol/EtOAc, 95/5→85/15) to obtain the allyl glycoside 107 in the form of a colorless oil (4.5 g, 92%).

Rf=0.5 (Tol/EtOAc, 85/15).

$^1$H NMR (CDCl$_3$), δ7.45-7.12 (m, 35H, CH$_{Ph}$), 5.87 (m, 1H, CH═), 5.61 (m, 1H, H-2$_A$), 5.32 (d, 1H, J$_{1,2}$=3.4 Hz, H-1$_E$), 5.31 (m, 1H, J$_{trans}$=17.2 Hz, ═CH$_2$), 5.23 (m, 1H, J$_{cis}$=10.3 Hz, ═CH$_2$), 5.06 (d, 1H, J=10.5 Hz, H$_{Bn}$), 5.05 (d, 1H, J$_{1,2}$=2.2 Hz, H-1$_A$), 5.00-4.89 (m, 5H, H$_{Bn}$), 4.82 (d, 1H, J=12.2 Hz, H$_{Bn}$), 4.81 (bs, 1H, H-1$_B$), 4.74-4.64 (m, 5H, H$_{Bn}$), 4.53 (d, 1H, J=11.0 Hz, H$_{Bn}$), 4.38 (d, 1H, J=12.0 Hz, H$_{Bn}$), 4.26 (dd, 1H, J$_{2,3}$=3.2 Hz, J$_{3,4}$=9.6 Hz, H-3$_A$), 4.20-4.09 (m, 3H, H$_{All}$, H-3$_E$, H-5$_E$), 4.03 (dd, 1H, J$_{2,3}$=2.9 Hz, H-2$_B$), 3.97 (m, 1H, H$_{All}$), 3.96-3.90 (m, 2H, H-5$_A$, H-3$_B$), 3.83 (pt, 1H, J$_{4,5}$=9.5 Hz, H-4$_E$), 3.75 (dq, 1H, J$_{4,5}$=9.4 Hz, H-5$_B$) 3.71-3.66 (m, 2H, H-6a$_E$, H-2$_E$), 3.63-3.57 (m, 2H, H-4$_A$, H-6b$_E$), 3.53 (pt, 1H, J$_{4,5}$=9.4 Hz, H-4$_B$), 2.55 (m, 4H, 2CH$_{2Lev}$), 2.11 (s, 3H, CH$_{3Lev}$), 1.42 (d, 3H, J$_{5,6}$=6.2 Hz, H-6$_A$), 1.37 (d, 3H, J$_{5,6}$=6.2 Hz, H-6$_B$).

$^{13}$C NMR (CDCl$_3$), δ206.2 (C$_{Lev}$), 171.8 (C$_{Lev}$), 138.7-137.7 (C$_{Ph}$), 133.9 (CH═), 129.1-127.6 (CH$_{Ph}$), 117.2 (═CH$_2$), 99.2 (C-1$_A$, $^1$J$_{CH}$=173.4 Hz), 97.9 (C-1$_B$, $^1$J$_{CH}$=170.8 Hz), 92.9 (C-1$_E$, $^1$J$_{CH}$=168.9 Hz), 82.1 (C-3$_E$), 80.5 (C-4$_B$), 79.9 (C-4$_A$), 79.6 (C-3$_B$), 79.5 (C-2$_E$), 77.8 (C-4$_E$), 76.2, 75.6, 75.5, (3C, C$_{Bn}$), 75.1 (C-2$_B$), 75.0, 73.4, 72.8 (3C, C$_{Bn}$), 72.3 (C-3$_A$), 72.2 (C$_{Bn}$), 70.3 (C-5$_E$), 68.4 (C-5$_A$), 68.3 (C-6$_E$), 68.1 (C-5$_B$), 68.0 (C-2$_A$), 67.7 (C$_{All}$), 38.0 (CH$_{2Lev}$), 29.7 (CH$_{3Lev}$), 28.2 (CH$_{2Lev}$), 18.1, 18.0 (C-6$_A$*, C-6$_B$*).

HRMS (ESI$^+$): [M+Na]$^+$ C$_{75}$H$_{84}$O$_{16}$Na m/z theoretical: 1263.5657
m/z measured: 1263.5437
[M+NH$_4$]$^+$ C$_{75}$H$_{84}$O$_{16}$NH$_4$ m/z theoretical: 1258.6104
m/z measured: 1258.5887

Allyl(2,3,4,6-tetra-O-benzyl-α-D-glucopyranosyl)-(1→3)-(2-O-benzoyl-4-O-benzyl-α-L-rhamnopyranosyl)-(1→2)-3,4-di-O-benzyl-α-L-rhamnopyranoside 107'

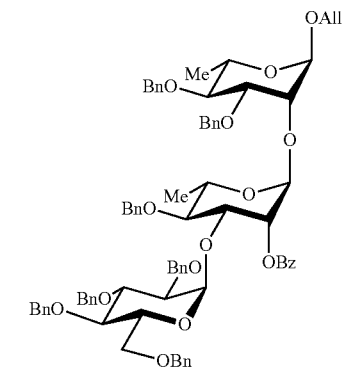

Chemical Formula: $C_{77}H_{82}O_{15}$
Exact Mass: 1246.57
Molecular Weight: 1247.47

Triflic acid (16 µL, 186 µmol, 0.2 eq.) is added to a suspension of acceptor 58 (463 mg, 1.2 mmol), donor 80' (953 mg, 932 µmol) and molecular sieve 4 Å (500 mg) in Tol (10 mL), stirred under argon at −30° C. The reaction is continued while the ethanol-dry ice bath returns to RT (about 1 h). The bath is withdrawn and stirring is continued for 1 h, after which time monitoring by TLC (DCM/EtOAc, 98/2) indicates the presence of a new main compound that is less polar than 58. The reaction is stopped by adding triethylamine (300 µL), then the reaction mixture is filtered and concentrated in a rotary evaporator. The raw reaction product is purified by silica gel chromatography (Chex/EtOAc, 100/0→80/20) to obtain the allyl glycoside 107' in the form of a colorless oil (1.08 g, 93%).

Rf=0.5 (Chex/EtOAc, 8/2).

$^1$H NMR (CDCl$_3$), δ8.09-7.08 (m, 40H, CH$_{Ph}$), 5.89 (m, 1H, CH=), 5.84 (dd, 1H, J$_{1,2}$=2.1 Hz, H-2$_A$), 5.37 (d, 1H, J$_{1,2}$=3.4 Hz, H-1$_E$), 5.28 (m, 1H, J$_{trans}$=17.3 Hz, =CH$_2$), 5.20 (m$_{Superposed}$, 1H, =CH$_2$), 5.19 (m$_{Superposed}$, 1H, H-1$_A$), 5.00 (d, 1H, J=10.2 Hz, H$_{Bn}$), 4.96 (d, 1H, J=10.8 Hz, H$_{Bn}$), 4.86 (d, 1H, J=10.9 Hz, H$_{Bn}$), 4.84 (d, 1H, J=10.9 Hz, H$_{Bn}$), 4.78 (d, 1H, J$_{1,2}$=1.8 Hz, H-1$_B$), 4.75 (d, 1H, J=10.9 Hz, H$_{Bn}$), 4.72 (s, 2H, H$_{Bn}$), 4.67-4.63 (m, 3H, H$_{Bn}$), 4.60 (d, 1H, J=12.1 Hz, H$_{Bn}$), 4.46 (m, 2H, H$_{Bn}$), 4.39 (dd, 1H, J$_{2,3}$=3.1 Hz, J$_{3,4}$=9.8 Hz, H-3$_A$), 4.36 (d, 1H, J=12.0 Hz, H$_{Bn}$), 4.15 (m, 1H, H$_{All}$), 4.08-4.03 (m, 3H, H-3$_E$, H-5$_E$, H-2$_B$), 3.97-3.90 (m, 3H, H$_{All}$, H-5$_A$, H-3$_B$), 3.79 (dd, 1H, J$_{4,5}$=9.4, J$_{3,4}$=9.7 Hz, H-4$_E$), 3.76-3.69 (m, 3H, H-5$_B$, H-6a$_E$, H-4$_A$), 3.62 (dd, 1H, J$_{1,2}$=3.4, J$_{2,3}$=9.7 Hz, H-2$_E$), 3.59 (m, 1H, J$_{5,6}$=1.7 Hz, H-6b$_E$), 3.56 (pt, 1H, J$_{4,5}$=9.4 Hz, H-4$_B$), 1.43 (d, 3H, J$_{5,6}$=6.2 Hz, H-6$_A$), 1.35 (d, 3H, J$_{5,6}$=6.2 Hz, H-6$_B$).

$^{13}$C NMR (CDCl$_3$), δ166.0 (C$_{Bz}$), 139.1-127.7 (C$_{Ph}$), 117.6 (=CH$_2$), 99.6 (C-1$_A$), 98.2 (C-1$_B$), 93.1 (C-1$_E$), 82.4 (C-3$_E$), 80.9 (C-4$_B$), 80.3 (C-4$_A$), 80.1 (C-3$_B$), 79.3 (C-2$_E$), 77.8 (C-4$_E$), 76.7, 76.0, 75.9, 75.3, (4C, C$_{Bn}$), 75.1 (C-2$_B$), 73.8 (C$_{Bn}$), 72.9 (C-3$_A$), 72.6, 72.5 (2C, C$_{Bn}$), 70.6 (C-5$_E$), 68.8 (2C, C-2$_A$, C-5$_B$*), 68.6 (C-6$_E$), 68.4 (C-5$_A$*), 68.0 (C$_{All}$), 18.5, 18.4 (C-6$_A$*, C-6$_B$*).

HRMS (ESI$^+$): [M+Na]$^+$ C$_{77}$H$_{82}$O$_{15}$Na m/z theoretical: 1269.5552
m/z measured: 1269.5563

Allyl(2,3,4,6-tetra-O-benzyl-α-D-glucopyranosyl)-(1→3)-(4-O-benzyl-α-L-rhamnopyranosyl)-(1→2)-3,4-di-O-benzyl-α-L-rhamnopyranoside 108

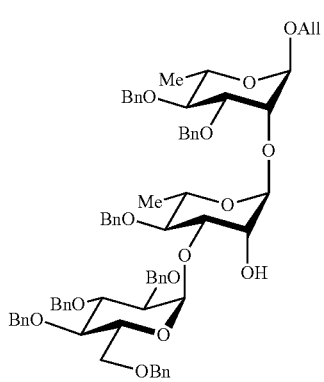

Chemical Formula: C$_{70}$H$_{78}$O$_{14}$
Exact Mass: 1142.5392
Molecular Weight: 1143.3599

Route a.

After adding 0.5 M methanolic NaOMe (2.5 mL, 1.25 mmol, 4 eq.) to the allyl glycoside 107' (385 mg, 308 μmol) in solution in DCM/MeOH mixture 1/1 (10 mL), the reaction mixture is refluxed and stirred for 3 h, after which time monitoring by TLC (Chex/EtOAc, 7/3) indicates the disappearance of 107' and the appearance of a more polar product (Rf=0.6). After it returns to RT, the reaction mixture is neutralized by adding Dowex X8 (H$^+$) ion-exchange resin, and then filtered on a frit. The resin is washed with DCM/MeOH mixture and the solvents are evaporated. The yellow oil obtained is purified by silica gel flash chromatography (Chex/EtOAc, 10/0→7/3) to give the alcohol 108 in the form of a colorless oil (303 mg, 86%).

Route b.

After adding 0.5 M methanolic NaOMe (12.2 mL, 6.1 mmol, 1.7 eq.) to the allyl glycoside 107 (4.5 g, 3.6 mmol) in solution in MeOH (200 mL), the reaction mixture is refluxed and stirred for 1 h, after which time monitoring by TLC (Chex/EtOAc, 7/3) indicates the disappearance of 107 (Rf=0.5) and the appearance of a more polar product (Rf=0.6). After it returns to RT, the reaction mixture is neutralized by adding Dowex X8 (H$^+$) ion-exchange resin, then filtered on a frit. The resin is washed with DCM/MeOH mixture and the solvents are evaporated. The yellow oil obtained is purified by silica gel chromatography (Tol/EtOAc, 98/2→9/1) to give the alcohol 108 in the form of a colorless oil (3.9 g, 94%).

Rf=0.6 (Chex/EtOAc, 7/3).

$^1$H NMR (CDCl$_3$), δ7.47-7.19 (m, 35H, CH$_{Ph}$), 5.93 (m, 1H, CH=), 5.32 (m, 1H, J$_{trans}$=17.2 Hz, =CH$_2$), 5.25 (m, 1H, J$_{cis}$=10.3 Hz, =CH$_2$), 5.22 (bs, 1H, H-1$_A$), 5.05-4.99 (m, 3H, H$_{Bn}$), 4.97 (d, 1H, J$_{1,2}$=3.5 Hz, H-1$_B$), 4.91-4.88 (m, 2H, H$_{Bn}$), 4.84 (d, 1H, J$_{1,2}$=1.6 Hz, H-1$_E$), 4.83-4.67 (m, 6H, H$_{Bn}$), 4.60 (d, 1H, J=12.0 Hz, H$_{Bn}$), 4.54 (d, 1H, J=11.0 Hz, H$_{Bn}$), 4.36 (d, 1H, J=12.0 Hz, H$_{Bn}$), 4.19 (m, 1H, H$_{All}$), 4.14-4.09 (m, 4H, H-2$_A$, H-2$_B$, H-3$_A$, H-3$_E$), 4.04-3.95 (m, 3H, H$_{All}$, H-5$_E$, H-3$_B$), 3.92 (dq, 1H, J$_{4,5}$=9.7 Hz, H-5$_A$), 3.80 (pt, 1H, J$_{4,5}$=9.8 Hz, H-4$_E$), 3.75 (pt, 1H, J$_{4,5}$=9.4 Hz, H-5$_B$), 3.66 (dd, 1H, J$_{2,3}$=3.6 Hz, J$_{3,4}$=9.6 Hz, H-2$_E$), 3.75 (pt, 1H, J$_{3,4}$=9.3 Hz, H-4$_A$), 3.55-3.49 (m, 2H, H-6a$_E$, H-4$_B$), 3.45 (dd, 1H, J$_{5,6aE}$=1.8 Hz, J$_{6aE,6bE}$=10.8 Hz, H-6b$_E$), 1.43 (d, 3H, J$_{5,6}$=6.3 Hz, H-6$_A$), 1.39 (d, 3H, J$_{5,6}$=6.2 Hz, H-6$_B$).

RMN $^{13}$C (CDCl$_3$), δ138.7-137.6 (C$_{Ph}$), 133.9 (CH=), 129.1-127.0 (CH$_{Ph}$), 117.2 (=CH$_2$), 101.0 (C-1$_A$, $^1$J$_{CH}$=170.3 Hz), 98.1 (C-1$_B$, $^1$J$_{CH}$=170.3 Hz), 94.0 (C-1$_E$, $^1$J$_{CH}$=166.7 Hz), 82.4 (C-3$_E$), 80.6 (C-4$_B$), 80.0 (C-3$_B$), 79.3 (C-4$_A$), 79.0 (C-2$_E$), 77.8 (C-4$_E$), 76.5 (C-3$_A$), 75.6, 75.6, 75.5 (3C, C$_{Bn}$), 75.0 (C-2$_B$), 74.9, 74.4, 73.4, 72.5 (4C, C$_{Bn}$), 70.7 (C-5$_E$), 68.1 (C-5$_B$), 68.0 (C-6$_E$), 67.7 (C-5$_A$), 67.7 (C$_{All}$), 67.4 (C-2$_A$), 18.0, 17.9 (C-6$_A$*, C-6$_B$*).

HRMS (ESI$^+$): [M+Na]$^+$ C$_{70}$H$_{78}$O$_{14}$Na m/z theoretical: 1165.5289
m/z measured: 1165.5283
[M+NH$_4$]$^+$ C$_{70}$H$_{78}$O$_{14}$NH$_4$ m/z theoretical: 1160.5735
m/z measured: 1160.5674

Propyl α-D-glucopyranosyl-(1→3)-α-L-rhamnopyranosyl-(1→2)-α-L-rhamnopyranoside VII

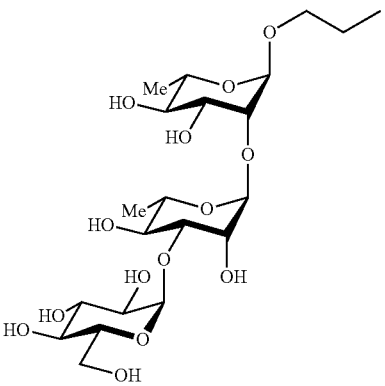

Chemical Formula: C$_{21}$H$_{38}$O$_{14}$
Exact Mass: 514.23
Molecular Weight: 514.52

Pd/C 10% (250 mg) is added to a degassed solution of alcohol 108 (260 mg, 209 μmol) in ethanol (10 mL) supplemented with 1M hydrochloric acid (155 μL). The suspension is placed under hydrogen atmosphere (1 bar) and stirred overnight at RT. Monitoring by TLC (iPrOH/H$_2$O/NH$_3$, 7/1/02) shows the disappearance of 108 and the appearance of a new, more polar compound. The reaction mixture is filtered on Celite, and the filtrate is concentrated in a rotary evaporator. The residue obtained is purified by HPLC (Kromasil C-18 column, 0.01 M aqueous TFA/CH$_3$CN, 100/0→60/40 in 20 min, 5 mL/min, 215 nm) to give the free tetrasaccharide VII in the form of a white powder after lyophilization (83 mg, 77%).

Rf=0.5 (iPrOH/H$_2$O/NH$_3$, 4/1/2).

$^1$H NMR (D$_2$O), δ5.09 (d, 1H, $J_{1,2}$=387 Hz, H-1$_E$), 4.98 (d, 1H, $J_{1,2}$=1.7 Hz, H-1$_A$), 4.88 (d, 1H, $J_{1,2}$=1.2 Hz, H-1$_C$), 4.25 (m, 1H, H-2$_A$), 3.94 (m, 1H, H-5$_E$), 3.90 (dd, 1H, H-2$_B$), 3.85-3.49 (m, 6H, H-3$_A$, H-3$_B$, H-3$_E$, H-6a$_E$, H-6b$_E$, H-5$_A$), 3.69 (dq, 1H, $J_{4,5}$=9.6 Hz, H-5$_B$), 3.64-3.48 (m, 4H, OCH$_2$, H-2$_E$, H-4$_A$, OCH$_2$), 3.52 (m, 1H, H$_{Pr}$), 3.44 (t, 2H, H-4$_E$, H-4$_B$) 1.59 (sex, 2H, CH$_2$), 1.27 (d, 6H, $J_{5,6}$=6.2 Hz, H-6$_A$, H-6$_C$), 0.90 (t, 3H, J=7.4 Hz, CH$_3$).

$^{13}$C NMR (D$_2$O), δ 102.4 (C-1$_C$, $^1J_{CH}$=175 Hz), 99.0 (C-1$_B$, $^1J_{CH}$=170.5 Hz), 95.7 (C-1$_E$, $^1J_{CH}$=168.8 Hz), 79.5 (C-2$_B$), 75.6 (C-3$_A$), 72.6 (C-4$_2$*), 72.1 (C-2$_E$), 71.8 (C-5$_E$), 70.7 (C-3$_B$), 70.5 (C-4$_A$), 70.2 (C$_{Pr}$), 69.9 (C-4$_E$), 69.7 (C-5$_A$), 69.1 (C-5$_B$), 67.1 (C-2$_A$), 60.8 (C-6$_E$), 22.3 (CH$_2$), 17.2, 17.0 (C-6$_A$, C-6$_B$), 10.3 (CH$_3$). MS (ESI$^+$) for C$_{29}$H$_{51}$NO$_1$ m/z theoretical 514.2. found 515.1 [M+H]$^+$.

Method 14:

Allyl(2-deoxy-4,6-O-isopropylidene-3-O-levulinoyl-2-trichloroacetamido-β-D-glucopyranosyl)-(1→2)-[2,3,4,6-tetra-O-benzyl-α-D-glucopyranosyl-(1→3)]-4-O-benzyl-α-L-rhamnopyranoside 111

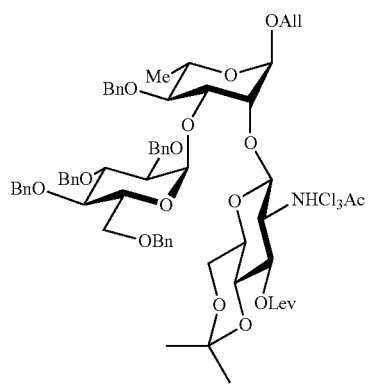

Chemical Formula: C$_{66}$H$_{76}$Cl$_3$NO$_{17}$
Exact Mass: 1259.4179
Molecular Weight: 1261.6651

The alcohol 38 (2.0 g, 1.7 mmol) is dissolved in DCM (15 mL), then DMAP (420 mg, 3.4 mmol, 2 eq.) is added to the reaction mixture. In another flask, DCC (532 mg, 2.6 mmol, 1.5 eq.) and levulinic acid (317 μL, 3.0 mmol, 1.8 eq.) are stirred in DCM (15 mL) and then added to the reaction mixture. The reaction mixture is then stirred for 1 h, after which time monitoring by TLC (Tol/EtOAc, 7/3) shows the formation of a less polar main compound (Rf=0.5) and the disappearance of 38 (Rf=0.35). The DCU is filtered on Celite and the filtrate is taken up in H$_2$O (15 mL). The aqueous phase is extracted with DCM (3×100 mL). The organic phases are combined and washed with NaHCO$_{3sat}$ solution (3×50 mL), NaCl$_{sat}$ solution (3×50 mL), filtered on a phase-separating filter and concentrated in a rotary evaporator. The oil obtained is purified by silica gel chromatography (Tol/EtOAc, 85/15→8/2) to give the levulinoyl ester 111 (1.9 g, 90%).

Rf=0.5 (Tol/EtOAc, 7/3).

$^1$H NMR (CDCl$_3$), δ7.44-7.08 (m, 26H, NH, CH$_{Ph}$), 5.94 (m, 1H, CH=), 5.29 (m, 1H, $J_{trans}$=17.2 Hz, =CH$_2$), 5.21 (m, 1H, $J_{cis}$=10.4 Hz, =CH$_2$), 5.11 (d, 1H, $J_{1,2}$=3.5 Hz, H-1$_E$), 5.10-5.07 (m, 4H, H$_{Bn}$), 4.80-4.69 (m, 5H, H-1$_A$, H$_{Bn}$, H-3$_D$, H$_{Bn}$, H-1$_D$), 4.59-4.54 (m, 2H, H$_{Bn}$), 4.90 (d, 1H, J=11.0 Hz, H$_{Bn}$), 4.32 (d, 1H, J=12.0 Hz, H$_{Bn}$), 4.18-4.07 (m, 5H, H$_{All}$, H-2$_D$, H-3$_E$, H-3$_A$, H-5$_E$), 3.99 (m, 1H, $J_{1,2}$=2.3 Hz, $J_{2,3}$=4.8 Hz, H-2$_A$), 3.94 (m, 1H, H$_{All}$), 3.90 (dd, 1H, $J_{1,2}$=3.6 Hz, $J_{2,3}$=9.7 Hz, H-2$_E$), 3.85 (dd, 1H, $J_{5,6a}$=5.4 Hz, $J_{6a,6b}$=10.7 Hz, H-6a$_D$), 3.79 (pt, 1H, $J_{3,4}$=10.0 Hz, H-4$_E$), 3.74-3.69 (m, 2H, H-6b$_D$, H-5$_A$), 3.67 (pt, 1H, $J_{3,4}$=9.6 Hz, H-4$_D$), 3.45 (pt, 1H, $J_{3,4}$=9.6 Hz, H-4$_A$), 3.41 (m, 2H, H-6a$_E$, H-6b$_E$), 2.76-2.63 (m, 5H, H-5$_D$, 2CH$_{2Lev}$), 2.20 (s, 3H, CH$_{3Lev}$), 1.47 (s, 3H, H$_{iPr}$), 1.42 (s, 3H, H$_{iPr}$), 1.39 (d, 3H, $J_{5,6}$=6.3 Hz, H-6$_A$).

$^{13}$C NMR (CDCl$_3$), δ206.4 (C$_{Lev}$), 172.6 (C$_{Lev}$), 162.5 (C$_{NTCA}$), 139.0-138.5 (C$_{Ph}$), 134.2 (CH=), 129.6-127.7 (CH$_{Ph}$), 117.6 (=CH$_2$), 101.8 (C-1$_D$, $^1J_{CH}$=163.0 Hz), 100.1 (C$_{iPr}$), 98.7 (C-1$_A$, $^1J_{CH}$=171.6 Hz), 95.1 (C-1$_E$, $^1J_{CH}$=165.2 Hz), 93.2 (CCl$_3$), 83.8 (C-3$_E$), 80.2 (C-4$_A$), 79.3 (C-2$_E$), 79.1 (C-4$_E$), 76.4, 75.5, 75.3 (3C, C$_{Bn}$), 75.0 (C-3$_A$), 74.7 (C$_{Bn}$), 74.6 (C-2$_A$), 73.8 (C$_{Bn}$), 73.3 (C-3$_D$), 71.6 (C-4$_D$), 70.3 (C-5$_E$), 68.7 (C-5$_A$), 68.3, 68.2 (2C, C$_{All}$*, C-6$_E$*), 67.5 (C-5$_D$), 62.4 (C-6$_D$), 56.9 (C-2$_D$), 38.4 (CH$_{2Lev}$), 30.2 (CH$_{3Lev}$), 29.4 (C$_{iPr}$), 28.5 (CH$_{2Lev}$), 19.3 (C$_{iPr}$), 18.3 (C-6$_A$).

HRMS (ESI$^+$): [M+Na]$^+$ C$_{66}$H$_{76}$NO$_{17}$$^{35}$Cl$_3$Na m/z theoretical:
1282.4076
m/z measured:
1282.4189
[M+NH$_4$]$^+$ C$_{66}$H$_{76}$NO$_{17}$$^{35}$Cl$_3$NH$_4$ m/z theoretical:
1277.4523
m/z measured:
1277.4634

(2-Deoxy-4,6-O-isopropylidene-3-O-levulinoyl-2-trichloroacetamido-β-D-glucopyranosyl)-(1→2)-[2,3,4,6-tetra-O-benzyl-α-D-glucopyranosyl-(1→3)]-4-O-benzyl-α-L-rhamnopyranose 112

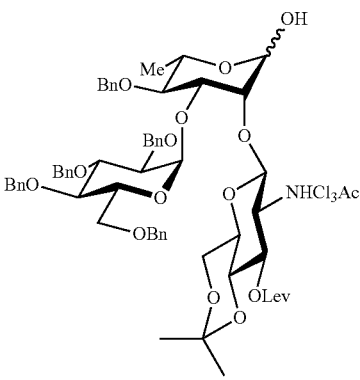

Chemical Formula: C$_{63}$H$_{72}$Cl$_3$NO$_{17}$
Exact Mass: 1219.3866
Molecular Weight: 1221.6013

(1,5-Cyclooctadienebis(methyldiphenylphosphine)-iridium(I)hexafluorophosphate) (30 mg) is dissolved in THF (11 mL) with stirring. The mixture is submitted to cycles of vacuum/argon degassing, 5 cycles of vacuum/hydrogen degassing and is then placed under hydrogen for 15 min. The mixture is then submitted to 5 cycles of vacuum/argon degassing for a second time. The solution of levulinoyl ester 111 (1.8 g, 1.5 mmol) in THF (15 mL) is transferred to the solution of activated catalyst. Monitoring by TLC (Tol/EtOAc, 8/2) shows the disappearance of 111 (Rf=0.5) and the appearance of a somewhat less polar product (Rf=0.55).

Diiodine (740 mg, 2.9 mmol, 2 eq.) in solution in THF/$H_2O$ mixture (8/2, 10 mL) is added to the reaction mixture. Monitoring by TLC (Tol/EtOAc, 8/2 and DCM/MeOH, 98/2) indicates the disappearance of the intermediate (Rf=0.55 and 1, respectively) and the appearance of a new, much more polar compound (Rf=0 and 0.3, respectively). To stop the reaction, 10% $NaHSO_3$ aqueous solution (4 mL) is added in portions to the mixture until the black coloration disappears. The reaction mixture is taken up in DCM (50 mL) and the aqueous phase is extracted with DCM (3×50 mL). The organic phases are combined and washed with $NaCl_{sat}$ solution (3×15 mL), with $H_2O$ (3×15 mL) and then dried on a phase-separating filter and concentrated in a rotary evaporator. The yellow oil obtained is purified by silica gel chromatography (DCM/MeOH, 99/1→97/3) to obtain predominantly the α anomer 112 in the form of a yellow oil (1.4 g, 80%).

Rf=0.3 (DCM/MeOH, 98/2).

$^1$H NMR ($CDCl_3$), δ7.45-7.05 (m, 26H, NH, $CH_{Ph}$), 5.16 (d, 1H, $J_{1,2}$=2.2 Hz, H-1$_A$), 5.14 (d, 1H, $J_{1,2}$=3.7 Hz, H-1$_E$), 5.12-5.07 (m, 4H, $H_{Bn}$), 4.78-4.68 (m, 4H, H-3$_D$, $H_{Bn}$, H-1$_D$, $H_{Bn}$), 4.58-4.44 (m, 3H, $H_{Bn}$), 4.30 (d, 1H, J=12.0 Hz, $H_{Bn}$), 4.21 (dd, 1H, $J_{2,3}$=2.9 Hz, $J_{3,4}$=9.6 Hz, H-3$_A$), 4.16-4.07 (m, 3H, H-2$_D$, H-3$_E$, H-5$_E$), 4.01 (m, 1H, $J_{1,2}$=2.0 Hz, $J_{2,3}$=4.5 Hz, H-2$_A$), 3.95 (dq, 1H, $J_{4,5}$=9.4 Hz, H-5$_A$), 3.90 (dd, 1H, $J_{1,2}$=2.4 Hz, $J_{2,3}$=9.6 Hz, H-2$_E$), 3.85 (dd, 1H, $J_{5,6a}$=5.1 Hz, $J_{6a,6b}$=10.4 Hz, H-6a$_D$), 3.76 (pt, 1H, $J_{3,4}$=9.2 Hz, H-4$_E$), 3.70 (m, 1H, H-6b$_D$), 3.66 (pt, 1H, $J_{3,4}$=9.5 Hz, H-4$_D$), 3.45 (pt, 1H, $J_{3,4}$=9.5 Hz, H-4$_A$), 3.39 (m, 2H, H-6a$_E$, H-6b$_E$), 3.30 (m, 1H, OH-1), 2.77-2.61 (m, 5H, H-5$_D$, $2CH_{2Lev}$), 2.19 (s, 3H, $CH_{3Lev}$), 1.47 (s, 3H, $H_{iPr}$), 1.42 (s, 3H, $H_{iPr}$), 1.38 (d, 3H, $J_{5,6}$=6.2 Hz, H-6$_A$).

$^{13}$C NMR ($CDCl_3$), δ206.2 ($C_{Lev}$), 172.2 ($C_{Lev}$), 162.1 ($C_{NTCA}$), 138.6-137.6 ($C_{Ph}$), 129.3-127.2 ($CH_{Ph}$), 101.4 (C-1$_D$, $^1J_{CH}$=167.7 Hz), 99.7 ($C_{iPr}$), 94.6 (C-1$_E$, $^1J_{CH}$=167.2 Hz), 93.9 (C-1$_A$, $^1J_{CH}$=171.7 Hz), 92.8 ($CCl_3$), 83.4 (C-3$_E$), 79.7 (C-4$_A$), 78.8 (C-2$_E$), 78.7 (C-4$_E$), 76.2, 75.9, 75.1 (3C, $C_{Bn}$), 74.5 (C-2$_A$), 74.4 ($C_{Bn}$), 74.1 (C-3$_A$), 73.3 ($C_{Bn}$), 72.8 (C-3$_D$), 71.2 (C-4$_D$), 69.9 (C-5$_E$), 68.3 (C-5$_A$), 67.8 (C-6$_E$), 67.1 (C-5$_D$), 62.0 (C-6$_D$), 56.4 (C-2$_D$), 38.0 ($CH_{2Lev}$), 29.8 ($CH_{3Lev}$), 28.9 ($C_{iPr}$), 28.0 ($CH_{2Lev}$), 18.9 ($C_{iPr}$), 17.9 (C-6$_A$).

HRMS (ESI$^+$): [M+Na]$^+$ $C_{63}H_{72}NO_{17}{}^{35}Cl_3Na$ m/z theoretical:
1242.3763
m/z measured:
1242.3856

[M+NH$_4$]$^+$ $C_{66}H_{76}NO_{17}{}^{35}Cl_3NH_4$ m/z theoretical:
1237.4209
m/z measured:
1237.4213

(2-Deoxy-4,6-O-isopropylidene-3-O-levulinoyl-2-trichloroacetamido-β-D-glucopyranosyl)-(1→2)-[2,3,4,6-tetra-O-benzyl-α-D-glucopyranosyl-(1→3)]-4-O-benzyl-α-L-rhamnopyranose trichloroacetimidate 109

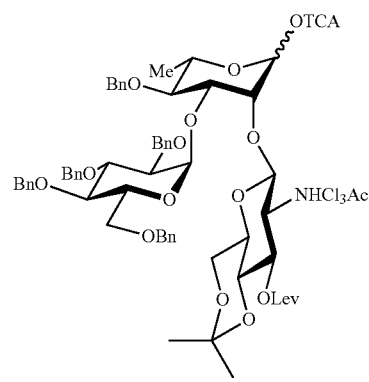

Chemical Formula: $C_{65}H_{72}Cl_6N_2O_{17}$
Exact Mass: 1362.2962
Molecular Weight: 1365.9884

The hemiacetal 112 (1.3 g, 1.1 mmol) is dissolved in DCE (10 mL) and stirred under argon at −5° C. and then DBU (44 μL, 308 μmol, 0.28 eq.) and trichloroacetonitrile (525 μL, 5.2 mmol, 5 eq.) are added. The reaction mixture is stirred at this temperature for 15 min and then it is loaded, without any treatment, on a silica gel column (flash chromatography, Chex/EtOAc+5% NEt$_3$, 7/3→1/1) to obtain the trichloroacetimidate 109 as a yellow oil (1.2 g, 85%).

Rf=0.45 (Chex/EtOAc, 6/4).

$^1$H NMR ($CDCl_3$), δ8.65 (s, 1H, NH), 7.45-7.06 (m, 26H, NH, $CH_{Ph}$), 6.22 (s, 1H, H-1$_A$), 5.11-5.01 (m, 5H, H-1$_E$, 4$H_{Bn}$), 4.80 (pt, 1H, $J_{3,4}$=9.9 Hz, H-3$_D$), 4.78 (m, 2H, $H_{Bn}$) 4.73 (d, 1H, $J_{1,2}$=8.4 Hz, H-1$_D$), 4.57-4.49 (m, 3H, $H_{Bn}$), 4.33 (d, 1H, J=12.9 Hz, $H_{Bn}$), 4.18-4.07 (m, 5H, H-2$_D$, H-3$_A$, H-2$_A$, H-3$_E$, H-5$_E$), 3.93-3.85 (m, 3H, H-5$_A$, H-2$_E$, H-6a$_D$), 3.82-3.74 (m, 2H, H-4$_E$, H-6b$_D$), 3.71 (pt, 1H, $J_{3,4}$=9.6 Hz, H-4$_D$), 3.56 (pt, 1H, $J_{3,4}$=9.6 Hz, H-4$_A$), 3.42 (m, 2H, H-6a$_E$, H-6b$_E$), 2.85 (m, 1H, H-5$_D$), 2.77-2.58 (m, 4H, $2CH_{2Lev}$), 2.20 (s, 3H, $CH_{3Lev}$), 1.49 (s, 3H, $H_{iPr}$), 1.43 (s, 3H, $H_{iPr}$), 1.42 (d, 3H, $J_{5,6}$=6.0 Hz, H-6$_A$).

$^{13}$C NMR ($CDCl_3$), δ206.0 ($C_{Lev}$), 172.3 ($C_{Lev}$), 162.1 ($C_{NTCA}$), 160.2 (C=NH), 138.5-137.4 ($C_{Ph}$), 129.2-127.4 ($CH_{Ph}$), 101.3 (C-1$_D$, $^1J_{CH}$=159.2 Hz), 99.8 ($C_{iPr}$), 96.9 (C-1$_A$, $^1J_{CH}$=182.9 Hz), 95.0 (C-1$_E$, $^1J_{CH}$=165.6 Hz), 92.7 ($CCl_3$), 91.1 ($CCl_3$), 83.3 (C-3$_E$), 79.2 (C-4$_A$), 78.7 (C-2$_E$), 78.6 (C-4$_E$), 76.3, 75.3, 75.0, 74.4 (4C, $C_{Bn}$), 74.3 (C-3$_A$), 73.3 ($C_{Bn}$), 72.7 (C-3$_D$), 72.2 (C-2$_A$), 71.2 (C-4$_D$), 71.1 (C-5$_A$), 70.1 (C-5$_E$), 67.9 (C-6$_E$), 67.3 (C-5$_D$), 61.9 (C-6$_D$), 56.5 (C-2$_D$), 38.0 ($CH_{2Lev}$), 29.8 ($CH_{3Lev}$), 29.0 ($C_{iPr}$), 28.1 ($CH_{2Lev}$), 18.9 ($C_{iPr}$), 17.9 (C-6$_A$).

Allyl(2-deoxy-4,6-O-isopropylidene-3-O-levulinoyl-2-trichloroacetamido-β-D-glucopyranosyl)-(1→2)-([2,3,4,6-tetra-O-benzyl-α-D-glucopyranosyl-(1→3)]-4-O-benzyl-α-L-rhamnopyranosyl)-(1→2)-3,4-di-O-benzyl-α-L-rhamnopyranoside 113

Allyl(2-deoxy-4,6-O-isopropylidene-3-O-levulinoyl-2-trichloroacetamido-β-D-glucopyranosyl)-(1→2)-([2,3,4,6-tetra-O-benzyl-α-D-glucopyranosyl-(1→3)]-4-O-benzyl-β-L-rhamnopyranosyl)-(1→2)-3,4-di-O-benzyl-α-L-rhamnopyranoside 114

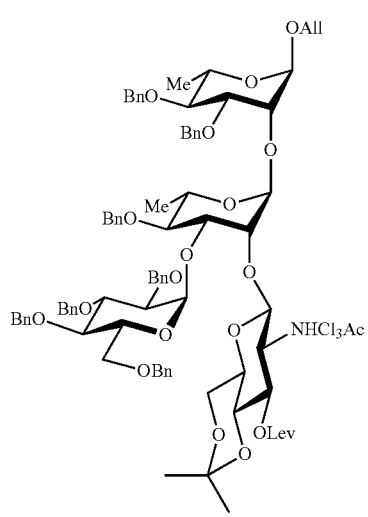

Chemical Formula: $C_{86}H_{98}Cl_3NO_{21}$
Exact Mass: 1585.5697
Molecular Weight: 1588.0514

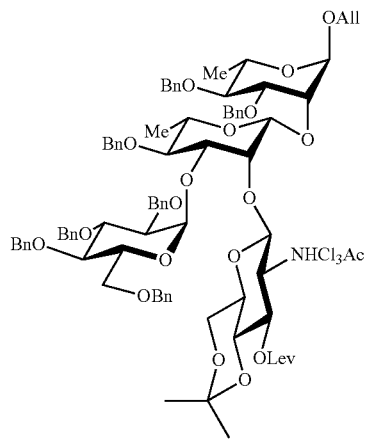

Chemical Formula: $C_{86}H_{98}Cl_3NO_{21}$
Exact Mass: 1585.5697
Molecular Weight: 1588.0514

TMSOTf (10.0 μL, 56 μmol, 0.3 eq.) is added to a solution of acceptor 58 (71 mg, 185 μmol) and donor 109 (380 mg, 280 μmol, 1.5 eq.) in DCM (5 mL), in the presence of molecular sieve 4 Å (160 mg), stirred under argon at −78° C. After stirring for 15 min, monitoring by TLC (Tol/EtOAc, 7/3) indicates the disappearance of 58 (Rf=0.5) and the appearance of two new, more polar compounds (Rf=0.6 and 0.65). The reaction is stopped by adding triethylamine (1 mL), then the reaction mixture is filtered and concentrated in a rotary evaporator. The yellow oil obtained is purified by silica gel chromatography (Tol/EtOAc, 9/1→1/1), obtaining, in the order of elution, the α anomer 113 in the form of a colorless oil (130 mg, 44%), then the β anomer 114 in the form of a colorless oil (130 mg, 44%).

113: Rf=0.65 (Tol/EtOAc, 7/3).

$^1$H NMR (CDCl$_3$), δ: α: 7.49-7.07 (m, 36H, NH, CH$_{Ph}$), 5.89 (m, 1H, CH=), 5.27 (m, 1H, J$_{trans}$=17.2 Hz, =CH$_2$), 5.21 (m, 1H, J$_{cis}$=10.3 Hz, =CH$_2$), 5.16 (d, 1H, J$_{1,2}$=3.6 Hz, H-1$_E$), 5.13-5.05 (m, 5H, H-1$_A$, 4H$_{Bn}$), 4.93 (d, 1H, J=10.8 Hz, H$_{Bn}$), 4.83-4.76 (m, 5H, H-3$_D$, 2H$_{Bn}$, H-1$_D$, H-1$_B$), 4.73-4.48 (m, 6H, H$_{Bn}$), 4.32 (d, 1H, J=12.0 Hz, H$_{Bn}$), 4.20-4.09 (m, 6H, H-3$_E$, H-2$_D$, H-2$_A$, H-3$_A$, H$_{All}$, H-5$_E$), 4.00 (dd, 1H, J$_{1,2}$=2.9 Hz, J$_{2,3}$=5.0 Hz, H-2$_B$), 3.98 (m, 1H, H$_{All}$), 3.95-3.89 (m, 2H, H-3$_B$, H-2$_E$), 3.83 (pt, 1H, J$_{3,4}$=9.2 Hz, H-4$_B$), 3.81 (m, 1H, H-5$_B$), 3.73 (dq, 1H, J$_{4,5}$=9.4 Hz, J$_{5,6}$=6.1 Hz, H-5$_A$), 3.64 (pt, 1H, J$_{3,4}$=9.5 Hz, H-4$_D$), 3.54-3.45 (m, 5H, H-6a$_D$, H-4$_A$, H-4$_B$, H-6a$_E$, H-6b$_E$), 3.38 (m, 1H, H-6b$_D$), 2.77 (m, 1H, H-5$_D$), 2.77-2.62 (m, 4H, 2CH$_{2Lev}$), 2.20 (s, 3H, CH$_{3Lev}$), 1.44 (s, 3H, H$_{iPr}$), 1.40 (d, 3H, J$_{5,6}$=6.3 Hz, H-6$_B$), 1.39 (s, 3H, H$_{iPr}$), 1.32 (d, 3H, J$_{5,6}$=6.2 Hz, H-6$_A$).

$^{13}$C NMR (CDCl$_3$), δ: α: 206.2 (C$_{Lev}$), 172.3 (C$_{Lev}$), 162.2 (C$_{NTCA}$), 138.6-137.5 (C$_{Ph}$), 133.8 (CH=), 129.2-127.3 (CH$_{Ph}$), 117.2 (=CH$_2$), 101.3 (C-1$_D$, $^1$J$_{CH}$=162.0 Hz), 100.9 (C-1$_A$, $^1$J$_{CH}$=171.3 Hz), 99.7 (C$_{iPr}$), 97.9 (C-1$_B$, $^1$J$_{CH}$=170.2 Hz), 94.6 (C-1$_E$, $^1$J$_{CH}$=165.1 Hz), 92.8 (CCl$_3$), 83.4 (C-3$_E$), 80.4 (C-4$_B$), 79.8 (C-4$_A$), 79.5 (C-2$_E$), 78.6 (C-4$_E$), 78.4 (C-3$_B$), 76.1, 75.3, 75.2, 74.9 (4C, C$_{Bn}$), 74.8 (C-2$_B$), 74.4 (C-3$_A$), 74.1 (C$_{Bn}$), 73.8 (C-2$_A$), 73.5 (C$_{Bn}$), 72.9 (C-3$_D$), 72.1 (C$_{Bn}$), 71.3 (C-4$_D$), 69.9 (C-5$_E$), 68.6 (C-5$_B$), 68.0 (C-5$_A$), 67.9 (C-6$_E$), 67.7 (C$_{All}$), 67.2 (C-5$_D$), 61.7 (C-6$_D$), 56.6 (C-2$_D$), 38.0 (CH$_{2Lev}$), 29.7 (CH$_{3Lev}$), 29.0 (C$_{iPr}$), 28.1 (CH$_{2Lev}$), 19.0 (C$_{iPr}$), 18.0 (C-6$_A$), 17.9 (C-6$_B$).

HRMS (ESI$^+$): [M+Na]$^+$ C$_{86}$H$_{98}$NO$_{21}$$^{35}$Cl$_3$Na m/z theoretical:
1608.5594
m/z measured:
1608.5730
[M+NH$_4$]$^+$ C$_{86}$H$_{98}$NO$_{21}$$^{35}$Cl$_3$NH$_4$ m/z theoretical:
1603.6041
m/z measured:
1603.6112

114: Rf=0.6 (Tol/EtOAc, 7/3).

$^1$H NMR (CDCl$_3$), δ: β: 7.66-7.05 (m, 36H, NH, CH$_{Ph}$), 5.89 (m, 1H, CH=), 5.31 (m, 1H, J$_{trans}$=17.2 Hz, =CH$_2$), 5.21 (m, 1H, J$_{cis}$=10.3 Hz, =CH$_2$), 5.20 (s, 2H, H$_{Bn}$), 5.11 (d, 1H, J$_{1,2}$=3.5 Hz, H-1$_E$), 5.05 (d, 2H, H$_{Bn}$), 4.95-4.89 (m, 4H, H-1$_D$, H-3$_D$, 2H$_{Bn}$), 4.86 (m, 1H, J$_{1,2}$=2.7 Hz, H-1$_B$), 4.79 (d, 1H, J=10.5 Hz, H$_{Bn}$), 4.64-4.48 (m, 7H, 3H$_{Bn}$, H-1$_A$, 3H$_{Bn}$), 4.34 (d, 1H, J=12.2 Hz, H$_{Bn}$), 4.30-4.11 (m, 6H, H-2$_D$, H$_{All}$, H-2$_B$, H-2$_A$, H-3$_E$, H-5$_E$), 4.00 (m, 1H, H$_{All}$), 3.99-3.93 (m, 2H, H-3$_B$, H-2$_E$), 3.88 (dd, 1H, J$_{5,6a}$=5.2 Hz, J$_{6a,6b}$=10.6 Hz, H-6a$_D$), 3.80 (dd, 1H, J$_{2,3}$=2.5 Hz, J$_{3,4}$=9.5 Hz, H-3$_A$), 3.78-3.67 (m, 3H, H-5$_B$, H-4$_E$, H-6b$_D$), 3.60-3.40 (m, 5H, H-4$_D$, H-4$_A$, H-4$_B$, H-6a$_E$, H-6b$_E$), 3.28 (dq, 1H, J$_{4,5}$=9.2 Hz, J$_{5,6}$=6.2 Hz, H-5$_A$), 2.83 (m, 1H, H-5$_D$), 2.78-2.64 (m, 4H, 2CH$_{2Lev}$), 2.18 (s, 3H, CH$_{3Lev}$), 1.37 (s, 3H, H$_{iPr}$), 1.40 (m, 6H, H-6$_A$, H-6$_B$), 1.32 (s, 3H, H$_{iPr}$).

$^{13}$C NMR (CDCl$_3$), δ: β: 206.1 (C$_{Lev}$), 172.2 (C$_{Lev}$), 162.0 (C$_{NTCA}$), 139.1-137.5 (C$_{Ph}$), 134.0 (CH=), 129.1-127.3 (CH$_{Ph}$), 117.2 (=CH$_2$), 100.7 (C-1$_D$, $^1$J$_{CH}$=163.8 Hz), 99.7 (C$_{iPr}$), 97.5 (C-1$_A$, $^1$J$_{CH}$=155.1 Hz), 96.9 (C-1$_B$, $^1$J$_{CH}$=167.2 Hz), 94.1 (C-1$_E$, $^1$J$_{CH}$=167.7 Hz), 92.8 (CCl$_3$), 83.7 (C-3$_E$), 81.0 (C-4$_B$), 79.7 (C-4$_A$), 78.7 (C-4$_E$), 77.8 (C-2$_E$), 77.4 (C-3$_B$), 76.4 (C-3$_A$), 76.2, 75.3, 75.1, 74.6, 73.6 (5C, C$_{Bn}$), 73.3 (3C, C-2$_A$*, C-2$_B$*, C-3$_D$*), 73.5 (C$_{Bn}$), 72.4 (C-5$_A$), 71.3 (C-4$_D$), 71.0 (C$_{Bn}$), 69.9 (C-5$_E$), 68.0 (2C, C-5$_B$*,

C-6$_E$*), 67.8 (C$_{All}$), 67.0 (C-5$_D$), 62.4 (C-6$_D$), 56.7 (C-2$_D$), 38.0 (CH$_{2Lev}$), 29.8 (CH$_{3Lev}$), 29.0 (C$_{iPr}$), 28.1 (CH$_{2Lev}$), 19.9 (C$_{iPr}$), 18.4 (C-6$_A$), 18.0 (C-6$_B$).

HRMS (ESI$^+$): [M+Na]$^+$ C$_{86}$H$_{98}$NO$_{21}$$^{35}$Cl$_3$Na m/z theoretical:
1608.5594
m/z measured:
1608.5914
[M+NH$_4$]$^+$ C$_{86}$H$_{98}$NO$_{21}$$^{35}$Cl$_3$NH$_4$ m/z theoretical:
1603.6041
m/z measured:
1603.6248
Method 14a:

Allyl(3-O-acetyl-2-deoxy-4,6-O-isopropylidene-2-trichloroacetamido-β-D-glucopyranosyl)-(1→2)-[2,3,4,6-tetra-O-benzyl-α-D-glucopyranosyl-(1→3)]-(4-O-benzyl-α-L-rhamnopyranosyl)-(1→2)-3,4-di-O-benzyl-α-L-rhamnopyranoside 115

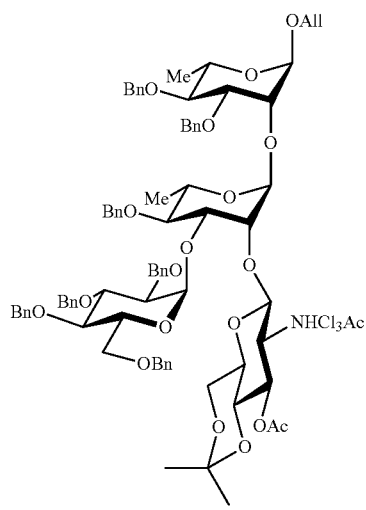

Chemical Formula: C$_{83}$H$_{94}$Cl$_3$NO$_{20}$
Exact Mass: 1529.5435
Molecular Weight: 1531.9882

TMSOTf (69.0 μL, 380 μmol, 0.3 eq.) is added to a solution of acceptor 108 (1.5 g, 1.3 mmol) and donor 2 (1.2 g, 2.2 mmol, 1.7 eq.) in Tol (30 mL), in the presence of molecular sieve 4 Å (1.1 g), stirred under argon at −40° C. After stirring for 1 h, monitoring by TLC (Tol/EtOAc, 85/15) indicates the disappearance of 108 (Rf=0.5) and the appearance of a new, more polar compound (Rf=0.45). The reaction is stopped by adding triethylamine (1 mL), then the reaction mixture is filtered and concentrated in a rotary evaporator. The yellow oil obtained is purified by silica gel chromatography (Tol/EtOAc, 95/5→1/1) to obtain the allyl glycoside 115 as a white solid (1.9 g, 95%).

Rf=0.45 (Tol/EtOAc, 85/15).

$^1$H NMR (CDCl$_3$), δ7.54-7.09 (m, 36H, NH, CH$_{Ph}$), 5.91 (m, 1H, CH═), 5.30 (m, 1H, J$_{trans}$=17.2 Hz, ═CH$_2$), 5.23 (m, 1H, J$_{cis}$=10.5 Hz, ═CH$_2$), 5.23-5.19 (m, 2H, H-1$_E$, H$_{Bn}$), 5.15 (bs, 1H, H-1$_A$), 5.11 (d, 1H, J=10.9 Hz, H$_{Bn}$), 5.08 (d, 1H, J=11.0 Hz, H$_{Bn}$), 4.96 (d, 1H, J=10.8 Hz, H$_{Bn}$), 4.88-4.78 (m, 5H, H$_{Bn}$, H-1$_D$, H-3$_D$, 2H$_{Bn}$), 4.75-4.66 (m, 3H, H$_{Bn}$), 4.63-4.58 (m, 3H, H-1$_B$, 2H$_{Bn}$), 4.52 (d, 1H, J=11.0 Hz, H$_{Bn}$), 4.36 (d, 1H, J=12.0 Hz, H$_{Bn}$), 4.25-4.12 (m, 6H, H-2$_D$, H-3$_E$, H-2$_A$, H-3$_A$, H$_{All}$, H-5$_E$), 4.03 (dd, 1H, J$_{2,3}$=2.8 Hz, H-2$_B$), 4.01-3.92 (m, 3H, H$_{All}$, H-2$_E$, H-3$_B$), 3.88-3.80 (m, 2H, H-4$_E$, H-5$_A$), 3.75 (dq, 1H, J$_{4,5}$=9.4 Hz, H-5$_B$), 3.68 (pt, 1H, J$_{3,4}$=9.5 Hz, H-4$_D$), 3.57-3.40 (m, 6H, H-6a$_D$, H-4$_A$, H-4$_B$, H-6a$_E$, H-6b$_E$, H-6b$_D$), 2.82 (m, 1H, H-5$_D$), 2.11 (s, 3H, H$_{Ac}$), 1.49 (s, 3H, H$_{iPr}$), 1.44 (d, 3H, J$_{5,6}$=6.2 Hz, H-6$_A$), 1.41 (s, 3H, H$_{iPr}$), 1.36 (d, 3H, J$_{5,6}$=6.2 Hz, H-6$_B$).

$^{13}$C NMR (CDCl$_3$), δ170.8 (C$_{Ac}$), 162.2 (C$_{NTCA}$), 138.6-137.6 (C$_{Ph}$), 133.9 (CH═), 129.1-127.4 (CH$_{Ph}$), 117.2 (═CH$_2$), 101.4 (C-1$_D$, $^1$J$_{CH}$=164.1 Hz), 101.0 (C-1$_A$, $^1$J$_{CH}$=172.5 Hz), 99.7 (C$_{iPr}$), 97.9 (C-1$_B$, $^1$J$_{CH}$=167.9 Hz), 94.6 (C-1$_E$, $^1$J$_{CH}$=167.1 Hz), 92.8 (CCl$_3$), 83.5 (C-3$_E$), 80.5 (C-4$_B$), 79.8 (C-4$_A$), 79.6 (C-3$_B$), 78.6 (C-4$_E$), 78.2 (C-2$_E$), 76.2, 75.3, 75.2, 75.0 (4C, C$_{Bn}$), 74.9 (C-2$_B$), 74.4 (C-3$_A$), 74.0 (C$_{Bn}$), 73.9 (C-2$_A$), 73.5 (C$_{Bn}$), 72.6 (C-3$_D$), 72.2 (C$_{Bn}$), 71.3 (C-4$_D$), 70.0 (C-5$_E$), 68.7 (C-5$_A$), 68.0 (C-5$_B$), 67.9 (C-6$_E$), 67.7 (C$_{All}$), 67.4 (C-5$_D$), 61.8 (C-6$_D$), 56.6 (C-2$_D$), 29.0 (C$_{iPr}$), 20.9 (C$_{Ac}$), 19.1 (C$_{iPr}$), 18.0 (C-6$_B$), 17.9 (C-6$_A$).

HRMS (ESI$^+$): [M+Na]$^+$ C$_{83}$H$_{94}$NO$_{20}$$^{35}$Cl$_3$Na m/z theoretical:
1552.5332
m/z measured:
1552.5430
[M+NH$_4$]$^+$ C$_{83}$H$_{94}$NO$_{20}$$^{35}$Cl$_3$NH$_4$ m/z theoretical:
1547.5779
m/z measured:
1547.5880

Allyl(2-deoxy-4,6-O-isopropylidene-2-trichloroacetamido-β-D-glucopyranosyl)-(1→2)-[2,3,4,6-tetra-O-benzyl-α-D-glucopyranosyl-(1→3)]-(4-O-benzyl-α-L-rhamnopyranosyl)-(1→2)-3,4-di-O-benzyl-α-L-rhamnopyranoside 110

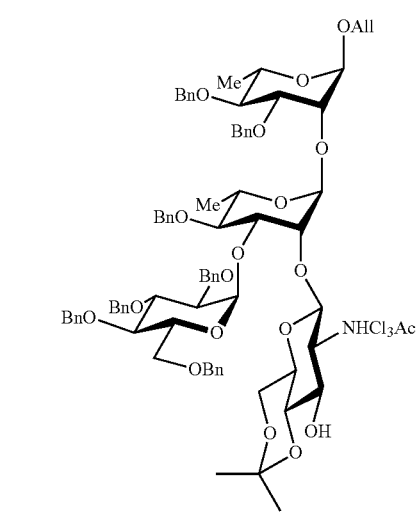

Chemical Formula: C$_{81}$H$_{92}$Cl$_3$NO$_{19}$
Exact Mass: 1487.5329
Molecular Weight: 1489.9515

The allyl glycoside 115 (1.9 g, 1.3 mmol) is dissolved in MeOH (20 mL), then potassium carbonate (175 mg, 1.3 mmol, 1 eq.) is added to the reaction mixture. After stirring overnight, monitoring by TLC (Tol/EtOAc, 7/3) indicates the disappearance of 115 (Rf=0.8) and the appearance of a more polar product (Rf=0.45). The solvents are then evaporated and the yellow oil obtained is purified by silica gel chromatography (Tol/EtOAc, 9/1→7/3) to give the alcohol 110 (1.7 g, 92%) as a white solid.

Rf=0.45 (Tol/EtOAc, 7/3).

$^1$H NMR (CDCl$_3$), δ7.43-7.08 (m, 36H, NH, CH$_{Ph}$), 5.88 (m, 1H, CH═), 5.29 (m, 1H, J$_{trans}$=17.2 Hz, ═CH$_2$), 5.23-5.20 (m, 2H, H-1$_E$, ═CH$_2$), 5.14-5.05 (m, 4H, H$_{Bn}$, H-1$_A$, 2H$_{Bn}$), 4.95 (d, 1H, J=10.8 Hz, H$_{Bn}$), 4.90 (d, 1H, J=12.0 Hz, H$_{B'}$), 4.83-4.77 (m, 3H, 2H$_{Bn}$, H-1$_B$), 4.70-4.61 (m, 5H, 2H$_{Bn}$, H-1$_D$, 2H$_{Bn}$), 4.58-4.52 (m, 2H, H$_{Bn}$), 4.37 (d, 1H, J=12.0 Hz, H$_{Bn}$), 4.19-4.13 (m, 5H, H-3$_A$, H-2$_A$, H-3$_E$, H$_{All}$, H-5$_E$), 4.02 (dd, 1H, J$_{2,3}$=2.8 Hz, H-2$_B$), 4.01-3.92 (m, 5H, H$_{All}$, H-3$_B$, H-2$_D$, H-4$_E$, H-2$_E$), 3.80 (dq, 1H, J$_{4,5}$=9.2 Hz, H-5$_A$), 3.73 (dq, 1H, J$_{4,5}$=9.4 Hz, H-5$_B$), 3.56 (dd, 1H, J$_{5,6}$=5.3 Hz, J$_{6a,6b}$=10.8 Hz, H-6a$_D$), 3.52-3.47 (m, 4H, H-6a$_E$, H-6b$_E$, H-4$_A$, H-4$_B$), 3.42-3.35 (m, 2H, H-4$_D$, H-6b$_D$), 2.85 (m, 1H, OH), 2.82 (m, 1H, H-5$_D$), 2.45 (pt, 1H, J$_{3,4}$=9.7 Hz, H-3$_D$), 1.47 (s, 3H, H$_{iPr}$), 1.46 (s, 3H, H$_{iPr}$), 1.41 (d, 3H, J$_{5,6}$=6.2 Hz, H-6$_A$), 1.35 (d, 3H, J$_{5,6}$=6.2 Hz, H-6$_B$).

$^{13}$C NMR (CDCl$_3$), δ163.7 (C$_{NTCA}$), 138.6-137.5 (C$_{Ph}$), 133.8 (CH=), 129.3-127.4 (CH$_{Ph}$), 117.2 (=CH$_2$), 101.0 (C-1$_D$, $^1$J$_{CH}$=159.1 Hz), 101.0 (C-1$_A$, $^1$J$_{CH}$=170.3 Hz), 99.7 (C$_{iPr}$), 97.9 (C-1$_B$, $^1$J$_{CH}$=168.6 Hz), 94.1 (C-1$_E$, $^1$J$_{CH}$=166.2 Hz), 92.7 (CCl$_3$), 83.3 (C-3$_E$), 80.5 (C-4$_B$), 79.8 (C-4$_A$), 79.7 (C-2$_E$), 79.5 (C-3$_B$), 78.7 (C-4$_E$), 76.3, 75.4, 75.3, 74.9 (5C, C$_{Bn}$), 74.7 (C-2$_B$), 74.1 (C-3$_A$), 74.0 (C-4$_D$), 73.5 (C$_{Bn}$), 73.3 (C-2$_A$), 73.0 (C-3$_D$), 72.1 (C$_{Bn}$), 70.0 (C-5$_E$), 68.7 (C-5$_A$), 68.0 (C-5$_B$), 67.9 (C-6$_E$), 67.7 (C$_{All}$), 67.1 (C-5$_D$), 61.4 (C-6$_D$), 58.8 (C-2$_D$), 29.1 (C$_{iPr}$), 19.0 (C$_{iPr}$), 18.0 (C-6$_B$), 17.8 (C-6$_A$).

HRMS (ESI$^+$): [M+Na]$^+$ C$_{81}$H$_{92}$NO$_{19}$$^{35}$Cl$_3$Na m/z theoretical:
1510.5227
m/z measured:
1510.5243
[M+NH$_4$]$^+$ C$_{81}$H$_{92}$NO$_{19}$$^{35}$Cl$_3$NH$_4$ m/z theoretical:
1505.5673
m/z measured:
1505.5669

Method 14b:

Allyl(3-O-acetyl-2-deoxy-4,6-O-isopropylidene-2-trichloroacetamido-β-D-glucopyranosyl)-(1→2)-[2,3,4,6-tetra-O-benzyl-α-D-glucopyranosyl-(1→3)]-(4-O-benzyl-α-L-rhamnopyranosyl)-(1→2)-3,4-di-O-benzyl-α-L-rhamnopyranoside 115'

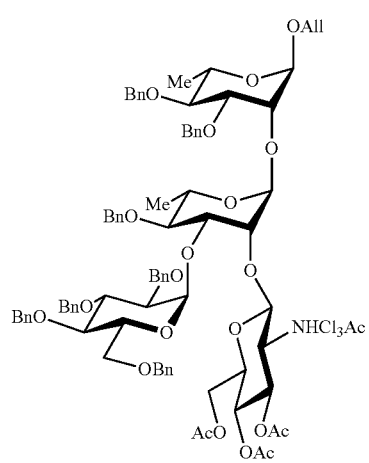

Chemical Formula: C$_{84}$H$_{94}$Cl$_3$NO$_{22}$
Exact Mass: 1573.53
Molecular Weight: 1576.00

Triflic acid (4 μL, 45 μmol, 0.3 eq.) is added to a suspension of acceptor 108 (163 mg, 143 μmol), donor 1 (110 mg, 185 μmol, 1.3 eq.) and molecular sieve 4 Å (350 mg), in Tol (5 mL), stirred under argon at −40° C. After stirring for 1 h at this temperature followed by 1.5 h of stirring at RT, after which donor 1 (20 mg, 34 μmol, 0.23 eq.) is added. Stirring is continued overnight at RT. Monitoring by TLC (Chex/EtOAc, 7/3) indicates the presence of a new compound that is more polar than 108. The reaction is stopped by adding triethylamine and then the reaction mixture is filtered and concentrated in a rotary evaporator. The raw reaction product is purified by silica gel flash chromatography (Chex/EtOAc, 100/0→70/30) to obtain the allyl glycoside 115' (196 mg, 87%).

Rf=0.33 (Chex/EtOAc, 7/3).

$^1$H NMR (CDCl$_3$), δ7.54-7.09 (m, 36H, NH, CH$_{Ph}$), 5.91 (m, 1H, CH=), 5.30 (m, 1H, J$_{trans}$=17.2 Hz, =CH$_2$), 5.23 (m, 1H, J$_{cis}$=10.5 Hz, =CH$_2$), 5.23-5.19 (m, 2H, H-1$_E$, H$_{Bn}$), 5.15 (bs, 1H, H-1$_A$), 5.11 (d, 1H, J=10.9 Hz, H$_{Bn}$), 5.08 (d, 1H, J=11.0 Hz, H$_{Bn}$), 4.96 (d, 1H, J=10.8 Hz, H$_{Bn}$), 4.88-4.78 (m, 5H, H$_{Bn}$, H-1$_D$, H-3$_D$, 2H$_{Bn}$), 4.75-4.66 (m, 3H, H$_{Bn}$), 4.63-4.58 (m, 3H, H-1$_B$, 2H$_{Bn}$), 4.52 (d, 1H, J=11.0 Hz, H$_{Bn}$), 4.36 (d, 1H, J=12.0 Hz, H$_{Bn}$), 4.25-4.12 (m, 6H, H-2$_D$, H-3$_E$, H-2$_A$, H-3$_A$, H$_{All}$, H-5$_E$), 4.03 (dd, 1H, J$_{2,3}$=2.8 Hz, H-2$_B$), 4.01-3.92 (m, 3H, H$_{All}$, H-2$_E$, H-3$_B$), 3.88-3.80 (m, 2H, H-4$_E$, H-5$_A$), 3.75 (dq, 1H, J$_{4,5}$=9.4 Hz, H-5$_B$), 3.68 (pt, 1H, J$_{3,4}$=9.5 Hz, H-4$_D$), 3.57-3.40 (m, 6H, H-6a$_D$, H-4$_A$, H-4$_B$, H-6a$_E$, H-6b$_E$, H-6b$_D$), 2.82 (m, 1H, H-5$_D$), 2.11 (s, 3H, H$_{Ac}$), 1.49 (s, 3H, H$_{iPr}$), 1.44 (d, 3H, J$_{5,6}$=6.2 Hz, H-6$_A$), 1.41 (s, 3H, H$_{iPr}$), 1.36 (d, 3H, J$_{5,6}$=6.2 Hz, H-6$_B$).

RMN $^{13}$C (CDCl$_3$), δ170.8 (C$_{Ac}$), 162.2 (C$_{NTCA}$), 138.6-137.6 (C$_{Ph}$), 133.9 (CH=), 129.1-127.4 (CH$_{Ph}$), 117.2 (=CH$_2$), 101.4 (C-1$_D$, $^1$J$_{CH}$=164.1 Hz), 101.0 (C-1$_A$, $^1$J$_{CH}$=172.5 Hz), 99.7 (C$_{iPr}$), 97.9 (C-1$_B$, $^1$J$_{CH}$=167.9 Hz), 94.6 (C-1$_E$, $^1$J$_{CH}$=167.1 Hz), 92.8 (CCl$_3$), 83.5 (C-3$_E$), 80.5 (C-4$_B$), 79.8 (C-4$_A$), 79.6 (C-3$_B$), 78.6 (C-4$_E$), 78.2 (C-2$_E$), 76.2, 75.3, 75.2, 75.0 (4C, C$_{Bn}$), 74.9 (C-2$_B$), 74.4 (C-3$_A$), 74.0 (C$_{Bn}$), 73.9 (C-2$_A$), 73.5 (C$_{Bn}$), 72.6 (C-3$_D$), 72.2 (C$_{Bn}$), 71.3 (C-4$_D$), 70.0 (C-5$_E$), 68.7 (C-5$_A$), 68.0 (C-5$_B$), 67.9 (C-6$_E$), 67.7 (C$_{All}$), 67.4 (C-5$_D$), 61.8 (C-6$_D$), 56.6 (C-2$_D$), 29.0 (C$_{iPr}$), 20.9 (C$_{Ac}$), 19.1 (C$_{iPr}$), 18.0 (C-6$_B$), 17.9 (C-6$_A$).

HRMS (ESI$^+$): [M+Na]$^+$ C$_{84}$H$_{94}$NO$_{22}$$^{35}$Cl$_3$Na m/z theoretical:
1598.5234
m/z measured:
1598.5170

Allyl(2-trichloroacetamido-β-D-glucopyranosyl)-(1→2)-[2,3,4,6-tetra-O-benzyl-α-D-glucopyranosyl-(1→3)]-(4-O-benzyl-α-L-rhamnopyranosyl)-(1→2)-3,4-di-O-benzyl-α-L-rhamnopyranoside 115''

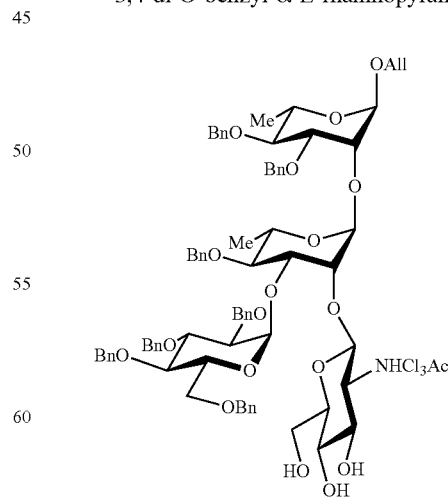

Chemical Formula: C$_{78}$H$_{88}$Cl$_3$NO$_{19}$
Exact Mass: 1447.50
Molecular Weight: 1449.89

0.5 M MeONa methanolic solution (1.4 mL, 0.75 mmol, 6 eq.) is added to a suspension of tetrasaccharide 115' (185 mg, 117 µmol) in methanol (5 mL). After stirring at RT for 3 h, monitoring by TLC (CDCM/MeOH, 95/5) indicates the presence of a new, more polar compound. The reaction mixture is neutralized by adding Dowex X8 (H$^+$) ion-exchange resin and filtered. The filtrate is concentrated in a rotary evaporator, then the raw reaction product is purified by silica gel flash chromatography (DCM/MeOH, 95/5) to obtain the triol 115'' (135 mg, 79%).

Rf=0.58 (DCM/MeOH, 9/1).

$^1$H NMR (CDCl$_3$), δ7.54-7.09 (m, 36H, NH, CH$_{Ph}$), 5.91 (m, 1H, CH=), 5.30 (m, 1H, J$_{trans}$=17.2 Hz, =CH$_2$), 5.23 (m, 1H, J$_{cis}$=10.5 Hz, =CH$_2$), 5.23-5.19 (m, 2H, H-1$_E$, H$_{Bn}$), 5.15 (bs, 1H, H-1$_A$), 5.11 (d, 1H, J=10.9 Hz, H$_{Bn}$), 5.08 (d, 1H, J=11.0 Hz, H$_{Bn}$), 4.96 (d, 1H, J=10.8 Hz, H$_{Bn}$), 4.88-4.78 (m, 5H, H$_{Bn}$, H-1$_D$, H-3$_D$, 2H$_{Bn}$), 4.75-4.66 (m, 3H, H$_{Bn}$), 4.63-4.58 (m, 3H, H-1$_B$, 2H$_{Bn}$), 4.52 (d, 1H, J=11.0 Hz, H$_{Bn}$), 4.36 (d, 1H, J=12.0 Hz, H$_{Bn}$), 4.25-4.12 (m, 6H, H-2$_D$, H-3$_E$, H-2$_A$, H-3$_A$, H$_{All}$, H-5$_E$), 4.03 (dd, 1H, J$_{2,3}$=2.8 Hz, H-2$_B$), 4.01-3.92 (m, 3H, H$_{All}$, H-2$_E$, H-3$_B$), 3.88-3.80 (m, 2H, H-4$_E$, H-5$_A$), 3.75 (dq, 1H, J$_{4,5}$=9.4 Hz, H-5$_B$), 3.68 (pt, 1H, J$_{3,4}$=9.5 Hz, H-4$_B$), 3.57-3.40 (m, 6H, H-6a$_D$, H-4$_A$, H-4$_B$, H-6a$_E$, H-6b$_E$, H-6b$_D$), 2.82 (m, 1H, H-5$_D$), 2.11 (s, 3H, H$_{Ac}$), 1.49 (s, 3H, H$_{iPr}$), 1.44 (d, 3H, J$_{5,6}$=6.2 Hz, H-6$_A$), 1.41 (s, 3H, H$_{iPr}$), 1.36 (d, 3H, J$_{5,6}$=6.2 Hz, H-6$_B$).

$^{13}$C NMR (CDCl$_3$), δ170.8 (C$_{Ac}$), 162.2 (C$_{NTCA}$), 138.6-137.6 (C$_{Ph}$), 133.9 (CH=), 129.1-127.4 (CH$_{Ph}$), 117.2 (=CH$_2$), 101.4 (C-1$_D$, $^1$J$_{CH}$=164.1 Hz), 101.0 (C-1$_A$, $^1$J$_{CH}$=172.5 Hz), 99.7 (C$_{iPr}$), 97.9 (C-1$_B$, $^1$J$_{CH}$=167.9 Hz), 94.6 (C-1$_E$, $^1$J$_{CH}$=167.1 Hz), 92.8 (CCl$_3$), 83.5 (C-3$_E$), 80.5 (C-4$_B$), 79.8 (C-4$_A$), 79.6 (C-3$_B$), 78.6 (C-4$_E$), 78.2 (C-2$_E$), 76.2, 75.3, 75.2, 75.0 (4C, C$_{Bn}$), 74.9 (C-2$_B$), 74.4 (C-3$_A$), 74.0 (C$_{Bn}$), 73.9 (C-2$_A$), 73.5 (C$_{Bn}$), 72.6 (C-3$_D$), 72.2 (C$_{Bn}$), 71.3 (C-4$_D$), 70.0 (C-5$_E$), 68.7 (C-5$_A$), 68.0 (C-5$_2$), 67.9 (C-6$_E$), 67.7 (C$_{All}$), 67.4 (C-5$_D$), 61.8 (C-6$_D$), 56.6 (C-2$_D$), 29.0 (C$_{iPr}$), 20.9 (C$_{Ac}$), 19.1 (C$_{iPr}$), 18.0 (C-6$_2$), 17.9 (C-6$_A$).

HRMS (ESI$^+$): [M+Na]$^+$ C$_{78}$H$_{88}$NO$_{19}$$^{35}$Cl$_3$Na m/z theoretical:
1472.4913
m/z measured:
1772.4921

Propyl 2-acetamido-2-deoxy-β-D-glucopyranosyl-(1→2)-[α-D-glucopyranosyl-(1→3)]-α-L-rhamnopyranosyl-(1→2)-α-L-rhamnopyranoside VIII

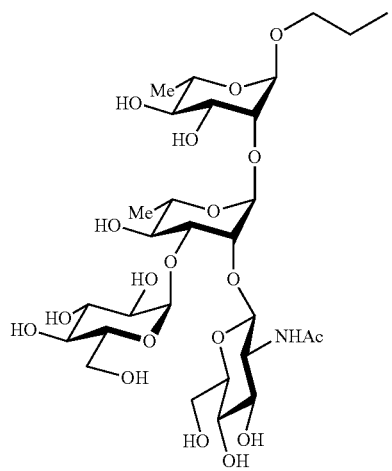

Chemical Formula: C$_{29}$H$_{51}$NO$_{19}$
Exact Mass: 717.31
Molecular Weight: 717.71

Route 1.

Pd/C 10% (108 mg) is added to a degassed solution of triol 115'' (108 mg, 75 µmol) in ethanol (10 mL) supplemented with 1M hydrochloric acid (110 µL). The suspension is placed under hydrogen atmosphere (1 bar) and stirred overnight at RT. Monitoring by TLC (iPrOH/H$_2$O/NH$_3$, 7/1/02) shows the disappearance of 115'' and the appearance of a new, more polar compound. The reaction mixture is filtered on Celite, and the filtrate is concentrated in a rotary evaporator. The residue is taken up in ethanol (10 mL), to which Et$_3$N (100 µL) is added. The medium is degassed, Pd/C 10% (100 mg) is added and the reaction mixture is stirred under hydrogen atmosphere overnight. Monitoring by TLC again indicates the presence of a more polar compound. After filtration of the suspension and evaporation of the filtrate, the residue obtained is purified by HPLC (Kromasil C-18 column, 0.01 M aqueous TFA/CH$_3$CN, 100/0→60/40 in 20min, 5 mL/min, 215 nm) to give the target tetrasaccharide VIII in the form of a white powder after lyophilization (36 mg, 68%).

Route 2.

A solution of triflic acid (2 µL, 23 µmol, 0.35 eq.) in anhydrous toluene (98 µL) is added to a suspension of acceptor 108 (82 mg, 66 µmol), of donor 1 (80 mg, 135 µmol, 2 eq.) and of molecular sieve 4 Å (200 mg), in Tol (2 mL), stirred under argon at −30° C. After stirring for 1 h at this temperature followed by 1 h of stirring at RT, after which time donor 1 (10 mg, 17 µmol, 0.25 eq.) is added to the reaction mixture cooled to −30° C., stirring continues for 3 h while the bath slowly returns to RT. The reaction is stopped by adding triethylamine and then the reaction mixture is filtered and concentrated in a rotary evaporator. The raw reaction product is purified by silica gel flash chromatography (Chex/EtOAc, 100/0→70/30) to obtain 115' (100 mg). The allyl glycoside is dissolved in 1 mL of DCM and 0.5 M methanolic solution of sodium methoxide (500 µL) is added. After stirring at RT for 3 h, monitoring by TLC (CDCM/MeOH, 9/1) indicates the presence of a new, more polar compound detected with ninhydrin. The reaction mixture is neutralized by adding Dowex X8 (H$^+$) ion-exchange resin, and filtered. The filtrate is concentrated in a rotary evaporator, then the raw reaction product is taken up in ethanol (2 mL) and treated with acetic anhydride (1 mL). After 2 h at RT, the volatile substances are coevaporated with toluene and the raw reaction product is chromatographed (DCM/MeOH, 95/5) to obtain the acetamidotriol (54 mg, 67%). The latter is taken up in ethanol (5 mL) supplemented with 1M hydrochloric acid (110 µL) and the solution is degassed. Pd/C 10% (50 mg) is added and the suspension is placed under hydrogen atmosphere (1 bar) and stirred overnight at RT. After filtration, concentration, purification by HPLC and lyophilization, the target tetrasaccharide VIII is isolated (19 mg, 40% starting from 108).

Rf=0.32 (iPrOH/H$_2$O/NH$_3$, 4/1/2).

$^1$H NMR (D$_2$O), δ5.06 (d, 1H, J$_{1,2}$=3.7 Hz, H-1$_E$), 4.83 (d, 1H, J$_{1,2}$=1.6 Hz, H-1$_A$), 4.76 (d, 1H, J$_{1,2}$=1.3 Hz, H-1$_C$), 4.73 (d, 1H, J$_{1,2}$=8.6 Hz, H-1$_D$), 4.18 (m, 1H, H-2$_A$), 3.95 (m, 1H, H-5$_E$), 3.88 (m, 1H, H-5$_C$), 3.83-3.79 (m, 2H, H-3$_A$, H-6a$_D$), 3.74 (m, 1H, H-2$_D$), 3.72 (m, 1H, H-3$_E$), 3.70-3.67 (m, 3H, H-2$_C$, H-6a$_E$, H-6b$_E$), 3.65-3.59 (m, 4H, H-6b$_D$, H-3$_C$, H-5$_A$, H-2$_E$), 3.52 (m, 1H, H$_{Pr}$), 3.42-3.28 (m, 6H, H-4$_E$, H$_{Pr}$, H-4$_D$, H-5$_D$, H-3$_D$, H-4$_C$), 3.23 (pt, 1H, J$_{3,4}$=9.7 Hz, H-4$_A$), 2.01 (s, 3H, H$_{NAc}$), 1.49 (sex, 2H, CH$_2$), 1.16 (d, 3H, J$_{5,6}$=6.2 Hz, H-6$_A$), 1.12 (d, 3H, J$_{5,6}$=6.3 Hz, H-6$_C$), 0.80 (t, 3H, J=7.4 Hz, CH$_3$).

$^{13}$C NMR (D$_2$O), δ174.5 (C$_{NAc}$), 101.8 (C-1$_D$, $^1$J$_{CH}$=160.3 Hz), 101.6 (C-1$_C$, $^1$J$_{CH}$=170.5 Hz), 99.0 (C-1$_A$, $^1$J$_{CH}$=172.7 Hz), 94.8 (C-1$_E$, $^1$J$_{CH}$=169.8 Hz), 81.7 (C-3$_D$), 76.4 (C-4$_D$), 74.7 (C-2$_A$), 74.1 (C-3$_A$), 73.5 (C-3$_E$), 72.2 (C-4$_C$), 71.7 (C-5$_E$), 71.6 (C-2$_E$), 71.2 (C-2$_C$), 71.0 (C-4$_A$), 70.5 (C-3$_C$), 70.0 (C$_{Pr}$), 69.6 (C-5$_D$), 69.3 (C-5$_C$), 69.1 (C-5$_A$), 68.6 (C-4$_E$), 60.9 (C-6$_D$), 60.6 (C-6$_E$), 55.9 (C-2$_D$), 22.8 (C$_{NAc}$), 22.3 (CH$_2$), 17.0, 16.7 (C-6$_A$, C-8$_C$), 10.2 (CH$_3$).

MS (ESI$^+$) for C$_{29}$H$_{51}$NO$_{19}$: m/z theoretical 717.32. found 718.3 [M+Na]$^+$ Method 15:

Allyl(2-acetamido-2-deoxy-β-D-glucopyranosyl)-(1→2)-[2,3,4,6-tetra-O-benzyl-α-D-glucopyranosyl-(1→3)]-4-O-benzyl-α-L-rhamnopyranoside 117

Allyl(2-deoxy-2-methylcarbamate-β-D-glucopyranosyl)-(1→2)-[2,3,4,6-tetra-O-benzyl-α-D-glucopyranosyl-(1→3)]-4-O-benzyl-α-L-rhamnopyranoside 118

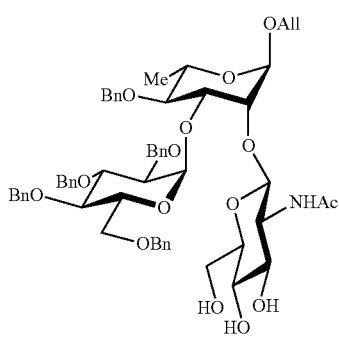

Chemical Formula: $C_{58}H_{69}NO_{15}$
Exact Mass: 1019.4667
Molecular Weight: 1020.1662

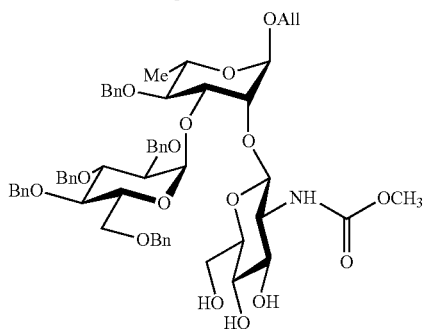

Chemical Formula: $C_{58}H_{69}NO_{16}$
Exact Mass: 1035.4616
Molecular Weight: 1036.1656

After adding 0.5 M NaOMe (4.8 mL, 2.4 mmol, 6 eq.) to the tri-O-acetyl 22 (500 mg, 400 µmol) in solution in DCM (38 mL), the reaction mixture is stirred for 9 h and monitored by TLC (DCM/MeOH, 92/8 and EtOAc/MeOH, 98/2). After observing the disappearance of 22 and the appearance of a more polar product detected with ninhydrin (Rf=0.35 and 0.2, respectively), the reaction mixture is diluted by adding MeOH (77 mL), and then acetic anhydride (300 µL, 3.2 mmol, 8 eq.) is added to the reaction mixture. After stirring for 2 h, the appearance of a new product is observed in TLC (Rf=0.4 and 0.25, respectively). The solvents are then evaporated and the solid obtained is purified by silica gel chromatography (DCM/MeOH, 98/2→95/5), giving, in the order of elution, the unwanted carbamate 118 as a white solid (20 mg, 5%) and then the triol 117 as a white solid (371 mg, 90%).

117: Rf=0.4 (DCM/MeOH, 92/8).
$^1$H NMR (CDCl$_3$), δ7.41-7.08 (m, 26H, NH, CH$_{Ph}$), 5.88 (m, 1H, CH=), 5.29 (m, 1H, $J_{trans}$=17.2 Hz, =CH$_2$), 5.21 (m, 1H, $J_{cis}$=10.4 Hz, =CH$_2$), 5.09-5.06 (m, 2H, H-1$_E$, H$_{Bn}$), 5.01-4.96 (m, 2H, H-1$_A$, H$_{Bn}$), 4.91-4.87 (m, 2H, H$_{Bn}$), 4.81-4.76 (m, 2H, J=10.3 Hz, H$_{Bn}$), 4.63-4.58 (m, 2H, H$_{Bn}$), 4.50 (d, 1H, J=10.9 Hz, H$_{Bn}$), 4.62 (m, 1H, H-1$_D$), 4.34 (m, 1H, H$_{Bn}$), 4.19-4.08 (m, 4H, H-3$_A$, H-5$_E$, H$_{All}$, H-3$_E$), 4.01 (m, 1H, H$_{All}$), 3.91 (bs, 1H, H-2$_A$), 3.87-3.81 (m, 5H, H-2$_E$, H-4$_E$, H-2$_D$, H-6a$_D$, H-6b$_D$), 3.72 (m, 1H, H-5$_A$), 3.51 (pt, 1H, $J_{3,4}$=9.0 Hz, H-4$_D$), 3.51-3.45 (m, 3H, H-4$_A$, H-6a$_E$, H-6b$_E$), 3.13 (m, 1H, H-5$_D$), 2.80 (pt, 1H, $J_{2,3}$=9.2 Hz, H-3$_D$), 2.21 (s, 3H, H$_{NAc}$), 1.40 (d, 3H, $J_{5,6}$=6.2 Hz, H-6$_A$).
$^{13}$C NMR (CDCl$_3$), δ173.3 (C$_{NAc}$), 138.6-137.5 (C$_{Ph}$), 134.2 (CH=), 129.5-127.8 (CH$_{Ph}$), 117.8 (=CH$_2$), 103.0 (C-1$_D$, $^1J_{CH}$=155.6 Hz), 98.5 (C-1$_A$, $^1J_{CH}$=174.8 Hz), 94.6 (C-1$_E$, $^1J_{CH}$=167.9 Hz), 83.7 (C-3$_E$), 80.2 (C-4$_A$), 79.2, 79.0 (2C, C-2$_E$, C-4$_E$), 77.1 (C-3$_D$), 76.9 (C-2$_A$), 76.5, 75.8 (2C, C$_{Bn}$), 75.7 (C-5$_D$), 75.6, 75.3 (2C, C$_{Bn}$), 74.6 (C-3$_A$), 73.8 (C$_{Bn}$), 71.8 (C-4$_E$), 70.3 (C-5$_E$), 68.7 (C-5$_A$), 68.3 (C$_{All}$), 68.2 (C-6$_E$), 62.7 (C-6$_D$), 57.4 (C-2$_D$), 23.6 (C$_{NAc}$), 18.2 (C-6$_A$).
HRMS (ESI$^+$): [M+H]$^+$ $C_{58}H_{70}NO_{15}$ m/z theoretical:
1020.4745
m/z measured:
1020.4739
[M+Na]$^+$ $C_{58}H_{69}NO_{35}Na$ m/z theoretical:
1042.4565
m/z measured:
1042.4545

118: Rf=0.45 (DCM/MeOH, 92/8).
$^1$H NMR (CDCl$_3$), δ7.42-7.08 (m, 25H, CH$_{Ph}$), 6.52 (d, 1H, $J_{NH,2}$=7.0, NH), 5.90 (m, 1H, CH=), 5.29 (m, 1H, $J_{trans}$=17.2 Hz, =CH$_2$), 5.20 (m, 1H, $J_{cis}$=10.4 Hz, =CH$_2$), 5.11-4.96 (m, 5H, 2H$_{Bn}$, H-1$_E$, 2H$_{Bn}$), 4.92 (bs, 1H, H-1$_A$), 4.84-4.79 (m, 2H, H$_{Bn}$), 4.73 (d, 1H, J=10.4 Hz, H$_{Bn}$), 4.63-4.55 (m, 2H, H$_{Bn}$), 4.45-4.42 (m, 2H, H-1$_D$, H$_{Bn}$), 4.29 (m, 1H, H-3$_E$), 4.15 (m, 1H, H$_{All}$), 4.12-4.09 (m, 2H, H-3$_A$, H-5$_E$), 3.98 (m, 1H, H$_{All}$), 4.87 (m, 1H, H-2$_A$), 3.87-3.70 (m, 8H, H-4$_E$, OMe, H-6a$_D$, H-6b$_D$, H-2$_E$, H-5$_A$), 3.63 (m, 1H, H-2$_D$), 3.51 (m, 2H, H-4$_A$, H-4$_D$), 3.33 (m, 2H, H-6a$_E$, H-6b$_E$), 2.90 (m, 1H, H-5$_D$), 2.61 (pt, 1H, $J_{2,3}$=9.8 Hz, H-3$_D$), 1.40 (d, 3H, $J_{5,6}$=6.2 Hz, H-6$_A$).
$^{13}$C NMR (CDCl$_3$), δ159.4 (C$_{NOMe}$), 139.7-137.8 (C$_{Ph}$), 134.2 (CH=), 129.4-127.9 (CH$_{Ph}$), 117.9 (=CH$_2$), 103.2 (C-1$_D$, $^1J_{CH}$=161.6 Hz), 98.6 (C-1$_A$, $^1J_{CH}$=171.5 Hz), 95.8 (C-1$_E$, $^1J_{CH}$=170.5 Hz), 83.1 (C-3$_E$), 80.1 (C-2$_E$), 79.9 (C-4$_A$), 78.7 (C-4$_E$), 78.1 (C-2$_A$), 77.1 (C-3$_D$), 76.1 (C$_{Bn}$), 76.0 (C-3$_A$), 75.7, 75.6, 75.4 (3C, C$_{Bn}$), 75.2 (C-5$_D$), 73.8 (C$_{Bn}$), 71.5 (C-4$_D$), 70.6 (C-5$_E$), 69.0 (C-5$_A$), 68.3 (C$_{All}$), 68.1 (C-6$_E$), 62.7 (C-6$_D$), 58.4 (C-2$_D$), 52.9 (OMe), 18.1 (C-6$_A$).
HRMS (ESI$^+$): [M+Na]$^+$ $C_{58}H_{69}NO_{16}Na$ m/z theoretical:
1058.4514
m/z measured:
1058.4514
[M+NH$_4$]$^+$ $C_{58}H_{69}NO_{16}NH_4$ m/z theoretical:
1053.4960
m/z measured:
1053.4946

Allyl(2-acetamido-2-deoxy-4,6-O-isopropylidene-β-D-glucopyranosyl)-(1→2)-[2,3,4,6-tetra-O-benzyl-α-D-glucopyranosyl-(1→3)]-4-O-benzyl-α-L-rhamnopyranoside 119

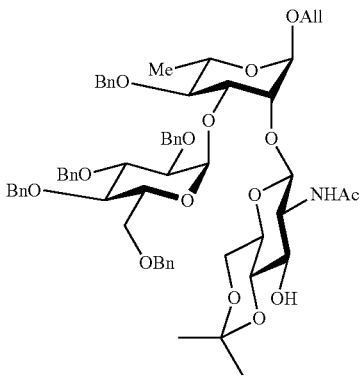

Chemical Formula: $C_{61}H_{73}NO_{15}$
Exact Mass: 1059.4980
Molecular Weight: 1060.2300

Route 1:

The triol 117 (270 mg, 265 µmol) and 2-methoxypropene (76 µL, 795 µmol, 3 eq.) are dissolved in DMF (3 mL). CSA (6.2 mg, 26 µmol, 0.1 eq.) is added in portions to the reaction mixture. The reaction mixture is then stirred at RT and the reaction is monitored by TLC (Chex/EtOAc, 1/1 and DCM/MeOH, 92/8). After stirring overnight, the transformation of the starting product (Rf=0.05 and 0.4, respectively) to a less polar product (Rf=0.35 and 0.75, respectively) is almost complete. The reaction mixture is neutralized with triethylamine (100 µL) and then concentrated in a rotary evaporator. The solid obtained is purified by silica gel chromatography (Chex/EtOAc, 1/1) to give the alcohol 119 as a white solid (240 mg, 85%).

Route 2:

TMSOTf (92.3 µL, 514 µmol, 0.2 eq.) is added to a solution of acceptor 21 (2.1 g, 2.6 mmol) and of donor 1 (1.8 g, 3.1 mmol, 1.2 eq.) in DCM (50 mL), in the presence of molecular sieve 4 Å (2.0 g), stirred under argon at −78° C. After stirring for 3 h, the ethanol-dry ice bath is withdrawn and stirring is continued for 30 min, after which time monitoring by TLC (Chex/EtOAc, 7/3) indicates the disappearance of 21 (Rf=0.5) and the appearance of a new, more polar compound (Rf=0.2). The reaction is stopped by adding triethylamine (0.2 mL), then the reaction mixture is filtered and then concentrated in a rotary evaporator. The yellow oil obtained is purified by silica gel chromatography (Chex/EtOAc, 8/2→7/3) to obtain a white solid (3.5 g).

After adding 0.5 M NaOMe (33.6 mL, 16.8 mmol, 6 eq.) to the preceding raw product (3.5 g, 2.8 mmol) in solution in DCM (270 mL), the reaction mixture is stirred for 9 h and monitored by TLC (DCM/MeOH, 92/8 and EtOAc/MeOH, 98/2). After observing the disappearance of the starting product and the appearance of a more polar product detected with ninhydrin (Rf=0.35 and 0.2, respectively), the reaction mixture is diluted by adding MeOH (540 mL), and then acetic anhydride (2.1 mL, 22.4 mmol, 8 eq.) is added to the reaction mixture. After stirring for 2 h, the appearance of a new product is observed in TLC (Rf=0.4 and 0.25, respectively). The solvents are then evaporated and the solid obtained is purified by silica gel chromatography (DCM/MeOH, 98/2→95/5) to give a white solid (2.7 g).

The previous raw product (2.7 g, 2.6 mmol) and 2-methoxypropene (758 µL, 7.9 mmol, 3 eq.) are dissolved in DMF (17 mL). CSA (61.2 mg, 263 µmol, 0.1 eq.) is added in portions to the reaction mixture. The reaction mixture is then stirred at RT and the reaction is monitored by TLC (Chex/EtOAc, 1/1 and DCM/MeOH, 92/8). After stirring for 6 h, the transformation of the starting product (Rf=0.05 and 0.4, respectively) to a less polar product (Rf=0.35 and 0.75, respectively) is almost complete. The reaction mixture is neutralized with triethylamine (0.1 mL) and then concentrated in a rotary evaporator. The solid obtained is purified by silica gel chromatography (Chex/EtOAc, 1/1) to give the alcohol 119 as a white solid (2.4 g, 87%).

Route 3:

After adding 0.5 M NaOMe (3.7 mL, 1.9 mmol, 6 eq.) to the allyl glycoside 23 (375 mg, 310 µmol) in solution in DCM (30 mL), the reaction mixture is stirred for 9 h and monitored by TLC (Chex/EtOAc, 1/1 and Chex/EtOAc, 6/4). After observing the disappearance of 23 and the appearance of a more polar product (Rf=0.2 and 0.15, respectively), the reaction mixture is diluted by adding MeOH (60 mL), and then acetic anhydride (234 µL, 2.5 mmol, 8 eq.) is added to the reaction mixture. After stirring for 2 h, the appearance of a new product is observed in TLC (Rf=0.3 in Chex/EtOAc, 1/1). The solvents are then evaporated and the solid obtained is purified by silica gel chromatography (Chex/EtOAc, 1/1) to give the alcohol 119 as a white solid (258 mg, 90%).

Route 4:

TMSOTf (16.0 µL, 92 µmol, 0.3 eq.) is added to a solution of acceptor 21 (250 mg, 310 µmol) and of donor 2 (220 mg, 400 µmol, 1.3 eq.) in DCM (8 mL), in the presence of molecular sieve 4 Å (250 mg), stirred under argon at −78° C. After stirring for 6 h, the ethanol-dry ice bath is withdrawn and stirring is continued for 30 min, after which time monitoring by TLC (Chex/EtOAc, 7/3) indicates the almost complete disappearance of the acceptor (Rf=0.5) and the appearance of a new, more polar compound (Rf=0.35). The reaction is stopped by adding triethylamine (0.1 mL), then the reaction mixture is filtered and then concentrated in a rotary evaporator. The yellow oil obtained is purified by silica gel chromatography (Chex/EtOAc, 8/27/3) to obtain a white solid (375 mg).

After adding 0.5 M NaOMe (3.7 mL, 1.9 mmol, 6 eq.) to the preceding raw product (375 mg, 310 µmol) in solution in DCM (30 mL), the reaction mixture is stirred for 9 h and monitored by TLC (Chex/EtOAc, 1/1 and Chex/EtOAc, 6/4). After observing the disappearance of the starting product and the appearance of a more polar product (Rf=0.2 and 0.15, respectively), the reaction mixture is diluted by adding MeOH (60 mL), and then acetic anhydride (234 µL, 2.5 mmol, 8 eq.) is added to the reaction mixture. After stirring for 2 h, the appearance of a new product is observed in TLC (Rf=0.3 in Chex/EtOAc, 1/1). The solvents are then evaporated and the solid obtained is purified by silica gel chromatography (Chex/EtOAc, 1/1) to give the alcohol 119 as a white solid (258 mg, 80%).

Rf=0.35 (Chex/EtOAc, 1/1).

$^1$H NMR (CDCl$_3$), δ7.31-6.96 (m, 26H, NH, CH$_{Ph}$), 5.88 (m, 1H, CH=), 5.29 (m, 1H, J$_{trans}$=17.3 Hz, =CH$_2$), 5.21 (m, 1H, J$_{cis}$=10.4 Hz, =CH$_2$), 5.09-5.06 (m, 2H, J$_{1,2}$=5.6 Hz, H-1$_E$, H$_{Bn}$), 4.98 (m, 1H, J=11.9 Hz, H$_{Bn}$), 4.86 (m, 2H, H$_{Bn}$), 4.84 (bs, 1H, J$_{1,2}$=1.7 Hz, H-1$_A$), 4.80-4.74 (m, 2H, H$_{Bn}$), 4.63-4.57 (m, 2H, J=11.9 Hz, H$_{Bn}$), 4.50 (m, 1H, J=9.6 Hz, H$_{Bn}$), 4.37-4.30 (m, 2H, J$_{1,2}$=8.3 Hz, H$_{Bn}$, H-1$_D$), 4.19-4.07 (m, 4H, H-3$_A$, H-5$_E$, H$_{All}$, H-3$_E$), 3.96 (m, 1H, H$_{All}$), 3.89-3.70 (m, 7H, H-2$_A$, H-6a$_D$, H-2$_E$, H-4$_E$, H-2$_D$, H-5$_A$, H-6b$_D$), 3.53 (pt, 1H, J$_{3,4}$=9.3 Hz, H-4$_D$), 3.51 (m, 2H, H-6a$_E$, H-6b$_E$), 3.45 (pt, 1H, J$_{3,4}$=9.6 Hz, H-4$_A$), 2.87 (m, 1H, H-5$_D$), 2.81 (pt, 1H J$_{2,3}$=9.2 Hz, H-3$_D$), 2.20 (s, 3H, H$_{NAc}$), 1.52 (s, 3H, H$_{iPr}$), 1.48 (s, 3H, H$_{iPr}$), 1.39 (d, 3H, J$_{5,6}$=6.2 Hz, H-6$_A$).

$^{13}$C NMR (CDCl$_3$), δ173.3 (C$_{NAc}$), 138.5-137.5 (C$_{Ph}$), 134.2 (CH=), 129.5-127.7 (CH$_{Ph}$), 117.7 (=CH$_2$), 102.8 (C-1$_D$, $^1$J$_{CH}$=155.2 Hz), 100.1 (C$_{iPr}$), 98.6 (C-1$_A$, $^1$J$_{CH}$=172.4 Hz), 94.6 (C-1$_E$, $^1$J$_{CH}$=169.1 Hz), 83.7 (C-3$_E$), 80.2 (C-4$_A$), 79.9 (C-2$_E$), 79.1 (C-4$_E$), 76.6 (C-2$_A$), 76.5, 76.1, 75.8, 75.4 (4C, C$_{Bn}$), 74.8 (C-3$_A$), 74.6 (C-3$_D$), 74.5 (C-4$_D$), 73.8 (C$_{Bn}$), 70.4 (C-5$_E$), 68.8 (C-5$_A$), 68.3 (C$_{All}$), 68.2 (C-6$_E$), 67.3 (C-5$_D$), 62.3 (C-6$_D$), 58.9 (C-2$_D$), 29.5 (C$_{iPr}$), 23.6 (C$_{NAc}$), 19.3 (C$_{iPr}$), 18.2 (C-6$_A$).

HRMS (ESI$^+$): [M+H]$^+$ C$_{61}$H$_{74}$NO$_{15}$ m/z theoretical:

1060.5058 m/z measured:

1060.5066

[M+Na]$^+$ C$_{61}$H$_{73}$NO$_{15}$Na m/z theoretical:

1082.4878 m/z measured:

1082.4875

Allyl(2-deoxy-4,6-O-isopropylidene-2-acetamido-β-D-glucopyranosyl)-(1→2)-[2,3,4,6-tetra-O-benzyl-α-D-glucopyranosyl-(1→3)]-(4-O-benzyl-α-L-rhamnopyranosyl)-(1→2)-3,4-di-O-benzyl-α-L-rhamnopyranoside 116

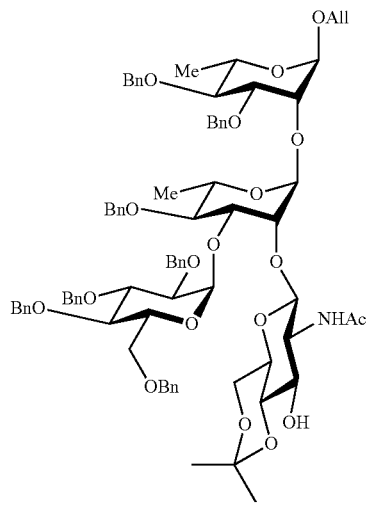

Chemical Formula: $C_{81}H_{95}NO_{19}$
Exact Mass: 1385.6498
Molecular Weight: 1386.6163

After adding 0.5 M NaOMe (5.7 mL, 2.8 mmol, 6.9 eq.) to the allyl glycoside 115 (630 mg, 412 µmol) in solution in DCM (45 mL), the reaction mixture is stirred for 6.5 h and monitored by TLC (DCM/MeOH, 98/2 and Tol/EtOAc, 85/15). After observing the disappearance of 115 and the appearance of a more polar product detected with ninhydrin (Rf=0.45 and 0, respectively), the reaction mixture is diluted by adding MeOH (91 mL), and then acetic anhydride (386 µL, 4.1 mmol, 10 eq.) is added to the reaction mixture. After stirring for 2 h, the appearance of a new product is observed in TLC (Rf=0.5 and 0.1, respectively). The solvents are then evaporated and the solid obtained is purified by silica gel chromatography (Tol/EtOAc, 6/4→4/6) to give the alcohol 116 as a white solid (470 mg, 83%).

Rf=0.35 (Tol/EtOAc, 6/4).

$^1$H NMR (CDCl$_3$), δ7.43-7.07 (m, 36H, NH, CH$_{Ph}$), 5.89 (m, 1H, CH=), 5.27 (m, 1H, J$_{trans}$=17.2 Hz, =CH$_2$), 5.20 (m, 1H, J$_{cis}$=11.7 Hz, =CH$_2$), 5.18 (d, 1H, J$_{1,2}$=3.7 Hz, H-1$_E$), 5.11-5.09 (m, 2H, H-1$_A$, H$_{Bn}$), 5.02-4.88 (m, 4H, H$_{Bn}$), 4.83-4.79 (m, 2H, H$_{Bn}$), 4.77 (d, 1H, J$_{1,2}$=1.6 Hz, H-1$_B$), 4.72-4.53 (m, 6H, H$_{Bn}$), 4.10-4.35 (m, 2H, H$_{Bn}$, H-1$_D$), 4.19-4.11 (m, 4H, H-3$_A$, H-5$_E$, H$_{All}$, H-3$_E$), 4.06 (dd, 1H, J$_{2,3}$=2.2 Hz, H-2$_A$), 4.02 (dd, 1H, J$_{2,3}$=2.9 Hz, H-2$_B$), 3.94-3.79 (m, 6H, H$_{All}$, H-4$_E$, H-3$_B$, H-2$_E$, H-2$_D$, H-5$_A$), 3.73 (dq, 1H, J$_{4,5}$=9.4 Hz, H-5$_B$), 3.59-3.46 (m, 6H, H-6a$_D$, H-6b$_D$, H-6a$_E$, H-6b$_E$, H-4$_D$, H-4$_A$, H-4$_B$), 2.83 (m, 1H, H-5$_D$), 2.78 (pt, 1H, J$_{3,4}$=9.2 Hz, H-3$_D$), 1.50 (s, 3H, H$_{iPr}$), 1.48 (s, 3H, H$_{iPr}$), 1.40 (d, 3H, J$_{5,6}$=6.2 Hz, H-6$_A$), 1.35 (d, 3H, J$_{5,6}$=6.2 Hz, H-6$_B$).

$^{13}$C NMR (CDCl$_3$), δ172.9 (C$_{NAc}$), 138.5-137.1 (C$_{Ph}$), 133.8 (CH=), 129.2-127.4 (CH$_{Ph}$), 117.2 (=CH$_2$), 102.4 (C-1$_D$, $^1$J$_{CH}$=162.8 Hz), 101.0 (C-1$_A$, $^1$J$_{CH}$=177.5 Hz), 99.6 (C$_{iPr}$), 97.8 (C-1$_B$, $^1$J$_{CH}$=169.0 Hz), 94.1 (C-1$_E$, $^1$J$_{CH}$=167.0 Hz), 83.3 (C-3$_E$), 80.5 (C-4$_B$), 80.0 (C-4$_A$), 79.4 (C-2$_E$), 79.2 (C-3$_B$), 78.7 (C-4$_E$), 76.3 (C$_{Bn}$), 75.9 (C-2$_A$), 75.7 (C$_{Bn}$), 75.5 (C-2$_B$), 75.4 75.3, 75.0 (3C, C$_{Bn}$), 74.2 (C-3$_A$), 74.1 (C-4$_D$), 74.0 (C-3$_D$), 73.5, 72.0 (2C, C$_{Bn}$), 70.1 (C-5$_E$), 68.8 (C-5$_A$), 67.9 (2C, C-5$_B$, C-6$_E$), 67.7 (C$_{All}$), 66.9 (C-5$_D$), 61.7 (C-6$_D$), 58.5 (C-2$_D$), 29.1 (C$_{iPr}$), 23.2 (C$_{NAc}$), 19.0 (C$_{iPr}$), 18.1 (C-6$_B$), 17.7 (C-6$_A$).

HRMS (ESI$^+$): [M+H]$^+$ $C_{81}H_{95}NO_{19}$ m/z theoretical: 1386.6577
m/z measured: 1386.6625
[M+Na]$^+$ $C_{81}H_{95}NO_{19}$Na m/z theoretical: 1408.6396
m/z measured: 1408.6478

Allyl(2-O-acetyl-3,4-di-O-benzyl-α-L-rhamnopyranosyl)-(1→3)-(2-acetamido-2-deoxy-4,6-O-isopropylidene-β-D-glucopyranosyl)-(1→2)-[2,3,4,6-tetra-O-benzyl-α-D-glucopyranosyl-(1→3)]-(4-O-benzyl-α-L-rhamnopyranosyl)-(1→2)-3,4-di-O-benzyl-α-L-rhamnopyranoside 116'

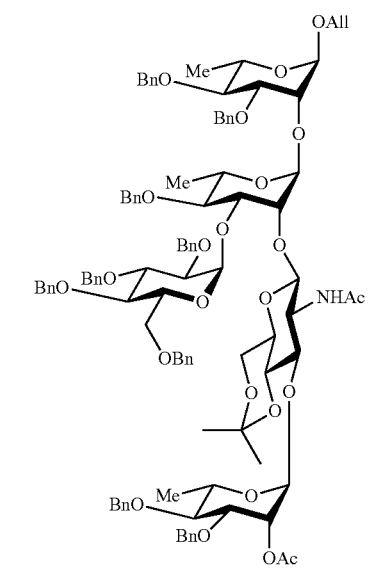

Chemical Formula: $C_{103}H_{119}NO_{24}$
Exact Mass: 1753.81
Molecular Weight: 1755.04

Triflic acid (2 µL, 23 µmol, 0.2 eq.) is added to a solution of acceptor 116 (128 mg, 94 µmol), donor 39 (97 mg, 188 µmol, 2 eq.) and molecular sieve 4 Å (200 mg) in toluene (1.5 mL), stirred under argon at −40° C. After stirring for 1 h at this temperature followed by 2 h of stirring at RT, monitoring by TLC (DCM/MeOH, 97.5/2.5) indicates the presence of a new, less polar compound, whereas 116 is at most still present in trace amounts. The reaction is stopped by adding triethylamine (0.2 mL), then the reaction mixture is filtered and concentrated in a rotary evaporator. The raw reaction product is purified by silica gel flash chromatography (Chex/EtOAc, 100/0→50/50) to obtain the allyl glycoside 116' as a white solid (116 mg, 71%).

Rf=0.58 (DCM/MeOH, 98.5/2.5).

$^1$H NMR (CDCl$_3$), δ7.44-7.06 (m, 50H, CH$_{Ph}$), 6.38 (d, 1H, NH), 5.85 (m, 1H, CH=), 5.18 (m, 1H, H-1$_E$), 5.04 (s, 1H, H-1$_A$), 5.13 (s, 1H, H-2$_C$), 5.32-4.97 (m, 15H, H$_{All}$, H$_{Bn}$), 4.72 (s, 1H, H-1$_B$), 4.63 (s, 1H, H-1$_C$), 4.33 (d, 1H, J=12.0 Hz, H$_{Bn}$), 4.27 (d, 1H, J$_{1,2}$=8.6 Hz, H-1$_D$), 4.21-4.08 (m, 5H, H-3$_E$, H-5$_E$, H-2$_D$, H-3$_A$, H$_{All}$), 3.98-3.87 (m, 8H, H-2$_A$, H-3$_C$, H-5$_C$, H-2$_B$, H$_{All}$, H-3$_B$, H-2$_E$, H-4$_E$), 3.75 (dq, 1H, J$_{4,5}$=9.3 Hz, J$_{5,6}$=6.6 Hz, H-5$_A$), 3.69 (dq, 1H, J$_{4,5}$=9.4 Hz, J$_{5,6}$=6.1 Hz, H-5$_B$), 3.52-3.41 (m, 8H, H-6a$_D$, H-6b$_D$, H-6a$_E$, H-6b$_E$, H-4$_A$, H-4$_B$, H-4$_D$, H-4$_C$), 2.74 (m, 1H, J$_{5,6}$=5.3 Hz, J$_{4,5}$=9.8 Hz, H-5$_D$), 2.62 (pt, 1H, J$_{3,4}$=J$_{4,5}$=9.4 Hz, H-3$_D$), 2.28 (s, 3H, H$_{Ac}$), 2.08 (s, 3H, H$_{NAc}$), 2.05 (s, 3H, H$_{Ac}$), 1.39 (s, 6H, H$_{iPr}$), 1.33-1.30 (m, 6H, H-6$_A$, H-6$_B$), 1.24 (d, 3H, J$_{5,6}$=6.3 Hz, H-6$_C$).

$^{13}$C NMR (CDCl$_3$), δ170.9 (C$_{Ac}$), 170.5 (C$_{NAc}$), 139.2-18.7 (C$_{Ph}$), 134.2 (CH=), 129.7-127.8 (CH$_{Ph}$), 117.6 (=CH$_2$), 103.8 (C-1$_D$), 101.5 (C-1$_A$), 99.6 (C$_{iPr}$), 98.8 (C-1$_B$), 98.2 (C-1$_C$), 94.4 (C-1$_E$), 83.7 (C-3$_E$), 80.8-78.9 (7C, C-3$_D$, C-4$_B$, C-2$_E$, C-4$_C$, C-4$_A$, C-3$_B$, C-4$_E$), 78.1 (C-3$_C$), 76.6 (C$_{Bn}$), 76.4 (C-2$_A$), 75.6 (C-2$_B$), 76.0-75.4 (7C, C$_{Bn}$), 74.6 (C-3$_A$), 73.9 (C$_{Bn}$), 72.4 (C-4$_D$), 72.3, 71.8 (2C, C$_{Bn}$), 70.3 (2C, C-2$_C$, C-5$_E$), 69.2 (C-5$_A$), 68.2 (C-5$_B$), 68.0 (2C, C-6$_E$, C$_{All}$), 67.8 (C-5$_C$), 67.5 (C-5$_D$), 62.3 (C-6$_D$), 55.7 (C-2$_D$), 29.5 (C$_{iPr}$), 24.4 (C$_{NAc}$), 21.5 (C$_{Ac}$), 19.5 (C$_{iPr}$), 18.4, 87.3, 18.0 (C-6$_A$, C-6$_B$, C-6$_C$).

HRMS (ESI$^+$): [M+H]$^+$ C$_{103}$H$_{119}$NO$_{24}$ m/z theoretical: 1755.8234
m/z measured: 1755.8301

Propyl(2-O-acetyl-α-L-rhamnopyranosyl)-(1→3)-(2-acetamido-2-deoxy-β-D-glucopyranosyl)-(1→2)-[α-D-glucopyranosyl-(1→3)]-α-L-rhamnopyranosyl-(1→2)-α-L-rhamnopyranoside IX

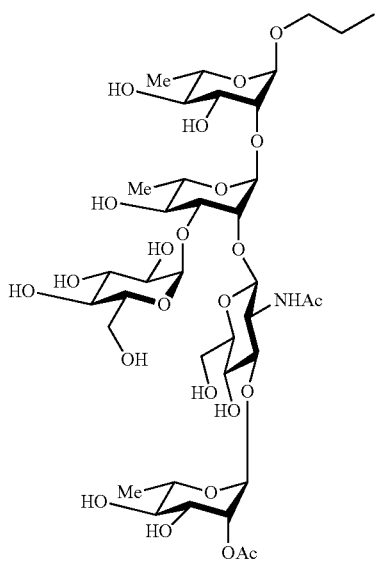

Chemical Formula: C$_{37}$H$_{63}$NO$_{24}$
Exact Mass: 905.37
Molecular Weight: 905.89

50% aqueous TFA solution (2 mL) is slowly added to a solution of the allyl glycoside 116' (105 g, 84 µmol) in DCM (2 mL) at 0° C. The reaction mixture is stirred for 1 h at this temperature, then 15 min at RT. Monitoring by TLC (DCM/MeOH, 95/5) indicates the complete disappearance of 116' and the appearance of a new, more polar compound 116". The reaction mixture is concentrated by coevaporation with toluene (3×10 mL). The raw reaction product (103 mg) is sufficiently pure, according to NMR analyses, to be used as in the debenzylation stage.

Pd/C 10% (100 mg) is added to a degassed solution of diol 116" (102 mg, 60 µmol) in ethanol (4 mL). The suspension is placed under hydrogen atmosphere (1 bar) and stirred at RT for 6 h. Monitoring by TLC (iPrOH/H$_2$O/NH$_3$, 7/1/2) shows the disappearance of 116" and the presence of a more polar compound. The reaction mixture is filtered on Celite, and the filtrate is concentrated in a rotary evaporator. After filtration of the suspension and evaporation of the filtrate, the residue obtained is purified by HPLC (Kromasil C-18 column, 0.01 M aqueous TFA/CH$_3$CN, 100/0→70/30 in 20 min, 5.5 mL/min, 215 nm) to give the target tetrasaccharide VIII in the form of a white powder after lyophilization (36 mg, 68%).

Rf=0.41 (iPrOH/NH$_3$/H$_2$O, 7/1/2).

$^1$H NMR (CDCl$_3$), δ7.40-7.06 (m, 50H, CH$_{Ph}$), 6.38 (d, 1H, J$_{NH,2}$=9.1 Hz, NH), 5.86 (m, 1H, CH=), 5.44 (dd, 1H, J$_{2,3}$=3.0 Hz, H-2$_{B'}$), 5.26 (m, 1H, J$_{trans}$=17.2 Hz, =CH$_2$), 5.20-5.17 (m, 2H, =CH$_2$, H-1$_E$), 5.07 (d, 1H, J$_{1,2}$=1.6 Hz, H-1$_A$), 5.05 (d, 1H, J$_{1,2}$=1.8 Hz, H-1$_{B'}$), 5.02-4.75 (m, 9H, 4H$_{Bn}$, H-2$_C$, 4H$_{Bn}$), 4.75 (d, 1H, J$_{1,2}$=1.4 Hz, H-1$_B$), 4.70 (bs, 1H, H-1$_C$), 4.68-4.57 (m, 9H, H$_{Bn}$), 4.50 (d, 1H, J=11.0 Hz, H$_{Bn}$), 4.42-4.33 (m, 2H, H$_{Bn}$), 4.28 (d, 1H, J$_{1,2}$=8.6 Hz, H-1$_D$), 4.21-4.08 (m, 6H, H-3$_E$, H-5$_E$, H-2$_D$, H-3$_A$, H$_{All}$, H-3$_C$), 3.99 (dd, 1H, J$_{2,3}$=2.6 Hz, H-2$_A$), 3.96-3.84 (m, 7H, H-5$_C$, H-2$_B$, H$_{All}$, H-3$_B$, H-3$_{B'}$, H-2$_E$, H-4$_E$), 3.81-3.73 (m, 2H, H-5$_A$, H-5$_{B'}$), 3.71 (dq, 1H, J$_{4,5}$=9.4 Hz, H-5$_B$), 3.54-3.38 (m, 8H, H-6a$_D$, H-6b$_D$, H-6a$_E$, H-6b$_E$, H-4$_A$, H-4$_B$, H-4$_D$, H-4$_C$, H-4$_{B'}$), 2.75-2.64 (m, 6H, H-5$_D$, 2CH$_{2Lev}$, H-3$_D$), 2.31 (s, 3H, H$_{NAc}$), 2.18 (s, 3H, CH$_{3Lev}$), 2.05 (s, 3H, H$_{Ac}$), 1.42 (s, 3H, H$_{iPr}$), 1.39 (s, 3H, H$_{iPr}$), 1.35-1.31 (m, 9H, H-6$_A$*, H-6$_B$*, H-6$_{B'}$*), 1.24 (d, 3H, J$_{5,6}$=6.2 Hz, H-6$_C$).

$^{13}$C NMR (CDCl$_3$), δ206.1 (C$_{Lev}$), 171.7 (C$_{Lev}$), 170.4 (C$_{Ac}$), 170.0 (C$_{NAc}$), 138.6-137.5 (C$_{Ph}$), 133.8 (CH=), 129.3-127.7 (CH$_{Ph}$), 117.1 (=CH$_2$), 103.6 (C-1$_D$, $^1$J$_{CH}$=159.0 Hz), 101.1 (C-1$_A$, $^1$J$_{CH}$=172.8 Hz), 99.5 (C-1$_{B'}$, $^1$J$_{CH}$=167.8 Hz), 99.2 (C$_{iPr}$), 97.9 (C-1$_B$, $^1$J$_{CH}$=172.8 Hz), 97.8 (C-1$_C$, $^1$J$_{CH}$=172.8 Hz), 94.2 (C-1$_E$, $^1$J$_{CH}$=165.3 Hz), 83.4 (C-3$_E$), 80.5 (C-3$_D$), 80.4 (C-4$_B$), 80.2 (C-2$_E$), 80.1 (C-4$_{B'}$), 80.0 (C-4$_C$), 79.8 (C-4$_A$), 79.2 (C-3$_B$), 78.5 (C-4$_E$), 78.2 (C-3$_C$), 77.9 (C-3$_{B'}$), 76.2 (C-2$_A$), 76.1, 75.7, 75.4 (3C, C$_{Bn}$), 75.3 (C-2$_B$), 75.2, 75.1, 75.0, 74.5 (4C, C$_{Bn}$), 74.5 (C-3$_A$), 73.5 (C$_{Bn}$), 73.2 (C-2$_C$), 72.1 (C-4$_D$), 71.9, 71.4 (2C, C$_{Bn}$), 70.0 (C-5$_E$), 69.3 (C-2$_{B'}$), 68.9 (C-5$_A$), 68.5 (C-5$_{B'}$), 67.9 (C-6$_E$), 67.8 (C-5$_B$), 67.7 (C$_{All}$), 67.3 (C-5$_C$), 67.2 (C-5$_D$), 62.0 (C-6$_D$), 55.0 (C-2$_D$), 38.1 (CH$_{2Lev}$), 29.8 (CH$_{3Lev}$), 29.2 (C$_{iPr}$), 28.2 CH$_{2Lev}$), 24.1 (C$_{NAc}$), 21.0 (C$_{Ac}$), 19.1 (C$_{iPr}$), 18.0, 17.9, 17.8, 17.7 (C-6$_A$*, C-6$_B$*, C-6$_{B'}$*, C-6$_C$*).

HRMS (ESI$^+$): [M+Na]$^+$ C$_{37}$H$_{63}$NO$_{24}$Na m/z theoretical: 928.3638
m/z measured: 928.3660

Method 16:

Allyl(3,4-di-O-benzyl-2-O-levulinoyl-α-L-rhamnopyranosyl)-(1→3)-(2-O-acetyl-4-O-benzyl-α-L-rhamnopyranosyl)-(1→3)-(2-deoxy-4,6-O-isopropylidene-2-acetamido-β-D-glucopyranosyl)-(1→2)-[2,3,4,6-tetra-O-benzyl-α-D-glucopyranosyl-(1→3)]-4-O-benzyl-α-L-rhamnopyranoside 120

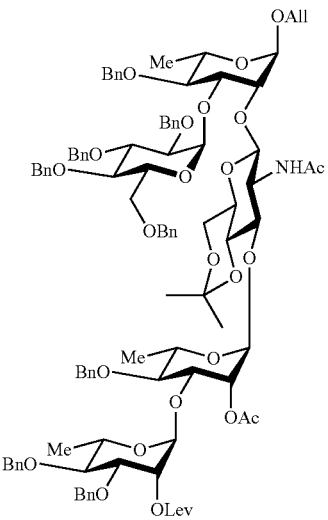

Chemical Formula: C$_{101}$H$_{119}$NO$_{26}$
Exact Mass: 1761.8020
Molecular Weight. 1763.0167

TfOH (23.0 µL, 263 µmol, 0.9 eq.) is added to a solution of acceptor 119 (310 mg, 290 µmol) and of donor 47 (379 mg, 440 µmol, 1.5 eq.) in Tol (10 mL), in the presence of molecular sieve 4 Å (1.7 g), stirred under argon at 0° C. After stirring for 15 min, monitoring by TLC (Chex/EtOAc, 1/1) indicates the disappearance of 119 (Rf=0.1) and the appearance of a new, more polar compound (Rf=0.35). The reaction is stopped by adding triethylamine (0.2 mL), then the reaction mixture is filtered and concentrated in a rotary evaporator. The yellow oil obtained is purified by silica gel chromatography (Tol/EtOAc, 8/2→6/4) to obtain the allyl glycoside 120 as a slightly contaminated white solid (383 mg, 74%).

Rf=0.35 (Chex/EtOAc, 1/1).

$^1$H NMR (CDCl$_3$), δ7.45-7.07 (m, 40H, CH$_{Ph}$), 6.47 (d, 1H, J$_{NH,2}$=9.0 Hz, NH), 5.90 (m, 1H, CH=), 5.46 (dd, 1H, J$_{2,3}$=3.0 Hz, H-2$_B$), 5.29 (m, 1H, J$_{trans}$=17.2 Hz, =CH$_2$), 5.20 (m, 1H, J$_{cis}$=10.4 Hz, =CH$_2$), 5.15 (d, 1H, J$_{1,2}$=3.5 Hz, H-1$_E$), 5.09 (d, 1H, J$_{1,2}$=1.2 Hz, H-1$_B$), 5.07-4.98 (m, 4H, H$_{Bn}$), 4.94 (dd, 1H, J$_{2,3}$=2.7 Hz, H-2$_C$), 4.93-4.88 (m, 3H, H$_{Bn}$), 4.84 (bs, 1H, H-1$_A$), 4.77 (bs, 1H, H-1$_C$), 4.67-4.60 (m, 5H, H$_{Bn}$), 4.53-4.33 (d, 4H, H$_{Bn}$), 4.28 (d, 1H, J$_{1,2}$=8.6 Hz, H-1$_D$), 4.21-4.13 (m, 6H, H-3$_E$, H-2$_D$, H-5$_E$, H-3$_C$, H$_{All}$, H-3$_A$), 4.00 (dq, 1H, J$_{4,5}$=9.6 Hz, H-5$_C$), 3.97-3.83 (m, 6H, H$_{All}$, H-3$_B$, H-2$_E$, H-2$_A$, H-4$_E$, H-6a$_D$), 3.79 (dq, 1H, J$_{4,5}$=9.4 Hz, H-5$_B$), 3.73 (m, 1H, H-6b$_D$), 3.70 (dq, 1H, J$_{4,5}$=9.5 Hz, H-5$_A$), 3.52 (pt, 1H, J$_{3,4}$=9.3 Hz, H-4$_D$), 3.58-3.40 (m, 5H, H-4$_A$, H-6a$_E$, H-6b$_E$, H-4$_C$, H-4$_B$), 2.76-2.68 (m, 6H, H-5$_D$, 2CH$_{2Lev}$, H-3$_D$), 2.35 (s, 3H, H$_{NAc}$), 2.19 (s, 3H, CH$_{3Lev}$), 2.06 (s, 3H, H$_{Ac}$), 1.48 (s, 3H, H$_{iPr}$), 1.45 (s, 3H, H$_{iPr}$), 1.38 (d, 3H, J$_{5,6}$=6.2 Hz, H-6$_A$), 1.34 (d, 3H, J$_{5,6}$=6.2 Hz, H-6$_B$), 1.27 (d, 3H, J$_{5,6}$=6.2 Hz, H-6$_C$).

$^{13}$C NMR (CDCl$_3$), δ206.1 (C$_{Lev}$), 171.8 (C$_{Lev}$), 170.5 (C$_{Ac}$), 170.1 (C$_{NAc}$), 138.7-137.5 (C$_{Ph}$), 134.0 (CH=), 129.4-127.8 (CH$_{Ph}$), 117.1 (=CH$_2$), 103.7 (C-1$_D$, $^1$J$_{CH}$=159.9 Hz), 99.5 (C-1$_B$, $^1$J$_{CH}$=169.7 Hz), 99.3 (C$_{iPr}$), 98.4 (C-1$_A$, $^1$J$_{CH}$=182.1 Hz), 97.5 (C-1$_C$, $^1$J$_{CH}$=170.6 Hz), 94.4 (C-1$_E$, $^1$J$_{CH}$=170.1 Hz), 83.5 (C-3$_E$), 80.7 (C-3$_D$), 80.4 (C-2$_E$), 80.1, 80.0 (C-4$_B$*, C-4$_C$*), 79.8 (C-4$_A$), 78.5 (C-4$_E$), 78.2 (C-3$_C$), 77.9 (C-3$_B$), 76.7 (C-2$_A$), 76.1, 75.9, 75.5, 75.4, 75.1, 75.0 (6C, C$_{Bn}$), 74.8 (C-3$_A$), 73.4 (C$_{Bn}$), 73.3 (C-2$_C$), 72.4 (C-4$_D$), 71.3 (C$_{Bn}$), 70.0 (C-5$_E$), 69.3 (C-2$_B$), 68.6 (C-5$_A$), 68.5 (C-5$_B$), 67.9 (C-6$_E$), 67.8 (C$_{All}$), 67.4 (C-5$_D$), 67.3 (C-5$_C$), 62.2 (C-6$_D$), 55.0 (C-2$_D$), 38.1 (CH$_{2Lev}$), 29.8 (CH$_{3Lev}$), 29.2 (C$_{iPr}$), 28.3 (CH$_{2Lev}$), 24.1 (C$_{NAc}$), 21.1 (C$_{Ac}$), 19.1 (C$_{iPr}$), 17.9, 17.8, 17.7 (C-6$_A$*, C-6$_B$*, C-6$_C$*).

HRMS (ESI$^+$): [M+H]$^+$ C$_{101}$H$_{119}$NO$_{26}$ m/z theoretical: 1762.8098 m/z measured: 1762.8198

[M+Na]$^+$ C$_{101}$H$_{119}$NO$_{26}$Na m/z theoretical: 1784.7917 m/z measured: 1784.7988

Allyl(3,4-di-O-benzyl-2-O-levulinoyl-α-L-rhamnopyranosyl)-(1→3)-2-O-acetyl-4-O-benzyl-α-L-rhamnopyranosyl)-(1→3)-(2-deoxy-4,6-O-isopropylidene-2-acetamido-β-D-glucopyranosyl)-(1→2)-[2,3,4,6-tetra-O-benzyl-α-D-glucopyranosyl-(1→3)]-(4-O-benzyl-α-L-rhamnopyranosyl)-(1→2)-3,4-di-O-benzyl-α-L-rhamnopyranoside 121

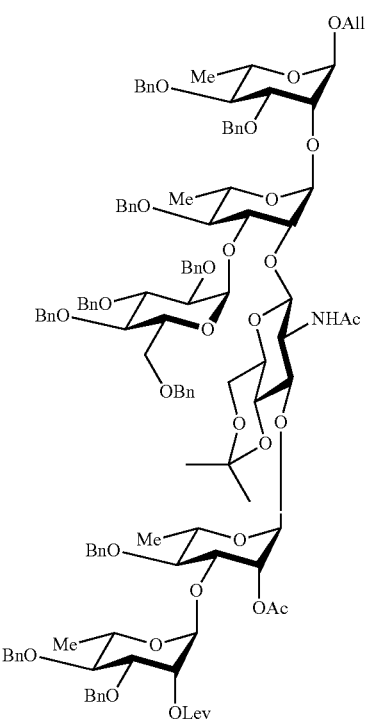

Chemical Formula: C$_{121}$H$_{141}$NO$_{30}$
Exact Mass: 2087.9538
Molecular Weight: 2089.4029

TMSOTf (18.0 µL, 100 µmol, 0.9 eq.) is added to a solution of acceptor 116 (150 mg, 110 µmol) and of donor 47 (140 mg, 160 µmol, 1.5 eq.) in Tol (5 mL), in the presence of molecular sieve 4 Å (620 mg), stirred under argon at 0° C. After stirring for 45 min, monitoring by TLC (Tol/EtOAc, 75/25 and Chex/EtOAc, 1/1) indicates the disappearance of 116 (Rf=0.05 and Rf=0.15, respectively) and the appearance of a new, less polar compound (Rf=0.55 and Rf=0.2). The reaction is stopped by adding triethylamine (0.5 mL), then the reaction mixture is filtered and concentrated in a rotary evaporator. The yellow oil obtained is purified by silica gel chromatography (Tol/EtOAc, 75/25/1/1), obtaining, in the order of elution, the allyl glycoside 121 as a slightly contaminated white solid (149 mg, 65%).

Rf=0.55 (Chex/EtOAc, 1/1).

$^1$H NMR (CDCl$_3$), δ7.40-7.06 (m, 50H, CH$_{Ph}$), 6.38 (d, 1H, J$_{NH,2}$=9.1 Hz, NH), 5.86 (m, 1H, CH=), 5.44 (dd, 1H, J$_{2,3}$=3.0 Hz, H-2$_{B'}$), 5.26 (m, 1H, J$_{trans}$=17.2 Hz, =CH$_2$), 5.20-5.17 (m, 2H, =CH$_2$, H-1$_E$), 5.07 (d, 1H, J$_{1,2}$=1.6 Hz, H-1$_A$), 5.05 (d, 1H, J$_{1,2}$=1.8 Hz, H-1$_{B'}$), 5.02-4.75 (m, 9H, 4H$_{Bn}$, H-2$_C$, 4H$_{Bn}$), 4.75 (d, 1H, J$_{1,2}$=1.4 Hz, H-1$_B$), 4.70 (bs, 1H, H-1$_C$), 4.68-4.57 (m, 9H, H$_{Bn}$), 4.50 (d, 1H, J=11.0 Hz, H$_{Bn}$), 4.42-4.33 (m, 2H, H$_{Bn}$), 4.28 (d, 1H, J$_{1,2}$=8.6 Hz, H-1$_D$), 4.21-4.08 (m, 6H, H-3$_E$, H-5$_E$, H-2$_D$, H-3$_A$, H$_{All}$, H-3$_{C'}$), 3.99 (dd, 1H, J$_{2,3}$=2.6 Hz, H-2$_A$), 3.96-3.84 (m, 7H, H-5$_C$, H-2$_B$, H$_{All}$, H-3$_B$, H-3$_{B'}$, $_H$2$_E$, H-4$_E$), 3.81-3.73 (m, 2H, H-5$_A$, H-5$_{B'}$), 3.71 (dq, 1H, J$_{4,5}$=9.4 Hz, H-5$_B$), 3.54-3.38 (m, 8H, H-6a$_D$, H-6b$_D$, H-6a$_E$, H-6b$_E$, H-4$_A$, H-4$_B$, H-4$_D$, H-4$_C$, H-4$_{B'}$), 2.75-2.64 (m, 6H, H-5$_D$, 2CH$_{2Lev}$, H-3$_D$), 2.31 (s, 3H, H$_{NAc}$), 2.18 (s, 3H, CH$_{3Lev}$), 2.05 (s, 3H, H$_{Ac}$), 1.42 (s, 3H, H$_{iPr}$), 1.39 (s, 3H, H$_{iPr}$), 1.35-1.31 (m, 9H, H-6$_A$*, H-6$_B$*, H-6$_{B'}$*), 1.24 (d, 3H, J$_{5,6}$=6.2 Hz, H-6$_C$).

$^{13}$C NMR (CDCl$_3$), δ206.1 (C$_{Lev}$), 171.7 (C$_{Lev}$), 170.4 (C$_{Ac}$), 170.0 (C$_{NAc}$), 138.6-137.5 (C$_{Ph}$), 133.8 (CH═), 129.3-127.7 (CH$_{Ph}$), 117.1 (═CH$_2$), 103.6 (C-1$_D$, $^1$J$_{CH}$=159.0 Hz), 101.1 (C-1$_A$, $^1$J$_{CH}$=172.8 Hz), 99.5 (C-1$_{B'}$, $^1$J$_{CH}$=167.8 Hz), 99.2 (C$_{iPr}$), 97.9 (C-1$_B$, $^1$J$_{CH}$=172.8 Hz), 97.8 (C-1$_C$, $^1$J$_{CH}$=172.8 Hz), 94.2 (C-1$_E$, $^1$J$_{CH}$=165.3 Hz), 83.4 (C-3$_E$), 80.5 (C-3$_D$), 80.4 (C-4$_B$), 80.2 (C-2$_E$), 80.1 (C-4$_{B'}$), 80.0 (C-4$_C$), 79.8 (C-4$_A$), 79.2 (C-3$_B$), 78.5 (C-4$_E$), 78.2 (C-3$_C$), 77.9 (C-3$_{B'}$), 76.2 (C-2$_A$), 76.1, 75.7, 75.4 (3C, C$_{Bn}$), 75.3 (C-2$_B$), 75.2, 75.1, 75.0, 74.5 (4C, C$_{Bn}$), 74.5 (C-3$_A$), 73.5 (C$_{Bn}$), 73.2 (C-2$_C$), 72.1 (C-4$_D$), 71.9, 71.4 (2C, C$_{Bn}$), 70.0 (C-5$_E$), 69.3 (C-2$_{B'}$), 68.9 (C-5$_A$), 68.5 (C-5$_{B'}$), 67.9 (C-6$_E$), 67.8 (C-5$_B$), 67.7 (C$_{All}$), 67.3 (C-5$_C$), 67.2 (C-5$_D$), 62.0 (C-6$_D$), 55.0 (C-2$_D$), 38.1 (CH$_{2Lev}$), 29.8 (CH$_{3Lev}$), 29.2 (C$_{iPr}$), 28.2 (CH$_{2Lev}$), 24.1 (C$_{NAc}$), 21.0 (C$_{Ac}$), 19.1 (C$_{iPr}$), 18.0, 17.9, 17.8, 17.7 (C-6$_A$*, C-6$_B$*, C-6$_C$*).

HRMS (ESI$^+$): [M+H]$^+$ C$_{121}$H$_{141}$NO$_{30}$ m/z theoretical:

2088.9617 m/z measured:

2088.9619

[M+Na]$^+$ C$_{121}$H$_{141}$NO$_{30}$Na m/z theoretical:

2110.9436 m/z measured:

2110.9497

Allyl(3,4-di-O-benzyl-2-O-levulinoyl-α-L-rhamnopyranosyl)-(1→3)-2-O-acetyl-4-O-benzyl-α-L-rhamnopyranosyl)-(1→3)-(2-deoxy-4,6-O-isopropylidene-2-trichloroacetamido-β-D-glucopyranosyl)-(1→2)-[2,3,4,6-tetra-O-benzyl-α-D-glucopyranosyl-(1→3)]-(4-O-benzyl-α-L-rhamnopyranosyl)-(1→2)-3,4-di-O-benzyl-α-L-rhamnopyranoside 122

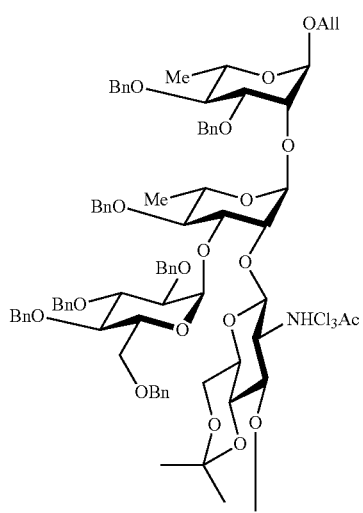

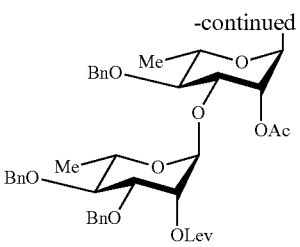

Chemical Formula C$_{121}$H$_{138}$Cl$_3$NO$_{30}$
Exact Mass: 2189.8369
Molecular Weight: 2192.7381

TMSOTf (61.0 μL, 340 μmol, 0.3 eq.) is added to a solution of acceptor 110 (1.7 g, 1.1 mmol) and of donor 47 (1.5 g, 1.7 mmol, 1.5 eq.) in Tol (35 mL), in the presence of molecular sieve 4 Å (975 mg), stirred under argon at −40° C. After stirring for 1 h, monitoring by TLC (Tol/EtOAc, 8/2) indicates the disappearance of 110 (Rf=0.3) and the appearance of a new, less polar compound (Rf=0.45). The reaction is stopped by adding triethylamine (0.5 mL), then the reaction mixture is filtered and concentrated in a rotary evaporator. The yellow oil obtained is purified by silica gel chromatography (Tol/EtOAc, 95/5→7/3), obtaining, in the order of elution, the allyl glycoside 122 as a white solid (1.45 g, 59%) and then the diol 123 as a white solid (505 mg, 21%).

Rf=0.45 (Tol/EtOAc, 8/2).

$^1$H NMR (CDCl$_3$), δ7.45-7.10 (m, 50H, CH$_{Ph}$), 6.94 (d, 1H, J$_{NH,2}$=8.8 Hz, NH), 5.92 (m, 1H, CH═), 5.46 (dd, 1H, J$_{1,2}$=1.9 Hz, J$_{2,3}$=3.0 Hz, H-2$_{B'}$), 5.30 (m, 1H, J$_{trans}$=17.2 Hz, ═CH$_2$), 5.25-5.22 (m, 2H, H-1$_E$, ═CH$_2$), 5.15-5.05 (m, 6H, H-1$_A$, 2H$_{Bn}$, H-1$_{B'}$, H-2$_C$, H$_{Bn}$), 4.98-4.93 (m, 3H, H$_{Bn}$), 4.89-4.83 (m, 3H, H$_{Bn}$), 4.81 (d, 1H, J$_{1,2}$=1.4 Hz, H-1$_B$), 4.76 (d, 1H, J$_{1,2}$=1.4 Hz, H-1$_C$), 4.72-4.60 (m, 8H, H$_{Bn}$), 4.58 (d, 1H, J$_{1,2}$=3.8 Hz, H-1$_D$), 4.54 (d, 1H, J=11.0 Hz, H$_{Bn}$), 4.45 (d, 1H, J=11.3 Hz, H$_{Bn}$), 4.37 (d, 1H, J=12.0 Hz, H$_{Bn}$), 4.21 (pt, 1H, J$_{3,4}$=9.3 Hz, H-3$_E$), 4.19-4.14 (m, 5H, H-3$_C$, H$_{All}$, H-3$_A$, H-2$_A$, H-5$_E$), 4.07-3.86 (m, 9H, H-2$_B$, H-2$_D$, H$_{All}$, H-5$_C$, H-5$_{B'}$, H-3$_B$, H-3$_{B'}$, H-2$_E$, H-4$_E$), 3.80 (dq, 1H, J$_{4,5}$=9.5 Hz, H-5$_A$), 3.74 (dq, 1H, J$_{4,5}$=9.4 Hz, H-5$_B$), 3.60-3.43 (m, 8H, H-6a$_D$, H-4$_A$, H-4$_B$, H-6a$_E$, H-6b$_E$, H-4$_D$, H-4$_{B'}$, $_H$4$_C$), 3.35 (m, 1H, J$_{6a,6b}$=10.4 Hz, H-6b$_D$), 2.82 (m, 1H, H-5$_D$), 2.75-2.69 (m, 5H, 2CH$_{2Lev}$, H-3$_D$), 2.21 (s, 3H, CH$_{3Lev}$), 2.14 (s, 3H, H$_{Ac}$), 1.44-1.43 (m, 9H, H$_{iPr}$, H-6$_A$), 1.39 (d, 3H, J$_{5,6}$=6.8 Hz, H-6$_{B'}$), 1.37 (d, 3H, J$_{5,6}$=6.2 Hz, H-6$_B$), 1.37 (d, 3H, J$_{5,6}$=6.2 Hz, H-6$_C$).

$^{13}$C NMR (CDCl$_3$), δ206.3 (C$_{Lev}$), 171.8 (C$_{Lev}$), 169.6 (C$_{Ac}$), 162.0 (C$_{NTCA}$), 138.7-137.6 (C$_{Ph}$), 133.9 (CH═), 129.4-127.5 (CH$_{Ph}$), 117.2 (═CH$_2$), 101.2 (C-1$_D$, $^1$J$_{CH}$=163.9 Hz), 100.9 (C-1$_A$, $^1$J$_{CH}$=172.0 Hz), 99.4 (C$_{iPr}$), 99.0 (C-1$_{B'}$, $^1$J$_{CH}$=168.3 Hz), 98.0 (C-1$_B$, $^1$J$_{CH}$=168.7 Hz), 97.6 (C-1$_C$, $^1$J$_{CH}$=170.4 Hz), 94.3 (C-1$_E$, $^1$J$_{CH}$=167.5 Hz), 93.1 (CCl$_3$), 83.1 (C-3$_E$), 80.4, 80.1, 79.9, 79.7, 79.6, 79.0 (7C, C-3$_B$*, C-3$_{B'}$*, C-4$_A$*, C-4$_B$*, C-4$_{B'}$*, C-4$_C$*, C-4$_E$*), 78.7 (C-3$_D$), 77.6 (C-2$_E$), 76.8 (C-3$_C$), 76.2, 75.4, 75.3, 75.2, 75.0, 74.9, 74.8 (7C, C$_{Bn}$), 74.3 (C-2$_B$), 74.2 (C-3$_A$), 73.5 (C$_{Bn}$), 73.4 (C-2$_A$), 72.6 (C-4$_D$), 72.1 (C-2$_C$), 72.0, 71.5 (2C, C$_{Bn}$), 69.9 (C-5$_E$), 69.4 (C-2$_{B'}$), 68.7 (C-5$_A$), 68.5 (C-5$_{B'}$), 68.0 (C-5$_B$), 67.9 (C-6$_E$), 67.8 (C-5$_C$), 67.7 (C$_{All}$), 67.0 (C-5$_D$), 61.8 (C-6$_D$), 57.4 (C-2$_D$), 38.2 (CH$_{2Lev}$), 29.9 (CH$_{3Lev}$), 29.2 (C$_{iPr}$), 28.2 (CH$_{2Lev}$), 21.2 (C$_{Ac}$), 19.1 (C$_{iPr}$), 18.3, 18.1, 18.0, 17.9 (C-6$_A$*, C-6$_B$*, C-6$_{B'}$*, C-6$_C$*).

HRMS (ESI+): [M+H]+ $C_{121}H_{138}NO_{30}{}^{35}Cl_3$ m/z theoretical:
2190.8447
m/z measured:
2190.8403
[M+Na]+ $C_{121}H_{138}NO_{30}{}^{35}Cl_3Na$ m/z theoretical:
2212.8267
m/z measured:
2212.8215

Allyl(3,4-di-O-benzyl-2-O-levulinoyl-α-L-rhamnopyranosyl)-(1→3)-2-O-acetyl-4-O-benzyl-α-L-rhamnopyranosyl)-(1→3)-(2-deoxy-2-trichloroacetamido-β-D-glucopyranosyl)-(1→2)-[2,3,4,6-tetra-O-benzyl-α-D-glucopyranosyl-(1→3)]-(4-O-benzyl-α-L-rhamnopyranosyl)-(1→2)-3,4-di-O-benzyl-α-L-rhamnopyranoside 123

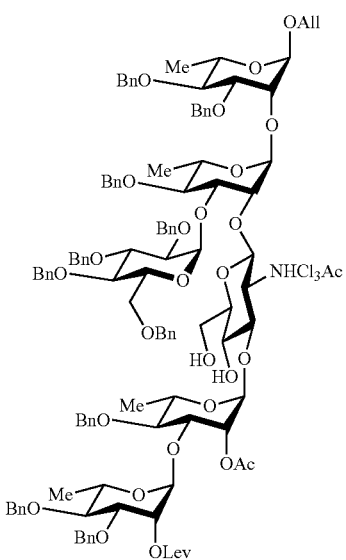

Chemical Formula: $C_{118}H_{134}Cl_3NO_{30}$
Exact Mass: 2149.8056
Molecular Weight: 2152.6743

50% aqueous TFA solution (8 mL) is slowly added to a solution of the allyl glycoside 122 (1.9 g, 880 μmol) in DCM (30 mL) at 0° C. The reaction mixture is stirred for 2 h at this temperature, after which time monitoring by TLC (Tol/EtOAc, 7/3) indicates the complete disappearance of 122 (Rf=0.55) and the appearance of a new, more polar compound (Rf=0.4). The reaction mixture is concentrated by coevaporation with Tol (3×10 mL). The yellow oil obtained is purified by silica gel chromatography (Tol/EtOAc, 8/2→6/4) to obtain the diol 123 as a white solid (1.7 g, 89%).

Rf=0.4 (Tol/EtOAc, 7/3).

$^1$H NMR (CDCl$_3$), δ7.62-7.13 (m, 50H, CH$_{Ph}$), 7.04 (d, 1H, J$_{NH,2}$=8.8 Hz, NH), 5.94 (m, 1H, CH=), 5.53 (dd, 1H, J$_{2,3}$=3.0 Hz, H-2$_{B'}$), 5.44 (bs, 1H, H-1$_A$), 5.34 (m, 1H, J$_{trans}$=17.2 Hz, =CH$_2$), 5.34 (d, 1H, J$_{1,2}$=3.6 Hz, H-1$_E$), 5.26 (m, 1H, J$_{cis}$=10.4 Hz, =CH$_2$), 5.22-5.11 (m, 5H, 2H$_{Bn}$, H-1$_{B'}$, H-2$_C$, H$_{Bn}$), 5.07-4.88 (m, 7H, H$_{Bn}$), 4.82-4.78 (m, 3H, 2H$_{Bn}$, H-1$_B$), 4.75-4.64 (m, 8H, H$_{Bn}$), 4.60 (bs, 1H, H-1$_C$), 4.56 (d, 1H, J$_{1,2}$=8.8 Hz, H-1$_D$), 4.44 (m, 2H, H$_{Bn}$), 4.30-4.18 (m, 7H, H-3$_C$, H-2$_A$, H-3$_A$, H-3$_E$, H-5$_E$, H-2$_B$, H$_{All}$), 4.05-3.70 (m, 7H, H$_{All}$, H-2$_D$, H-3$_B$, H-3$_{B'}$, H-5$_C$, 4$_E$, H-2$_E$), 3.88 (dq, 1H, J$_{4,5}$=9.4 Hz, H-5$_{B'}$), 3.81 (dq, 1H, J$_{4,5}$=9.6 Hz, H-5$_B$), 3.78 (dq, 1H, J$_{4,5}$=10.0 Hz, H-5$_A$), 3.72 (m, 1H, H-6a$_D$), 3.61-3.56 (m, 4H, H-4$_B$, H-6a$_E$, H-6b$_E$, H-4$_A$), 3.54 (pt, 1H, J$_{3,4}$=9.5 Hz, H-4$_C$), 3.48 (pt, 1H, J$_{3,4}$=9.4 Hz, H-4$_{B'}$), 3.10 (m, 2H, H-4$_D$, H-5$_D$), 3.05 (m, 1H, H-6b$_D$), 2.78 (m, 4H, 2CH$_{2Lev}$), 2.24 (s, 3H, CH$_{3Lev}$), 2.23 (s, 3H, H$_{Ac}$), 2.19 (m, 1H, H-3$_D$), 1.50 (d, 3H, J$_{5,6}$=6.3 Hz, H-6$_A$), 1.46 (d, 3H, J$_{5,6}$=6.2 Hz, H-6$_B$), 1.38 (d, 3H, J$_{5,6}$=6.1 Hz, H-6$_{B'}$), 1.37 (d, 3H, J$_{5,6}$=6.1 Hz, H-6$_C$).

$^{13}$C NMR (CDCl$_3$), δ206.1 (C$_{Lev}$), 171.7 (C$_{Lev}$), 170.0 (C$_{Ac}$), 162.2 (C$_{NTCA}$), 138.8-137.6 (C$_{Ph}$), 133.9 (CH=), 129.4-127.5 (CH$_{Ph}$), 117.1 (=CH$_2$), 101.1 (C-1$_D$, $^1$J$_{CH}$=165.4 Hz), 100.2 (C-1$_A$, $^1$J$_{CH}$=175.4 Hz), 99.1 (C-1$_{B'}$, $^1$J$_{CH}$=171.8 Hz), 98.5 (C-1$_C$, $^1$J$_{CH}$=173.3 Hz), 98.3 (C-1$_B$, $^1$J$_{CH}$=168.3 Hz), 94.1 (C-1$_E$, $^1$J$_{CH}$=166.9 Hz), 93.3 (CCl$_3$), 87.2 (C-3$_D$), 83.1 (C-3$_E$), 80.6 (C-3$_B$), 80.5 (2C, C-2$_E$, C-4$_B$), 80.1 (C-4$_{B'}$), 79.7 (C-4$_A$), 79.5 (C-4$_C$), 78.8 (C-4$_E$), 77.7 (C-3$_{B'}$), 77.3 (C-3$_C$), 76.3 (C$_{Bn}$), 75.6 (C-5$_D$), 75.5, 75.4, 75.3, 75.0 (6C, C$_{Bn}$), 74.1, 74.0 (C-2$_B$*, C-3$_A$*), 73.5, 72.9 (2C, C$_{Bn}$), 72.1 (C-2$_C$), 71.4 (C$_{Bn}$), 71.3 (2C, C-2$_A$, C-4$_D$), 70.1 (C-5$_E$), 69.4 (2C, C-2$_{B'}$, C-5$_C$), 68.9 (C-5$_A$), 68.7 (C-5$_{B'}$), 68.4 (C-5$_B$), 68.0 (C-6$_E$), 67.6 (C$_{All}$), 62.8 (C-6$_D$), 55.5 (C-2$_D$), 38.2 (CH$_{2Lev}$), 29.9 (CH$_{3Lev}$), 28.3 (CH$_{2Lev}$), 21.1 (C$_{Ac}$), 18.1, 18.0, 17.8, 17.9 (C-6$_A$*, C-6$_B$*, C-6$_{B'}$*, C-6$_C$*).

HRMS (ESI+): [M+H]+ $C_{118}H_{134}NO_{30}{}^{35}Cl_3$ m/z theoretical:
2150.8135
m/z measured:
2150.84857
[M+Na]+ $C_{118}H_{134}NO_{30}{}^{35}Cl_3Na$ m/z theoretical:
2172.7954
m/z measured:
2172.8081

Allyl(3,4-di-O-benzyl-2-α-L-rhamnopyranosyl)-(1→3)-2-O-acetyl-4-O-benzyl-α-L-rhamnopyranosyl)-(1→3)-(2-deoxy-2-trichloroacetamido-β-D-glucopyranosyl)-(1→2)-[2,3,4,6-tetra-O-benzyl-α-D-glucopyranosyl-(1→3)]-(4-O-benzyl-α-L-rhamnopyranosyl)-(1→2)-3,4-di-O-benzyl-α-L-rhamnopyranoside 124

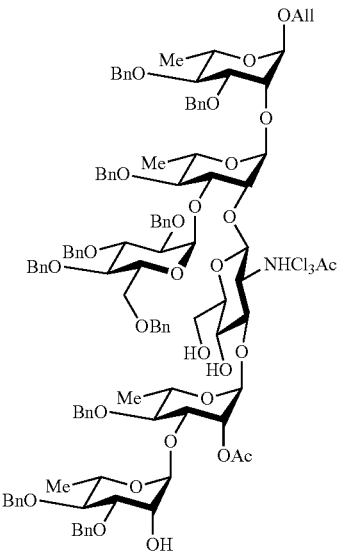

Chemical Formula: $C_{113}H_{128}Cl_3NO_{28}$
Exact Mass: 2051.7688
Molecular Weight: 2054.5743

The diol 123 (700 mg, 320 μmol) is dissolved in pyridine/acetic acid mixture (3/2, 5 mL). Hydrazine monohydrate (158 μL, 3.2 mmol, 10 eq.) is added dropwise to the reaction mixture. After stirring for 25 min at 0° C., monitoring by TLC (Tol/EtOAc, 7/3) indicates the disappearance of 123 (Rf=0.4) and the appearance of a more polar product (Rf=0.35). The reaction mixture is then taken up in cold water (10 mL) and the aqueous phase is quickly extracted with DCM (3×50 mL). The organic phases are combined and washed with saturated NaCl solution, filtered on a phase-separating filter and concentrated in a rotary evaporator. The oil obtained is purified by silica gel chromatography (Tol/EtOAc, 9/1→7/3) to obtain the triol 124 as a white solid (560 mg, 84%).

Rf=0.35 (Tol/EtOAc, 7/3).

$^1$H NMR (CDCl$_3$), δ7.44-7.07 (m, 50H, CH$_{Ph}$), 7.02 (d, 1H, J$_{NH,2}$=8.6 Hz, NH), 5.90 (m, 1H, CH=), 5.40 (bs, 1H, H-1$_A$), 5.30 (d, 1H, J$_{1,2}$=3.6 Hz, H-1$_E$), 5.29 (m, 1H, J$_{trans}$=17.2 Hz, =CH$_2$), 5.22 (m, 1H, J$_{cis}$=10.4 Hz, =CH$_2$), 5.18-5.12 (m, 4H, H$_{Bn}$, H-1$_{B'}$, H-2$_C$, H$_{Bn}$), 5.16-4.99 (m, 3H, H$_{Bn}$), 4.93 (d, 1H, J=10.9 Hz, H$_{Bn}$), 4.85-4.81 (m, 2H, H$_{Bn}$), 4.77-4.66 (m, 7H, 3H$_{Bn}$, H-1$_B$, 3H$_{Bn}$), 4.62-4.54 (m, 6H, 5H$_{Bn}$, H-1$_C$), 4.51 (d, 1H, J$_{1,2}$=8.4 Hz, H-1$_D$), 4.38 (d, 1H, J=11.9 Hz, H$_{Bn}$), 4.23-4.13 (m, 7H, H-2$_B$, H-3$_C$, H-3$_E$, H-3$_A$, H$_{All}$, H-5$_E$, H-2$_A$), 5.53 (m, 1H, H-2$_{B'}$), 4.00-3.87 (m, 6H, H$_{All}$, H-2$_D$, H-3$_B$, H-5$_C$, H-4$_E$, H-2$_E$), 3.84-3.81 (m, 1H, H-3$_{B'}$, H-5$_{B'}$), 3.78 (m, 1H, H-5$_B$), 3.72 (m, 1H, H-5$_A$), 3.65 (m, 1H, H-6a$_D$), 3.55-3.49 (m, 5H, H-6a$_E$, H-6b$_E$, H-4$_B$, H-4$_A$, H-4$_{B'}$), 3.47 (pt, 1H, J$_{3,4}$=9.5 Hz, H-4$_C$), 3.04 (m, 2H, H-4$_D$, H-5$_D$), 2.94 (m, 1H, H-6b$_D$), 2.20 (s, 3H, H$_{Ac}$), 2.15 (m, 1H, H-3$_D$), 1.46 (d, 3H, J$_{5,6}$=6.2 Hz, H-6$_A$), 1.42 (d, 3H, J$_{5,6}$=6.2 Hz, H-6$_B$), 1.33-1.30 (m, 6H, H-6$_C$, H-6$_{B'}$).

$^{13}$C NMR (CDCl$_3$), δ170.0 (C$_{Ac}$), 162.3 (C$_{NTCA}$), 138.7-137.4 (C$_{Ph}$), 133.8 (CH=), 129.4-127.4 (CH$_{Ph}$), 117.1 (=CH$_2$), 101.1 (C-1$_D$, $^1$J$_{CH}$=161.0 Hz), 100.6 (C-1$_{B'}$, $^1$J$_{CH}$=171.0 Hz), 100.1 (C-1$_A$, $^1$J$_{CH}$=174.7 Hz), 98.3 (C-1$_C$, $^1$J$_{CH}$=170.4 Hz), 98.2 (C-1$_B$, $^1$J$_{CH}$=170.4 Hz), 94.0 (C-1$_E$, $^1$J$_{CH}$=163.1 Hz), 93.1 (CCl$_3$), 87.1 (C-3$_D$), 83.1 (C-3$_E$), 80.5 (C-3$_B$), 80.4 (C-4$_B$), 80.3 (C-2$_E$), 80.0 (C-4$_A$), 79.7 (2C, C-3$_{B'}$, C-4$_{B'}$), 79.4 (C-4$_C$), 78.7 (C-4$_E$), 77.7 (C-3$_C$), 76.3 (C$_{Bn}$), 75.5 (C-5$_D$), 75.4, 75.4, 75.3, 75.0, 74.9 (6C, C$_{Bn}$), 74.1 (C-2$_A$), 73.9 C-3$_A$), 73.5, 72.8 (2C, C$_{Bn}$), 72.0 (C-2$_C$), 71.7 (C$_{Bn}$), 71.3 (C-4$_D$), 71.0 (C-2$_B$), 70.0 (C-5$_E$), 69.1 (C-5$_C$), 68.8 (2C, C-2$_{B'}$, C-5$_A$), 68.4, 68.3 (C-5$_B$*, C-5$_{B'}$*), 67.8 (C-6$_E$), 67.6 (C$_{All}$), 62.7 (C-6$_D$), 55.3 (C-2$_D$), 21.2 (C$_{Ac}$), 18.0, 17.8 (4C, C-6$_A$*, C-6$_B$*, C-6$_{B'}$*, C-6$_C$*).

HRMS (ESI$^+$): [M+Na]$^+$ C$_{113}$H$_{128}$NO$_{28}$$^{35}$Cl$_3$Na m/z theoretical:

2074.7585 m/z measured:

2074.7581

[M+NH$_4$]$^+$ C$_{113}$H$_{128}$NO$_{28}$$^{35}$Cl$_3$NH$_4$ m/z theoretical:

2069.8032 m/z measured:

2069.7925

Propyl α-L-rhamnopyranosyl-(1→3)-(2-O-acetyl-α-L-rhamnopyranosyl)-(1→3)-(2-acetamido-2-deoxy-β-D-glucopyranosyl)-(1→2)-[α-D-glucopyranosyl-(1→3)]-α-L-rhamnopyranosyl-(1→2)-α-L-rhamnopyranoside XIII

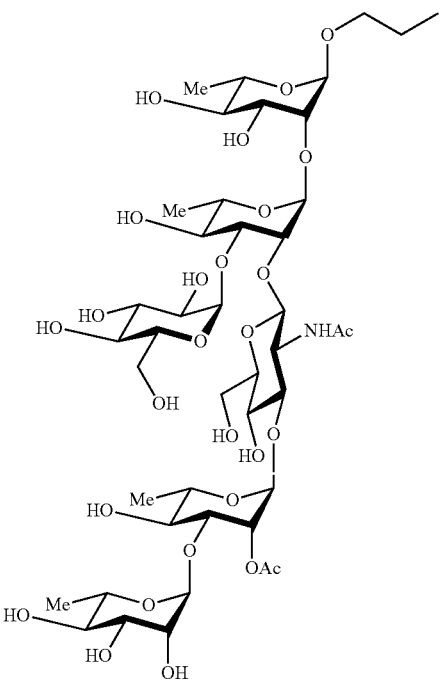

Chemical Formula: C$_{43}$H$_{73}$NO$_{28}$
Exact Mass: 1051.4319
Molecular Weight: 1052.0296

Pd—C 10% (400 mg) is added to a degassed solution of triol 124 (400 mg, 195 μmol) in absolute ethanol (20 mL). The suspension is saturated with hydrogen at 50 bar and stirred at RT for 10 days. Monitoring by TLC (iPrOH/H$_2$O/NH$_3$, 4/1/0.5 and Tol/EtOAc, 7/3) shows the disappearance of 124 (Rf=1 and 0.35, respectively) and the appearance of a new, more polar compound (Rf=0.65 and 0, respectively). The reaction mixture is filtered on an Acrodisc LC 25 mm filter, and the filtrate is concentrated in a rotary evaporator. The residue obtained is purified on a C-18 column (H$_2$O/CH$_3$CN, 100/0→70/30) to give the target XIII as a white solid (131 mg, 64%).

Rf=0.65 (iPrOH/H$_2$O/NH$_3$, 4/1/0.5)

$^1$H NMR (D$_2$O), δ5.10 (d, 1H, J$_{1,2}$=3.7 Hz, H-1$_E$), 5.00 (d, 1H, J$_{1,2}$=1.6 Hz, H-1$_A$), 4.91 (dd, 1H, J$_{1,2}$=1.9 Hz, J$_{2,3}$=3.1 Hz, H-2$_C$), 4.89 (d, 1H, J$_{1,2}$=1.4 Hz, H-1$_{B'}$), 4.80 (bs, 2H, H-1$_B$, H-1$_C$), 4.71 (m, 1H, H-1$_D$), 4.35 (m, 1H, H-2$_A$), 4.02-3.92 (m, 3H, H-5$_C$, H-5$_E$, H-2$_{B'}$), 3.89-3.51 (m, 14H, H-3$_C$, H-2$_B$, H-3$_A$, H-6a$_D$, H-2$_D$, H-3$_B$, H-3$_E$, H-6a$_E$, H-6b$_E$, H-5$_A$, H-6b$_D$, H-2$_E$, H-5$_B$, H-3$_{B'}$, H$_{Pr}$), 3.49 (pt, 1H, J$_{3,4}$=10.0 Hz, H-4$_C$), 3.47-3.30 (m, 8H, H-4$_D$, H$_{Pr}$, H-5$_{B'}$, H-4$_E$, H-4$_B$, H-4$_{B'}$, H-5$_D$, H-3$_D$), 3.26 (pt, 1H, J$_{3,4}$=9.6 Hz, H-4$_A$), 2.08 (s, 3H, H$_{Ac}$), 2.03 (s, 3H, H$_{NAc}$), 1.50 (sex, 2H, CH$_2$), 1.22-1.13 (m, 12H, H-6$_B$, H-6$_A$, H-6$_{B'}$, H-6$_C$), 0.82 (t, 3H, J=7.4 Hz, CH$_3$);

$^{13}$C NMR (D$_2$O), δ174.4 (C$_{NAc}$), 173.2 (C$_{Ac}$), 102.7 (C-1$_{B'}$, $^1$J$_{CH}$=170.6 Hz), 101.4 (C-1$_D$, $^1$J$_{CH}$=166.0 Hz), 101.2 (C-1$_A$, $^1$J$_{CH}$=173.5 Hz), 98.4 (C-1$_C$, $^1$J$_{CH}$=167.8 Hz), 98.1 (C-1$_B$, $^1$J$_{CH}$=171.5 Hz), 94.2 (C-1$_E$, $^1$J$_{CH}$=172.8 Hz), 82.6 (C-3$_D$), 79.1 (C-2$_B$), 77.0 (C-3$_C$), 76.0 (C-5$_D$), 74.1 (C-2$_A$), 73.3 (C-3$_A$), 73.0 (C-3$_E$), 72.4 (C-2$_C$), 71.9 (C-4$_B$), 71.7 (C-4$_{B'}$), 71.3, 71.2, 71.1 (C-5$_E$, C-2$_E$, C-4$_C$), 70.7 (C-4$_A$), 70.1 (C-3$_{B'}$), 69.9 (2C, C-2$_{B'}$, C-3$_B$), 69.7 (C$_{Pr}$), 69.4, 69.3 (3C, C-4$_E$, C-5$_A$, C-5$_{B'}$), 68.8 (C-5$_C$), 68.6 (C-5$_B$), 68.1 (C-4$_D$), 60.6 (C-6$_D$), 60.3 (C-6$_E$), 55.3 (C-2$_D$), 22.7 (C$_{NAc}$), 21.9 (CH$_2$), 20.2 (C$_{Ac}$), 16.8, 16.6, 16.5, 16.3 (C-6$_A$*, C-6$_B$*, C-6$_{B'}$*, C-6$_C$*), 9.8 (CH$_3$);

HRMS (ESI$^+$): [M+H]$^+$ C$_{43}$H$_{73}$NO$_{28}$ m/z theoretical: 1052.4397
m/z measured: 1052.4360
[M+Na]$^+$ C$_{43}$H$_{73}$NO$_{28}$Na m/z theoretical: 1074.4216
m/z measured 1074.4202

Method 17:

Allyl(3,4-di-O-benzyl-2-α-L-rhamnopyranosyl)-(1→3)-4-O-benzyl-α-L-rhamnopyranosyl)-(1→3)-(2-deoxy-2-trichloroacetamido-β-D-glucopyranosyl)-(1→2)-[2,3,4,6-tetra-O-benzyl-α-D-glucopyranosyl-(1→3)]-(4-O-benzyl-α-L-rhamnopyranosyl)-(1→2)-3,4-di-O-benzyl-α-L-rhamnopyranoside 125

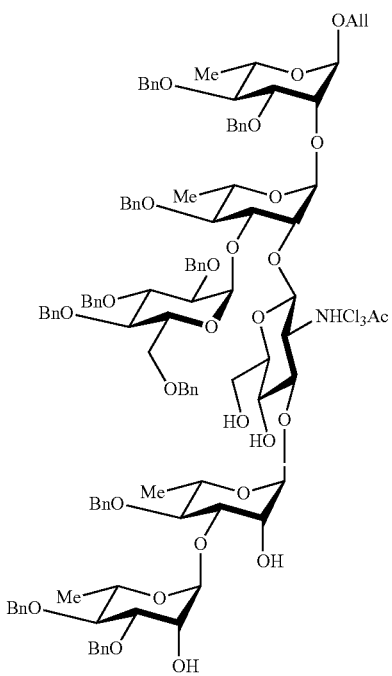

Chemical Formula: C$_{111}$H$_{126}$Cl$_3$NO$_{27}$
Exact Mass: 2009.7583
Molecular Weight: 2012.5376

After adding 0.5 M NaOMe (745 μL, 370 μmol, 1 eq.) to the diol 123 (800 mg, 370 μmol) in solution in MeOH (20 mL), the reaction mixture is heated to 60° C. and stirred for 1 h, after which time monitoring by TLC (Tol/EtOAc, 6/4) indicates the disappearance of 123 (Rf=0.6) and the appearance of a more polar product (Rf=0.45). After it returns to RT, the reaction mixture is neutralized by adding DOWEX (H$^+$) ion-exchange resin, then filtered on a frit. The resin is washed with DCM/MeOH mixture and the solvents are evaporated.

The yellow oil obtained is purified by silica gel chromatography (Tol/EtOAc, 8/2→7/3) to give the tetraol 125 as a white solid (688 mg, 92%).

Rf=0.45 (Tol/EtOAc, 6/4)

$^1$H NMR (CDCl$_3$), δ7.44-7.05 (m, 50H, CH$_{Ph}$), 6.86 (d, 1H, J$_{NH,2}$=8.6 Hz, NH), 5.89 (m, 1H, CH=), 5.36 (bs, 1H, H-1$_A$), 5.28 (m, 2H, =CH$_2$, H-1$_E$), 5.21 (m, 1H, J$_{cis}$=10.4 Hz, =CH$_2$), 5.17 (d, 1H, J$_{1,2}$=1.6 Hz, H-1$_{B'}$), 5.14-5.07 (m, 2H, H$_{Bn}$), 5.03-5.490 (m, 4H, H$_{Bn}$), 4.82 (d, 1H, J=11.0 Hz, H$_{Bn}$), 4.74-4.51 (m, 13H, H-1$_B$, H$_{Bn}$), 4.47 (d, 1H, J$_{1,2}$=7.0 Hz, H-1$_D$), 4.47 (d, 1H, J$_{1,2}$=1.6 Hz, H-1$_C$), 4.38 (d, 1H, J=11.9 Hz, H$_{Bn}$), 4.19 (dd, 1H, J$_{2,3}$=2.4 Hz, H-2$_B$), 4.17-4.12 (m, 5H, H$_{All}$, H-5$_E$, H-3$_A$, H-2$_A$), 4.06-4.03 (m, 2H, H-3$_C$, H-2$_{B'}$), 3.99-3.82 (m, 9H, H$_{All}$, H-2$_C$, H-2$_D$, H-3$_B$, H-5$_C$, H-5$_{B'}$, H-4$_E$, H-2$_E$, H-3$_{B'}$), 3.78-3.64 (m, 3H, H-5$_B$, H-5$_A$, H-6a$_D$), 3.59-3.45 (m, 6H, H-4$_{B'}$, H-6a$_E$, H-6b$_E$, H-4$_B$, H-4$_A$, H-4$_C$), 3.07-3.03 (m, 2H, H-5$_D$, H-4$_D$), 2.94 (m, 1H, H-6b$_D$), 2.23 (m, 1H, H-3$_D$), 1.44 (d, 3H, J$_{5,6}$=6.2 Hz, H-6$_{B'}$), 1.43 (d, 3H, J$_{5,6}$=6.1 Hz, H-6$_A$), 1.40 (d, 3H, J$_{5,6}$=6.2 Hz, H-6$_B$), 1.32 (d, 3H, J$_{5,6}$=6.1 Hz, H-6$_C$).

$^{13}$C NMR (CDCl$_3$), δ161.9 (C$_{NTCA}$), 138.7-137.5 (C$_{Ph}$), 133.9 (CH=), 129.1-127.3 (CH$_{Ph}$), 117.1 (=CH$_2$), 101.0 (C-1$_D$, $^1$J$_{CH}$=162.7 Hz), 100.8 (C-1$_C$, $^1$J$_{CH}$=169.2 Hz), 100.1 (C-1$_A$, $^1$J$_{CH}$=180.3 Hz), 100.0 (C-1$_{B'}$, $^1$J$_{CH}$=180.3 Hz), 98.3 (C-1$_B$, $^1$J$_{CH}$=170.3 Hz), 94.0 (C-1$_E$, $^1$J$_{CH}$=168.6 Hz), 93.2 (CCl$_3$), 86.5 (C-3$_D$), 83.0 (C-3$_E$), 80.5 (C-3$_B$), 80.4 (2C, C-2$_E$, C-4$_B$), 79.8, 79.7, 79.6 (4C, C-4$_A$*, C-3$_{B'}$*, C-4$_B$*, C-4$_C$*), 78.8 (C-4$_E$), 78.3 (C-3$_C$), 76.3 (C$_{Bn}$), 75.5 (C-5$_D$), 75.4, 75.3, 75.2, 74.9 (6C, C$_{Bn}$), 74.0 (C-3$_A$), 73.8 (C-2$_A$), 73.5, 72.8, 72.0 (3C, C$_{Bn}$), 71.3 (C-2$_B$), 71.1 (C-4$_D$), 70.4 (C-2$_C$), 70.0 (C-5$_E$), 68.9 (C-5$_C$), 68.8 (2C, C-5$_A$, C-2$_{B'}$), 68.7 (C-5$_{B'}$), 68.3 (C-5$_B$), 67.9 (C-6$_E$), 67.6 (C$_{All}$), 62.7 (C-6$_D$), 55.8 (C-2$_D$), 18.1, 18.0, 17.8 (4C, C-6$_A$*, C-6$_B$*, C-6$_{B'}$*, C-6$_C$*).

HRMS (ESI$^+$): [M+Na]$^+$ C$_{111}$H$_{126}$NO$_{27}$$^{35}$Cl$_3$Na m/z theoretical: 2032.7480
m/z measured: 2032.7448

Propyl α-L-rhamnopyranosyl-(1→3)-(α-L-rhamnopyranosyl)-(1→3)-(2-acetamido-2-deoxy-β-D-glucopyranosyl)-(1→2)-[α-D-glucopyranosyl-(1→3)]-α-L-rhamnopyranosyl-(1→2)-α-L-rhamnopyranoside XXV

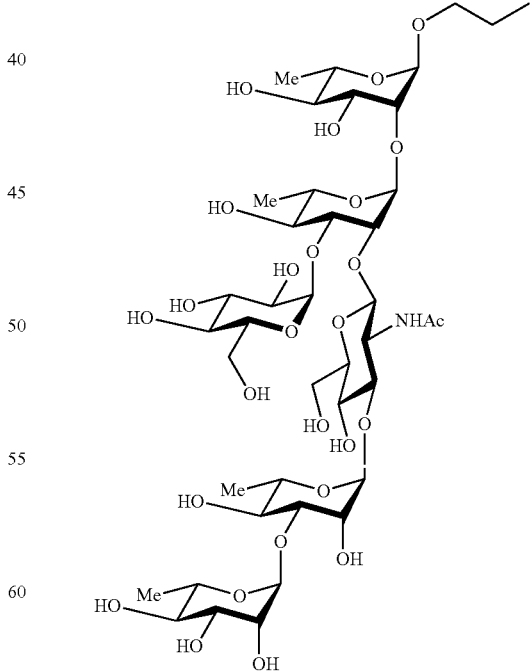

Chemical Formula: C$_{41}$H$_{71}$NO$_{27}$
Exact Mass: 1009.4213
Molecular Weight: 1009.9929

Pd—C 10% (340 mg) is added to a degassed solution of tetraol 125 (580 mg, 289 μmol) in absolute ethanol (15 mL). The suspension is saturated with hydrogen at 50 bar and stirred at RT for 10 days. Monitoring by TLC (iPrOH/H$_2$O/NH$_3$, 4/1/0.5 and Tol/EtOAc, 6/4) shows the disappearance of 125 (Rf=1 and 0.45, respectively) and the appearance of a new, more polar compound (Rf=0.2 and 0, respectively). The reaction mixture is filtered on an Acrodisc LC 25 mm filter, and the filtrate is concentrated in a rotary evaporator. The residue obtained is purified on a C-18 column (H$_2$O/CH$_3$CN, 100/0→70/30) to give the target XIV in the form of a white solid (240 mg, 82%).

Rf=0.2 (iPrOH/H$_2$O/NH$_3$, 4/1/0.5)

$^1$H NMR (D$_2$O), δ5.20 (d, 1H, J$_{1,2}$=3.7 Hz, H-1$_E$), 5.10 (d, 1H, J$_{1,2}$=1.6 Hz, H-1$_A$), 5.01 (d, 1H, J$_{1,2}$=1.2 Hz, H-1$_{B'}$), 4.90 (m, 1H, H-1$_B$), 4.84 (d, 1H, J$_{1,2}$=1.9 Hz, H-1$_C$), 4.82 (d, 1H, J$_{1,2}$=9.5 Hz, H-1$_D$), 4.44 (m, 1H, H-2$_A$), 4.06-3.99 (m, 3H, H-2$_{B'}$, H-5$_E$, H-5$_C$), 3.95-3.61 (m, 17H, H-2$_B$, H-3$_A$, H-6a$_D$, H-2$_C$, H-2$_D$, H-3$_B$, H-3$_E$, H-3$_{B'}$, H-6a$_E$, H-6b$_E$, H-3$_C$, H-5$_B$, H-5$_A$, H-6b$_D$, H-2$_E$, H-5$_{B'}$, H$_{Pr}$), 3.55-3.38 (m, 8H, H$_{Pr}$, H-4$_C$, H-4$_D$, H-4$_E$, H-3$_D$, H-4$_B$, H-4$_{B'}$, H-5$_D$), 3.35 (pt, 1H, J$_{3,4}$=9.7 Hz, H-4$_A$), 2.11 (s, 3H, H$_{NAc}$), 1.59 (sex, 2H, CH$_2$), 1.31 (d, 3H, J$_{5,6}$=6.3 Hz, H-6$_B$), 1.28 (d, 3H, J$_{5,6}$=6.3 Hz, H-6$_{B'}$), 1.26 (d, 3H, J$_{5,6}$=6.3 Hz, H-6$_A$), 1.23 (d, 3H, J$_{5,6}$=6.3 Hz, H-6$_C$), 0.91 (t, 3H, J=7.4 Hz, CH$_3$);

$^{13}$C NMR. (D$_2$O), δ174.0 (C$_{NAc}$), 102.4 (C-1$_{B'}$, $^1$J$_{CH}$=171.2 Hz), 101.5 (C-1$_D$, $^1$J$_{CH}$=163.6 Hz), 101.3 (C-1$_C$, $^1$J$_{CH}$=169.8 Hz), 101.2 (C-1$_A$, $^1$J$_{CH}$=169.8 Hz), 98.2 (C-1$_B$, $^1$J$_{CH}$=170.5 Hz), 94.4 (C-1$_E$, $^1$J$_{CH}$=171.2 Hz), 81.7 (C-3$_D$), 79.1 (C-2$_B$), 78.1 (C-3$_C$), 76.0 (C-5$_D$), 74.2 (C-2$_A$), 73.5 (C-3$_A$), 73.2 (C-3$_E$), 72.2 (C-4$_B$), 72.0 (C-4$_{B'}$), 71.4 (C-5$_E$), 71.3 (C-2$_E$) 71.3 (C-4$_C$), 70.8 (C-4$_A$), 70.5 (C-2$_C$), 70.2 (C-3$_{B'}$), 70.2 (C-2$_{B'}$), 70.0 (C-3$_B$), 69.8 (C$_{Pr}$), 69.5 (C-4$_E$), 69.4 (C-5$_A$), 69.0 (2C, C-5$_C$, C-5$_B$), 68.7 (C-5$_{B'}$), 68.3 (C-4$_D$), 60.7 (C-6$_D$), 60.4 (C-6$_E$), 55.5 (C-2$_D$), 22.6 (C$_{NAc}$), 21.9 (CH$_2$), 16.8, 16.7, 16.5 (4C, C-6$_A$*, C-6$_B$*, C-6$_{B'}$*, C-6$_C$*), 9.9 (CH$_3$);

HRMS (ESI$^+$): [M+H]$^+$ C$_{41}$H$_{71}$NO$_{27}$ m/z theoretical:
1010.4292
m/z measured:
1010.4295
[M+Na]$^+$ C$_{41}$H$_{71}$NO$_{27}$Na m/z theoretical:
1032.4111
m/z measured:
1032.4116

Section V—Larger Targets

TABLE 14

Higher oligosaccharides representative of the fragments of the O antigen of S. flexneri serotype 3a and/or X

| Hexasaccharides | Octasaccharides | Decasaccharides | > |
|---|---|---|---|
| Methods 16 and 17: (cf. section 4) B$_{Ac}$CD(E)AB XVII BCD(E)AB XVIII | Methods 18 and 19: D(E)AB$_{Ac}$CD(E)A XIX D(E)ABCD(E)A XX | Methods 20 and 21: B$_{Ac}$CD(E)AB$_{Ac}$CD(E)A XXI BCD(E)ABCD(E)A XXII | |
| Methods 22 and 23: D(E)AB$_{Ac}$CD XXIII D(E)ABCD XXIV | Methods 24 and 25: B$_{Ac}$CD(E)AB$_{Ac}$CD XXV BCD(E)ABCD XXVI | Methods 26 and 27: D(E)AB$_{Ac}$CD(E)AB$_{Ac}$C XXVII D(E)AB$_{Ac}$CD(E)AB$_{Ac}$C XXVIII | |

Analysis by back synthesis, taking into account the higher-order fragments of the 0 antigens of S. flexneri 3a and X, namely having at least 6 residues, made it possible to select a limited number of common synthons which, when combined according to sequences appropriate to each of the targets, can provide access to all of the oligosaccharides of interest. As stated above, the acceptor synthons can be extended at their non-reducing end by iterative incorporation of the required donor monosaccharides or disaccharides, suitably functionalized. Moreover, the allyl glycosides can be extended at their reducing end after selective deallylation and activation, permitting their coupling on the required pre-functionalized acceptor monosaccharides or disaccharides.

Scheme 77: Key synthons used

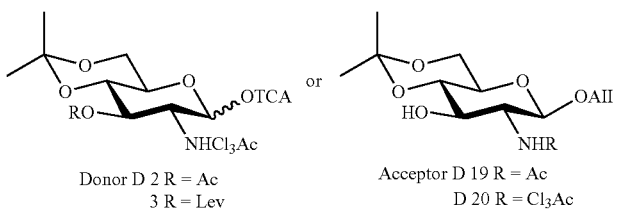

Donor D 2 R = Ac
3 R = Lev

Acceptor D 19 R = Ac
D 20 R = Cl$_3$Ac

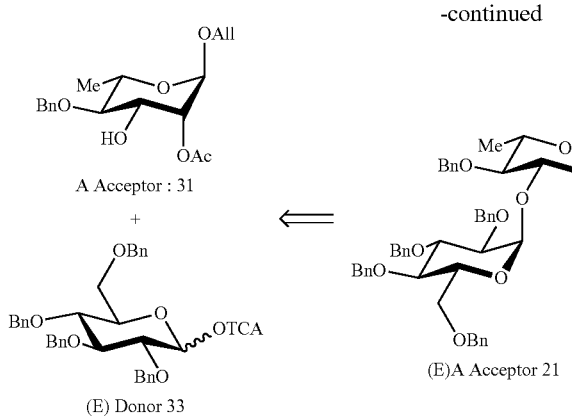

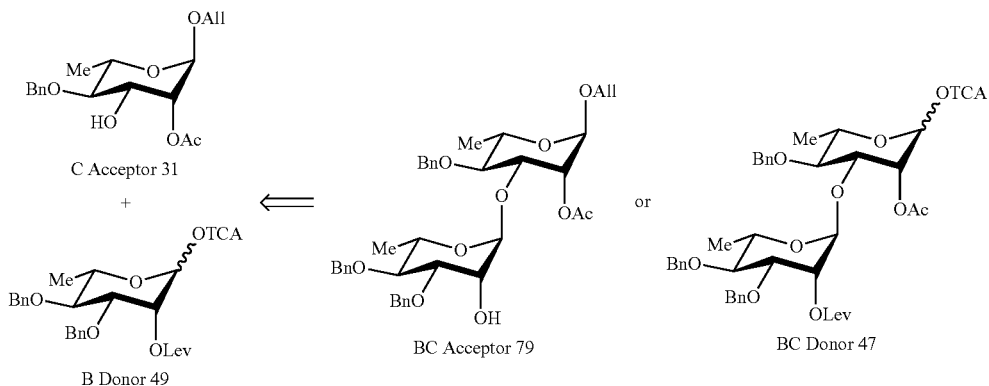

Several examples of combination are proposed below. The corresponding syntheses are under development for some of the methods. A fully protected octasaccharide has already been synthesized.

Note also that the use of an anomeric allyl function opens the way to specific further modifications of this position, for example grafting onto a substrate or a carrier. Various methodologies have been proposed in this direction in the literature.

Methods 18 and 19: Targets D(E)AB$_{Ac}$CD(E)A (XIX) and D(E)ABCD(E)A (XX)

The present invention thus relates to the method of preparation of the octasaccharide D(E)AB$_{Ac}$CD(E)A (XIX), as defined in list L1, characterized in that it comprises the following stages:

condensation of the acceptor pentasaccharide 66 and of the donor disaccharide 80 leading to the acceptor heptasaccharide 126;

delevulinoylation of the heptasaccharide 126 leading to the heptasaccharide 127 preferably in conventional conditions of selective deprotection of the levilinates, for example in the presence of hydrazine monohydrate;

condensation of the acceptor heptasaccharide 127 and of the donor monosaccharide 3 leading to the octasaccharide 128, preferably in a solvent such as dichloromethane, 1,2-dichloroethane, toluene, acetonitrile or their equivalents usually employed in industry in the presence of a Lewis acid such as TMSOTf, triflic acid, trimethylsilyl trifluoromethane sulfonate;

delevulinoylation of the octasaccharide 128 leading to the acceptor octasaccharide 128a;

deprotection in two stages, including acid hydrolysis of the isopropylidene functions and then debenzylation and reduction of the trichloroacetamide functions of the octasaccharide 128a, preferably under hydrogen atmosphere in the presence of palladium, leading to the octasaccharide D(E)AB$_{Ac}$CD(E)A (scheme 78).

The invention also relates to the method of preparation of the octasaccharide D(E)ABCD(E)A) (XX), as defined in list L1, characterized in that it comprises the following stages:

condensation of the acceptor pentasaccharide 66 and of the donor disaccharide 80 leading to the acceptor heptasaccharide 126;

delevulinoylation of the heptasaccharide 126 leading to the heptasaccharide 127 preferably in conventional conditions of selective deprotection of the levilinates, for example in the presence of hydrazine monohydrate;

condensation of the acceptor heptasaccharide 127 and of the donor monosaccharide 3 leading to the octasaccharide 128, preferably in the presence of a Lewis acid such as TMSOTf, triflic acid, trimethylsilyl trifluoromethane sulfonate;

transesterification of the octasaccharide 128 and then acid hydrolysis of the isopropylidenes and debenzylation and reduction of the trichloroacetamide functions leading to the octasaccharide D(E)ABCD(E)A preferably by treatment under hydrogen pressure in the presence of palladium on charcoal (scheme 78).

Scheme 78
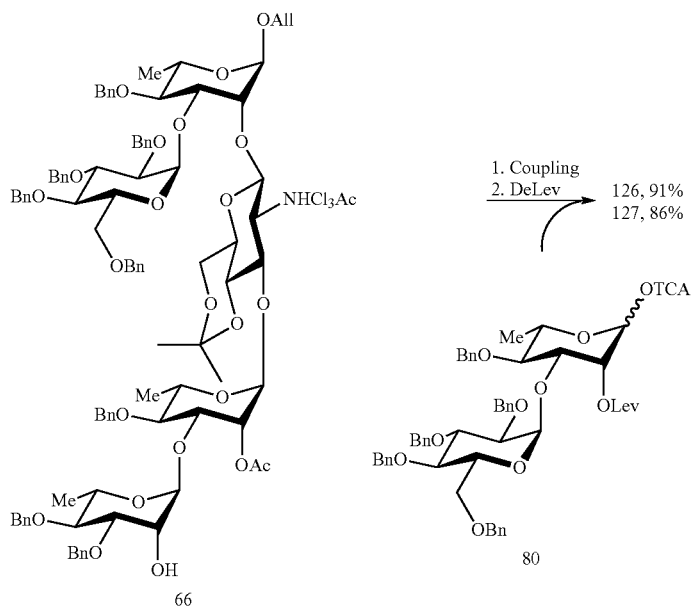
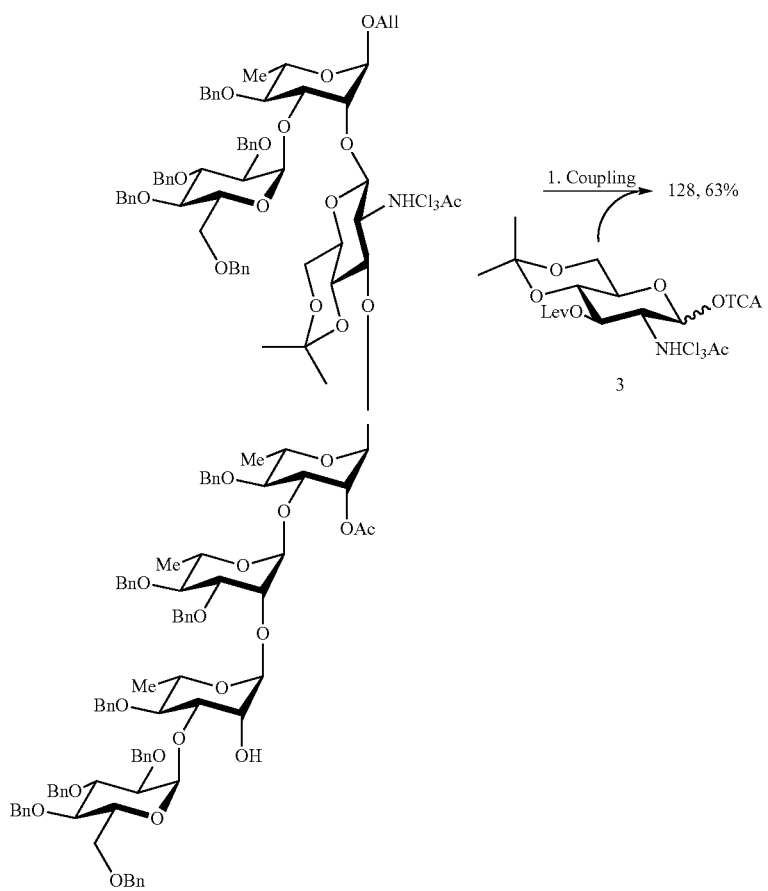

-continued
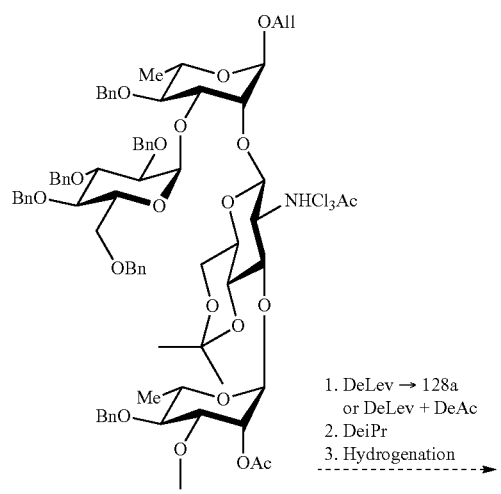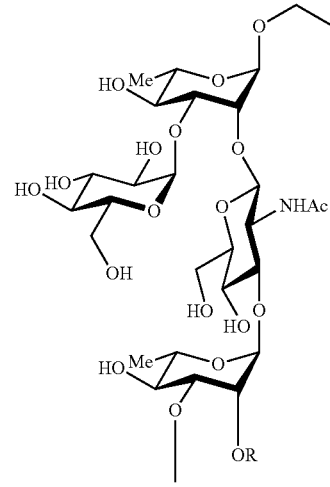
1. DeLev → 128a
   or DeLev + DeAc
2. DeiPr
3. Hydrogenation
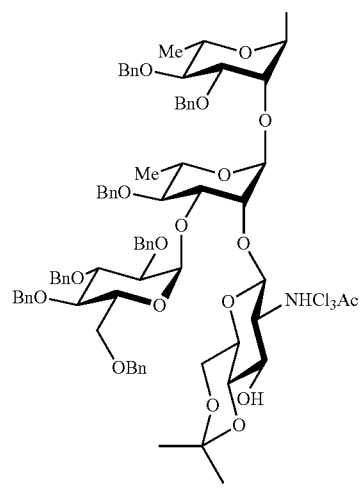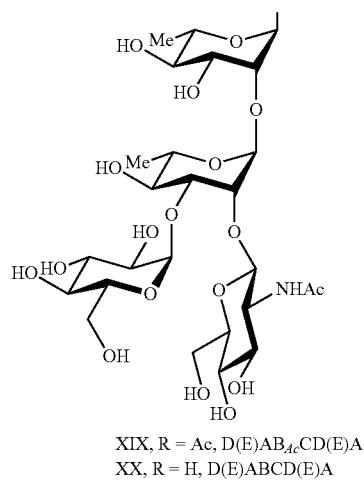
XIX, R = Ac, D(E)AB$_{Ac}$CD(E)A
XX, R = H, D(E)ABCD(E)A Experimental Application of Methods 18 and 19
Method 18:

Allyl(2,3,4,6-tetra-O-benzyl-α-D-glucopyranosyl)-(1→3)-(4-O-benzyl-2-O-levulinoyl-α-L-rhamnopyranosyl)-(1→2)-(3,4-di-O-benzyl-α-L-rhamnopyranosyl)-(1→3)-(2-O-acetyl-4-O-benzyl-α-L-rhamnopyranosyl)-(1→3)-(2-deoxy-4,6-O-isopropylidene-2-trichloroacetamido-β-D-glucopyranosyl)-(1→2)-[2,3,4,6-tetra-O-benzyl-α-D-glucopyranosyl-(1→3)]-4-O-benzyl-α-L-rhamnopyranoside 126

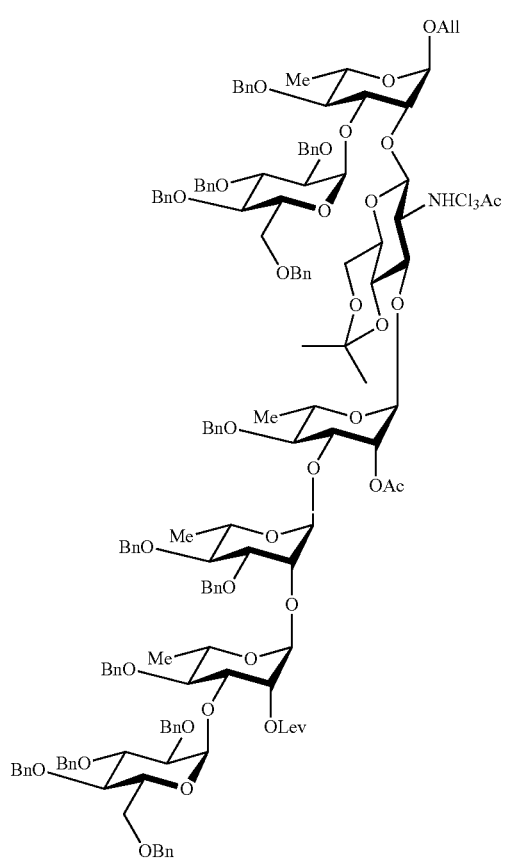

Chemical Formula: $C_{148}H_{166}Cl_3NO_{35}$
Exact Mass: 2622.0306
Molecular Weight: 2625.2463

TMSOTf (14.0 μL, 75.0 μmol, 0.3 eq.) is added to a solution of acceptor 66 (440 mg, 248 μmol) and of donor 80 (380 mg, 370 μmol, 1.5 eq.) in Tol (6 mL), in the presence of molecular sieve 4 Å (236 mg), stirred under argon at −5° C. After stirring for 20 min, monitoring by TLC (Tol/EtOAc, 8/2) indicates the disappearance of 66 (Rf=0.15) and the appearance of a new, less polar compound (Rf=0.4). The reaction is stopped by adding triethylamine (0.5 mL), then the reaction mixture is filtered and concentrated in a rotary evaporator. The raw product obtained (248 μmol) is dissolved in DMF (10 mL) containing 2-methoxypropene (48.0 μL, 498 μmol, eq.). CSA (480 mg, 2.0 mmol, 8 eq.) is added in portions to the reaction mixture until pH 2 is obtained. The reaction mixture is stirred at RT and the reaction is monitored by TLC (Tol/EtOAc, 8/2). After stirring for 2 h, the MeOH formed is evaporated in a rotary evaporator and 2-methoxypropene (24.0 μL, 250 μmol, 1 eq.) is added again. After stirring for 1 h, the reaction mixture is neutralized with triethylamine (0.2 mL) and then concentrated in a rotary evaporator. The yellow oil obtained is purified by silica gel chromatography (Tol/EtOAc, 9/1→7/3) to obtain the allyl glycoside 126 as a white solid (596 mg, 91%).

Rf=0.4 (Tol/EtOAc, 8/2).
$^1$H NMR (CDCl$_3$), δk
$^{13}$C NMR (CDCl$_3$), δk
HRMS (ESI$^+$): [M+Na]$^+$ not visible m/z theoretical: m/z measured:

Allyl(2,3,4,6-tetra-O-benzyl-α-D-glucopyranosyl)-(1→3)-(4-O-benzyl-α-L-rhamnopyranosyl)-(1→2)-(3,4-di-O-benzyl-α-L-rhamnopyranosyl)-(1→3)-(2-O-acetyl-4-O-benzyl-α-L-rhamnopyranosyl)-(1→3)-(2-deoxy-4,6-O-isopropylidene-2-trichloroacetamido-β-D-glucopyranosyl)-(1→2)-[2,3,4,6-tetra-O-benzyl-α-D-glucopyranosyl-(1→3)]-4-O-benzyl-α-L-rhamnopyranoside 127

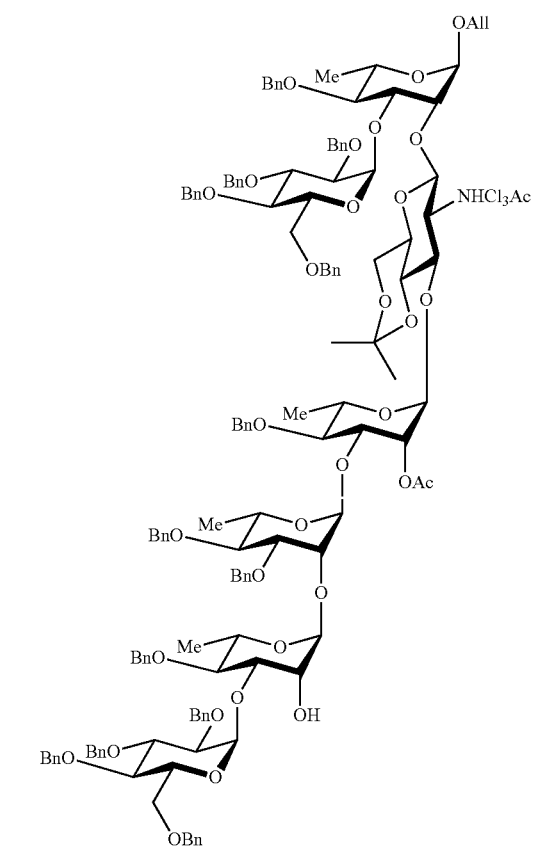

Chemical Formula: $C_{143}H_{160}Cl_3NO_{33}$
Exact Mass: 2523.9938
Molecular Weight: 2527.1464

The allyl glycoside 126 (1.23 g, 468 μmol) is dissolved in pyridine/acetic acid mixture (3/2, 10 mL). Hydrazine monohydrate (227 μL, 4.7 mmol, 10 eq.) is added dropwise to the reaction mixture. After stirring for 35 min at 0° C., monitoring by TLC (Tol/EtOAc, 7/3) indicates the appearance of a slightly less polar product (Rf=0.6). The reaction mixture is then taken up in cold water (20 mL) and the aqueous phase is quickly extracted with DCM (3×80 mL). The organic phases are combined and washed with saturated NaCl solution, filtered on a phase-separating filter and concentrated in a rotary evaporator. The oil obtained is purified by silica gel chromatography (Tol/EtOAc, 9/1→8/2) to obtain the alcohol 127 as a white solid (1.05 g, 870).

Rf=0.6 (Tol/EtOAc, 7/3).
$^1$H NMR (CDCl$_3$), δk
$^{13}$C NMR (CDCl$_3$), δk
HRMS (ESI$^+$): [M+NH$_4$]$^+$ C$_{143}$H$_{160}$NO$_{33}$$^{35}$Cl$_3$NH$_4$ m/z theoretical: 2542.0281
m/z measured:
2542.0186

Allyl(2-deoxy-4,6-O-isopropylidene-3-O-levulinoyl-2-trichloroacetamido-β-D-glucopyranose)-(1→2)-[2,3,4,6-tetra-O-benzyl-α-D-glucopyranosyl-(1→3)]-(4-O-benzyl-α-L-rhamnopyranosyl)-(1→2)-(3,4-di-O-benzyl-α-L-rhamnopyranosyl)-(1→3)-(2-O-acetyl-4-O-benzyl-α-L-rhamnopyranosyl)-(1→3)-(2-deoxy-4,6-O-isopropylidene-2-trichloroacetamido-β-D-glucopyranosyl)-(1→2)-[2,3,4,6-tetra-O-benzyl-α-D-glucopyranosyl-(1→3)]-4-O-benzyl-α-L-rhamnopyranoside 128

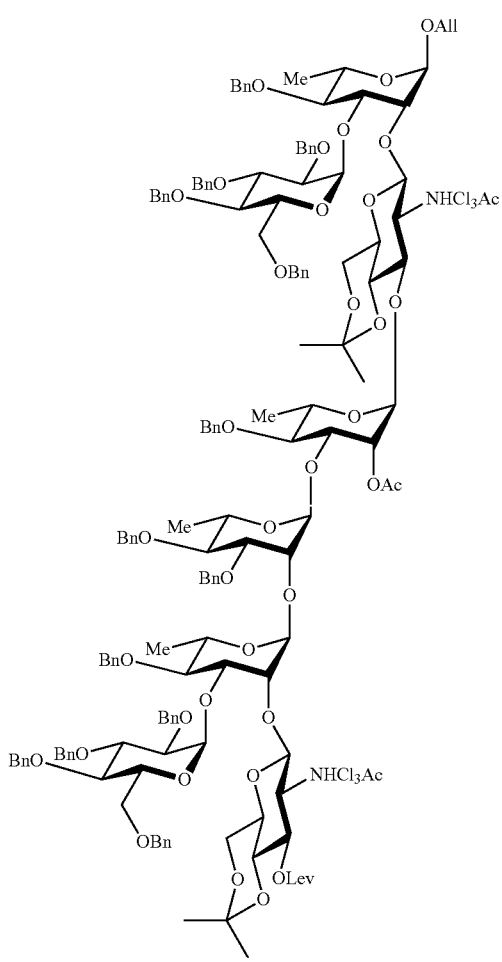

Chemical Formula: C$_{159}$H$_{180}$Cl$_6$N$_2$O$_{40}$
Exact Mass: 2967.0244
Molecular Weight: 2971.8379

TMSOTf (12.5 μL, 70.0 μmol, 0.35 eq.) is added to a solution of acceptor 127 (455 mg, 180 μmol) and of donor 3 (380 mg, 314 μmol, 1.7 eq.) in Tol (8 mL), in the presence of molecular sieve 4 Å (173 mg), stirred under argon at 0° C. After stirring for 20 min, monitoring by TLC (Tol/EtOAc, 7/3) indicates the disappearance of 127 (Rf=0.6) and the appearance of a new, less polar compound (Rf=0.5). The reaction is stopped by adding triethylamine (0.5 mL), then the reaction mixture is filtered and concentrated in a rotary evaporator. The raw product obtained (180 μmol) is dissolved in DMF (8 mL) containing 2-methoxypropene (35.0 μL, 360 μmol, 2 eq.). CSA (250 mg, 1.1 mmol, 6 eq.) is added in portions to the reaction mixture until pH 2 is obtained. The reaction mixture is stirred at RT and the reaction is monitored by TLC (Tol/EtOAc, 7/3). After stirring for 2 h, the MeOH formed is evaporated in a rotary evaporator and 2-methoxypropene (17.5 μL, 180 μmol, 1 eq.) is added again. After stirring for 1 h, the reaction mixture is neutralized with triethylamine (0.2 mL) and then concentrated in a rotary evaporator. The yellow oil obtained is purified by silica gel chromatography (Tol/EtOAc, 9/1→75/25) to obtain the allyl glycoside 128 as a white solid (340 mg, 63%.

Rf=0.5 (Tol/EtOAc, 7/3).
$^1$H NMR (CDCl$_3$), δk
$^{13}$C NMR (CDCl$_3$), δk
HRMS (ESI$^+$): [M+Na]$^+$ not visible m/z theoretical:
m/z measured:

Methods 20 and 21: Targets B$_{Ac}$CD(E)AB$_{Ac}$CD(E)A (XXI) and BCD(E)ABCD(E)A (XXII)

The invention further relates to the method of preparation of the decasaccharide B$_{Ac}$CD(E)AB$_{Ac}$CD(E)A (XXI), as defined in list L1, characterized in that it comprises the following stages:

condensation of the acceptor octasaccharide 128 and of the donor disaccharide 47 leading to the decasaccharide 129;

delevulinoylation of the decasaccharide 129 leading to the decasaccharide 130;

cleavage of the isopropylidene group, notably by acid hydrolysis, of the decasaccharide 130 leading to the decasaccharide 132;

deprotection by hydrogenolysis of the decasaccharide 132 leading to the decasaccharide B$_{Ac}$CD(E)AB$_{Ac}$CD(E)A preferably by treatment under hydrogen pressure in the presence of palladium on charcoal (scheme 79).

The invention further relates to the method of preparation of the decasaccharide BCD(E)ABCD(E)A (XXII), as defined in list L1, characterized in that it comprises the following stages:

condensation of the acceptor octasaccharide 128 and of the donor disaccharide 47 leading to the decasaccharide 129;

simultaneous delevulinoylation and deacetylation by transesterification of the decasaccharide 129 leading to the decasaccharide 131;

cleavage of the isopropylene group, notably by acid hydrolysis, of the decasaccharide 131 leading to the decasaccharide 133;

deprotection of the decasaccharide 133 leading to the decasaccharide BCD(E)ABCD(E)A preferably by treatment under hydrogen pressure in the presence of palladium on charcoal (scheme 79).

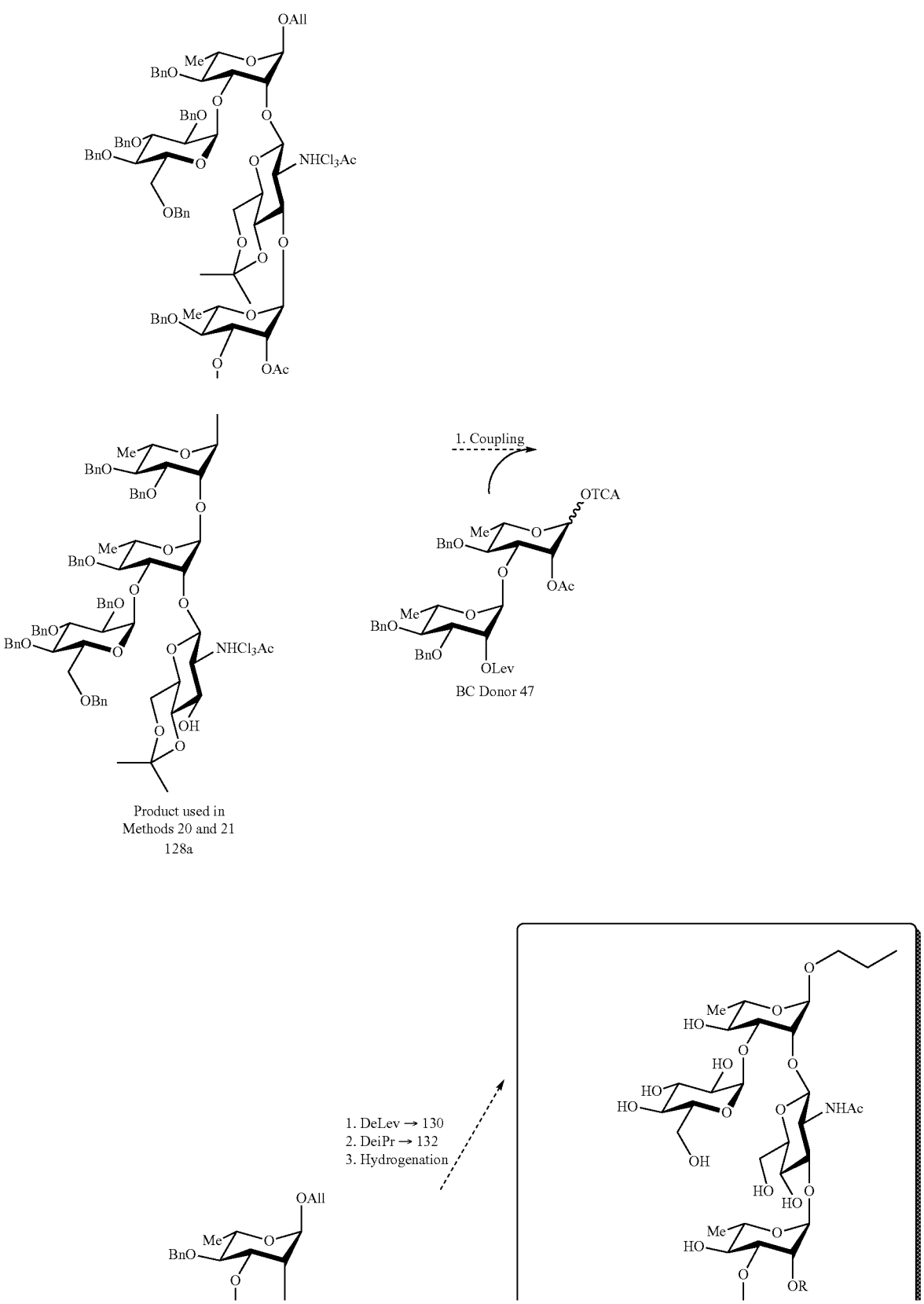

267
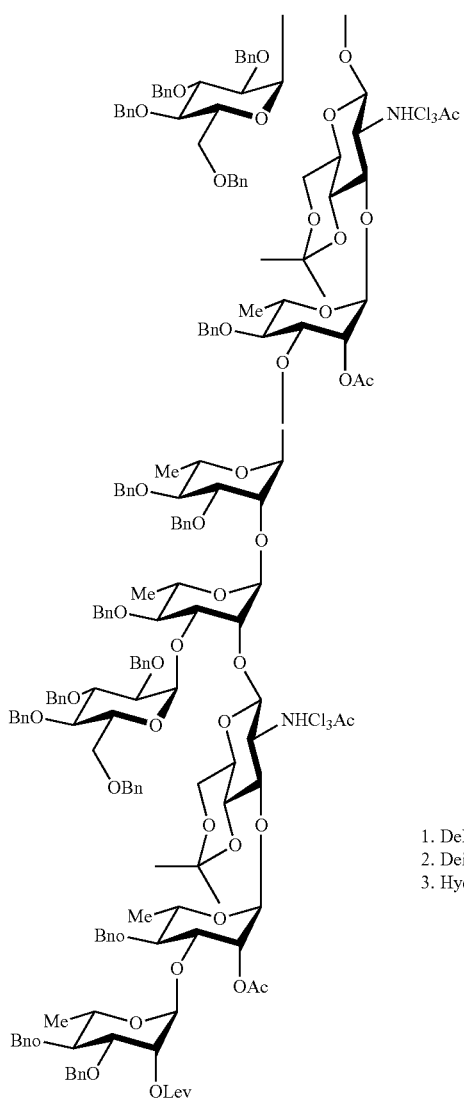
129
268 -continued
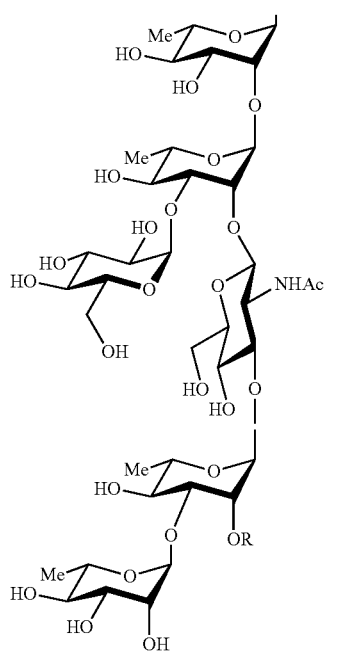
XXI, R = Ac, B$_{Ac}$CD(E)AB$_{Ac}$CD(E)A
1. DeLev → 131
2. DeiPr → 133
3. Hydrogenation
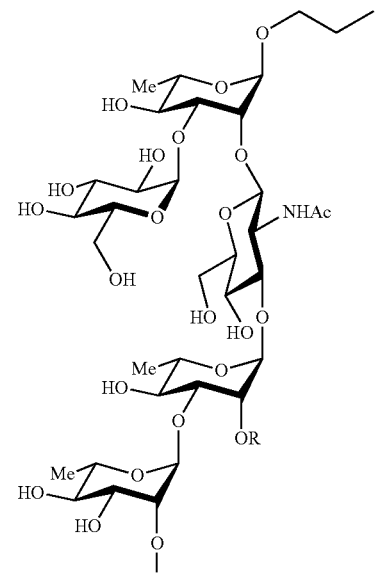

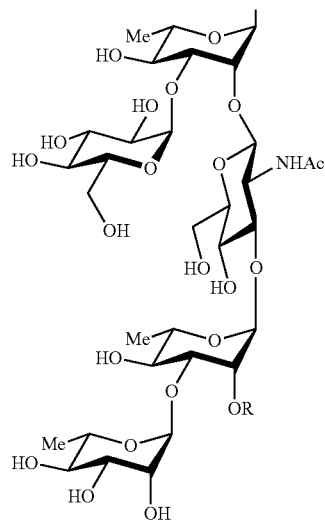

XXII, R = H, BCD(E)ABCD(E)A

Methods 22 and 23: Targets D(E)AB$_{Ac}$CD (XXIII) and D(E)ABCD (XXIV)

The invention relates to the method of preparation of the hexasaccharide D(E)AB$_{Ac}$CD (XXIII), as defined in list L1, characterized in that it comprises the following stages:
- condensation of the acceptor monosaccharide 20 and of the donor tetrasaccharide 86 leading to the acceptor pentasaccharide 134;
- delevulinoylation of the pentasaccharide 134 leading to the pentasaccharide 135;
- condensation of the acceptor pentasaccharide 135 and of the donor monosaccharide 3 leading to the hexasaccharide 136;
- delevulinoylation of the hexasaccharide 136 leading to the hexasaccharide 136a;
- two-stage deprotection of the hexasaccharide 136a including a stage of acid hydrolysis of the isopropylidene functions and then debenzylation and concomitant reduction of the trichloroacetamide functions leading to the hexasaccharide D(E)AB$_{Ac}$CD preferably by treatment under hydrogen pressure in the presence of palladium on charcoal (scheme 80).

The invention also relates to the method of preparation of the hexasaccharide D(E)ABCD (XXIV), as defined in list L1, characterized in that it comprises the following stages:
- condensation of the acceptor monosaccharide 20 and of the donor tetrasaccharide 86 leading to the pentasaccharide 134;
- delevulinoylation of the pentasaccharide 134 leading to the acceptor pentasaccharide 135;
- condensation of the acceptor pentasaccharide 135 and of the donor monosaccharide 3 leading to the hexasaccharide 136;
- transesterification of the hexasaccharide 136 and then acid hydrolysis of the isopropylidene functions followed by hydrogenolysis of the benzyl functions and concomitant reduction of the trichloroacetamide functions leading to the hexasaccharide D(E)ABCD preferably under hydrogen pressure in the presence of palladium on charcoal (scheme 80).

Scheme 80

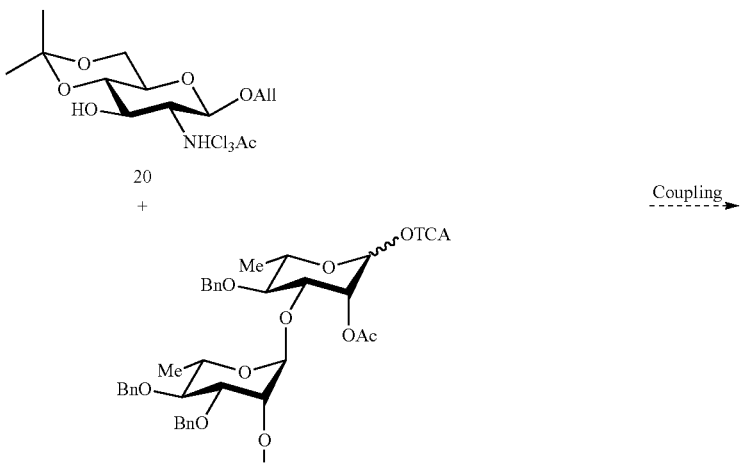

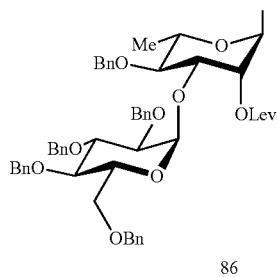
86
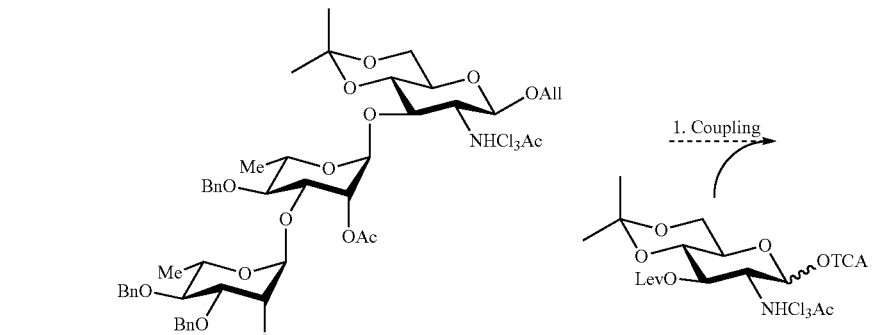
DeLev { 134 R = Lev
135 R = H
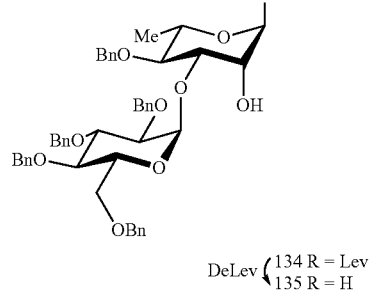
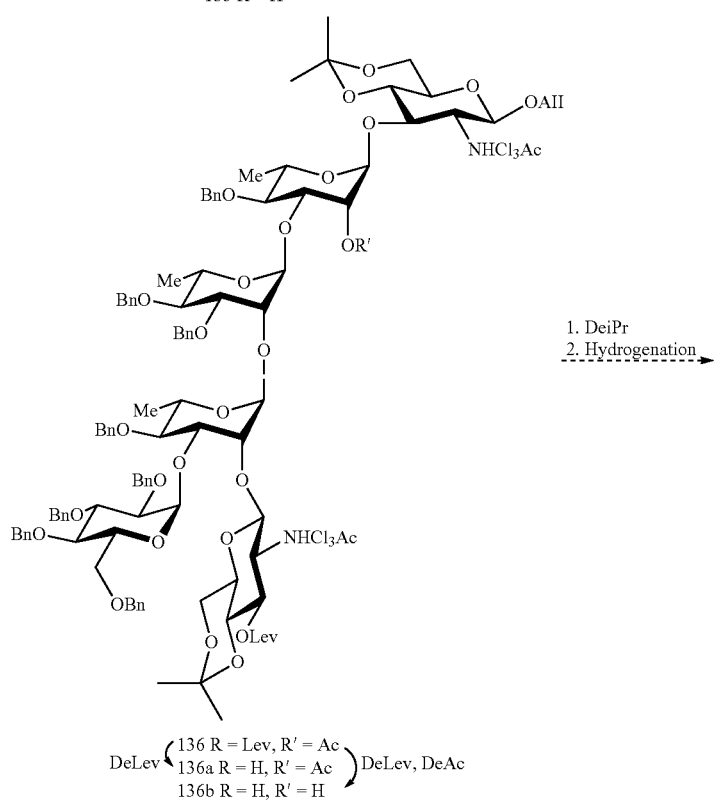
DeLev { 136 R = Lev, R' = Ac
136a R = H, R' = Ac } DeLev, DeAc
136b R = H, R' = H

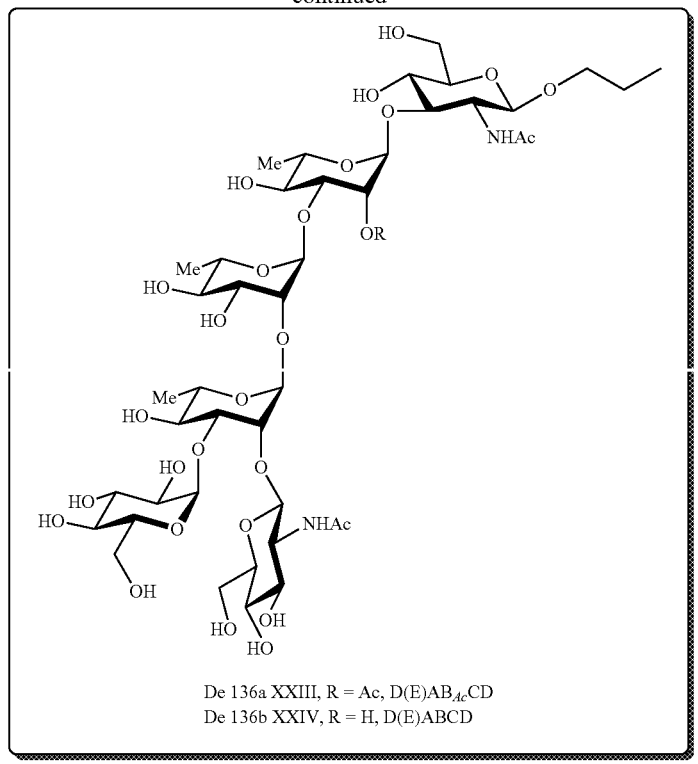

De 136a XXIII, R = Ac, D(E)AB$_{Ac}$CD
De 136b XXIV, R = H, D(E)ABCD

Methods 24 and 25: Targets B$_{Ac}$CD(E)AB$_{Ac}$CD (XXV) and BCD(E)ABCD (XXVI)

The invention relates to the method of preparation of the octasaccharide B$_{ac}$CD(E)AB$_{Ac}$CD (XXV), as defined in list L1, characterized in that it comprises the following stages:
- condensation of the acceptor hexasaccharide 136 and of the donor disaccharide 47 leading to the octasaccharide 137;
- delevulinoylation of the octasaccharide 137 leading to the acceptor octasaccharide 137a;
- two-stage deprotection of the hexasaccharide 137a including a stage of acid hydrolysis of the isopropylidene functions then debenzylation and concomitant reduction of the trichloroacetamide functions leading to the octasaccharide B$_{ac}$CD(E)AB$_{Ac}$CD preferably by treatment under hydrogen pressure in the presence of palladium on charcoal (scheme 81).

The invention relates to the method of preparation of the octasaccharide BCD(E)ABCD (XXVI), as defined in claim 1, 12 or 13, characterized in that it comprises the following stages:
- condensation of the acceptor hexasaccharide 136 and of the donor disaccharide 47 leading to the octasaccharide 137;
- transesterification of the octasaccharide 137 and then acid hydrolysis of the isopropylidene functions followed by hydrogenolysis of the benzyl functions and concomitant reduction of the trichloroacetamide functions leading to the octasaccharide BCD(E)ABCD preferably under hydrogen pressure in the presence of palladium on charcoal (scheme 81).

Scheme 81

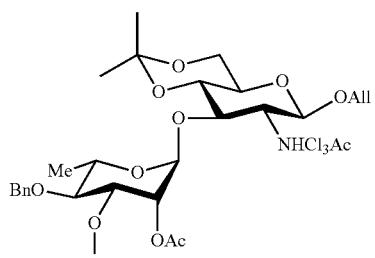

-continued
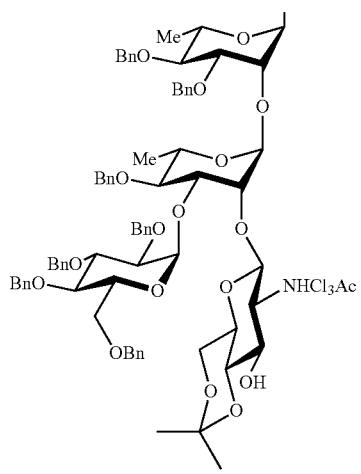
Product used in
Methods 24 and 25
136a
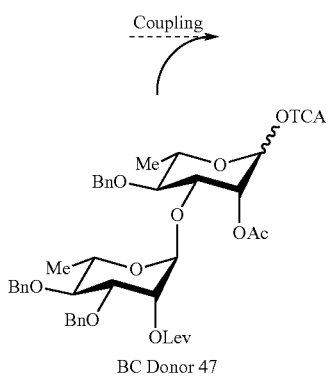
BC Donor 47
Coupling
1. DeiPr
2. Hydrogenation
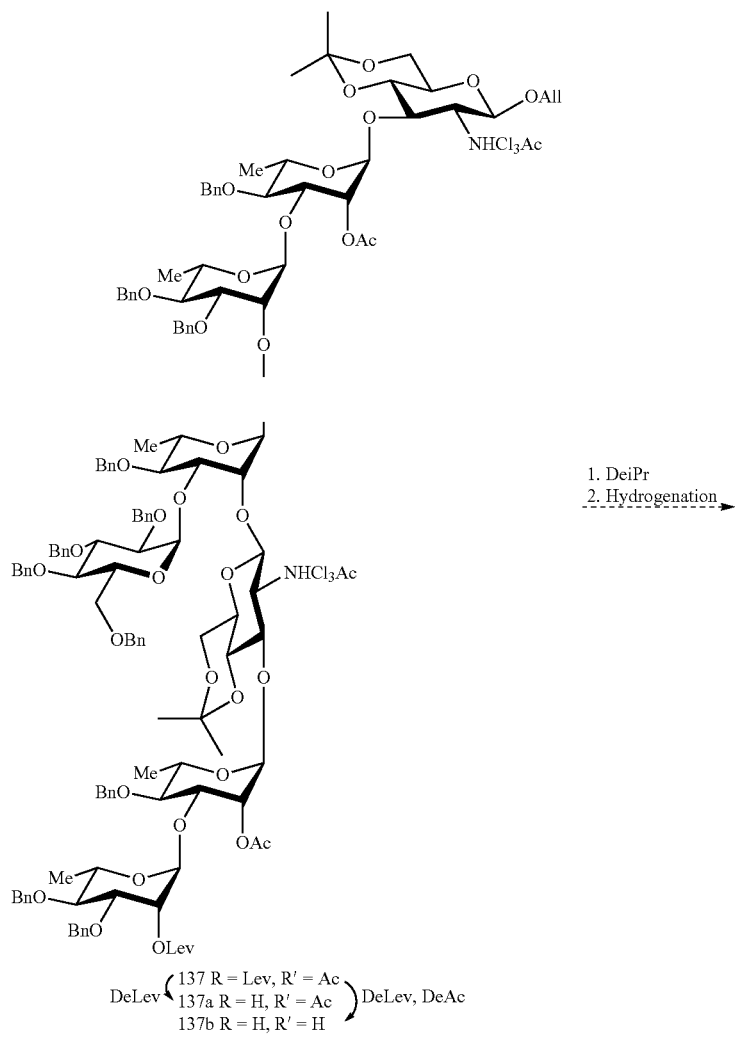
DeLev { 137 R = Lev, R' = Ac
137a R = H, R' = Ac } DeLev, DeAc
137b R = H, R' = H

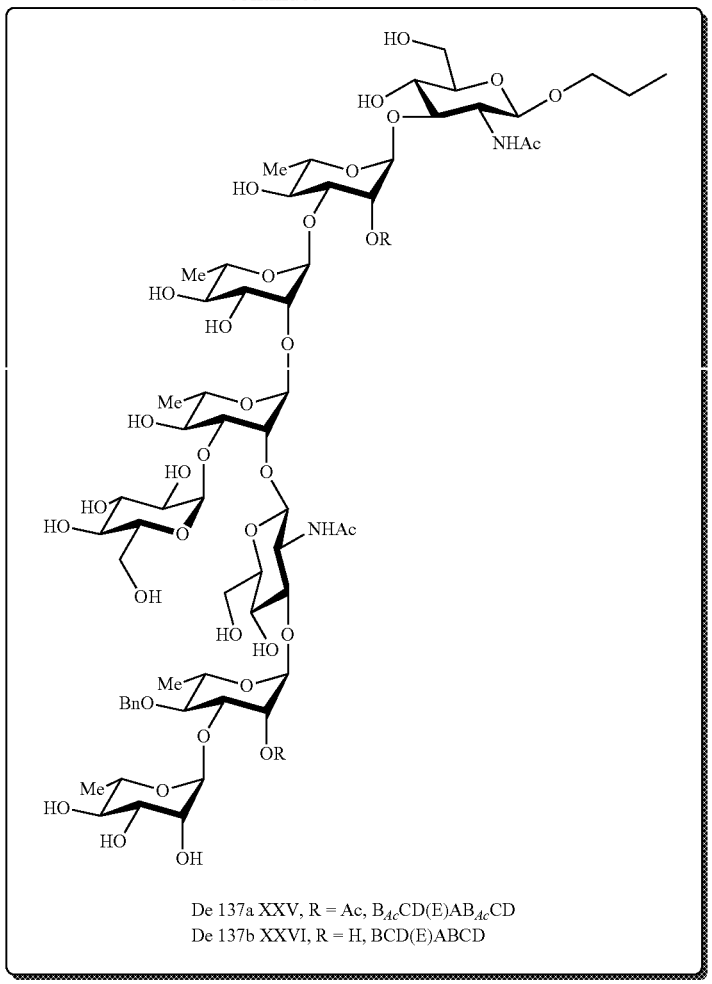

De 137a XXV, R = Ac, B$_{Ac}$CD(E)AB$_{Ac}$CD
De 137b XXVI, R = H, BCD(E)ABCD

Methods 26 and 27: Targets D(E)AB$_{Ac}$CD(E)AB$_{Ac}$C (XXVII) and D(E)ABCD(E)ABC (XXVIII)

The invention relates to the method of preparation of the decasaccharide D(E)AB$_{Ac}$CD(E)AB$_{Ac}$C (XXVII), as defined in list L1, characterized in that it comprises the following stages:

- condensation of the acceptor tetrasaccharide 85 and of the donor monosaccharide 3 leading to the pentasaccharide 138a;
- delevulinoylation of the pentasaccharide 138a leading to the acceptor pentasaccharide 138b;
- condensation of the acceptor pentasaccharide 138b and of the donor disaccharide 47 leading to the heptasaccharide 139a;
- delevulinoylation of the heptasaccharide 139a leading to the heptasaccharide 139b;
- condensation of the acceptor heptasaccharide 139b and of the donor disaccharide 80 leading to the nonasaccharide 140a;
- delevulinoylation of the nonasaccharide 140a leading to the acceptor nonasaccharide 140b;
- condensation of the acceptor nonasaccharide 140b and of the donor monosaccharide 3 leading to the decasaccharide 141a;
- delevulinoylation of the decasaccharide 141a leading to the acceptor decasaccharide 141b;
- two-stage deprotection of the decasaccharide 141b including a stage of acid hydrolysis of the isopropylidene functions and then debenzylation and concomitant reduction of the trichloroacetamide functions leading to the decasaccharide D(E)AB$_{Ac}$CD(E)AB$_{Ac}$C preferably by treatment under hydrogen pressure in the presence of palladium on charcoal (scheme 82).

The invention relates to the method of preparation of the decasaccharide D(E)ABCD(E)ABC (XXVIII), as defined in list L1, characterized in that it comprises the following stages:

- condensation of the acceptor tetrasaccharide 85 and of the donor monosaccharide 3 leading to the pentasaccharide 138a;
- delevulinoylation of the acceptor pentasaccharide 138a leading to the acceptor pentasaccharide 138b;
- condensation of the pentasaccharide 138b and of the donor disaccharide 47 leading to the heptasaccharide 139a;
- delevulinoylation of the heptasaccharide 139a leading to the acceptor heptasaccharide 139b;
- condensation of the acceptor heptasaccharide 139b and of the donor disaccharide 80 leading to the nonasaccharide 140;
- delevulinoylation of the nonasaccharide 140a leading to the acceptor nonasaccharide 140b;
- condensation of the acceptor nonasaccharide 140b and of the donor monosaccharide 3 leading to the decasaccharide 141a;
- two-stage deprotection of the decasaccharide 141a including a stage of transesterification, a stage of acid hydrolysis of the isopropylidene functions and then debenzylation and concomitant reduction of the trichloroacetamide functions leading to the decasaccharide D(E)ABCD(E)ABC preferably by treatment under hydrogen pressure in the presence of palladium on charcoal (scheme 82).

Scheme 82
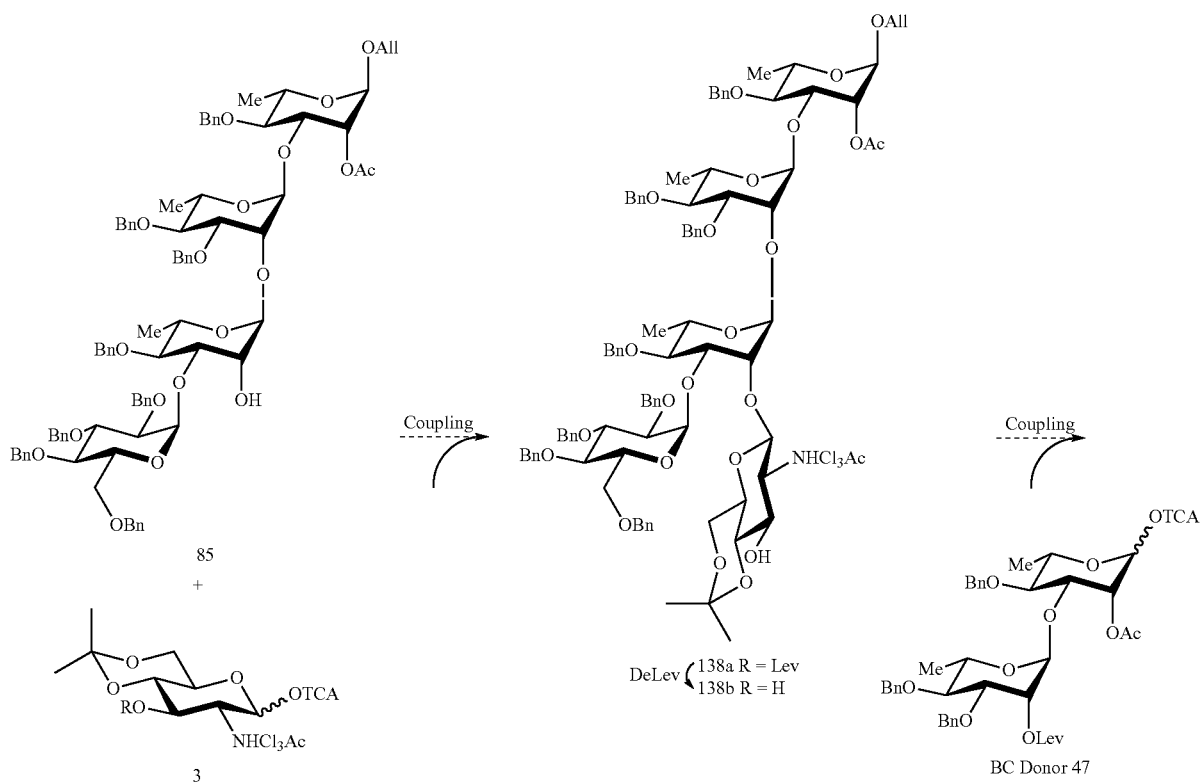
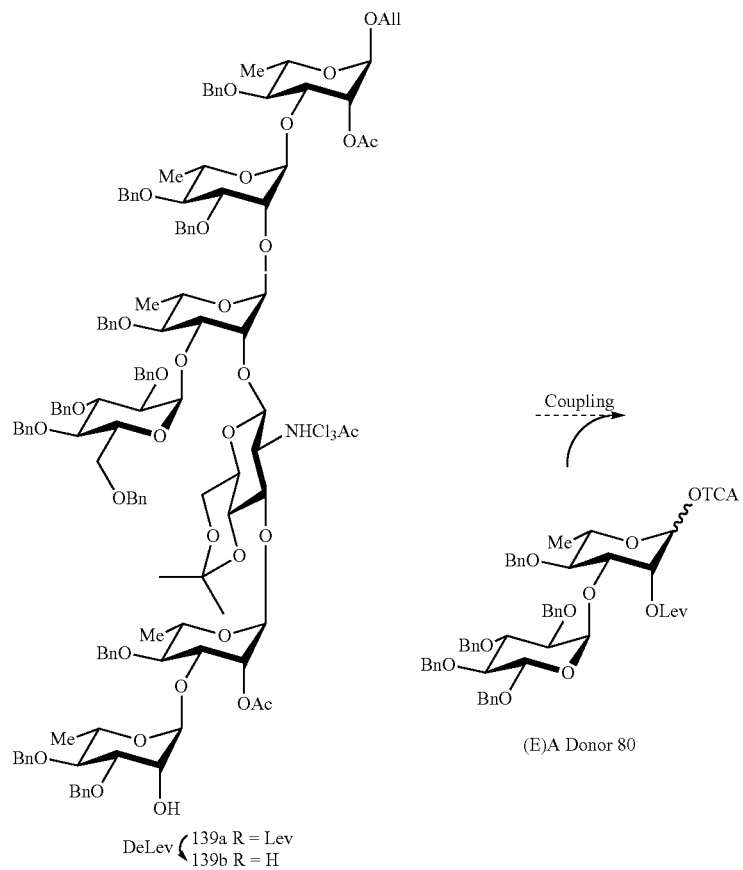

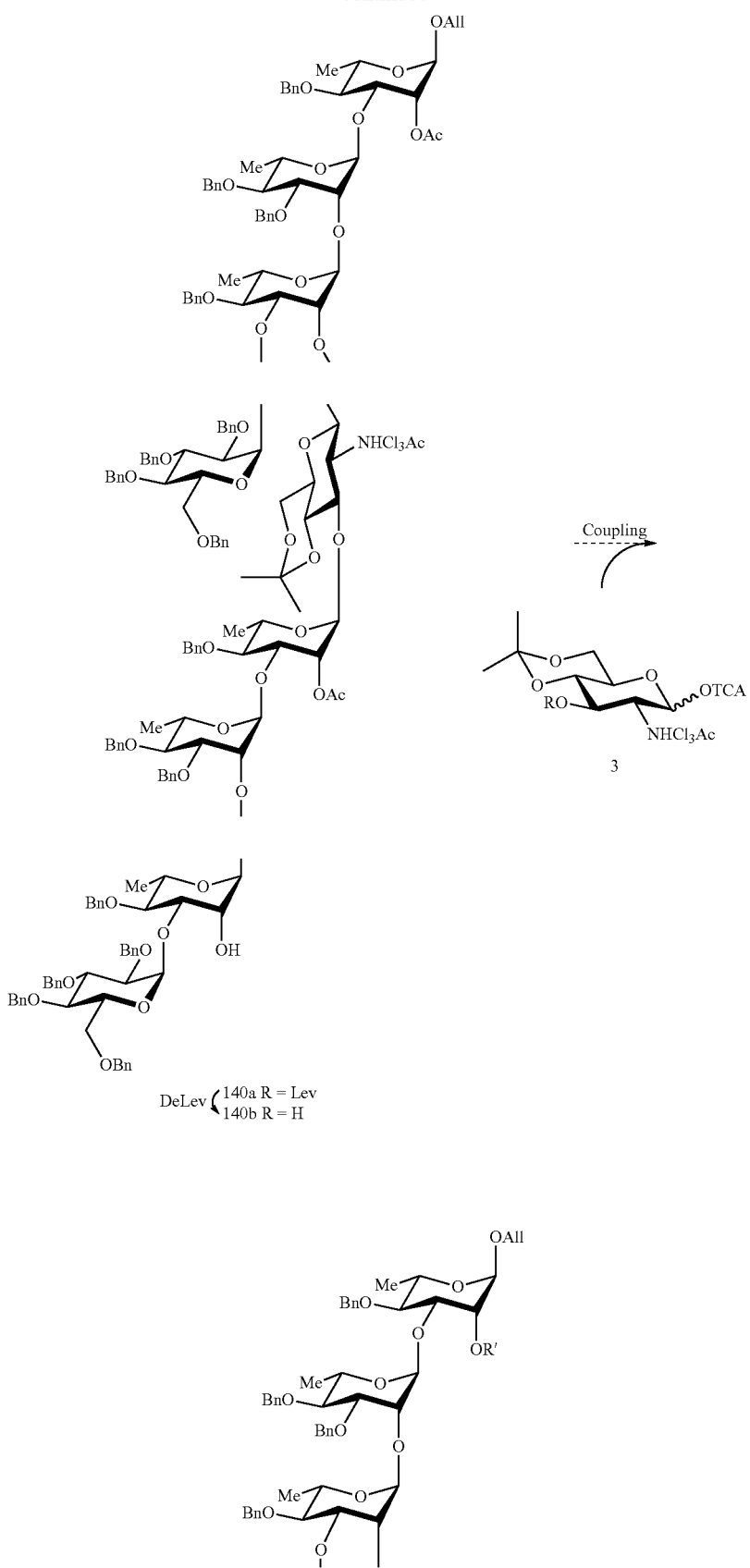

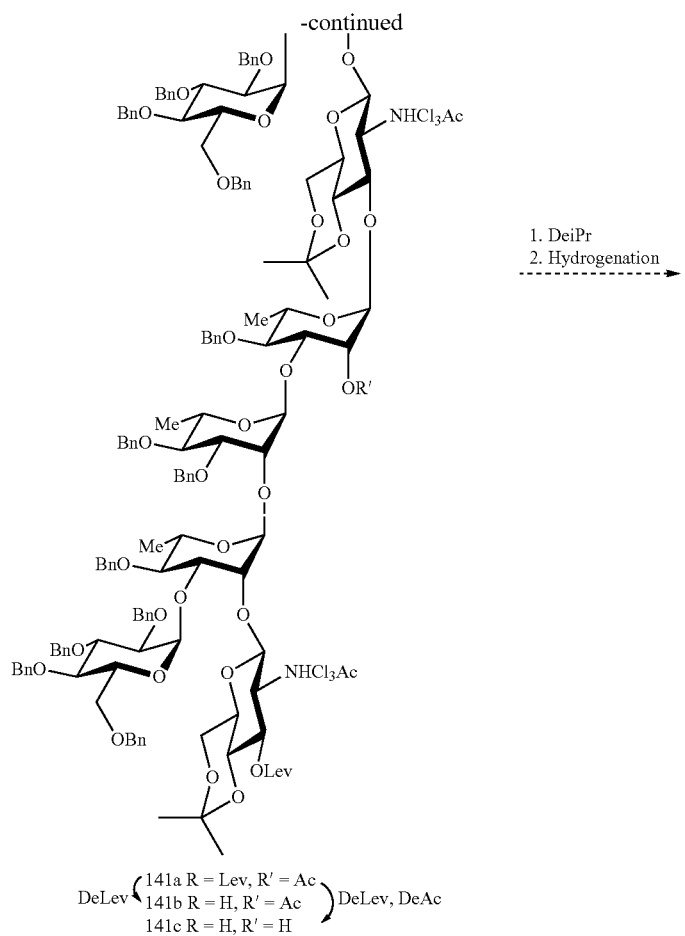
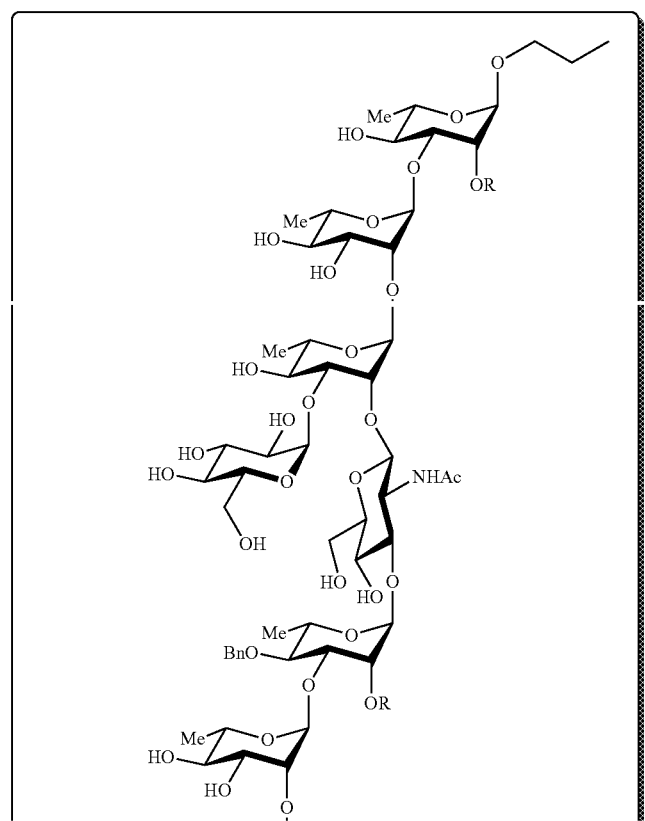

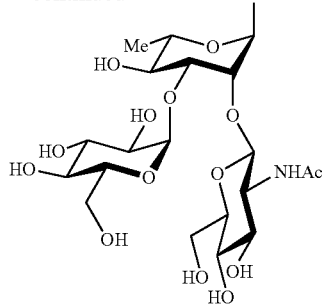

De 141b XXVII, R = Ac, D(E)AB$_{4c}$CD(E)AB$_{4c}$C
De 141c XXVIII, R = H, D(E)ABCD(E)ABC

Example of Demonstration of the Biological Activity of the Saccharides According to the Invention 1. Production of the Monoclonal Antibodies (mAbs)

Protocol 1) Four BP2 mice received, by the intraperitoneal route (i.p.), $5 \times 10^6$ live bacteria of the strain S. flexneri 3a every 3 weeks. After 8 injections, the mouse that had developed the best antibody response to the LPS of S. flexneri 3a received a booster injection 3 days before being sacrificed for carrying out cellular fusion with splenocytes obtained from the spleen. Two mAbs of type IgG (G17-12 and G17-37) specifically recognizing the LPS of S. flexneri 3a were obtained and characterized.

Protocol 2) Ten Balb/C mice and four BP2 mice were immunized by i.p. injection with virulent live bacteria of the strain S. flexneri 3a, every three weeks, using $2 \times 10^6$ bacteria for the first 2 immunizations and $5 \times 10^6$ for the next 4. As the anti-LPS 3a antibody response was too weak for performing cellular fusion, an additional series of 4 injections was carried out. Two mAbs of type IgM, G19-2 and L18-9, were obtained.

2. Characterization of the Oligosaccharide Determinants Recognized by the mAbs

The oligosaccharide determinants recognized by the four mAbs obtained were characterized by measuring, by inhibition ELISA, the interaction of the various oligosaccharides synthesized with these mAbs.

1) First, a standard curve OD=f(concentration of the mAb) was established for each antibody.

For this, purified LPS from S. flexneri 3a was fixed in the wells of ELISA plates (96-well plate), at a concentration of 25 µg/ml in a carbonate buffer pH 9.6, at 4° C., overnight. After washing the wells with a solution of PBS/Tween 20 (0.05%) 1% and a stage of saturation with PBS/BSA 1% for 30 minutes at 4° C., various concentrations of each mAb were incubated for 30 minutes at 4° C. After a washing stage, a secondary antibody coupled to alkaline phosphatase and specific to the mouse IgGs or IgMs was added at a dilution of 1/5000 (Sigma-Aldrich) for 1 h at 37° C. After washing, the enzymatic reaction was carried out with the specific substrate of alkaline phosphatase (12 mg of p-nitrophenylphosphate in 1.2 ml of Tris-HCl buffer 1M (pH 8.8) and 10.8 ml of 5M NaCl). Once the color reaction had developed, the plates were read at 405 nm (Dynatech MR 4000 plate reader). The standard curve OD=f(Ab concentration) was refined with the equation $Y=aX^2+bX+c$, where Y corresponds to the OD and X to the antibody concentration. A correlation factor ($r^2$) of 0.99 was generally obtained.

2) The concentration of oligosaccharide capable of inhibiting 50% of the fixation of the mAb on LPS 3a was then determined as follows.

Each mAb was used at a given concentration, defined as the first concentration tested giving a maximum OD on the standard curve (the first point at the start of the plateau of the curve). Various concentrations of each of the oligosaccharides to be tested were then incubated separately with the mAb at constant concentration, overnight at 4° C., in 1% PBS-BSA buffer. Measurement of the free antibody concentration was carried out as stated above, after incubation of the mAb/oligosaccharide mixtures at 4° C. for 30 minutes on plates covered with LPS 3a and using the standard curve obtained in parallel on the same plate. For each mAb and each oligosaccharide, a value called $IC_{50}$ was then calculated, corresponding to the concentration of oligosaccharide permitting 50% inhibition of the fixation of the mAb on LPS 3a.

The following tables present the results obtained for the oligosaccharides available to date, in interaction with the two mIgGs and one of the two mAb IgMs.

In addition, $IC_{50}$ characterizing the interaction of these antibodies with LPS 3a was also defined. The values are 19 ng/ml for L18-9 (mIgM); 39 ng/ml for G19-2 (mIgM); and 450 ng/ml for G17-12 and G17-37 (mIgG). It is important to note that here the value is expressed in ng/ml as it is very difficult to evaluate the molecular weight of the LPS without knowing precisely the length of the chains and therefore the number of repetitions of the oligosaccharide base unit.

TABLE 1 mIgG C7-37 and mIgG G7-12

| Saccharide | Abbreviated name | $IC_{50}$ with mIgG C7-37 | $IC_{50}$ with mIgG G7-12 |
|---|---|---|---|
| EA-OPr | A | >5 mM | >2.5 mM |
| EAB-OPr | B | >5 mM | >2.5 mM |
| DEA-OPr | C | >5 mM | >2.5 mM |
| DEA-OMethyl | D | >5 mM | >2.5 mM |
| DEAB-OPr | I | >5 mM | >2.5 mM |
| C(2,3-OAc)D(E)AB-OPr | E | >5 mM | >2.5 mM |
| C(OH)D(E)A-OPr | F | >5 mM | >2.5 mM |
| C(2-OAc)DEA-OPr | J | >5 mM | >2.5 mM |
| EABC(2-OAc)-OPr | G | 0.41 mM | 0.45 mM |
| EABC-OPr | H | >5 mM | >2.5 mM |
| DEABC(2-OAc)-OPr | K | +/−4 mM | >2.5 mM |
| DEABC)-OPr | L | >5 mM | >2.5 mM |
| EABC(2-OAc)D-OPr | M | 0.28 mM | 0.315 mM |
| EABCD-OPr | N | >1 mM | >2.5 mM |

TABLE 1-continued

| | mIgG C7-37 and mIgG G7-12 | | |
|---|---|---|---|
| Saccharide | Abbreviated name | $IC_{50}$ with mIgG C7-37 | $IC_{50}$ with mIgG G7-12 |
| BCDEA-Opr-Oac | O | 0.195 mM | 0.175 mM |
| BCDEA-Opr | P | >1 mM | >2.5 mM |
| BCDEAB-Opr | Q | >5 mM | >2.5 mM |
| BC(2-OAc)D(E)AB-OPr | R | 0.23 mM | 0.205 mM |

It is important to note: (i) that there is no difference between these two antibodies for recognition of the oligosaccharides. As they are obtained from one and the same limit dilution, it is very probable that it is in fact one and the same mAb; (ii) these results demonstrate the crucial role of acetylation of residue C in recognition.

TABLE 2

| | IgM (G 19-2) | |
|---|---|---|
| EA-OPr | A | >2.5 mM |
| EAB-OPr | B | >2.5 mM |
| DEA-OPr | C | >2.5 mM |
| DEA-OMethyl | D | >2.5 mM |
| DEAB-OPr | I | >2.5 mM |
| C(2,3-OAc)D(E)AB-OPr | E | >2.5 mM |
| C(OH)D(E)A-OPr | F | >2.5 mM |
| C(2-OAc)DEA-OPr | J | >2.5 mM |
| EABC(2-OAc)-OPr | G | 1.43 mM |
| EABC-Opr | H | >2.5 mM |
| DEABC(2-OAc)-OPr | K | >2.5 mM |
| DEABC)-OPr | L | >2.5 mM |
| EABC(2-OAc)D-OPr | M | 1.28 mM |
| EABCD-OPr | N | >2.5 mM |
| BCDEA-Opr-Oac | O | 1.98 mM |
| BCDEA-Opr | P | >2.5 mM |
| BCDEAB-Opr | Q | >2.5 mM |
| BC(2-OAc)D(E)AB-OPr | R | 2.2 mM |

The same oligosaccharides G, M, O and R are recognized by this mIgM antibody and by the mIgGs (tables 1 and 2) confirming the importance of the presence of the acetyl. Provision of residues additional to the oligosaccharide sequence G does not improve the recognition. The values obtained here are higher, indicating that the interaction is weaker than that observed with the mIgGs.

REFERENCES

1. Blatter, G.; Beau, J. M.; Jacquinet, J. C. *Carbohydr. Res.* 1994, 260, 189-202.
2. Kinzy, W.; Schmidt, R. R. *Liebigs Ann Chem* 1987, 407-415.
3. Shiozaki, M.; Kobayashi, Y.; Arai, M.; Watanabe, T.; Hiraoka, T.; Nishijima, M.; Kuge, S.; Otsuka, T.; Akamatsu, Y. *J Med Chem* 1991, 34, 2643-2646.
4. Hasegawa, A.; Ozaki, M.; Kiso, M.; Azuma, I. *J. Carbohydr. Chem.* 1984, 3, 331-341.
5. Myers, A. G.; Gin, D. Y.; Rogers, D. H. *J Am Chem Soc* 1993, 115, 2036-2038.
6. Oikawa, M.; Tanaka, T.; Fukuda, M.; Kusumoto, S. *Tetrahadron Lett* 2004, 45, 4039-4042.
7. Coutant, C.; Jacquinet, J. C. *J. Chem. Soc., Perkin Trans.* 1 1995, 1573-1581.
8. Bergmann, Max; Zervas, Leonidas *Ber. Dtsch. Chem. Ges.* 1931, 64, 975-980.
9. Medgyes, A.; Farkas, E.; Liptak, A.; Pozsgay, V. *Tetrahedron* 1997, 53, 4159-4178.
10. Myszka, H.; Bednarczyk, D.; Najder, M.; Kaca, W. *Carbohydr. Res.* 2003, 338, 133-141.
11. Inouye, Y.; Onodera, K.; Kitaoka, S.; Hirano, S. *J. Am. Chem. Soc.* 1956, 78, 4722-4724.
12. Inouye, Y.; Onodera, K.; Kitaoka, S.; Hirano, S. *J. Chem. Soc.* 1960, 25, 1265-1267.
13. Ponticelli, F.; Trendafilova, A.; Valoti, M.; Saponara, S.; Sgaragli, G. P. *Carbohydr. Res.* 2001, 330, 459-468.
14. Chittaboina, S.; Hodges, B.; Wang, Q. *Lett. Org. Chem.* 2006, 3, 35-38.
15. Excoffier, Gerard; Gagnaire, Didier; Utille, Jean-Pierre. *Carbohydr. Res.* 1975, 39, 368-373.
16. Lindhorst, T. K. *Essentials of Carbohydrate Chemistry and Biochemistry*; WILEY-VCH, 2000, 50.
17. Zhang, J.; Kovac, P. *J. Carbohydr. Chem.* 1999, 18, 461-469.
18. Furstner, A.; Muller, T. *J. Am. Chem. Soc.* 1999, 121, 7814-7821.
19. Larson, D. P.; Heathcock, C. H. *J. Org. Chem.* 1997, 62, 8406-8418.
20. Urban, F. J.; Moore, B. S.; Breitenbach, R. *Tetrahedron Lett.* 1990, 31, 4421-4424.
21. Yamazaki, F.; Sato, S.; Nukada, T.; Ito, Y.; Ogawa, T. *Carbohydr. Res.* 1990, 201, 31-50.
22. Lindhorst, T. K. *Essentials of Carbohydrate Chemistry and Biochemistry*; WILEY-VCH, 2000, 88.
23. Schmidt, R. R.; Jung, K-H. Oligosaccharide synthesis with Trichloroacetimidates Chapter 12. In *Modern Synthetic Methods in Carbohydrate Chemistry*; Hanessian, S. Ed.; Marcel Dekker Inc: New York, 1997; pp. 283-312.
24. Calinaud, P.; Gelas, J. Synthesis of Isopropylidene, Benzylidene, and Related Acetals Chapter 1. In *Preparative Carbohydrate Chemistry*; Hanessian, S. Ed.; Marcel Dekker Inc: New York, 1997; pp. 3-34.
25. Barili, P. L.; Berti, G.; Catelani, G.; Colonna, F.; Marra, A. *Tetrahedron Lett.* 1986, 27, 2307-2310.
26. Chittenden, G. J. F. *Carbohydr. Res.* 1980, 87, 219-226.
27. Chittenden, G. J. F. *Carbohydr. Res.* 1982, 108, 81-87.
28. Grindley, T. B.; Cote, C. J. P.; Wickramage, C. *Carbohydr. Res.* 1985, 140, 215-238.
29. Posner, G. H.; Loomis, G. L.; Sawaya, H. S. *Tetrahedron Lett.* 1975, 1373-1376.
30. Gelas, J.; Horton, D. *Carbohydr. Res.* 1978, 67, 371-387.
31. Wolfrom, M. L.; Diwadkar, A. B.; Gelas, J.; Horton, D. *Carbohydr. Res.* 1974, 35, 87-96.
32. Hasegawa, A.; Nakajima, M. *Carbohydr. Res.* 1973, 29, 239-245.
33. Hasegawa, A.; Kiso, M. *Carbohydr. Res.* 1978, 63, 91-98.
34. Schmidt, R. R.; Michel, J.; Roos, M. *Liebigs Ann. Chem.* 1984, 1343-1357.
35. Schmidt, R. R.; Stumpp, M. *Liebigs Ann. Chem.* 1983, 1249-1256.
36. Wegmann, B.; Schmidt, R. R. *J. Carbohydr. Chem.* 1987, 6, 357-375.
37. Alessi, Frederic; Doutheau, Alain; Anker, Daniel; Condemine, Guy; Robert-Baudouy, Janine. *Tetrahedron* 1996, 52, 4625-4636.
38. Crich, D.; Dudkin, V. *J Am Chem Soc* 2001, 123, 6819-6825.
39. Nashed, M. A.; Anderson, L. *J. Chem. Soc.-Chem. Commun.* 1982, 1274-1276.
40. Oltvoort, J. J.; Vanboeckel, C. A. A.; Dekoning, J. H.; Vanboom, J. H. *Synthesis-Stuttgart* 1981, 305-308.
41. Hecker, S. J.; Minich, M. L.; Lackey, K. *J. Org. Chem.* 1990, 55, 4904-4911.
42. Gigg, R.; Payne, S.; Conant, R. *J. Carbohydr. Chem.* 1983, 2, 207-223.

43. Pinto, B. M.; Morissette, D. G.; Bundle, D. R. *J. Chem. Soc., Perkin Trans.* 1 1987, 9-14.
44. Mulard, L. A.; Ughetto-Monfrin, J. *J. Carbohydr. Chem.* 2000, 19, 503-526.
45. Mulard, L. A.; Clement, M. J.; Segat-Dioury, F.; Delepierre, M. *Tetrahedron* 2002, 58, 2593-2604.
46. Lindhorst, T. K. *Essentials of Carbohydrate Chemistry and Biochemistry*; WILEY-VCH, 2000, 42.
47. Pinto, B. M.; Reimer, K. B.; Tixidre, A. *Carbohydr. Res.* 1991, 210, 199-219.
48. Smith, A. B.; Rivero, R. A.; Hale, K. J.; Vaccaro, H. A. *J. Am. Chem. Soc.* 1991, 113, 2092-2112.
49. Mulard, L. A.; Ughetto-Monfrin, J. *J. Carbohydr. Chem.* 1999, 18, 721-753.
50. Schmidt, R. R.; Michel, J. *Tetrahedron Lett.* 1984, 25, 821-824.
51. Zhang, K. Q.; Li, S. C.; Mao, J. M.; Chen, H. M.; Cai, M. S. *Chemical Journal of Chinese Universities-Chinese* 1997, 18, 1469-1473.
52. Schmidt, R. R.; Kinzy, W. ANOMERIC-OXYGEN ACTIVATION FOR GLYCOSIDE SYNTHESIS—THE TRICHLOROACETIMIDATE METHOD. In *Advances in Carbohydrate Chemistry and Biochemistry*, Vol 50, 1994; Vol. 50; pp. 21-123.
53. Hoffmann, M. G.; Schmidt, R. R. *Liebigs Ann. Chem.* 1985, 2403-2419.
54. Chapman, A. W. *Journal of Chemical Society* 1925, 127, 1992-1998.
55. Mumm, O; Hesse, H; Volquartz, H *Ber. Dtsch. Chem. Ges.* 1915, 48, 379-391.
56. Wiberg, K. B.; Rowland, B. I. *J. Am. Chem. Soc.* 1955, 77, 2205-2209.
57. Nifantev, N. E.; Amochaeva, V. Y.; Shashkov, A. S. *Bioorg. Khim* 1992, 18, 562-569.
58. Mulard, L. A.; Glaudemans, C. P. *Carbohydr. Res.* 1998, 311, 121-33.
59. Heathcock, C. H.; Ratcliffe, R. *J. Am. Chem. Soc.* 1971, 93, 1746.
60. Zemplen, G. *Ber. Dtsch. Chem. Ges.* 1920, 60, 1555-1564.
61. Donohoe, T. J.; Logan, J. G.; Laffan, D. D. P. *Org. Lett.* 2003, 5, 4995-4998.
62. Belot, F.; Guerreiro, C.; Baleux, F.; Mulard, L. A. *Chem. Eur. J.* 2005, 11, 1625-1635.
63. Backinowsky, L. V.; Gomtsyan, A. R.; Byramova, N. E.; Kochetkov, N. K. *Bioorg. Khim* 1984, 10, 79-87.
64. Bakinovskii, L. V.; Gomtsyan, A. R.; Bairamova, N. E.; Kochetkov, N. K. *Bioorg. Khim* 1985, 11, 254-263.
65. Nifantev, N. E.; Shashkov, A. S.; Khatuntseva, E. A.; Tsvetkov, Y. E.; Sherman, A. A.; Kochetkov, N. K. *Bioorg. Khim* 1994, 20, 1001-1012.
66. Koenigs, Wilhelm; Knorr, Eduard. *Chem. Ber.* 1901, 34, 957-981.
67. Castro Palomino, Julio C.; Hernandez Rensoli, Marylin; Verez Bencomo, Vicente. *J. Carbohydr. Chem.* 1996, 15, 137-146.
68. Fekete, A.; Gyergyoi, K.; Kover, K. E.; Bajza, I.; Liptak, A. *Carbohydr. Res.* 2006, 341, 1312-1321.
69. Geyer, K.; Seeberger, P. H. *Helv. Chim. Acta* 2007, 90, 395-403.
70. Li, A. X.; Kong, F. Z. *Carbohydr. Res.* 2004, 339, 2499-2506.
71. Ning, J.; Zhang, W. H.; Yi, Y. T.; Yang, G. B.; Wu, Z. K.; Yi, J.; Kong, F. Z. *Biorg. Med. Chem.* 2003, 11, 2193-2203.
72. Yang, F.; He, H. M.; Du, Y. G.; Lu, M. J. *Carbohydr. Res.* 2002, 337, 1165-1169.
73. Zeng, Y.; Ning, J.; Kong, F. Z. *Tetrahedron Lett.* 2002, 43, 3729-3733.
74. Zeng, Y.; Ning, J.; Kong, F. Z. *Carbohydr. Res.* 2003, 338, 307-311.
75. Zhang, G. H.; Fu, M. K.; Ning, J. *Carbohydr. Res.* 2005, 340, 597-602.
76. Demchenko, A.; Stauch, T.; Boons, G. J. *Synlett* 1997, 818-&.
77. Demchenko, A. V.; Rousson, E.; Boons, G. J. *Tetrahedron Lett.* 1999, 40, 6523-6526.
78. Manabe, S.; Ito, Y.; Ogawa, T. *Synlett* 1998, 628-+.
79. Nishimur, D; Hasegawa, A.; Nakajima, M. *Agricultural and Biological Chemistry* 1972, 36, 1767-&.
80. Leblanc, Y.; Fitzsimmons, B. J.; Adams, J.; Perez, F.; Rokach, J. *J. Org. Chem.* 1986, 51, 789-793.
81. Nicolaou, K. C.; Reddy, K. R.; Skokotas, G.; Sato, F.; Xiao, X. Y.; Hwang, C. K. *J. Am. Chem. Soc.* 1993, 115, 3558-3575.
82. Kitagawa, I.; Baek, N. I.; Ohashi, K.; Sakagami, M.; Yoshikawa, M.; Shibuya, H. *Chemical & Pharmaceutical Bulletin* 1989, 37, 1131-1133.
83. Lubineau, A.; Basset-Carpentier, K.; Auge, C. *Carbohydr. Res.* 1997, 300, 161-167.
84. Zhang, S. Q.; Li, Z. J.; Wang, A. B.; Cai, M. S.; Feng, R. *Carbohydr. Res.* 1998, 308, 281-285.
85. Baeschlin, D. K.; Green, L. G.; Hahn, M. G.; Hinzen, B.; Ince, S. J.; Ley, S. V. *Tetrahedron: Asym* 2000, 11, 173-197.
86. Belot, F.; Wright, K.; Costachel, C.; Phalipon, A.; Mulard, L. A. *J. Org. Chem.* 2004, 69, 1060-74.
87. Pozsgay, V.; Coxon, B. *Carbohydr. Res.* 1994, 257, 189-215.
88. Hassner, A.; Strand, G.; Rubinstein, M.; Patchornik, A. *J. Am. Chem. Soc.* 1975, 97, 1614-1615.
89. Vanboom, J. H.; Burgers, P. M. J. *Tetrahedron Lett.* 1976, 4875-4878.
90. Kosemura, S.; Yamamura, S.; Kakuta, H.; Mizutani, J.; Hasegawa, K. *Tetrahedron Lett.* 1993, 34, 2653-2656.
91. Yamamura, T.; Hada, N.; Kaburaki, A.; Yamano, K.; Takeda, T. *Carbohydr. Res.* 2004, 339, 2749-2759.
92. Kovac, P.; Edgar, K. J. *J. Org. Chem.* 1992, 57, 2455-2467.
93. Mulard, L. A.; Clement, M. J.; Imberty, A.; Delepierre, M. *Eur. J. Org. Chem.* 2002, 2486-2498.
94. Nagashima, N.; Ohno, M. *Chem. Lett.* 1987, 141-144.
95. Westerduin, P.; De Haan, P. E.; Dees, M. J.; Van Boom, J. H. *Carbohydr. Res.* 1988, 180, 195-205.
96. Bousquet, E.; Khitri, M.; Lay, L.; Nicotra, F.; Panza, L.; Russo, G. *Carbohydr. Res.* 1998, 311, 171-181.
97. Jeker, N.; Tamm, C. *Helv. Chico. Acta* 1988, 71, 1895-1903.
98. Jeker, N.; Tamm, C. *Helv. Chico. Acta* 1988, 71, 1904-1913.
99. Koeners, H. J.; Verhoeven, J.; Vanboom, J. H. *Tetrahedron Lett.* 1980, 21, 381-382.
100. Koeners, H. J.; Verhoeven, J.; Vanboom, J. H. *Recl. Trav. Chico. Pays-Bas-J. Roy. Neth. Chem. Soc.* 1981, 100, 65-72.
101. Osborn, H. M. I. *Carbohydrates*; Academic Press, New York, 2003, 26.
102. Ravida, A.; Liu, X. Y.; Kovacs, L.; Seeberger, P. H. *Org. Lett.* 2006, 8, 1815-1818.
103. Kong, F. Z. *Carbohydr. Res.* 2007, 342, 345-373.
104. Dong, L.; Roosenberg, J. M.; Miller, M. J. *J. Am. Chem. Soc.* 2002, 124, 15001-15005.
105. Zhu, Y. L.; Kong, F. Z. *Synlett* 2000, 1783-1787.
106. Lindhorst, T. K. *J. Carbohydr. Chem.* 1997, 16, 237-243.

107. Franks, N. E.; Montgomery, R. *Carbohydr. Res.* 1968, 6, 286-298.
108. Srivastava, V. K.; Schuerch, C. *J. Org. Chem.* 1981, 46, 1121-1126.
109. Glushka, J. N.; Perlin, A. S. *Carbohydr. Res.* 1990, 205, 305-321.
110. Kordes, M.; Winsel, H.; de Meijere, A. *Eur. J. Org. Chem.* 2000, 3235-3245.
111. Rips, R.; Derappe, Ch; Buu-Hoi, N. P. *J. Org. Chem.* 1960, 25, 390-392.
112. Meldgaard, M.; Hansen, F. G.; Wengel, J. *J. Org. Chem.* 2004, 69, 6310-6322.
113. Elliott, W. J.; Fried, J. *J. Org. Chem.* 1978, 43, 2708-2710.
114. Belot, F.; Rabuka, D.; Fukuda, M.; Hindsgaul, O. *Tetrahedron Lett.* 2002, 43, 7743-7747.
115. Belot, F.; Costachel, C.; Wright, K.; Phalipon, A.; Mulard, L. A. *Tetrahedron Lett.* 2002, 43, 8215-8218.
116. Nishikawa, T.; Urabe, D.; Tomita, M.; Tsujimoto, T.; Iwabuchi, T.; Isobe, M. *Org. Lett.* 2006, 8, 3263-3265.

The invention claimed is:

1. A conjugate specific to *Shigella flexneri* of serotype 3a and/or X, consisting of at least one saccharide selected from the group consisting of:
   $(X)_x\text{-}\{D(E)A\}_n\text{-}(Y)_y$
   $(X)_x\text{-}\{(E)AB\}_n\text{—}(Y)_y$
   $(X)_x\text{-}\{CD(E)A\}_n\text{-}(Y)_y$
   $(X)_x\text{-}\{D(E)AB\}_n\text{—}(Y)_y$
   $(X)_x\text{-}\{(E)ABC\}_n\text{—}(Y)_y$
   $(X)_x\text{-}\{BCD(E)A\}_n\text{-}(Y)_y$
   $(X)_x\text{-}\{CD(E)AB\}_n\text{—}(Y)_y$
   $(X)_x\text{-}\{D(E)ABC\}_n\text{—}(Y)_y$
   $(X)_x\text{-}\{(E)ABCD\}_n\text{—}(Y)_y$,
in which:
   A represents a residue α-L-Rhap-(1,2),
   B represents a residue α-L-Rhap-(1,3),
   C represents a residue α-L-Rhap-(1,3) or a residue [2-O-acetyl] α-L-Rhap-(1,3),
   D represents a residue β-D-GlcNAcp-(1,2) and
   E represents a residue α-D-Glcp-(1,3),
   x and y represent independently 0 or 1,
   X and Y represent a mono-, di- or oligosaccharide and are selected independently from the group consisting of A, B, C, D, E, AB, BC, CD, DA, (E)A, ABC, BCD, CDA, DAB, (E)AB, D(E)A, ABCD, BCDA, CDAB, DABC, (E)ABC, D(E)AB, CD(E)A, (E)ABCD, D(E)ABC, CD(E)AB and BCD(E)A,
   X and Y are such that the sequence of the group -ABCD- is always conserved, and
   n is an integer between 1 and 10
   said oligo- or polysaccharide being bound to a substrate molecule M, wherein M is selected from the group consisting of proteins, peptides, polylactic acids, polyglycolic acids, lipid aggregates and inactivated viral particles.

2. The conjugate as claimed in claim 1, wherein the substrate molecule M is selected from the group consisting of peptides and proteins having at least one epitope T selected from the group consisting of protein IpaD, peptide PADRE, tetanus toxin, protein KLH or protein $CRM_{197}$.

3. The conjugate as claimed in claim 1, wherein said saccharide is directly bound to said substrate molecule M.

4. The conjugate as claimed in claim 1, wherein said saccharide is bound to said substrate molecule M via a spacer.

5. The conjugate as claimed in claim 1, wherein the ratio of saccharide to molecule M is between 1:1 and 200:1 and wherein the saccharide is selected from the group consisting of:
   $(X)_x\text{-}\{D(E)A\}_n\text{-}(Y)_y$
   $(X)_x\text{-}\{(E)AB\}_n\text{—}(Y)_y$
   $(X)_x\text{-}\{CD(E)A\}_n\text{-}(Y)_y$
   $(X)_x\text{-}\{D(E)AB\}_n\text{-}(Y)_y$
   $(X)_x\text{-}\{(E)ABC\}_n\text{—}(Y)_y$
   $(X)_x\text{-}\{BCD(E)A\}_n\text{-}(Y)_y$
   $(X)_x\text{-}\{CD(E)AB\}_n\text{-}(Y)_y$
   $(X)_x\text{-}\{D(E)ABC\}_n\text{—}(Y)_y$
   $(X)_x\text{-}\{(E)ABCD\}_n\text{-}(Y)_y$,
in which:
   A represents a residue α-L-Rhap-(1,2),
   B represents a residue α-L-Rhap-(1,3),
   C represents a residue α-L-Rhap-(1,3) or a residue [2-O-acetyl] α-L-Rhap-(1,3),
   D represents a residue β-D-GlcNAcp-(1,2) and
   E represents a residue α-D-Glcp-(1,3),
   x and y represent independently 0 or 1,
   X and Y represent a mono-, di- or oligosaccharide and are selected independently from the group consisting of A, B, C, D, E, AB, BC, CD, DA, (E)A, ABC, BCD, CDA, DAB, (E)AB, D(E)A, ABCD, BCDA, CDAB, DABC, (E)ABC, D(E)AB, CD(E)A, (E)ABCD, D(E)ABC, CD(E)AB and BCD(E)A,
   X and Y are such that the sequence of the group -ABCD- is always conserved, and
   n is an integer between 1 and 10.

6. The conjugate as claimed in claim 1, wherein the saccharide is selected from the group consisting of the tetrasaccharides, the pentasaccharides and the multimers of the latter complying with the sequence of the group -ABCD-.

7. The conjugate as claimed in claim 6, wherein said saccharide is selected from the group consisting of:
   [CD(E)A], [D(E)AB], [(E)ABC], [BCD(E)A], [CD(E)AB], [D(E)ABC], [(E)ABCD], $[BCD(E)A]_n$, $[CD(E)AB]_n$, $[D(E)ABC]_n$, $[(E)ABCD]_n$, [BCD(E)AB], [D(E)ABCD], [D(E)ABCD(E)A], [BCD(E)ABCD], [BCD(E)ABCD(E)A], and [D(E)ABCD(E)ABC], with n being between 2 and 5.

8. An immunogenic composition containing a conjugate as claimed in claim 1 and at least one pharmaceutically acceptable excipient.

9. The composition as claimed in claim 8, wherein said saccharide is a pentasaccharide or a multimer of the latter.

10. The immunogenic composition as claimed in claim 8, wherein it additionally comprises an immunogen.

11. The composition as claimed in claim 8, wherein it is formulated for parenteral, oral, intranasal or intradermal administration.

12. A kit for diagnosis of an infection with *Shigella flexneri* of serotype 3a or X, wherein it comprises at least one conjugate as claimed in claim 1.

13. A method of preparation of a conjugate as claimed in claim 1, wherein it comprises the covalent reaction of a saccharide derivative selected from the group consisting of:
   $\{D(E)A\}_n\text{-O—R—Z}$
   $\{(E)AB\}_n\text{—O—R—Z}$
   $\{CD(E)A\}_n\text{-O—R—Z}$
   $\{D(E)AB\}_n\text{—O—R—Z}$
   $\{(E)ABC\}_n\text{—O—R—Z}$
   $\{BCD(E)A\}_n\text{-O—R—Z}$
   $\{CD(E)AB\}_n\text{—O—R—Z}$
   $\{D(E)ABC\}_n\text{—O—R—Z}$
   $\{(E)ABCD\}_n\text{—O—R—Z}$ in which A, B, C, D, E and n have the same definition as in claim 1, Z represents a functional group and R represents an alkyl group having from 1 to 12 carbon atoms with a suitable substrate molecule M.

14. The method as claimed in claim 13, wherein the covalent reaction comprises prior activation of the molecule M.

15. A method of preparation of a conjugate as claimed in claim 1, wherein it comprises the following stages:
  a) conjugation of a saccharide derivative selected from the group consisting of:
   {D(E)A}$_n$-O—R—Z
   {(E)AB}$_n$—O—R—Z
   {CD(E)A}$_n$-O—R—Z
   {D(E)AB}$_n$—O—R—Z
   {(E)ABC}$_n$—O—R—Z
   {BCD(E)A}$_n$-O—R—Z
   {CD(E)AB}$_n$—O—R—Z
   {D(E)ABC}$_n$—O—R—Z
   {(E)ABCD}$_n$—O—R—Z
   in which A, B, C, D, E and n have the same definition as in claim 1, Z represents a functional group and R represents an alkyl group having from 1 to 12 carbon atoms with a spacer to obtain a derivatized molecule containing said spacer, and
  b) reaction of the derivatized molecule containing the spacer with the molecule M.

16. A method of preparation of a conjugate as claimed in claim 1, wherein it comprises the following stages:
  a) conjugation of a molecule M to a suitable spacer to obtain a derivatized substrate molecule M containing the spacer, and
  b) reaction of said derivatized substrate molecule M with a saccharide derivative selected from the group consisting of:
   {D(E)A}$_n$-O—R—Z
   {(E)AB}$_n$—O—R—Z
   {CD(E)A}$_n$-O—R—Z
   {D(E)AB}$_n$—O—R—Z
   {(E)ABC}$_n$—O—R—Z
   {BCD(E)A}$_n$-O—R—Z
   {CD(E)AB}$_n$—O—R—Z
   {D(E)ABC}$_n$—O—R—Z
   {(E)ABCD}$_n$—O—R—Z
   in which A, B, C, D, E and n have the same definition as in claim 1, Z represents a functional group and R represents an alkyl group having from 1 to 12 carbon atoms.

17. The method of preparation of a conjugate as claimed in claim 15, wherein the spacer is a small molecule having a molecular weight of less than 500 dalton.

18. The method of preparation of a conjugate as claimed in claim 15, wherein the spacer is a homo-bifunctional molecule.

19. The method of preparation of a conjugate as claimed in claim 15, wherein the spacer is a hetero-bifunctional molecule.

* * * * *